United States Patent
Boschelli et al.

(10) Patent No.: US 6,689,772 B1
(45) Date of Patent: Feb. 10, 2004

(54) 3-CYANOQUINOLINES, 3-CYANO-1,6-NAPHTHYRIDINES, AND 3-CYANO-1,7-NAPHTHYRIDINES AS PROTEIN KINASE INHIBITORS

(75) Inventors: Diane Harris Boschelli, New City, NY (US); Yanong Wang, Nanuet, NY (US); Frank Charles Boschelli, New City, NY (US); Dan Maarten Berger, New City, NY (US); Nan Zhang, Bayside, NY (US); Dennis William Powell, Cortlandt Manor, NY (US); Fei Ye, Audubon, PA (US); Ayako Yamashita, Englewood, NJ (US); Frenel Fils DeMorin, Thousand Oaks, CA (US); Biqi Wu, Nanuet, NY (US); Hwei-Ru Tsou, New City, NY (US); Elsebe Geraldine Overbeek-Klumpers, Baam (NL); Allan Wissner, Ardsley, NY (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/318,213

(22) Filed: Dec. 12, 2002

Related U.S. Application Data

(62) Division of application No. 09/820,070, filed on Mar. 28, 2001, now Pat. No. 6,521,618.
(60) Provisional application No. 60/219,322, filed on Mar. 28, 2000.

(51) Int. Cl.[7] ............ A61K 31/33; A61K 31/535; A61K 31/4375; C07D 47/02
(52) U.S. Cl. ............ 514/183; 514/231.5; 514/313; 514/300; 514/314; 546/122
(58) Field of Search .................. 514/183, 231.5, 514/313, 300, 314; 546/122

(56) References Cited

U.S. PATENT DOCUMENTS

| | | | |
|---|---|---|---|
| 4,332,952 A | 6/1982 | Schnur | 548/226 |
| 4,343,804 A | 8/1982 | Munson, Jr. et al. | 424/258 |
| 5,104,882 A | 4/1992 | Young et al. | 514/311 |
| 5,232,916 A | 8/1993 | Zamboni et al. | 514/151 |
| 5,240,916 A * | 8/1993 | Caley et al. | |
| 5,480,883 A | 1/1996 | Spada et al. | 514/249 |
| 5,650,415 A | 7/1997 | Tang et al. | 514/312 |
| 5,814,630 A | 9/1998 | Barker et al. | 514/234.5 |
| 5,866,572 A | 2/1999 | Barker et al. | 514/234.5 |
| 5,955,464 A | 9/1999 | Barker | 514/289 |
| 5,958,947 A * | 9/1999 | Papadopoulou-Rosenzweig et al. | |
| 6,002,008 A | 12/1999 | Wissner et al. | 546/160 |

FOREIGN PATENT DOCUMENTS

| | | |
|---|---|---|
| DE | 19532714 | 3/1997 |
| EP | 0349062 | 1/1990 |
| EP | 0456442 | 11/1991 |
| EP | 0499415 | 8/1992 |
| EP | 0527534 | 2/1993 |
| EP | 837 063 | 4/1998 |
| GB | 2264710 | 9/1993 |
| WO | WO 85/01939 | 5/1985 |
| WO | WO 94/04526 | 3/1994 |
| WO | WO 94/04527 | 3/1994 |
| WO | WO 95/32948 | 12/1995 |
| WO | WO 96/02509 | 2/1996 |
| WO | WO 96/09294 | 3/1996 |
| WO | WO 97/19927 | 6/1997 |
| WO | WO 97/44036 | 11/1997 |
| WO | WO 97/44322 | 11/1997 |
| WO | WO 97/02434 | 1/1998 |
| WO | WO 98/02437 | 1/1998 |
| WO | WO 98/13350 | 4/1998 |
| WO | WO 98/20007 | 5/1998 |
| WO | WO 98/42670 | 10/1998 |
| WO | WO 98/43960 | 10/1998 |
| WO | WO 98/57936 | 12/1998 |
| WO | WO 99/35146 | 7/1999 |
| WO | WO 0018740 A | 6/2000 |
| WO | WO 0018761 A | 6/2000 |

OTHER PUBLICATIONS

Missbach, M., Bone, 24, 437 (1999).
Garrett, M.D., Current Opin. Genetics Devel., 9, 104 (1999).
R.D. Larsen, Current Opion in Drug Discovery and Development, 2, No. 6, 651–667 (1999).
Ellis, L.M., J. Biol. Chem., 273, 1052(1998).
Schwarzberg, P.L., Oncogene, 17, 1463–1468 (1998).
Campbell, S.L., Oncogene, 17, 1395–1413 (1998).
Webster, K.R., Exp. Opin. Invest. Drugs, 7, 865–887 (1998).
Glazer, R.I., Current Pharm. Design, 4(3) 277–290 (1998).
Traxler, P.M., Exp. Opin. Ther. Patents, 8 1599–1625 (1998).
Wolf, D.G., Arch. Virology 143 (6), 1223–1232 (1998).
Bridges, A.J., Emerging Drugs, 3, 279 (1998).
Myers, M., Current Pharm. Design, 3, 473 (1997).
He, Z., J. Virology, 71, 405–411(1997).

(List continued on next page.)

Primary Examiner—Mukund J. Shah
Assistant Examiner—Sudhaker B Patel
(74) Attorney, Agent, or Firm—Joy S. Goudie

(57) ABSTRACT

This invention provides compounds of Formula (I), having the structure

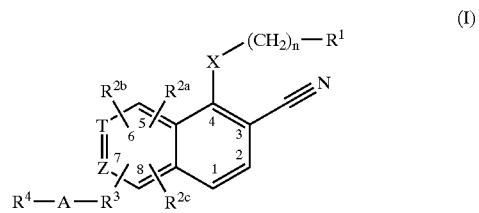

where T, Z, X, A, $R^1$, $R^{2a}$, $R^{2b}$, $R^{2c}$, $R^3$, $R^4$, and n are defined herein, or a pharmaceutically acceptable salt thereof which are useful as antineoplastic agents and in the treatment of osteoporosis and polycystic kidney disease.

28 Claims, No Drawings

OTHER PUBLICATIONS

Sivaraman, V.S., J. Clin. Invest., 99, 1478–1483 (1997).
O'Reilly, M.S., Cell, 88, 277–285 (1997).
Loomis, W.F., Cell Sci., 110, 1141–1145 (1997).
Staley, C.A., Cell Growth Differentiation, 8, 269–274 (1997).
Shawver, L.K., Drug Discovery Today, 2, 50–63 (1997).
Davies, D.E., Biochem. Pharmacol., 51, 1101–1110 (1996).
O'Reilly, M.S., Nature Medicine, 2, 689–692 (1996).
Rusch, V., Cytokine Growth Factor Rev., 7, 133–141 (1996).
Rains, E.W., BioEssays, 18, 271–282 (1996).
Alcalde, E., Tetrahedron, 52, 15171 (1996).
Seger. R., FASEB, 9, 726–735 (1995).
Sato, T.N., Nature, 376, 70–74 (1995).
Gattone, V.H., Developmental Biology, 169(2), 504–510(1995).
Nauta, J., Pediatric Res., 37(6), 755–763(1995).
Du, J., Amer. J. Physiol., 269(2 Pt 1), 487–495(1995).
Folkman, J., Nature Medicine, 1, 27–31(1995).
Mattsson. E., Trends Cardiovas. Med. 5, 200–204 (1995).
Shaw, Trends Parmacol. Sci., 16, 401–404 (1995).
Strawn, L.M., J. Biol. Chem. 269, 21215–21222 (1994).
O'Reilly, M.S., Cell, 79, 315–328 (1994).
Modjtahed, E., Int. J. Oncol. 4, 277 (1994).
Windscheif P. M., Synthesis, 87 (1994).
Wilson, P.D., Eur. J. Cell Biol., 61(1), 131, (1993).
Boyce, B.F., J. Clin. Invest., 90, 1622–1627 (1992).
Ife, R., J. Med. Chem., 35 (18), 3413–3422 (1992).
Denat, F., J. Organ. Metallic Chem., 423, 173–182 (1992).
Nister, M., J. Biol. Chem. 266, 16755–16763 (1991).
Soriano, P., Cell, 64, 693–702 (1991).
Gullick, W .J., Brit. Med. Bull., vol. 47, 87–98 (1991).
Slamon, D.J., Science, 244, 707–712 (1989).
Macias, A., Anticancer Res., 7, 459–464 (1987).
Slamon, D.J., Science, 235, 177–182 (1987).
Reiss, M., Cancer Res., 51, 6254–6262 (1991).
Theodoridis, G., Pesticide Science, 30(3), 259 (1990).
Richard C. Larock, Comprehensive Organic Transformations, VCH publishers, 411–415 (1989).
M. Yamamoto, J. Chem. Soc. Chem. Comm., 8, 560(1998).
Ross, S.T., J. Med. Chem., 30, 1309 (1987).
Johnson, A., J. Org. Chem., 41, 1320(1976).
PCT International Search Nov. 7, 2001.

* cited by examiner

… proliferation and migration responses in many cell types. Src activity has been shown to be elevated in breast, colon (~90%), pancreatic (>90%) and liver (>90%) tumors. Greatly increased Src activity is also associated with metastasis (>90%) and poor prognosis. Antisense Src message impedes growth of colon tumor cells in nude mice [Staley, C. A., *Cell Growth Differentiation*, 8, 269 (1997)], suggesting that Src inhibitors should slow tumor growth. In addition to its role in cell proliferation, Src also acts in stress response pathways, including the hypoxia response. Nude mice studies with colon tumor cells expressing antisense Src message have reduced vascularization [Ellis, L. M., *J. Biol. Chem.*, 273, 1052 (1998)], which suggests that Src inhibitors would be anti-angiogenic as well as anti-proliferative.

In addition to its role in cancer, Src also appears to play a role in osteoporosis. Mice genetically engineered to be deficient in Src production were found to exhibit osteopetiosis, the failure to resorb bone [Soriano, P., *Cell*, 64, 693 (1991); Boyce, B. F., *J. Clin., Invest.*, 90, 1622 (1992)]. This defect was characterized by a lack of osteoclast activity. Since osteoclasts normally express high levels of Src, inhibition of Src kinase activity may be useful in the treatment of osteoporosis [Missbach, M., *Bone*, 24, 437 (1999)].

Two members of the cytoplasmic protein TKs, lck and ZAP-70 are predominately expressed on T-cells and natural killer (NK) cells. Inhibitors of these kinases can suppress the immune system and therefore have possible therapeutic potential to treat autoimmune diseases such as rheumatoid arthritis, sepsis, and transplant rejection [Myers, M., *Current Pharm. Design*, 3, 473 (1997)].

Besides TKs, there are additional kinases including those that phosphorylate serine and/or threonine residues on proteins. A major pathway in the cellular signal transduction cascade is the mitogen-activated protein kinase (MAPK) pathway which consists of the MAP kinase kinases (MAPKK), including mek, and their substrates, the MAP kinases (MAPK), including erk [Seger, R., *FASEB*, 9, 726 (1995)]. When activated by phosphorylation on two serine residues by upstream kinases, such as members of the raf family, mek catalyzes the phosphorylation of threonine and tyrosine residues on erk. The activated erk then phosphorylates and activates both transcription factors in the nucleus and other cellular targets. Over-expression and/or over-activation of mek or erk is associated with various human cancers [Sivaraman, V. S., *J. Clin. Invest.*, 99, 1478 (1997)].

As mentioned above, members of the raf family of kinases phosphorylate serine residues on mek. There are three serine/threonine kinase members of the raf family known as a-raf, b-raf and c-raf. While mutations in the raf genes are rare in human cancers, c-raf is activated by the ras oncogene which is mutated in a wide number of human tumors. Therefore inhibition of the kinase activity of c-raf may provide a way to prevent ras medicated tumor growth [Campbell, S. L., *Oncogene*, 17, 1395 (1998)].

The cyclin-dependent kinases (cdks), including cdc2/cyclin B, cdk2/cyclin A, cdk2/cyclin E and cdk4/cyclin D, and others, are serine/threonine kinases that regulate mammalian cell division. Increased activity or activation of these kinases is associated with the development of human tumors [Garrett, M. D., *Current Opin. Genetics Devel.*, 9, 104 (1999); Webster, K. R., *Exp. Opin. Invest. Drugs*, 7, 865 (1998)]. Additional serine/threonine kinases include the protein kinases A, B, and C. These kinases, are known as PKA or cyclic AMP-dependent protein kinase, PKB or Akt, and PKC, and all three play key roles in signal transduction pathways responsible for oncogenesis [Glazer, R. I., *Current Pharm. Design*, 4(3), 277 (1998)]. Compounds capable of inhibiting the kinase activity of mek, erk, raf, cdc2/cyclin B, cdk2/cyclin A, cdk2/cyclin E, cdk4/cyclin D, PKA, Akt or PKC may be useful in the treatment of diseases characterized by abnormal cellular proliferation, such as cancer.

The serine/threonine kinase UL97 is a virion-associated protein kinase which is required for the replication of human cytomegalovirus [Wolf, D. G., *Arch. Virology* 143(6), 1223 (1998) and He, Z., *J. Virology*, 71, 405(1997)]. Compounds capable of inhibiting the kinase activity of UL97 may be useful antiviral therapeutics. Since certain bacteria require the action of a histidine kinase for proliferation [Loomis, W. F., *J. Cell Sci.* 110, 1141 (1997)], compounds capable of inhibiting such histidine kinase activity may be useful antibacterial agents.

Some 3-cyanoquinoline derivatives are inhibitors of tyrosine kinases and are described in the application WO9843960 (U.S. Pat. No. 6,002,008). These 3-cyanoquinolines may be substituted at carbon-5 through carbon-8 with an unsubstituted phenyl, alkene or alkyne group. A 3-cyanoquinoline with a 4-(2-methylanilino) substituent having gasitic ($H^+/K^+$)-ATPase inhibitory activity at high concentrations has been described [Ife, R., *J. Med. Chem.*, 35(18) 3413 (1992)].

Some 3-cyanoquinolines are claimed as inhibitors of tumor necrosis factor (TNF) or phosphodiesterase IV. The application WO982007 claims 3-cyanoquinolines that may be unsubstituted at carbon-2 and substituted at carbon-4 with an aryloxy, cycloalkoxy, heteroaryloxy or anilino group. However these compounds must contain at carbon-8 a hydroxy, thioalkyl, alkoxy of 1 to 6 carbon atoms or cycloalkoxy group optionally substituted with one or more halogens. These compounds must also contain at carbon-5 an imidazole, oxazole, or thiazole ring attached to the quinoline ring at carbon-2 and this hereroaryl ring must be fused to a 6-membered aromatic ring that may contain 1 or 2 nitrogen atoms in the ring. The application WO9857936 also claims 3-cyanoquinolines as inhibitors of tumor necrosis factor (TNF) or phosphodiesterase IV. These compounds may be unsubstituted at carbon-2 but must contain at carbon-8 a hydroxy, thioalkyl, alkoxy of 1 to 6 carbon atoms or cycloalkoxy group optionally substituted with one or more halogens. These compounds must contain at carbon-5 an aryl or heteroaryl ring that may be substituted. In addition these compounds may contain a aryloxy, cycloalkoxy, or heteroaryloxy group at carbon-4. However when an amino group is present at carbon-4 the amino group must be substituted by an alkylcarbonyl, alkoxycarbonyl, arylsulfonyl, heteroarylsulfonyl, heterocyclosulfonyl, arylcarbonyl, heteroarylcarbonyl, heterocyclocarbonyl or alkylsulfonyl group.

The applications WO9744036 and WO9744322 claim additional 3-cyanoquinolines as inhibitors of tumor necrosis factor (TNF) of phosphodiesterase IV but these applications do not claim the substituents at carbon-5 through carbon-8 of the 3-cyanoquinolines claimed herein.

The applications WO9404526 and WO9404527 claim 3-cyanoquinolines as pesticides. These 3-cyanoquinolines may be unsubstituted at carbon-2, but differ from the compounds claimed herein that they must contain at carbon-4 a group of formula —Y(CH$_2$)$_2$-phenyl, —Y(CH$_2$)$_2$-pyridine or —Y(CH$_2$)$_2$-pyridazine, where Y is O, CH$_2$, NH or N-alkyl. These applications also do not claim the substituents at carbon-5 through carbon-8 of the 3-cyanoquinolines claimed herein.

A series of patent applications, WO9719927, WO9602509, and WO9532948 claim 3-cyanoquinolines as neurokinin inhibitors. However these compounds must contain at carbon-4 of the quinoline a group of the formula C(X)NRR wherein X is O, S or N—CN and in addition carbon-2 of the quinoline can not be unsubstituted.

Several patents and patent applications claim 3-cyanoquinolines as inhibitors of leukotriene biosynthesis. While some of these, including U.S. Pat. No. 5,232,916, U.S. Pat. No. 5,104,882, EP349062 and DE19532714, claim compounds with the substituents at carbon-4 and at carbon-5 through carbon-8 of the cyanoquinoline claimed herein, all of the compounds must contain a substituent at carbon-2.

Several patent applications claim 3-cyanoquinolines as angiotensin II antagonists. EP499415 claims 3-cyanoquinolines, unsubstituted at carbon-2 and substituted at carbon-4 with a group of the formula NRCH$_2$Ph, wherein R is H or lower, alkyl and Ph is phenyl which must be substituted by a tetrazole, C(O)NHtetrazole or other specified groups. This application does not claim the substituents at carbon-5 through carbon-8 of the 3-cyanoquinolines claimed herein. A series of patent applications EP527534, EP156442 and CB2264710 claim 3-cyanoquinolines, unsubstituted at carbon-2 and substituted at carbon-4 with a group of the formula OCH$_2$Ph, but these applications do not claim the substituents at carbon-5 through carbons-8 of the 3-cyanoquinolines claimed herein.

U.S. Pat. No. 5,480,883 describes a series of compounds including quinolines as tyrosine kinase inhibitors. These quinoline compounds are unsubstituted at carbon-3. Patent application WO9609294 describes quinazolines and quinolines substituted at carbon-4 by anilino, phenoxy and thiophenoxy groups as tyrosine kinase inhibitors, however the quinoline compounds are unsubstituted at carbon-3. U.S. Pat. No. 5,650,415 describes quinolines substituted at carbon-4 by a benzylamino or benzylthio group as tyrosine kinase inhibitors. These quinolines however must contain an ethyl ester group at carbon-3. Additional quinoline compounds substituted with an ethyl ester at carbon-3 and an anilino group at carbon-4 are claimed in U.S. Pat. No. 4,343,804 as antisecretory and antiulcer compounds.

Patent application WO9813350 describes 3-fluoroquinolines, quinolines, 1,6-naphthyridines and 1,7-naphthyridines substituted at carbon-4 by anilino, phenoxy and thiophenoxy groups as tyrosine kinase inhibitors, but does not include the 3-cyano group contained in the quinoline, 1,6-naphthyridine and 1,7-naphthyridine compounds of the present invention.

Several patents and patent applications disclose quinazolines with anilino groups it carbon-4 and substituted at carbons-5 to 8 with a phenyl, naphthyl, alkene, alkyne or a 5–6 membered heteroaryl group as kinase inhibitors. U.S. Pat. No. 5,814,630 describes quinazolines substituted at carbon-7 with a phenyl, naphthyl or 5–6 membered heteroaromatic ring. U.S. Pat. No. 5,866,572 describes 4-anilinoquinazolines substituted at carbon-6 with a phenyl, naphthyl or 5–6 membered heteroaryl group that may be directly attached to the quinoline or attached via a carbonyl, alkyl or hydroxymethylene linker. U.S. Pat. No. 5,955,464 describes 4-anilinoquinazolines substituted at carbon-6 by a nitrogen containing heteroaryl group that is linked to the quinazoline via a nitrogen atom. The application EP837063 describes quinazolines that are substituted at carbons-5 to 8 with one or more optionally substituted 5- or 6-membered heteroaryl, or phenyl rings either directly attached to the quinazoline or attached via an alkene or alkyne linker.

Additionally, the application WO98024134 describes quinazolines and quinolines, as kinase inhibitors, unsubstituted at carbon-3, that are substituted at carbons-5 to 8 with one or more optionally substituted 5- or 6-membered heteroalyl or phenyl rings. Patent applications WO9802437 and WO9935146 further describe ring systems, including quinolines, 1,6-naphthyridines and 1.7-naphthyridines with anilino groups at carbon-4 and substituted at carbons-5 to 8 with one or more optionally substituted 5- or 6-membered heteroaryl or phenyl rings, as kinase inhibitors and which do not disclose the 3-cyano group of the present invention.

The compounds of the present invention are 3-cyanoquinolines with a suitably substituted heteroaryl, bicyclic heteroaryl, aryl, alkene or alkyne group at carbon-5, carbon-6, carbon-7, or carbon-8. Alternative names for 3-cyanoquinolines include 3-quinolinecarbonitriles and quinoline-3-carbonitriles. Also included in the present invention, are 3-cyano-1,6-naphthyridines with a suitably substituted heteroaryl, bicyclic heteroaryl, alkene or alklyne group at carbon-5, carbon-7, or carbon-8 and 3-cyano-1,7-naphthyridines with a suitably substituted heteroaryl, bicyclic heteroaryl, aryl, alkene or alkyne group at carbon-5, carbon-6, or carbon-8. The compounds of the present invention inhibit the activity of protein kinases that are required for cell growth and differentiation and are therefore useful for the treatment of certain diseases that result from activity of these protein kinases. The compounds of this invention are anti-cancer agents and are useful for the treatment of cancer in mammals. Further, the compounds of this invention are useful for the treatment of polycystic kidney disease in mammals.

SUMMARY OF THE INVENTION

In accordance with the present invention there is provided compounds represented by Formula (I):

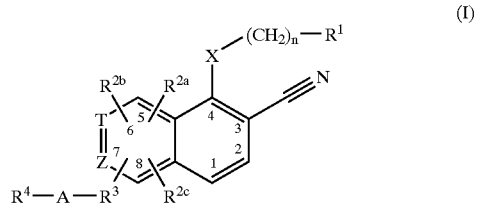

wherein:

X is —NH—, —NR$^5$—, —O—, or —S(O)$_m$—;

n is an integer of 0 or 1;

m is an integer of 0 to 2;

q is an integer of 0 to 5;

p is an integer of 2 to 5;

s is an integer of 0 to 5;

r is an integer of 0 to 5;

J is halogen;

A is —(C(R$^9$)$_2$)$_r$—, —C(O)—, —C(O)(C(R$^9$)$_2$)$_r$—, —(C(R$^9$)$_2$)$_r$C(O)—, -cycloalkyl- or is absent;

T and Z are each independently carbon or N, provided that both T and Z are not simultaneously N;

R$^1$ is selected from a cycloalkyl ring of 3 to 10 carbon atoms, optionally substituted with one or more independently selected alkyl groups of 1 to 6 carbon atoms; aryl of 6 to 12 carbon atoms optionally substituted with 1 to 4 substituents which may be the same or different independently selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$^2$)$_q$—, —NH(C(R$^9$)$_2$)$_q$—, —NR$^{10}$(C(R$^9$)$_2$)$_q$—, —(C(R$^9$)$_2$)$_q$(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;

a heteroaryl ring having 5 or 6 atoms containing 1 to 4 heteoatoms or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—,—(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;

a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, —J, —NO$_2$, —NH$_2$, —OH, —SH —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$) R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, NH(C(R$^9$)$_2$)$_q$—, —NR$^{10}$(C(R$^9$)$_2$)$_q$, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms; and a moiety of the formula

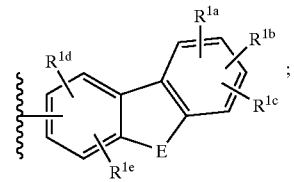

E is —NH—, —NR$^5$—, —O—, —S(O)$_m$—, —C(O)—, —CH$_2$—, —CHR$^5$— or —CR$^5$R$^5$—;

Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ring of 3 to 8 atoms, optionally containing 1 or 2 additional heteroatoms which may be the same or different selected from N, O and S;

R$^{1a}$, R$^{1b}$, R$^{1c}$, R$^{1d}$ and R$^{1e}$ are each, independently selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH—, —R$^6$OR$^5$, —R$^6$NH$_2$, —R$^6$NHR$^5$, —R$^6$Q, —R$^6$SH, —R$^6$S(O)$_m$ R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O) OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, -aryl, —CH$_2$aryl, —NHaryl, —Oaryl, —S(O)$_m$aryl, —R$^{11}$, —OR$^{11}$, —NHR$^{11}$ and —R$^6$OC(O)Q;

R$^{2a}$, R$^{2b}$, and R$^{2c}$, are each, independently selected from —H, -aryl, —CH$_2$aryl, —Oaryl, —S(O)$_m$, —J, —NO$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^7$OR$^5$, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O) OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$R$^{12}$, —(C(R$^9$)$_2$)$_q$R$^{12}$,

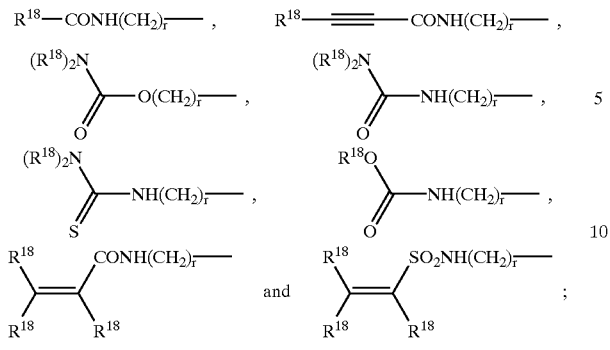

G is —NH—, —NR$^{10}$—, —O— of —S(O)$_m$—;

R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_q$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$—(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_q$H, —G(C(R$^9$)$_2$)$_q$OR$^{10}$, —G(C(R$^9$)$_{2)}$$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H—, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_q$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteoatoms or particularly 1 or 2 heteroatoms which may be the same or different, selected from N, O and S where the heteroaryl ring may be optionally substituted with to 4 substituents which may be the same or different selected from R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_q$H, —G(C(R$^9$)$_2$)$_p$OR$^{10}$, —G(C(R$^9$)$_2$)$_p$R$^{12}$ and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_q$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —Q(C(R$^9$)$_2$)$_p$OH;

aryl of 6 to 12 carbon atoms optionally substituted wit 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{11}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_Q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

R$^6$ is a divalent group selected from alkyl of 1 to 6 carbon atoms, alkenyl of 2 to 6 carbon atoms, and alkynyl of 2 to 6 carbon atoms;

R$^7$ is a divalent alkyl group of 2 to 6 carbon atoms;

R$^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —R$^6$R$^{12}$, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)

$R^7NHR^5$, $-N(R^5)R^7Q$, $-OR^7OH$, $-OR^7OR^5$, $-OR^7NH_2$, $-OR^7NHR^5$, $-OR^7Q$, $-OC(O)R^5$, $-NHC(O)R^5$, $-NHC(O)NHR^5$, $-OR^6C(O)R^5$, $-NHR^6C(O)R^5$, $-C(O)R^5$, $-C(O)OR^5$, $-C(O)NHR^5$, $-C(O)Q$, $-R^6C(O)H$, $-R^6C(O)R^5$, $-R^6C(O)OH$, $-R^6C(O)OR^5$, $-R^6C(O)NH_2$, $-R^6C(O)NHR^5$, $-R^6C(O)Q$, $-R^6OC(O)R^5$, $-R^6OC(O)NH_2$, $-R^6OC(O)NHR^5$ and $-R^6OC(O)Q$; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from $-H$, -aryl, $-CH_2$aryl, $-NH$ary, $-O$aryl, $-S(O)_m$aryl, $-J$, $-NO_2$, $-NH_2$, $-OH$, $-SH$, $-CN$, $-N_3$, $-COOH$, $-CONH_2$, $-NHC(O)NH_2$, $-C(O)H$, $-CF_3$, $-OCF_3$, $-R^5$, $-OR^5$, $-NHR^5$, $-Q$, $-S(O)_mR^5$, $-NHSO_2R^5$, $-R^{11}$, $-OR^{11}$, $-NHR^{11}$, $-R^6OH$, $-R^6OR^5$, $-R^6NH_2$, $-R^6NHR^5$, $-R^6Q$, $-R^6SH$, $-R^6S(O)_mR^5$, $-NHR^7OH$, $-NHR^7R^5$, $-N(R^5)R^7OH$, $-N(R^5)R^7OR^5$, $-NHR^7NH_2$, $-NHR^7NHR^5$, $-NHR^7Q$, $-N(R^5)R^7NH_2$, $-N(R^5)R^7NHR^5$, $-N(R^5)R^7Q$, $-OR^7OH$, $-OR^7OR^5$, $-OR^7NH_2$, $-OR^7NHR^5$, $-OR^7Q$, $-OC(O)R^5$, $-NHC(O)R^5$, $-R^6R^{12}$, $-NHC(O)NHR^5$, $-OR^6C(O)R^5$, $-NHR^6C(O)R^5$, $-C(O)R^5$, $-C(O)OR^5$, $-C(O)NHR^5$, $-C(O)Q$, $-R^6C(O)H$, $-R^6C(O)R^5$, $-R^6C(O)OH$, $-R^6C(O)OR^5$, $-R^6C(O)NH_2$, $-R^6C(O)NHR^5$, $-R^6C(O)Q$, $-R^6C(O)R^5$, $-R^6OC(O)NH_2$, $-R^6C(O)NHR^5$ and $-R^6OC(O)Q$; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from $-H$, -aryl, $-CH_2$aryl, $-NH$aryl, $-O$aryl, $-S(O)_m$aryl, $-J$, $-NO_2$, $-NH_2$, $-OH$, $-SH$, $-CN$, $-N_3$, $-COOH$, $-CONH_2$, $-NHC(O)NH_2$, $-C(O)H$, $-CF_3$, $-OCF_3$, $-R^5$, $-OR^5$, $-NHR^5$, $-Q$, $-S(O)_mR^5$, $-NHSO_2R^5$, $-R^{11}$, $-OR^{11}$, $-NHR^{11}$, $-R^6OH$, $-R^6OR^5$, $-R^6NH_2$, $-R^6NHR^5$, $-R^6Q$, $-R^6SH$, $-R^6R^{12}$, $-R^6S(O)_mR^5$, $-NHR^7OH$, $-NHR^7OR^5$, $-N(R^5)R^7OH$, $-N(R^5)R^7OR^5$, $-NHR^7NH_2$, $-NHR^7NHR^5$, $-NHR^7Q$, $-N(R^5)R^7NH_2$, $-N(R^5)R^7NHR^5$, $-N(R^5)R^7Q$, $-OR^7OH$, $-OR^7OR^5$, $-OR^7NH_2$, $-OR^7NHR^5$, $-OR^7Q$, $-OC(O)R^5$, $-NHC(O)R^5$, $-NHC(O)NHR^5$, $-OR^6C(O)R^5$, $-NHR^6C(O)R^5$, $-C(O)R^5$, $-C(O)OR^5$, $-C(O)NHR^5$, $-C(O)Q$, $-R^6C(O)H$, $-R^6C(O)R^5$, $-R^6C(O)OH$, $-R^6C(O)OR^5$, $-R^6C(O)NH_2$, $-R^6C(O)NHR^5$, $-R^6C(O)Q$, $-R^6OC(O)R^5$, $-R^6OC(O)NH_2$, $-R^6OC(O)NHR^5$ and $-R^6OC(O)Q$;

$R^9$ is independently $-H$, $-F$ or $-R^5$;

$R^{10}$ is an alkyl group of 1 to 12 carbon atoms, preferred is 1 to 6 carbon atoms;

$R^{11}$ is a cycloalkyl group of 3 to 10 carbon atoms;

$R^{12}$ is $-N(O)_nR^{13}R^{14}$ or $-N^+(R^{10}R^{13}R^{14})J^-$;

provided that when $R^{12}$ is $N(O)_nR^{13}R^{14}$ and n is 1, $R^{13}$ or $R^{14}$ are not H;

$R^{13}$ and $R^{14}$ are independently selected from a group consisting of $-H$, $-R^5$, $-R^{11}$, $-(C(R^9)_2)_q$aryl-$R^{15}$, $-(C(R^9)_2)_q$heteroaryl-$R^{15}$, $-(C(R^9)_2)_q$heterocyclyl-$R^{15}$, $-(C(R^9)_2)_pOR^{16}$, $-(C(R^9)_2)_pNR^{16}R^{17}$, $-(C(R^9)_2)_pS(O)_mR^{16}$, $-(C(R^9)_2)_pCO_2R^{16}$, $-(C(R^9)_2)_pC(O)NHR^{16}$ and $-(C(R^9)_2)_pC(O)R^{15}$; fur-ther provided that $R^3$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, $-R^5$, $-R^{11}$, $-(C(R^9)_2)_q$aryl$R^{15}$, $-(C(R^9)_2)_q$heteroaryl$R^{15}$, $-(C(R^9)_2)_q$heterocyclyl$R^{15}$, $-(C(R^9)_2)_qCO_2R^{16}$, $-(C(R^9)_2)_qC(O)NHR^{16}$, and $-(C(R^9)_2)_qC(O)R^{15}$; or optionally substituted on carbon by $-F$, $-(C(R^7)_2)_qOR^{16}$, $-(C(R^7)_2)_qNR^{16}R^{17}$, and $-(C(R^9)_2)_qS(O)_mR^{16}$; or optionally substituted on nitrogen by $-(C(R^9)_2)_pOR^{16}$, $-(C(R^9)_2)_pNR^{16}R^{17}$, and $-(C(R^9)_2)_pS(O)_mR^{16}$;

$R^{15}$ is independently selected from a group consisting of $-H$, $-R^5$, $-R^{11}$, $-(C(R^9)_2)_q$aryl, $-(C(R^9)_2)_q$heteroalyl, $-(C(R^9)_2)_q$hetetocyclyl, $-(C(R^9)_2)_qOH$, $-(C(R^9)_2)_qOR^{10}$, $-(C(R^9)_2)_qNH_2$, $-(C(R^9)_2)_qNHR^{10}$, $-(C(R^9)_2)_qS(O)_mR^{10}$, $-(C(R^9)_2)_qCO_2R^{10}$, $-(C(R^9)_2)_qCONHR^{10}$, $-(C(R^9)_2)_qCONR^{10}R^{10}$, $-(C(R^9)_2)_qCOR^{10}$, $(C(R^9)_2)_qCO_2H$, and $-(C(R^9)_2)_qCONH_2$;

$R^{16}$ and $R^{17}$ are independently selected from n group consisting of $-H$, $-R^5$, $-R^{11}$, $-(C(R^9)_2)_q$aryl, $-(C(R^9)_2)_q$heteroaryl, $-(C(R^9)_2)_q$heterocyclyl, $-(C(R^9)_2)_pOH$, $-(C(R^9)_2)_pOR^{10}$, $-(C(R^9)_2)_pNH_2$, $-(C(R^9)_2)_pNHR_2$, $-(C(R^9)_2)_pNR^{10}R^{10}$, $-(C(R^9)_2)_pS(O)_mR^{10}$, $-(C(R^9)_2)_pCO_2R^{10}$, $-(C(R^9)_2)_pCONHR^{10}$, $-(C(R^9)_2)_pCONR^{10}R^{10}$, $-(C(R^9)_2)_pCOR^{10}$, $-(C(R^9)_2)_pCO_2H$, and $-(C(R^9)_2)_pCONH_2$;

$R^{18}$ is independently selected from the group consisting of $-H$, -aryl, $-R^5$, $-R^6NH_2$, $-R^6NHR^5$ and $-R^6Q$;

provided that, when T and Z are carbon, A is absent, r is 0 and $R^4$ is $-(C(R^9)_2)_rH$, then,
  a. $R^3$ is not unsubstituted thiophene, furan, thiazole, imidazole, 1,2,3-triazole, 1,2,4-triazole, tetrazole, pyridine, phenyl, alkenyl or alkynyl; or
  b. $R^3$ is not monosubstituted by $-R^{10}$, $-(C(R^9)_2)_qOH$, or $-(C(R^9)_2)_qOR^{10}$ when $R^3$ is thiophene, furan, thiazole, imidazole, 1,2,3-triazole, 1,2,4-triazole, tetrazole or pyridine; and
  c. $R^{13}$ and $R^{14}$ are not alkyl of 1 to 6 carbon atoms when $R^3$ is thiophene, furan, thiazole, imidazole, 1,2,3-triazole, 1,2,4-triazole, tetrazole or pyridine when $R^3$ is substituted by $-(C(R^9)_2)_sR^{12}$ and $R^{12}$ is $-NR^{13}R^{14}$;

further provided that, when T and Z are carbon, A is absent and $R^4$ is phenyl, then,
  a. $R^4$ is not substituted by $-NO_2$, $-CN$, $-CO_2H$, $-CONH_2$, $-CO_2R^{10}$, $-CONHR^{10}$, $-(C(R^9)_2)_qOH$, $-(C(R^9)_2)_qOR^{10}$, $-(C(R^9)_2)_qNHR^{10}$, $-(C(R^9)_2)_qJ$ or $-(C(R^9)_2)_qNH_2$ or unsubstituted when $R^3$ is thiophene, furan, thiazole, imidazole, 1,2,3-triazole, 1,2,4-triazole, tetrazole or pyridine; and
  b. $R^{13}$ and $R^{14}$ are not independently alkyl of 1 to 3 carbon atoms when $R^3$ is thiophene, furan, thiazole, imidazole, 1,2,3-triazole, 1,2,4-triazole, tetrazole or pyridine, wherein $R^4$ is substituted by $-(C(R^9)_2)_sR^{12}$ and s is 0 and $R^{12}$ is $-NR^{13}R^{14}$;

additionally provided that, when T and Z are carbon, then,
  a. carbon-8 is not substituted by $-OH$, $-OR^{10}$, $-SR^{10}$, or $-OR^{11}$ when carbon-5 is substituted by an imidazole, oxazole or thiazole ring that is fused to a 6-membered aryl or heteroaryl ring heaving 0 to 2 nitrogen atoms and wherein the fused bicyclic heteroaryl ring is attached to carbon-5 of Formula (I) via carbon-2 of the imidazole, oxazole or thiazole ring; and b. carbon-8 is not substituted by —OH, —OR$^{10}$, —SR$^{10}$, or —OR$^{11}$ when X is —O— and carbon-5 is substituted by aryl or heteroaryl;

further provided that when either T or Z are N, then R$^{2c}$ is absent; or a pharmaceutically acceptable salt thereof.

Among the preferred groups of compounds of Formula (I) of this invention including pharmaceutically acceptable salts thereof are those in the subgroups below, wherein the other variables of Formula (I) in the subgroups are as defined above wherein:

a) X is —NH—, —NR$^5$— and —O—;
b) T and Z are carbon;
c) T is N and Z is carbon;
d) T is carbon and Z is N;
e) T and Z are carbon, n is 0 and X is —NH—;
f) T is carbon and Z, is N, n is 0 and X is —NH—;
g) T is N and Z is carbon, n is 0 and X is —NH—;
h) T and Z are carbon, n is 0, X is —NH— and R$^1$ is aryl;
i) T is carbon and Z is N, n is 0, X is —NH— and R$^1$ is aryl;
j) T is N and Z is carbon, n is 0, X is —NH— and R$^1$ is aryl;

Among the additionally preferred groups of compounds of Formula (I) of this invention including pharmaceutically acceptable salts thereof are those in the subgroups below, wherein the other valuables of Formula (I) in the subgroups are as defined above wherein:

a) 3-cyanoquinolines, 3-cyano-1,6-naphthyridines and 3-cyano-1,7-naphthyridines of Formula (I) wherein:
X is —NH—;
n is 0;
R$^1$ is a phenyl ring optionally substituted with 1 to 4 substituents which may be the same or different independently selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$, —NR$^{10}$(C(R$^9$)$_2$)$_q$, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$(NR$^{10}$—, —C≡C—, cis and trans —CH=CH— and cycloalkyl of 3 to 10 carbon atoms; or a pharmaceutically acceptable salt thereof.

b) 3-cyanoquinolines, of Formula (I) wherein:
T and Z are carbon;
X is —NH—;
n is 0;
R$^1$ is a phenyl ring optionally substituted with 1 to 4 substituents which may be the same or different independently selected form —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^6$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$, —S(O)$_m$ (C(R$^9$)$_2$)$_q$—, —NH(C(R$^9$)$_2$)$_q$, —NR$^{10}$(C(R$^9$)$_2$)$_q$, —(C(R$^9$)$_2$)$_q$—, —(C(R$^9$)$_2$)$_q$O—, —(C(R$^9$)$_2$)$_q$ S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;
or pharmaceutically acceptable salt thereof.

d) 3-cyanoquinolines of Formula (I) wherein:
X is —NH—;
T and Z are carbon;
n is 0;
A is absent;
R$^1$ is a phenyl ring optionally substituted with 1 to 4 substituents which may be the same or different independently selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, R$^6$C(O)OR$^5$, —R$^6$C(O)NH$_2$, —R$^6$C(O)NHR$^5$, R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH═CH— and cycloalkyl of 3 to 10 carbon atoms;

or pharmaceutically acceptable salt thereof.

e) 3-cyanoquinolines of Formula (I) wherein:
T and Z are carbon;
X is —NH—;
n is 0;
R$^1$ is a phenyl ring substituted with 1 to 4 substituents which may be the same or different independently selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$; —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH═CH— and cycloalkyl of 3 to 10 carbon atoms;
A is absent;
R$^4$ is (C(R$^9$)$_2$)$_r$H;
r is 0;

or a pharmaceutically acceptable salt thereof.

Among the broadly preferred groups of compounds of Formula (I) of this invention including pharmaceutically acceptable salts thereof are those in the subgroups below, wherein the other variables of Formula (I) in the subgroups are as defined above wherein:

a) 3-cyanoquinolines of Formula (I) wherein:
T and Z are carbon;
R$^{2a}$ and R$^{2b}$ are hydrogen;
R$^{2c}$ is selected from —H, —J, —CF$_3$, —OCF$_3$, —R$^5$, —OR$^5$, —OR$^{11}$, —OR$^7$OH, —OR$^7$OR$^5$ and —S(O)$_m$R$^5$;
X is —NH—;
n is 0;
R$^1$ is phenyl optionally substituted with 1 to 4 substituents which may he the same or different independently selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NH$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NH$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H, —O(C(R$^9$)$_2$)$_q$—, —S(O)$_m$(C(R$^9$)$_2$)$_q$—, —NH(C(R$^9$)$_2$)$_q$—, —NHR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH═CH— and cycloalkyl of 3 to 10 carbon atoms;

or a pharmaceutically acceptable salt thereof.

b) 3-cyanoquinolines of Formula (I) wherein:
T and Z are carbon;
R$^{2a}$ and R$^{2b}$ are hydrogen;
R$^{2c}$ is selected from —H, —J, —CF$_3$, —OCF$_3$, —R$^5$, —OR$^5$, —OR$^{11}$, —OR$^7$OH, —OR$^7$OR$^5$ and —S(O)$_m$R$^5$;
X is —NH—;
n is 0;
R$^1$ is phenyl optionally substituted with 1 to 4 substituents which may be the same or different independently selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_M$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, (C(R$^9$)$_2$)$_q$NH—, —(C(R$^9$)$_2$)$_q$NR$^{10}$—, —C≡C—, cis and trans —CH═CH— and cycloalkyl of 3 to 10 carbon atoms;

A is absent;
or a pharmaceutically acceptable salt thereof.

c) 3-cyanoquinolines of Formula (I) wherein:
T and Z are carbon;
$R^{2a}$ and $R^{2b}$ are hydrogen;
$R^{2c}$ is selected from —H, —J, —$CF_3$, —$OCF_3$, —$R^5$, —$OR^5$, —$OR^5$, —$OR^7OH$, —$OR^7OR^5$ and —$S(O)_m R^5$;
X is —NH—;
n is 0;
$R^1$ is phenyl optionally substituted with 1 to 4 substituents which may be the same or different independently selected from —H, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_m R^5$, —$NHSO_2R^5$, —$R^6OH$, —$R^6OR^5$, —$R^6NH_2$, —$R^6NHR^5$, —$R^6Q$, —$R^6SH$, —$R^6S(O)_m R^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NH^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$, —$R^6OC(O)Q$ and $YR^8$ groups wherein Y is independently selected from —C(O)—, —C(O)O—, —OC(O)—, —C(O)NH—, —NHC(O)—, —$NHSO_2$—, —$SO_2NH$—, —C(OH)H—, —$O(C(R^9)_2)_q$—, —$S(O)_m (C(R^9)_2)_q$—, —$NH(C(R^9)_2)_q$—, —$NR^{10}(C(R^9)_2)_q$—, —$(C(R^9)_2)_q$—, —$(C(R^9)_2)_q O$—, —$(C(R^9)_2)_q S(O)_m$—, —$(C(R^9)_2)_q NH$, —$(C(R^9)_2)_q NR^{10}$—, —C≡C—, cis and trans —CH=CH— and cycloalkyl of 3 to 10 carbon atoms;
$R^4$ is —$(C(R^9)_2)_r H$;
r is 0;
A is absent;
$R^3$ is attached to carbon-7 of Formula (I) and is selected from aryl, heteroaryl, bicyclic heteroaryl, alkenyl, alkynyl wherein each aryl, heteroaryl, bicyclic heteroaryl, alkenyl, and alkynyl is optionally substituted by one or more of —$R^{10}$, —$(C(R^9)_2)_s R^{12}$, —CHO, 1,3-dioxolane, —$CONH_2$, —$CO_2R^{10}$, —$CONHR^{10}$, —$COR^{10}$, —$(C(R^9)_2)_q OH$, —$(C(R^9)_2)_q OR^{10}$, —$(C(R^9)_2)_q NHR^{10}$, —$(C(R^9)_2)_q NH_2$, $G(C(R^9)_2)_p OR^{10}$, $G(C(R^9)_2)_p OH$, and $G(C(R^9)_2)_s R^{12}$;
or a pharmaceutically acceptable salt thereof.

d) 3-cyanoquinolines of Formula (I) wherein:
T and Z are carbon;
$R^{2a}$ and $R^{2b}$ are hydrogen;
$R^{2c}$ is selected from —H, —J, —$CF_3$, —$OCF_3$, —$R^5$, —$OR^5$, —$OR^{11}$, —$OR^7OH$, —$OR^7OR^5$ and —$S(O)_m R^5$;
X is —NH—;
n is 0;
$R^1$ is phenyl optionally substituted with 1 to 4 substituents which may be the same or different independently selected from —H, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_m R^5$, —$NHSO_2R^5$, —$R^6OH$, —$R^6OR^5$, —$R^6NH_2$, —$R^6NHR^5$, —$R^6Q$, —$R^6SH$, —$R^6S(O)_m R^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$, —$R^6OC(O)Q$ and $YR^8$ groups wherein Y is independently selected from —C(O)—, —C(O)O—, —OC(O)—, —C(O)NH—, —NHC(O)—, —$NHSO_2$—, —$SO_2NH$—, —C(OH)H—, —$O(C(R^9)_2)_q$—, —$S(O)_m(C(R^9)_2)_q$—, —$NH(C(R^9)_2)_q$—, —$NR^{10}(C(R^9)_2)_q$—, —$(C(R^9)_2)_q$—, —$(C(R^9)_2)_q O$—, —$(C(R^9)_2)_q S(O)_m$—, —$(C(R^9)_2)_q NH$—, —$(C(R^9)_2)_q NR^{10}$—, —C≡C—, cis and trans —CH=CH— and cycloalkyl of 3 to 10 carbon atoms;
$R^4$ is —$(C(R^9)_2)_r H$;
r is 0;
A is absent;
$R^3$ is attached to carbon-6 of Formula (I) and is selected form aryl, heteroaryl, bicyclic heteroaryl, alkenyl, alkynyl wherein each aryl, heteroaryl, bicyclic heteroaryl, alkenyl, and alkynyl is optionally substituted by one or more of —$R^{10}$, —$(C(R^9)_2)_s R^{12}$, —CHO, 1,3-dioxolane, —$CONH_2$, —$CO_2R^{10}$, —$CONHR^{10}$, —$COR^{10}$, —$(C(R^9)_2)_q OH$, —$(C(R^9)_2)_q OR^{10}$, —$(C(R^9)_2)_q NHR^{10}$, —$(C(R^9)_2)_q NH_2$, $G(C(R^9)_2)_p OR^{10}$, —$G(C(R^9)_2)_p OH$, and $G(C(R^9)_2)_p R^{12}$;
or a pharmaceutically acceptable salt thereof.

Among the more preferred groups of compounds of Formula (I) of this invention including pharmaceutically acceptable salts thereof are those in the subgroups below wherein the other variables of Formula (I) in the subgroups are as defined above wherein:

a) 3-cyanoquinolines of Formula (I) wherein:
T and Z are carbon;
$R^{2a}$ and $R^{2b}$ are hydrogen;
$R^{2c}$ is attached to carbon-6 or carbon-7 of Formula (I) and is selected from —H, —J, —$CF_3$, —$OCF_3$, —$R^5$, —$OR^5$, —$OR^{11}$, —$OR^7OH$, —$OR^7OR^5$ and —$S(O)_m R^5$;
X is —NH—;
n is 0;
$R^1$ is phenyl optionally substituted with 1 to 4 substituents which may be the same or different independently selected from —H, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_m R^5$, —$NHSO_2R^5$, —$R^6OH$, —$R^6OR^5$, —$R^6NH_2$, —$R^6NHR^5$, —$R^6Q$, —$R^6SH$, —$R^6S(O)_m R^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$, —$R^6OC(O)Q$ and —$YR^8$ groups wherein Y is independently selected from —C(O)—, —C(O)O—, —OC(O)—, —C(O)NH—, —NHC(O)—, —$NHSO_2$—, —$SO_2NH$—, —C(OH)H—, —$O(C(R^9)_2)_q$—, —$S(O)_m(C(R^9)_2)_q$—, —$NH(C(R^9)_2)_q$—, —$NR^{10}(C(R^9)_2)_q$—, —$(CR^9)_2)_q$—, —(C $(R^9)_2)_qO$—, —$(C(R^9)_2)_qS(O)_m$—, —$(C(R^9)_2)_q$NH—, —$(C(R^9)_2)_qNR^{10}$—, —C≡C—, cis and trans —CH=CH— and cycloalkyl of 3 to 10 carbon atoms;

$R^4$ is —$(C(R^9)_2)_rH$;

r is 0;

A is absent;

$R^3$ is attached to carbon-6 or carbon-7 of Formula (I) and is selected from aryl, heteroaryl, bicyclic heteroaryl, alkenyl, alkynyl wherein each aryl, heteroaryl, bicyclic heteroaryl, alkenyl, alkynyl is optionally substituted by one or more of —$R^{10}$, —$(C(R^9)_2)_sR^{12}$, —CHO, and 1,3-dioxolane;

or a pharmaceutically acceptable salt thereof.

b) 3-cyanoquinolines of Formula (I) wherein:

T and Z are carbon;

X is —NH—;

n is 0;

$R^1$ is phenyl optionally substituted with 1 to 4 substituents which may be the same or different independently selected from —H, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_mR^5$, —$NHSO_2R^5$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$, —$R^6OC(O)Q$ and $YR^8$ groups wherein Y is independently selected from —C(O)—, —C(O)O—, —OC(O)—, —C(O)NH—, —NHC(O)—, —$NHSO_2$—, —$SO_2NH$—, —C(OH)H—, —$O(C(R^9)_2)_q$—, —$S(O)_m(C(R^9)_2)_q$—, —$NH(C(R^9)_2)_q$—, —$NR^{10}(CR^9)_2)_q$—, —$(C(R^9)_2)_q$—, —$(C(R^9)_2)_qO$—, —$(C(R^9)_2)_qS(O)_m$—, —$(C(R^9)_2)_qNH$—, —$(C(R^9)_2)_qNR^{10}$—, —C≡C—, cis and trans —CH=CH— and cycloalkyl of 3 to 10 carbon atoms;

$R^{2a}$ and $R^{2b}$ are H;

$R^{2c}$ is attached to carbon-6 of Formula (I) and is selected from —H, —J, —$CF_3$, —$OCF_3$, —$R^5$, —$OR^5$, —$OR^{11}$, —$OR^7OH$, —$OR^7OR^5$ and —$S(O)_mR^5$;

$R^3$ is attached to carbon-7 of Formula (I) and is selected from heteroaryl, phenyl, alkenyl of 2 to 6 carbon atoms or alkynyl of 2 to 6 carbon atoms with each heteroaryl, phenyl, alkenyl and alkynyl group further substituted by one or more of the group —$(C(R^9)_2)_sR^{12}$;

A is absent;

$R^4$ is $(C(R^9)_2)_rH$;

r is 0;

or a pharmaceutically acceptable salt thereof.

c) 3-cyanoquinolines of Formula (I) wherein:

T and Z are carbon;

X is —NH—;

n is 0;

$R^1$ is phenyl optionally substituted with 1 to 4 substituents which may be the same or different independently selected from —H, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_mR^5$, —$NHSO_2R^5$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NH$—$R^5$, —$R^6C(O)Q$, —$R^6OC(O)R^5$, —$R^6OC(O)NH_2$, —$R^6OC(O)NHR^5$, —$R^6OC(O)Q$ and —$YR^8$ groups wherein Y is independently selected from —C(O)—, —C(O)O—, —OC(O)—, —C(O)NH—, —NHC(O)—, —$NHSO_2$—, —$SO_2NH$—, —C(OH)H—, —$O(C(R^9)_2)_q$—, —$S(O)_m(C(R^9)_2)_q$—, —$NH(C(R^9)_2)_q$—, —$NR^{10}(CR^9)_2)_q$—, —$(C(R^9)_2)_q$—, —$(C(R^9)_2)_qO$—, —$(C(R^9)_2)_qS(O)_m$—, —$(C(R^9)_2)_qNH$—, —$(C(R^9)_2)_qNR^1$—, —C≡C—, cis and trans —CH=CH— cycloalkyl of 3 to 10 carbon atoms;

$R^{2a}$ and $R^{2b}$ are H;

$R^{2c}$ is attached to carbon-7 of Formula (I) and is selected from —H, —J, —$CF_3$, —$OCF_3$, —$R^5$, —$OR^5$, —$OR^{11}$, —$OR^7OH$, —$OR^7OR^5$ and —$S(O)_mR^5$;

$R^3$ is attached to carbon-6 of Formula (I) and is selected from heteroaryl, phenyl, alkenyl of 2 to 6 carbon atoms or alkynyl of 2 to 6 carbon atoms with each heteroaryl, phenyl, alkenyl and alkynyl group substituted by one or more of the group —$(C(R^9)_2)_sR^{12}$;

A is absent;

$R^4$ is —$(C(R^9)_2)_rH$;

r is 0;

or a pharmaceutically acceptable salt thereof.

d) 3-cyanoquinolines of Formula (I) wherein:

X is —NH—;

T and Z are carbon;

n is 0;

$R^{2a}$ and $R^{2b}$ are H;

$R^{2c}$ attached to carbon-6- or carbon-7 of Formula (I) and is selected from —H, —J, —$CF_3$, —$OCF_3$, —$R^5$, —$OR^5$, —$OR^{11}$, —$OR^7OH$, —$OR^7OR^5$ and —$S(O)_mR^5$;

$R^1$ is phenyl optionally substituted which 1 to 4 substituents which may be the same or different independently selected from —H, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_mR^5$, —$NHSO_2R^5$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^7)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$, —$R^6OC(O)Q$ and —$YR^8$ groups wherein Y is independently selected form —C(O)—, —C(O)O—, —OC(O)—, —C(O)NH—, —NHC(O)—, —$NHSO_2$—, —SO₂NH—, —C(OH)H—, —O(C(R⁹)₂)_q—, —S(O)_m(C(R⁹)₂)_q—, —NH(C(R⁹)₂)_q—, —NR¹⁰(C(R⁹)₂)_q—, —(C(R⁹)₂)_q—, —(C(R⁹)₂)_qO—, —(C(R⁹)₂)_qS(O)_m—, —(C(R⁹)₂)_qNH—, —(C(R⁹)₂)_qNR¹⁰, —C≡C—, cis- and trans- —CH=CH— and cycloalkyl of 3 to 10 carbon atoms;
R³ is attached to carbon-6 or carbon-7 of Formula (I) and is alkenyl of 2 carbon atoms;
A is absent;
or a pharmaceutically acceptable salt thereof.
e) 3-cyanoquinolines of Formula (I) wherein:
X is —NH—;
T and Z are carbon;
n is 0;
R^{2a} and R^{2b} are H;
R^{2c} is attached to carbon-6 or carbon-7 of Formula (I) and is selected from —H, —J, —CF₃, —OCF₃, —R⁵, —OR⁵, —OR¹¹, —OR⁷OH, —OR⁷OR⁵ and —S(O)_mR⁵;
R¹ is phenyl optionally substituted with 1 to 4 substituents which may be the same or different independently selected from —H, —J, —NO₂, —NH₂, —OH, —SH, —CN, —N₃, —COOH, —CONH₂, —NHC(O)NH₂, —C(O)H, —CF₃, —OCF₃, —R⁵, —OR⁵, —NHR⁵, —Q, —S(O)_mR⁵, —NHSO₂R⁵, —R⁶OH, —R⁶OR⁵, —R⁶NH₂, —R⁶NHR⁵, —R⁶Q, —R⁶SH, —R⁶S(O)_mR⁵, —NHR⁷OH, —NHR⁷OR⁵, —N(R⁵)R⁷OH, —N(R⁵)R⁷OR⁵, —NHR⁷NH₂, —NHR⁷NHR⁵, —NHR⁷Q, —N(R⁵)R⁷NH₂, —N(R⁵)R⁷NHR⁵, —N(R⁵)R⁷Q, —OR⁷OH, —OR⁷OR⁵, —OR⁷NH₂, —OR⁷NHR⁵, —OR⁷Q, —OC(O)R⁵, —NHC(O)R⁵, —NHC(O)NHR⁵, —OR⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O)OR⁵, —R⁶C(O)NH₂, —R⁶C(O)NHR⁵, —R⁶C(O)Q, —R⁶OC(O)R⁵, —R⁶OC(O)NH₂, —R⁶OC(O)NHR⁵, —R⁶OC(O)Q and YR⁸ groups wherein Y is independently selected from —C(O)—, —C(O)O—, —OC(O)—, —C(O)NH—, —NHC(O)—, —NHSO₂—, —SO₂NH—, —C(OH)H—, —O(C(R⁹)₂)_q—, —S(O)_m (C(R⁹)₂)_q—, —NH(C(R⁹)₂)_q—, —NR¹⁰(C(R⁹)₂)_q—, —(C(R⁹)₂)_q—, —(C(R⁹)₂)_qO—, —(C(R⁹)₂)_qS(O)_m—, —(C(R⁹)₂)_qNH—, —(C(R⁹)₂)_qNR¹⁰—, —C≡C—, cis and trans —CH=CH— and cycloalkyl of 3 to 10 carbon atoms;
R³ is attached to carbon-6 or carbon-7 of Formula (I) and is alkynyl of 2 carbon atoms;
A is absent;
or a pharmaceutically acceptable salt thereof.

Preferred compounds of the invention or a pharmaceutically acceptable salt thereof are:
4-(4-Chloro-2-fluoroanilino)-7-[5-(4-morpholinylmethyl)-3-thienyl]-3-quinolinecarbonitrile,
4-(2,4-Dichloro-5-methoxyanilino)-7-[(E)-2-(4-pyridinyl)ethenyl]-3-quinolinecarbonitrile,
4-(2,4-Dichloro-5-methoxyanilino)-7-[(E)-2-(2-pyridinyl)ethenyl]-3-quinolinecarbonitrile,
4-(2,4-Dichloroanilino)-7-[(E)-2-(4-pyridinyl)ethenyl]-3-quinolinecarbonitrile,
4-(2,4-Dichloro-5-methoxyanilino)-7-[5-(1,3-dioxolan-2-yl)-2-furyl]-3-quinolinecarbonitrile,
4-(2,4-Dichloro-5-methoxyanilino)-7-(5-formyl-2-furyl)-3-quinolinecarbonitrile,
7-[5-(4-Morpholinylmethyl)-3-thienyl]-4-(4-phenoxyanilino)-3-quinolinecarbonitrile,
4-(4-Benzylanilino)-7-[5-(4-morpholinylmethyl)-3-thienyl]-3-quinolinecarbonitrile,
4-(2,4-Dichloroanilino)-7-{5-[2-(4-morpholinyl)ethyl]-2-thienyl}-3-quinolinecarbonitrile,
4-(2,4-Dichloroanilino)-7-{5-[(4-ethyl-1-piperazinyl)methyl]-3-thienyl}-3-quinolinecarbonitrile,
4-(2,4-Dichloroanilino)-7-[5-(4-morpholinyl)-1-pentynyl]-3-quinolinecarbonitrile,
4-(2,4-Dichloroanilino)-7-[(E/Z)-5-(4-morpholinyl)-1-pentynyl]-3-quinolinecarbonitrile,
4-(2,4-Dichloroanilino)-7-[5-(4-morpholinylmethyl)-2-furyl]-3-quinolinecarbonitrile,
4-(2,4-Dichloroanilino)-7-(3-hydroxy-1-propynyl)-3-quinolinecarbonitrile,
4-(2,4-Dichloroanilino)-7-[3-(dimethylamino)-1-propynyl]-3-quinolinecarbonitrile,
4-(2,4-Dichloroanilino)-7-[(E/Z)-6-(4-morpholinyl)-1-hexenyl]-3-quinolinecarbonitrile,
7-[4,5-Bis(4-morpholinylmethyl)-2-thienyl]-4-(2,4-dichloroanilino)-3-quinolinecarbonitrile,
4-(2,4-Dichloroanilino)-7-[5-(2-pyridinyl)-2-thienyl]-3-quinolinecarbonitrile,
4-(2,4-Dichloro-5-methoxyanilino)-7-{5-[(4-ethyl-1-piperazinyl)methyl]-3-thienyl}-3-quinolinecarbonitrile,
7-[4,5-Bis(4-morpholinylmethyl)-2-thienyl]-4-(2,4-dichloro-5-methoxyanilino)-3-quinolinecarbonitrile,
4-(2,4-Dichloro-5-methoxyanilino)-7-{5-[(E)-3-(4-morpholinyl)-1-propenyl]-2-thienyl}-3-quinolinecarbonitrile,
4-(2,4-Dichloro-5-methoxyanilino)-7-{5-[4-(4-morpholinyl)butyl]-2-thienyl}-3-quinolinecarbonitrile,
4-(2,4-Dichloro-5-methoxyanilino)-7-[5-(4-morpholinylmethyl)-2-thienyl]-3-quinolinecarbonitrile,
4-(2,4-Dichloro-5-methoxyanilino)-7-[5-(4-morpholinylmethyl)-3-thienyl]-3-quinolinecarbonitrile,
4-(2,4-Dichloroanilino)-7-[5-(4-morpholinylmethyl)-3-thienyl]-3-quinolinecarbonitrile,
4-(2,4-Dichloro-5-methoxyanilino)-7-[3-(4-morpholinylmethyl)phenyl]-3-quinolinecarbonitrile,
4-(2,4-Dichloro-5-methoxyanilino)-7-{4-[2-(4-morpholinyl)ethyl]phenyl}-3-quinolinecarbonitrile,
4-(2,4-Dichloro-5-methoxyanilino)-7-{3-[2-(4-morpholinyl)ethyl]phenyl)-3-quinolinecarbonitrile,
4-(2,4-Dichloro-5-methoxyanilino)-7-[4-(4-morpholinylmethyl)phenyl]-3-quinolinecarbonitrile,
4-(2,4-Dichloro-5-methoxyanilino)-7-{4-[(4-ethyl-1-piperazinyl)methyl]phenyl-3-quinolinecarbonitrile,
4-(2,4-Dichloro-5-methoxyanilino)-7-{4-[(4-ethyl-1-piperazinyl)methyl]phenyl}-methoxy-3-quinolinecarbonitrile,
4-(2,4-Dichloro-5-methoxyanilino)-7-{4-[2-(4-ethyl-1-piperazinyl)ethyl]phenyl}-3-quinolinecarbonitrile,
4-{3-Chloro-4-[(1-methyl-1H-imidazol-2-yl)sulfanyl]anilino}-7-[5-(4-morpholinylmethyl)-3-thienyl]-3-quinolinecarbonitrile,
7-[3,4-Bis(4-morpholinylmethyl)phenyl]-4-(2,4-dichloro-5-methoxyanilino)-3-quinolinecarbonitrile,
7-[3,4-Bis(4-morpholinylmethyl)phenyl]-4-(3-chloro-4-[(1-methyl-1H-imidazol-2-yl)sulfanyl]anilino}-3-quinolinecarbonitrile, 4-(2,4-Dichloro-5-methoxyanilino)-6-methoxy-7-[5-(4-morpholinylmethyl)-3-thienyl]-3-quinolinecarbonitrile, 4-(2,4-Dichloro-5-methoxyanilino)6-methoxy-7-[4-(4-morpholinylmethyl)phenyl]3-quinolinecarbonitrile, 4-(2,4-Dichloro-5-methoxyanilino)-6-methoxy-7-{3-[2-(4-morpholinyl)ethyl]phenyl}-3-quinolinecarbonitrile, 4-(2,4-Dichloro-5-methoxyanilino)-6-methoxy-7-[3-(4-morpholinylmethyl]phenyl}-3-quinolinecarbonitrile, 4-(2,4-Dichloro-5-methoxyanilino)-6-methoxy-7-{4-[2-(4-morpholinyl)ethyl]phenyl}-3-quinolinecarbonitrile, 4-(2,4-Dichloro-5-methoxyanilino)-7-{5-[(4-ethyl-1-piperazinyl)methyl]-2-furyl-3-quinolinecarbonitrile, 4-(2,4-Dichloro-5-methoxyanilino)-7-[5-(1,3-dioxolan-2-yl)-3-thienyl]-3-quinolinecarbonitrile, 4-(2,4-Dichloro-5-methoxyanilino)-7-(5-formyl-3-thienyl)-3-quinolinecarbonitrile, 4-(2,4-Dichloroanilino)-7-(5-formyl-3-thienyl)-3-quinolinecarbonitrile, 4-(2,4-Dichloro-5-methoxyanilino)-6-(5-formyl-3-thienyl)-3-quinolinecarbonitrile, 4-(2,4-Dichloro-5-methoxyanilino)-7-{5-[(4-methyl-1-piperazinyl)methyl]-3-thienyl}-3-quinolinecarbonitrile, (2R)-1-({5-[3-Cyano-4-(2,4-dichloro-5-methoxyanilino)-7-quinolinyl]-2-furyl}methyl)-2-pyrrolidinecarboxamide, 7-[5-(4-Morpholinylmethyl)-3-pyridinyl]-4-(4-phenoxyanilino)-3-quinolinecarbonitrile, 4-(2,4-Dichloro-5-methoxyanilino)-7-[5-(4-morpholinylmethyl)-3-pyridinyl]-3-quinolinecarbonitrile, 4-(2,4-Dichloro-5-methoxyanilino)-6-[5-(4-morpholinylmethyl)-3-thienyl]-3-quinolinecarbonitrile, 4-(2,4-Dichloro-5-methoxyanilino)-7-[5-(1,3-dioxolan-2-yl)-2-thienyl]-3-quinolinecarbonitrile, 4-(2,4-Dichloro-5-methoxyanilino)-7-(5-formyl-2-thienyl)-3-quinolinecarbonitrile, 4-(2,4-Dichloro-5-methoxyanilino)-7-[5-(4-morpholinylmethyl)-2-furyl]-3-quinolinecarbonitrile, 4-(2,4-Dichloro-5-methoxyanilino)-7-[(E)-2-(4-methoxyphenyl)ethenyl]-3-quinolinecarbonitrile, 4-(2,4-Dichloro-5-methoxyanilino)-7-{5-[(4-methyl-1-piperazinyl)methyl]-2-thienyl}-3-quinolinecarbonitrile, 7-[5-(4-Morpholinylmethyl)-2-pyridinyl]-4-(4-phenoxyanilino)-3-quinolinecarbonitrile, 4-(2,4-Dichloro-5-methoxyanilino)-7-[5-(4-morpholinylmethyl)-2-pyridinyl]-3-quinolinecarbonitrile, 4-(2,4-Dichloro-5-methoxyanilino)-7-[5-({[2-(phenylsulfonyl)ethyl]amino}methyl)-2-furyl]-3-quinolinecarbonitrile, 4-(2,4-Dichloro-5-methoxyanilino)-6-methoxy-7-(1H-pyrrol-1-yl)-3-quinolinecarbonitrile, 4-(3-Bromoanilino)-6-(2-formyl-1H-pyrrol-1-yl)-3-quinolinecarbonitrile, 4-(3-Chloro-4-fluoro-phenylamino)-7-methoxy-6-(1H-pyrrol-1-yl)-3-quinolinecarbonitrile, 4-{3-Chloro-4-[(1-methyl-1H-imidazol-2-yl)sulfanyl]anilino}-7-(4-formylphenyl)-3-quinolinecarbonitrile, 4-{3-Chloro-4-[(1-methyl-1H-imidazol-2-yl)sulfanyl]anilino}-7-[4-(4-morpholinylmethyl)phenyl]-3-quinolinecarbonitrile, 4-(2,4-Dichloro-5-methoxyanilino)-7-{1-[2-(4-morpholinyl)ethyl]-1H-imidazol-5-yl}-3-quinolinecarbonitrile, 4-(2,4-Dichloro-5-methoxyanilino)-7-[4-(4-morpholinylmethyl)-3-thienyl]-3-quinolinecarbonitrile, 4-(2,4-Dichloro-5-methoxyanilino)-7-[2-(4-morpholinylmethyl)-3-thienyl]-3-quinolinecarbonitrile, 4-(2,4-Dichloro-5-methoxyanilino)-7-[4-(4-morpholinyl)phenyl]-3-quinolinecarbonitrile, 4-(2,4-Dichloro-5-methoxyanilino)-7-[4-(4-morpholinylmethyl)-2-thienyl]-3-quinolinecarbonitrile, 4-(2,4-Dichloro-5-methoxyanilino)-7-(5-formyl-1-methyl-1H-pyrrol-2-yl)-3-quinolinecarbonitrile, 4-(2,4-Dichloro-5-methoxyanilino)-7-[1-methyl-5-(4-morpholinylmethyl)-1H-pyrrol-2-yl]-3-quinolinecarbonitrile, 4-(2,4-Dichloro-5-methoxyanilino)-7-(1-methyl-5-[(4-methyl-1-piperazinyl)methyl]-1H-pyrrol-2-yl}-3-quinolinecarbonitrile, 4-(2,4-Dichloro-5-methoxyanilino)-7-[1-methyl-5-({[2-(phenylsufonyl)ethyl]amino}methyl)-1H-pyrrol-2-yl]-3-quinolinecarbonitrile, 4-(2,4-Dichloro-5-methoxyanilino)-7-[1-methyl-5-({[2-(methylsulfonyl)ethyl]amino}-methyl)-1H-pyrrol-2-yl]-3-quinolinecarbonitrile, 4-(2,4-Dichloro-5-methoxyanilino)-7-[5-({[2-(2-pyridinyl)ethyl]amino}methyl)-2-furyl]-3-quinolinecarbonitrile, 4-(2,4-Dichloro-5-methoxyanilino)-7-(5-{[4-(2-hydroxyethyl)-1-piperazinyl]methyl}-2-furyl)-3-quinolinecarbonitrile, 7-(5-{[Bis(2-hydroxyethyl)amino]methyl}-2-furyl)-4-(2,4-dichloro-5-methoxyanilino)-3-quinolinecarbonitrile, 4-(2,4-Dichloro-5-methoxyanilino)-7-[5-({[2-(methylsulfonyl)ethyl]amino}methyl)-furyl]-3-quinolinecarbonitrile, 4-(2,4-Dichloro-5-methoxyanilino)-7-[5-(1-piperidinylmethyl)-2-thienyl]-3-quinolinecarbonitrile, 4-{2-Chloro-4-fluoro-5-methoxyanilino)-7-[5-(4-morpholinylmethyl)-3-thienyl]-3-quinolinecarbonitrile, 4-{2-Chloro-5-methoxy-4-methoxyanilino)-7-[5-(4-morpholinylmethyl)-3-thienyl]-3-quinolinecarbonitrile, 4-(2,4-Dichloro-5-methoxyanilino)-7-[6-4-morpholinylmethyl)-3-pyridinyl]-3-quinolinecarbonitrile, 7-[4,5-Bis(4-morpholinylmethyl)-2-thienyl]-4-(2,4-dichloro-5-methoxyanilino)-6-methoxy-3-quinolinecarbonitrile, 4-(2,4-Dichloro-5-methoxyanilino)-7-(4-formylphenyl)-3-quinolinecarbonitrile, (2R)-1-{4-[3-Cyano-4-(2,4-dichloro-5-methoxyanilino)-7-quinolinyl]benzyl}-2-pyrrolidinecarboxamide, 4-(2,4-Dichloro-5-methoxyanilino)-7-[4-({[2-(phenylsulfonyl)ethyl]amino}methyl)phenyl]-3-quinolinecarbonitrile, 4-(2,4-Dichloro-5-methoxyanilino)-7-{4-[(dimethylamino)methyl]phenyl}-3-quinolinecarbonitrile, 4-(2,4-Dichloro-5-methoxyanilino)-7-{4-[(diethylamino)methyl]phenyl}-3-quinolinecarbonitrile, 4-(2,4-Dichloro-5-methoxyanilino)-7-[4-({[2-(methylsufonyl)ethyl]amino}methyl)phenyl]-3-quinolinecarbonitrile, 4-(2,4-Dichloro-5-methoxyanilino)-7-{5-[(4-hydroxy-1-piperidinyl)methyl]-2-thienyl}-3-quinolinecarbonitrile, 4-(2,4-Dichloro-5-methoxyanilino)-7-[2-(4-methoxyphenyl)ethynyl]-3-quinolinecarbonitrile, 4-(2,4-Dichloro-5-methoxyanilino)-7-[2-(2-pyridinyl)ethynyl]-3-quinolinecarbonitrile, 4-(2,4-Dichloro-5-methoxyanilino)-7-pyrrol-1-yl-3-quinolinecarbonitrile, 4-(2,4-Dichloro-5-methoxyanilino)-7-{(2-[(dimethylamino)methyl]-1H-pyrrol-1-yl}-3-quinolinecarbonitrile, 7-[5-(1,3-Dioxolan-2-yl)-3-thienyl]-4-[3-methyl-4-(2-pyridinylmethoxy)anilino]-3-quinolinecarbonitrile, 4-[3-Methyl-4-(2-pyridinylmethoxy)anilino]-7-[5-(4-morpholinylmethyl)-3-thienyl]-3-quinolinecarbonitrile, 4-[(2,4-Dichloro-5-methoxyanilino]-7-(2-formyl-1-methyl-1H-imidazol-5-yl)quinoline-3-carbonitrile, 4-({3-Chloro-4-[(1-methyl-1H-imidazol-2-yl)sulfanyl]phenyl}amino)-7-[4-(1-piperazinylmethyl)phenyl]-3-quinolinecarbonitrile, 4-({3-Chloro-4-[(1-methyl-1H-imidazol-2-yl)sulfanyl]phenyl}amino)-7-{4-[(4-isopropyl-1-piperazinyl)methyl]phenyl}-3-quinolinecarbonitrile, (E)-3-[3-Cyano-4-(2,4-dichloro-1-methoxyanilino)-7-quinolinyl]-2-propenoic acid, (1-{4-[3-Cyano-4-(2,4-dichloro-5-methoxyanilino)-7-quinolinyl]benzyl}-4-piperidinyl)acetic acid, 4-(2,4-Dichloro-5-methoxyanilino)-7-[4-(hydroxymethyl)phenyl]-3-quinolinecarbonitrile, 7-[4-(Chloromethyl)phenyl]-4-(2,4-dichloro-5-methoxyanilino)-3-quinolinecarbonitrile, 4-[(2,4-Dichloro-5-methoxyphenyl)amino]-7-[4-(1H-1,2,3-triazol-1-methyl)phenyl]-3-quinolinecarbonitrile, 4-(2,4-Dichloro-5-methoxyanilino)-7-(1H-pyrrol-2-yl)-3-quinolinecarbonitrile, 4-[(2,4-Dichloro-5-methoxyanilino]-7-[4-(1H-tetraazol-5-yl)phenyl]-3-quinolinecarbonitrile, 4-({3-Chloro-4-[(1-methyl-1H-imidazol-2-yl)sulfanyl]phenyl}amino)-7-(5-{[(2-hydroxyethyl)(methyl)amino]methyl}-2-pyridinyl)-3-quinolinecarbonitrile, Methyl 1-{[6-(4-(3-chloro-4-[(1-methyl-1H-imidazol-2-yl)sulfanyl]anilino}-3-cyano-7-quinolinyl)-3-pyridinyl]methyl}-4-piperidinecarboxylate, 4-({3-Chloro-4-[(1-methyl-1H-imidazol-2-yl)sulfanyl]phenyl}amino)-7-[5-(4-ethyl-1-piperazinyl)-2-pyridinyl]-3-quinolinecarbonitrile, 4-({3-Chloro-4-[(1-methyl-1H-imidazol-2-yl)sulfanyl]phenyl}amino)-7-[6-(4-morpholinylmethyl)-3-pyridinyl]-3-quinolinecarbonitrile, 4-({3-Chloro-4-[(1-methyl-1H-imidazol-2-yl)sulfanyl]phenyl}amino)-7-[6-(4-thiomorpholinyl)-3-pyridinyl]-3-quinolinecarbonitrile, 4-(2,4-Dichloro-5-methoxyanilino)-7-[3-(morpholin-4-ylmethyl)-pyridin-2-yl]-3-quinolinecarbonitrile, 4-(2,4-Dichloro-5-methoxylanilino)-7-(3-formyl)-3-quinolinecarbonitrile, 4-(2,4-Dichloro-5-methoxyanilino)-7-{3-[(4-methyl-1-piperazinyl)methyl]phenyl}-3-quinolinecarbonitrile, 4-(2,4-Dichloro-5-methoxyanilino)-7-(2-formylphenyl)-3-quinolinecarbonitrile, 4-(2,4-Dichloro-5-methoxyanilino)-7-[2-(4-morpholinylmethyl)phenyl]-3-quinolinecarbonitrile, 4-(2,4-Dichloro-5-methoxyanilino)-7-(1-naphthyl)-3-quinolinecarbonitrile, 4-(2,4-Dichloro-5-methoxyanilino)-7-(2-naphthyl)-3-quinolinecarbonitrile, N-{3-[3-Cyano-4-(2,4-dichloro-5-methoxyanilino)-7-quinolinyl]phenyl}acetamide, 7-(1-Benzofuran-2-yl)-4-(2,4-dichloro-5-methoxyanilino)-3-quinolinecarbonitrile, 7-(1-Benzothien-2-yl)-4-2,4-dichloro-5-methoxyanilino)-3-quinolinecarbonitrile, 4-[3-Cyano-4-(2,4-dichloro-5-methoxyanilino)-7-quinolinyl]benzoic acid, 4-(2,4-Dichloro-5-methoxyanilino)-7-(3-nitrophenyl)-3-quinolinecarbonitrile, 4-{3-Chloro-4-[(1-methyl-1H-imidazol-2-yl)sulfanyl]anilino}-6-methoxy-7-[4-(4-morpholinylmethyl)phenyl]-3-quinolinecarbonitrile, 7-[3,4-Bis(4-morpholinylmethyl)phenyl-4-{3-chloro-4-[(1-methyl-1H-imidazol-2-yl)sulfanyl]anilino}-6-methoxy-3-quinolinecarbonitrile, 4-{3-Chloro-4-[(1-methyl-1H-imidazol-2-yl)sulfanyl]anilino}-6-methoxy-7-[5-(4-morpholinylmethyl)-3-thienyl]-3-quinolinecarbonitrile, 4-{3-Chloro-4-[(1-methyl-1H-imidazol-2-y)sulfanyl]anilino}-6-methoxy-7-{5-[(4-methyl-1-piperazinyl)methyl]-3-thienyl}-3-quinolinecarbonitrile, 4-{3-Chloro-4-[(1-methyl-1H-imidazol-2-yl)sulfanyl]anilino}-6-methoxy-7-(4-methoxyphenyl)-3-quinolinecarbonitrile, 4-[(2,4-Dichloro-5-methoxyphenyl)amino]-7-[4-(4-morpholinyl)phenyl]-3-quinolinecarbonitrile, 4-({3-Chloro-4-[(1-methyl-1H-imidazol-2-yl)sulfanyl]phenyl}amino)-7-[4-(4-morpholinylcarbonyl)phenyl]-3-quinolinecarbonitrile, 4-(2,4-Dichloro-5-methoxyanilino)-7-{4-[(2-methoxy)ethoxyl]phenyl}-3-quinolinecarbonitrile, 4-(2-Chloro-5-methoxyanilino)-7-[5-(4-morpholinylmethyl)-3-thienyl]-3-quinolinecarbonitrile, 4-[4-(Benzyloxy)-3-chloroanilino]-7-[3,4-bis(4-morpholinylmethyl)phenyl]-3-quinolinecarbonitrile, 7-[3,4-Bis(4-morpholinylmethyl)phenyl]-4-(2-chloro-5-methoxy-4-methylanilino)-3-quinolinecarbonitrile, 4-{3-Chloro-4-[(1-methyl-1H-imidazol-2-yl)sulfanyl]anilino}-7-{4-[(4-hydroxy-1-piperidinyl)methyl]phenyl}-3-quinolinecarbonitrile, 4-{3-Chloro-4-[(1-methyl-1H-imidazol-2-yl)sulfanyl]anilino}-7-{4-[(4-methyl-1-piperazinyl)methyl]phenyl}-3-quinolinecarbonitrile, 4-{3-Chloro-4-[(1-methyl-1H-imidazol-2-yl)sulfanyl]anilino}-7-[4-(1-piperidinylmethyl)phenyl]-3-quinolinecarbonitrile, tert-Butyl 4-{4-[4-({3-chloro-4-[(1-methyl-1H-imidazol-2-yl)sulfanyl]phenyl}amino)-3-cyano-7-quinolinyl]benzyl}-1-piperazinecarboxylate, 4-({3-Chloro-4-[(1-methyl-1H-imidazol-2-yl)sulfanyl] phenyl}amino)-7-{4-[(4-morpholinyl)methyl]phenyl}-3-quinolinecarbonitrile, 4-(2,4-Dichloro-5-methoxyanilino)-7-[(E)-2-phenylethenyl]-3-quinolinecarbonitrile, 4-(2,4-Dichloro-5-methoxyanilino)-7-(2-phenylethynyl)-3-quinolinecarbonitrile, 4-(2,4-Dichloro-5-methoxyanilino)-7-[2-(4-methylphenyl)ethynyl]-3-quinolinecarbonitrile, tert-Butyl (E)-3-[3-cyano-4-(2,4-dichloro-5-methoxyanilino)-7-quinolinyl]-2-propenoate, 4-(2,4-Dichloro-5-methoxyanilino)-7-(3-hydroxy-1-propynyl)-3-quinolinecarbonitrile, Ethyl (1-{4-[3-Cyano-4-(2,4-dichloro-5-methoxyanilino)-7-quinolinyl]benzyl}-4-piperidinyl) acetate, Ethyl 1-{4-[3-cyano-4-(2,4-dichloro-5-methoxyanilino)-7-quinolinyl]benzyl}-2-piperidinecarboxylate, 4-(2,4-Dichloro-5-methoxyanilino)-7-[3-(4-morpholinyl)-1-propynyl]-3-quinolinecarbonitrile, 1-{4-[3-Cyano-4-(2,4-dichloro-5-methoxyanilino)-7-quinolinyl]benzyl}-2-piperidinecarboxylic acid, Ethyl 1-(4-{3-cyano-4-[(2,4-dichloro-5-methoxyphenyl) amino]-7-quinolinyl}benzyl)-3-piperidinecarboxylate, 1-(4-{3-Cyano-4-[(2,4-dichloro-5-methoxyphenyl) amino]-7-quinolinyl}benzyl)-3-piperidinecarboxylic acid, 4-[(2,4-Dichloro-5-methoxyphenyl)amino]-7-{4-[(1,1-dioxido-4-thiomorpholinyl)methyl]phenyl}-3-quinolinecarbonitrile, 4-[(2,4-Dichloro-5-methoxyphenyl)amino]-7-{4-[(1-oxido-4-thiomorpholinyl)methyl]phenyl}-3-quinolinecarbonitrile, 7-(3-Chloro-1-propynyl)-4-[(2,4-dichloro-5-methoxyphenyl)amino]-3-quinolinecarbonitrile, 4-[(2,4-Dichloro-5-methoxyphenyl)amino]-7-[4-(4-thiomorpholinylmethyl)phenyl]-3-quinolinecarbonitrile, 4-{3-Chloro-4-[(1-methyl-1H-imidazol-2-yl)sulfanyl] anilino}-7-[5-(4-morpholinylmethyl)-2-furyl-3-quinolinecarbonitrile, 4-{3-Chloro-4-[(-methyl-1H-imidazol-2-yl)sulfanyl] anilino}-7-[5-(1-piperidinylmethyl)-2-furyl]-3-quinolinecarbonitrile, 4-{3-Chloro-4-[(1-methyl-1H-imidazol-2-yl)sulfanyl] anilino}-7-{5-[(4-ethyl-1-piperazinyl)methyl]-2-furyl}-3-quinolinecarbonitrile, 4-{3-Chloro-4-[(1-methyl-1H-imidazol-2-yl)sulfanyl] anilino}-7-(5-{[4-(2-hydroxyethyl)-1-piperazinyl] methyl}-2-furyl)-3-quinolinecarbonitrile, 4-({3-Chloro-4-[(1-methyl-1H-imidazol-2-yl)sulfanyl] phenyl}amino)-7-(5-formyl-2-furyl)-3-quinolinecarbonitrile, 4-{3-Chloro-4-[(1-methyl-1H-imidazol-2-yl)sulfanyl] anilino}-7-{5-[(4-hydroxy-1-piperidinyl)methyl]-2-thienyl}-3-quinolinecarbonitrile, 4-{3-Chloro-4-[(1-methyl-1H-imidazol-2-yl)sulfanyl] anilino}-7-[5-(1-piperidinylmethyl)-2-thienyl]-3-quinolinecarbonitrile, 4-{3-Chloro-4-[(1-methyl-1H-imidazol-2-yl)sulfanyl] anilino}-7-(5-{[4-(2-hydroxyethyl)-1-piperazinyl] methyl}-2-thienyl)-3-quinolinecarbonitrile, 4-(2,4-Dichloro-5-methoxyanilino)-7-[5-(hydroxymethyl)-1-methyl-1H-pyrrol-2-yl]-3-quinolinecarbonitrile, 4-(2,4-Dichloro-5-methoxyanilino)-7-(3-formyl-2-thienyl)-3-quinolinecarbonitrile, tert-Butyl 2-[3-cyano-4-(2,4-dichloro-5-methoxyanilino)-7-quinolinyl]-1H-pyrrole-1-carboxylate, 7-[1,1'-Biphenyl]-4-yl-4-(2,4-dichloro-5-methoxyanilino)-3-quinolinecarbonitrile, 4-(2,4-Dichloro-5-methoxyanilino)-6-methoxy-7-[3-(4-morpholinyl)-1-propynyl]-3-quinolinecarbonitrile, 4-(4-Chloro-5-methoxy-2-methylanilino)-7-[5-(4-morpholinylmethyl)-3-thienyl]-3-quinolinecarbonitrile, 7-[4,5-Bis(4-morpholinylmethyl)-2-thienyl]-4-(4-phenoxyanilino)-3-quinolinecarbonitrile, 7-[4,5-Bis(4-morpholinylmethyl)-2-thienyl]-4-{3-chloro-4-[(1-methyl-1H-imidazol-2-yl)sulfanyl]anilino}-3-quinolinecarbonitrile, 4-{3-Chloro-4-[(1-methyl-1H-imidazol-2-yl)sulfanyl] anilino}-7-(5-formyl-2-pyridinyl)-3-quinolinecarbonitrile, 4-{3-Chloro-4-[(1-methyl-1H-imidazol-2-yl)sulfanyl] anilino}-7-{5-[(4-ethyl-1-piperidinyl)methyl]-2-pyridinyl}-3-quinolinecarbonitrile, 4-{3-Chloro-4-[(1-methyl-1H-imidazol-2-yl)sulfanyl] anilino}-7-{5-[(4-hydroxy-1-piperidinyl)methyl]-2-pyridinyl}-3-quinolinecarbonitrile, 4-{3-Chloro-4-[(1-methyl-1H-imidazol-2-yl)sulfanyl] anilino}-7-(5-{[4-(1-pyrrolidinyl)-1-piperidinyl] methyl}-2-pyridinyl)-3-quinolinecarbonitrile, 7-(3-Aminophenyl)-4-[(2,4-dichloro-5-methoxyphenyl) amino]-3-quinolinecarbonitrile, 1-{[6-{4-(3-chloro-4-[(1-methyl-1H-imidazol-2-yl) sulfanyl]anilino}-3-cyano-7-quinolinyl)-3-pyridinyl] methyl]-2-pyridinyl}-4-piperidinecarboxylic acid, 1-{6-[3-Cyano-4-(2,4-dichloro-5-methoxyphenylamino)-quinolin-7-yl]-pyridin-3-ylmethyl}-piperidine-4-carboxylic acid methyl ester, 1-{6-[3-Cyano-4-(2,4-dichloro-5-methoxyphenylamino)-quinolin-7-yl]-pyridin-3-ylmethyl}-piperidine-4-carboxylic acid, 4-({3-Chloro-4-[(1-methyl-1H-imidazol-2-yl)sulfanyl] phenyl}amino)-7-(5-chloro-2-pyridinyl)-3-quinolinecarbonitrile, 4-[(2,4-Dichloro-5-methoxyphenyl)amino]-7-[5-(4-ethyl-1-piperazinyl)-2-pyridinyl]-3-quinolinecarbonitrile, 4-({3-Chloro-4-[(1-methyl-1H-imidazol-2-yl)sulfanyl] phenyl}amino)-7-[5-(1-pyridinyl)-3-quinolinecarbonitrile, 4-({3-Chloro-4-[(1-methyl-1H-imidazol-2-yl)sulfanyl] phenyl}amino)-6-[5-(4-ethyl-1-piperazinyl)-2-pyridinyl]-3-quinolinecarbonitrile, 4-({3-Chloro-4-[(1-methyl-1H-imidazol-2-yl)sulfanyl] phenyl}amino)-6-[5-(4-morpholinylmethyl)-2-pyridinyl]-3-quinolinecarbonitrile, 4-({3-Chloro-4-[(1-methyl-1H-imidazol-2-yl)sulfanyl] phenyl}amino)-6-{5-[(4-methyl-1-piperazinyl) methyl]-2-pyridinyl}-3-quinolinecarbonitrile, 4-({3-Chloro-4-[(1-methyl-1H-imidazol-2-yl)sulfanyl] phenyl}amino)-6-[6-(4-morpholinyl)-3-pyridinyl-3-quinolinecarbonitrile, 4-(2,4-Dichloro-5-methoxyanilino)-7-[6-(4-morpholinyl)-3-pyridinyl-3-quinolinecarbonitrile, 4-(2,4-Dichloro-5-methoxyanilino)-7-[2-(4-morpholinyl)-5-pyrimidinyl]-3-quinolinecarbonitrile, 4-{(3-Chloro-4-[(1-methyl-1H-imidazol-2-yl)sulfanyl]
anilino}-7-[5-(4-morpholinylmethyl)-3-
quinolinecarbonitrile, 4-(2,4-Dichloro-5-methoxyanilino)-7-{5-[(4-methyl-1-
piperazinyl)methyl]-2-pyridinyl}-3-
quinolinecarbonitrile, 4-{3-Chloro-4-[(1-methyl-1H-imidazol-2-yl)sulfanyl]
anilino}-7-{5-[(4-methyl-1-piperazinyl)methyl]-2-
pyridinyl}-3-quinolinecarbonitrile, 4-{3-Chloro-4-[(1-methyl-1H-imidazol-2-yl)sulfanyl]
anilino}-7-[6-(4-morpholinyl]-3-pyridinyl]-3-
quinolinecarbonitrile, 4-{3-Chloro-4-[(1-methyl-1H-imidazol-2-yl)sulfanyl]
anilino}-7-[2-(4-morpholinyl]-5-pyrimidinyl]-3-
quinolinecarbonitrile, 4-(2,4-Dichloro-5-methoxyanilino)-7-{5-[(4-hydroxy-1-
piperidinyl)methyl]-3-thienyl}-3-
quinolinecarbonitrile, 4-(2,4-Dichloro-5-methoxyanilino)-7-{6-[4-(4-
morpholinylmethyl)phenoxy]-3-pyridinyl)-3-
quinolinecarbonitrile, 4-(2,4-Dichloro-5-methoxyanilino)-7-(4-
methoxyphenyl)-3-quinolinecarbonitrile, 4-{3-Chloro-4-[(1-methyl-1H-imidazol-2-yl)sulfanyl]
anilino}-7-[6-(4-ethyl-1-piperazinyl)-3-pyridinyl]-3-
quinolinecarbonitrile, 4-{3-Chloro-4-[(1-methyl-1H-imidazol-2-yl)sulfanyl]
anilino}-7-[6-(4-methyl-1-piperazinyl)-3-pyridinyl]-3-
quinolinecarbonitrile, 4-(2,4-Dichloro-5-methoxyanilino)-7-[6-(4-ethyl-1-
piperazinyl)-3-pyridinyl]-3-quinolinecarbonitrile, 4-(2,4-Dichloro-5-methoxyanilino)-7-[6-(4-methyl-1-
piperazinyl)-3-pyridinyl]-3-quinolinecarbonitrile, 4-{3-Chloro-4-[(1-methyl-1H-imidazol-2-yl)sulfanyl]
anilino}-7-[6-(4-morpholinylmethyl)-2-pyridinyl]-3-
quinolinecarbonitrile, 4-(2,4-Dichloro-5-methoxyanilino)-7-[6-(4-
morpholinylmethyl)-2-pyridinyl]-3-
quinolinecarbonitrile, 4-{3-Chloro-4-[(1-methyl-1H-imidazol-2-yl)sulfanyl]
anilino}-7-{6-[(4-ethyl-1-piperazinyl)methyl]2-
pyridinyl}-3-quinolinecarbonitrile, 4-{3-Chloro-4-[(1-methyl-1H-imidazol-2-yl)sulfanyl]
anilino}-7-{6-[(4-methyl-1-piperazinyl)methyl]-2-
pyridinyl}-3-quinolinecarbonitrile, 4-((3-Chloro-4-[(1-methyl-1H-imidazol-2-yl)sulfanyl]
phenyl}amino)-4-(4-morpholinylmethyl)-2-pyridinyl]-
3-quinolinecarbonitrile, 4-[(2,4-Dichloro-5-methoxyphenyl)amino]-7-[4-(4-
morpholinylmethyl)-2-pyridinyl]-3-
quinolinecarbonitrile, 4-({3-Chloro-4-[(1-methyl-1H-imidazol-2-yl)sulfanyl]
phenyl}amino)-7-{4-[(4-ethyl-1-piperazinyl)methyl]-
2-pyridinyl}-3-quinolinecarbonitrile, 4-({3-Chloro-4-[(1-methyl-1H-imidazol-2-yl)sulfanyl]
phenyl}amino)-7-{4-[(4-methyl-1-piperazinyl)
methyl]-2-pyridinyl}-3-quinolinecarbonitrile, 4-({3-Chloro-4-[(1-methyl-1H-imidazol-2-yl)sulfanyl]
phenyl}amino)-7-[3-(4-morpholinylmethyl)-2-
pyridinyl]-3-quinolinecarbonitrile, 4-({3-Chloro-4-[(1-methyl-1H-imidazol-2-yl)sulfanyl]
phenyl}amino)-7-{3-[(4-ethyl-1-piperazinyl)methyl]-
2-pyridinyl}-3-quinolinecarbonitrile, 4-({3-Chloro-4-[(1-methyl-1H-imidazol-2-yl)sulfanyl]
phenyl}amino)-7-{3-[(4-methyl-1-piperazinyl)
methyl]-2-pyridinyl}-3-quinolinecarbonitrile, 4-({3-Chloro-4-[(1-methyl-1H-imidazol-2-yl)sulfanyl]
phenyl}amino)-7-{6-[4-(1-pyrrolidinyl)-1-
piperidinyl]-3-pyridinyl}-3-quinolinecarbonitrile, 4-({3-Chloro-4-[(1-methyl-1H-imidazol-2-yl)sulfanyl]
phenyl}amino)-7-[6-(1-piperidinyl)-3-pyridinyl]-3-
quinolinecarbonitrile, 4-({3-Chloro-4-[(1-methyl-1H-imidazol-2-yl)sulfanyl]
phenyl}amino)-7-{6-[(2-methoxyethyl)(methyl)
amino]3-pyridinyl}-3-quinolinecarbonitrile, Ethyl 1-{5-[4-({3-chloro-4-[(1-methyl-1H-imidazol-2-yl)
sulfanyl]phenyl}amino)-3-cyano-7-quinolinyl]-2-
pyridinyl}-4-piperidinecarboxylate, 4-({3-Chloro-4-[(1-methyl-1H-imidazol-2-yl)sulfanyl]
phenyl}amino)-7-[6-(4-hydroxy-1-piperidinyl)-3-
pyridinyl]-3-quinolinecarbonitrile, 4-({3-Chloro-4-[(1-methyl-1H-imidazol-2-yl)sulfanyl]
phenyl}amino)-7-{6-[4-(2-hydroxyethyl)-1-
piperazinyl]-3-pyridinyl}-3-quinolinecarbonitrile, 4-({3-Chloro-4-[(1-methyl-1H-imidazol-2-yl)sulfanyl]
phenyl}amino)-7-{6-[(2-hydroxyethyl)(methyl)
amino]-3-pyridinyl}-3-quinolinecarbonitrile, 4-({3-chloro-4-[(1-methyl-1H-imidazol-2-yl)sulfanyl]
phenyl}amino)-7-(5-{[4-(2-hydroxyethyl)-1-
piperazinyl]-methyl}-2-pyridinyl)-3-
quinolinecarbonitrile, 4-(2,4-Dichloro-5-methoxyanilino)-7-{4-[(4-methyl-1-
piperazinyl)methyl]phenyl}-3-quinolinecarbonitrile, 4-({3-Chloro-4-[(1-methyl-1H-imidazol-2-yl)sulfanyl]
phenyl}amino)-7-(5-thiomorpholinylmethyl)-2-
pyridinyl}-3-quinolinecarbonitrile, 4-({3-Chloro-4-[(1-methyl-1H-imidazol-2-yl)sulfanyl]
phenyl}amino)-7-{6-[(4-ethyl-1-piperazinyl)methyl]-
3-pyridinyl}-3-quinolinecarbonitrile, 4-({3-Chloro-4-[(1-methyl-1H-imidazol-2-yl)sulfanyl]
phenyl}amino)-7-{6-[(4-methyl-1-piperazinyl)
methyl]-3-pyridinyl}-3-quinolinecarbonitrile, 4-({3-Chloro-4-[(1-methyl-1H-imidazol-2-yl)sulfanyl]
phenyl}amino)-7-(6-formyl-3-pyridinyl)-3-
quinolinecarbonitrile, 4-({3-Chloro-4-[(1-methyl-1H-imidazol-2-yl)sulfanyl]
phenyl}amino)-7-{6-[(4-hydroxy-1-piperidinyl)
methyl]-3-pyridinyl)-3-quinolinecarbonitrile, 4-({3-Chloro-4-[(1-methyl-1H-imidazol-2-yl)sulfanyl]
phenyl}amino)-7-[6-(1-piperidinylmethyl)-3-
pyridinyl]-3-quinolinecarbonitrile, 4-({3-Chloro-4-[(1-methyl-1H-imidazol-2-yl)sulfanyl]
phenyl}amino)-7-{6-[(4-isopropyl-1-piperazinyl)
methyl]-3-pyridinyl}-3-quinolinecarbonitrile, 4-(2,4-Dichloro-5-methoxyanilino)-7-[1-methyl-2-(4-
morpholinylmethyl)-1H-imidazol-5-yl]-3-
quinolinecarbonitrile, 4-(2,4-Dichloro-5-methoxyanilino)-7-{1-methyl-2-[(4-
methyl-1-piperazinyl)methyl]-1H-imidazol-5-yl}-3-
quinolinecarbonitrile, 4-(2,4-Dichloro-5-methoxyanilino)-7-(2-formyl-1-
methyl-1H-imidazol-5-yl)-6-methoxy-3-
quinolinecarbonitrile, 4-(2,4-Dichloro-5-methoxyanilino)-7-[4-({[2-(2-
pyridinyl)ethyl]amino}methyl)phenyl]-3-
quinolinecarbonitrile, 4-(2,4-Dichloro-5-methoxyanilino)-7-(4-{[4-(2-hydroxyethyl)-1-piperazinyl]methyl}phenyl)-3-quinolinecarbonitrile, Methyl 1-{4-[3-cyano-4-(2,4-dichloro-5-methoxyanilino)-7-quinolinyl]benzyl}-4-piperidinecarboxylate, 4-(2,4-Dichloro-5-methoxyanilino)-6-methoxy-7-[1-methyl-2-(4-morpholinylmethyl)-1H-imidazol-5-yl]-3-quinolinecarbonitrile, 4-(2,4-Dichloro-5-methoxyanilino)-6-methoxy-7-{1-methyl-2-[(4-methyl-1-piperazinyl)methyl]-1H-imidazol-5-yl}-3-quinolinecarbonitrile, 4-(2-Chloro-5-methoxy-4-methylanilino)-7-[4-(4-morpholinylmethyl)phenyl]-3-quinolinecarbonitrile, 4-(2-Chloro-4-fluoro-5-methoxyanilino)-7-[(4-(4-morpholinylmethyl)phenyl]-3-quinolinecarbonitrile, 4-(2-Chloro-5-methoxyanilino)-7-[4-(4-morpholinylmethyl)phenyl]-3-quinolinecarbonitrile, 1-{4-[3-Cyano-4-(2,4-dichloro-5-methoxyanilino)-7-quinolinyl]benzyl}-4-piperidinecarboxylic acid, 4-{3-chloro-4-[(1-methyl-1H-imidazol-2-yl)sulfanyl]anilino}-7-{4-[(4-methyl-1-piperazinyl)methyl]phenyl}-3-quinolinecarbonitrile, Additionally, preferred compounds of the invention or a pharmaceutically acceptable salt thereof are:

4-{3-chloro-4-[(1-methyl-1H-imidazol-2-yl)sulfanyl]anilino}-7-[4-({[2-(dimethylamino)ethyl]amino}methyl)phenyl]-3-quinolinecarbonitrile, 4-{3-chloro-4-[(1-methyl-1H-imidazol-2-yl)sulfanyl]anilino}-7-(4-{[4-(1-pyrrolidinyl)-1-piperidinyl]methyl}phenyl)-3-quinolinecarbonitrile, 4-{3-chloro-4-[(1-methyl-1H-imidazol-2-yl)sulfanyl]anilino}-7-(4-{[(4-pyridinylmethyl)amino]methyl}phenyl)-3-quinolinecarbonitrile, 4-{3-chloro-4-[(1-methyl-1H-imidazol-2-yl)sulfanyl]anilino}-7-{4[(dimethylamino)methyl]phenyl}-3-quinolinecarbonitrile, 4-{3-chloro-4-[(1-methyl-1H-imidazol-2-y)sulfanyl]anilino})-7-(4-{[(2-hydroxyethyl)amino]methyl}phenyl)-3-quinolinecarbonitrile, 4-{3-chloro-4-[(1-methyl-1H-imidazol-2-yl)sulfanyl]anilino}-7-[4-({[3-(4-morpholinyl)propyl]amino}methyl)phenyl]-3-quinolinecarbonitrile, 4-{3-chloro-4-[(1-methyl-1H-imidazol-2-yl)sulfanyl]anilino}-7-{4-[(4-ethyl-1-piperazinyl)methyl]phenyl}-3-quinolinecarbonitrile, 4-{3-chloro-4-[(1-methyl-1H-imidazol-2-yl)sulfanyl]anilino}-7-(4-{[4-(2-hydroxyethyl)-1-piperazinyl]methyl}phenyl)-3-quinolinecarbonitrile, 4-{3-chloro-4-[(1-methyl-1H-imidazol-2-yl)sulfanyl]anilino}-7-{3-[(4-hydroxy-1-piperidinyl)methyl]phenyl}-3-quinolinecarbonitrile, 4-{3-chloro-4-[(1-methyl-1H-imidazol-2-yl)sulfanyl]anilino}-7-[3-({[2-dimethylamino)ethyl]amino}methyl)phenyl]-3-quinolinecarbonitrile, 4-{3-chloro-4-[(1-methyl-1H-imidazol-2-yl)sulfanyl]anilino}-7-(3-{[4-(1-pyrrolidinyl)-1-piperidinyl]methyl}phenyl)-3-quinolinecarbonitrile, 4-{3-chloro-4-[(1-methyl-1H-imidazol-2-yl)sulfanyl]anilino}-7-(3-{[(4-pyridinylmethyl)amino]methyl}phenyl)-3-quinolinecarbonitrile, 4-{3-chloro-4-(1-methyl-1H-imidazol-2-yl)sulfanyl]anilino}-7-{3-[(dimethylamino)methyl]phenyl}-3-quinolinecarbonitrile, 4-{3-chloro-4-[(1-methyl-1H-imidazol-2-yl)sulfanyl]anilino}-7-[3-(4-morpholinylmethyl)phenyl]-3-quinolinecarbonitrile, 4-{3-chloro-4-[(1-methyl-1H-imidazol-2-yl)sulfanyl]anilino}-7-(3-{[(2-hydroxyethyl)amino]methyl}phenyl)-3-quinolinecarbonitrile, 4-{3-chloro-4-[(1-methyl-1H-imidazol-2-yl)sulfanyl]anilino}-7-{3-[(4-methyl-1-piperazinyl)methyl]phenyl}-3-quinolinecarbonitrile, 4-{3-chloro-4-[(1-methyl-1H-imidazol-2-yl)sulfanyl]anilino}-7-[3-({[3-(4-morpholinyl)propyl]amino}methyl)phenyl]-3-quinolinecarbonitrile, 4-{3-chloro-4-[(1-methyl-1H-imidazol-2-yl)sulfanyl]anilino}-7-[3-(1-piperidinylmethyl)phenyl]3-quinolinecarbonitrile, 4-{3-chloro-4-[(1-methyl-1-imidazol-2-yl)sulfanyl]anilino}-7-{3-[(4-ethyl-1-piperazinyl)methyl]phenyl}-3-quinolinecarbonitrile, 4-{3-chloro-4-[(1-methyl-1H-imidazol-2-yl)sulfanyl]anilino}-7-(3-{[4-(2-hydroxyethyl)-1-piperazinyl]methyl}phenyl)-3-quinolinecarbonitrile, 4-{3-chloro-4-[(1-methyl-1H-imidazol-2-yl)sulfanyl]anilino}-7-{5-[(4-hydroxy-1-piperidinyl)methyl]-2-furyl}-3-quinolinecarbonitrile, 4-{3-chloro-4-[(1-methyl-1H-imidazol-2-yl)sulfanyl]anilino}-7-[5-({[2-(dimethylamino)ethyl]amino}methyl)-2-furyl]-3-quinolinecarbonitrile, 4-{3-chloro-4-[(1-methyl-1H-imidazol-2-yl)sulfanyl]anilino}-7-(5-{[4-(1-pyrrolidinyl)-1-piperidinyl]methyl}-2-furyl)-3-quinolinecarbonitrile, 4-{3-chloro-4-[(1-methyl-1H-imidazol-2-yl)sulfanyl]anilino}-7-(5-{[(2-hydroxyethyl)amino]methyl-2-furyl)-3-quinolinecarbonitrile, 4-{3-chloro-4-[(1-methyl-1H-imidazol-2-yl)sulfanyl]anilino}-7-{5-[(4-methyl-1-piperazinyl)methyl]-2-furyl}-3-quinolinecarbonitrile, 4-{3-chloro-4-[(1-methyl-1H-imidazol-2-yl)sulfanyl]anilino}-7-[5-({[3-(4-morpholinyl)propyl]amino}methyl)-2-furyl]-3-quinolinecarbonitrile, 4-{3-chloro-4-[(1-methyl-1H-imidazol-2-yl)sulfanyl]anilino}-7-[5-({[2-(dimethylamino)ethyl]amino}methyl)-2-thienyl]-3-quinolinecarbonitrile, 4-{3-chloro-4-[(1-methyl-1H-imidazol-2-yl)sulfanyl]anilino}-7-(5-{[4-(1-pyrrolidinyl)-1-piperidinyl]methyl}-2-thienyl)-3-quinolinecarbonitrile, 4-{3-chloro-4-[(1-methyl-1H-imidazol-2-yl)sulfanyl]anilino}-7-(5-{[(2-hydroxyethyl)amino]methyl}-2-thienyl)-3-quinolinecarbonitrile, 4-{3-chloro-4-[(1-methyl-1H-imidazol-2-yl)sulfanyl]anilino}-7-[5-({[3-(4-morpholinyl)propyl]amino}methyl)-2-thienyl]-3-quinolinecarbonitrile, 4-{3-chloro-4-[(1-methyl-1H-imidazol-2-yl)sulfanyl]anilino}-7-{5-[(4-ethyl-1-piperazinyl)methyl]-2-thienyl}-3-quinolinecarbonitrile, 4-{3-chloro-4-[(1-methyl-1H-imidazol-2-yl)sulfanyl]anilino}-7-[5-({[2-(dimethylamino)ethyl]amino}methyl)-2-pyridinyl]-3-quinolinecarbonitrile, 4-{3-chloro-4-[(1-methyl-1H-imidazol-2-yl)sulfanyl]anilino}-7-[5-({[3-(4-morpholinyl)propyl]amino}methyl)-2-pyridinyl]-3-quinolinecarbonitrile, 4-(2,4-dimethylanilino)-7-{4-[(4-hydroxy-1-piperidinyl)methyl]phenyl}-3-quinolinecarbonitrile, 7-[4-({[2-(dimethylamino)ethyl]amino}methyl)phenyl]-4-(2,4-dimethylanilino)-3-quinolinecarbonitrile, 4-(2,4-dimethylanilino)-7-(4-{[4-(1-pyrrolidinyl)-1-piperidinyl]methyl}phenyl)-3-quinolinecarbonitrile, 4-(2,4-dimethylanilino)-7-(4-{[(4-pyridinylmethyl)amino]methyl}phenyl)-3-quinolinecarbonitrile, 4-(2,4-dimethylanilino)-7-[4-({[2-(1H-imidazol-4-yl)ethyl]amino}methyl)phenyl]-3-quinolinecarbonitrile, 4-(2,4-dimethylanilino)-7-[4-(4-morpholinylmethyl)phenyl]-3-quinolinecarbonitrile, 4-(2,4-dimethylanilino)-7-(4-{[(2-hydroxyethyl)amino]methyl}phenyl)-3-quinolinecarbonitrile, 4-(2,4-dimethylanilino)-7-{4-[(4-methyl-1-piperazinyl)methyl]phenyl}-3-quinolinecarbonitrile, 4-(2,4-dimethylanilino)-7-[4-({[3-(4-morpholinyl)propyl]amino}methyl)phenyl]-3-quinolinecarbonitrile, 4-(2,4-dimethylanilino)-7-(4-(1-piperidinylmethyl)phenyl]-3-quinolinecarbonitrile, 4-(2,4-dimethylanilino)-7-{4-[(4-ethyl-1-piperazinyl)methyl]phenyl}-3-quinolinecarbonitrile, 4-(2,4-dimethylanilino)-7-(4-{[4-(2-hydroxyethyl)-1-piperazinyl]methyl}phenyl)-3-quinolinecarbonitrile, 4-(2,4-dimethylanilino)-7-{3-[(4-hydroxy-1-piperidinyl)methyl]phenyl}-3-quinolinecarbonitrile, 7-[3-({[2-(dimethylamino)ethyl]amino}methyl)phenyl]-4-(2,4-dimethylanilino)-3-quinolinecarbonitrile, 4-(2,4-dimethylanilino)-7-(3-{[4-(1-pyrrolidinyl)-1-piperidinyl]methyl}phenyl)-3-quinolinecarbonitrile, 4-(2,4-dimethylanilino)-7-(3-{[(4-pyridinylmethyl)amino]methyl}phenyl)-3-quinolinecarbonitrile, 4-(2,4-dimethylanilino)-7-[3-({[2-(1H-imidazol-4-yl)ethyl]amino}methyl)phenyl]-3-quinolinecarbonitrile, 4-(2,4-dimethylanilino)-7-[3-(4-morpholinylmethyl)phenyl]-3-quinolinecarbonitrile, 4-(2,4-dimethylanilino)-7-(3-{[(2-hydroxyethyl)amino]methyl}phenyl)-3-quinolinecarbonitrile, 4-(2,4-dimethylanilino)-7-{3-[(4-methyl-1-piperazinyl)methyl]phenyl}-3-quinolinecarbonitrile, 4-(2,4-dimethylanilino)-7-[3-({[3-(4-morpholinyl)propyl]amino}methyl)phenyl]-3-quinolinecarbonitrile, 4-(2,4-dimethylanilino)-7-[3-(1-piperidinylmethyl)phenyl]-3-quinolinecarbonitrile, 4-(2,4-dimethylanilino)-7-{3-[(4-ethyl-1-piperazinyl)methyl]phenyl}-3-quinolinecarbonitrile, 4-(2,4-dimethylanilino)-7-(3-{[4-(2-hydroxyethyl)-1-piperazinyl]methyl}phenyl)-3-quinolinecarbonitrile, 4-(2,4-dimethylanilino)-7-{5-[(4-hydroxy-1-piperidinyl)methyl]-2-furyl}-3-quinolinecarbonitrile, 7-[5-({[2-(dimethylamino)ethyl]amino}methyl)-2-furyl]-4-(2,4-dimethylanilino)-3-quinolinecarbonitrile, 4-(2,4-dimethylanilino)-7-(5-{[4-(1-pyrrolidinyl)-1-piperidinyl]methyl}-2-furyl)-3-quinolinecarbonitrile, 4-(2,4-dimethylanilino)-7-(5-{[(4-pyridinylmethyl)amino]methyl}-2-furyl)-3-quinolinecarbonitrile, 4-(2,4-dimethylanilino)-7-[5-({[2-(1H-imidazol-4-yl)ethyl]amino}methyl)-2-furyl]3-quinolinecarbonitrile, 4-(2,4-dimethylanilino)-7-[5-(4-morpholinylmethyl)-2-furyl]-3-quinolinecarbonitrile, 4-(2,4-dimethylanilino)-7-(5-{[(2-hydroxyethyl)amino]methyl}-2-furyl)-3-quinolinecarbonitrile, 4-(2,4-dimethylanilino)-7-{5-[(4-methyl-1-piperazinyl)methyl]-2-furyl}-3-quinolinecarbonitrile, 4-(2,4-dimethylanilino)-7-[5-(1-piperidinylmethyl)-2-furyl]-3-quinolinecarbonitrile, 4-(2,4-dimethylanilino)-7-{5-[(4-ethyl-1-piperazinyl)methyl]-2-furyl}-3-quinolinecarbonitrile, 4-(2,4-dimethylanilino)-7-(5-{[4-(2-hydroxyethyl)-1-piperazinyl]methyl}-2-furyl)-3-quinolinecarbonitrile, 4-(2,4-dimethylanilino)-7-{5-[(4-hydroxy-1-piperidinyl)methyl]-2-thienyl}-3-quinolinecarbonitrile, 7-[5-({[2-(dimethylamino)ethyl]amino}methyl)-2-thienyl]-4-(2,4-dimethylanilino)-3-quinolinecarbonitrile, 4-(2,4-dimethylanilino)-7-(5-{[4-(1-pyrrolidinyl)-1-piperidinyl]methyl}-2-thienyl)-3-quinolinecarbonitrile, 4-(2,4-dimethylanilino)-7-(5-{[(4-pyridinylmethyl)amino]methyl}-2-thienyl)-3-quinolinecarbonitrile, 4-(2,4-dimethylanilino)-7-[5-({[2-(1H-imidazol-4-yl)ethyl]amino}methyl)-2-thienyl]-3-quinolinecarbonitrile, 4-(2,4-dimethylanilino)-7-[5-(4-morpholinylmethyl)-2-thienyl]-3-quinolinecarbonitrile, 4-(2,4-dimethylanilino)-7-(5-{[(2-hydroxyethyl)amino]methyl}-2-thienyl)-3-quinolinecarbonitrile, 4-(2,4-dimethylanilino)-7-{5-[(4-methyl-1-piperazinyl)methyl]-2-thienyl}-3-quinolinecarbonitrile, 4-(2,4-dimethylanilino)-7-{5-[(4-ethyl-1-piperazinyl)methyl]-2-thienyl}-3-quinolinecarbonitrile, 4-(2,4-dimethylanilino)-7-(5-{[4-(2-hydroxyethyl)-1-piperazinyl]methyl}-2-thienyl)-3-quinolinecarbonitrile, 4-(2,4-dimethylanilino)-7-{5-[(4-hydroxy-1-piperidinyl)methyl]-3-thienyl}-3-quinolinecarbonitrile, 7-[5-({[2-(dimethylamino)ethyl]amino}methyl)-3-thienyl]-4-(2,4-dimethylanilino)-3-quinolinecarbonitrile, 4-(2,4-dimethylanilino)-7-(5-{[4-(1-pyrrolidinyl)-1-piperidinyl]methyl}-3-thienyl)-3-quinolinecarbonitrile, 4-(2,4-dimethylanilino)-7-(5-{[(4-pyridinylmethyl)amino]methyl}-3-thienyl)-3-quinolinecarbonitrile, 4-(2,4-dimethylanilino)-7-[5-{[2-(1H-imidazol-4-yl)ethyl]amino}methyl)-3-thienyl]-3-quinolinecarbonitrile, 4-(2,4-dimethylanilino)-7-[5-(4-morpholinylmethyl)-3-thienyl]-3-quinolinecarbonitrile, 4-(2,4-dimethylanilino)-7-(5-{[(2-hydroxyethyl)amino]methyl}-3-thienyl)-3-quinolinecarbonitrile, 4-(2,4-dimethylanilino)-7-{5-[(4-methyl-1-piperazinyl)methyl]-3-thienyl}-3-quinolinecarbonitrile, 4-(2,4-dimethylanilino)-7-[5-({[3-(4-morpholinyl)propyl]amino}methyl)-3-thienyl]-3-quinolinecarbonitrile, 4-(2,4-dimethylanilino)-7-[5-(1-piperidinylmethyl)-3-thienyl]-3-quinolinecarbonitrile, 4-(2,4-dimethylanilino)-7-{5-[(4-ethyl-1-piperazinyl)methyl]-3-thienyl}-3-quinolinecarbonitrile, 4-(2,4-dimethylanilino)-7-(5-{[4-(2-hydroxyethyl)-1-piperazinyl]methyl}-3-thienyl)-3-quinolinecarbonitrile, 4-(4-bromo-2-chloro-6-methylanilino)-7-{5-[(4-hydroxy-1-piperidinyl)methyl]-2-furyl}-3-quinolinecarbonitrile, 4-(4-bromo-2-chloro-6-methylanilino)-7-[5-({[2-(dimethylamino)ethyl]amino}methyl)-2-furyl]-3-quinolinecarbonitrile, 4-(4-bromo-2-chloro-6-methylanilino)-7-(5-{[4-(1-pyrrolidinyl)-1-piperidinyl]methyl}-2-furyl)-3-quinolinecarbonitrile, 4-(4-bromo-2-chloro-6-methylanilino)-7-(5-{[(4-pyridinylmethyl)amino]methyl}-2-furyl)-3-quinolinecarbonitrile, 4-(4-bromo-2-chloro-6-methylanilino)-7-[5-({[2-(1H-imidazol-4-yl)ethyl]amino}methyl)-2-furyl]-3-quinolinecarbonitrile, 4-(4-bromo-2-chloro-6-methylanilino)-7-[5-(4-morpholinylmethyl)-2-furyl]-3-quinolinecarbonitrile, 4-(4-bromo-2-chloro-6-methylanilino)-7-(5-{[(2-hydroxyethyl)amino]methyl}-2-furyl)-3-quinolinecarbonitrile, 4-(4-bromo-2-chloro-6-methylanilino)-7-{5-[(4-methyl-1-piperazinyl)methyl]-2-furyl}-3-quinolinecarbonitrile, 4-(4-bromo-2-chloro-6-methylanilino)-7-[5-({[3-(4-morpholinyl)propyl]amino}methyl)-2-furyl]-3-quinolinecarbonitrile, 4-(4-bromo-2-chloro-6-methylanilino)-7-[5-(1-piperidinylmethyl)-2-furyl]-3-quinolinecarbonitrile, 4-(4-bromo-2-chloro-6-methylanilino)-7-{5-[(4-ethyl-1-piperazinyl)methyl]-2-furyl}-3-quinolinecarbonitrile, 4-(4-bromo-2-chloro-6-methylanilino)-7-(5-{[4-(2-hydroxyethyl)-1-piperazinyl]methyl}-2-furyl)-3-quinolinecarbonitrile, 4-(4-bromo-2-chloro-6-methylanilino)-7-{5-[(4-hydroxy-1-piperidinyl)methyl]-2-thienyl}-3-quinolinecarbonitrile, 4-(4-bromo-2-chloro-6-methylanilino)-7-[5-({[2-(dimethylamino)ethyl]amino}methyl)-2-thienyl]-3-quinolinecarbonitrile, 4-(4-bromo-2-chloro-6-methylanilino)-7-(5-{[4-(1-pyrrolidinyl)-1-piperidinyl]methyl}-2-thienyl)-3-quinolinecarbonitrile, 4-(4-bromo-2-chloro-6-methylanilino)-7-(5-{[(4-pyridinylmethyl)amino]methyl}-2-thienyl)-3-quinolinecarbonitrile, 4-(4-bromo-2-chloro-6-methylanilino)-7-[5-{[2-(1H-imidazol-4-yl)ethyl]amino}methyl]-2-thienyl]-3-quinolinecarbonitrile, 4-(4-bromo-2-chloro-6-methylanilino)-7-[5-(4-morpholinylmethyl)-2-thienyl]-3-quinolinecarbonitrile, 4-(4-bromo-2-chloro-6-methylanilino)-7-(5-{[(2-hydroxyethyl)amino]methyl}-2-thienyl)-3-quinolinecarbonitrile, 4-(4-bromo-2-chloro-6-methylanilino)-7-{5-[(4-methyl-1-piperazinyl)methyl]-2-thienyl}-3-quinolinecarbonitrile, 4-(4-bromo-2-chloro-6-methylanilino)-7-[5-({[3-(4-morpholinyl)propyl]amino}methyl)-2-thienyl-3-quinolinecarbonitrile, 4-(4-bromo-2-chloro-6-methylanilino)-7-[5-(1-piperidinylmethyl)-2-thienyl]-3-quinolinecarbonitrile, 4-({3-chloro-4'-[(4-hydroxy-1-piperidinyl)methyl]-5-methyl[1,1'-biphenyl]-4-yl)amino)-7-{4-[(4-hydroxy-1-piperidinyl)methyl]phenyl}-3-quinolinecarbonitrile, 4-{[3-chloro-4'-({[2-(dimethylamino)ethyl]amino}methyl)-5-methyl[1,1'-biphenyl]-4-yl]amino}-7-({[2-(dimethylamino)ethyl]amino}methyl)phenyl]-3-quinolinecarbonitrile, 4-[(3-chloro-5-methyl-4'-{[4-(1-pyrrolidinyl)-1-piperidinyl]methyl}[(1,1'-biphenyl]-4-yl)amino]-7-(4-{[4-(1-pyrrolidinyl)-1-piperidinyl]methyl}phenyl)-3-quinolinecarbonitrile, 4-{[3-chloro-5-methyl-4'-(4-morpholinylmethyl)[1,1'-biphenyl]-4-yl]amino}-7-[4-morpholinylmethyl)phenyl]-3-quinolinecarbonitrile, 4-[(3-chloro-4'-([(2-hydroxyethyl)amino]methyl}-5-methyl[1,1'-biphenyl]-4-yl)amino]-7-(4-{[(2-hydroxyethyl)amino]methyl}phenyl)-3-quinolinecarbonitrile, 4-({3-chloro-5-methyl-4'-[(4-methyl-1-piperazinyl)methyl][1,1'-biphenyl]-4-yl}amino)-7-{4-[(4-methyl-1-piperazinyl)methyl]phenyl}-3-quinolinecarbonitrile, 4-{[3-chloro-5-methyl-4'-({[3-(4-morpholinyl)propyl]amino}methyl)[1,1'-biphenyl]-4-yl]amino}-7-[4-({[3-(4-morpholinyl)propyl]amino}methyl)phenyl]-3-quinolinecarbonitrile, 4-{[3-chloro-5-methyl-4'-(1-piperidinylmethyl)[1,1'-biphenyl)-4-yl]amino}-7-[4-({[3-(4-morpholinyl)propyl]amino}methyl)phenyl]-3-quinolinecarbonitrile, 4-({3-chloro-4'-[(4-ethyl-1-piperazinyl)methyl]-5-methyl[1,1'-biphenyl]-4-yl}amino]-7-{4-[(4-ethyl-1-piperazinyl)methyl]phenyl}-3-quinolinecarbonitrile, 4-[(3-chloro-4'-{[4-(2-hydroxyethyl)-1-piperazinyl]methyl}-5-methyl[1,1'-biphenyl]-4-yl)amino]-7-(4-{[4-(2-hydroxyethyl)-1-piperazinyl]methyl}phenyl)-3-quinolinecarbonitrile, 4-({(3-chloro-3'-[(4-hydroxy-1-piperidinyl)methyl]-5-methyl[1,1'-biphenyl]-4-yl}amino)-7-{3-[(4-hydroxy-1-piperidinyl)methyl]phenyl}-3-quinolinecarbonitrile, 4-{[3-chloro-3'-({[2-(dimethylamino)ethyl]amino}methyl)-5-methyl[1,1'-biphenyl]-4-yl]amino}-7-[3-({[2-(dimethylamino)ethyl]amino}methyl)phenyl]-3-quinolinecarbonitrile, 4-[(3-chloro-5-methyl-3'-{[4-(1-pyrrolidinyl)-1-piperidinyl]methyl}[1,1'-biphenyl]-4-yl)amino]-7-(3-{[4-(1-pyrrolidinyl)-1-piperidinyl]methyl}phenyl)-3-quinolinecarbonitrile, 4-[(3-chloro-5-methyl-3'-{[(4-pyridinylmethyl)amino]methyl}[1,1'-biphenyl]-4-yl)amino]-7-(3-{[(4-pyridinylmethyl)amino]methyl}phenyl)-3-quinolinecarbonitrile, 4-{[3-chloro-3'-({[2-(1H-imidazol-4-yl)ethyl]amino}methyl)-5-methyl[1,1'biphenyl]-4-yl]amino}-7-[3-({[2-(1H-imidazol-4-yl)ethyl]amino}methyl)phenyl]-3-quinolinecarbonitrile, 4-{[3-chloro-5-methyl-3'-(4-morpholinylmethyl)[1,1'-biphenyl]-4-yl]amino}-7-[3-(4-morpholinylmethyl)phenyl]-3-quinolinecarbonitrile, 4-[(3-chloro-3'-{[(2-hydroxyethyl)amino]methyl}-5-methyl[1,1'-biphenyl]-4-yl)amino]-7-{[(2-hydroxyethyl)amino]methyl}phenyl}-3-quinolinecarbonitrile, 4-({3-chloro-5-methyl-3'-[(4-methyl-1-piperazinyl)methyl][1,1'-biphenyl]-4-yl}amino)-7-{3-[(4-methyl-1-piperazinyl)methyl]phenyl}-3-quinolinecarbonitrile, 4-{[3-chloro-5-methyl-3'-({[3-(4-morpholinyl)propyl]amino}methyl)[1,1'-biphenyl]-4-yl]amino}-7-[3-({[3-(4-morpholinyl)propyl]amino}methyl)phenyl]-3-quinolinecarbonitrile, 4-{[3-chloro-5-methyl-3'-(1-piperidinylmethyl)[1,1'-biphenyl]-4-yl]amino}-7-[3-(1-piperidinylmethyl)phenyl]-3-quinolinecarbonitrile, 4-({3-chloro-3'-[(4-ethyl-1-piperazinyl)methyl]-5-methyl[1,1'-biphenyl]-4-yl}amino)-7-{3-[(4-ethyl-1-piperazinyl)methyl]phenyl}-3-quinolinecarbonitrile, 4-[(3-chloro-3'-{[4-(2-hydroxyethyl)-1-piperazinyl]methyl}-5-methyl[1,1'-biphenyl]-4-yl)amino]-7-(3-{[4-(2-hydroxyethyl)-1-piperazinyl]methyl}phenyl)-3-quinolinecarbonitrile, 4-(2-chloro-4-[5-({[2-(dimethylamino)ethyl]amino}methyl)-3-thienyl]-6-methylanilino]-7-[5-({[2-(dimethylanilino)ethyl]amino}methyl)-3-thienyl]-3-quinolinecarbonitrile, 4-[2-chloro-6-methyl-4-(5-{[4-(1-pyrrolidinyl)-1-piperidinyl]methyl}-3-thienyl)anilino]-7-(5-{[4-(1-pyrrolidinyl)-1-piperidinyl]methyl}-3-thienyl)-3-quinolinecarbonitrile, 4-[2-chloro-6-methyl-4-(5-{[(4-pyridinylmethyl)amino]methyl}-3-thienyl)anilino]7-(5-{[(4-piperidinylmethyl)amino]methyl}-3-thienyl)-3-quinolinecarbonitrile, 4-{2-chloro-4-[5-({[2-(1H-imidazol-4-yl)ethyl]amino}methyl)-3-thienyl]-6-methylanilino-7-[5-({[2-(1H-imidazol-4-yl)ethyl]amino}methyl)-3-thienyl]-3-quinolinecarbonitrile, 4-(2-chloro-6-methyl-4-[5-(4-morpholinylmethyl)-3-thienyl]anilino}-7-[5-(4-morpholinylmethyl)-3-thienyl]-3-quinolinecarbonitrile, 4-(2-chloro-6-methyl-4-{5-[(4-methyl-1-piperazinyl)methyl]-3-thienyl}anilino)-7-{5-[(4-methyl-1-piperazinyl)methyl]-3-thienyl}-3-quinolinecarbonitrile, 4-{2-chloro-6-methyl-4-[5-({[3-(4-morpholinyl)propyl]amino}methyl)-3-thienyl]anilino}-7-[5-({[3-(4-morpholinyl)propyl]amino}methyl)-3-thienyl]-3-quinolinecarbonitrile, 4-{2-chloro-6-methyl-4-[5-(1-piperidinylmethyl)-3-thienyl]anilino}-7-[5-(1-piperidinylmethyl)-3-thienyl]-3-quinolinecarbonitrile, 4-(2-chloro-4-{5-[(4-ethyl-1-piperazinyl)methyl]-3-thienyl}-6-methylanilino)-7-{5-[(4-ethyl-1-piperazinyl)methyl]-3-thienyl}-3-quinolinecarbonitrile, 4-[2-chloro-4-(5-{[4-(2-hydroxyethyl)-1-piperazinyl]methyl}-3-thienyl)-6-methylanilino]-7-(5-{[4-(2-hydroxyethyl)-1-piperazinyl]methyl}-3-thienyl)-3-quinolinecarbonitrile, 4-[(3-chloro-4-phenoxyphenyl)amino]-7-[4-({[3-(4-morpholinyl)propyl]amino}methyl)phenyl]-3-quinolinecarbonitrile, 4-[(3-chloro-4-phenoxyphenyl)amino]-7-{4-[(4-ethyl-1-piperazinyl)methyl]phenyl}-3-quinolinecarbonitrile, 4-[(3-chloro-4-phenoxyphenyl)amino]-7-(4-{[4-(2-hydroxyethyl)-1-piperazinyl]methyl}phenyl)-3-quinolinecarbonitrile, 4-[(3-chloro-4-phenoxyphenyl)amino]-7-[3-({[2-(dimethylamino)ethyl]amino}methyl)phenyl]-3-quinolinecarbonitrile, 4-[(3-chloro-4-phenoxyphenyl)amino]-7-(3-{[4-(1-pyrrolidinyl)-1-piperidinyl]methyl}phenyl)-3-quinolinecarbonitrile, 4-[(3-chloro-4-phenoxyphenyl)amino]-7-(3-{[(4-pyridinylmethyl)amino]methyl}phenyl)-3-quinolinecarbonitrile, 4-[(3-chloro-4-phenoxyphenyl)amino]-7-[3-({[3-(4-morpholinyl)propyl]amino}methyl)phenyl]-3-quinolinecarbonitrile, 4-[(3-chloro-4-phenoxyphenyl)amino]-7-{3-[(4-ethyl-1-piperazinyl)methyl]phenyl}-3-quinolinecarbonitrile, 4-[(3-chloro-4-phenoxyphenyl)amino]-7-{5-[(4-hydroxy-1-piperidinyl)methyl]-2-furyl}-3-quinolinecarbonitrile, 4-[(3-chloro-4-phenoxyphenyl)amino]-7-[5-({[2-(dimethylamino)ethyl]amino}methyl)-2-furyl]-3-quinolinecarbonitrile, 4-[(3-chloro-4-phenoxyphenyl)amino]-7-(5-{[4-(1-pyrrolidinyl)-1-piperidinyl]methyl}-2-furyl)-3-quinolinecarbonitrile, 4-[(3-chloro-4-phenoxyphenyl)amino]-7-(5-{[(4-pyridinylmethyl)amino]methyl}-2-furyl)-3-quinolinecarbonitrile, 4-[(3-chloro-4-phenoxyphenyl)amino]-7-[5-({[2-(1H-imidazol-4-yl)ethyl]amino}methyl)-2-furyl]-3-quinolinecarbonitrile, 4-[(3-chloro-4-phenoxyphenyl)amino]-7-5[-(4-morpholinylmethyl)-2-furyl]-3-quinolinecarbonitrile, 4-[(3-chloro-4-phenoxyphenyl)amino]-7-(5-{[(2-hydroxyethyl)amino]methyl}-2-furyl)-3-quinolinecarbonitrile, 4-[(3-chloro-4-phenoxyphenyl)amino]-7-{5-[(4-methyl-1-piperazinyl)methyl]-2-furyl}-3-quinolinecarbonitrile, 4-[(3-chloro-4-phenoxyphenyl)amino]-7-[5-({[3-(4-morpholinyl)propyl]amino}methyl)-2-furyl]-3-quinolinecarbonitrile, 4-[(3-chloro-4-phenoxyphenyl)amino]-7-[5-(1-piperidinylmethyl)-2-furyl]-3-quinolinecarbonitrile, 4-[(3-chloro-4-phenoxyphenyl)amino]-7-{5-[(4-ethyl-1-piperazinyl)methyl]-2-furyl}-3-quinolinecarbonitrile, 4-[(3-chloro-4-phenoxyphenyl)amino]-7-(5-{[4-(2-hydroxyethyl)-1-piperazinyl]methyl}-2-furyl)-3-quinolinecarbonitrile, 4-[(3-chloro-4-phenoxyphenyl)amino]-7-[5-({[2-(dimethylamino)ethyl]amino}methyl)-2-thienyl]-3-quinolinecarbonitrile, 4-[(3-chloro-4-phenoxyphenyl)amino]-7-(5-{[4-(1-pyrrolidinyl)-1-piperidinyl]methyl}-2-thienyl)-3-quinolinecarbonitrile, 4-[(3-chloro-4-phenoxyphenyl)amino]-7-(5-{[(4-pyridinylmethyl)amino]methyl}-2-thienyl)-3-quinolinecarbonitrile, 4-[(3-chloro-4-phenoxyphenyl)amino]-7-[5-(4-morpholinylmethyl)-2-thienyl]-3-quinolinecarbonitrile, 4-[(3-chloro-4-phenoxyphenyl)amino]-7-{5-[(4-methyl-1-piperazinyl)methyl]-2-thienyl}-3-quinolinecarbonitrile, 4-[(3-chloro-4-phenoxyphenyl)amino]-7-{5-[(4-ethyl-1-piperazinyl)methyl]-2-thienyl}-3-quinolinecarbonitrile, 4-[(3-chloro-4-phenoxyphenyl)amino]-7-{5-[(4-hydroxy-1-piperidinyl)methyl]-3-thienyl}-3-quinolinecarbonitrile, 4-[(3-chloro-4-phenoxyphenyl)amino]-7-[5-({[2-(dimethylamino)ethyl]amino}methyl)-3-thienyl]-3-quinolinecarbonitrile, 4-[(3-chloro-4-phenoxyphenyl)amino]-7-(5-{[4-(1-pyrrolidinyl)-1-piperidinyl]methyl}-3-thienyl)-3-quinolinecarbonitrile, 4-[(3-chloro-4-phenoxyphenyl)amino]-7-(5-{[(4-pyridinylmethyl)amino]methyl}-3-thienyl)-3-quinolinecarbonitrile, 4-[(3-chloro-4-phenoxyphenyl)amino]-7-[5-({[2-(1H-imidazol-4-yl)ethyl]amino}methyl)-3-thienyl]-3-quinolinecarbonitrile, 4-[(3-chloro-4-phenoxyphenyl)amino]-7-[5-(4-morpholinylmethyl)-3-thienyl]-3-quinolinecarbonitrile, 4-[(3-chloro-4-phenoxyphenyl)amino]-7-(5-{[(2-hydroxyethyl)amino]methyl}-3-thienyl)-3-quinolinecarbonitrile, 4-[(3-chloro-4-phenoxyphenyl)amino]-7-{5-[(4-methyl-1-piperazinyl)methyl]-3-thienyl}-3-quinolinecarbonitrile, 4-[(3-chloro-4-phenoxyphenyl)amino]-7-[5-({[3-(4-morpholinyl)propyl]amino}methyl)-3-thienyl]-3-quinolinecarbonitrile, 4-[(3-chloro-4-phenoxyphenyl)amino]-7-[5-(1-piperidinylmethyl)-3-thienyl]-3-quinolinecarbonitrile, 4-[(3-chloro-4-phenoxyphenyl)amino]-7-{5-[(4-ethyl-1-piperazinyl)methyl]-3-thienyl)-3-quinolinecarbonitrile, 4-[(3-chloro-4-phenoxyphenyl)amino]-7-(5-{[4-(2-hydroxyethyl)-1-piperazinyl]methyl}-3-thienyl)-3-quinolinecarbonitrile, 4-[(3-chloro-4-phenoxyphenyl)annoy]-7-[5-({[3-(4-morpholinyl)propyl]amino}methyl)-2-pyridinyl]-3-quinolinecarbonitrile, 4-{[3-chloro-4-(phenylsulfanyl)phenyl]amino}-7-{4-[(4-hydroxy-1-piperidinyl)methyl]phenyl}-3-quinolinecarbonitrile, 4-{[3-chloro-4-(phenylsulfanyl)phenyl]amino}-7-(4-{[(4-pyridinylmethyl)amino]methyl}phenyl)-3-quinolinecarbonitrile, 4-{[3-chloro-4-(phenylsulfanyl)phenyl]amino}-7-[4-({[2-(1H-imidazol-4-yl)ethyl]amino}methyl)phenyl]-3-quinolinecarbonitrile, 4-{[3-chloro-4-(phenylfanyl)phenyl]amino}-7-[4-(4-morpholinylmethyl)phenyl]-3-quinolinecarbonitrile, 4-{[3-chloro-4-(phenylsulfanyl)phenyl]amino}-7-(4-{[(2-hydroxyethyl)amino]methyl}phenyl)-3-quinolinecarbonitrile, 4-[3-chloro-4-(phenylsulfanyl)phenyl]amino)-7-{4-[(4-methyl-1-piperazinyl)methyl]phenyl}-3-quinolinecarbonitrile, 4-{[3-chloro-4-(phenylsulfanyl)phenyl]amino}-7-[4-({[3-(4-morpholinyl)propyl]amino}methyl)phenyl]-3-quinolinecarbonitrile, 4-{[3-chloro-4-(phenylsulfanyl)phenyl]amino}-7-{4-[(4-ethyl-1-piperazinyl)methyl]phenyl}-3-quinolinecarbonitrile, 4-{[3-chloro-4-(phenylsulfanyl)phenyl]amino}-7-(4-{[4-(2-hydroxyethyl)-1-piperazinyl]methyl}phenyl)-3-quinolinecarbonitrile, 4-{[3-chloro-4-(phenylsulfanyl)phenyl]amino}-7-{3-[(4-hydroxy-1-piperidinyl)methyl]phenyl}-3-quinolinecarbonitrile, 4-{[3-chloro-4-(phenylsulfanyl)phenyl]amino}-7-[3-({[2-(dimethylamino)ethyl]amino}methyl)phenyl]-3-quinolinecarbonitrile, 4-{[3-chloro-4-(phenylsulfanyl)phenyl]amino}-7-(3-{[4-(1-pyrrolidinyl)-1-piperidinyl]methyl}phenyl)-3-quinolinecarbonitrile, 4-{[3-chloro-4-(phenylsulfanyl)phenyl]amino}-7-(3-{[(2-hydroxyethyl)amino]methyl}phenyl)-3-quinolinecarbonitrile, 4-{[3-chloro-4-(phenylsulfanyl)phenyl]amino}-7-[3-({[3-(4-morpholinyl)propyl]amino}methyl)phenyl]-3-quinolinecarbonitrile, 4-{[3-chloro-4-(phenylsulfanyl)phenyl]amino}-7-(3-{[4-(2-hydroxyethyl)-1-piperazinyl]methyl}phenyl)-3-quinolinecarbonitrile, 4-{[3-chloro-4-(phenylsulfanyl)phenyl]amino}-7-{5-[(4-hydroxy-1-piperidinyl)methyl]-2-furyl}-3-quinolinecarbonitrile, 4-{[3-chloro-4-(phenylsulfanyl)phenyl]amino}-7-[5-({[2-(dimethylamino)ethyl]amino}methyl)-2-furyl]-3-quinolinecarbonitrile, 4-{[3-chloro-4-(phenylsulfanyl)phenyl]amino}-7-(5-{[4-(1-pyrrolidinyl)-1-piperidinyl]methyl}-2-furyl)-3-quinolinecarbonitrile, 4-{[3-chloro-4-(phenylsulfanyl)phenyl]amino}-7-(5-{[(4-pyridinylmethyl)amino]methyl}-2-furyl)-3-quinolinecarbonitrile, 4-{[3-chloro-4-(phenylsulfanyl)phenyl]amino}-7-[5-({[2-(1H-imidazol-4-yl)ethyl]methyl}-2-furyl)-3-quinolinecarbonitrile, 4-{[3-chloro-4-(phenylsulfanyl)phenyl]amino}-7-[5-(4-morpholinylmethyl)-2-furyl]3-quinolinecarbonitrile, 4-{[3-chloro-4-(phenylsulfanyl)phenyl]amino}-7-(5-{[(2-hydroxyethyl)amino]methyl}-2-furyl)-3-quinolinecarbonitrile, 4-{[3-chloro-4-(phenylsulfanyl)phenyl]amino}-7-{5-[(4-methyl-1-piperazinyl)methyl]-2-furyl}-3-quinolinecarbonitrile, 4-[3-chloro-4-(phenylsulfanyl)phenyl]amino}-7-[5-({[3-(4-morpholinyl)propyl]amino}methyl)-2-furyl]-3-quinolinecarbonitrile, 4-{[3-chloro-4-(phenylsulfanyl)phenyl]amino}-7-{5-[(4-ethyl-1-piperazinyl)methyl]-2-furyl}-3-quinolinecarbonitrile, 4-{[3-chloro-4-(phenylsulfanyl)phenyl]amino}-7-[5-({[2-(dimethylamino)ethyl]amino}methyl)-2-thienyl]-3-quinolinecarbonitrile, 4-{[3-chloro-4-(phenylsulfanyl)phenyl]amino}-7-(5-{[4-(1-pyrrolidinyl)-1-piperidinyl]methyl}-2-thienyl)-3-quinolinecarbonitrile, 4-{[3-chloro-4-(phenylsulfanyl)phenyl]amino}-7-[5-(4-morpholinylmethyl)-2-thienyl]-3-quinolinecarbonitrile, 4-{[3-chloro-4-(phenylsulfanyl)phenyl]amino}-7-{5-[(4-methyl-1-piperazinyl)methyl]-2-thienyl}-3-quinolinecarbonitrile, 4-{[3-chloro-4-(phenylsulfanyl)phenyl]amino}-7-[5-({[3-(4-morpholinyl)propyl]amino}methyl)-2-thienyl]-3-quinolinecarbonitrile, 4-[3-chloro-4-(phenylsulfanyl)phenyl]amino}-7-{5-[(4-ethyl-1-piperazinyl)methyl]-2-thienyl}-3-quinolinecarbonitrile, 4-{[3-chloro-4-(phenylsulfanyl)phenyl]amino}-7-{5-[(4-hydroxy-1-piperidinyl)methyl]-3-thienyl}-3-quinolinecarbonitrile, 4-{[3-chloro-4-(phenylsulfanyl)phenyl]amino}-7-[5-({[2-(dimethylamino)ethyl]amino}methyl)-3-thienyl]-3-quinolinecarbonitrile, 4-{[3-chloro-4-(phenylsulfanyl)phenyl]amino}-7-(5-{[4-(1-pyrrolidinyl)-1-piperidinyl]methyl}-3-thienyl)-3-quinolinecarbonitrile, 4-{[3-chloro-4-(phenylsulfanyl)phenyl]amino}-7-(5-{[(4-pyridinylmethyl)amino]methyl}-3-thienyl)-3-quinolinecarbonitrile, 4-{[3-chloro-4-(phenylsulfanyl)phenyl]amino}-7-[5-({[2-(1H-imidazol-4-yl)ethyl]amino}methyl)-3-thienyl]-3-quinolinecarbonitrile, 4-{[3-chloro-4-(phenylsulfanyl)phenyl]amino}-7-[5-(4-morpholinylmethyl)-3-thienyl]-3-quinolinecarbonitrile, 4-{[3-chloro-4-(phenylsulfanyl)phenyl]amino}-7-(5-{[(2-hydroxyethyl)amino]methyl}-3-thienyl)-3-quinolinecarbonitrile, 4-{[3-chloro-4-(phenylsulfanyl)phenyl]amino}-7-{5-[(4-methyl-1-piperazinyl)methyl]-3-quinolinecarbonitrile, 4-{[3-chloro-4-(phenylsulfanyl)phenyl]amino}-7-[5-({[3-(4-morpholinyl)propyl]amino}methyl)-3-thienyl]-3-quinolinecarbonitrile, 4-{[3-chloro-4-(phenylsulfanyl)phenyl]amino}-7-[5-(1-piperidinylmethyl)-3-thienyl]-3-quinolinecarbonitrile, 4-{[3-chloro-4-(phenylsulfanyl)phenyl]amino}-7-{5-[(4-ethyl-1-piperazinyl)methyl]-3-thienyl}-3-quinolinecarbonitrile, 4-{[3-chloro-4-(phenylsulfanyl)phenyl]amino}-7-(5-{[4-(2-hydroxyethyl)-1-piperazinyl]methyl-3-thienyl)-3-quinolinecarbonitrile, 4-{[3-chloro-4-(3-furylmethyl)phenyl]amino}-7-{4-[(4-hydroxy-1-piperidinyl)methyl]phenyl}-3-quinolinecarbonitrile, 4-{[3-chloro-4-(3-furylmethyl)phenyl]amino}-7-[4-({[2-(dimethylamino)ethyl]amino}methyl)phenyl]-3-quinolinecarbonitrile, 4-{[3-chloro-4-(3-furylmethyl)phenyl]amino}-7-(4-{[4-(1-pyrrolidinyl)-1-piperidinyl]methyl}phenyl)-3-quinolinecarbonitrile, 4-{[3-chloro-4-(3-furylmethyl)phenyl]amino}-7-(4-{[(4-pyridinylmethyl)amino]methyl}phenyl)-3-quinolinecarbonitrile, 4-{[3-chloro-4-(3-furylmethyl)phenyl]amino}-7-[4-({[2-(1-imidazol-4-yl)ethyl]amino}methyl)phenyl]-3-quinolinecarbonitrile, 4-{[3-chloro-4-(3-furylmethyl)phenyl]amino}-7-[4-(4-morpholinylmethyl)phenyl]-3-quinolinecarbonitrile, 4-{[3-chloro-4-(3-furylmethyl)phenyl]amino}-7-(4-{[(2-hydroxyethyl)amino]methyl}phenyl)-3-quinolinecarbonitrile, 4-{[3-chloro-4-(3-furylmethyl)phenyl]amino}-7-{4-[(4-methyl-1-piperazinyl)methyl]phenyl}-3-quinolinecarbonitrile, 4-{[3-chloro-4-(3-furylmethyl)phenyl]amino}-7-[4-({[3-(4-morpholinyl)propyl]amino}methyl)phenyl]-3-quinolinecarbonitrile, 4-{[3-chloro-4-(3-furylmethyl)phenyl]amino}-7-[4-(1-piperidinylmethyl)phenyl]-3-quinolinecarbonitrile, 4-{[3-chloro-4-(3-furylmethyl)phenyl]amino}-7-{4-[(4-ethyl-1-piperazinyl)methyl]phenyl}-3-quinolinecarbonitrile, 4-[3-chloro-4-(3-furylmethyl)phenyl]amino}-7-(4-{[4-(2-hydroxyethyl)-1-piperazinyl]methyl}phenyl)-3-quinolinecarbonitrile, 4-{[4-(3-furylmethyl)phenyl]amino}-7-(4-{[(4-pyridinylmethyl)amino]methyl}phenyl)-3-quinolinecarbonitrile, 4-{[4-(3-furylmethyl)phenyl]amino}-7-[4-({[2-(1H-imidazol-4-yl)ethyl]amino}methyl)phenyl]-3-quinolinecarbonitrile, 4-{[4-(3-furylmethyl)phenyl]amino}-7-[4-(4-morpholinylmethyl)phenyl]-3-quinolinecarbonitrile, 4-{[4-(3-furylmethyl)phenyl]amino}-7-(4-{[(2-hydroxyethyl)amino]methyl}phenyl)-3-quinolinecarbonitrile, 4-{[4-(3-furylmethyl)phenyl]amino}-7-{4-[(4-methyl-1-piperazinyl)methyl]phenyl}-3-quinolinecarbonitrile, 4-{[4-(3-furylmethyl)phenyl]amino}-7-[4-(1-piperidinylmethyl)phenyl]-3-quinolinecarbonitrile, 7-{4-[(4-ethyl-1-piperazinyl)methyl]phenyl}-4-{[4-(3-furylmethyl)phenyl]amino}-3-quinolinecarbonitrile, 4-{[4-(3-furylmethyl)phenyl]amino}-7-(4-{[4-(2-hydroxyethyl)-1-piperazinyl]methyl}phenyl)-3-quinolinecarbonitrile, 4-{[4-(3-furylmethyl)phenyl]amino}-7-{3-[(4-hydroxy-1-piperidinyl)methyl]phenyl}-3-quinolinecarbonitrile, 7-[3-({[2-(dimethylamino)ethyl]amino}methyl)phenyl]-4-{[4-(3-furylmethyl)phenyl]amino}-3-quinolinecarbonitrile, 4-{[4-(3-furylmethyl)phenyl]amino}-7-(3-{[4-(1-pyrrolidinyl)-1-piperidinyl]methyl}phenyl)-3-quinolinecarbonitrile, 4-{[4-(3-furylmethyl)phenyl]amino}-7-(3-{[(4-pyridinylmethyl)amino]methyl}phenyl)-3-quinolinecarbonitrile, 4-{[4-(3-furylmethyl)phenyl]amino}-7-[3-({[2-(1H-imidazol-4-yl)ethyl]amino}methyl)phenyl]-3-quinolinecarbonitrile, 4-{[4-(3-furylmethyl)phenyl]amino}-7-[3-(4-morpholinylmethyl)phenyl]-3-quinolinecarbonitrile, 4-[4-(3-furylmethyl)phenyl]amino}-7-(3-{[(2-hydroxyethyl)amino]methyl}phenyl)-3-quinolinecarbonitrile, 4-{[4-(3-furylmethyl)phenyl]amino}-7-{3-[(4-methyl-1-piperazinyl)methyl]phenyl}-3-quinolinecarbonitrile, 4-{[4-(3-furylmethyl)phenyl]amino)-7-[3-({[3-(4-morpholinyl)propyl]amino}methyl)phenyl]-3-quinolinecarbonitrile, 7-{3-[(4-ethyl-1-piperazinyl)methyl]phenyl}-4-{[4-(3-furylmethyl)phenyl]amino}-3-quinolinecarbonitrile, 4-{[4-(3-furylmethyl)phenyl]amino}-7-(3-{[4-(2-hydroxyethyl)-1-piperazinyl]methyl}phenyl)-3-quinolinecarbonitrile, 4-{[4-(3-furylmethyl)phenyl]amino}-7-{5-[(4-hydroxy-1-piperidinyl)methyl]-2-pyridinyl}-3-quinolinecarbonitrile, 7-[5-({[2-(dimethylamino)ethyl]amino}methyl)-2-pyridinyl]-4-{[4-(3-furylmethyl)phenyl]amino}-3-quinolinecarbonitrile, 4-{[4-(3-furylmethyl)phenyl]amino}-7-{5-[(2-hydroxyethyl)amino]methyl}-2-pyridinyl)-3-quinolinecarbonitrile, 4-{[4-(3-furylmethyl)phenyl]amino}-7-[5-({[3-(4-morpholinyl)propyl]amino}methyl)-2-pyridinyl]-3-quinolinecarbonitrile, 4-{[4-(3-furylmethyl)phenyl]amino}-7-(5-{[4-(2-hydroxyethyl)-1-piperazinyl]methyl}-2-pyridinyl)-3-quinolinecarbonitrile, 4-{[4-(3-furylmethyl)phenyl]amino}-7-{5-[(4-hydroxy-1-piperidinyl)methyl]-3-thienyl}-3-quinolinecarbonitrile, 4-{[4-(3-furylmethyl)phenyl]amino}-7-(5-{[4-(1-pyrrolidinyl)-1-piperidinyl]methyl}-3-thienyl)-3-quinolinecarbonitrile, 4-{[4-(3-furylmethyl)phenyl]amino}-7-(5-{[(4-pyridinylmethyl)amino]methyl}-3-quinolinecarbonitrile, 4-{[4-(3-furylmethyl)phenyl]amino}-7-[5-(4-morpholinylmethyl)-3-thienyl]-3-quinolinecarbonitrile, 4-{[4-(3-furylmethyl)phenyl]amino}-7-(5-{[(2-hydroxyethyl)amino]methyl}-3-thienyl)-3-quinolinecarbonitrile, 4-{[4-(3-furylmethyl)phenyl]amino}-7-{5-[(4-methyl-1-piperazinyl)methyl]-3-thienyl}-3-quinolinecarbonitrile, 4-{[4-(3-furylmethyl)phenyl]amino}-7-[5-({[3-(4-morpholinyl)propyl]amino}methyl)-3-thienyl]-3-quinolinecarbonitrile, 4-{[4-(3-furylmethyl)phenyl]amino}-7-[5-(1-piperidinylmethyl)-3-thienyl]-3-quinolinecarbonitrile, 7-{5-[(4-ethyl-1-piperazinyl)methyl]-3-thienyl]-4-{[4-(3-furylmethyl)phenyl]amino}-3-quinolinecarbonitrile, 4-[4-(3-furylmethyl)phenyl]amino}-7-(5-{[4-(2-hydroxyethyl)-1-piperazinyl]methyl}-3-thienyl)-3-quinolinecarbonitrile, 4-(2,4-dichloro-5-methoxyanilino)-7-(4-{[4-(1-pyrrolidinyl)-1-piperidinyl]methyl}phenyl)-3-quinolinecarbonitrile, 4-(2,4-dichloro-5-methoxyanilino)-7-(4-{[(4-pyridinylmethyl)amino]methyl}phenyl)-3-quinolinecarbonitrile, 4-(2,4-dichloro-5-methoxyanilino)-7-[4-({[2-(1H-imidazol-4-yl)ethyl]amino}methyl)phenyl]-3-quinolinecarbonitrile, 4-(2,4-dichloro-5-methoxyanilino)-7-(4-{[(2-hydroxyethyl)amino]methyl}phenyl)-3-quinolinecarbonitrile, 4-(2,4-dichloro-5-methoxyanilino)-7-[4-({[3-(4-morpholinyl)propyl]amino}methyl)phenyl]-3-quinolinecarbonitrile, 4-(2,4-dichloro-5-methoxyanilino)-7-{5-[(4-hydroxy-1-piperidinyl)methyl]-2-furyl}-3-quinolinecarbonitrile, 4-(2,4-dichloro-5-methoxyanilino)-7-[5-({[2-(dimethylamino)ethyl]amino}methyl)-2-furyl]-3-quinolinecarbonitrile, 4-(2,4-dichloro-5-methoxyanilino)-7-(5-{[4-(1-pyrrolidinyl)-1-piperidinyl]methyl}2-furyl)-3-quinolinecarbonitrile, 4-(2,4-dichloro-5-methoxyanilino)-7-(5-{[(4-pyridinylmethyl)amino]methyl}-2-furyl)-3-quinolinecarbonitrile, 4-(2,4-dichloro-5-methoxyanilino)-7-[5-({[2-(1H-imidazol-4-yl)ethyl]amino}methyl)-2-furyl]-3-quinolinecarbonitrile, 4-(2,4-dichloro-5-methoxylanilino)-7-(5-{[(2-hydroxyethyl)amino]methyl}-2-furyl)-3-quinolinecarbonitrile, 4-(2,4-dichloro-51-methoxyanilino)-7-[5-({[3-(4-morpholinyl)propyl]amino}methyl)-2-furyl]-3-quinolinecarbonitrile, 4-(2,4-dichloro-5-methoxyanilino)-7-[5-(1-piperidinylmethyl)-2-furyl]-3-quinolinecarbonitrile, 4-(2,4-dichloro-5-methoxyanilino)-7-{5-[(4-ethyl-1-piperazinyl)methyl]-2-furyl}-3-quinolinecarbonitrile, 4-(2,4-dichloro-5-methoxyanilino)-7-(5-{[4-(1-pyrrolidinyl)-1-piperidinyl]methyl}2-thienyl)-3-quinolinecarbonitrile, 4-(2,4-dichloro-5-methoxyanilino)-7-{5-[(4-ethyl-1-piperazinyl)methyl]-2-thienyl}-3-quinolinecarbonitrile, 4-(2,4-dichloro-5-methoxyanilino)-7-(5-({[2-(dimethylamino)ethyl]amino}methyl)-3-thienyl]-3-quinolinecarbonitrile, 4-(2,4-dichloro-5-methoxyanilino)-7-(5-{[(4-pyridinylmethyl)amino]methyl}-3-thienyl)-3-quinolinecarbonitrile, 4-(2,4-dichloro-5-methoxyanilino)-7-[5-({[2-(1H-imidazol-4-yl)ethyl]amino}methyl)-3-thienyl]-3-quinolinecarbonitrile, 4-(2,4-dichloro-5-methoxyanilino)-7-{5-[(4-hydroxy-1-piperidinyl)methyl]-2-pyridinyl}-3-quinolinecarbonitrile, 4-(2,4-dichloro-5-methoxyanilino)-7-[5-({[2-(dimethylamino)ethyl]amino}methyl)-2-pyridinyl]-3-quinolinecarbonitrile, 4-(2,4-dichloro-5-methoxyanilino)-7-(5-{[4-(1-pyrrolidinyl)-1-piperidinyl]methyl}2-pyridinyl)-3-quinolinecarbonitrile, 4-(2,4-dichloro-5-methoxyanilino)-7-{5-[(2-hydroxyethyl)amino]methyl}-2-pyridinyl}-3-quinolinecarbonitrile, 4-(2,4-dichloro-5-methoxyanilino)-7-[5-({[3-(4-morpholinyl)propyl]amino}methyl)-2-pyridinyl]-3-quinolinecarbonitrile, 4-(2,4-dichloro-5-methoxyanilino)-7-[(5-{[4-(2-hydroxyethyl)-1-piperazinyl]methyl}-2-pyridinyl]-3-quinolinecarbonitrile, 7-{4-[(4-hydroxy-1-piperidinyl)methyl]phenyl}-4-(3,4,5-trimethoxyanilino)-3-quinolinecarbonitrile, 7-[4-(4-morpholinylmethyl)phenyl]-4-(3,4,5-trimethoxyanilino)-3-quinolinecarbonitrile, 7-(4-{[(2-hydroxyethyl)amino]methyl}phenyl)-4-(3,4,5-trimethoxyanilino)-3-quinolinecarbonitrile, 7-{4-[(4-methyl-1-piperazinyl)methyl]phenyl}-4-(3,4,5-trimethoxyanilino)-3-quinolinecarbonitrile, 7-[4-(1-piperidinylmethyl)phenyl]-4-(3,4,5-trimethoxyanilino)-3-quinolinecarbonitrile, 7-{4-[(4-ethyl-1-piperazinyl)methyl]phenyl}-4-(3,4,5-trimethoxyanilino)-3-quinolinecarbonitrile, 7-{3-[(4-hydroxy-1-piperidinyl)methyl]phenyl}-4-(3,4,5-trimethoxyanilino)-3-quinolinecarbonitrile, 7-[3-({[2-(dimethylamino)ethyl]amino}methyl)phenyl]-4-(3,4,5-trimethoxyanilino)-3-quinolinecarbonitrile, 7-(3-{[4-(1-pyrrolidinyl)-1-piperidinyl]methyl}phenyl)-4-(3,4,5-trimethoxyanilino)-3-quinolinecarbonitrile, 7-(3-{[(4-pyridinylmethyl)amino]methyl}phenyl)-4-(3,4,5-trimethoxyanilino)-3-quinolinecarbonitrile, 7-[3-({[2-(1H-imidazol-4-yl)ethyl]amino}methyl)phenyl]-4-(3,4,5-trimethoxyanilino)-3-quinolinecarbonitrile, 7-[3(4-morpholinylmethyl)phenyl]-4-(3,4,5-trimethoxyanilino)-3-quinolinecarbonitrile, 7-(3-{[(2-hydroxyethyl)amino]methyl}phenyl)-4-(3,4,5-trimethoxyanilino)-3-quinolinecarbonitrile, 7-{3-[(4-methyl-1-piperazinyl)methyl]phenyl}-4-(3,4,5-trimethoxyanilino)-3-quinolinecarbonitrile, 7-[3-({[3-(4-morpholinyl)propyl]amino}methyl)phenyl]-4-(3,4,5-trimethoxyanilino)-3-quinolinecarbonitrile, 7-[3-(1-piperidinylmethyl)phenyl]-4-(3,4,5-trimethoxyanilino)-3-quinolinecarbonitrile, 7-((3-{[4-(2-hydroxyethyl)-1-piperazinyl]methyl}phenyl)-4-(3,4,5-trimethoxyanilino)-3-quinolinecarbonitrile, 7-(5-{[4-(1-pyrrolidinyl)-1-piperidinyl]methyl}-2-furyl)-4-(3,4,5-trimethoxyanilino)-3-quinolinecarbonitrile, 7-{5-[(4-hydroxy-1-piperidinyl)methyl]-2-thienyl}-4-(3,4,5-trimethoxyanilino)-3-quinolinecarbonitrile, 7-[5-({[2-(1H-imidazol-4-yl)ethyl]amino}methyl)-2-thienyl]-4-(3,4,5-trimethoxyanilino)-3-quinolinecarbonitrile, 7-{5-[(4-methyl-1-piperazinyl)methyl]-2-thienyl}-4-(3,4,5-trimethoxyanilino)-3-quinolinecarbonitrile, 7-{5-[(4-ethyl-1-piperazinyl)methyl]-2-thienyl}-4-(3,4,5-trimethoxyanilino)-3-quinolinecarbonitrile, 7-(5-{[4-(2-hydroxyethyl)-1-piperazinyl]methyl}-2-thienyl)-4-(3,4,5-trimethoxyanilino)-3-quinolinecarbonitrile, 7-(5-{[(4-pyridinylmethyl)amino]methyl}-3-thienyl)-4-(3,4,5-trimethoxyanilino)-3-quinolinecarbonitrile, 7-[5-(4-morpholinylmethyl)-3-thienyl]-4-(3,4,5-trimethoxyanilino)-3-quinolinecarbonitrile, 7-(5-{[(2-hydroxyethyl)amino]methyl}-3-thienyl)-4-(3,4,5-trimethoxyanilino)-3-quinolinecarbonitrile, 7-{5-[(4-methyl-1-piperazinyl)methyl]-3-thienyl}-4-(3,4,5-trimethoxyanilino)-3-quinolinecarbonitrile, 7-{5-[(4-hydroxy-1-piperidinyl)methyl]-2-pyridinyl}-4-(3,4,5-trimethoxyanilino)-3-quinolinecarbonitrile, 7-(5-{[4-(1-pyrrolidinyl)-1-piperidinyl]methyl}-2-pyridinyl)-4-(3,4,5-trimethoxyanilino)-3-quinolinecarbonitrile, 7-(5-{[(2-hydroxyethyl)amino]methyl}-2-pyridinyl)-4-(3,4,5-trimethoxyanilino)-3-quinolinecarbonitrile, 7-[5-({[3-(4-morpholinyl)propyl]amino}methyl)-2-pyridinyl]-4-(3,4,5-trimethoxyanilino)-3-quinolinecarbonitrile, and 7-[(5-{[4-(2-hydroxyethyl)-1-piperazinyl]methyl})-2-pyridinyl]-4-(3,4,5trimethoxyanilino)-3-quinolinecarbonitrile, For the compounds of Formula (I) defined above and referred to herein, unless otherwise noted, the following terms are defined:

Halogen, as used herein means chloro, fluoro, bromo and iodo.

Alkyl as used herein means a branched or straight chain having from 1 to 12 carbon atoms and more preferably from 1 to 6 carbon atoms. Exemplary alkyl groups include methyl, ethyl, propyl, isopropyl, butyl, isobultyl, t-butyl, pentyl and hexyl optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialklylamino, thioalkyl, alkoxycarbonyl and acyl.

Alkenyl as used herein means a branched or straight chain having from 2 to 12 carbon atoms and more preferably from 2 to 6 carbon atoms, the chain containing at least one carbon-carbon double bond and all possible configurational isomers. Alkenyl, may be used synonymously with the term olefin and includes alkylidenes. Exemplary alkenyl groups include ethenyl, propenyl, 1,4-butadienyl, 3-hexen-1-yl and the like optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

An alkynyl group is defined as straight or branched carbon chain of 2 to 6 carbon atoms that contains at least one carbon-carbon triple bond and includes propynyl and the like optionally substituted with phenyl, phenyl optionally substituted with one or more substituents preferably from one to three substituents independently selected from alkyl, alkoxy, perhaloalkyl, halogen, nitro, hydroxy, amino, carboxy, carboxyalkyl, alkylamino and dialkylamino, thioalkyl, alkoxycarbonyl and acyl.

Alkoxy as used herein means an alkyl-O— group in which the alkyl group is as previously described. Exemplary alkoxy groups include methoxy, methoxy, n-propoxy, i-propoxy, n-butoxy, t-butoxy and polyethers including —O—$(CH_2)_2OCH_3$.

Cycloalkyl as used herein means a simple carbocycle having a saturated ring having from 3 to 10 carbon atoms and more preferably from 3 to 6 carbon atoms optionally substituted with 1 to 3 independently selected alkyl groups of 1 to 12 carbon atoms. Exemplary cycloalkyl rings include cyclopropyl, cyclobutyl, cyclopentyl, cyclohexyl and adamantyl and the like.

Aryl is used herein means a mono or bicyclic aromatic ring having from 6 to 12 carbon atoms. Monocyclic rings preferably have 6 members and bicyclic rings preferably have 8, 9, 10 or 12 membered ring structures. Exemplary aryl groups include phenyl, alpha-naphithyl, beta-naphthyl, indene, and the like independently substituted with one or more substituents and more preferably with 1 to 4 substituents.

Heteroaryl denotes an unsubstituted or optionally substituted monocyclic 5 or 6 membered ring, which contains 1 to 4, or particularly 1 or 2 heteroatoms which may be the same or different. Nitrogen, oxygen and sulfur are the preferred heteroatoms, provided that the heteroaryl does not contain O—O, S—S or S—O bonds. Specific examples include thiophene, furan, pyrrol, pyrazole, imidazole, 1,2,3-triazole, 1,2,4-triazole, tetrazole, thiazole, oxazole, isothiazole, isoxazole, 1,3,4-oxadiazole, 1,2,4-oxadiazole, 1,3,4-thiadiazole, pyridine, pyrimidine, pyrazine, pyridazine and 1,3,5-triazine. The heteroaryl ring may be oxidized when a heteroatom is a nitrogen atom to provide the corresponding N-oxide, including pyridine-N-oxide. The heteroaryl ring may be oxidized on a sulfur atom to provide the corresponding sulfoxide or sulfone, including thiophene-1-oxide. The heterocyclic ring may contain a carbonyl group on one of the carbon atoms, such as 1,3,4-oxadiazol-2-one.

Bicyclic heteroaryl as used herein refers to saturated or partially unsaturated bicyclic fused rings having 8 to 20 ring atoms containing 1 to 4 heteroatoms which may be the same or different independently selected from nitrogen, oxygen and sulfur optionally substituted with 1 to 3 independently selected substituents which may be the same or different provided that the bicyclic heteroaryl does not contain O—O, S—S or S—O bonds. Specific examples include: indole, 2,3-dihydroindole, 2-indazole, isoindazole, quinoline, isoquinoline, tetrahydroquinoline, benzofuran, benzothiophene, benzimidazole, benzotriazole, benzothiazole, benzoxazole, benzisoxazole, 1,2-benzopyran, cinnoline, phthalazine, quinazoline, 1,8-naphthyridine, pyrido[3,2-b]pyridine, pyrido[3,4-b]pyridine, pyrido[4,3-b]pyridine, pyrido[2,3-d]pyrimidine, purine, and ptenidine and the like. Either or both rings of the bicyclic ring system may be partially saturated, or fully saturated. The bicyclic group may be oxidized on a nitrogen atom to provide the corresponding N-oxide, such as quinoline-N-oxide. The bicyclic group may be oxidized on a sulfur atom to provide the corresponding sulfoxide or sulfone, such as benzothiophene-1-oxide. The bicyclic ring system may contain a carbonyl group on one of the carbon atoms, such as 2-indanone.

Heterocyclyl means a saturated or partially unsaturated monocyclic radical containing preferably 3 to 8 ring atoms, more preferably 3 to 7 ring atoms and most preferably 5 to 6 ring atoms selected from carbon, nitrogen, oxygen and sulfur with at least 1 and preferably 1 to 4, more preferably 1 to 2 nitrogen, oxygen or sulfur as ring atoms. Specific examples include but are not limited to morpholine, thiomorpholine, thiomorpholine-S-oxide, thiomorpholine-S,S-dioxide, piperidine, piperazine, pyrrolidine, aziridine, oxirane, tetrahydrothiophene, tetrahydrofuran, 1,2-pyran, 1,4-pyran, dioxane, 1,3-dioxolane and tetralhydropyran. The heterocyclyl ring may be oxidized on a tri-substituted nitrogen atom to provide the corresponding N-oxide, such as N-ethylpiperazine-N-oxide, or the heterocyclyl ring may contain a carbonyl group on one of the carbon atoms, such as pyrrolidinone.

Thioalkyl as used herein means an alkyl-S— group in which the alkyl group is as previously described. Thioalkyl groups include thiomethyl and the like.

A carboxy group is defined as —C(O)OH, and an alkoxycarbonyl group is defined as —C(O)OR where R is alkyl of 1 to 6 carbon atoms and includes methoxycarbonyl, allyloxycarbonyl and the like.

Carboxyalkyl is defined as HOOC-alkyl of 1 to 12 carbon atoms.

Alkylamino is defined as a nitrogen atom substituted with an alkyl of 1 to 12 carbon atoms.

Dialkylamino is defined as a nitrogen atom disubstituted with an alkyl of 1 to 12 carbon atoms.

An acyl group is defined as a group —C(O)R where R is an alkyl or aryl radical and includes acetyl, trifluoroacetyl, benzoyl and the like.

Phenyl as used herein refers to a 6-membered aromatic ring.

Where terms are used in combination, the definition for each individual part of the combination applies unless defined otherwise. For instance, perhaloalkyl refers to an alkyl group, as defined above and perhalo refers to all hydrogen atoms on the alkyl group being substituted with a halogen as define above. An example is trifluoromethyl.

Some of the compounds of the invention have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diasteieomeric mixture of isomers. The absolute configuration of any compound may be determined by conventional X-ray crystallography. Optically active isomers may be prepared, for example, by resolving racemic derivatives or by asymmetric synthesis. The resolution can be carried out by the methods known to those skilled in the art such as in the presence of a resolving agent, by chromatography, or combinations thereof.

The compounds of Formula (I) may be obtained as inorganic or organic salts using methods known to those skilled in the art (Richard C. Larock, Comprehensive Organic Transformations, VCH publishers 411–415, 1989). It is well known to one skilled in the art that an appropriate salt form is chosen based on physical and chemical stability, flowability, hydroscopicity and solubility.

Pharmaceutically acceptable salts of the compounds of Formula (I) with an acidic moiety may be formed from organic and inorganic bases. For example with alkali metals or alkaline earth metals such as sodium, potassium, lithium, calcium, or magnesium or organic bases and N-tetraalkylammonium salts such as N-tetrabutylammonium salts. Similarly, when a compound of this invention contains a basic moiety, salts may be formed from organic and inorganic acids. For example salts may be formed from acetic, propionic, lactic, citic, tartaric, succinic, fumaric, maleic, malonic, mandelic, malic, phthalic, hydrochloric, hydrobromic, phosphoric, nitric, sulfuric, methanesulfonic, naphthialenesulfonic, benzenesulfonlic, toluenesulfonic, camphorsulfonic, and similarly known acceptable acids. The compounds can also be used in the form of esters, carbamates and other conventional prodrug forms, which when administered in such form, convert to the active moiety in vivo.

The present invention accordingly provides a pharmaceutical composition which comprises a compound of this invention in combination or association with a pharmaceutically acceptable carrier. In particular, the present invention provides a pharmaceutical composition which comprises an effective amount of a compound of this invention and a pharmaceutically acceptable carrier.

The compounds of this invention are certain substituted 3-cyanoquinolines, 3-cyano-1,6-naphthyridine and 3-cyano-1,7-naphthyridine containing compounds.

The quinoline, 1,6-nphthyridine and 1,7-naphthyridine ring systems will be numbered as indicated in the formulae:

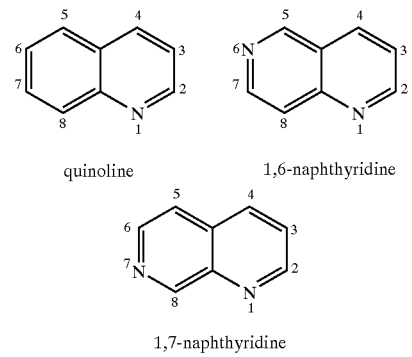

quinoline      1,6-naphthyridine 1,7-naphthyridine

In addition to the utilities, described herein some of the compounds of this invention are intermediates useful for the preparation of other compounds of this invention.

DESCRIPTION OF THE PREFERRED EMBODIMENTS

The compounds of this invention may be prepared from: (a) commercially available starting materials (b) known starting materials which may be prepared as described in literature procedures or (c) new intermediates described in the schemes and experimental procedures herein.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps. Appropriate consideration must be made as to the protection of reactive functional groups to prevent undesired side reactions. For example, it may be necessary to protect primary or secondary amino or hydroxyl groups. Suitable protecting groups include, but are not limited to, tert-butoxycarbonyl (BOC), trimethylsilylethanesulfonamide (SES), benzyloxycarbonyl (CBZ) and benzyl (Bn) protecting groups. The BOC protecting group may be removed by treatment with in acid such as trifluoroacetic acid or concentrated hydrochloric acid and the SES protecting group may be removed with a fluoride salt, such as cesium fluoride or tetrabutylammonium fluoride. The CBZ and Bn protection groups may be removed by catalytic hydrogenation. Additional suitable protecting groups for hydroxy substituents include, but are not limited to, t-butyldimethylsilyl (TBDMS), tetrahydropyranyl (THP), or isopropyl (i-Pr) protecting groups. The TBDMS and THP protecting groups may be removed by treatment with an acid such as acetic acid or hydrochloric acid while the i-Pr protecting group may be removed by aluminum trichloride.

Substituents on the starting materials may be incompatible with some of the reaction conditions. Such restrictions to the substituents which are compatible with the reaction conditions will be apparent to one skilled in the salt. Reactions were run under inert atmospheres where appropriate.

The preparation of the compounds and intermediates of this invention encompassed by Formula (I) is described as follows where key intermediates for the preparation of compounds of Formula (I) are compounds of Formulae (II), (III), and (IV) wherein LG is attached to a carbon atom and designates a leaving group preferably Br, I or OTf where OTf designates a trifluoromethanesulfonate (triflate) group.

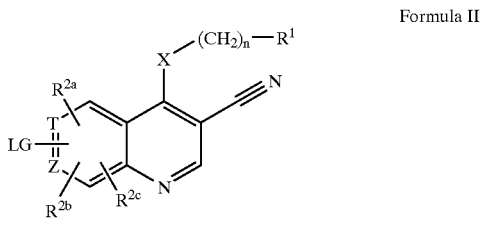

Formula II

T and Z are carbon

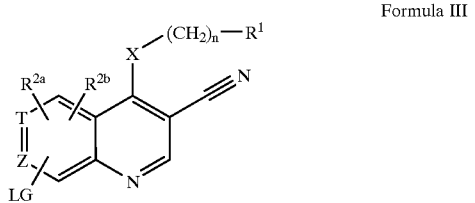

Formula III

T is nitrogen
Z is carbon

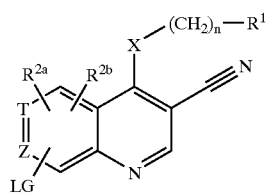

Formula IV

T is carbon
Z is nitrogen

As shown in Scheme 1, a 3-bromoaniline 1 where T and Z are carbon atoms and $R^{2a}$, $R^{2b}$ and $R^{2c}$ are hereinbefore defined and LG is bromo and ethyl(ethoxymethylene)cyano acetate 2 may be heated at temperatures ranging from 60 to 120° C. either neat or in an inert solvent which includes toluene and the like followed by cyclization in a 3:1 mixture of diphenyl ether and biphenyl at an optimal temperature of 260° C. to provide a mixture of isomers 7-bromo-4-oxo-1,4-dihydroquinoline-3-carbonitrile 3a and 5-bromo-4-oxo-1,4-dihydroquinoline-3-carbonitrile 3b. The isomers may be separated by either recrystallization or chromatography. Heating of 7-bromo-4-oxo-1,4-dihydroquinoline-3-cabonitrile 3a with a chlorinating reagent selected from phosphorus oxychloride and oxalyl chloride either neat or in an inert solvent which includes methylene chloride, provides the corresponding 7-bromo-4-chloro-3-cyanoquinoline 4 where T and Z are carbon atoms and $R^{2a}$, $R^{2b}$ and $R^{2c}$ are hereinbefore defined and LG is bromo. Reaction of 7-bromo-4-chloro-3-cyanoquinoline 4 with an aniline, phenol, thiophenol, amine, alcohol or thiol reagent 5 having the formula $HX-(CH_2)_n-R^1$, wherein $R^1$, X and n are hereinbefore defined, gives the 3-cyanoquinolines of Formula (II) where the leaving group LG may be bromo, where T and Z are carbon atoms, X, $R^1$, $R^{2a}$, $R^{2b}$ and $R^{2c}$ are hereinbefore defined. The condensation may be accelerated by heating the reaction mixture together with a catalytic amount or one equivalent of pyridime hydrochloride or by using organic bases selected from triethylamine, 4-dimethylaminopyridine, and diazabicyclo[5.4.0]undec-7-ene and the like or sodium hydride in an inert solvent, which includes tetrahydrofuan and the like or sodium or potassium alkoxides in the absence of solvent or in an inert solvent.

SCHEME 1

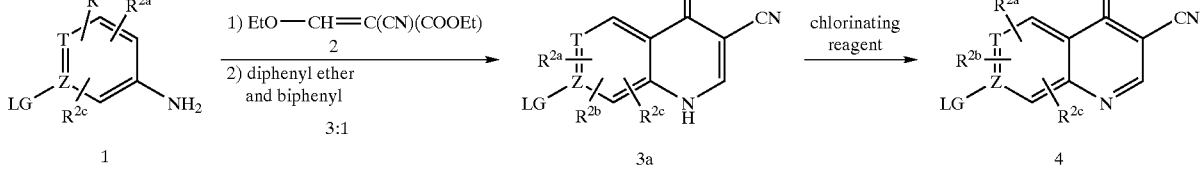

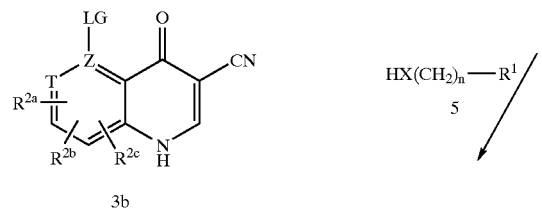

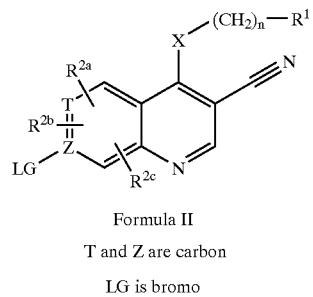

Formula II
T and Z are carbon
LG is bromo

The reaction sequence shown in Scheme 1 may be modified by substitution of 3-iodoaniline for 3-bromoaniline 1, where the LG may be iodo in place of bromo with the resulting compounds of Formula (II) now containing a 7-iodo group.

before defined, which when reacted with an aniline, phenol, thiophenol, amine, alcohol or thiol reagent 5 of the formula HX—$(CH_2)_n$—$R^1$, wherein $R^1$, X and n are as previously defined, gives the 3-cyanoquinolines of Formula (II) where the leaving group LG may be bromo.

SCHEME 2

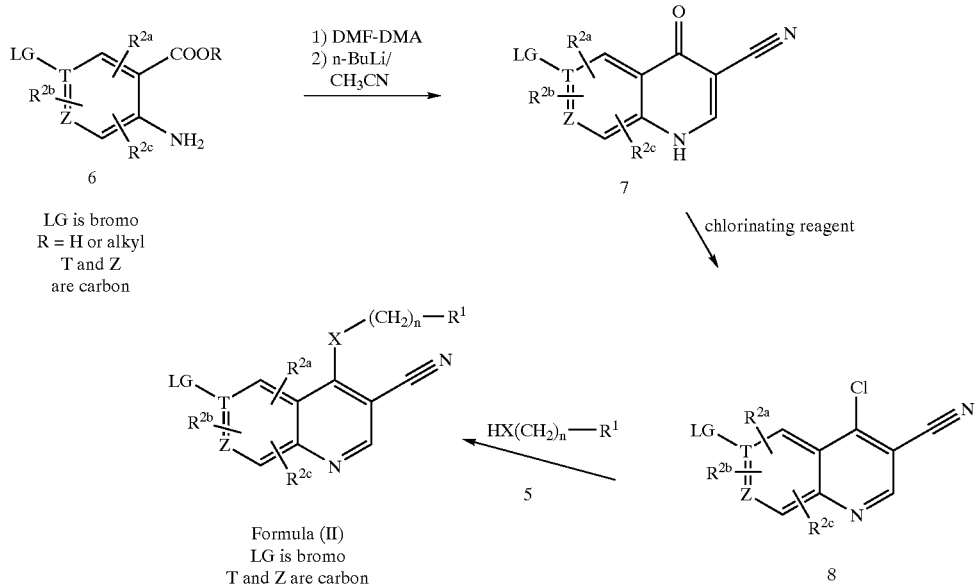

Scheme 2 shows an alternate route for the preparation of compounds of Formula (II). Reaction of 5-bromoanthranilic acid or ester 6 where T and Z are carbon atoms and $R^{2a}$, $R^{2b}$ and $R^c$ are hereinbefore defined with N,N'-dimethylformamide dimethyl acetal (DMF-DMA), in the presence or absence of a co-solvent selected from dimethylformamide and toluene gives the corresponding intermediate amidine which may be further reacted with the lithium anion of acetonitrile prepared by using a base which includes n-butyllithium, lithium di-isopropylamine, or the like in an inert solvent, preferably tetrahydrofuran, to give 6-bromo-4-oxo-1,4-dihydroquinoline-3-carbonitrile 7. Heating 6-bromo-4-oxo-1,4-dihydroquinoline-3-carbonitrile 7 with a chlorinating reagent selected from phosphorus oxychloride and oxalyl chloride either neat or in a solvent such as methylene chloride, provides the corresponding 6-bromo-4-chloro-3-cyanoquinoline 8 where T and Z are carbon atoms and $R^{2a}$, $R^{2b}$ and $R^{2c}$ are herein- Alternatively compounds of Formulae (II), (III) or (IV) containing a triflate (-OTf) leaving group may be prepared as shown in Scheme 3. The phenolic group of an ester of formula 9 where T and Z are carbon atoms and $R^{2a}$, $R^{2b}$ and $R^{2c}$ are hereinbefore defined is protected with a benzyl group and subsequent nitration provides the 2-nitro derivative 10. Removal of the benzyl group, formation of the triflate and reduction of the nitro group provides the aniline 11 where T and Z are carbon atoms and $R^{2a}$, $R^{2b}$ and $R^{2c}$ are hereinbefore declined. Further reaction of aniline 11 with N,N'-dimethylformamide dimethyl acetal (DMF-DMA), in the presence or absence of a co-solvent selected from toluene and N,N-dimethylformamide, gives the corresponding intermediate amidine which is further reacted with the lithium anion of acetonitrile prepared by using a base which includes n-butyllithium, lithium di-isopropylamine, or the like in an inert solvent, preferably tetrahydrofuran, to give quinoline-3-carbonitrile 12. Heating quinoline-3-carbonitrile 12 with a chlorinating reagent selected from phosphorus oxychloride and oxalyl chloride either neat or in it solvent such as methylene chloride, provides the corresponding 4-chloro-3-cyanoquinoline 13 where T and Z are carbon atoms and $R^{2a}$, $R^{2b}$ and $R^{2c}$ are hereinbefore defined, which when reacted with an aniline, phenol, thiophenol, amine, alcohol or thiol reagent 5 of the formula HX—$(CH_2)_n$—$R^1$, wherein $R^1$, X and n are as previously defined, gives the 3-cyanoquinolines of Formula (II) where the leaving group LG is -OTf where T and Z are carbon atoms and $R^{2a}$, $R^{2b}$ and $R^{2c}$ are hereinbefore defined.

by nitration to afford a 2-bromo-4-nitro-pyridine-N-oxide which following subsequent reduction using iron in the presence of ammonium chloride provides a 4-amino-2-bromopyridine 16. Using conditions analogous to those in Scheme 1, a 4-amino-2-bromopyridine 16 and ethyl (ethoxymethylene)cyano acetate 2 are heated at temperatures ranging from 60 to 120° C. either neat or in an inert solvent which includes toluene and the like followed by cyclization in a 3:1 mixture of diphenyl ether and biphenyl

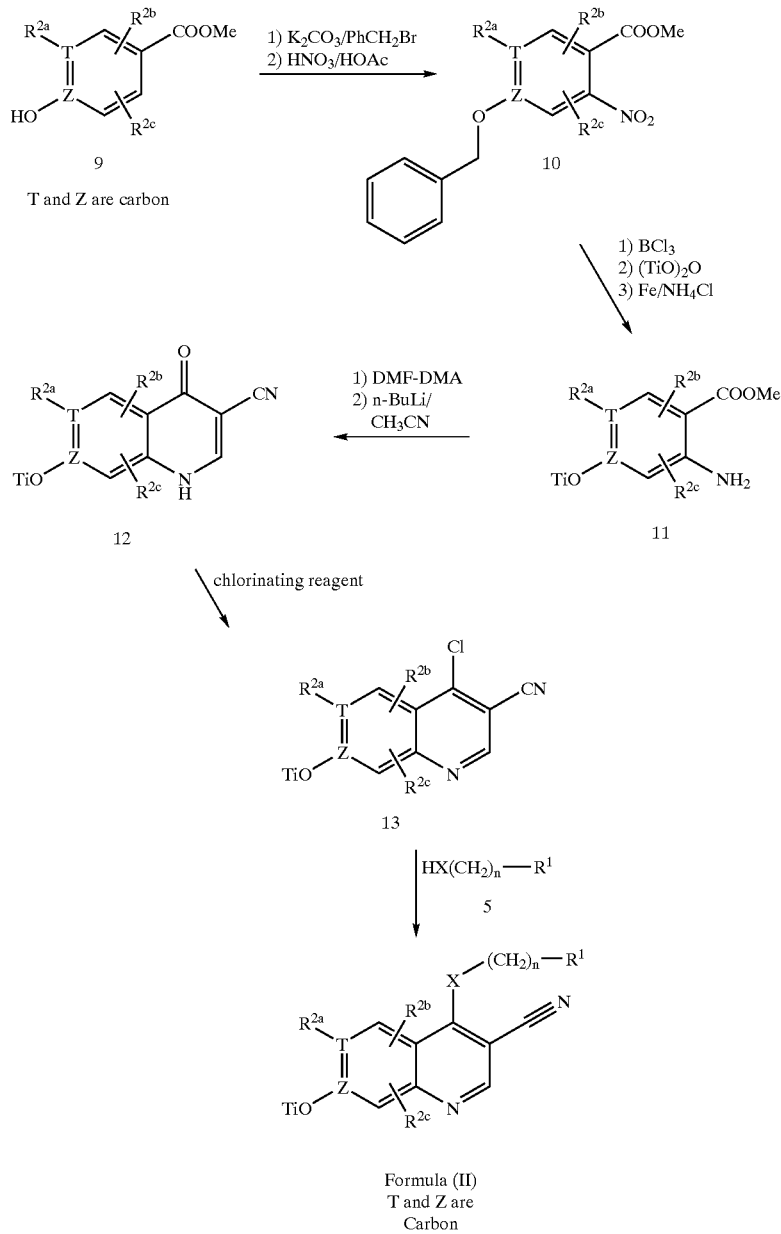

SCHEME 3

Formula (II)
T and Z are Carbon

The compounds of Formulae (III) and (IV) may be prepared by routes analogous to those shown in Schemes 1–3. As shown in Scheme 4 oxidation of a 2-bromopyridine 14, where T is a nitrogen atom, Z is a carbon atom, $R^{2a}$, $R^{2b}$ are hereinbefore defined and $R^{2c}$ is absent and LG is bromo, using m-chloroperbenzoic acid forms the N-oxide followed at an optimal temperature of 260° C. to provide a 7-bromo-4-oxo-1,4,-dihydro-1,6-naphthyridine-3-carbonitrile 17 where T is a nitrogen atom, Z is a carbon atom, $R^{2a}$ and $R^{2b}$ are hereinbefore defined. Heating of a 7-bromo-4-oxo-1,4-dihydro-1,6-naphthyridine-3-carbonitrile 17 with a chlorinating agent selected from phosphorus oxychloride and oxalyl chloride either neat or in a solvent such as methylene chloride, provides the corresponding 7-bromo-4-chloro-1,6-naphthyridine-3-carbonitrile 18. Reaction of a 7-bromo-4-chloro-1,6-naphthyridine-3-carbonitrile 18 with an aniline, phenol, thiophenol, amine, alcohol or thiol reagent 5 of the formula HX—$(CH_2)_n$—$R^1$, wherein $R^1$, X and n are as previously defined, gives the 3-cyano-1,6-naphthyridines of Formula (III) where the leaving group LG is bromo and where T is a nitrogen atom, Z is a carbon atom, $R^{2a}$, $R^{2b}$, X, $R^1$ and n are hereinbefore defined.

organolithium may then be treated with an organoboron reagent of formula $Q^1$—$BL^1L^2$ 22 where $Q^1$ is defined as a leaving group selected from alkoxy and the like to provide compounds of formula $R^4$—A—$R^3$—$BL^1L^2$ 19. Organoboron reagents of formula $Q^1$—$BL^1L^2$ 9 include alkyl borates including tri-isopropyl borate, wherein one of the tri-isopropyl groups functions as the leaving group $Q^1$. Suitable $L^1$ and $L^2$ groups are independently hydroxy, alkyl of 1 to 12 carbon atoms or alkoxy of 1 to 12 carbon atoms. In addition, the ligands $L^1L^2$ may be taken together with the

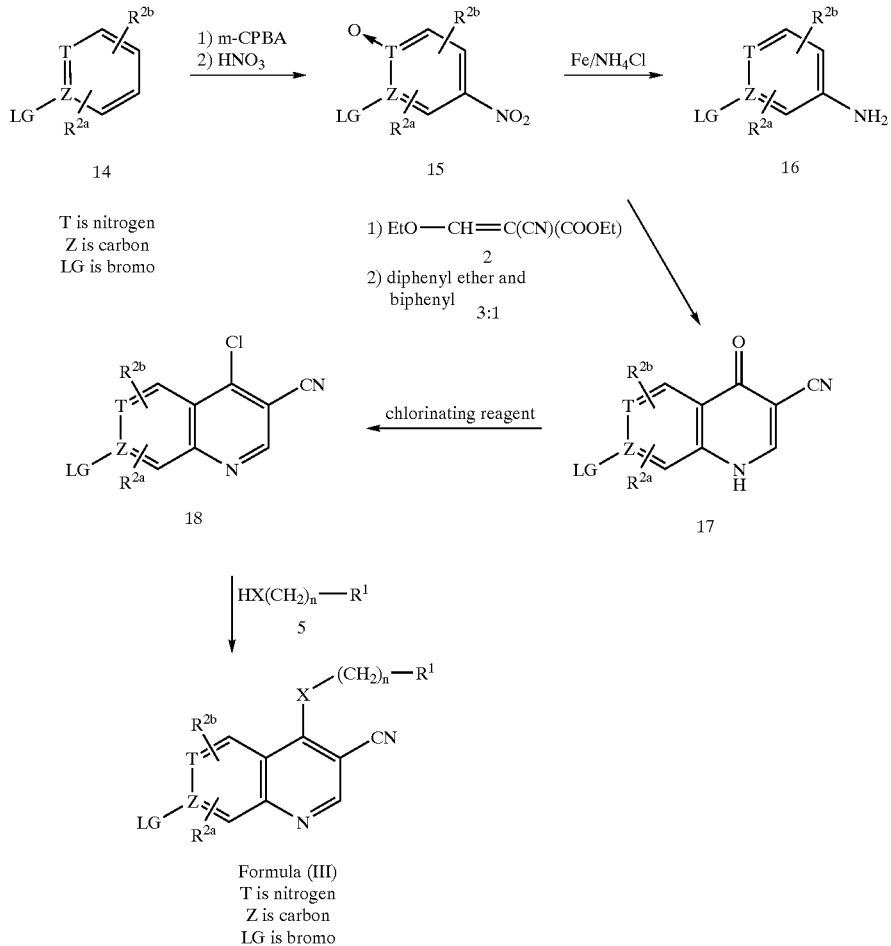

SCHEME 4

Compounds of Formulae (II), (III) and (IV) may be converted to compounds of Formula (I) of the invention by replacement of the leaving group (LG) of Formulae (II), (III) and (IV) with organometallic reagents and formation of a carbon-carbon bond. The organometallic reagents, which are organoboron and organotin reagents may be prepared as shown in Scheme 5.

Organoboron reagents of formula $R^4$—A—$R^3$—$BL^1L^2$ 19, wherein $R^3$ is aryl, heteroaryl, and bicyclic heteroaryl, $L^1$ and $L^2$ are suitable ligands independently selected from alkoxy, alkyl and hydroxy and readily obtained by standard procedures, (R. D. Larsenl, Current Opinoion Drug Discovery and Development, 2, No. 6, 651–667(1999). Compounds of formula $R^4$—A—$R^3$—H 20 or $R^4$—A—$R^3$—Br 21 may be converted to the corresponding in organolithium by treatment with a lithium base which include n-BuLi. The boron to which they are attached to form a cyclic boron ester, where $L^1L^2$ may be oxyethyleneoxy and the like. Alternatively a compound of formula $R^4$—A—$R^3$—Br 21 may be treated with an organoboron compound such as bis(pinacolato)diboron and the like in the presence of potassium acetate and a palladium catalyst including [1,1'-bis(diphenylphosphino)ferrocene]dichloropalladium(II) complex with dichloromethane in a solvent selected from dimethyl sulfoxide, N,N-dimethylformamide (DMF), and dioxane and the like to provide the organoboron compound of formula $R^4$—A—$R^3$—$BL^1L^2$ 19.

Organotin reagents of formula $R^4$—A—$R^3$—$SnR_3$ 24 may be readily obtained by standard procedures. Compounds of formula $R^4$—A—$R^3$—H 20 or $R^4$—A—$R^3$—Br 21 may be converted to the corresponding organolithium compound by treatment with a lithium base which includes n-BuLi. The organolithium compound may then be treated with an organotin compound of formula $Q^1$—$SnR_3$ 23 which include tri-n-butylstannyl chloride where $Q^1$ is a chloro leaving group to afford organotin reagents of formula $R^4$—A—$R^3$—$SnR_3$ 24. Organoboron reagents of formula 19 and organotin reagant of formula 24 may be generated in situ and used without purification.

SCHEME 5

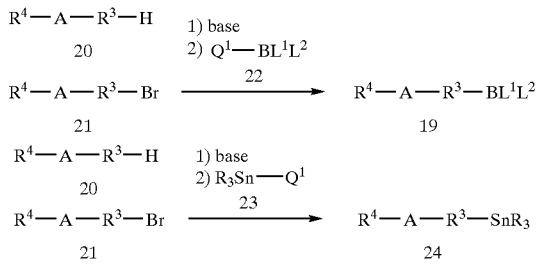

Scheme 6 shows a route for the preparation of compounds of Formula (I) from the reaction of compounds of Formulae (II), (III) and (IV) in a solvent selected from tetrahydrofuran, dioxane, and ethylene glycol dimethyl ether and the like at temperatures preferably 60 to 150° C. with reagents $R^4$—A—$R^3$—$BL^1L^2$ 19 or $R^4$—A—$R^3$—$SnR_3$ 24 in the presence of catalysts which include tetrakis(triphenylphosphine)palladium(0), palladium(II)chloride, nickel(II)bromide and the like, where A, $R^3$ and $R^4$ are hereinbefore defined.

SCHEME 6

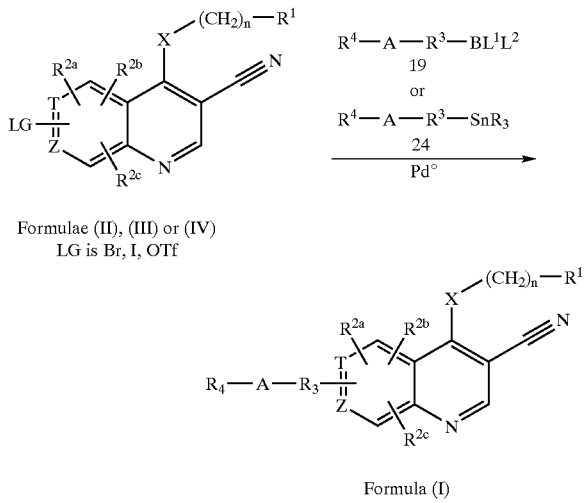

Specifically as shown in Scheme 7 compounds of Formula (I) wherein $R^3$ is an alkene may be prepared via reaction of compounds of formula $R^4$—A—CH=$CH_2$ 25 with compounds of Formula (II), (III) or (IV) in the presence of triphenylphosphine and a palladium catalyst, which include palladium acetate. Preferred solvents include trialkylamines such as triethylamine, or alternatively N,N-dimethylformamide with an equivalent of a base which include sodium bicarbonate. Similarly, compounds of Formula (I) wherein $R^3$ is an alkyne group may be obtained by reaction of compounds of formula $R^4$—A—C≡CH 26 with compounds of Formula (II), (III) or (IV) in the presence of triphenylphosphine, copper(I)iodide and a palladium catalyst, which include dichloro bis(triphenylphosphine)palladium(I).

SCHEME 7

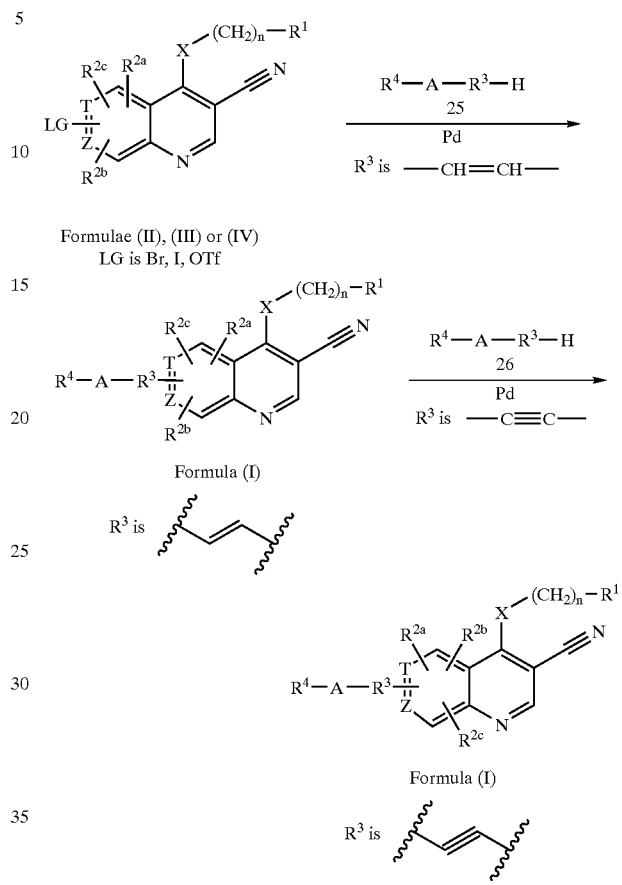

As shown in Scheme 8, an alternate route to some compounds of Formula (I) involves reaction of compounds of Formulae (II), (III) and (IV) with a stannane reagent 27 where $R^3$ is an aryl, heteroaryl, or bicyclic heteroaryl which include 2-(tributylstannyl)-5-(1,3-dioxolan-2-yl)furan, 2-(1,3-dioxolan-2-yl)-1-methyl-5-(tributylatannyl)imidazole. The stannane reagent 27 may be reacted with compounds of Formulae (II), (III) and (IV) in an inert solvent which includes tetrahydrofuran or dioxane and the like in the presence of a palladium catalyst such as bis(triphenylphosphine)palladium(II)chloride or 1,4-bis(diphenylphosphino)butane palladium(II)chloride to afford an acetal 29. The acetal protecting group may be removed by acid hydrolysis, preferably using aqueous hydrochloric acid with a cosolvent such as tetrahydrofuran, to give the aldehyde 29. Alternatively the aldehyde 29 may be obtained directly by reaction of compounds of Formulae (II), (III) and (IV) with a boronic acid reagent 30 where $R^3$ is aryl, heteroaryl and bicyclic heteroaryl which include 4-formylphenyl boronic acid and the like, to also give aldehyde 29. The boronic acid reagent 30 may be reacted with compounds of Formulae (II), (III) and (IV) in a solvent selected from tetrahydrofuran and dioxane in the presence of a palladium catalyst which includes bis(triphenylphosphine)palladium(II)chloride or 1,4-bis(diphenylphosphino)butane palladium(II)chloride. Aldehyde 29 may be treated with an amine 31 of formula $HNR^{13}R^{14}$, in a solvent selected from methylene chloride, dioxane and tetrahydrofuan, in the presence of a reducing agent such as sodium triacetoxyborohydride or sodium cyanoborohydride with the optional addition of a catalyst which includes acetic acid and the like.

SCHEME 8

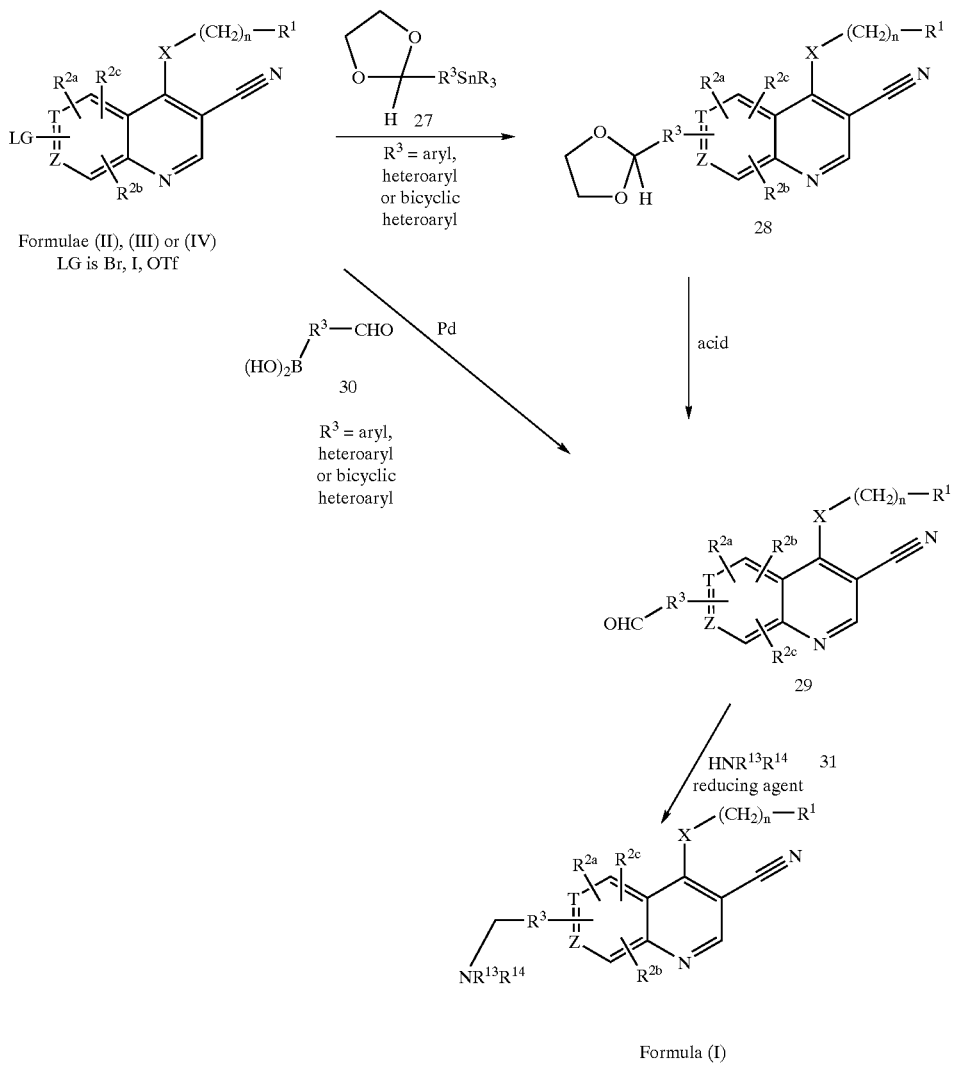

Alternatively compounds of the invention may be prepared by the routes shown in Schemes 9 and 10 where the olganotin reagent $R^4$—A—$R^3$—$SnR_3$ 24 or organoboron reagent $R^4$—A—$R^3$—$BL^1L^2$ 19, may be coupled to cyano compound 32 where T, Z, $R^{2a}$, $R^{2b}$ and $R^{2c}$ are hereinbefore defined to give intermediate 33 which may then be converted to the 4-chloro intermediate 34 by reaction with a chlorinating reagent selected from phosphorous oxychloride, oxalyl chloride and polymer supported triphenylphosphine and carbon tetrachloride, which when reacted with an aniline, phenol, thiophenol, amine, alcohol or thiol reagent 5 of the formula HX—$(CH_2)_n$—$R^1$, wherein $R^1$, X and n are as previously defined, gives compounds of Formula, (I) of the invention

SCHEME 9

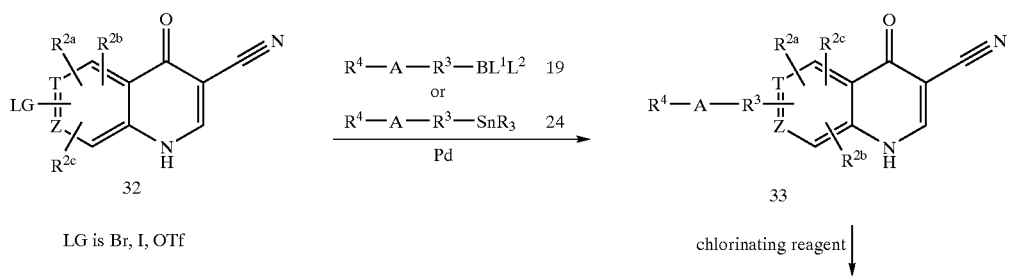

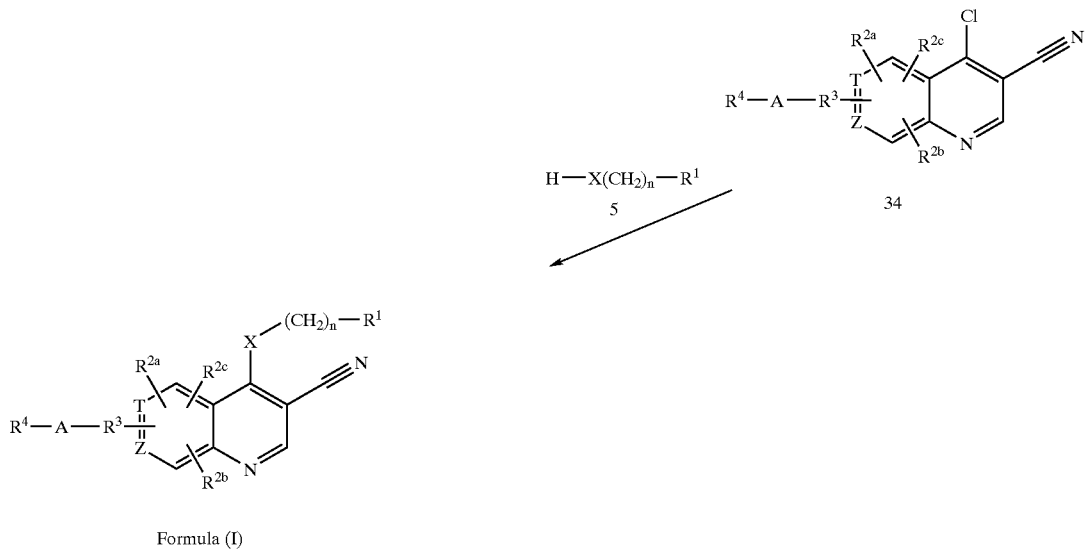

Formula (I)

Referring to Scheme 10, compounds of the formula $R^4$—A—CH=$CH_2$ 25 coupled to cyano compound 32 where T, Z, $R^{2a}$, $R^{2b}$ and $R^{2c}$ are hereinbefore defined give intermediate 35 which may then be converted to the 4-chloro intermediate 36 by reaction with a chlorinating reagent selected from phosphorous oxychloride, oxalyl chloride and polymer supported triphenylphosphine and carbon tetrachloride, which when reacted with an aniline, phenol, thiophenol, amine, alcohol or thiol reagent 5 of the formula HX—$(CH_2)_n$—$R^1$, wherein $R^1$, X and n are as previously defined, to give compounds of Formula (I).

SCHEME 10

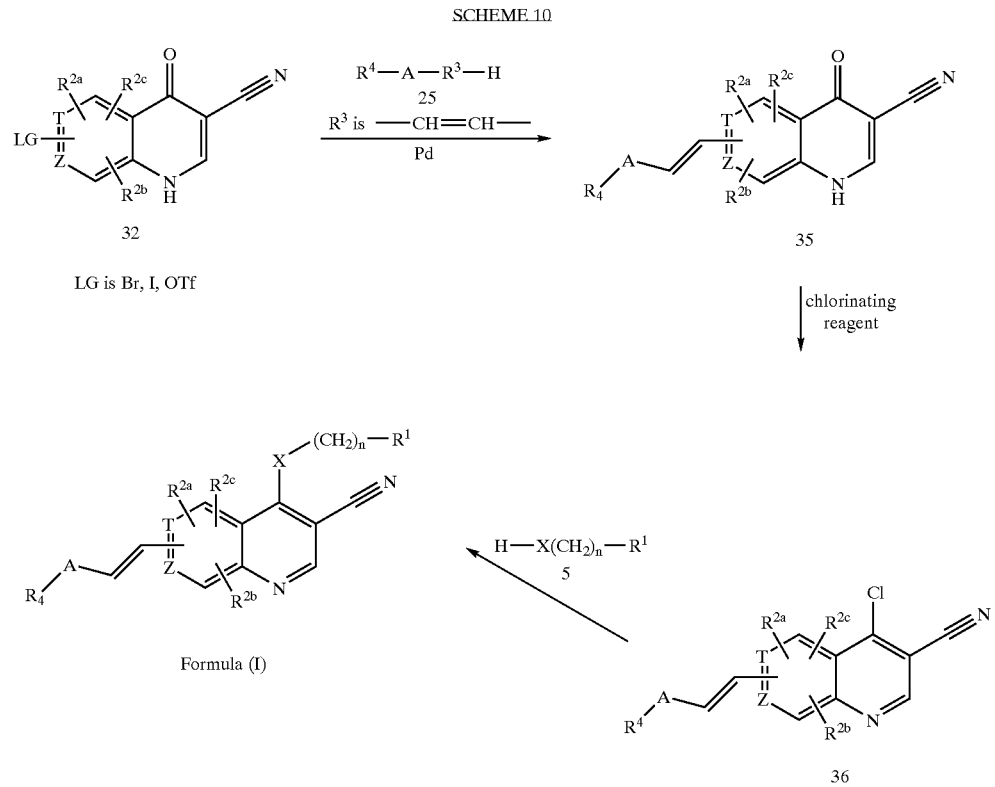

Additional key intermediates for the preparation of compounds of Formula (I) are compounds of Formulae (V), (VI), and (VII), when in the primary amino group is attached to a carbon atom.

Formula V

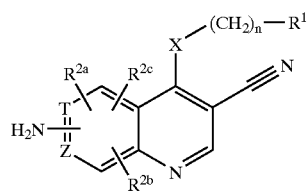

T and Z are carbon

Formula VI

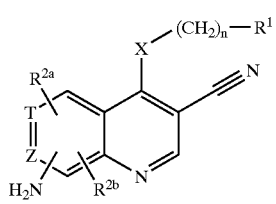

T is nitrogen
Z is carbon

Formula VII

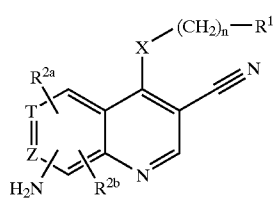

T is carbon
Z is nitrogen

Compounds of Formula (V) where T and Z are carbon atoms and $R^{2a}$, $R^{2b}$ and $R^{2c}$ are hereinbefore defined may be prepared as shown in Scheme 11. A 3-nitroaniline 37 where $R^{2a}$, $R^{2b}$ and $R^{2c}$ are hereinbefore defined and ethyl (ethoxymethylene)cyano acetate 2 are heated at temperatures ranging from 60 to 190° C. either neat or in a solvent such as toluene followed by cyclization in a 3:1 mixture of diphenyl ether and biphenyl at all optimal temperature of 260° C. to provide a mixture of 7-nitro-4-oxo-1,4-dihydro-3-quinolinecarbonitrile 38a and 5-nitro-4-oxo-1,4-dihydro-3-quinolinecarbonitrile 38b which may be separated by either recrystallization or chromatography. Heating of 7-nitro-4-oxo-1,4-dihydro-3-quinolinecarbonitrile 38a with a chlorinating agent selected from phosphorus oxychloride and oxalyl chloride either neat or in a solvent such as methylene chloride, provides the corresponding 4-chloro-7-nitro-3-cyanoquinoline 39 followed by reaction with an aniline, phenol, thiophenol, amine, alcohol or thiol reagent of formula $HX$—$(CH_2)n$—$R^1$ 5 wherein $R^1$, X and n are hereinbefore defined gives the 4-substituted 7-nitro-3-cyanoquinolines 40 where $R^{2a}$, $R^{2b}$, $R^{2c}$, $R^1$, X and n are hereinbefore defined and T and Z are carbon atoms. The condensation may be accelerated by heating the reaction mixture together with a catalytic amount or one equivalent of pyridine hydrochloride or by using bases such as triethylamine, 4-dimethylaminopyridine, diazabicyclo [5.4.0]undec-7-ene or sodium hydride in an inert solvent, such as tetrahydrofuran, or sodium or potassium alkoxides in an inert solvent, or in the absence of solvent. The nitro group may be reduced with iron and ammonium chloride in methanol and water, or with iron and acetic acid in methanol to give the 3-cyanoquinolines of Formula (V).

SCHEME 11

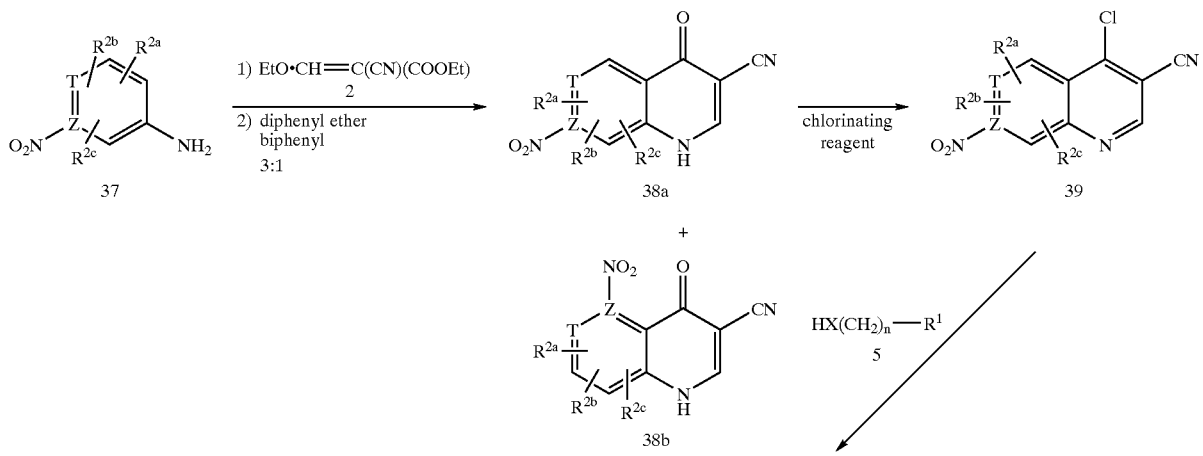

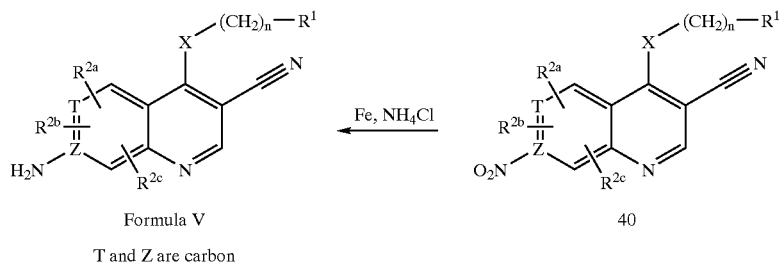

Formula V

T and Z are carbon

Scheme 12 shows an alternate route for the preparation of compounds of Formula (V). Reaction of a 3-nitroaniline 37 where $R^{2a}$, $R^{2b}$ and $R^{2c}$ are hereinbefore defined with acetic anhydride (Ac$_2$O) in water gives the corresponding acetamide 41. Reaction of the acetamide 41 with iron and ammonium chloride in methanol and water yields N-(3-aminophenyl)acetamide 42 which may be further reacted with ethyl(ethoxylmethylene)cyano acetate 2 with heating at temperatures ranging from 60 to 120° C. either neat or in an inert solvent which includes toluene followed by cyclization in a 3:1 mixture of diphenyl ether and biphenyl at an optimal temperature of 260° C. to provide a mixture of N-(3-cyano-4-oxo-1,4-dihydro-7-quinolinyl)acetamide 43a and N-(3-cyano-4-oxo-1,4-dihydro-5-quinolinyl)acetamide 43b which may be separated by either recrystallization or chromatography. Heating of N-(3-cyano-4-oxo-1,4-dihydro-7-quinolinyl)acetamide 43a with a chlorinating agent selected from phosphorus oxychloride and oxalyl chloride either neat or in a solvent which includes methylene chloride, provides the corresponding N-(4-chloro-3-cyano-7-quinolinyl)acetamide 44 followed by reaction with an aniline, phenol, thiophenol, amine, alcohol or thiol reagent of formula 5 HX—(CH$_2$)$_n$—R$^1$, wherein R$^1$, X and n are hereinbefore defined, followed by acid hydrolysis to give the 3-cyanoquinolines of Formula (V). The condensation may be accelerated by heating the reaction mixture together with a catalytic amount or one equivalent of pyridine hydrochloride or by using bases such as triethylamine, 4-dimethylaminopyridine, diazabicyclo[5.4.0]undec-7-ene or sodium hydride in an inert solvent, such as tetrahydrofuran, or sodium or potassium alkoxides in an inert solvent or in the absence of solvent.

SCHEME 12

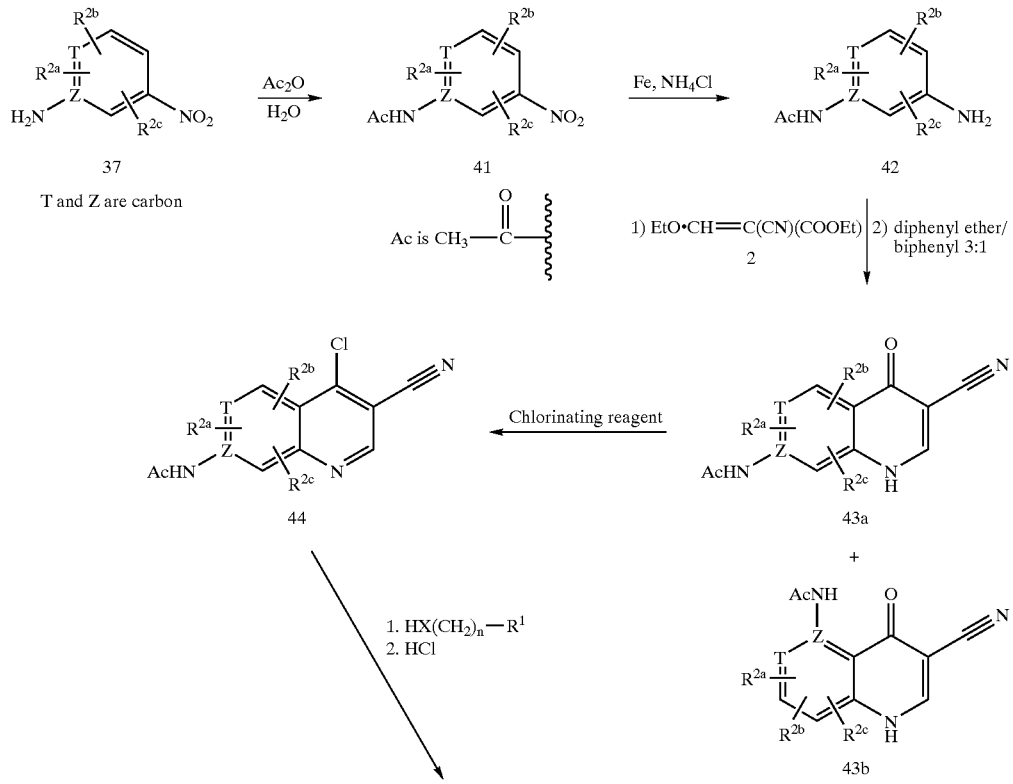

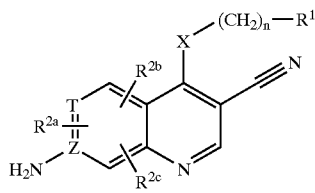

Formula (V)

T and Z are carbon

Compounds of Formulae (V), (VI), and (VII) may be converted to compounds of Formula (I) of the invention by additional, routes as shown in Schemes 13, 14, 15 and 16. As outlined in Scheme 13, reaction of the amino group bonded to a carbon atom of Formulae (V), (VI) and (VII) where T, Z, $R^{2a}$, $R^{2b}$, $R^{2c}$, $R^1$, X and n are hereinbefore defined with 2,5-dimethoxytetrahydrofuran 45 where A and $R^4$ are hereinbefore defined, in acetic acid or N,N-dimethylformamide containing 4-chloropyridine hydrochloride at temperatures ranging from 70 to 110° C. affords compounds of formula I where $R^3$ is pyrrole and T, Z, $R^{2a}$, $R^{2b}$, $R^{2c}$, $R^1$, X A, $R^4$ and n are hereinbefore defined.

SCHEME 13

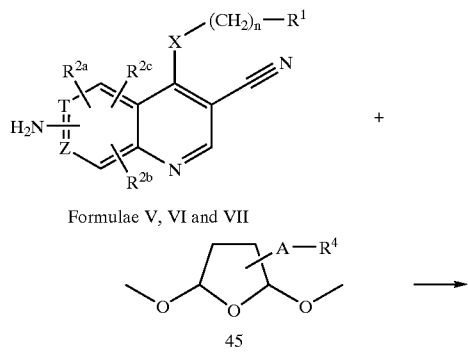

Formulae V, VI and VII

Formula I
$R^3$ is pyrrole

Specifically as outlined in Scheme 14, reaction of the amino group bonded to a carbon atom of Formulae (V), (VI) and (VII) where T, Z, $R^{2a}$, $R^{2b}$, $R^{2c}$, $R^1$, X and n are hereinbefore defined may be reacted with furfuyl aldehyde 46 catalyzed by acids which include Amberlite IR-120 in 2-ethoxyethanol to give the corresponding pyrrole carboxaldehyde 47 which may be treated with an amine 31 of formula $HNR^{13}R^{14}$ where $R^{13}$ and $R^{14}$ are hereinbefore defined, which may be either a primary or secondary amine, in a solvent selected from methanol, dioxane, tetrahydrofuan and methylene chloride, with the optional addition of a cosolvent which includes N,N-dimethylformamide, in the presence of a reducing agent such as sodium triacetoxyborohydride or sodium cyanoborohydride with the optional addition of a catalyst such as acetic acid to afford compounds of formula I where $R^3$ is pyrrole, A is absent, $R^4$ is —$(C(R^9)_2)_r$H and r is 0.

It should be noted that compounds of formula 47 are also compounds of formula I where $R^3$ is pyrrole, A is absent, $R^4$ is —$(C(R^9)_2)_r$H and r is 0.

SCHEME 14

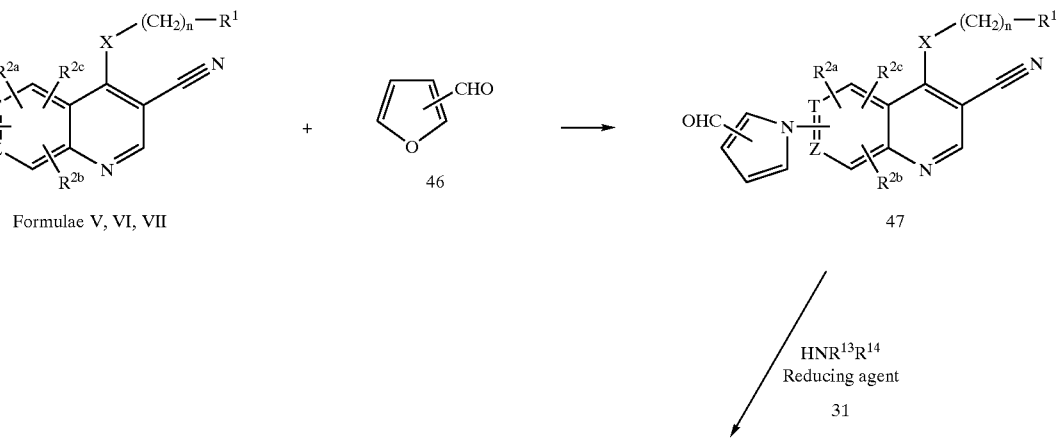

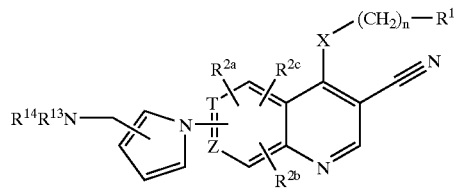

Formula I
R³ is pyrrole, A is absent,
R⁴ is $(C(R^9)_2)_rH$ and r is 0

Alternatively, Scheme 15 shows that the pyrrole carboxaldehyde 47 may be reduced to alcohol 48 using a reducing agent such as sodium borohydride. The resulting alcohol 48 may then be converted to pyrrole 49 having a leaving group LG selected from Cl, Br, p-toluelnesulfonate (TsO), methanesufonate (MsO) and trifluoromethanesulfonate (TfO). For example the alcohol may be converted into the corresponding chloride by a reagent such as thionyl chloride or phosphorus oxychloide in the presence of pyridine, or by hydrogen chloride. The leaving group LG may then be displaced by treatment with a primary or secondary amine of formula $R^{13}R^{14}NH$, 31 where $R^{13}$ and $R^{14}$ are hereinbefore defined, which may be either a primary or secondary amine to afford compounds of formula I where $R^3$ is pyrrole, A is absent, $R^4$ is —$(C(R^9)_2)_rH$ and r is 0.

It should be noted that compounds of formula 48 are also compounds of formula I where $R^3$ is pyrrole, A is absent, $R^4$ is —$(C(R^9)_2)_rH$ and r is 0.

As outlined in Scheme 16, reaction of the amino group bonded to a carbon atom of Formulae (V), (VI) and (VII) where T, Z, $R^{2a}$, $R^{2b}$, $R^{2c}$, $R^1$, X and n are hereinbefore defined, with 2,5-dimethoxytetrahydrofuran 50 in acetic acid or N,N-dimethylformamide containing 4-chloropyridine hydrochloride at temperatures ranging from 70 to 110° C. affords pyrrole 51 where T, Z, $R^{2a}$, $R^{2b}$, $R^{2c}$, $R^1$, X, and n are hereinbefore defined. Compounds of formula 51 are also compounds of Formula I where $R^3$ is pyrrole, A is absent, $R^4$ is —$(C(R^9)_2)_rH$ and r is 0. Further reaction of pyrrole 51 with paraformaldehyde and an amine 31 of formula $HNR^{13}R^{14}$ as the hydrochloride, where $R^{13}$ and $R^{14}$ are hereinbefore defined, which may be either a primary or secondary amine, in at solvent selected from methanol, dioxane, tetrahydrofuran and methylene chloride, with the optional addition of a cosolvent which includes N,N-dimethylformamide affords pyrrole compounds of Formula I.

SCHEME 15

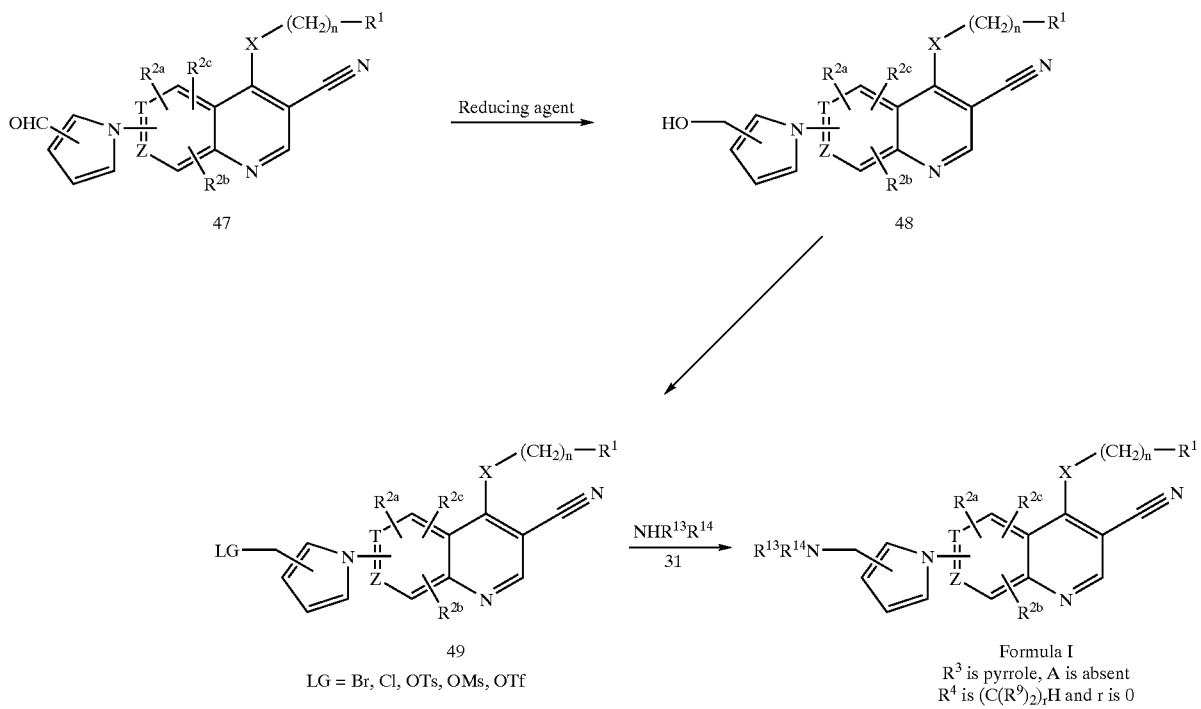

47

48

49
LG = Br, Cl, OTs, OMs, OTf

Formula I
R³ is pyrrole, A is absent
R⁴ is $(C(R^9)_2)_rH$ and r is 0

SCHEME 16

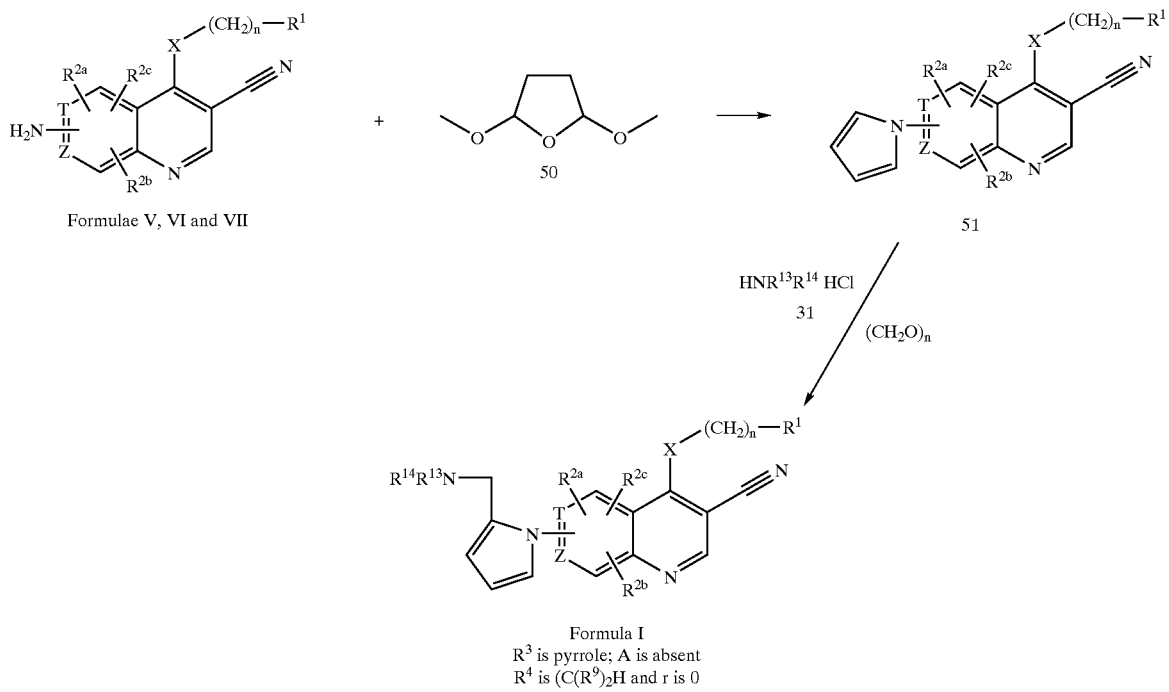

Scheme 17 shows an alternative route for the conversion of compounds of Formulae (II), (III) and (IV) to compounds of Formula (I) of the invention by initial reaction of compounds of Formulae (II), (III) and (IV), wherein the LG is bromo, with hexabutylditin, also known as bis(tributyltin), in N,N-dimethylformamide in the presence of a base such as triethylamine and a catalyst such as tetrakis (triphenylphosphine)pallidium(0) at elevated temperatures, preferably around 100° C. to provide the corresponding tin derivative 52. Reaction of 52 with bromo derivative 21 in a solvent such as N,N-dimethylformamide in the presence of a a catalyst such as dichlorobis(triphenylphosphine) pallidium(II) at elevated temperatures, provides compounds of Formula (I) of the invention wherein $R^1$, $R^{2a}$, $R^{2b}$, $R^{2c}$, $R^3$, $R^4$, n, A, T, X, and Z are hereinbefore defined.

SCHEME 17

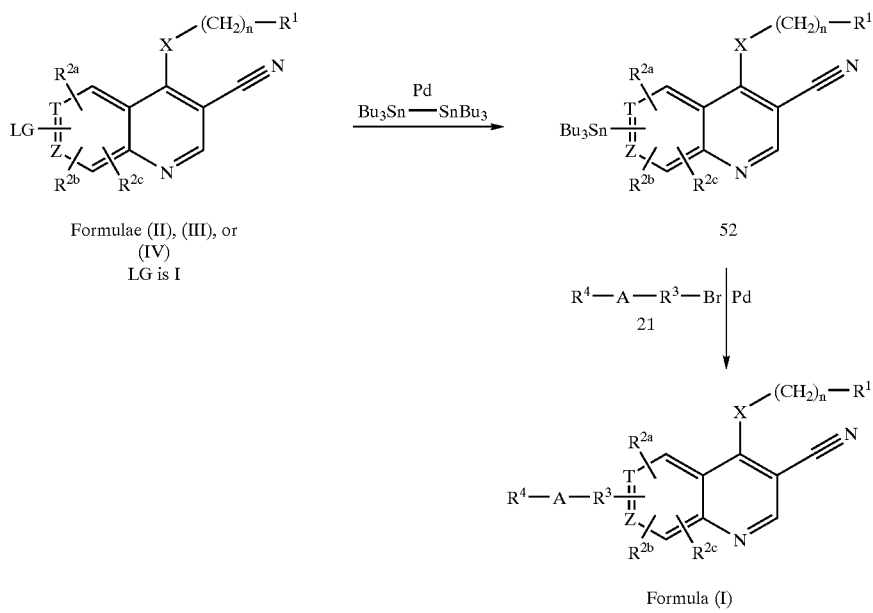

Scheme 18 shows an alternate route for the preparation of compounds of Formula (I) from 29. The carboxaldehyde group of 29 may be reduced to an alcohol 53 with a reducing agent such as sodium bomohydride. The resulting alcohol 53 may then be converted to 54 which has a leaving group LG selected from Cl, Br, p-toluenesulfonate (TsO), methanesulfonate (MsO) and trifluoromethanesulfonate (TfO). For example the alcohol is converted into the corresponding chloride by a reagent such as thionyl chloride or phosphorus oxychloride in the presence of pyridine, or by hydrogen chloride. The alcohol may also be converted to the chloride with 1-chloro-N,N, 2-trimethylpropenylamine in the presence of pyridine. The leaving group LG may then be displaced by treatment with a primary or secondary amine of formula $R^{13}R^{14}NH$, 31, where $R^{13}$ and $R^{14}$ are hereinbefore defined, which may be either a primary or secondary amine to afford compounds of Formula (I) of the invention wherein $R^1$, $R^{2a}$, $R^{2b}$, $R^{2c}$, $R^3$, $R^{13}$, $R^{14}$, n, T, X, and Z are hereinbefore defined, A is absent and $R^4$ is $-C((R^9)_2)_rH$ where r is 0.

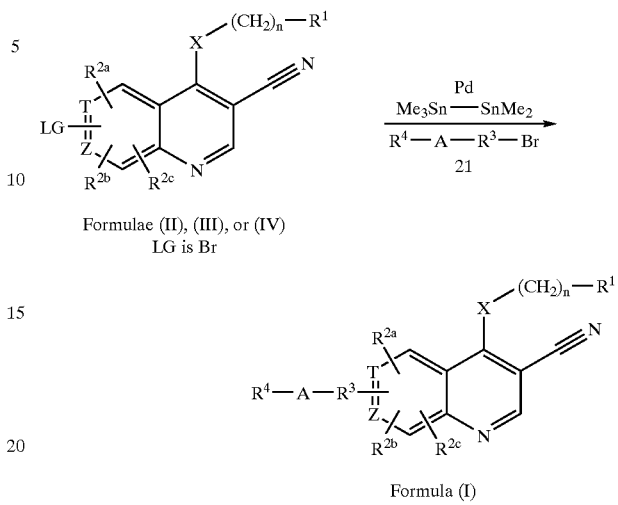

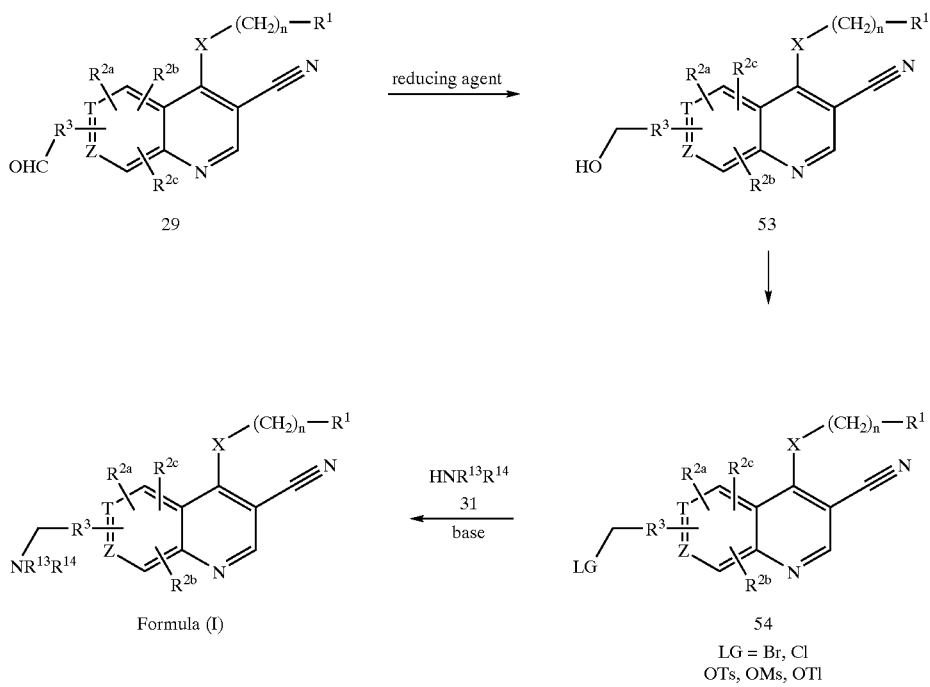

Scheme 19 shows a route for the conversion of compounds of Formulae (II), (III) and (IV) to compounds of Formula (I) of the invention by reaction of compounds of Formulae (II), (III) and (IV), wherein the LG is bromo, with bromo derivative 21 in the presence of hexamethylditin and a catalyst such as tetrakis(triphenylphosphine)pallidium(0) in dioxane at elevated temperatures to provide compounds of Formula (I) of the invention wherein $R^1$, $R^{2a}$, $R^{2b}$, $R^{2c}$, $R^3$, $R^4$, n, A,T, X, and Z are hereinbefore defined.

Scheme 20 depicts the preparation of compounds of Formula (I) of the invention whereby compounds of Formulae (II), (III) and (IV), wherein the LG is bromo, may be reacted with bromo containing aldehydes of structure 55 in the presence of hexamethylditin and a catalyst such as tetrakis(triphenylphosphine)pallidium(0) in dioxane at elevated temperatures to provide compounds of structure 29. Aldehyde 29 may be treated with an amine 31 of formula $HNR^{13}R^{14}$ in a solvent selected from methylene chloride, dioxane and tetrahydrofuran in the presence of a reducing agent such as sodium triacetoxyborohydride or sodium cyanoborohydride with the optional addition of a catalyst which includes acetic acid and the like to provide compounds of Formula (I) of the invention wherein $R^1$, $R^{2a}$, $R^{2b}$, $R^{2c}$, $R^3$, $R^{13}$, $R^{14}$, n, T, X, and Z are hereinbefore defined, A is absent and $R^4$ is —$C((R^9)_2)_rH$ where r is 0.

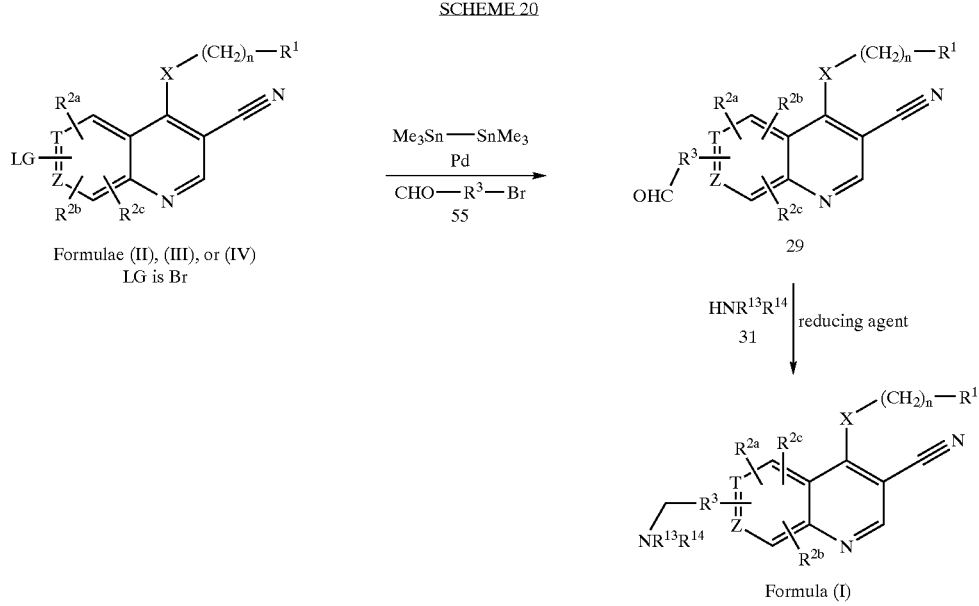

SCHEME 20

Formulae (II), (III), or (IV)
LG is Br

Formula (I)

Standard Pharmacological Test Procedures

Evaluation of representative compounds of this invention in several standard pharmacological test procedures indicated that the compounds of this invention possess significant antiproliferative activity and are inhibitors of protein tyrosine kinases. Based on the activity shown in the standard pharmacological test procedures, the compounds of this invention are therefore useful as antineoplastic agents. In particular, these compounds are useful in treating, inhibiting the growth of, or eradicating neoplasms such as those of the breast, kidney, bladder, mouth, larynx, esophagus, stomach, colon, ovary, lung, pancreas, liver, prostate and skin.

In addition to having antineoplastic properties, the compounds of the present invention are expected to be useful in treating a variety of protein tylosine kinase associated disorders including, but not limited to, osteoporosis, osteoarthritis, restenosis, atherosclerosis, fibroplasia, angiofibromas, hemangiomas, diabetes, acute and chronic nephropathies, Kaposi's sarcoma, atheroma, neovascular glaucoma, neovascularization associated with macular degeneration, rheumatoid arthritis, psoriatic arthritis, transplant rejection, T-cell mediated hypersensitivity diseases, including gluten-sensitive eniteropatily (Celiac disease), contact and delayed-type hypersensitivity, psoriasis, contact dermatitis, protection from ischemic or reperfusion injury such as that incurred during organ transplantation, stroke or myocardial infarction, transplantation tolerance induction, lupus, graft versus host disease, glomerulonephritis, serum sickness, respiratory and skin allergies, autoimmune alopecia, pernicious anemia, Hashimoto's thyroiditis, autoimmune hyperthyroidism, Addison's disease, multiple sclerosis, inflammatory bowel disease, acute inflammatory responses (for example acute respiratory distress syndrome), Behcet's disease, atopic dermatitis, systemic sclerosis and eczema.

The test procedures used and results obtained are shown below.

c-Src Kinase Assay

Inhibitors of Src (partially purified preparation purchased from Upstate Biotechinologies) tyrosine kinase activity are analyzed in an ELISA format. The Boehringer Mannheim Tyrosine Kinase Assay Kit (Catalog number 1-534505) with a cdc2 substrate peptide containing Tyr15 is used for the assay. Horseradish Peroxidase (HRP)-conjugated anti-phosphotyrosine is used to detect phosphorylated peptide via a color reaction. Conditions recommended by the manufacturer are employed.

Reaction conditions: Five micmoliter aliquots of each compound prepared fresh at the time of the assay are added as a solution in 10 mM HEPES pH 7.5, 10% DMSO to the reaction well. Thirty-five microliters of reaction mix containing Src, bluffer and peptide/bovine serum albumin mix are acided to the compound wells and incubated at 30° C. for 10 minutes (reaction buffer: 50 mM TrisHCl pH 7.5, 10 nM $MgCl_2$, 0.1 mM ECTA, 0.5 mM $Na_3VO_4$). The reaction is started by addition of 10 microliters of ATP, incubated at 30° C. for 1 hour, and stopped by addition of 20 microliters of 0.5M EDTA. The reaction mixture with the phosphorylated peptide is then transferred to a streptavidin-coated microtiter plate (provided in the kit) and allowed to bind for 20 minutes. Unbound peptide and reaction mixture is decanted and the plate is washed with PBS six times. HRP-conjugated phosphotyrosine antibody supplied in the kit is incubated with the plate for one hour, then decanted. The plate is again washed with PBS six times. Substrate (provided in the kit) is added and absorbance at 405 nm is measured.

Activity is determined as % inhibition as calculated by the formula: (1−Abs/Abs(max)×100% inhibition. Where multiple concentrations of the test agent are used, an $IC_{50}$ (concentration which gives 50%. inhibition) may be determined. The results obtained for representative compounds of this invention are listed in Table 1. Multiple entries for a given compound indicate that it is tested multiple times.

Anchorage Independent Src-transformed Fibroblast Proliferation Assay

Rat2 fibroblasts stably transformed with a plasmid containing a CMV promotor controlled v-Src/-Hu c-Src fusion gene in which the catalytic domain of human c-Src was inserted in place of the v-Src catalytic domain in the v-Src gene are used for the measurement of src dependent suspension growth. Ultra-low cluster plates (Costar #3474) are seeded with 10,000 cells per well on Day 1. Compound is added in serial two-fold dilutions from 10 micromoar to 0.009 micromolar on Day 2 and MTS reagent (Promega) is added on Day 5 (100 microliters of MTS/medium mix+100 microliters of medium already on the cells and the absorbance is measured at 490 nm. The results are analyzed as follows to yield an $IC_{50}$ for proliferation (micromolar units) as follows: % inhibition=(Abs490 nm sample−blank)/ (Abs490 nm no cmpd control−blank)×100%. The results obtained for representative compounds of this invention are listed in Table 1. Multiple entries for a given compound indicate that it was tested multiple times.

TABLE I

| Example | ELISA c-src $IC_{50}$ nM | anch-indep src-tx fib $IC_{50}$ μM |
|---|---|---|
| 1 | 25 | |
| 2 | 2 | 0.27, 0.19, 0.13 |
| 3 | 11 | 10, 4.1 |
| 4 | 14 | |
| 5 | 4.3 | 0.20 |
| 6 | 4 | 1.60 |
| 9 | 6 | 2.70 |
| 10 | 2.4 | 0.90 |
| 11 | 43 | >10 |
| 12 | 77 | >10 |
| 13 | 10.4, 4.0 | 1.51, 1.59 |
| 14 | 40% at 1 μM | |
| 15 | 63 | >10 |
| 16 | 44 | >10 |
| 17 | 0.7, 2.1, 3.1 | 0.31 |
| 18 | 180 | |
| 19 | 2.0, 1.7 | 0.16 |
| 20 | 1.1, 0.8 | 0.04, 0.03 |
| 21 | 40/9.0 | 1.7/4.7 |
| 22 | 6.8 | 0.60 |
| 23 | 2.0 | 0.09 |
| 24 | 2.1, 3.7 | 0.5, 0.15, 0.18, 0.18 |
| 25 | 3.6, 6.0, 4.9 | 1.3, 0.93 |
| 26 | 24 | |
| 27 | 8.0, 18, 1 | 1.02 |
| 28 | 25 | 4.10 |
| 29 | 4.1, 2.5 | 0.54, 0.50 |
| 30 | 4.4, 1.5 | 0.03, 1.10, 0.82 |
| 31 | 8.3, 5.6 | 0.08, 2.07, 1.93 |
| 32 | 2.7 | 2.0, 1.9 |
| 34 | 3 | |
| 36 | 1.9 | 0.16, 0.20 |
| 37 | 19 | 1.59, 1.49 |
| 38 | 81 | 12.7, 10.6 |
| 39 | 220 | |
| 40 | 10 | |
| 41 | 2.4 | 0.38 |
| 42 | 2.7 | |
| 43 | 1.7 | |
| 44 | 25 | |
| 45 | 51 | |
| 46 | 0.61 | 0.16 |
| 47 | 1.1 | 1.17 |
| 49 | 13 | 1.68 |
| 50 | 111 | |
| 51 | 8.2 | 0.42 |
| 52 | 11 | |
| 53 | 2.9 | 0.25 |
| 54 | 62 | >10 |
| 55 | 0.73 | 0.22 |
| 57 | 0.9 | 0.05 |
| 58 | 11 | 5.1 |
| 59 | 12, 15 | |
| 64 | 950 | >10 |
| 65 | 200 | >10 |
| 66 | 380 | >10 |
| 67 | 3.0. 4.9 | 0.11 |
| 68 | 1.5 | 0.12 |
| 69 | 110 | >10 |
| 70 | 25 | 6.0 |
| 71 | 26, 24 | 6.8 |
| 72 | 78 | >10 |
| 73 | 58, 75 | >10 |
| 74 | 40 | 1.40 |
| 75 | 24 | 0.29 |
| 76 | 22 | 1.1 |
| 77 | 21 | 0.42 |
| 78 | 1.3 | 0.14 |
| 79 | 1.7 | 0.13 |
| 80 | 1.5 | 0.08 |
| 81 | 1.1 | 0.13 |
| 82 | 0.48 | 0.05 |
| 83 | 42 | 3.90 |
| 84 | 7.5 | 0.77 |
| 85 | 36, 41 | 10.2 |
| 86 | 1.1 | 0.21 |
| 87 | 0.46 | 0.22 |
| 88 | 3.0 | 0.85 |
| 89 | 0.52, 0.84 | 0.09 |
| 90 | 10% at 100 nM | >10 |
| 91 | 3.1 | >10 |
| 92 | 8.6 | 2.11 |
| 93 | 610, 680 | >10 |
| 96 | 240 | |
| 99 | 44 | >10 |
| 100 | 0.57 | 0.34, 0.40 |
| 101 | 15 | >10 |
| 102 | 18 | 7.5 |
| 103 | | 4.3, >10 |
| 104 | 14 | 0.56 |
| 105 | 10 | >10, 5.9, >10 |
| 111 | 410 | >10 |
| 112 | 36 | 7.3 |
| 113 | 10 | 1.4 |
| 114 | 2,200 | >10 |
| 115 | 5,000 | >10 |
| 116 | 25% at 10 μM | >10 |
| 117 | 210, 160, 120 | 6.9 |
| 118 | 160 | 3.0 |
| 119 | 130 | >10 |
| 120 | 170 | >10 |
| 121 | 4.8, 1.8 | >10 |
| 122 | 44% at 10 μM | |
| 128 | 3.2 | 0.64 |
| 131 | 2.0 | 0.09 |
| 133 | 7.0 | 0.73 |
| 139 | 300, 340 | >10 |
| 140 | 240, 200 | >10 |
| 141 | 750 | >10 |
| 142 | 31 | >10 |
| 143 | 26 | >10 |
| 144 | 4.0 | 0.092 |
| 145 | 17% at 10 nM | >10 |
| 146 | 22 | 6.5 |
| 147 | 0.47 | 4.6 |
| 148 | 8.6 | 2.1 |
| 149 | 0.67 | 2.5 |
| 150 | 13, 6.6 | 0.50, 0.52 |
| 151 | 4.7 | 0.34, 0.49, 0.20 |
| 152 | | 4.8, 3.8 |
| 153 | | 2.8, 2.7 |
| 162 | 76 | >10 |
| 163 | >1,000 | >10 |
| 164 | >1,000 | >10 |
| 165 | 28% at 10 nM | >10 |
| 166 | 5.5 | 0.72 |
| 167 | 12, 16 | 0.9 |
| 174 | 95 | 5.6 |
| 176 | 1.7 | 0.09 |
| 177 | 0.69 | 2.1, 0.88 |

TABLE I-continued

| Example | ELISA c-src IC$_{50}$ nM | anch-indep src-tx fib IC$_{50}$ μM |
|---|---|---|
| 179 | 0.23 | 0.27 |
| 185 | 3.4 | 0.46. 8.3, >10 |
| 186 | 30 | >10 |
| 188 | 0.86 | 0.07, 0.13 |
| 192 | 2.1 | 0.17 |
| 193 | 34 | >10 |
| 194 | 12 | >10 |
| 197 | 4.4 | 0.34, 0.20, 0.73 |
| 198 | 1.9 | 0.24, 0.84, 0.14 |
| 200 | 1.4 | 0.25, 0.73 |
| 204 | 6.4 | 1.1 |
| 218 | 3.1, 45 | 0.6 |
| 226 | 31 | |
| 227 | 25 | |
| 228 | 46 | >10 |
| 229 | 2.3 | 0.45 |
| 230 | 0.63, 2.52, 7.1 | 0.064, 0.22, 0.14 |
| 231 | 6.8 | 0.39 |
| 232 | 78 | 3.5 |
| 233 | 28 | |
| 234 | 7.2 | 0.72 |
| 235 | 4.1 | 0.79 |
| 236 | 3.0 | 0.57 |
| 237 | 0.18, 0.55, 0.18 | 0.49, 0.52, 0.41 |

Raf1 Kinase Cascade Assay Procedure

Raf-1 (c-Raf) is used to phosphorylate and activate inactive GST-MEK1 which then can phosphorylate and activate inactive p42 GST-MAPK, which subsequently is measured for phosphorylation of the TEY sequence (aa's 202–204) by a phospho-specific antibody from Sigma (cat. #77439219041) Reagents: Sf9 insect cell lysate containing full length 6his-tagged recombinant human c-Raf. (Specific Activity: ~200 U/ml). Human Non-active Mek-1-GST and human GST-MAP kinase (recombinant proteins produced in E. coli).

Stock Solutions Raf Assay:
  Assay Dilution Buffer (ADB): 20 mM MOPS, pH 7.2, 25 mM β-glycerol phosphate, 5 mM EGTA, 1 mM sodium orthovanadate, 1 mM dithiothreitol.
  Magnesium/ATP Cocktail: 500 μM cold ATP and 75 mM magnesium chloride in ADB.
  Active Kinase: Human Active c-Raf: Use at 0.4 U per assay point.
  Non-active GST-MEK1: Use at 0.1 μg per assay point.
  Non-active GST-p42 MAP Kinase: Use at 1.0 μg per assay point.
Stock Solutions ELISA:
  TBST—Tris (50 mM, pH 7.5), NaCl (150 mM), Tween-20 (0.05%)
  Superblock (Pierce)
  Anti-GST Ab (Pharmacia)
  Anti-Phospho MAPK (Sigma)
  Anti-Mouse Ab/Europium conjugate (Wallac)
Assay Procedure:
  First Stage: c-Raf Dependent Activation of GST-MEK and GST-MAPK
  Add 20 ml of ADB per assay (i.e. per well of a 96 well plate)
  Add 10 ml of 0.5 mM cold ATP and 75 mM magnesium chloride in ADB.
  Add 2 ml of c-Raf (0.4 U/assay), in conjunction with 1.6 ml non-active MEK1 (0.4 mg/assay).
  Add 4 ml of non-active GST-p42 MAP Kinase (1.0 mg/assay).
  Incubate for 60 minutes at 30° C. in a shaking incubator.
  Transfer this mixture to an anti-GST Ab coated 96 well plate (Nunc Immunosorb plates coated o/n with a-GST, then blocked with Pierce Superblock).
  Incubate for 60 minutes at 30° C. in a shaking incubator
  Wash 3× with TBST, add Anti-Phospho MAPK (Sigma) (1:3000)
  Incubate for 60 minutes at 30° C. in a shaking incubator
  Wash 3× with TBST, add Anti-Mouse Ab/Europium conjugate (Wallac) (1:500)
  Incubate for 60 minutes at 30° C. in a shaking incubator
  Wash 3× with TBST, Read plates in Wallac Victor model Plate Reader.
  Collect data analyze in Excel for single point and IC50 determinations.
  Single point assay—% inhibition at 10 mg/ml (% Inhibition=1–cpd.treated sample/untreated control). IC$_{50}$ determinations—done on compounds from single point assays with >80% inhibition. Typically Raf-1 assay is run at compound concentrations from 10 μM to 30 nM in half log dilutions. (% inhibition is determined for each compound concentration). The results obtained for representative compounds of this invention are listed in Table 2.

Cell Based Screen for Inhibitors of Raf Kinase
Materials
  Cell Lines: Human adenocarcinoma cell line LoVo which is known to be growth inhibited by low nM concentrations of a reference standard inhibitor of Ras and human adenocarcinoma cell line CaCo-2, which is known to be growth resistant to the same reference compound.
  Cell Media: RPMI 1640 with 10% Fetal Bovine Serum supplemented with L-glutamine and Pennicilin/Streptomycin.
  Compounds: Supplied usually as a 10 mM stock in 100% DMSO.
  Normal Saline: 150 mM NaCl
  Trichloroacetic Acid (TCA): 50% (w/v) in water
  Sulforhodamine B (SRB): 0.4% (w/v) in 1% Acetic Acid
  Tris Base: 10 min in water
Methods
  Cells are plated at 2000 cells per well for cell line LoVo and 1500 cells for cell line CaCo-2 in 96 well plates. Cells are plated in media (200 μl) and allowed to adhere overnight at 37° C. At 24 hours post plating, compounds are added directly at a volume of 0.5 μl. For the qualitative screen (compounds screened at 25 μM) compound is added directly to cells. For the quantitative screen, compound is first diluted in DMSO to generate concentrations of compound or reference standard of: 1, 5, 10 and 25 μM. It is advisable to make the dilutions in an identical 96 well plate so that compounds may be added using a multichannel micropipettor set at 0.5 μl. The cells are then incubated for four days after which the media is removed using a 12 well manifold by first tipping the plate forward at a 45 degree angle and then inserting the manifold in an upright orientation to prevent the tips of the manifold from disturbing cells it the bottom of the plate. 200 μl of normal saline is then added to each well using an 8 well multichannel pipettor, followed by the careful addition of 50 μl of 50% TCA. The plates are then incubated for 2 hours at 4° C., after which the supernatant is removed using the same technique as above and the plated washed twice with 200 μl water. The plates are then air dried and 50 μl of SRB stock solution is carefully added so that the entire bottom of each well is covered. This again may be used using an 8 well multichannel pipettor. The SRB is incubated with fixed cells for 15 minutes at room temperature after which the SRB is removed with the manifold as described above and the plates washed twice with 350 μl of 1% acetic acid per well each time. The plates are then air dried after which the bound SRB is released from protein by the addition of 200 μl of Tris base. Resolubilizing the SRB is aided by placing the plates on a rotator for 15–30 minutes. The absorbance of each well is determined at 550 or 562 nm using a microtiter plate reader.

Each compound or dilution thereof is performed in triplicate. Outliers are identified by visual inspection of the data. Each plate should have a "0" control (vehicle only).

Qualitative screen: To calculate % inhibition of a compound at 25 μM, the following formula is used: 1-(experimental absorbance @ 25 μM compound/"0" control absorbance)×100=% inhibition at 25 μM. Compounds having >50% inhibition at 25 μM are placed in the quantitative assay.

Quantitative Assay: A standard curve is constructed by plotting the concentration of compound against the average absorbance calculated at that concentration. A curve is plotted and the concentration at which the curve passes through the 50% the absorbance mark seen in the "0" control well is the $IC_{50}$ calculated for that compound. Multiple entries for a given compound indicate that it was tested multiple times. The results obtained for representative compounds of this invention in Table 2.

TABLE 2

| Example | raf $IC_{50}$ nM | LoVo $IC_{50}$ μM | CaCo-2 $IC_{50}$ μM |
|---|---|---|---|
| 7 | 8.0 | 3.7 | >10 |
| 8 | 6.0 | >10 | >10 |
| 33 | 6.0 | 0.006 | 1.9, 0.78 |
| 35 | 22, 4.0, 13 | <0.005, <0.005, <0.005, 0.006 | >10 |
| 48 | 90 | | |
| 56 | 1.0 | 0.29, 0.44, 0.31 | 1.0, 1.0, 0.6 |
| 62 | 27 | | |
| 63 | 5.0 | 3.8 | 2.2 |
| 94 | 89 | | |
| 95 | 40 | | |
| 97 | 16 | 0.033 | >1 |
| 98 | 10 | 0.0071 | 0.64 |
| 106 | 9.2 | 0.0064 | >1 |
| 107 | 8.0 | 0.025 | >1 |
| 108 | 1.5 | 0.0026 | 0.39 |
| 109 | 5.4 | 0.0068 | 0.98 |
| 110 | 4.3 | 0.01 | >1 |
| 123 | 80 | 0.04 | 1.5 |
| 124 | 33 | 0.15, 0.03 | 1.2, 2.9 |
| 125 | 4.0 | 0.02, 0.015 | 1.9, 2.8 |
| 126 | 20 | 0.075 | >1 |
| 127 | 180 | | |
| 129 | 7.0 | 0.042 | >1 |
| 132 | 300, 330 | 0.43 | 7.0 |
| 134 | 80 | 0.0046 | >1 |
| 135 | 9.0, 10 | 0.0068 | >1 |
| 136 | 2.5, 1.8 | 0.011 | >1 |
| 137 | 90 | 0.0485 | >1 |
| 138 | 5.6 | 0.0062 | 0.81 |
| 154 | 9.0, 11 | 0.0068 | >1 |
| 155 | 20 | | |
| 156 | 9.0, 12 | 0.0056 | 1 |
| 157 | 9.0, 5.0 | 0.0245 | >1 |
| 159 | 2.0 | 0.0042 | 0.71 |
| 160 | 3.8 | 0.0041 | 0.62 |
| 161 | 4.0 | 0.0056 | >1 |
| 168 | 27.28 | 2.0 | 4.6 |
| 169 | 8.0 | 0.04, 0.047 | 0.6, 1.4 |
| 170 | 30 | 0.05 | >10, 5 |
| 171 | 10 | 0.008, 0.005, <0.005, <0.005 | 2.2, 2.7, >1 |
| 172 | 7.4 | 0.0079 | >1 |
| 173 | 22 | 0.025 | >1 |
| 175 | 8.0 | 0.33 | >1 |
| 178 | 4,000 | | |
| 180 | 3.7 | 0.0056 | 0.93 |
| 181 | 80 | | |
| 182 | >10,000 | | |
| 183 | 1,500 | | |
| 184 | 1,400 | | |
| 187 | 1.0, 5.0 | 0.008, 0.009, 0.018, 0.0077, 0.0096, 0.0126, 0.007, 0.009 | >10, >10, 5.5 |
| 189 | 2.7 | 0.006 | 1.25 |
| 190 | 0.9 | 0.002 | >10, >1 |
| 191 | 1.0 | 0.03 | >10 |
| 195 | 3.0, 2.0 | 0.0023, 0.002, 0.0022, 0.0037, 0.005, 0.0027, 0.0033, 0.0028 | 0.47, 0.43, 0.77. 0.71, 0.85, >1, >1 |
| 196 | 2.8 | <0.005, 0.0029 | 1.1, 0.55 |
| 199 | 17 | 0.0095 | >1, >1 |
| 201 | 5.0, 7.5 | 0.0084 | >1 |
| 202 | 4.5, 13 | 0.0065 | >1 |
| 203 | 22 | 0.0097 | >1 |
| 205 | 27 | 0.275 | 0.94 |
| 206 | 28 | 0.28 | >1 |
| 207 | 8,000 | | |
| 208 | 8,100 | | |
| 209 | 1,900 | | |
| 210 | 1.8 | 0.0032 | 0.59 |
| 211 | 6.0 | 0.0053 | >1 |
| 212 | 2.0 | 0.004 | 0.78 |
| 213 | 40 | 0.0452 | >1 |
| 214 | 2.5 | 0.0057 | >1 |
| 215 | 2.3 | 0.0035 | >1 |
| 216 | 2.0 | 0.007 | >1 |
| 217 | 8.0 | 0.036 | >1 |
| 219 | 32 | 0.015 | >1 |
| 220 | 14 | 0.0077 | >1 |
| 221 | 12 | 0.074 | >1 |
| 221 | 12 | 0.074 | >1 |
| 135 | 30 | | |
| 238 | 45 | | |
| 239 | 48 | | |
| 240 | 42 | | |
| 241 | 13 | | |
| 243 | 18 | | |
| 244 | 48 | | |
| 245 | 18 | | |
| 246 | 28 | | |
| 247 | 20 | | |
| 248 | 190 | | |
| 249 | 180 | | |
| 250 | 190 | | |
| 251 | 190 | | |
| 252 | 200 | | |
| 253 | 180 | | |
| 254 | 40 | | |
| 255 | 180 | | |
| 256 | 190 | | |
| 257 | 150 | | |
| 258 | 140 | | |
| 259 | 50 | | |
| 260 | 20 | | |
| 261 | 15 | | |
| 262 | 24 | | |
| 263 | 17 | | |
| 264 | 160 | | |
| 265 | 14 | | |
| 266 | 9 | | |
| 267 | 35 | | |
| 268 | 35 | | |

TABLE 2-continued

| Example | raf IC$_{50}$ nM | LoVo IC$_{50}$ μM | CaCo-2 IC$_{50}$ μM |
|---|---|---|---|
| 269 | 9 | | |
| 270 | 180 | | |
| 271 | 210 | | |
| 422 | 40 | | |
| 439 | 15 | | |
| 448 | 21 | | |
| 450 | 19 | | |
| 452 | 23 | | |
| 456 | 17 | | |
| 460 | 55 | | |
| 462 | 50 | | |
| 463 | 27 | | |

Based on the results obtained for representative compounds of this invention, the compounds of this invention are antineoplatic agents which are useful in treating, inhibiting the growth of, or eradicating neoplasms. In particular, the compounds of this invention are useful in treating, inhibiting the growth of, or eradicating neoplasms that either express Src or raf or neoplasms that depend at least in part on the Src or raf pathways. Such neoplasms include those of the breast, kidney, bladder, mouth, larynx, esophagus, stomach, colon, ovary, lung, pancreas, skin, liver, prostate or brain. Based on the results obtained, the compounds of this invention are also useful in the treatment of osteoporosis.

As may be appreciated from the data in Tables 1 and 2, the compounds according to the invention are endowed with valuable biological properties useful in the treatment of certain diseases that are the result of deregulation of protein kinases.

The compounds of this invention may be formulated neat or may be combined with one or more pharmaceutically acceptable carriers for administration. For example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solution or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 1000 mg/kg of animal body weight, optionally given in divided doses two to four times a day, or in sustained release form. For most large mammals the total daily dosage is from about 1 to 1000 mg, preferably from about 2 to 500 mg. Dosage forms suitable for internal use comprise from about 0.5 to 1000 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The compounds of this invention may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt may be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, polyol (e.g., glycerol, propylene glycol and liquid polyethylene glycol), suitable mixtures thereof, and vegetable oils.

For the treatment of cancer, the compounds of this invention may be administered in combination with other antitumor substances or with radiation therapy. These other substances or radiation treatments may be given at the same or at different times as the compounds of this invention. These combined therapies may effect synergy and result in improved efficacy. For example, the compounds of this invention may be used in combination with mitotic inhibitors such as taxol or vinblastine, alkylating agents such as cisplatin or cyclophosamide, antimetabolites such as 5-fluorouracil or hydroxyurea, DNA intercalators such as adriamycin or bleomycin, topoisomerase inhibitors such as etoposide or camptothecin, antiangiogenic agents such is angiostatin, and , antiestrogens such is tamoxifen.

As used in accordance with this invention, the term providing an effective amount of a compound means either directly administering such compound, or administering a prodrug, derivative, or analog which will form an effective amount of the compound within the body.

The invention will be more fully described in conjunction with the following specific examples which are not to be construed as limiting the scope of the invention.

REFERENCE EXAMPLE 1

6-Bromo-4-oxo-1,4-dihydro-quinoline-3-carbonitrile

A solution of 5-bromoanthranilic acid (21.6 g, 100 mmol) and dimethylformamide dimethylacetal (50 mL) in dimethylformamide (150 mL) was heated at 155–160° C. for 8 hours then cooled to room temperature. The volatiles were removed in vacuo to provide 28.5 g of the intermediate amidine.

Lithium diisopropylamide (LDA) was generated from isopropylamine (9.84 mL, 70.2 mmol) and 2.5 M n-butyl lithium (29.5 mL, 70.2 mmol) in tetrahydrofuran (150 ml) at −78° C. Acetonitrile (3.67 mL, 70.2 mmol) was added and the resulting white suspension was stirred at −78° C. for 1 hour. A solution of 10 g of the amidine in 100 mL of tetrahydrofuran was added and stirring was continued for 1 hour at −78° C. and then 1 hour at room temperature. The reaction was quenched by addition of acetic acid (15 mL). The volatiles were removed in vacuo and water was added to the residue. The aqueous solution was basified to pH 9 by the addition of ammonium hydroxide. The white precipitate was collected, suspended in methylene chloride and filtered to provide 6-bromo-4-oxo-1,4-dihydro-quinoline-3-carbonitrile as a white solid;

$^1$H NMR (DMSO-$d_6$) δ 7.60 (d, J=9 Hz, 1H), 7.93 (dd, J=9, 2 Hz, 1H), 8.20 (d, J=2 Hz, 1H), 8.77 (s, 1H); MS (ES) m/z 248.7 (M+1). Analysis for $C_{10}H_5BrN_2O$: Calcd: C, 48.22; H, 2.02; N, 11.25; Br, 32.08. Found: C, 48.18; H, 2.18; N, 11.24; Br, 32.09.

REFERENCE EXAMPLE 2

6-Bromo-4-chloro-3-quinolinecarbonitrile

A mixture of 6-bromo-4-oxo-1,4-dihydroquinoline-3-carbonitrile (1.3 g, 4.86 mmol) and 8 mL of phosphorous oxychloride was heated at reflux for 30 minutes. The dark brown solution was cooled to room temperature and 10 mL of hexane was added. The resultant solid was collected by filtration washing with hexane, water, and hexane to provide 1.05 g of 6-bromo-4-chloro-3-quinolinecarbonitrile as a tan solid;

$^1$H NMR (DMSO-$d_6$) δ 8.12 (d, J=9 Hz, 1H), 8.19 (dd, J=9, 2 Hz, 1H), 8.45 (d, J=2 Hz, 1H), 9.23 (s, 1H); MS (ES) m/z 267.1, 269.0 (M+1). Analysis for $C_9H_4BrClN_2$: Calcd: C, 44.90; H, 1.51; N, 10.47. Found: C, 44.53; H, 1.63; N, 10.27.

REFERENCE EXAMPLE 3

6-Bromo-4-(2,4-dichloro-5-methoxyanilino)-3-quinolinecarbonitrile

A mixture of 2,4-dichloro-5-methoxy aniline (prepared by the procedure described in WO 8501939-A1) (730 mg, 3.77 mmol) and sodium hydride (180 mg of a 60% dispersion in oil, 4.5 mmol) in 30 mL of tetrahydrofuran was heated at reflux for 1 hour. The mixture was cooled, 6-bromo-4-chloro-3-quinolinecarbonitrile (600 mg, 2.24 mmol) was added and the mixture was heated at reflux for 50 minutes. After cooling to room temperature, the reaction mixture was partitioned between ethyl acetate and saturated sodium bicarbonate. The organic layer was washed with saturated sodium chloride, dried over magnesium sulfate, filtered and concentrated in vacuo. The resultant solid was purified by flash chromatography eluting with a gradient of 3:1 to 1:1 hexane:ethyl acetate to provide 530 mg (53% yield) of 6-bromo-4-(2,4-dichloro-5-methoxyanilino)-3-quinolinecarbonitrile as tan crystals, mp 232–234° C.;

$^1$H NMR (DMSO-$d_6$/trifluoroacetic acid) δ 3.89 (s, 3H), 7.58 (s, 1H), 7.88 (s, 1H), 8.01 (d, J=7 Hz, 1H), 8.30 (dd, J=7, 2 Hz, 1H), 9.12 (d, J=2 Hz, 1H), 9.29 (s, 1H); MS (ES) m/z 424.2 (M+1). Analysis for $C_{17}H_{10}BrClN_3O$: Calcd: C, 48.26; H, 2.38; N, 9.93. Found: C, 48.36; H, 2.45; N, 9.88.

REFERENCE EXAMPLE 4

7-Bromo-4-oxo-1,4-dihydroquinoline-3-carbonitrile

A mixture of ethyl(ethoxymethylene)cyanoacetate (30 g, 180 mmol) and 3-bromoaniline (25.0 g, 145 mmol) in 300 mL of toluene was heated at reflux for 7 hours. Upon cooling to room temperature a white solid formed. The solid was collected by filtration washing with toluene. The olefin (30.0 g, 101 mmol) was dissolved in 600 mL of a 3 to 1 mixture of diphenyl ether and biphenyl and the solution was heated at 259–260° C. (internal temperature) with the ethanol formed in the reaction removed by distillation. After heating overnight, the solution was cooled to room temperature and poured into hexane. The precipitate was collected to provide 22.0 g of a solid that was combined with 275 mL of dimethylformamide, heated at 100° C. and then filtered to provide 9.0 g (36% yield) of 7-bromo-4-oxo-1,4-dihydroquinoline-3-carbonitrile;

$^1$H NMR (DMSO-$d_6$) δ −7.64 (dd, J=9, 2 Hz, 1H), 7.82 (d, J=2 Hz, 1H), 8.04 (d, J=9 Hz, 1H), 8.78 (s, 1H); MS (ES) m/z 248.8 (M+1). Analysis for $C_{10}H_5BrN_2O$: Calcd: C, 48.22; H, 2.02; N, 11.25. Found: C, 48.31; H, 1.93; N, 11.33.

REFERENCE EXAMPLE 5

7-Bromo-4-chloro-3-quinolinecarbonitrile

To suspension of 7-bromo-4-oxo-1,4-dihydroquinoline-3-carbonitrile (1.0 g, 4.02 mmol) in methylene chloride was added oxalyl chloride (1.75 mL, 20 mmol) followed by dimethylformamide (78 μL, 1.00 mmol). The mixture was stirred at room temperature for 3 hours and additional oxalyl chloride (1.75 mL, 20 mmol) and dimethylformamide (78 μL, 1.00 mmol) were added. The reaction mixture was stirred at room temperature overnight and then diluted with methylene chloride. Ice water was added and the aqueous layer was basified to pH 9 with sodium carbonate. The organic layer was washed with water, dried over magnesium sulfate, filtered and concentrated in vacuo to provide 1.0 g (93% yield) of 7-bromo-4-chloro-3-quinolinecarbonitrile as a light yellow solid;

$^1$H NMR (DMSO-$d_6$) δ 8.07 (dd, J=9, 2 Hz, 1H), 8.26 (d, J=9 Hz, 1H), 8.46 (d, J=2 Hz, 1H), 9.22 (s, 1H); MS (ES) m/z 268.7 (M+1). Analysis for $C_{10}H_4BrClN_2$: Calcd: C, 44.90; H, 1.51; N, 10.47; Br, 29.87; Cl, 13.25. Found: C, 45.00; H, 1.76; N, 10.40; Br, 30.25; Cl, 13.47.

REFERENCE EXAMPLE 6

7-Bromo-4-(2,4-dichloroanilino)-3-quinolinecarbonitrile

A mixture of 2,4-dichloroaniline (1.213 g, 7.49 mmol) and sodium hydride (300 mg of a 60% dispersion in oil, 7.50 mmol) in 50 mL of tetrahydrofuran was heated at reflux for 15 minutes. The mixture was cooled, 7-bromo-4-chloro-3-quinolinecarbonitrile (1.00 g, 3.75 mmol) was added and the mixture was heated at reflux for 30 minutes. After cooling to room temperature the reaction mixture was partitioned between ethyl acetate and water. The organic layer was dried over magnesium sulfate, filtered and concentrated in vacuo. The resultant solid was purified by flash silica gel chromatography eluting with 3:1 hexane:ethyl acetate to provide 927 mg (63% yield) of 7-bromo-4-(2,4-dichloroanilino)-3-quinolinecarbonitrile as a light yellow solid, mp 180–183° C.;

$^1$H NMR (DMSO-$d_6$/trifluoroacetic acid) δ 7.53–7.65 (m, 1H), 7.83 (d, J=2 Hz, 1H), 7.93–7.99 (m, 2H), 8.13 (d, J=2

Hz, 1H), 8.53 (d, J=9 Hz, 1H), 8.83 (s, 1H); MS (ES) m/z 392, 394, 396 (M+1). Analysis for $C_{16}H_8BrCl_2N_3$: Calcd: C, 48.89; H, 2.05; N, 10.69. Found: C, 48.53; H, 2.18; N, 10.61.

REFERENCE EXAMPLE 7

7-Bromo-4-(4-chloro-2-fluoroanilino)-3-quinolinecarbonitrile

A mixture of 7-bromo-4-chloro-3-quinolinecarbonitrile (5.0 g, 18.69 mmol), 4-chloro-2-fluoroaniline (3.27 g, 22.43 mmol) and pyridine hydrochloride (2.2 g 18.69 mmol) in 150 mL of ethoxyethanol was heated at reflux for 4 hours. After cooling, the solvent was removed in vacuo and the residue was diluted with ice water, basified (pH 9) with ammonium hydroxide, and extracted into ethyl acetate. The extracts were washed with saturated sodium chloride, dried over sodium sulfate and concentrated. The residue was treated with diethyl ether, and the yellow solid was collected by filtration. The filtrate was concentrated and purified by flash silica gel chromatography eluting with methylene chloride:diethyl ether:methanol (9:1:0.1) to provide 3.0 g (43%) of 7-bromo-4-(4-chloro-2-fluoroanilino)-3-quinolinecarbonitrile as a light brown solid;

$^1$NMR (DMSO-$d_6$) δ 7.38 d, J=9 Hz, 1H), 7.47–7.53 (m, 1H), 7.62 (dd, =3, 9 Hz, 1H), 7.84 (d, J=9 Hz, 1H), 8.13 (s, 1H), 8.44 (d, J=9 Hz, 1H), 8.62 (s, 1H); MS (ES) m/z 377.7 (M+1). Analysis for $C_{16}H_8BrClFN_3$: Calcd: C, 51.03; H, 2.14; N, 11.16. Found: C, 50.67; H, 2.20; N, 11.02.

REFERENCE EXAMPLE 8

7-Bromo-4-(2,4-dichloro-5-methoxyanilino)-3-quinolinecarbonitrile

A mixture of 2,4-dichloro-5-methoxy aniline (prepared by the procedure described in WO 8501939-A1) (202 mg, 1.05 mmol), 7-bromo-4-chloro-3-quinolinecarbonitrile (267 mg, 1.0 mmol) and pyridine hydrochloride (20 mg) in 10 mL of ethoxyethanol was heated at reflux for 1.5 hours, and concentrated. The residue was treated with saturated sodium bicarbonate. The solids were filtered and dried. The product was then dissolved in ethyl acetate and filtered through hydrous magnesium silicate. The filtrate was concentrated, and the resulting solids were triturated with a small quantity of ethyl acetate to give the first crop of product as a yellow solid. The filtrate was purified by flash silica gel chromatography, eluting with 1:1 hexane:ethyl acetate to give a second crop of product, providing a total of 216 mg (51% yield) of 7-bromo-4-(2,4-dichloro-5-methoxyanilino)-3-quinolinecarbonitrile as a yellow solid, mp 192–193° C.;

$^1$H NMR (DMSO-$d_6$/trifluoroacetic acid) δ 3.91 (s, 3H), 7.59 (s, 1H), 7.86 (s, 1H), 8.15 (dd, J=9, 2 Hz, 1H), 8.26 (d, J=2 Hz, 1H), 8.74 (d, J=9 Hz, 1H), 9.28 (s, 1H); MS (ES) m/z 424.0 (M+1). Analysis for $C_{17}H_{10}BrCl_2N_3O$: Calcd: C, 48.26; H, 2.38; N, 9.93. Found: C, 48.06; H, 2.53; N, 9.71.

REFERENCE EXAMPLE 9

4-(4-Benzylanilino)-7-bromo-3-quinolinecarbonitrile

A mixture of 4-aminodiphenylmethane (604 mg, 33 mmol) 7-bromo-4-chloro-3-quinolinecarbonitrile (800 mg, 3.0 mmol) and pyridine hydrochloride (30 mg) in 15 mL of ethoxyethanol was heated at reflux for 1 hour. The mixture was cooled, poured into 5% sodium carbonate solution, and stirred. The product was filtered, washed with water, and dried to provide 1.20 g (96% yield) of 4-(4-benzylanilino)-7-bromo-3-quinolinecarbonitrile as a tan solid, mp 195–197° C.;

$^1$H NMR (DMSO-$d_6$) δ 3.99 (s, 2H), 7.26 (m, 9H), 7.81 (dd, J=9, 2 Hz, 1H), 8.12 (d, J=2 Hz, 1H), 8.41 (d, J=9 Hz, 1H), 8.57 (s, 1H), 9.91 (s, 1H); MS (ES ) m/z 416.1 (M+1). Analysis for $C_{23}H_{16}BrN_3$: Calcd: C, 66.68; H, 3.89; N, 10.14. Found: C, 66.67; H, 3.96; N, 9.81.

REFERENCE EXAMPLE 10

7-Bromo-4-(4-phenoxyanilino)-3-quinolinecarbonitrile

A mixture of 4-phenoxyaniline (204 mg, 1.1 mmol), 7-bromo-4-chloro-3-quinolinecarbonitrile (267 mg, 1.0 mmol) and pyridine hydrochloride (20 mg) in 10 mL of ethoxyethanol was heated at reflux for 1 hour. The mixture was cooled, poured into 5% sodium carbonate solution, and stirred. The product was filtered, washed with water, and dried to provide 396 mg (95% yield) of 7-bromo-4-(4-phenoxyanilino)-3-quinolinecarbonitrile as a tan solid, mp 205–207° C.;

$^1$H NMR (DMSO-$d_6$) δ 7.05 (m, 4H), 7.10 (t, J=7 Hz, 1H), 7.27 (dd, J=7, 2 Hz, 2H), 7.37 (m, 2H), 7.72 (dd, J=9, 2 Hz, 1H), 8.01 (d, J=2 Hz, 1H), 8.41 (t, J=4 Hz, 2H), 10.02 (s, 1H); MS (ES) m/z 416.1 (M+1). Analysis for $C_{22}H_{14}BrN_3O$: Calcd: C, 63.48; H, 3.39; N, 10.09. Found: C, 63.12; H, 3.29; N, 10.00.

REFERENCE EXAMPLE 11

Ethyl 2-Cyano-3-(3-iodophenylamino)acrylate (E/Z 1:1)

A mixture of 3-iodoaniline (5.0 g, 22.83 mmol) and ethyl(ethoxymethylene)cyanoacetate (3.86 g, 22.83 mmol) was heated at 120° C. for 30 minutes. The resultant solid mixture was cooled to room temperature and slurried in hexane (100 mL), filtered and washed with hexane to give 7.67 g (98% yield) of a 1:1 mixture of the E and Z isomers of ethyl 2-cyano-3-(3-iodophenylamino)acrylate as a white solid, mp 140–141° C.;

$^1$H NMR (DMSO-$d_6$) δ 1.25 (t, J=7 Hz, 1.5H), 1.25 (t, J=7 Hz, 1.5H), 4.18 (q, J=7 Hz, 1H), 4.22 (q, J=7 Hz, 1H), 7.15 (t, J=8 Hz, 0.5H), 7.16 (t, J=8 Hz, 0.5H), 7.44 (dd, J=8, 2 Hz, 0.5H), 7.48 (dd, J=8, 2 Hz, 0.5H), 7.51 (d, J=8 Hz, 0.5H), 7.52 (d, J=8 Hz, 0.5H), 7.81 (t, J=2 Hz, 0.5H), 7.96 (t, J=2 Hz, 0.5H), 8.31 (d, J=14 Hz, 0.5H), 8.48 (d, J=14 Hz, 0.5H), 10.65 (d, J=14 Hz, 0.5H), 10.75 (d, J=14 Hz, 0.5H); MS (ES) m/z 341.3 (M−1). Analysis for $C_{12}H_{11}IN_2O_2$: Calcd: C, 42.13; H, 3.24; N, 8.19. Found: C, 42.08; H, 3.34; N, 7.93.

REFERENCE EXAMPLE 12

4-Chloro-7-iodo-3-quinolinecarbonitrile

A mixture of ethyl 2-cyano-3-(3-iodophenylamino) acrylate (E/Z 1:1) (5.0 g, 14.61 mmol) in a 3 to 1 mixture of diphenyl ether and biphenyl (150 mL) was heated at reflux for 4 hours. After cooling to room temperature, the reaction mixture was poured into hexane (1.0 L). The precipitated solids were collected by filtration and thoroughly washed with hexane to give 3.60 g of crude 7-iodo-4-oxo-1,4-dihydroquinoline-3-carbonitrile as a light brown solid.

A mixture of crude 7-iodo-4-oxo-1,4-dihydroquinoline-3-carbonitrile (2.2 g, 7.43 mmol) and phosphorous oxychloride (14 mL) was heated at reflux for 45 minutes, then cooled to room temperature. The resultant mixture was evaporated to remove excess phosphorous oxychloride. The residue was slurried in aqueous saturated bicarbonate and water (1:1) (200 mL) and extracted with ethyl acetate. The combined extracts were dried over sodium sulfate, concentrated on silica gel (5 g) and purified by flash silica gel chromatography, eluting with ethyl acetate/hexane (1:10), to give 1.40 g (60% yield) of 4-chloro-7-iodo-3-quinolinecarbonitrile as a white solid, mp 165–167° C.;

$^1$H NMR (DMSO-d$_6$) δ 8.07 (d, J=9 Hz, 1H), 8.20 (dd, J=9 Hz, 1H), 8.64 (d, J=2 Hz, 1H), 9.20 (s, 1H); MS (ES) m/z 315.1 (M+1). Analysis for C$_{10}$H$_4$ClIN$_2$: Calcd: C, 38.19; H, 1.28; N, 8.91. Found: C, 38.24; H, 1.44; N, 8.65.

REFERENCE EXAMPLE 13

4-(2,4-Dichloro-5-methoxyanilino)-7-iodo-3-quinolinecarbonitrile

A mixture of 4-chloro-7-iodo-3-quinolinecarbonitrile (1.0 g, 3.18 mmol), 2,4-dichloro-5-methoxyaniline (prepared by the procedure described in WO 8501939-A1) (746 mg, 3.82 mmol) and pyridine hydrochloride (441 mg, 3.82 mmol) in 2-ethoxyethanol (16 mL) was heated at 100–110° C. for 2 hours. The resultant mixture was cooled to room temperature and diluted with water (50 mL) and aqueous saturated sodium bicarbonate (50 mL). The precipitated solids were collected by filtration, washed with aqueous saturated sodium bicarbonate and water and dried to give 1.42 g (94% yield) of 4-(2,4-dichloro-5-methoxyanilino)-7-iodo-3-quinolinecarbonitrile as a light yellow solid, mp 243–245° C.;

$^1$H NMR (DMSO-d$_6$) δ 3.86 (s, 3H), 6.44 (s, 1H), 7.81 (s, 1H), 8.15 (dd, J=9, 2 Hz, 1H), 8.33 (d, J=2 Hz, 1H), 8.40 (d, J=9 Hz, 1H), 8.90 (s, 1H); MS (ES) m/z 470.1 (M+1). Analysis for C$_{12}$H$_{10}$Cl$_2$IN$_3$O-0.65H$_2$O: Calcd: C, 42.38; H, 2.36; N, 8.72. Found: C, 42.01; H, 2.09; N, 8.75.

REFERENCE EXAMPLE 14

7-Bromo-4-{3-chloro-4-[(1-methyl-1H-imidazol-2-yl)sulfanyl]anilino}-3-quinolinecarbonitrile Following the procedure for Reference Example 7, a reaction mixture of 350 mg (1.3 mmol) of 7-bromo-4-chloro-3-quinolinecarbonitrile 376 mg (1.57 mmol) of 3-chloro-4-[(1-methyl-1H-imidazol-2-yl)thio]benzenamine (prepared by the procedure described in U.S. Pat. No. 4,973,599) and 151 mg (1.31 mmol) of pyridine hydrochloride in 8.0 mL of 2-ethoxyethanol was heated at 110–120° C. for 1 hour to yield 402 mg of 7-bromo-4-{3-chloro-4-[(1-methyl-1H-imidazol-2-yl)sulfanyl]anilino}-3-quinolinecarbonitrile as a bright yellow solid, mp 258–261° C.;

$^1$H NMR (DMSO-d$_6$) δ 8.84 (s, 1H), 8.51 (d, J=9 Hz, 1H), 8.22 (d, J=2 Hz, 1H), 7.91 (d, J=2 Hz, 1H), 7.90 (d, J=2 Hz, 1H), 7.75 (d, J=2 Hz, 1H), 7.60 (d, J=1.8 Hz, 1H); 7.30 (dd, J=8, 2 Hz, 1H), 7.18 (d, J=8 Hz, 1H), 3.77 (s, 3H); MS (ES) m/z 469.9, 471.9 (M+1). Analysis for C$_{20}$H$_{13}$BrClN$_5$S-1.8HCl: Calcd: C, 44.78; H, 2.78; N, 13.06. Found: C, 44.74; H, 2.78; N, 13.12.

REFERENCE EXAMPLE 15

Methyl 5-Methoxy-2-nitro-4-(benzyloxy)benzoate

Nitric acid (27 mL of a 70% solution) was added dropwise to a suspension of methyl 3-methoxy-4-(benzyloxy) benzoate (14.5 g, 53.0 mmol) in 150 mL of acetic acid. The mixture was stirred at room temperature for 15 minutes and then was heated at 50° C. for 4 hours. The reaction was cooled to room temperature and poured into ice. The precipitate was collected by filtration, washed with water and dried to provide 16.4 g of methyl 5-methoxy-2-nitro-4-(benzyloxy)benzoate as an off-white solid, mp 104–105° C.;

MS (ES) m/z 318.1 (M+1). Analysis for C$_{16}$H$_{15}$NO$_6$: Calcd: C, 60.57; H, 4.76; N, 4.41. Found: C, 60.39; H, 4.70; N, 4.28.

REFERENCE EXAMPLE 16

Methyl 4-Hydroxy-5-methoxy-2-nitrobenzoate

To a −78° C. solution of methyl 5-methoxy-2-nitro-4-(benzyloxy)benzoate (5 g, 15.6 mmol) in 100 mL of dichloromethane was added dropwise a solution of boron trichloride (46 mL of a 1M solution in methylene chloride, 46 mmol). After 5 minutes, 130 mL of methanol was added and the solution was allowed to warm to room temperature. The solvents were removed in vacuo and the residue was partitioned between methylene chloride and saturated aqueous sodium bicarbonate. The aqueous layer was extracted with additional methylene chloride and the organic layers were combined and dried over sodium sulfate. The solution was passed through a plug of hydrous magnesium silicate, concentrated in vacuo and dried to provide 3.5 g (97%) of methyl 4-hydroxy-3-methoxy-6-nitrobenzoate as a yellow solid, mp 101–102° C.;

MS (ES) m/z 226.1 (M+1). Analysis for C$_9$H$_9$NO$_6$: Calcd: C: 47.58; H: 3.99; N: 6.17. Found: C: 47.60; H: 3.94; N: 6.14.

REFERENCE EXAMPLE 17

Methyl 5-Methoxy-2-nitro-4-{[(trifluoromethyl) sulfonyl]oxy}benzoate

To a solution of methyl 4-hydroxy-3-methoxy-6-nitrobenzoate (1.0 g, 4.4 mmol) in a mixture of 10 mL of methylene chloride and 1 mL of pyridine, trifluoromethanesulfonic anhydride (0.73 mL, 6.6 mmol) was added dropwise. The reaction mixture was stirred at room temperature for 2 hours, then washed sequentially with 2N hydrochloric acid, water and saturated sodium bicarbonate. The organic layer was dried over sodium sulfate, filtered and concentrated in vacuo. The residue was dried to provide 1.4 g of methyl 5-methoxy-2-nitro-4-{[(trifluoromethyl)sulfonyl] oxy}-benzoate as a tan solid, mp 69–70° C.;

MS (ES) m/z 360.1 (M+1). Analysis for C$_{10}$H$_8$F$_3$NO$_8$S: Calcd: C, 33.43; H, 2.24; N, 3.90. Found: C, 33.66; H, 2.20; N, 3.83.

REFERENCE EXAMPLE 18

Methyl 2-Amino-5-methoxy-4-{[(trifluoromethyl) sulfonyl]oxy}benzoate

A mixture of methyl 5-methoxy-2-nitro-4-{ [(trifluoromethyl)sulfonyl]oxy}benzoate (1.50 g, 4.1 mmol), ammonium chloride (2.17 g, 41 mmol) and iron (1.17 g, 21 mmol) in 30 mL of ethanol and 10 mL of water was heated at reflux for several hours. The reaction was cooled to room temperature and the ethanol was removed in vacuo. Sodium bicarbonate was added to the residue and the mixture was extracted with ethyl acetate. The organic layer was washed with water followed by saturated sodium bicarbonate. The organic layer was then dried over sodium sulfate and passed through a plug of hydrous magnesium silicate to provide 1.49 g of methyl 2-amino-5-methoxy-4-{[(trifluoromethyl) sulfonyl]oxy}benzoate as off-white solid, mp 85–87° C.; MS (ES) m/z 330.1 (M+1). Analysis for C$_{10}$H10F$_3$NO$_6$S: Calcd: C, 36.48; H, 3.06; N, 4.25. Found: C, 36.66; H, 3.09; N, 4.22.

REFERENCE EXAMPLE 19

Methyl 2-{[(E)-(Dimethylamino)methylidene]
amino}-5-methoxy-4-{[(trifluoromethyl)sulfonyl]
oxy}benzoate A solution of methyl 2-amino-5-methoxy-4-{[(trifluoromethyl)sulfonyl]oxy}benzoate (9.5 g, 28.8 mmol) and 25 mL of dimethylformamide dimethylacetal was heated at 110° C. for several hours then cooled to room temperature and diluted with toluene. The mixture was concentrated in vacuo to give 10.2 g of methyl 2-{[(E)-(dimethylamino)methylidene]amino}-5-methoxy-4{[(trifluoromethyl)sulfonyl]oxy}benzoate as a thick oil;

MS (ES) m/z 385.1 (M+1). Analysis for $C_{13}H_{15}F_3N_2O_6S$: Calcd: C, 40.63; H, 3.93; N, 7.29. Found: C, 40.48; H, 3.86; N, 6.99.

REFERENCE EXAMPLE 20

3-Cyano-6-methoxy-4-oxo-1,4-dihydro-7-quinolinyl
Trifluoromethanesulfonate

To a solution of n-butyl lithium (25 mL of a 2.5M solution in hexane, 62.5 mmol) in 50 mL of tetrahydrofuran was added a solution of acetonitrile (5.0 mL, 95.7 mmol) in 80 mL of tetrahydrofuran. The reaction mixture was stirred at −78° C. for 15 minutes. A solution of methyl 2-{[(E)-(dimethylamino)methylidene]amino}-5-methoxy-4{[(trifluoromethyl)sulfonyl]oxy}benzoate (8.0 g 20.8 mmol) in 20 mL of tetrahydrofuran was added and stirring was continued for 2 hours at −78° C. The reaction was quenched by the addition of 15 mL of acetic acid and the mixture was allowed to warm to room temperature. The volatiles were removed in vacuo and water was added to the residue. The white precipitate was collected and purified by flash silica gel chromatography eluting with 10% hexane in ethyl acetate to provide 5.0 g of 3-cyano-6-methoxy-4-oxo-1,4-dihydro-7-quinolinyl trifluoromenthanesulfonate as a yellow solid, mp>240° C. (dec);

MS (ES) m/z 349.5 (M+1). Analysis for $C_{12}H_7F_3N_2O_5S$-0.13$H_2O$: Calcd: C, 41.09; H, 2.09; N, 7.97. Found: C, 40.97; H, 2.18; N, 7.58.

REFERENCE EXAMPLE 21

4-Chloro-3-cyano-6-methoxy-7-quinolinyl
Trifluoromethanesulfonate

To a solution of 3-cyano-6-methoxy-4-oxo-1,4-dihydro-7-quinolinyl trifluoromethanesulfonate (5.0 g, 14 mmol) in oxalyl chloride (30 mL of a 2M solution in dichloromethane) was slowly added 1 mL of dimethylformamide. The reaction mixture was heated at 40° C. for 3 h then cooled to room temperature and concentrated in vacuo. The residue was added to crushed ice and the resulting precipitate was collected and washed with water. The solid was dissolved in methylene chloride, dried over sodium sulfate and passed through a plug of hydrous magnesium silicate. The filtrate was concentrated in vacuo to provide 3.2 g (62%) of 4-chloro-3-cyano-6-methoxy-7-quinolinyl trifluoromethanesulfonate as an off-white solid, mp 112–113° C.;

MS (ES) m/z 367.0 (M+1). Analysis for $C_{12}H_6ClF_3N_2O_4S$-0.24$H_2O$: Calcd: C, 38.83; H, 1.76; N, 7.51; Found: C, 38.84; H, 1.76; N, 7.51.

REFERENCE EXAMPLE 22

3-Cyano-4-(2,4-dichloro-5-methoxyanilino)-6-
methoxy-7-quinolinyl Trifluoromethanesulfonate A mixture of 4-chloro-3-cyano-6-methoxy-7-quinolinyl trifluoromethanesulfonate (200 mg, 0.54 mmol), 2,4-dichloro-5-methoxyaniline (114 mg, 0.59 mmol) prepared by the procedure described in WO 8501939-A1 and pyridine hydrochloride (62 mg, 0.54 mmol) in 5 mL of ethoxyethanol was heated at 110° C. for 2 hours then cooled to room temperature and partitioned between saturated sodium bicarbonate and ethyl acetate. The organic layer was dried over sodium sulfate, filtered and concentrated in vacuo. The residue was purified by flash silica gel chromatography eluting with 3:2 ethyl acetate:hexane to provide 254 mg of 3-cyano-4-(2,4-dichloro-5-methoxyanilino)-6-methoxy-7-quinolinyl trifluoromethanesulfonate as an off-white solid, mp 220–223° C.;

MS (ES) m/z 523.9 (M+1). Analysis for $C_{19}H_{12}Cl_2F_3N_3O_5S$: Calcd: C, 43.69; H, 2.32; N, 8.05. Found: C, 43.87; H, 2.34; N, 7.91.

REFERENCE EXAMPLE 23

1-[(4-Bromo-2-thienyl)methyl]-4-ethylpiperazine

Sodium cyanoborohydride (1.07 g, 17.01 mmol) was added to a mixture of 4-bromo-2-thiophenecarboxaldehyde (2.50 g, 13.08 mmol), N-ethylpiperazine (1.49 g, 13.08 mmol) and acetic acid (942 mg, 15.70 mmol) in 6 mL of ethanol and the mixture was stirred at room temperature for 4 hours, then poured into saturated sodium bicarbonate and extracted with methylene chloride. The organic layer was extracted with 10% aqueous hydrochloric acid and the aqueous layer was neutralized with 10N sodium hydroxide and saturated sodium bicarbonate. The aqueous layer was extracted with methylene chloride and the combined methylene chloride extracts were dried over magnesium sulfate, filtered and concentrated in vacuo. The residue was recrystallized from hexane to provide 170 mg of a light yellow solid. Concentration of the mother liquor provided an additional 2.02 g of 1-[(4-bromo-2-thienyl)methyl]-4-ethylpiperazine, mp 168–169° C.;

$^1$H NMR (DMSO-$d_6$) δ 1.22 (t, J=7 Hz, 3H), 2.75–3.55 (m, 10H), 3.77 (s, 2H), 7.05 (s, 1H), 7.61 (s, 1H); MS (ES) m/z 289.2 (M+1).

REFERENCE EXAMPLE 24

4-{[2-(4-Morpholinylmethyl)-3-thienyl]
methyl}morpholine

Using an analogous procedure to that described for Reference Example 23, 4-{[2-(4-morpholinylmethyl)-3-thienyl]methyl}morpholine was prepared from 2,3-bisthiophene-carboxaldehyde and morpholine in 34% yield as a white solid, mp 58–60° C.;

$^1$H NMR (DMSO-$d_6$) δ 2.25–2.35 (m, 4H), 2.41 (t, J=4 Hz, 4H), 3.42 (s, 2H), 3.53–3.58 (m, 8H), 3.65 (s, 2H), 6.92 (d, J=5 Hz, 1H), 7.34 (d, J=5 Hz, 1H); MS (ES) m/z 283.2 (M+1); Calcd: C, 59.54; H, 7.85; N, 9.92. Found: C, 59.26; H, 3.90; N, 10.14.

REFERENCE EXAMPLE 25

4-[(5-Bromo-2-thienyl)methyl]morpholine

Using an analogous procedure to that described for Reference Example 23, 4[(5-bromo-2-thienyl)methyl]morpholine was prepared from 5-bromo-2-carboxaldehyde and morpholine in 40% yield as a semi-solid;

$^1$H NMR (DMSO-$d_6$) δ 2.90–3.10 (m, 2H), 3.20–3.35 (m, 2H), 3.60–3.75 (m, 2H), 3.85–4.00 (m, 2H), 4.35 (s, 2H), 7.10–7.30 (m, 2H); MS (ES) m/z 289.1 (M+1)

REFERENCE EXAMPLE 26

4-(5-Hexenyl)morpholine

A mixture of 6-bromohexene (2.0 g, 12.27 mmol), morpholine (2.15 g, 24.66 mmol) and a catalytic amount of sodium iodide in ethylene glycol dimethyl ether was heated at 80° C. for 1 hour to give a thick solid cake which was cooled to room temperature and slurried with hexane. The suspension was filtered and washed with hexane and diethyl ether. The filtrate was concentrated and dried in vacuo to give 1.75 g (84% yield) of 4-(5-hexenyl)morpholine as a colorless oil;

$^1$H NMR (DMSO-$d_6$) δ 1.35–1.60 (m, 4H), 2.06 (dt, J=17, 7 Hz, 2H), 2.33 (t, J=7 Hz, 2H), 2.44 (t, J=5 Hz, 4H), 3.72 (t, J=5 Hz, 4H), 4.93–5.03 (m, 1H), 5.74–5.87 (m, 2H); MS (ES) m/z 170.1 (M+1).

REFERENCE EXAMPLE 27

4-[(E)-3-(3-Thienyl)-2-propenoyl]morpholine

A mixture of 3-(2-thienyl)acrylic acid (2.0 g, 12.97 mmol), morpholine (2.37 g, 27.25 mmol), 1-(3-dimethylaminopropyl)-3-ethylcarbodiimide hydrochloride (2.43 g, 14.27 mmol) and a catalytic amount of 4-dimethylaminopyridine in methylene chloride (70 mL) was stirred at room temperature for 2 hours and diluted with methylene chloride to a volume of 150 ml. The resultant mixture was washed with 5% hydrochloric acid (50 mL×2), saturated aqueous sodium bicarbonate (50 mL), and water (50 mL) and concentrated. The residue was slurried in hexane, filtered and washed with hexane to give 1.78 g of 4-[(E)-3-(3-thienyl)-2-propenoyl]morpholine as is a white solid, mp 141–142° C.;

$^1$H NMR (DMSO-$d_6$) δ 3.60–3.80 (m, 8H), 6.64 (d, J=15 Hz, 1H), 7.04 (dd, J=5, 4 Hz, 1H), 7.23 (d, J=4 Hz, 1H), 7.32 (d, J=5 Hz, 1H), 7.84 (d, J=15 Hz, 1H); MS (ES) m/z 224.1 (M+1).

REFERENCE EXAMPLE 28

4-[(E)-3-(2-Thienyl)-2-propenyl]morpholine

Lithium aluminum hydride (10M in tetrahydrofuran, 8.96 mL, 8.96 mmol) was added to a stirring mixture of 4-[(E)-3-(3-thienyl)-2-propenoyl]morpholine (1.0 g, 4.48 mmol) and tetrahydrofuran (22 mL) at room temperature. The mixture was heated to 45° C. for 2 hours. Ten percent hydrochloric acid (3.7 mL) was added dropwise to destroy the excess lithium aluminum hydride. The resultant mixture was diluted with 20 mL of water and 10 ml of 1N sodium hydroxide and extracted with methylene chloride (940 mL×4). The combined organic layers were washed with saturated sodium chloride and water, dried over sodium sulfate and concentrated to give a light yellow syrup which was purified by flash silica gel column chromatography, eluting with 1% methanol in methylene chloride) to give 450 mg (48%) of 4-[(E)-3-(2-thienyl)-2-propenyl]morpholine as a colorless oil;

$^1$H NMR (DMSO-$d_6$) δ 2.52 (t, J=5 Hz, 4H), 3.13 (d, J=7 Hz, 2H), 3.75 (t, J=5 Hz, 4H), 6.09 (dt, J=16, 7 Hz, 1H), 6.66 (d, J=16 Hz, 1H), 6.83–6.97 (m, 2H), 7.14 (dd, J=5, 1 Hz, 1H); MS (ES) m/z 209.9 (M+1).

REFERENCE EXAMPLE 29

4-[4-(2-Thienyl)butyl]morpholine

Using an analogous procedure to that described for Reference Example 27, 4-[4-(2-thienyl)butanoyl]morpholine was prepared from 4-(2-thienyl)butyric acid and morpholine in 71% yield as a colorless oil;

$^1$H NMR (CDCl$_3$): δ 1.99–2.08 (m, 2H), 2.35 (t, J=7 Hz, 2H), 2.91 (t, J=7 Hz), 2H), 3.40 (t, J=5 Hz, 2H), 3.55–3.70 (m, 6H), 6.80 (dd, J=3, 1 Hz, 6.92 (dd, J=5, 3 Hz, 1H), 7.12 (dd, J=5, 1 Hz, 1H); MS (ES) m/z 239.9 (M+1). Analysis for C$_{12}$H$_{17}$NO$_2$S-0.2H$_2$O: Calcd: C, 59.32; H, 7.20; N, 5.77. Found: C, 59.38; H, 6.96; N, 5.64.

REFERENCE EXAMPLE 30

4-[4-(2-Thienyl)butyl]morpholine

Using an analogous procedure to that described for Reference Example 28, 4-[4-(2-thienyl)butyl]morpholine was prepared from reduction of 4-[4-(2-thienyl)butanoyl] morpholine with lithium aluminum hydride in 86% yield as a colorless oil;

$^1$H NMR (DMSO-$d_6$) δ 1.40–1.55 (m, 2H), 1.56–1.68 (m, 2H), 2.20–2.35 (m, 4H), 2.82 (t, J=10 Hz, 2H), 3.27–3.40 (m, 4H), 3.55 (t, J=5 Hz, 2H), 6.83 (dd, J=3, 1 Hz, 1H), 6.92 (dd, J=5, 3 Hz, 1H), 7.31 (dd, J=5, 1 Hz, 1H); MS (ES) m/z 226.2 (M+1).

REFERENCE EXAMPLE 31

4-(3-Bromobenzyl)morpholine

To a mixture of 5.0 g (27.0 mmol) of 3-bromobenzaldehyde, 2.35 (27.0 mmol) of morpholine and 1.95 g (32.4 mmol) of acetic acid in 100 mL of ethanol was added 2.21 g (35.1 mmol) of sodium cyanoborohydride in portions over 5 minutes. The resulting mixture was stirred at room temperature for 15 hours. After removal of ethanol in vacuo, the residue was partitioned between 40 mL of methylene chloride and 40 mL of saturated aqueous sodium bicarbonate solution. The layers were separated, and the aqueous layer was extracted with 2×20 mL methylene chloride. The organic layers were combined and extracted with 3×50 mL of a 1N hydrochloric acid solution. The combined aqueous solution was neutralized with 5N sodium hydroxide, then sodium bicarbonate. The milky aqueous solution was extracted with 3×50 mL methylene chloride, and the combined organic layers were dried over magnesium sulfate. Following removal of the magnesium sulfate by filtration, and removal of methylene chloride in vacuo, 3.5 g of 4-(3-bromobenzyl)morpholine was obtained as a clear oil;

$^1$H NMR (DMSO-$d_6$) δ 7.50 (d, J=1 Hz, 1H), 7.47–7.43 (m, 1H), 7.33–7.26 (m, 2H), 3.57 (t, J=5 Hz, 4H), 3.46 (s, 2H), 2.34 (t, J=5 Hz, 4H); MS (ES) m/z 256.2, 258.1 (M+1). Analysis for C$_{11}$H$_{14}$BrNO: Calcd: C, 51.58; H, 5.51; N, 5.47. Found: C, 51.62; H, 5.27; N, 5.31.

REFERENCE EXAMPLE 32

1-Ethyl-4-[2-(4-iodophenyl)acetyl]piperazine

A mixture of 4.00 g (15.3 mmol) of 4-iodophenylacetic acid, 1.74 g (15.3 mmol) of ethylpiperazine, 3.22 g (16.8 mmol) of 1-[3-(dimethylamino)propyl]-3-ethylcarbodiimide hydrochloride and 0.01 g (0.082 mmol) of 4-(dimethylamino)-pyridine in 35 mL of methylene chloride was stirred at room temperature for 15 hours. The mixture was washed with 30 mL water, then extracted with 3×30 mL 1N hydrochloric acid. The combined aqueous layers were neutralized with 10N sodium hydroxide, then potassium bicarbonate. The milky solution was extracted with 3×40 mL of ethyl acetate, and the combined organic layers were dried over magnesium sulfate. After filtering off the magnesium sulfate, the solvent was removed in vacuo to provide 3.6 g of 1-ethyl-4-[2-(4-iodophenyl)acetyl]piperazine as a white solid, mp 81–83° C.;

$^1$H NMR (DMSO-d$_6$) δ 7.65 (d, J=8 Hz, 2H), 7.03 (d, J=8 Hz, 2H), 3.66 (s, 2H), 3.44 (m, 4H), 2.34–2.27 (m, 6H), 0.98 (t, J=7 Hz, 3H); MS (ES) m/z 359.1 (M+1). Analysis for C$_{14}$H$_{19}$IN$_2$C: Calcd: C, 46.94; H, 5.35; N, 7.82. Found: C, 46.85; H, 5.37; N, 7.83.

REFERENCE EXAMPLE 33

1-Ethyl-4-[2-(4-iodophenyl)ethyl]piperazine

To a solution of 3.52 g (9.83 mmol) of 1-ethyl-4-[2-(4-iodophenyl)acetyl]piperazine (Reference Example 32) in 30 mL of tetrahydrofuran was added 1.86 mL (19.7 mmol) of borane-methyl sulfide at room temperature while stirring. The reaction mixture was heated at reflux for 2 hours. After cooling, the mixture was quenched with methanol, followed by removal of the solvents in vacuo. The residue was taken up in 10 mL ethanol and 20 mL 1N sodium hydroxide. The reaction mixture was heated at reflux for 2 hours, then cooled to room temperature. The mixture was partitioned between 75 mL of ethyl acetate and 40 mL of water. Following separation of the layers, the aqueous layer was further extracted with 2×30 mL of ethyl acetate. The organic layers were combined, washed with saturated sodium chloride and then dried over magnesium sulfate. After filtering off the magnesium sulfate, the solvent was removed in vacuo to provide the crude product. This material was purified by passing through a short pad of silica gel, eluting with 95:5 methylene chloride/methanol, to provide 3.2 g of 1-ethyl-4-[2-(4-iodophenyl)ethyl]piperazine as a white wax;

$^1$H NMR (DMSO-d$_6$) δ 7.61 (d, J=8 Hz, 2H), 7.04 (d, J=8 Hz, 2H), 2.67 (t, J=7 Hz, 2H), 2.48–2.27 (m, 10H), 2.27 (t, J=7 Hz, 2H), 0.97 (t, J=7 Hz, 3H); MS (ES) m/z 345.1 (M+1). Analysis for C$_{14}$H$_{21}$IN$_2$.0.17CH$_2$Cl$_2$: Calcd: C, 47.45; H, 6.00; N, 7.81. Found: C, 47.83; H, 5.68; N, 7.43.

REFERENCE EXAMPLE 34

1-(4-Bromobenzyl)-4-ethylpiperazine

Using an analogous procedure to that described for Reference Example 31, 5.0 g (27.0 mmol) of 4-bromobenzaldehyde, 3.09 g (27.0 mmol) of ethyl piperazine, 1.95 g (32.4 mmol) of acetic acid and 2.21 g (35.1 mmol) of sodium cyanoborohydride in 100 mL of ethanol were allowed to react at room temperature. Workup provided 4.2 g of 1-(4-bromobenzyl)-4-ethylpiperazine as a yellow oil;

$^1$H NMR (DMSO-d$_6$) δ 7.50 (d, J=8 Hz, 2H), 7.25 (d, J=8 Hz, 2H), 3.41 (s, 2H), 2.36–2.30 (m, 8H), 2.29 (q, J=7 Hz, 2H), 0.97 (t, J=7 Hz, 3H); MS (ES) m/z 283.1, 285.1 (M+1). Analysis for C$_{13}$H$_{19}$BrN$_2$.0.3H$_2$O: Calcd: C, 54.10; H, 6.85; N, 9.71. Found: C, 54.25; H, 6.76; N, 9.71.

REFERENCE EXAMPLE 35

4-[2-(3-Bromophenyl)ethyl]morpholine

Using an analogous procedure to that described for Reference Example 33, a solution of 3.0 g (10.6 mmol) of 4-[(3-bromophenyl)acetyl]morpholine (prepared according to the procedure of WO 9842670) in 25 mL of dry tetrahydrofuran was allowed to react with 2.0 mL (21.1 mmol) of borane-methyl sulfide. Following the same workup and treatment with aqueous sodium hydroxide, 2.1 g of 4-[2-(3-bromophenyl)ethyl]morpholine was obtained as a clear oil;

$^1$H NMR (DMSO-d$_6$) δ 7.45 (d, J=1 Hz, 1H), 7.39–7.34 (m, 1H), 7.26–7.23 (m, 2H), 3.56 (t, J=5 Hz, 4H), 2.73 (t, J=7 Hz, 2H), 2.52–2.49 (m, 2H), 2.41 (t, J=5 Hz, 4H); MS (ES) m/z 270.2, 272.1 (M+1). Analysis for C$_{12}$H$_{16}$BrNO: Calcd: C, 53.35; H, 5.97; N, 5.18. Found: C, 53.16; H, 6.07; N, 5.46.

REFERENCE EXAMPLE 36

4-[4-Bromo-2-(4-morpholinylcarbonyl)benzoyl]morpholine

A mixture of 3.00 g (12.2 mmol) of 4-bromophthalic acid, 2.13 g (24.4 mmol) of morpholine, 5.16 g (26.9 mmol) of 1-[3-(dimethylamino)propyl]-3-ethylcarbodiimide hydrochloride and 0.01 g (0.082 mmol) of 4-(dimethylamino) pyridine in 30 mL of methylene chloride was stirred at room temperature for 15 hours. The mixture was washed with 30 mL of water, 2×20 mL of 1N hydrochloric acid and then with 2×20 mL of saturated sodium bicarbonate. After filtering off the magnesium sulfate, the solvent was removed in vacuo. The crude product was purified by flash silica gel chromatography, eluting with 97:3 methylene chloride/methanol to provide 3.5 g of 4-[4-bromo-2-(4-morpholinylcarbonyl)benzoyl]morpholine as a white foam;

$^1$H NMR (acetone-d$_6$) δ 7.68 (dd, J=8, 2 Hz, 1H), 7.58 (d, J=2 Hz, 1H), 7.35 (d, J=8 Hz, 1H), 3.65 (br s, 12H), 3.29 (br s, 4H); MS (ES) m/z 383.3, 385.2 (M+1). Analysis for C$_{16}$H$_{19}$BrN$_2$O$_4$: Calcd: C, 50.14; H, 5.00; N, 7.31. Found: C, 49.98; H, 4.76; N, 7.20.

REFERENCE EXAMPLE 37

4-[4-Bromo-2-(4-morpholinymethyl)benzyl]morpholine

Using an analogous procedure to that described for Reference Example 33, a solution of 2.10 g (5.48 mmol) of 4-[4-bromo-2-(4-morpholinylcarbonyl)benzoyl]morpholine in 25 mL of tetrahydrofuran was reacted with 2.10 mL (21.9 mmol) of borane-methyl sulfide. Following the same workup and treatment with aqueous sodium hydroxide, 1.6 g of 4-[4-bromo-2-(4-morpholinylmethyl)benzyl]morpholine was obtained as a clear oil;

$^1$H NMR (DMSO-d$_6$) δ 7.50 (d, J=2 Hz, 1H), 7.41 (dd, J=8, 2 Hz, 1H), 7.26 (d, J=8 Hz, 1H), 3.57–3.52 (m, 12H), 2.36–2.32 (m, 8H); MS (ES) m/z 355.3, 357.4 (M+1). Analysis for C$_{16}$H$_{23}$BrN$_2$O$_2$.0.15CH$_2$Cl$_2$: Calcd: C, 52.71; H, 6.38; N, 7.61. Found: C, 52.73; H, 6.11; N, 7.33.

REFERENCE EXAMPLE 38

4-[2-(4-Iodophenyl)acetyl]morpholine

Using an analogous procedure to that described for Reference Example 36, a mixture of 4.0 g (15.3 mmol) of 4-iodoacetic acid, 1.33 g (15.3 mmol) of morpholine, 3.22 g (16.8 mmol) of 1-[3-(dimethylamino)propyl]-3-ethylcarbodiimide hydrochloride and 0.01 g (0.082 mmol) of 4-(dimethylamino)pyridine in 35 mL of methylene chloride was reacted at room temperature. Workup provided 4.2 g of 4-[2-(4-iodophenyl)acetyl]morpholine as a white solid, mp 114–117° C.;

$^1$H NMR (DMSO-d$_6$) δ 7.66 (d, J=8 Hz, 2H), 7.03 (d, J=8 Hz, 2H), 3.68 (s, 2H), 3.54–3.42 (m, 8H); MS (ES) m/z 332.2 (M+1). Analysis for C$_{12}$H$_{14}$INO$_2$: Calcd: C, 43.52; H, 4.26; N, 4.23. Found: C, 43.74; H, 4.29; N, 4.43.

REFERENCE EXAMPLE 39

4-[2-(4-Iodophenyl)ethyl]morpholine

Using an analogous procedure to that described for Reference Example 33, a solution of 3.50 g (5.48 mmol) of 4-[2-(4-iodophenyl)acetyl]morpholine in 35 mL of tetrahydrofuran was reacted with 2.01 mL (21.1 mmol) of borane-methyl sulfide. Following the same workup and treatment with aqueous sodium hydroxide, 3.0 g of 4-[2-(4-iodophenyl)ethyl]morpholine was obtained as a white solid, mp 64–67° C.;

$^1$H NMR (DMSO-d$_6$) δ 7.62 (d, J=8 Hz, 2H), 7.06 (d, J=8 Hz, 2H), 3.55 (t, J=5 Hz, 4H), 2.69 (t, J=7 Hz, 2H), 2.47 (t, J=7 Hz, 2H), 2.39 (t, J=5 Hz, 4H); MS (ES) m/z 318.0 (M+1). Analysis for C$_{12}$H$_{16}$INO: Calcd: C, 45.44; H, 5.08; N, 4.42. Found: C, 45.58; H, 5.09; N, 4.56.

REFERENCE EXAMPLE 40

4-(4-Pentenyl)morpholine

Using an analogous procedure to that described for Reference Example 26, 4-(4-pentenyl)morpholine was prepared from 5-bromopentene and morpholine in 40% yield as colorless oil;

$^1$H NMR (DMSO-d$_6$), δ 1.54–1.61 (m, 2H), 2.07 (dt, J=8, 7 Hz, 2H), 2.34 (t, J=8 Hz, 2H), 2.44 (t, J=5 Hz, 4H), 3.72 (t, J=5 Hz, 4H), 4.90–5.06 (m, 2H), 5.75–5.88 (m, 1H); MS (ES) m/z 155.9 (M+1).

REFERENCE EXAMPLE 41

4-(4-Pentynyl)morpholine

Using an analogous procedure to that described for Reference Example 26, 4-(4-pentynyl)morpholine was prepared from 5-chloropentyne and morpholine in 31% yield as colorless oil;

$^1$H NMR (DMSO-d$_6$), δ 1.66–1.76 (m, 2H), 1.95 (t, J=3 Hz, 1H), 2.26 (dt, J=7, 3 Hz, 2H), 2.36–2.49 (m, 6H), 3.72 (t, J=5 Hz, 4H); MS (ES) m/z 153.9 (M+1).

REFERENCE EXAMPLE 42

4-[(5-Bromo-2-furanyl)methyl]morpholine

Using an analogous procedure to that described for Reference Example 23, 4-[(5-bromo-2-furanyl)methyl]morpholine was prepared from 5-bromo-2-furaldehyde and morpholine in 54% yield as a colorless oil;

$^1$H NMR (DMSO-d$_6$): δ 2.36 (t, J=5 Hz, 4H), 3.46 (s, 2H), 3.56 (t, J=5 Hz, 4H) 6.37 (d, J=3 Hz, 1H), 6.49 (d, J=3 Hz, 1H); MS (ES) m/z 248.1 (M+1).

REFERENCE EXAMPLE 43

Tributyl[5-(1,3-dioxolan-2-yl)-3-thienyl]stannane

To a −78° C. solution of 2-(4-bromo-2-thienyl)-1,3-dioxolane (4.41 g, 18.76 mmol) (prepared according to the procedure of Johnson, A., *J. Org. Chem.*, 41, 1320 (1976) in 20 mL of tetrahydrofuran was added tri-n-butylstannyl chloride (6.0 mL, 22.15 mmol) followed by 2.5M n-butyl lithium in hexane (10.0 mL, 25.0 mmol). The reaction mixture was stirred at −78° C. for 3.5 hours then partitioned between ethyl acetate and water. The organic layer was washed with water, dried over magnesium sulfate, filtered and concentrated in vacuo. The residue was purified by flash silica gel chromatography eluting with 8:1 hexane:ethyl acetate to provide 4.86 g of tributyl[5-(1,3-dioxolan-2-yl)-3-thienyl]stannane (58% yield) as a colorless oil;

$^1$H NMR (DMSO-d$_6$): δ 0.85 (t, J=6 Hz, 9H), 1.02 (dd, J=6 Hz, 6H), 1.28 (m, 6H), 1.50 (m, 6H), 3.88–4.07 (m, 4H), 6.06 (s, 1H), 7.20 (s, 1H), 7.50 (s, 1H); MS (ES) m/z 447.1 (M+1).

REFERENCE EXAMPLE 44

4-[(5-Bromo-3-pyridinyl)carbonyl]morpholine

A mixture of 5-bromonicotinic acid (5.05 g, 25 mmol) and carbonyldiimidazole (4.86 g, 30 mmol) in 100 mL of tetrahydrofuran was stirred at room temperature for two hours. Morpholine (5.0 g, 57.4 mmol) was added to the solution, and the mixture was stirred for one additional hour at room temperature. The mixture was partitioned between ethyl acetate and water. The ethyl acetate layer was washed with water and brine, dried over magnesium sulfate, and filtered through hydrous magnesium silicate. Concentration of the filtrate provided 2.73 g (40% yield) of 4-[(5-bromo-3-pyridinyl)carbonyl]morpholine as a white solid, mp 49–51° C.;

$^1$H NMR (DMSO-d$_6$) δ 3.32 (m, 4H), 3.63 (m, 4H), 8.15 (t, J=2 Hz, 1H), 8.61 (d, J=2 Hz, 1H), 8.80 (d, J=2 Hz, 1H); MS (E) m/z 271.2 (M+1). Analysis for C$_{10}$H$_{11}$BrN$_2$O$_2$; Calcd: C, 44.30; H, 4.09; N, 10.33. Found: C, 43.91; H, 3.99; N, 10.35.

REFERENCE EXAMPLE 45

4-[(5-Bromo-3-pyridinyl)methyl]morpholine

To a solution of 4-[(5-bromo-3-pyridinyl)carbonyl]morpholine (2.71 g, 10 mmol) in 100 mL of tetrahydrofuran was added 10 mL of 10 M borane-methyl sulfide complex (100 mmol). The mixture was stirred at room temperature for 20 hours, and quenched slowly with 100 mL of 1 N sodium hydroxide. The resulting mixture was stirred at room temperature for 24 hours. Ethyl acetate was added, and the layers were separated. The ethyl acetate layer was dried over magnesium sulfate. Removal of the solvent in vacuo gave a residue which was purified by flash silica gel chromatography eluting with a gradient of 2:1 to 1:1 hexane:ethyl acetate to provide 1.02 g (40% yield) of 4-[(5-bromo-3-pyridinyl)methyl]morpholine as a colorless oil;

$^1$H NMR (DMSO-d$_6$) δ 2.36 (t, J=4 Hz, 4H), 3.51 (s, 2H), 3.57 (t, J=4 Hz, 4H), 7.97 (t, J=2 Hz, 1H), 8.49 (d, J=2 Hz, 1H), 8.60 (d, J=2 Hz, 1H); MS (ES) m/z 257.2 (M+1). Analysis for C$_{10}$H$_{13}$BrN$_2$O-0.15H$_2$O; Calcd: C, 46.23; H, 5.16; N, 10.78. Found: C, 46.16; H, 5.09; N, 10.53.

REFERENCE EXAMPLE 46

4-(4-Bromobenzyl)morpholine

Using an analogous procedure to that described for Reference Example 31, 5.0 g (27.0 mmol) of 3-bromobenzaldehyde, 2.35 g (27.0 mmol) of morpholine, 1.95 g (32.4 mmol) of acetic acid and 2.21 g (35.1 mmol) of sodium cyanoborohydride in 100 mL of ethanol were reacted at room temperature. Workup provided 4.5 g of 4-(4-bromobenzyl)morpholine as a white solid, mp 68–71° C.;

$^1$H NMR (DMSO-d$_6$): δ 7.51 (d, J=8 Hz, 2H), 7.27 (d, J=8 Hz, 2H), 3.56 (t, J=5 Hz, 4H), 3.43 (s, 2H), 2.33 (t, J=5 Hz, 4H). MS (ES) m/z 256.1, 258.1 (M+1). Analysis for C$_{11}$H$_{14}$BrNO: Calcd: C, 51.58; H, 5.51; N, 5.47; Found: C, 51.76; H, 5.50; N, 5.35.

REFERENCE EXAMPLE 47

Tributyl[5-(1,3-dioxolan-2-yl)-2-thienyl]stannane

To a −78° C. solution of 2-(2-thienyl)-1,3-dioxolane (4.00 g, 25.64 mmol) (prepared according to the procedure of Johnson, A., *J. Org. Chem.*, 41, 1320 (1976) in 30 mL of tetrahydrofuran was added 2.5M n-butyl lithium in hexane (14.0 mL, 31.0 mmol). The reaction mixture was stirred at −78° C. for 10 minutes, then stirred at 0° C. for 30 minutes. The reaction mixture was cooled to −78° C. and tri-n-butylstannyl chloride (8.4 mL, 31.02 mmol) was added and the reaction mixture was allowed to warm to room temperature and stirred overnight. The reaction mixture was partitioned between ethyl acetate and water. The organic layer was washed with water, dried over magnesium sulfate, filtered and concentrated in vacuo. The residue was purified by flash silica gel chromatography eluting with 8:1 hexane-:ethyl acetate to provide 4.80 g of tributyl[5-(1,3-dioxolan-2-yl)-2-thienyl]stannane (42% yield) as an orange oil;

$^1$H NMR (DMSO-d$_6$): δ 0.85 (t, J=6 Hz, 9H), 1.08 (dd, J=6 Hz, 6H), 1.29 (m, 6H), 1.51 (m, 6H), 3.87–4.28 (m, 4H), 6.05 (s, 1H), 7.06 (d, J=3 Hz, 1H), 7.30 (d, J=3 Hz, 1H); MS (ES) m/z 447.1 (M+1).

REFERENCE EXAMPLE 48

4-{[6-(Tributylstannyl)-3-pyridinyl])methyl}morpholine

To a −78° C. solution of 2-bromo-5-(morpholinomethyl) pyridine (337.3 mg, 1.31 mmol) (prepared according to the procedure of Windscheif P.-M., *Syntheses*, 87 (1994) in 2.2 mL of tetrahydrofuran was added 2.5M n-butyl lithium in hexane (0.65 mL, 1.62 mmol). The reaction mixture was stirred at −78° C. for 30 minutes where upon a solution of tri-n-butylstannyl chloride (434.9 mg, 1.33 mmol) in tetrahydrofuran (0.7 mL) was added. The resulting reaction mixture was stirred at −78° C. for 4 hours, then allowed to warm to room temperature. The reaction mixture was partitioned between diethyl ether and water. The organic layer was washed with water, dried over sodium sulfate, filtered and concentrated in vacuo, to give 895.7 mg of the crude product as a yellow oil. An analytical sample was obtained via purification by preparative thin layer chromatography, with a developing solvent of 1:1 ethyl acetate/hexane, to provide 4-{[6-(tributylstannyl)-3-pyridinyl] methyl}morpholine as a yellow oil;

$^1$H NMR (DMSO-d$_6$) δ 0.88 (t, J=7 Hz, 9H), 1.12 (dd, J=6 Hz, 6H), 1.34 (m, 6H), 1.54 (m, 6H), 2.44 (t, J=5 Hz, 4H), 3.46 (s, 2H), 3.70 (m, 4H), 7.36 (d, J=8 Hz, 1H), 7.48 (m, 1H), 8.66 (s, 1H); MS (ES) m/z 469.2 (M+1). Analysis for C$_{22}$H$_{40}$N$_2$OSn: Calcd: C, 56.55; H, 8.63; N, 5.99. Found: C, 56.76; H, 8.28; N, 5.83.

REFERENCE EXAMPLE 49

2-(Phenylsulfonyl)ethanamine

An oven dried flask was charged with 2-(phenylsulfonyl) acetonitrile (5.0 g, 27.59 mmol) and tetrahydrofuran (2.67 mL) under nitrogen. The mixture was stirred and heated to reflux. Borane-methyl sulfide complex (3.26 mL, 30.35 mmol) was added at a rate that the reaction mixture gently refluxed (caution: gas evolution may be vigorous!). Dimethyl sulfide was distilled and collected during the addition. The reaction mixture was heated at reflux for an additional 30 minutes and then cooled to room temperature. 6.0N Hydrochloric acid (16.5 mL) was very slowly added to the solidified reaction mixture followed by heating at reflux for 20 minutes to give a clear solution. The reaction mixture was cooled to room temperature, basified with 10N sodium hydroxide to pH 8–9 and extracted with ethyl acetate. The combined extracts were dried over sodium sulfate, concentrated and purified by flash column chromatography eluting with 1% methanol in methylene chloride to give 3.25 g (64% yield) of 2-(phenylsulfonyl)ethanamine as a colorless oil;

$^1$HNMR (DMSO-d$_6$) δ 2.78 (t, J=7 Hz, 2H), 3.36 (t, J=7 Hz, 2H), 7.69 (t, J=7 Hz, 2H), 7.76 (t, J=7 Hz, 1H), 7.89 (d, J=7 Hz, 2H); MS (ES) m/z 186.0 (M+H).

REFERENCE EXAMPLE 50

N-(2-Methoxy-5-nitrophenyl)acetamide

To a stirred solution of 90 g (0.54 mol) of 2-methoxy-5-nitroaniline in 1100 mL of water was slowly added acetic acid (200 mL, 2.12 mol) at room temperature. The reaction mixture was stirred at room temperature for 1.5 hours and filtered. The solid was washed with water, ether, and dried to give 133 g of crude yellow product (90% yield), mp 172–177° C.;

$^1$H NMR (DMSO-d$_6$) δ 9.56 (s, 1H), 9.00 (d, J=3 Hz, 1H), 8.02 (dd, J=9 Hz, 3 Hz, 1H), 7.26 (d, J=9 Hz, 1H), 3.99 (s, 3H), 2.15 (s, 3H); MS (ES) m/z 211.1 (M+1).

REFERENCE EXAMPLE 51

N-(5-Amino-2-methoxyphenyl)acetamide

An amount of 30 g (0.14 mol) of N-(2-methoxy-5-nitrophenyl)acetamide was dissolved in 750 mL of methanol and 195 mL of water, and to this was added 40 g (0.72 mol) of iron powder, and 53 g (0.99 mol) of ammonium chloride at room temperature. The suspension was heated at 50° C. for 0.5 hour, then cooled to room temperature and filtered. The residue was washed with ethyl acetate, and the combined filtrate was evaporated to dryness. The solid was basified with saturated sodium bicarbonate solution, and extracted with ethyl acetate. The organic phase was dried over magnesium sulfate and evaporated to dryness to yield a brown solid (21 g, 83% yield), mp 83° C.;

$^1$H NMR (DMSO-d$_6$) δ 8.85 (broad s, 1H), 7.32 (d, J=2 Hz, 1H), 6.71 (d, J=8 Hz, 1H), 6.24 (dd, J=8 Hz, 2 Hz, 1H), 4.64 (s, 2H), 3.68 (s, 3H), 2.05 (s, 3H); MS (ES) m/z 181.1 (M+1). Analysis for C$_9$H$_{12}$N$_2$O$_2$: Calcd: C, 59.99; H, 6.71; N, 15.55. Found: C, 59.65; H, 6.63; N, 15.23.

REFERENCE EXAMPLE 52

Ethyl (E)-3-[3-(Acetylamino)-4-methoxyanilino]-2-cyano-2-propenoate and Ethyl (Z)-3-[3-(Acetylamino)-4-methoxyanilino]-2-cyano-2-propenoate An amount of 4.95 g (0.0275 mol) of N-(5-amino-2-methoxyphenyl)acetamide was heated with ethyl (ethoxymethylene)cyanoacetate (4.74 g, 0.028 mol), at 120° C. for 2 hours. The reaction mixture was evaporated to dryness to give a brown solid (7.9 g, 95% yield) with an Z/E isomer ratio of 2 to 1, mp 155–160° C.;

$^1$H NMR (DMSO-d$_6$) (Z isomer) δ 10.7 (d, J=14 Hz, 1H), 9.27 (broad s, 1H), 8.30 (d, J=14 Hz, 1H), 8.01 (broad s, 1H), 7.05 (m, 2H), 4.21 (m, 2H), 3.83 (s, 3H), 2.10 (s, 3H), 1.25 (m, 3H); (E isomer) δ 10.9 (d, J=14 Hz, 1H), 9.24 (broad s, 1H), 8.15 (d, J=14 Hz, 1H), 8.12 (broad s, 1H), 7.22 (m, 2H), 4.21 (m, 2H), 3.83 (s, 3H), 2.10 (s, 3H), 1.25 (m, 3H); HRMS (EI) m/z 304.1290 (M+1). Analysis for C$_{15}$H$_{17}$N$_3$O$_4$: Calcd: C, 59.40; H, 5.65; N, 13.85. Found: C, 59.03; H, 5.51; N, 13.55.

REFERENCE EXAMPLE 53

N-(3-Cyano-6-methoxy-4-oxo-1,4-dihydro-7-quinolinyl)acetamide

An amount of 1 g (0.003 mol) of ethyl (E)-3-[3-(acetylamino)-4-methoxyanilino]-2-cyano-2-propenoate and ethyl (Z)-3-[3-(acetylamino)-4-methoxyanilino]-2-cyano-2-propenoate was added to a stirring solution of biphenyl (16.3 mL, 0.10 mol) and diphenyl ether (48.8 mL, 0.30 mol) at 256° C. After stirring for 2 hours at 256° C., the reaction mixture was cooled to room temperature, diluted with diethyl ether (130 mL), filtered, and evaporated to dryness to give a gray solid (0.53 g, 62% yield), mp 305–310° C.;

$^1$H NMR (DMSO-d$_6$) δ 12.80 (s, 1H), 9.58 (s, 1H), 8.62 (s, 1H), 8.58 (m, 1H), 7.52 (s, 1H), 3.97 (s, 3H), 2.20 (s, 3H); HRMS (EI) m/z 257.0793 (M+1).

REFERENCE EXAMPLE 54

N-(4-Chloro-3-cyano-6-methoxy-7-quinolinyl)acetamide

An amount of 10 g (0.039 mol) of N-(3-cyano-6-methoxy-4-oxo-1,4-dihydro-7-quinolinyl)acetamide was stirred in 29 mL (0.31 mol) of phosphorus oxychloride, heated at 100° C. for 0.5 hour, and subsequently cooled to 0° C. To this was slowly added a saturated solution of sodium bicarbonate and ethyl acetate to extract the product. The organic phase was washed with saturated brine solution, dried over sodium sulfate, and evaporated to give a brown solid (9.8 g, 73% yield), mp 230–235° C.;

$^1$H NMR (DMSO-d$_6$) δ 9.77 (s, 1H), 8.98 (s, 1H), 8.94 (s, 1H), 7.50 (s, 1H), 4.11 (s, 3H), 2.25 (s, 3H); HRMS (EI) m/z 275.0466 (M+1).

REFERENCE EXAMPLE 55

N-[3-Cyano-4-(2,4-dichloro-5-methoxyanilino)-6-methoxy-7-quinolinyl]acetamide

An amount of 9.7 g (0.035 mol) of N-(4-chloro-3-cyano-6-methoxy-7-quinolinyl)acetamide was stirred in 97 ml of 2-ethoxyethanol. To this was added 2,4-dichloro-5-methoxyaniline (prepared by the procedure described in WO 8501939-A1) (7.4 g, 0.038 mol), and 4.1 g (0.035 mol) pyridine hydrochloride, and the mixture was heated at 135° C. for 3 hours. The solvent was evaporated and the solid was stirred in saturated sodium bicarbonate solution and extracted with ethyl acetate. The organic phase was washed with saturated brine solution, dried over sodium sulfate and evaporated to dryness to give a brown solid (10.7 g, 71% yield), mp 267–270° C.;

$^1$H NMR (DMSO-d$_6$) δ 9.28 (s, 1H), 8.37 (s, 1H), 7.98 (s, 1H), 7.83 (s, 1H), 7.40 (s, 1H), 6.82 (s, 1H), 3.92 (s, 3H), 3.79 (s, 3H), 2.16 (s, 3H); MS (ES) m/z 431.1 (M+1).

REFERENCE EXAMPLE 56

7-Amino-4-(2,4-dichloro-5-methoxyanilino)-6-methoxy-3-quinolinecarbonitrile

An amount of 5.0 g (0.012 mol) of N-[3-cyano-4-(2,4-dichloro-5-methoxyanilino)-6-methoxy-7-quinolinyl]acetamide was stirred in 37% hydrochloric acid (500 mL), and heated at 65° C. for 1 hour. The mixture was evaporated to a slurry, stirred in saturated sodium bicarbonate solution, and extracted with ethyl acetate. The organic phase was dried over sodium sulfate, filtered through a pad of silica gel, and evaporated to dryness to give a tan solid (1.9 g, 42% yield), mp 265° C. decomp.;

$^1$H NMR (DMSO-d$_6$) δ 9.29 (s, 1H), 8.27 (s, 1H), 7.70 (s, 1H), 7.66 (s, 1H), 7.23 (s, 1H), 6.98 (s, 1H), 5.93 (s, 2H), 3.96 (s, 3H), 3.84 (s, 3H); MS (ES) m/z 389.2 (M+1).

Analysis for $C_{18}H_{14}Cl_2N_4O_2$: Calcd: C, 55.54; H, 3.63; N, 14.39. Found: C, 55.80; H, 3.78; N, 14.67.

REFERENCE EXAMPLE 57

4-Methoxy-3-nitroaniline

A solution of 4-amino-2-nitrophenol (10.0 g, 64.9 mmol), cesium carbonate (21 g, 64 mmol), and methyl iodide (9.22 g, 64.9 mmol) in acetonitrile (1500 mL) was heated at reflux for 5 hours. The mixture was cooled to room temperature and subsequently filtered, evaporated, and purified by flash chromatography (chloroform) to give 5.03 g (46% yield) of a reddish oil.

$^1$H NMR (DMSO-d$_6$) δ 7.09–7.03 (m, 2H), 6.87 (d, J=3 Hz, 1H), 5.21 (bs, 2H), 3.77 (s, 3H); HRMS (EI) m/z 168.0497 (M+1). Analysis for $C_7H_8N_2O_3$: Calcd: C, 50.00; H, 4.80; N, 16.66. Found: C, 50.20; H, 5.07; N, 16.60.

REFERENCE EXAMPLE 58

Ethyl (E)-2-Cyano-3-(4-methoxy-3-nitroanilino)-2-propenoate and Ethyl (Z)-2-Cyano-3-(4-methoxy-3-nitroanilino)-2-propenoate A mixture of 200 mg (1.19 mmol) of 4-methoxy-3-nitroaniline and 203 mg (1.20 mmol) of ethyl (ethoxymethylene)cyanoacetate in toluene (20 mL) was heated at reflux for 18 hours. This mixture was cooled to room temperature and filtered. The solid was washed with diethyl ether, and dried to give 293 mg of a yellow solid (84% yield) with an Z/E isomer ratio of 2 to 1, mp 186–190° C.;

$^1$H NMR (DMSO-d$_6$) (Z isomer) δ 10.86 (broad s, 1H), 8.32 (broad s, 1H), 8.05 (d, J=3 Hz, 1H), 7.34 (dd, J=9 Hz, 3 Hz, 1H), 7.38 (d, J=9 Hz, 1H), 4.17 (m, 2H), 3.92 (s, 3H); 1.24 (m, 3H); (E isomer) δ 10.75 (d, J=13 Hz, 1H), 8.43 (d, J=13 Hz, 1H), 8.15 (d, J=3 Hz, 1H), 7.82 (dd, J=9 Hz, 3 Hz, 1H), 7.38 (d, J=9 Hz, 1H), 4.17 (m, 2H), 3.92 (s, 3H); 1.24 (m, 3H); HRMS (EI) m/z 291.0846 (M+1). Analysis for $C_{13}H_{13}N_3O_5$: Calcd: C, 53.61; H, 4.50; N, 14.43. Found: C, 53.48; H, 4.52; N, 14.46.

REFERENCE EXAMPLE 59

6-Methoxy-7-nitro-4-oxo-1,4-dihydro-3-quinolinecarbonitrile

An amount of 3.0 g (10.31 mmol) of ethyl (E)-2-cyano-3-(4-methoxy-3-nitroanilino)-2-propenoate and (Z)-2-cyano-3-(4-methoxy-3-nitroanilino)-2-propenoate was added to a stirring solution of biphenyl (50 mL, 0.32 mmol) and diphenyl ether (150 mL, 0.95 mmol), and heated at reflux for 2.5 hours. The reaction mixture was cooled to room temperature and subsequently filtered, washed with diethyl ether, and evaporated to dryness. The crude solid was stirred in boiling ethyl acetate (2200 mL) for one hour, and subsequently filtered and evaporated to give a light brown solid (910 mg, 36% yield), mp 305–309° C.;

$^1$H NMR (DMSO-d$_6$) δ 13.10 (broad s, 1H), 8.81 (s, 1H), 8.15 (s, 1H), 7.81 (s, 1H), 4.02 (s, 3H); HRMS (EI) m/z 245.0440 (M+1).

REFERENCE EXAMPLE 60

N-(2-Ethoxy-5-mitrophenyl)acetamide

An amount of 100 g (0.649 mol) of 2-amino-4-nitrophenol was added to a stirring solution of water (444 mL) and acetic anhydride (124 mL). After stirring for 5 hours at room temperature, the reaction mixture was filtered and the solid was subsequently washed with water, diethyl ether, and evaporated to dryness to give 125 g (0.637 mol) of crude intermediate. This intermediate was stirred in N,N-dimethylformamide (822 mL), and to this was added 204 g (1.48 mol) of potassium carbonate and 726 g (4.66 mol) of ethyl iodide. The mixture was heated at reflux for 18 hours, cooled to room temperature, and evaporated to dryness. The obtained solid was mixed with water, filtered, and washed consecutively with water and diethyl ether, and evaporated to give a golden solid (117 g, 82% yield), mp 195–198° C.;

$^1$H NMR (DMSO-$d_6$) δ 9.37 (bs, 1H), 8.98 (s, 1H), 7.98 (d, J=9 Hz, 1H), 7.24 (d, J=9 Hz, 1H), 4.28 (q, J=7 Hz, 2H), 2.17 (s, 3H), 1.43 (t, J=7 Hz, 3H).

REFERENCE EXAMPLE 61

N-(5-Amino-2-ethoxyphenyl)acetamide

An amount of 22.4 g (0.10 mole) of N-(2-ethoxy-5-nitrophenyl)acetamide was treated, according to the procedure described for the preparation of the intermediate N-(5-amino-2-methoxyphenyl)acetamide (Reference Example 51), to give 18.5 g (95% yield) of a reddish oil;

$^1$H NMR (DMSO-$d_6$) δ 8.69 (broad s, 1H), 7.30 (s, 1H), 6.72 (d, J=9 Hz, 1H), 6.23 (d, J=9 Hz, 1H), 4.25 (broad s, 2H), 3.91 (q, J=6.9 Hz, 2H), 2.06 (s, 3H), 1.29 (t, J=6.9 Hz, 3H); HRMS (EI) m/z 194.1075 (M+1). Analysis for $C_{10}H_{14}N_2O_2 \cdot 0.43H_2O$: Calcd: C, 59.44; H, 7.40; N, 13.77. Found: C, 59.83; H, 7.00; N, 13.40.

REFERENCE EXAMPLE 62

Ethyl (E)-3-[3-(Acetylamino)-4-ethoxyanilino]-2-cyano-9-propenoate and Ethyl (Z)-3-[3-(Acetylamino)-4-ethoxyanilino]-2-cyano-2-propenoate An amount of 17.3 g (89.1 mmol) of N-(5-amino-2-ethoxyphenyl)acetamide was treated, according to the procedure described for the preparation of ethyl (E)-3-[3-(acetylamino)-4-methoxyanilino]-2-cyano-2-propenoate (Reference Example 62), to give 26.8 g (95% yield) of a beige solid with an Z/E isomer ratio of 3 to 1, mp 185–188° C.;

$^1$H NMR (DMSO-$d_6$) (Z isomer) δ 10.70 (d, J=14 Hz, 1H), 9.10 (broad s, 1H), 8.29 (d, J=14 Hz, 1H), 7.99 (broad s, 1H), 7.03 (m, 2H), 4.23 (q, J=7 Hz, 2H), 3.34 (s, 3H), 2.11 (s, 3H), 1.26 (t, J=7 Hz, 6H); (E isomer) δ 10.90 (d, J=14 Hz, 1H), 9.10 (broad s, 1H), 8.15 (d, J=14 Hz, 1H), 8.10 (broad s, 1H), 7.19 (m, 2H), 4.12 (q, J=7 Hz, 2H), 3.34 (s, 3H), 2.11 (s, 3H), 1.36 (t, J=7 Hz, 6H); HRMS (EI) m/z 317.1356 (M+1). Analysis for $C_{16}H_{19}N_3O_4 \cdot 0.25H_2O$: Calcd: C, 59.71; H, 6.11; N, 13.01. Found: C, 60.05; H, 6.03; N, 12.68.

REFERENCE EXAMPLE 63

N-(3-Cyano-6-ethoxy-4-oxo-1,4-dihydro-7-quinolinyl)acetamide

An amount of 2.0 g (6.31 mmol) of ethyl (E)-3-[3-(acetylamino)-4-ethoxyanilino]-2-cyano-2-propenoate and ethyl (Z)-3-[3-(acetylamino)-4-ethoxyanilino]-2-cyano-2-propenoate was treated, according to the procedure described for the preparation of N-(3-cyano-6-methoxy-4-oxo-1,4-dihydro-7-quinolinyl)acetamide (Reference Example 53), to give 0.59 g (35% yield) of a brown solid, mp 240° C. (decomp);

$^1$H NMR (DMSO-$d_6$) δ 12.80 (broad s, 1H), 9.35 (s, 1H), 8.61 (s, 1H), 8.58 (broad s, 1H), 7.50 (s, 1H), 4.20 (q, J=7 Hz, 2H), 2.22 (s, 3H), 1.44 (t, J=7 Hz, 3H); HRMS (EI) m/z 271.0961 (M+1). Analysis for $C_{14}H_{13}N_3O_3 \cdot 0.25H_2O$: Calcd: C, 60.97; H, 4.94; N, 15.23. Found: C, 60.73; H, 4.58; N, 15.21.

REFERENCE EXAMPLE 64

N-(4-Chloro)-3-cyano-6-ethoxy-7-quinolinyl) acetamide

N-(3-Cyano-6-ethoxy-4-oxo-1,4-dihydro-7-quinolinyl) acetamide (406 mg, 1.5 mmol) was treated with 5.0 mL of phosphorus oxychloride by the method of Reference Example 54 to give 202 mg (46%) of a light yellow solid, mp 202–204° C.;

$^1$H NMR(DMSO-$d_6$) δ 9.53 (broad s, 1H), 8.97 (s, 1H), 8.92 (s, 1H), 7.47 (s, 1H), 4.40 (q, J=7 Hz, 2H), 2.27 (s, 1H), 1.49 (t, J=7 Hz, 3H); HRMS (EI) 289.0603 (M+1). Analysis for $C_{14}H_{12}N_3O_2Cl$: Calcd: C, 58.04; H, 4.17; N, 14.50; Cl, 12.24. Found: C, 58.16; H, 4.18; N, 14.57; Cl, 12.03.

REFERENCE EXAMPLE 65

N-[3-Cyano-4-(2,4-dichloro-5-methoxyanilino)-6-ethoxy-7-quinolinyl]acetamide

N-(4-Chloro-3-cyano-6-ethoxy-7-quinolinyl)acetamide (290 mg, 1 mmol) was reacted with 191 mg (1 mmol) of 2,4-dichloro-5-methoxyaniline (prepared by the procedure described in WO 8501939-A1) by the procedure of Reference Example 55. The product was recrystallized from ethyl acetate to yield 146 mg (33%) of the title product as yellow crystals, mp 245–248° C.;

$^1$H NMR(DMSO-$d_6$) δ 9.63 (s, 1H), 9.34 (s, 1H), 8.71 (s, 1H), 8.42 (s, 1H), 7.91 (s, 1H), 7.56 (s, 1H), 7.36 (s, 1H), 4.31 (q, J=7 Hz, 2H), 3.86 (s, 3H), 2.23 (s, 3H), 1.48 (t, J=7 Hz, 3H); HRMS (ESI) 445.0823 (M+1).

REFERENCE EXAMPLE 66

7-Amino-4-(2,4-dichloro-5-methoxyanilino)-6-ethoxy-3-quinolinecarbonitrile

N-[3-Cyano-4-(2,4-dichloro-5-methoxyanilino)-6-ethoxy-7-quinolinyl]acetamide (100 mg, 0.225 mmol), was hydrolyzed by the method of Reference Example 56, in a mixture of concentrated hydrochloric acid and water (2 1) to generate 74 mg (81%) of the title compound as a yellow solid, mp 230–233° C.;

$^1$H NMR(DMSO-$d_6$) δ 9.33 (broad s, 1H), 8.33 (s, 1H), 7.76 (s, 1H), 7.71 (s, 1H), 7.28 (s, 1H), 7.04 (s, 1H), 5.96 (broad s, 2H), 2.60 (q, J=7 Hz, 2H), 3.90 (s, 3H), 1.50 (t, J=7 Hz, 3H); HRMS (ESI) 403.0714 (M+1). Analysis for $C_{19}H_{16}N_4O_2Cl_2$: Calcd: C, 56.59; H, 4.00; N, 13.89; Cl, 17.58. Found: C, 56.73; H, 4.11; N, 13.66; Cl, 17.23.

REFERENCE EXAMPLE 67

4-(2-Imidazol-1-ylethyl)morpholine

To a solution of imidazole (6.81 g, 0.1 mol) in 50 mL of acetonitrile at room temperature was added sodium hydroxide (6.8 g, 0.17 mol). The mixture was stirred at room temperature for 30 minutes. Tetrabutylammonium hydrogen sulfate (1.35 g, 4 mmol) was added followed by 4-(2-chloroethyl)morpholine hydrochloride (20.5 g, 0.11 mol). The mixture was heated at reflux for 42 hours and then concentrated in vacuo. The residue was purified by flash silica gel chromatography eluting with a gradient of 5% methanol in diethyl ether to 20% methanol in diethyl ether to provide 4.20 g (23% yield) of 4-(2-imidazol-1-ylethyl) morpholine as a yellow oil;

$^1$H NMR (DMSO-d$_6$) δ 2.39 (t, J=4 Hz, 4H), 2.59 (t, J=7 Hz, 2H), 3.55 (t, J=4 Hz, 4H), 4.06 (t, J=7 Hz, 2H), 6.85 (s, 1H), 7.17 (s, 1H), 7.62 (s, 1H); MS (ES) m/z 182.0 (M+1). Analysis for C$_9$H$_{15}$N$_3$O-0.45H$_2$O: Calcd: C, 57.09; H, 8.46; N, 22.19. Found: C, 57.20; H, 8.55; N, 22.11.

REFERENCE EXAMPLE 68

4-{2-[5-(Tributylstannyl)-1H-imidazol-1-yl]ethyl}morpholine

To 1 mL of N,N,N',N'-tetramethylethylenediamine at −78° C. with stirring was added 2.5M n-bultyl lithium in hexane (1.92 mL, 4.8 mmol). The mixture was warmed to −20° C. 4-(2-Imidazol-1-ylethyl)morpholine (362 mg, 2.0 mmol) was added and the mixture was stirred at −20° C. for 30 minutes and at room temperature for 30 minutes. The mixture was cooled to −20° C., and tributyltin chloride (1.63 g, 5.0 mmol) was added. The reaction was warmed to room temperature, stirred for 20 hours, and partitioned between ethyl acetate and water. The layers were separated and the aqueous layer was extracted with ethyl acetate. The combined extracts were washed with brine, dried over magnesium sulfate and filtered. Removal of the solvent in vacuo gave a residue which as purified by flash silica gel chromatography eluting with 10% methanol in ethyl acetate to provide 124 mg (13% yield) of 4-{2-[5-(tributylstannyl)-1H-imidazol-1-yl]ethyl}morpholine as a yellow oil;

$^1$H NMR (DMSO-d$_6$) δ 0.86 (t, J=7 Hz, 9H), 1.07 (m, 6H), 1.29 (m, 6H), 1.48 (m, 6H), 2.38 (t, J=4 Hz, 4H), 2.57 (t, J=7 Hz, 2H), 3.56 (t, J=4 Hz, 4H), 4.00 (t, J=7 Hz, 2H), 6.83 (s, 1H), 7.84 (s, 1H); MS (ES) m/z 472.2 (M+1). Analysis for C$_{21}$H$_{41}$N$_3$OSn: Calcd: C, 53.63; H, 8.79; N, 8.94. Found: C, 53.26; H, 8.82; N, 8.99.

REFERENCE EXAMPLE 69

4-[(4-Bromo-3-thienyl)methyl]morpholine

Using an analogous procedure to that described for Reference Example 23, 4-[(4-bromo-3-thienyl)methyl]morpholine was prepared from 4-bromo-3-thiophenecarbaldehyde (prepared according to the procedure of U.S. Pat. No. 4,332,952) and morpholine in 55% yield as a colorless oil;

$^1$H NMR (DMSO-d$_6$) δ 2.41 (t, J=5 Hz, 4H), 3.42 (s, 2H), 3.56 (t, J=5 Hz, 4H), 7.48 (d, J=3 Hz, 1H), 7.67 (d, J=3 Hz, 1H); MS (ES) m/z 262.1 (M+1).

REFERENCE EXAMPLE 70

4-[(3-Bromo-2-thienyl)carbonyl]morpholine

Using an analogous procedure to that described for Reference Example 27, (4-[(3-bromo-2-thienyl)carbonyl]morpholine was prepared from 3-bromo-2-thiophenecarboxylic acid and morpholine in 83% yield as a colorless oil;

$^1$H NMR (DMSO-d$_6$) δ 3.34 (t, J=5 Hz, 4H), 3.63 (t, J=5 Hz, 4H), 7.15 (d, J=5 Hz, 1H), 7.79 (d, J=5 Hz, 1H); MS (ES) m/z 276.1 (M+1). Analysis for C$_9$H$_{10}$BrNO$_2$S: Calcd: C, 39.14; H, 3.65; N, 5.07. Found: C, 39.08; H, 3.55; N, 5.07.

REFERENCE EXAMPLE 71

4-[(3-Bromo-2-thienyl)methyl]morpholine

4-[(3-Bromo-2-thienyl)carbonyl]morpholine (927 mg, 3.36 mmol) was dissolved in 17 mL of tetrahydrofuran and borane-dimethyl sulfide complex (0.67 mL, 6.71 mmol) was added dropwise via (syringe. The mixture was heated at reflux for 30 minutes. Methanol (10 mL) was added and the solution was evaporated to dryness. Another 10 mL of methanol was added and the solution was evaporated again and sodium hydroxide (2.5M, 5.0 mL) and ethanol (10 mL) were added to the residue. The mixture was stirred at room temperature overnight, diluted with brine and extracted with ethyl acetate (50 mL×3). The combined extracts were dried over sodium sulfate, filtered and concentrated in vacuo to give 879 mg (100%) of 4-[(3-bromo-2-thienyl)methyl] morpholine as a colorless oil;

$^1$H NMR (DMSO-d$_6$) δ 2.43 (t, J=5 Hz, 4H), 3.57 (t, J=5 Hz, 4H), 3.65 (s, 2H), 7.04 (d, J=5 Hz, 1H), 7.60 (d, J=5 Hz, 1H); MS (ES) m/z 262.1 (M+1). Analysis for C$_9$H$_{12}$BrNOS: Calcd: C, 41.23; H, 4.61; N, 5.34. Found: C, 41.06; H, 4.53; N, 5.40.

REFERENCE EXAMPLE 72

2-(Methylsulfonyl)ethylamine Hydrochloride Salt

Using an analogous procedure to that described for Reference Example 49, 2-(methylsulfonyl)ethylamine hydrochloride salt was prepared from methanesulphonylacetonitrile in 87% yield as a white solid, mp 131–133° C.;

$^1$H NMR (DMSO-d$_6$) δ 63.12 (s, 3H), 3.22 (t, J=7 Hz, 2H), 3.51 (t, J=7 Hz, 2H), 8.30 (s, 3H); MS (ES) m/z 124.0 (M+1).

REFERENCE EXAMPLE 73

4-[(5-Bromo-3-thienyl)methyl]morpholine

Using in analogous procedure to that described for Reference Example 23, 4[(5-bromo-3-thienyl)methyl]morpholine was prepared from 5-bromo-3-thiophenecarbaldehyde (prepared according to the procedure of U.S. Pat. No. 5,597,832) and morpholine in 69% yield as a colorless oil;

$^1$H NMR (DMSO-d$_6$) δ 2.33 (t, J=5 Hz, 4H), 3.40 (s, 2H), 3.56 (t, J=5 Hz, 4H), 7.11 (d, J=2 Hz, 1H), 7.34 (d, J=2 Hz, 1H); MS (ES) m/z 262.0 (M+1).

REFERENCE EXAMPLE 74

7-Bromo-4-(2-chloro-4-fluoro-5-methoxyanilino)-3-quinolinecarbonitrile

A mixture of 2-chloro-4-fluoro-5-methoxy aniline (prepared by the procedure described in WO 8501939 A1) (300 mg, 1.71 mmol), 7-bromo-4-chloro-3-quinolinecarbonitrile (400 mg, 1.5 mmol) and pyridine hydrochloride (170 mg, 1.47 mmol) in 4 mL of ethoxyethanol was heated at reflux for 1.5 hours and concentrated. The residue was treated with saturated sodium bicarbonate and the resulting precipitate was collected by filtration and dried. The product was dissolved in ethyl acetate and filtered through hydrous magnesium silicate. The filtrate was concentrated, and the resulting solid was purified by flash silica gel chromatography, eluting with 1:1 hexane:ethyl acetate to give 400 mg (66% yield) of 7-bromo-4-(2-chloro-4-fluoro-5-methoxyanilino)-3-quinolinecarbonitrile as a white solid, mp 200–202° C.; MS (ES) m/z 405.9 (M+1). Analysis for $C_{17}H_{10}BrClFN_3O\cdot0.2H_2O$: Calcd: C, 49.78; H, 2.56; N, 10.24. Found: C, 49.64; H, 2.46; N, 10.01.

REFERENCE EXAMPLE 75

7-Bromo-4-(2-chloro-5-methoxy-4-methylanilino)-3-quinolinecarbonitrile

A mixture of 2-chloro-4-methyl-5-methoxy aniline (prepared by the procedure described in Theodoridis, G., *Pesticide Science*, 30(3), 259 (1990) (265 mg, 1.71 mmol), 7-bromo-4-chloro-3-quinolinecarbonitrile (400 mg, 1.5 mmol) and pyridine hydrochloride (170 mg) in 4 mL of ethoxyethanol was heated at reflux for 1.5 hours and concentrated. The residue was treated with saturated sodium bicarbonate and the resulting precipitate was collected by filtration and dried. The product was dissolved in ethyl acetate and filtered through hydrous magnesium silicate. The filtrate was concentrated, and the resulting solid was purified by flash silica gel chromatography, eluting with 3:1 hexane:ethyl acetate to give 210 mg (35% yield) of 7-bromo-4-(2-chloro-5-methoxy-4-methylanilino)-3-quinolinecarbonitrile as a white solid, mp 215–2170° C.;
$^1$H NMR (DMSO-d$_6$) δ 10.05 (s, 1H), 8.55 (s, 1H), 8.50 (d, J=9 Hz, 1H), 8.13 (s, 1H), 7.84 (d, J=9 Hz, 1H), 7.37 (s, 1H), 7.14 (s, 1H), 3.79 (s, 3H), 2.20 (s, 3H), MS (ES) m/z 402.0 (M+1). Analysis for $C_{18}H_{13}BrClN_3O$: Calcd: C, 53.69; H, 3.25; N, 10.44. Found: C, 53.60; H, 3.43; N, 10.28.

REFERENCE EXAMPLE 76

6-(4-Morpholinylmethyl)-3-pyridinyl 4-Methylbenzenesulfonate

To a solution of 6-formyl-3-pyridinyl 4-methylbenzenesulfonate (2.77 g, 10 mmol, prepared according to the procedure of Ross, S. T., *J. Med. Chem.*, 30, 1309 (1987) in 50 mL of methyl alcohol at room temperature was added morpholine (1.74 g, 20 mmol). The mixture was stirred at room temperature for one hour. Sodium cyanoborohydride (2.51 g, 40 mmol) was added in portions. The mixture was stirred at room temperature for one hour, and concentrated. The residue was partitioned between ethyl acetate and brine. The layers were separated and the organic layer was dried over magnesium sulfate. Removal of the solvent in vacuo gave a residue which was purified by silica gel chromatography eluting with ethyl acetate to provide 1.12 g (32% yield) of 6-(4-morpholinylmethyl)-3-pyridinyl 4-methylbenzenesulfonate as a white solid, mp) 68–69° C.;
$^1$H NMR (DMSO-d$_6$) δ 2.36 (t, J=5 Hz, 4H), 2.43 (s, 3H), 3.56 (s, 2H), 3.57 (t, J=5 Hz, 4H), 7.51 (m, 4H), 7.75 (d, J=9 Hz, 2H), 8.13 (dd, J=2, 1 Hz, 1H); MS (ES) m/z 349.1 (M+1). Analysis for $C_{17}H_{20}N_2O_4S\cdot0.45H_2O$: Calcd: C, 57.27; H, 5.91; N, 7.86. Found: C, 57.17; H, 5.64; N, 8.07.

REFERENCE EXAMPLE 77

6-(4-Morpholinylmethyl)-3-pyridinyl Trifluoromethanesulfonate

A suspension of 6-(4-morpholinylmethyl)-3-pyridinyl 4-methylbenzenesulfonate (800 mg, 2.30 mmol) in 50 mL of 2.5M sodium hydroxide in water was heated at reflux for one hour, until homogeneous. The mixture was cooled to room temperature, and neutralized with concentrated hydrochloric acid to pH 7. The solvent was removed in vacuo to give a white powder. To a suspension of this residue in 25 mL of dichloromethane at room temperature was added 2,6-lutidine (1.07 g, 10 mmol) followed by trifluoromethanesulfonic anhydride (2.82 g, 10 mmol). The mixture was stirred at room temperature for 30 minutes, and quenched with saturated sodium carbonate solution. The layers were separated and the aqueous layer was extracted with dichloromethane. The combined extracts were dried over magnesium sulfate, and filtered through hydrous magnesium silicate. Removal of the solvent in vacuo gave a residue which was purified by silica gel chromatography eluting with ethyl acetate to provide 112 mg (15% yield) of 6-(4-morpholinylmethyl)-3-pyridinyl trifluoromethanesulfonate as a brown oil;
$^1$H NMR (DMSO-d$_6$) δ 3.40 (s, 4H), 3.74 (s, 2H), 3.92 (s, 2H), 4.58 (s, 2H), 7.77 (d, J=9 Hz, 1H), 8.23 (dd, J=9, 3 Hz, 1H), 8.93 (d, J=3 Hz, 1H); MS (ES) m/z 327.0 (M+1).

REFERENCE EXAMPLE 78

7-Nitro-4-oxo-1,4-dihydro-quinoline-3-carbonitrile

A mixture of 50 g (0.361 mol) of 3-nitroaniline and 61.85 g (0.366 mol) of ethyl(ethoxymethylene)cyanoacetate was heated at 120° C. for 3 hours. This mixture was cooled to room temperature and filtered. The solid was washed with diethyl ether, and dried to give 95 g of ethyl 2-cyano-3-(3-nitroanilino)-2-propenoate as a yellow solid (quantitative yield).

An amount of 12 g (45.98 mmol) of ethyl 2-cyano-3-(3-nitroanilino)-2-propenoate was added to a refluxing solution (750 mL) of biphenyl and diphenyl ether (1:3 ratio) and refluxed for 8 hours. The reaction mixture was cooled to room temperature and subsequently filtered, washed with diethyl ether, and evaporated to dryness to give a brown solid (6.5 g, 66% yield, containing 20% of the 5-nitro-isomer);
HRMS (EI) 214.02618 (M–1). Analysis for $C_{10}H_5N_3O_3$-0.17H$_2$O: Calcd: C, 55.05; H, 2.46; N, 19.26. Found: C, 55.19; H, 2.22; N, 19.35.

REFERENCE EXAMPLE 79

4-Chloro-7-nitro-quinoline-3-carbonitrile

An amount of 5.5 g (0.026 mol) of 7-nitro-4-oxo-1,4-dihydro-quinoline-3-carbonitrile (Reference Example 78) was stirred in 38 mL (0.41 mol) of phosphorus oxychloride, heated to reflux for 3 hours, and subsequently cooled to 0° C. To this was slowly added ice water and a saturated solution of sodium bicarbonate. After stirring for 0.5 hour, the mixture was filtered, and the solids were subsequently washed with water and dried to give a brown solid (5.5 g, 91% yield; contains 20% 5-nitro-isomer), mp 275° C. decomp;
MS (ES) m/z 233.1 (M–1).

REFERENCE EXAMPLE 80

4-(2,4-Dichloro-5-methoxyanilino)-7-nitro-quinoline-3-carbonitrile

An amount of 3.0 g (0.013 mol) of 4-chloro-7-nitro-quinoline-3-carbonitrile was stirred in 30 mL of 2-ethoxyethanol. To this were added 2,4-dichloro-5-methoxyaniline (prepared by the procedure of WO 8501939-A1) (2.7 g, 0.014 mol), and 1.6 g (0.005 mol) pyridine hydrochloride and the mixture was heated at 80° C. for 2 hours. The solvent was evaporated, washed with ethyl acetate and dried to give a brown solid (5.3 g, 105%). The ethyl acetate wash was subsequently stirred with saturated bicarbonate solution, saturated brine solution, dried over sodium sulfate, and evaporated. The orange oily residue was purified by preparative thin layer chromatography (10% hexane in ethyl acetate), to give an orange solid (86 mg; contains 17% 5-nitro-isomer), mp 112–115° C.;

MS (ES) m/z 389.0 (M+1); HRMS (EI) m/z 389.01895 (M+1). Analysis for $C_{17}H_{10}Cl_2N_4O_3$: Calcd: C, 52.46; H, 2.59; N, 14.40. Found: C, 52.53; H, 2.67; N, 14.11.

REFERENCE EXAMPLE 81

7-Amino-4-(2,4-dichloro-5-methoxyanilino)-3-quinolinecarbonitrile

An amount of 4 g of 4-(2,4-dichloro-5-methoxyanilino)-7-nitro-3-quinolinecarbonitrile HCl-salt (Reference Example 80) was stirred in 100 mL of methanol and 25 mL of water, and to this was added at room temperature 2.9 g (0.052 mol) of iron powder. The suspension was heated to reflux for 3 hours, then cooled to room temperature and filtered. The residue was stirred with saturated bicarbonate solution and ethyl acetate. The organic phase was washed with brine, dried over sodium sulfate, and evaporated to give a tan solid (1.7 g, 46% yield; contains 17% 5-amino-isomer), mp 230–232° C.;

MS (ES) m/z 359.0 (M+1); HRMS (EI) m/z 359.04457 (M+1). Analysis for $C_{17}H_{12}Cl_2N_4O$: Calcd: C, 55.40; H, 3.53; N, 15.21. Found: C, 55.42; H, 3.75; N, 15.03.

REFERENCE EXAMPLE 82

7-Bromo-4-[3-methyl-4-(2-pyridinylmethoxy)anilino]-3-quinolinecarbonitrile

A mixture of 3-methyl-4-(2-pyridinylmethoxy)aniline (prepared by the procedure described in U.S. Pat. No. 5,955,464) (822 mg, 3.84 mmol), 7-bromo-4-chloro-3-quinolinecarbonitrile (935 mg, 3.5 mmol) and pyridine hydrochloride (406 mg) in 20 mL of ethoxyethanol was heated at reflux for 20 minutes. The reaction mixture was filtered while warm and the solids were washed with ethoxyethanol and diethyl ether. The solids were then suspended in 20 mL of water and 6 mL of concentrated aqueous ammonium hydroxide was added and the mixture was stirred for 30 min. The solids were collected washing with water to provide 1.335 g (86% yield) of 7-bromo-4-[3-methyl-4-(2-pyridinylmethoxy)anilino]-3-quinolinecarbonitrile as a tan solid, mp 238–241° C.;

MS (ES) m/z 445.1, 447.0 (M+1). Analysis for $C_{23}H_{17}BrN_4O\cdot2.0H_2O$: Calcd: C, 57.39; H, 4.40; N, 11.64. Found: C, 57.54; H, 4.33; N, 11.69.

REFERENCE EXAMPLE 83

4-(2,4-Dichloro-5-methoxyanilino)-7-tributylstannanyl-3-quinolinecarbonitrile A mixture of 4-(2,4-dichloro-5-methoxyanilino)-7-iodo-3-quinolinecarbonitrile (790 mg, 1.67 mmol) (Reference Example 13), bis(tributyltin) (0.97 mL, 1.91 mmol) and tetrakis(triphenylphosphine)palladium(0) (20 mg) in triethylamine (5.71 mL) and N,N-dimethylformamide (1.71 mL) was heated at 100–105° C. for 16 hours. The reaction mixture was evaporated and the residue was purified by flash column chromatography to give 645 mg (61%) of 4-(2,4-dichloro-5-methoxyphenylamino)-7-tributylstannanyl-3-quinolinecarbonitrile as a light yellow solid: mp 108–110° C.; MS (M+H)+.

REFERENCE EXAMPLE 84

2-[[(6-Bromo-3-pyridinyl)methyl](methyl)amino]ethanol

A mixture of 2-bromo-5-(bromomethyl)pyridine (470 mg, 1.87 mmol) (prepared by the procedure described in Windscheif, P. M., *Synthesis*, 87(1994) and 2-(methylamino) ethanol (935 mg, 12.4 mmol) in 10 mL of acetonitrile was stirred at room temperature for 16 hours then concentrated. The residue was partitioned between 5% aqueous sodium carbonate solution and ethyl acetate. The organic layer was separated, dried, and concentrated. The residue was purified by flash column chromatography, eluting with a gradient of ethyl acetate to 10% methanol in ethyl acetate to provide 362 mg (79%) of 2-[[(6-bromo-3-pyridinyl)methyl](methyl) amino]ethanol as a yellow oil,: MS 245.2 (M+H)+.

REFERENCE EXAMPLE 85

1-(6-Chloro-3-pyridinyl)-4-ethylpiperazine

A mixture of 5-bromo-2-chloropyridine (384 mg, 2.0 mmol), 1-ethylpiperazine (228 mg, 2.0 mmol), sodium tert-butoxide (576 mg, 6 mmol), tris(dibenzylideneacetone) dipalladium(0) (18.3 mg, 0.02 mmol), and 2-dicyclohexylphosphino-2'-(N,N-dimethylamino)biphenyl (23.6 mg, 0.06 mmol) in 10 mL of toluene was heated at reflux for 1 hour and concentrated. The residue was purified by flash column chromatography, eluting with 5% methanol in ethyl acetate to provide 269 mg (60%) of 1-(6-chloro-3-pyridinyl)-4-ethylpiperazine as a brown semi-solid: MS 225.9 (M+H)+.

REFERENCE EXAMPLE 86

1-(6-Bromo-3-pyridinyl)-4-ethylpiperazine 1-(6-Chloro-3-pyridinyl)-4-ethylpiperazine (903 mg, 4.0 mmol) in 30 mL of phosphorus tribromide was heated at 150° C. for four days and cooled to room temperature. The mixture was then poured onto an ice-water mixture, and the solution was neutralized with sodium carbonate. The product was extracted with ethyl acetate. The organic layer was separated, dried, and concentrated. The residue was purified by flash column chromatography, eluting with 5% methanol in ethyl acetate to provide 940 mg (87%) of 1-(6-bromo-3-pyridinyl)-4-ethylpiperazine as a brown solid: mp 30–31° C.; MS 269.8 (M+H)+.

REFERENCE EXAMPLE 87

3-Furyl(4-nitrophenyl)methanol

To a solution of 3-bromofuran (10.28 g, 70 mmol) in 200 mL of tetrahydrofuran at −78° C. was added n-butyllithium (2.5M in hexanes, 26.4 mL, 66 mmol). The solution was stirred at −78° C. for 10 minutes. A solution of 4-nitrobenzaldehyde (9.06 g, 60 mmol) in 80 mL of tetrahydrofuran was added, and the mixture was stirred at −78° C. for 10 min then warmed to room temperature. The reaction was quenched with an aqueous ammonium chloride solution, and the product was extracted with ethyl acetate. The organic layer was washed with saturated sodium chloride solution, dried over magnesium sulfate, and concentrated. The residue was purified by flash column chromatography, eluting with a gradient of 10% ethyl acetate in hexanes to ethyl acetate/hexanes (1:1) to provide 7.83 g (60%) of 3-furyl(4-nitrophenyl)methanol as a yellow solid: mp 50–52° C.; MS 219.0 (M+H)+.

REFERENCE EXAMPLE 88

4-(3-Furylmethyl)aniline

A mixture of 3-furyl(4-nitrophenyl)methanol (658 mg, 3.0 mmol) and palladium hydroxide (20 wt. % on carbon, 100 mg) in 20 mL of methanol was hydrogenated at 50 psi for 8 minutes, and filtered. The filtrate was concentrated, and the residue was purified by flash column chromatography, eluting with ethyl acetate/hexanes (1:2) to provide 253 mg (49%) of 4-(3-furylmethyl)aniline as a tan oil: MS: 174.2 (M+H)+.

REFERENCE EXAMPLE 89

3-Chloro-4-phenoxyaniline

A mixture of 3-chloro-4-fluoronitrobenzene (17.6 g, 0.1 mol), phenol (18.8 g, 0.2 mol), and sodium bicarbonate (25.2 g, 0.3 mol) in 200 mL of dimethylsulfoxide was heated at 80° C. for 30 minutes and then cooled to room temperature. The mixture was treated with saturated sodium chloride solution, and the product was extracted with ethyl acetate. The organic layer was washed with 0.1 N sodium hydroxide solution, water (×4) and saturated sodium chloride, dried over magnesium sulfate and concentrated. The residue was dissolved in a mixture of 100 mL of methanol and 100 mL of glacial acetic acid. Iron powder (22,4 g, 0.4 mol) was added, and the mixture was heated at reflux for 1 hour, cooled to room temperature, and filtered through Celite. The filtrate was concentrated, and the residue was treated with saturated sodium bicarbonate solution. The product was extracted with ethyl acetate. The organic layer was washed with saturated sodium chloride, dried over magnesium sulfate and filtered through Magnesol. Removal of the solvent provided 19.6 g, (89%) of 3-chloro-4-phenoxyaniline as a brown solid:

mp 31–33° C.; MS: 220.0 (M+H)+.

REFERENCE EXAMPLE 90

3-Chloro-4-(phenylthio)aniline

Using an analogous procedure to that described for Reference Example 89, replacement of phenol with thiophenol provided 3-chloro-4-(phenylthio)aniline as a brown solid in 58% yield: mp 48–50° C.; MS 236.0 (M+H)+.

REFERENCE EXAMPLE 91

1-(5-Bromo-2-pyridinyl)-4-piperidinol

A mixture of 2,5-dibromopyridine (1.00 g, 4.20 mmol), 4-hydroxypiperidine (4.25 g, 42 mmol) in 10 mL of acetonitrile was heated at reflux for 20 hours. After cooling, the mixture was concentrated and the residue was treated with water. The aqueous suspension was extracted with ethyl acetate. The organic phase was washed with brine, dried over sodium sulfate and filtered. Removal of the solvent gave a solid residue that was purified by flash column chromatography eluting with a gradient of 20% ethyl acetate in hexanes to 50% ethyl acetate in hexanes to provide 1.02 g (94.0%) of 1-(5-bromo-2-pyridinyl)-4-piperidinol as white rosette crystals: mp 91–93° C.; MS 257.2 (M+H)+.

REFERENCE EXAMPLES 92 AND 93

5-Bromo-2-(dibromomethyl)pyrdine and 5-Bromo-2-(bromomethyl)pyridine

A mixture of 5-bromo-2-methylpyridine (2.00 g, 11.6 mmol), N-bromosuccinimide (2.17 g, 12.2 mmol) and 2,2'-azabisisobutyronitrile (19.1 mg, 0.12 mmol) was heated at reflux in 30 mL of carbon tetrachloride under irradiation with a 300 Watt lamp. After 6 hours, the mixture was allowed to cool, the succinimide was filtered off, and the filtrate was concentrated in vacuo. Chloroform as added and the organic layer washed with saturated aqueous sodium bicarbonate, dried over sodium sulfate and concentrated to a solid residue that was purified by flash chromatography eluting with a gradient of 2% ethyl acetate in hexanes to 8% ethyl acetate in hexanes to provide 2.4 g (25%) of 5-bromo-2-(dibromomethyl)pyridine as a yellow solid: mp 59–61° C.; along with 5-bromo-2-(bromomethyl)pyridine (47%). (The preparation of 5-bromo-2-(bromomethyl)pyridine is reported in Bioorg. Med. Chem. Lett, 4, 99–104, 1994).

REFERENCE EXAMPLE 94

5-Bromo-2-pyridinecarbaldehyde

A mixture of 5-bromo-2-(dibromomethyl)pyridine (2.28 g, 9.51 mmol) (Reference Example 92) in 7 mL of morpholine was stirred at room temperature overnight. The mixture was partitioned between ethyl acetate and water. The organic phase was washed with brine, dried over sodium sulfate, filtered and concentrated in vacuo. The residue was purified by flash column chromatography eluting with a gradient of 3% methanol in dichloromethane to 10% methanol in dichloromethane to provide 0.79 g (44%) of 5-bromo-2-pyridinecarbaldehyde as an off-white solid: mp 90–92° C.; MS 186.0 (M+H)+.

REFERENCE EXAMPLE 95

1-[(5-Bromo-2-pyridinyl)methyl]-4-piperidinol

A mixture of 5-bromo-2-(bromomethyl)pyridine (600 mg, 2.4 mmol) (Reference Example 93), 4-hydroxypiperidine (293 mg, 2.9 mmol) and 1,1-diisopropylethylamine (308 mg, 2.4 mmol) in 5 mL of acetonitrile was stirred at room temperature for 1 hour. The reaction mixture was treated with brine and the product was extracted with ethyl acetate. The organic phase was washed with brine, dried over sodium sulfate, filtered and concentrated in vacuo. The residue was purified by flash column chromatography eluting with a gradient of 3% methanol in dichloromethane to 10% % methanol in dichloromethane to provide 496 mg (76%) of 1-[(5-bromo-2-pyridinyl)methyl]-4-piperidinol as an off-white solid: mp 52–54° C.; MS 217.18 (M+H)+.

REFERENCE EXAMPLE 96

4-{4-[(5-Bromo-2-pyridinyl)oxy]benzyl}morpholine

To a solution of 4-hydroxybenzaldehyde (2.0 g, 16.4 mmol), morpholine (1.4 g, 16.4 mmol) and acetic acid (1.2 g, 20.6 mmol) in 60 mL of anhydrous ethanol was added sodium cyanoborohydride (1.3 g, 21.3 mmol) in portions. The resulting mixture was stirred at room temperature overnight and then concentrated in vacuo. The residue was treated with water and neutralized with 6 N HCl. The aqueous solution was extract with ether and then treated with 28% aqueous ammonium hydroxide. The basified aqueous solution was extracted with ethyl acetate. The ethyl acetate phase was washed with brine, dried over sodium sulfate, filtered and concentrated in vacuo. The residue was purified by flash column chromatography eluting with 80% ethyl acetate in hexanes to all ethyl acetate to 2% methanol in ethyl acetate to 5% methanol in ethyl acetate to provide 2.09 g (66%) of the intermediate phenol as a white solid.

The intermediate phenol was added in portions to a suspension of sodium hydride (304 mg, 7.60 mmol) in 6 mL of dimethylformamide. The reaction mixture was stirred at room temperature for 10 minutes. A solution of 2,5-dibromopyridine (1.5 g, 6.33 mmol) in 4 mL of dimethylformamide was added. The resulting dark solution was heated at 80° C. for 17 hours and then at 150° C. for 7 hours. After cooling to room temperature, the mixture was concentrated in vacuo. The residue was treated with water and extracted with dichloromethane. The organic phase was washed with brine, dried over sodium sulfate, filtered and concentrated in vacuo. The residue was purified by flash column chromatography eluting with 50% ethyl acetate in hexanes to provide 1.70 g (77%) of 4-{4-[(5-bromo-2-pyridinyl)oxy]benzyl)morpholine as yellow oil: MS 349.0 (M+H)+.

REFERENCE EXAMPLE 97

1-[(4-Bromo-2-thienyl)methyl]-4-methylpiperazine

N-Methylpiperazine (0.65 g, 6.5 mmol) was added to a solution of 4-bromo-2-thiophenecarboxaldehyde (0.975 g, 5.0 mmol) in 30 mL of methylene chloride and 4 mL of dimethylformamide. The mixture was cooled to 0° C. and sodium triacetoxyborohydride (2.75 g, 13.0 mmol) was added. After stirring at 0° C. for 1.5 hours, a catalytic amount of acetic acid was added and the reaction mixture was allowed to warm to room temperature and stirred for 2 hours. The reaction was quenched by the addition of water and then partitioned between saturated sodium bicarbonate and methylene chloride. The organic layer was dried over sodium sulfate, filtered and concentrated in vacuum. The residue was purified by column chromatography, eluting with chloroform to provide 0.7 g (48%) of 1-[(4-bromo-2-thienyl)methyl]-4-methylpiperazine as a viscous liquid: MS 276.8 (M+H)+.

REFERENCE EXAMPLE 98

3-(2-Chloro-4-nitrobenzyl)furan

To a −78° C. solution of 3-bromofuran (3.2 mL, 35.60 mmol) in 40 mL of tetrahydrofuran was added tert-butyl lithium (42 mL of a 1.7 M solution in hexanes, 71.4 mmol) over 7 minutes. The reaction mixture was allowed to warm to −45° C. and then cooled again to −78° C. After stirring for 50 minutes, a solution of 2-chloro-4-nitrobenzaldehyde (5.32 g, 28.68 mmol) (prepared by the procedure described in U.S. Pat. No. 5,807,876) in 15 mL of tetrahydrofuran was added over 5 minutes. The reaction mixture was allowed to warm to room temperature and quenched with an aqueous solution of saturated ammonium chloride. The aqueous layer was extracted with diethyl ether. The organic layers were combined, washed with brine, dried over magnesium sulfate, filtered and concentrated in vacuo. The residue was purified by flash column chromatography eluting with 10% ethyl acetate in hexanes to provide 2.60 g (36%) of the intermediate carbinol as an oil. The above procedure was repeated to provide additional amounts of the carbinol.

To a suspension of the intermediate carbinol (3.70 g 14.59 mmol) and sodium iodide (8.74 g, 58.35 mmol) in 15 mL of acetonitrile on a water bath was added dimethyl dichlorosilane (3.45 mL, 29.17 mmol). The resulting mixture was stirred for 20 min then poured into ethyl acetate. The organic layer was washed with water, saturated sodium bicarbonate, saturated sodium thiosulfate and brine, then dried over magnesium sulfate, filtered and concentrated in vacuo. The residue was purified by flash column chromatography eluting with 1% ethyl acetate in hexanes to provide 2.50 g (72%) of 3-(2-chloro-4-nitrobenzyl)furan as an oil: MS (CI) 237.98 (M+H)+.

REFERENCE EXAMPLE 99

3-Chloro-4-(2-furylmethyl)aniline

A mixture of 3-(2-chloro-4-nitrobenzyl)furan (2.50 g, 10.52 mmol), iron powder (3.70 g, 66.25 mmol), ammonium chloride (5.60 g, 106 mmol) in 40 mL of water and 80 mL of methanol was heated at reflux for 6 hours. The mixture was cooled and filtered through a pad of Celite washing with ethyl acetate. The filtrate was concentrated to remove the ethyl acetate and methanol. The aqueous residue was partitioned between water and ethyl acetate. The organic layer was washed with brine, dried over sodium sulfate, filtered and concentrated in vacuo. The residue was purified by flash column chromatography eluting with 10% ethyl acetate in hexanes to provide 2.27 g (97%) of 3-chloro-4-(2-furylmethyl)aniline as a light yellow oil:

MS (ES) 207.9 (M+H)+.

The Reference Examples in Table 3 are listed with the chemical name, melting point and/or mass spectral data and the Reference Example procedure used in the preparation of the compound.

TABLE 3

| Ref. Ex. | Chemical Name | MP ° C. | mass spec. | Ref. Ex. pro. |
|---|---|---|---|---|
| 100 | 6-bromo-4-({3-chloro-4-[(1-methyl-1H-imidazol-2-yl)-sulfanyl]phenyl}-amino)-3-quinolinecarbonitrile | 275–277 | 470.0 (M + H) + | 13 |
| 101 | 7-bromo-4-(4-chloro-5-methoxy-2-methylanilino)-3-quinolinecarbonitrile | 97–100 | 402.0, 404.0 (M + H) + | 8 |
| 102 | 7-bromo-4-(2-chloro-5-methoxy-anilino)-3-quinoline-carbonitrile | 185–187 | 390.0 (M + H) + | 13 |
| 103 | 7-bromo-4-(5-methoxy-2-methylanilino)-3-quinoline-carbonitrile | 208–210 | 368.1 (M + H) + | 13 |
| 104 | 4-[4-(benzyloxy)-3-chloro-anilino]-7-bromo-3-quinoline-carbonitrile | 223–225 | 466.0 (M + H) + | 13 |
| 105 | 7-bromo-4-(3,4,5-trimethoxy-anilino)-3-quinolinecarbonitrile | 224–226 | 414.0, 416.0 (M + H) + | 13 |
| 106 | 7-bromo-4-[3-chloro-4-(phenylsulfanyl)anilino]-3-quinolinecarbonitrile | 237 (dec) | 465.9 (M + H) + | 13 |
| 107 | 7-bromo-4-(3-chloro-4-phenoxyanilino)-3-quinoline-carbonitrile | 210 (dec) | 450.0 (M + H) + | 13 |
| 108 | 7-bromo-4-(2,4-dimethyl-anilino)-3-quinoline-carbonitrile | 170–172 | 352.0 (M + H) + | 13 |
| 109 | 7-bromo-4-(4-bromo-2-chloro-6-methylanilino)-3-quinolinecarbonitrile | 188–190 | 449.9 (M + H) + | 6 |
| 110 | 7-bromo-4-(3-chloro-4-(3-furylmethyl)anilino]-3-quinolinecarbonitrile | 208–210 | 439.7 (M + H) + | 13 |
| 111 | 7-bromo-4-[4-(3-furylmethyl)-anilino]-3-quinoline-carbonitrile | 180–182 | 405.7 (M + H) + | 13 |
| 112 | 4-{3-chloro-4-[(1-methyl-1H-imidazol-2-yl)sulfanyl]anilino}-7-iodo-3-quinoline-carbonitrile | dec >240 | 517.5, 519.7 (M + H) + | 14 |

TABLE 3-continued

| Ref. Ex. | Chemical Name | MP ° C. | mass spec. | Ref. Ex. pro. |
|---|---|---|---|---|
| 113 | 4-[3-chloro-4-(phenyl-fanyl)-anilino-7-iodo-3-quinolinecarbonitrile | 240–245 | 514 (M + H) + | 13 |
| 114 | 4-(3-chloro-4-phenoxy-anilino)-7-iodo-3-quino-linecarbonitrile | 182–184 | 497.9 (M + H) + | 13 |
| 115 | 7-iodo-4-(3,4,5-trimethoxy-anilino)-3-quinoline-carbonitrile | 220–222 | 461.7, 462.7 (M + H) + | 13 |
| 116 | 4-(2,4-dimethylanilino)-7-iodo-3-quinoline-carbonitrile | >250 | 400.7 (M + H) + | 13 |
| 117 | 4-(4-bromo-2-chloro-6-methylanilino)-7-iodo-3-quinolinecarbonitrile | 140–142 | 497.4 (M + H) + | 13 |
| 118 | 4-[4-(3-furylmethyl)-anilino]-7-iodo-3-quinolinecarbonitrile | 193–195 | 451.70 (M + H) + | 13 |
| 119 | 4-[3-chloro-4-(3-furylmethyl)-anilino]-7-iodo-3-quinoline-carbonitrile | 163–165 | 485.7 (M + H) + | 13 |
| 120 | 4-{3-chloro-4-[(1-methyl-1H-imidazol-2-yl)sulfanyl]anilino}-3-cyano-6-methoxy-7-quinolinyl trifluoromethane-sulfonate | | 570.3 (M + H) + | 22 |
| 121 | 4-(5-bromo-2-pyridinyl)-morpholine | 73–74 | 243 (M + H) + | 91 |
| 122 | 1-[(6-bromo-3-pyridinyl)-methyl]-4-methylpiperazine | oil | 270 (M + H) + | 84 |
| 123 | 5-bromo-N-[2-(4-morpho-linyl)ethyl]-2-pyridinamine | oil | 285.9 (M + H) + | 91 |
| 124 | 1-(5-bromo-2-pyridinyl)-4-ethylpiperazine | 68–69 | 271.8 (M + H) + | 91 |
| 125 | 1-(5-bromo-2-pyridinyl)-4-methylpiperazine | 71–72 | 255.9 (M + H) + | 91 |
| 126 | 4-[(6-bromo-2-pyridinyl)methyl]morpholine | oil | 257.0 (M + H) + | 84 |
| 127 | 1-[(6-bromo-2-pyridinyl)methyl]-4-ethylpiperazine | oil | 283.8 (M + H) + | 84 |
| 128 | (4-[(2-bromo-4-pyridinyl)methyl]morpholine | oil | 256.8 (M + H) + | 84 |
| 129 | 1-[(2-bromo-4-pyridinyl)methyl]-4-ethylpiperazine | oil | 284.0 (M + H) + | 84 |
| 130 | 1-[(2-bromo-4-pyridinyl)methyl]-4-methylpiperazine | oil | 270.2 (M + H) + | 84 |
| 131 | 1-[(6-bromo-2-pyridinyl)methyl]-4-methylpiperazine | oil | 270.2 (M + H) + | 84 |
| 132 | 4-[(2-bromo-3-pyridinyl)methyl]morpholine | oil | 256.8 (M + H) + | 84 |
| 133 | 1-[(2-bromo-3-pyridinyl)methyl]-4-ethylpiperazine | oil | 283.8 (M + H) + | 84 |
| 134 | 1-[(2-bromo-3-pyridinyl)methyl]-4-methylpiperazine | oil | 270.2 (M + H) + | 84 |
| 135 | 1-(5-bromo-2-pyridinyl)-4-(1-pyrrolidinyl)piperidine | 110–112 | 310.3 (M + H) + | 91 |
| 136 | 5-bromo-N-(2-methoxyethyl)-N-methyl-2-pyridinamine | oil | 245.1 (M + H) + | 91 |
| 137 | 5-bromo-2-(1-piperidinyl)pyridine | 24–25 | 241.1 (M + H) + | 91 |
| 138 | 2-[4-(5-bromo-2-pyridinyl)-1-piperazinyl]ethanol | 100–102 | 285.8 (M + H) + | 91 |
| 139 | 2-[(5-bromo-2-pyridinyl)(methyl)amino]ethanol | 40–42 | 230.8 (M + H) + | 91 |
| 140 | 4-(5-bromo-2-pyridinyl)-thiomorpholine | oil | 258.8 (M + H) + | 91 |
| 141 | ethyl 1-(5-bromo-2-pyridinyl)-4-piperidinecarboxylate | 30–32 | 313.1 (M + H) + | 91 |
| 142 | 2-{4-[(6-bromo-3-pyridinyl)methyl]-1-piperazinyl}-ethanol | 57–59 | 300.1 (M + H) + | 84 |
| 143 | 6-bromo-3-(1-piperidinyl-methyl)pyridine | 52–54 | 255.2 (M + H) + | 84 |
| 144 | 1-[(6-bromo-3-pyridinyl)methyl]-4-piperidinol | 87–90 | 271.1 (M + H) + | 84 |
| 145 | 4-[(6-bromo-3-pyridinyl)methyl]-thiomorpholine | 88–89 | 273.1 (M + H) + | 84 |
| 146 | 4-[(5-bromo-2-pyridinyl)methyl]morpholine | 57–59 | 257.0 (M + H) + | 95 |
| 147 | 1-[(5-bromo-2-pyridinyl)methyl]-4-methylpiperazine | oil | 270.03 (M + H) + | 95 |
| 148 | 1-[(5-bromo-2-pyridinyl)methyl]-4-ethylpiperazine | oil | 283.98 (M + H) + | 95 |
| 149 | 5-bromo-2-(1-piperidinyl-methyl)pyridine | oil | 255.2 (M + H) + | 95 |

EXAMPLE 1

4-(4-Chloro-2-fluoroanilino)-7-[5-(4-morpholinylmethyl)-3-thienyl]-3-quinolinecarbonitrile 4-[(4-Bromo-2-thienyl)methyl]morpholine (prepared according to the procedure of U.S. Pat. No. 5,866,572) (208.8 mg, 0.80 mmol) was dissolved in 20 mL of tetrahydrofuran and the solution was cooled to −78° C. Triisopropylborate (0.202 mL, 0.80 mmol) was added followed by 2.5 M n-butyl lithium in hexane (0.392 mL, 0.98 mmol). The mixture was stirred at −78° C. for 30 minutes, then allowed to warm to room temperature. The solvent was removed in vacuo to provide diisopropyl[5-(morpholinomethyl)thien-3-yl]boronate.

A mixture of this boronate, 7-bromo-4-(4-chloro-2-fluoroanilino)-3-quinolinecarbonitrile (Reference Example 7) (150 mg, 0.40 mmol), tetrakis(triphenylphosphine) palladium (75 mg) and saturated sodium bicarbonate (4 mL) in 7 mL of ethylene glycol dimethyl ether was heated at 100° C. for 3 hours. The reaction mixture was cooled and treated with 1N sodium hydroxide then extracted with ethyl acetate. The organic layer was washed with saturated sodium chloride, dried over sodium sulfate and concentrated in vacuo. The residue was triturated with diethyl ether to provide 4-(4-chloro-2-fluoroanilino)-7-[5-(4-morpholinylmethyl)-3-thienyl)-3-yl)-3-quinoline-carbonitrile as a yellow solid;

$^1$H NMR (DMSO-d$_6$) δ 2.45–2.60 (m, 6H), 3.50–3.65 (m, 4H), 7.35–7.70 (m, 5H), 8.10 (dd, J=8, 4 Hz, 1H), 8.16 (s, 1H), 8.50 (d, J=4 Hz, 1H), 8.59 (s, 1H), 9.88 (br s, 1H); MS (ES) m/z 240 (M+2)$^{2+}$, 478.9 (M+1).

EXAMPLE 2

4-(2,4-Dichloro-5-methoxyanilino)-7-[(E)-2-(4-pyridinyl)ethenyl]-3-quinolinecarbonitrile A mixture of 7-bromo-4-(2,4-dichloro-5-methoxyanilino)-3-quinolinecarbonitrile (Reference Example 8) (250 mg, 0.59 mmol), 4-vinylpyridine (0.10 mL, 0.93 mmol), palladium(II)acetate (1.5 mg, 0.007 mmol) and tri-o-tolylphosphine (7 mg, 0.02 mmol) in 3 mL of triethylamine was heated at reflux for 16 hours. Additional triethylamine was added and the solids were removed by filtration, washing with ethyl acetate, methanol and water. The aqueous and organic layers of the filtrate were separated and the aqueous layer was extracted with additional ethyl acetate. The organic layers were combined, dried over sodium sulfate, filtered and concentrated in vacuo. The resultant solid was purified by flash silica gel chromatography eluting with 10% methanol in methylene chloride to provide 90 mg (34% yield) of 4-(2,4-dichloro-5-methoxyanilino)-7-[(E)-2-(4-pyridinyl)ethenyl]-3-quinoline-carbonitrile as a yellow solid, mp 255–257° C.;

$^1$HNMR (DMSO-d($_6$)) δ 3.84 (s, 3H), 7.49 (s, 1H), 7.73 (s, 1H), 7.84 (d, J=16 Hz, 1H), 8.12–8.21 (m, 3H), 8.27–8.36 (m, 3H), 8.81–8.90 (m, 3H), 9.23 (s, 1H); MS (ES) m/z 447.2 (M+1). Analysis for $C_{24}H_{16}Cl_2N_4O$-0.7$H_2O$: Calcd: C, 62.66; H, 3.81; N, 12.18. Found: C, 69.50; H, 3.79; N, 12.28.

EXAMPLE 3

4-(2,4-Dichloro-5-methoxyanilino)-7-[(E)-2-(2-pyridinyl)ethenyl]-3-quinolinecarbonitrile A mixture of 7-bromo-4-(2,4-dichloro-5-methoxyanilino)-3-quinolinecarbonitrile (Reference Example 8) (250 mg, 0.59 mmol), 2-vinylpyridine (0.10 mL, 0.93 mmol), palladium(II)acetate (1.5 mg, 0.007 mmol) and tri-o-tolylphosphine (7 mg, 0.02 mmol) in 5 mL of triethylamine was heated at reflux overnight. The mixture was concentrated in vacuo and the resultant solid was purified by preparative thin layer chromatography eluting with 10% methanol in methylene chloride to provide 25 mg (34% yield) of 4-(2,4-dichloro-5-methoxyanilino)-7-[(E)-2-(4-pyridinyl)ethenyl]-3-quinolinecarbonitrile as a yellow solid, mp 218–219° C.;

EXAMPLE 4

4-(2,4-Dichloroanilino)-7-[(E)-2-(4-pyridinyl)ethenyl]-3-quinolinecarbonitrile

A mixture of 7-bromo-4-(2,4-dichloroanilino)-3-quinolinecarbonitrile (Reference Example 6) (250 mg, 0.64 mmol), 4-vinylpyridine (0.11 mL, 1.02 mmol), palladium (II)acetate (3 mg, 0.015 mmol) and tri-o-tolylphosphine (8 mg, 0.022 mmol) in 5 mL of triethylamine was heated at reflux overnight. The solvent was removed in vacuo and the residue was partitioned between ethyl acetate and water. The organic layer was dried over magnesium sulfate, filtered and concentrated in vacuo. The resultant solid was purified by flash silica gel chromatography eluting with ethyl acetate to provide 80 mg (30% yield) of 4-(2,4-dichloroanilino)-7-[(E)-2-(4-pyridinyl)ethenyl]-3-quinolinecarbonitrile as a yellow solid, mp 240–2429° C.;

$^1$H NMR (DMSO-d$_6$/trifluoroacetic acid) δ 7.55–7.68 (m, 2H), 7.82–7.95 (m, 2H), 8.13–8.33 (m, 5H), 8.70 (d, J=9 Hz, 1H), 8.89–8.99 (m, 3H); MS (ES) m/z 417.3 (M+1). Analysis for $C_{23}H_{14}Cl_2N_4$: Calcd: C, 66.20; H, 3.38; N, 13.43. Found: C, 65.90; H, 3.17; N, 13.37.

EXAMPLE 5

4-(2,4-Dichloro-5-methoxyanilino)-7-[5-(1,3-dioxolan-2-yl)-2-furyl]-3-quinolinecarbonitrile A mixture of 4-(2,4-dichloro-5-methoxyanilino)-7-iodo-3-quinolinecarbonitrile (Reference Example 13) (200 mg, 0.42 mmol), tributyl[5-(1,3-dioxolan-2-yl)-2-furanyl] stannane (prepared according to the procedure of M. Yamamoto, *J. Chem. Soc. Chem. Comm.*, 8, 560 (1988) (220 mg, 0.50 mmol), and a catalytic amount of dichlorobis (triphenylphosphine)palladium(II) in 5 mL of dioxane was heated at reflux for 4 hours. The mixture was concentrated in vacuo and partitioned between ethyl acetate and saturated sodium chloride. The organic layer was washed with water, dried over sodium sulfate and concentrated in vacuo to provide 130 mg (64% yield) of 4-(2,4-dichloro-5-methoxyanilino)-7-[5-(1, 3-dioxolan-2-yl)-2-furyl] quinolinecarbonitrile as a yellow solid, mp 224–229° C.;

$^1$H NMR (DMSO-d$_6$/trifluoroacetic acid) δ 3.88 (s, 3H), 4.00–4.04 (m, 2H), 4.10–4.15 (m, 2H), 6.04 (s, 1H), 6.82 (d, J=4 Hz, 1H), 7.43 (d, J=4 Hz, 1H), 7.54 (s, 1H), 7.86 (s, 1H), 8.19 (s, 1H), 8.24 (d, J=9 Hz, 1H), 8.73 (d, J=9 Hz, 1H), 9/09 (s, 1H); MS (ES) m/z 482.3 (M+1). Analysis for $C_{24}H_{17}Cl_2N_3O_4$: Calcd: C, 59.77; H, 3.55; N, 8.71. Found: C, 59.70; H, 3.75; N, 8.61.

EXAMPLE 6

4-(2,4-Dichloro-5-methoxyanilino)-7-(5-formyl-2-furyl)-3-quinolinecarbonitrile

A solution of 4-(2,4-dichloro-5-methoxyanilino)-7-[5-(1, 3-dioxolan-2-yl)-2-furyl]-3quinolinecarbonitrile (Example 5) (90 mg, 0.19 mmol) in 2 mL of tetrahydrofuran and 1 mL of 2N hydrochloric acid was stirred at room temperature for 4 hours. The mixture was partitioned between ethyl acetate and saturated sodium bicarbonate. The organic layer was dried over sodium sulfate and filtered through silica gel. The filtrate was concentrated in vacuo to provide 40 mg (48% yield) of 4-(2,4-dichloro-5-methoxyanilino)-7-(5-formyl-2-furyl)-3-quinolinecarbonitrile as a yellow solid, mp>250° C.;

$^1$H NMR (DMSO-d$_6$/trifluoroacetic acid) δ 3.87 (s, 3H), 7.43 (s, 1H), 7.67 (d, J=4 Hz, 1H), 7.76 (d, J=4 Hz, 1H), 7.79 (s, 1H), 8.26 (d, J=9 Hz, 1H), 8.34 (s, 1H), 8.72 (d, J=9 Hz, 1H), 8.87 (s, 1H), 9.72 (s, 1H); MS (ES) m/z 438.3 (M+1). Analysis for $C_{22}H_{13}Cl_2N_3O_3$: Calcd: C, 60.29; H, 2.99; N, 9.59. Found: C, 60.25; H, 3.12; N, 9.34.

EXAMPLE 7

7-[5-(4-Morpholinylmethyl)-3-thienyl]-4-(4-phenoxyanilino)-3-quinolinecarbonitrile 4-[(4-Bromo-2-thienyl)methyl]morpholine (262 mg, 1.0 mmol) was dissolved in 20 mL of tetrahydrofuran and the solution was cooled to −78° C. 2.5M n-Butyl lithium in hexane (0.40 mL, 1.0 mmol) was added followed by tri-isopropylborate (209 mg, 1.1 mmol). The mixture was stirred at −78° C. for 30 minutes and then allowed to warm to room temperature. The solvent was removed in vacuo to provide the intermediate boronate.

A mixture of this boronate, 7-bromo-4-(4-phenoxyanilino)-3-quinolinecarbonitrile (Reference Example 10) (208 mg, 0.50 mmol) and tetrakis (triphenylphosphine)palladium(0) (96 mg, 0.082 mmol) was heated at reflux in 8.5 mL of ethylene glycol dimethyl ether and 5.1 mL of saturated sodium bicarbonate for 2 hours. The reaction was cooled to room temperature, quenched with 4.1 mL of 1N sodium hydroxide, and partitioned between ethyl acetate and saturated sodium chloride. The layers were separated and the ethyl acetate layer was dried over magnesium sulfate. Removal of the solvent in vacuo gave a residue which was purified by flash silica gel chromatography eluting with 5% methanol in methylene chloride to provide 83 mg (32% yield) of 7-[5-(4-morpholinylmethyl)-3-thienyl]-4-(4-phenoxyanilino)-3-quinolinecarbonitrile as a light tan solid, mp 221–223° C.;

$^1$H NMR (DMSO-d$_6$) δ 2.47 (t, J=4 Hz, 4H), 3.61, (t, J=4 Hz, 4H), 3.74 (s, 2H), 7.10 (m, 5H), 7.39 (m, 4H), 7.67 (s, 1H), 8.04 (dd, J=10, 2 Hz, 1H), 8.17 (dd, J=10, 2 Hz, 2H), 8.51 (d, J=10 Hz, 1H), 8.54 (s, 1H), 9.86 (s, 1H); MS (ES) m/z 519.1 (M+1). Analysis for $C_{31}H_{26}N_4O_2S$-0.25$H_2O$: Calcd: C, 71.17; H, 5.10; N, 10.71. Found: C, 71.16; H, 4.99; N, 10.51.

EXAMPLE 8

4-(4-Benzylanilino)-7-[5-(4-morpholinylmethyl)-3-thienyl]-3-quinolinecarbonitrile 4-[(4-Bromo-2-thienyl)methyl]morpholine (524 mg, 2.0 mmol) was dissolved in 40 mL of tetrahydrofuran and the solution was cooled to −78° C. 2.5M n-Butyl lithium in hexane (0.80 mL, 2.0 mmol) was added followed by tri-isopropylborate (418 mg, 2.2 mmol). The mixture was stirred at −78° C. for 30 minutes and then allowed to warm to room temperature. The solvent was removed in vacuo to provide the intermediate boronate.

A mixture of this boronate, 4-(4-benzylanilino)-7-bromo-3-quinolinecarbonitrile (Reference Example 9) (414 mg, 1.0 mmol) and tetrakis(triphenylphosphine)palladium(0) (200 mg, 0.17 mmol) was heated it reflux in 15 mL of ethylene glycol dimethyl ether and 10 mL of saturated sodium bicarbonate for 2 hours. The reaction was cooled to room temperature, quenched with 8 mL of 1N sodium hydroxide, and partitioned between ethyl acetate and saturated sodium chloride. The layers were separated and the ethyl acetate layer was dried over magnesium sulfate. Removal of the solvent in vacuo gave a residue which was purified by flash silica gel chromatography eluting with 5% methanol in methylene chloride to provide 86 mg (17% yield) of 4-(4-benzylanilino)-7-[5-(4-morpholinylmethyl)-3-thienyl]-3-quinolinecarbonitrile as a tan solid, mp 228–230° C.; p $^1$HNMR(DMSO-$d_6$) δ 2.46 (t, J=4 Hz, 4H), 3.60 (t, J=4 Hz, 4H), 3.74 (s, 2H), 3.99 (s, 2H), 7.25 (m, 9H), 7.66 (s, 1H), 8.01 (dd, J=9, 2 Hz, 1H), 8.17 (dd, J=13, 2 Hz, 2H), 8.46 (d, J=9 Hz, 1H), 8.55 (s, 1H), 9.91 (s, 1H); MS (ES) m/z 517.1 (M+1). Analysis for $C_{32}H_{28}N_4OS$-0.25$H_2O$: Calcd: C, 73.75; H, 5.41; N, 10.75. Found: C, 73.76; H, 5.46; N, 10.78.

EXAMPLE 9

4-(2,4-Dichloroanilino)-7-{5-[2-(4-morpholinyl)ethyl]-2-thienyl}-3-quinolinecarbonitrile 4-[2-(2-Thienyl)ethyl]morpholine (prepared according to the procedure of U.S. Pat. No. 5,8665,72) (200 mg, 1.00 mmol) was dissolved in 20 mL of tetrahydrofuran and the solution was cooled to −78° C. 2.5M n-Butyl lithium in hexane (0.40 mL, 1.00 mmol) was added and the mixture was stirred at −78° C. for 30 minutes. Tri-isopropylborate (209 mg, 1.11 mmol) was added and the reaction mixture was stirred at −78° C. for 30 minutes, then allowed to warm to room temperature. The solvent was removed in vacuo to provide the intermediate boronate.

A mixture of the boronate, 7-bromo-4-(2,4-dichloroanilino)-3-quinolinecarbonitrile (Reference Example 6) (200 mg, 0.508 mmol), and tetrakis(triphenylphosphine)palladium(0) (96 mg, 0.082 mmol) was heated at reflux in 8.4 mL of ethylene glycol dimethyl ether and 5.1 mL of saturated sodium bicarbonate for 5 hours. The reaction was quenched with 4.1 mL of 1N sodium hydroxide and partitioned between ethyl acetate and saturated sodium chloride. The layers were separated and the ethyl acetate layer was dried over magnesium sulfate. Removal of the solvent in vacuo gave a residue which was purified by flash silica gel chromatography eluting with 1:1 ethyl acetate-:hexane followed by 3% methanol in methylene chloride. The fractions containing product were concentrated and the solid was recrystallized from acetone and hexane to provide 69 mg (27% yield) of 4-(2,4-dichloroanilino)-7-{5-[2-(4-morpholinyl)ethyl]-2-thienyl}-3-quinolinecarbonitrile as a white solid, mp 168–169° C.;

$^1$H NMR (DMSO-$d_6$) δ 2.47 (t, J=5 Hz, 4H); 2.61 (t, J=7 Hz, 2H), 3.02 (t, J=7 Hz, 2H), 3.62 (t, J=5 Hz, 4H), 7.00 (d, J=4 Hz, 1H), 7.50–8.51 (m, 8H), 9.95 (s, 1H); MS (ES) m/z 511.1 (M+1). Analysis for $C_{26}H_{22}Cl_2N_4OS$-0.35$H_2O$: Calcd: C, 60.54; H, 4.42; N, 10.86. Found: C, 60.82; H, 4.46; N, 10,38.

EXAMPLE 10

4-(2,4-Dichloroanilino)-7-{5-[(4-ethyl-1-piperazinyl)methyl]-3-thienyl}-3-quinolinecarbonitrile 1-[(4-Bromo-2-thienyl)methyl]-4-ethylpiperazine (294 mg, 1.08 mmol) was dissolved in 15 mL of tetrahydrofuran and the solution was cooled to −78° C. Tri-isopropylborate (209 mg, 1.11 mmol) was added followed by 2.5 M n-Butyl lithium in hexane (0.40 mL, 1.00 mmol). The mixture was stirred at −78° C. for 30 minutes and then allowed to warm to room temperature. The solvent was removed in vacuo to provide the intermediate boronate.

A mixture of this boronate, 7-bromo-4-(2,4-dichloroanilino)-3-quinolinecarbonitrile (Reference Example 6) (200 mg, 0.509 mmol) and tetrakis(triphenylphosphine)palladium(0) (96 mg, 0.082 mmol) was heated at reflux in 8 mL of ethylene glycol dimethyl ether and 5 mL of saturated sodium bicarbonate for 2 hours. The reaction was cooled to room temperature, quenched with 4.1 mL of 1.0N sodium hydroxide, and partitioned between ethyl acetate and saturated sodium chloride. The layers were separated and the ethyl acetate layer was dried over magnesium sulfate. Removal of the solvent in vacuo gave a residue which was purified by flash silica gel chromatography eluting with 5% methanol in methylene chloride to provide 180 mg (67% yield) of 4-(2,4-dichloroanilino)-7-{5-[(4-ethyl-1-piperazinyl)methyl]-3-thienyl}-3-quinolinecarbonitrile as a white solid: mp 182–184° C.;

$^1$H NMR (DMSO-$d_6$) δ 1.22 (t, J=8 Hz, 3H), 2.50–2.52 (m, 2H), 2.90–3.10 (m, 2H), 3.16 (q, J=7 Hz, 2H), 3.40–3.50 (m, 2H), 3.80–4.20 (m, 4H), 7.55 (dd, J=9, 2 Hz, 1H), 7.60 (d, J=9 Hz, 1H), 7.72 (s, 1H), 7.83 (d, J=2 Hz, 1H), 8.12 (d, J=9 Hz, 1H), 8.19 (s, 1H), 8.24 (d, J=1 Hz, 1H), 8.60 (d, J=9 Hz, 1H), 8.75 (s, 1H); MS (ES) m/z 522.0 (M+1). Analysis for $C_{27}H_{25}Cl_2N_5S$-0.2$CH_2Cl_2$: Calcd: C, 60.55; H, 4.73; N, 12.98. Found: C, 60.43; H, 4.42; N, 12.56.

EXAMPLE 11

4-(2,4-Dichloroanilino)-7-[5-(4-morpholinyl)-1-pentynyl]-3-quinolinecarbonitrile A solution of 7-bromo-4-(2,4-dichloroanilino)-3-quinolinecarbonitrile (Reference Example 6) (200 mg, 0.509 mmol) and 4-(4-pentynyl)morpholine (117 mg, 0.763 mmol) in 5 mL of triethylamine was flushed with nitrogen for 10 minutes. Triphenylphosphine (10.1 mg, 0.039 mmol), copper(I)iodine (2.0 mg, 0.01 mmol) and dichlorobis(triphenylphosphine)palladium(II) (236 mg, 0.039 mmol) were added and the resulting mixture was heated at reflux for 12 hours and then stirred at room temperature overnight. The reaction mixture was diluted with triethylamine and filtered. The filtrate was concentrated and the residue was purified by flash silica gel chromatography eluting with 5% methanol in methylene chloride to provide 25 mg of 4-(2,4-dichloroanilino)-7-[5-(4-morpholinyl)-1-pentynyl]-3-quinolinecarbonitrile as a off-white solid, mp 131–133° C.;

$^1$H NMR (DMSO-$d_6$) δ 1.99 (m, 2H), 2.66 (t, J=7 Hz, 2H), 3.14 (m, 2H), 3.26 (t, J=8 Hz, 2H), 3.50 (d, J=11 Hz,

2H), 3.67 (t, J=12 Hz, 2H), 4.02 (d, J=11 Hz, 2H), 7.54 (s, 2H), 7.71 (d, J=9 Hz, 1H), 7.80 (s, 1H), 7.92 (s, 1H), 8.53 (d, J=9 Hz, 1H), 8.73 (s, 1H), 9.68 (s, 1H); MS (ES) m/z 465.4 (M+1).

EXAMPLE 12

4-(2,4-Dichloroanilino)-7-[(E/Z)-5-(4-morpholinyl)-1-pentenyl]-3-quinolinecarbonitrile A solution of 7-bromo-4-(2,4-dichloroanilino)-3-quinolinecarbonitrile (Reference Example 6) (200 mg, 0.509 mmol) and 4-(4-pentenyl)morpholine (118 mag, 0.763 mmol) in 5 mL of dimethylformamide was added to a mixture of triphenylphosphine (20 mg, 0.076 mmol), palladium acetate (6 mg, 0.025 mmol) and sodium bicarbonate (51 mg, 0.607). The resulting slurry was heated at 120° C. for 4 hours and then stirred at room temperature overnight. The reaction mixture was partitioned between ethyl acetate and water and the organic layer was dried over sodium sulfate, filtered and concentrated in vacuo. The residue was purified by flash silica gel chromatography eluting with 5% methanol in methylene chloride to provide 76 mg (32% yield) of 4-(2,4-dichloroanilino)-7-[(E/Z)-5-(4-morpholinyl)-1-pentenyl]-3-quinolinecarbonitrile as a white solid: mp 70–72° C.;

$^1$H NMR (DMSO-d$_6$) δ 1.85–2.85 (m, 4H), 3.00–3.25 (m, 4H), 3.50–4.00 (m, 6H), 5.53–5.86 (m, 1H), 6.70 (m, 1H), 7.52–7.93 (m, 5H), 8.47 (d, J=8 Hz, 1H), 8.65 (s, 1H), 9.78 (s, 1H); MS (ES) m/z 467.1 (M+1). Analysis for C$_{25}$H$_{24}$Cl$_2$N$_4$O-0.6H$_2$O: Calcd: C, 62.78; H, 5.30; N, 11.72. Found: C, 62.47; H, 5.21; N, 11.48.

EXAMPLE 13

4-(2,4-Dichloroanilino)-7-[5-(4-morpholinylmethyl)-2-furyl]-3-quinolinecarbonitrile Using an analogous procedure to that described for Product 10, 4-(2,4-dichloroanilino-7-[5-(4-morpholinylmethyl)-2-furyl]-3-quinolinecarbonitrile was prepared from 7-bromo-4-(2,4-dichloroanilino)-3-quinolinecarbonitrile (Reference Example 6) and 4-[(5-bromo-2-furyl)methyl]morpholine in 26% yield, mp 118–120° C.;

$^1$H NMR (DMSO-d$_6$) δ 2.50 (t, J=5 Hz, 4H), 3.60 (t, J=5 Hz, 4H), 3.63 (s, 2H), 6.53 (d, J=3 Hz, 1H), 8.12–8.27 (m, 6H), 8.46–8.60 (m, 2H), 9.93 (s, 1H); MS m/z 479.3 (M+1).

EXAMPLE 14

4-(2,4-Dichloroanilino)-7-(3-hydroxy-1-propynyl)-3-quinolinecarbonitrile

Using an analogous procedure to that described for Example 11, 4-(2,4-dichloroanilino)-7-(3-hydroxy-1-propynyl)-3-quinolinecarbonitrile was prepared from 7-bromo-4-(2,4-dichloroanilino)-3-quinolinecarbonitrile (Reference Example 6) and propargyl alcohol in 67% yield, mp 251–253° C.;

$^1$H NMR (DMSO-d$_6$) δ 4.40 (s, 2H), 7.56 (m, 2H), 7.75 (d, J=9 Hz, 1H), 7.83 (d, J=2 Hz, 1H), 7.91 (s, 1H), 8.57 (d, J=9 Hz, 1H), 8.85 (s, 1H); MS (ES) m/z 368.1 (M+1). Analysis for C$_{19}$H$_{11}$Cl$_2$N$_3$O-0.5CH$_2$Cl$_2$: Calcd: C, 57.02; H, 2.94; N, 10.23. Found: C, 57.22; H, 2.91; N, 10.34.

EXAMPLE 15

4-(2,4-Dichloroanilino)-7-[3-(dimethylamino)-1-propynyl]-3-quinolinecarbonitrile Using an analogous procedure to that described for Example 12, 4-(2,4-dichloroanilino)-7-[3-(dimethylamino)-1-propynyl]-3-quinolinecarbonitrile was prepared from 7-bromo-4-(2,4-dichloroanilino)-3-quinolinecarbonitrile (Reference Example 6) and 1-dimethylamino-2-propyne in 93% yield, mp 144–145° C.;

$^1$H NMR (DMSO-d$_6$) δ 2.29 (s, 6H), 3.55 (s, 2H), 7.49–7.89 (m, 5H), 8.40–8.55 (m, 2H), 10.03 (bs, 1H); MS (ES) m/z 395.2 (M+1).

EXAMPLE 16

4-(2,4-Dichloroanilino)-7-[(E/Z)-6-(4-morpholinyl)-1-hexenyl]-3-quinolinecarbonitrile Using an analogous procedure to that described for Example 12, 4-(2,4-dichloroanilino)-7-[(E/Z)-6-(4-morpholinyl)-1-hexenyl]-3-quinolinecarbonitrile was prepared from 7-bromo-4-(2,4-dichloroanilino)-3-quinolinecarbonitrile (Reference Example 6) and 4-(5-hexenyl)morpholine in 13% yield, mp 128–130° C.;

$^1$H NMR (DMSO-d$_6$) δ 1.40–1.55 (m, 4H), 2.29–2.84 (m, 6H), 3.45–3.58 (m, 6H), 5.45–5.70 (m, 1H), 6.63 (m, 1H), 7.51–7.80 (m, 5H), 8.45–8.55 (m, 2H), 9.86 (s, 1H); MS (ES) m/z 481.3 (M+1). Analysis for C$_{26}$H$_{26}$Cl$_2$N$_4$O-0.3CH$_2$Cl$_2$: Calcd: C, 69.30; H, 5.27; N, 11.05. Found: C, 62.54; H, 4.95; N, 11.16.

EXAMPLE 17

7-[4,5-Bis(4-morpholinylmethyl)-2-thienyl]-4-(2,4-dichloroanilino)-3-quinolinecarbonitrile Using an analogous procedure to that described for Example 9, 7-[4,5-bis(4-morpholinylmethyl)-2-thienyl]-4-(2,4-dichloroanilino)-3-quinolinecarbonitrile was prepared from 7-bromo-4-(2,4-dichloroanilino)-3-quinolinecarbonitrile (Reference Example 6) and 4-{[2-(4-morpholinylmethyl)-3-thienyl]methyl}morpholine in 49% yield, mp 118–125° C.;

$^1$H NMR (DMSO-d$_6$) δ 2.35–2.45 (m, 8H), 3.62 (s, 4H), 3.70–3.80 (m, 8H), 7.53 (d, J=9 Hz, 1H), 7.60 (d, J=9 Hz, 1H), 7.50–7.70 (m, 1H), 7.81 (s, 1H), 8.99 (d, J=8 Hz, 1H), 8.06 (s, 1H), 8.53 (d, J=8 Hz, 1H), 8.58 (s, 1H), 9.97 (s, 1H); MS (ES) m/z 594.1 (M+1).;

EXAMPLE 18

4-(2,4-Dichloroanilino)-7-[5-(2-pyridinyl)-2-thienyl]-3-quinolinecarbonitrile

Using an analogous procedure to that described for Example 10, 4-(2,4-dichloroanilino)-7-[5-(2-pyridinyl)-2-thienyl]-3-quinolinecarbonitrile was prepared from 7-bromo-4-(2,4-dichloroanilino)-3-quinolinecarbonitrile (Reference Example 6) and 2-pyridinyl-2-thiophene in 62% yield, mp 270° C. (dec);

$^1$H NMR (DMSO-d$_6$) δ 7.37 (dd, J=5, 3 Hz, 1H), 7.58 (dd, J=7, 2 Hz, 1H), 7.64 (d, J=6 Hz, 1H), 7.87 (d, J=2 Hz, 1H), 7.91 (dd, J=7, 2 Hz, 1H), 7.96 (s, 2H), 8.05 (d, J=6 Hz, 1H), 8.18 (s, 1H), 8.23 (d, J=7 Hz, 1H), 8.60 (d, J=3 Hz, 1H), 8.67 (d, J=7 Hz, 1H), 8.92 (s, 1H); MS (ES) m/z 473.1 (M+1). Analysis for C$_{25}$H$_{14}$Cl$_2$N$_4$S-0.5CH$_2$Cl$_2$: Calcd: C, 59.36; H, 2.92; N, 10.86. Found: C, 59.03; H, 2.79; N, 10.71.

EXAMPLE 19

4-(2,4-Dichloro-5-methoxyanilino)-7-{5-[(4-ethyl-1-piperazinyl)methyl]-3-thienyl}-3-quinolinecarbonitrile Using an analogous procedure to that described for Example 10, 4-(2,4-dichloro-5-methoxyanilino)-7-{5-[(4- ethyl-1-piperazinyl)methyl]-3-thienyl}-3-quinolinecarbonitrile was prepared from 7-bromo-4-(2,4-dichloro-5-methoxyanilino)-3-quinolinecarbonitrile (Reference Example 8) and 1-[(4-bromo-2-thienyl)methyl]-4-ethylpiperazine in 26% yield as a off-white solid, mp 118–120° C.;

$^1$H NMR (DMSO-d$_6$) δ 1.21 (t, J=7 Hz, 3H), 2.44–2.55 (m, 2H), 2.95–3.10 (m, 2H), 3.16 (q, J=7 Hz, 2H), 3.40–3.51 (m, 4H), 3.87 (s, 3H), 3.92 (s, 2H), 7.36 (s, 1H), 7.70 (s, 1H), 7.75 (s, 1H), 8.08 (d, J=9 Hz, 1H), 8.17 (s, 1H), 8.20 (s, 1H), 8.56 (d, J=9 Hz, 1H), 8.62 (s, 1H), 9.33 (s, 1H); MS (ES) m/z 552.2 (M+1). Analysis for $C_{28}H_{27}Cl_2N_5OS$-0.25$CH_2Cl_2$: Calcd: C, 59.08; H, 4.82; N, 12.21. Found: C, 58.96; H, 4.72; N, 11.98.

EXAMPLE 20

7-[4,5-bis(4-Morpholinylmethyl)-2-thienyl]-4-(2,4-dichloro-5-methoxyanilino)-3-quinolinecarbonitrile Using an analogous procedure to that described for Example 9, 7-[4,5-bis(4-morpholinylmethyl)-2-thienyl]-4-(2,4-dichloro-5-methoxyanilino)-3-quinolinecarbonitrile was prepared from 7-bromo-4-(2,4-dichloro-5-methoxyanilino)-3-quinolinecarbonitrile (Reference Example 8) and 4-{[2-(4-morpholinylmethyl)-3-thienyl]methyl}morpholine in 53% yield as a light yellow solid, mp 118–125° C.;

$^1$H NMR (DMSO-d$_6$) δ 2.35–2.45 (m, 4H), 3.25–3.35 (m, 4H), 3.55–3.65 (m, 8H), 3.73 (s, 3H), 3.86 (s, 4H), 7.41 (s, 1H), 7.64 (s, 1H), 7.76 (s, 1H), 7.95–8.10 (m, 2H), 8.45–8.60 (m, 2H), 10.00 (s, 1H); MS (ES) m/z 624.0 (M+1). Analysis for $C_{31}H_{31}Cl_2N_5O_3S$-0.7$CH_2Cl_2$: Calcd: C, 55.65; H, 4.76; N, 9.84. Found: C, 55.64; H, 4.61; N, 9.52.

EXAMPLE 21

4-(2,4-Dichloro-5-methoxyanilino)-7-{5-[(E)-3-(4-morpholinyl)-1-propenyl]-2-thienyl}-3-quinolinecarbonitrile Using an analogous procedure to that described for Example 9, 4-(2,4-dichloro-5-methoxyanilino)-7-{5-[(E)-(4-morpholinyl)-1-propenyl]-2-thienyl}-3-quinolinecarbonitrile was prepared from 7-bromo-4-(2,4-dichloro-5-methoxyanilino)-3-quinolinecarbonitrile (Reference Example 8) and 4-[(E)-3-(2-thienyl)-2-propenyl]morpholine in 20% yield, mp) 145° C. (dec);

$^1$H NMR (DMSO-d$_6$) δ 3.00–3.25 (m, 4H), 3.50–3.75 (m, 4H), 3.86 (s, 3H), 3.96 (d, J=7 Hz, 2H), 6.16 (dd, J=16, 7 Hz, 1H), 7.08 (d, J=16 Hz, 1H), 7.30–7.40 (m, 2H), 7.73 (s, 1H), 7.83 (d, J=3 Hz, 1H), 7.95–8.20 (m, 2H), 8.50–8.70 (m, 2H), 9.96 (bs, 1H); MS (ES) m/z 551.1 (M+1). Analysis for $C_{28}H_{24}Cl_2N_4O_2S$-2.0$H_2O$: Calcd: C, 59.23; H, 4.78; N, 9.50. Found: C, 59.59; H, 4.59; N, 9.00.

EXAMPLE 22

4-(2,4-Dichloro-5-methoxyanilino)-7-{5-[4-(4-morpholinyl)butyl]-2-thienyl}-3-quinolinecarbonitrile Using an analogous procedure to that described for Example 9, 4-(2,4-dichloro-5-methoxyanilino)-7-{5-[4-(4-morpholinyl)butyl]-2-thienyl}-3-quinolinecarbonitrile was prepared from 7-bromo-4-(2,4-dichloro-5-methoxyanilino)-3-quinolinecarbonitrile (Reference Example 8) and 4-[4-(2-thienyl)butyl]-morpholine in 51% yield, mp 188° C. (dec);

$^1$H NMR (DMSO-d$_6$) δ 1.50 (m, 2H), 1.70 (m, 2H), 2.25–2.40 (m, 4H), 2.87 (t, J=7 Hz, 2H), 3.30–3.50 (m, 4H), 3.56 (t, J=5 Hz, 2H), 3.86 (s, 3H), 6.96 (d, J=4 Hz, 1H), 7.20–7.45 (m, 1H), 7.55–7.80 (m, 3H), 7.81–8.12 (m, 2H), 8.40–8.60 (m, 1H), 10.01 (br s, 1H); MS (ES) m/z 567.3 (M+1). Analysis for $C_{29}H_{28}Cl_2N_4O_2S$-0.25$H_2O$: Calcd: C, 60.89; H, 5.01; N, 9.80. Found: C, 60.46; H, 4.97; N, 9.87.

EXAMPLE 23

4-(2,4-Dichloro-5-methoxyanilino)-7-[5-(4-morpholinylmethyl)-2-thienyl]-3-quinolinecarbonitrile Using an analogous procedure to that described for Example 10, 4-(2,4-dichloro-5-methoxyanilino)-7-[5-(4-morpholinylmethyl)-2-thienyl]-3-quinolinecarbonitrile was prepared from 7-bromo-4-(2,4-dichloro-5-methoxyanilino)-3-quinolinecarbonitrile (Reference Example 8) and 4-[(5-bromo-2-thienyl)methyl]morpholine in 24% yield, mp 188° C.;

$^1$H NMR (DMSO-d$_6$) δ 2.30–2.55 (m, 4H), 3.40–3.75 (m, 6H), 3.86 (s, 3H), 7.05–8.50 (m, 8H), 10.03 (s, 1H); MS (ES) m/z 525.2 (M+1). Analysis for $C_{26}H_{22}Cl_2N_4O_2S$-0.17$CH_2Cl_2$-0.17EtOAc: Calcd: C, 58.14; H, 4.29; N, 10.11. Found: C, 58.28; H, 4.06; N, 9.68.

EXAMPLE 24

4-(2,4-Dichloro-5-methoxyanilino)-7-[5-(4-morpholinylmethyl)-3-thienyl]-3-quinolinecarbonitrile Using an analogous procedure to that described for Example 10, 4-(2,4-dichloro-5-methoxyanilino)-7-[5-(4-morpholinylmethyl)-3-thienyl]-3-quinolinecarbonitrile was prepared from 7-bromo-4-(2,4-dichloro-5-methoxyanilino)-3-quinolinecarbonitrile (Reference Example 8) and 4-[(4-bromo-2-thienyl)methyl]morpholine in 41%, yield; mp, 216–217° C.;

$^1$H NMR (DMSO-d$_6$) δ 2.35–2.50 (m, 4H), 3.55–3.65 (m, 4H), 3.75 (s, 2H), 3.87 (s, 3H), 7.42 (s, 1H), 7.68 (s, 1H), 7.77 (s, 1H), 8.08 (d, J=9 Hz, 1H), 8.17 (s, 1H), 8.22 (s, 1H), 8.54 (d, J=9 Hz, 1H), 8.57 (s, 1H), 9.99 (s, 1H); MS (ES) m/z 525.2 (M+1). Analysis for $C_{26}H_{22}Cl_2N_4O_2S$: Calcd: C, 59.43; H, 4.22; N, 10.66. Found: C, 59.28; H, 3.93; N, 10.61.

EXAMPLE 25

4-(2,4-Dichloroanilino)-7-[5-(4-morpholinylmethyl)-3-thienyl]-3-quinolinecarbonitrile Using an analogous procedure to that described for Example 10, 4-(2,4-dichloroanilino)-7-[5-(4-morpholinylmethyl)-3-thienyl]-3-quinolinecarbonitrile was prepared from 7-bromo-4-(2,4-dichloroanilino)-3-quinolinecarbonitrile (Reference Example 6) and 4-[(4-bromo-2-thienyl)methyl]morpholine in 66% yield, mp 203–205° C.;

$^1$H NMR (DMSO-d$_6$) δ 2.35–2.45 (m, 4H), 3.60 (t, J=4 Hz, 4H), 3.75 (s, 2H), 7.50–7.62 (m, 2H), 7.67 (s, 1H), 7.80 (s, 1H), 8.09 (d, J=8 Hz, 1H), 8.16 (s, 1H), 8.21 (s, 1H), 8.52 (d, J=8 Hz, 1H), 8.57 (s, 1H), 9.92 (s, 1H); MS (ES) m/z 495.3 (M+1). Analysis for $C_{25}H_{20}Cl_2N_4OS$-0.5EtOAc: Calcd: C, 60.11; H, 4.47; N, 10.38. Found: C, 60.27; H, 4.48; N, 10.37.

EXAMPLE 26

4-(2,4-Dichloro-5-methoxyanilino)-7-[3-(4-morpholinylmethyl)phenyl]-3-quinolinecarbonitrile To a dry flask under a nitrogen atmosphere was added 200 mg (0.78 mmol) of 4-(3-bromobenzyl)morpholine, 0.218 g (0.86 mmol) of bis(pinacolato)diboron, 230 mg (2.34 mmol) of potassium acetate, 5 mL of dimethylsulfoxide and 32 mg (0.04 mmol) of [1,1'-bis(diphenylphosphino)ferrocene] dichloropalladium(II) complex with dichloromethane. The reaction mixture was heated at 80° C. for 2 hours. After cooling, the mixture was partitioned between 20 mL of toluene, 40 mL of ethyl acetate and 40 mL of water. The layers were separated and the aqueous layer was further extracted with 30 mL of ethyl acetate. The organic layers were combined and washed with 4×40 mL water. After drying over magnesium sulfate, removal of the solvents gave crude 4-[3-(4,4,5,5-tetramethyl-1,3,2-dioxaborolan-2-yl)benzyl]morpholine as a dark oil.

A mixture of 110 mg (0.26 mmol) of 7-bromo-4-(2,4-dichloro-5-methoxyanilino)-3-quinolinecarbonitrile (Reference Example 8), crude 4-[3-(4,4,5,5-tetramethyl-1,3,2-dioxaborolan-2-yl)benzyl]morpholine and 45 mg (0.04 mmol) of tetrakis(triphenylphosphine)palladium(0) was heated at reflux in 4 mL of ethylene glycol dimethyl ether and 2.5 mL of saturated aqueous sodium bicarbonate for 2 hours. After cooling, the mixture was partitioned between 50 mL of ethyl acetate and 40 ml of water. The layers were separated and the ethyl acetate layer was dried over magnesium sulfate. Removal of the solvent in vacuo gave a dark residue which was purified by flash silica gel chromatography eluting with a gradient of ethyl acetate to 95:5 ethyl acetate/methanol), to provide 70 mg of 4-(2,4-dichloro-5-methoxyanilino)-7-[3-(4-morpholinylmethyl)phenyl]-3-quinoline-carbonitrile as a yellow solid, mp 88–91° C.;

$^1$H NMR (DMSO-$d_6$) δ 10.05 (s, 1H), 8.61 (broad s, 2H), 8.19 (s, 1H), 8.08–7.97 (m, 1H), 7.85–7.72 (m, 3H), 7.51 (m, J=8 Hz, 1H), 7.43 (s, 1H), 7.41 (s, 1H), 3.87 (s, 3H), 3.61 (s, 2H), 3.59 (s, 4H), 2.42 (s, 4H); MS (ES) m/z 519.1, 521.0 (M+1). Analysis for $C_{28}H_{24}Cl_2N_4O_2 \cdot 0.5EtOAc$: Calcd: C, 63.95; H, 5.01; N, 9.94. Found: C, 63.64; H, 4.93; N, 9.97.

EXAMPLE 27

4-(2,4-Dichloro-5-methoxyanilino)-7-{4-[2-(4-morpholinyl)ethyl]phenyl}-3-quinolinecarbonitrile By the procedure used to prepare 4-[3-(4,4,5,5-tetramethyl-1,3,2-dioxaborolan-2-yl)benzyl]morpholine in Example 26, 800 mg (2.52 mmol) of 4-[2-(4-iodophenyl) ethyl]morpholine was reacted with 704 mg (2.77 mmol) of bis(pinacolato)diboron, 743 mg (7.57 mmol) of potassium acetate and 103 mg, (0.13 mmol) of [1,1'-bis (diphenylphosphino)ferrocene]dichloropalladium(II), complex with dichloromethane in 15 mL of anhydrous dimethylsulfoxide to provide crude 4-[4-(4,4,5,5-tetramethyl-1,3,2-dioxaborolan-2-yl)phenethyl]morpholine.

By the procedure of Example 26, 266 mg (0.63 mmol) of 7-bromo-4-(2,4-dichloro-5-methoxyanilino)-3-quinolinecarbonitrile (Reference Example 8) was reacted with crude 4-[4-(4,4,5,5-tetramethyl-1,3,2-dioxaborolan-2-yl)phenethyl]morpholine and 218 mg (0.19 mmol) of tetrakis(triphenylphosphine)palladium(0) in 7 mL of ethylene glycol dimethyl ether and 4 mL of saturated aqueous sodium bicarbonate to provide 230 mg of 4-(2,4-dichloro-5-methoxyanilino)-7-{4-[2-(4-morpholinyl)ethyl]phenyl}-3-quinolinecarbonitrile as a yellow solid after purification, mp>170° C. (dec);

$^1$H NMR (DMSO-$d_6$) δ 10.03 (s, 1H), 8.60 (m, 2H), 8.19 (s, 1H), 8.10–8.03 (m, 1H), 7.87–7.75 (m, 3H), 7.43–7.39 (m, 3H), 3.87 (s, 3H), 3.59 (m, 4H), 2.83 (t, J=7 Hz, 2H), 2.60–2.53 (m, 2H), 2.46 (broad s, 4H); MS (ES) m/z 533.1, 535.1 (M+1). Analysis for $C_{29}H_{26}Cl_2N_4O_2 \cdot 0.4$ MeOH: Calcd: C, 64.64; H, 5.09; N, 10.26. Found: C, 64.73; H, 5.00; N, 9.86.

EXAMPLE 28

4-(2,4-Dichloro-5-methoxyanilino)-7-{3-[2-(4-morpholinyl)ethyl]phenyl}-3-quinolinecarbonitrile By the procedure used to prepare 4-[3-(4,4,5,5-tetramethyl-1,3,2-dioxaborolan-2-yl)benzyl]morpholine, in Example 26, 1.0 g (3.70 mmol) of 4-(3-bromophenethyl) morpholine, was reacted with 1.03 g (4.07 mmol) of bis (pinacolato)diboron, 1.1 g (11.0 mm of potassium acetate and 0.3 g (0.37 mmol) of [1,1'-bis(diphenylphosphino) ferrocene]dichloropalladium(II), complex with dichloromethane in 25 mL of anhydrous dimethylsulfoxide to provide crude 4-[3-(4,4,5,5-tetramethyl-1,3,2-dioxaborolan-2-yl)phenethyl]morpholine. This material was purified by flash silica gel chromatography, eluting with a gradient of 99:1 methylene chloride/methanol to 97.5:2.5 methylene chloride/methanol, to provide 0.52 g of 4-[4-(4,4,5,5-tetramethyl-1,3,2-dioxaborolan-2-yl)benzyl]morpholine as a light brown liquid; MS (ES) m/z 318.3 (M+1).

By the procedure for Example 26, 107 mg (0.25 mmol) of 7-bromo-4-(2,4-dichloro-5-methoxyanilino)-3-quinolinecarbonitrile (Reference Example 8) was reacted with 0.160 g (0.50 mmol) of 4-[4-(4,4,5,5-tetramethyl-1,3,2-dioxaborolan-2-yl)benzyl]morpholine and 57 mg (0.05 mmol) of tetrakis(triphenylphosphine)palladium(0) in 6 mL of ethylene glycol dimethyl ether and 2.5 mL of saturated aqueous sodium bicarbonate to provide 115 mg of 4-(2,4-dichloro-5-methoxyanilino)-7-{3-[2-(4-morpholinyl)ethyl] phenyl}3-quinolinecarbonitrile as a yellow solid after purification, mp 146–148° C.;

$^1$H NMR (DMSO-$d_6$) δ 10.05 (s, 1H), 8.62 (broad s, 2H), 8.22 (m , 1H), 8.07–8.01 (m, 1H), 7.81–7.71 (m, 3H), 7.50–7.32 (m, 3H), 3.87 (s, 3H), 3.60 (broad s, 4H), 2.92–2.83 (m, 2H), 2.67–2.56 (m, 2H), 2.50 (broad s, 4H); MS (ES) m/z 533.1, 535.1 (M+1). Analysis for $C_{29}H_{26}Cl_2N_4O_2 \cdot 0.5EtOAc \cdot 0.15CH_2Cl_2$: Calcd: C, 63.38; H, 5.17; N, 9.49. Found: C, 63.54; H, 5.03; N, 9.31.

EXAMPLE 29

4-(2,4-Dichloro-5-methoxyanilino)-7-[4-(4-morpholinylmethyl)phenyl]-3-quinolinecarbonitrile By the procedure used to prepare 4-[3-(4,4,5,5-tetramethyl-1,3,2-dioxaborolan-2-yl)benzyl]morpholine in Example 26, 500 mg (1.95 mmol) of 4-(4-bromobenzyl) morpholine was reacted with 545 mg (2.15 mmol) of bis (pinacolato)diboron, 575 mg (5.86 mmol) of potassium acetate and 80 mg (0.098 mmol) of [1,1'-bis(diphenyl-phosphino)ferrocene]dichloropalladium(II), complex with dichloromethane in 10 mL of anhydrous dimethylsulfoxide to provide crude 4-[4-(4,4,5,5-tetramethyl-1,3,2-dioxaborolan-2-yl)benzyl]morpholine.

By the procedure for Example 26, 247 mg (0.59 mmol) of 7-bromo-4-(2,4-dichloro-5-methoxyanilino)-3-quinolinecarbonitrile (Reference Example 8) was reacted with crude 4-[4-(4,4,5,5-tetramethyl-1,3,2-dioxaborolan-2-yl)benzyl]morpholine and 150 mg (0.13 mmol) of tetrakis (triphenylphosphine)palladium(0) in 7 mL of ethylene glycol dimethyl ether and 4 ml of saturated aqueous sodium bicarbonate to provide 180 mg of 4-(2,4-dichloro-5-methoxyanilino)-7-{4-[2-(4-morpholinyl)ethyl]phenyl}-3-quinolinecarbonitrile as a yellow solid after purification, mp>180° C. (dec);

$^1$H NMR (DMSO-$d_6$) δ 10.03 (s, 1H), 8.60 (broad s, 2H), 8.20 (s, 1H), 8.08–8.00 (m, 1H), 7.92–7.84 (m, 2H), 7.76 (s, 1H), 7.50 (s, 1H), 7.47 (s, 1H), 7.42 (s, 1H), 3.87 (s, 3H), 3.60 (t, J=4.5 Hz, 4H), 3.54 (s, 2H), 2.42–2.38 (m, 4H); MS (ES) m/z 519.2, 521.2 (M+1). Analysis for $C_{28}H_{24}Cl_2N_4O_2 \cdot 0.4H_2O$: Calcd: C, 63.86; H, 4.75; N, 10.64. Found: C, 64.15; H, 4.57; N, 10.26.

EXAMPLE 30

4-(2,4-Dichloro-5-methoxyanilino)-7-{4-[(4-ethyl-1-piperazinyl)methyl]phenyl}-3-quinolinecarbonitrile By the procedure used to prepare 4-[3-(4,4,5,5-tetramethyl-1,3,2-dioxaborolan-2-yl)benzyl]morpholine in Example 26, 800 mg (2.82 mmol) of 1-(4-bromobenzyl)-4-ethylpiperazine, was reacted with 789 mg (3.11 mmol) of bis(pinacolato)diboron, 832 mg (8.47 mmol) of potassium acetate and 115 mg (0.14 mmol) of [1,1'-bis(diphenylphosphino)ferrocene]dichloropalladium(II), complex with dichloromethane in 15 mL of anhydrous dimethylsulfoxide to provide crude 1-ethyl-4-[4-(4,4,5,5-tetramethyl-1,3,2-dioxaborolan-2-yl)benzyl]piperazine. This material was divided into two equal portions, one of which was used in the subsequent step.

By the procedure of Example 26, 179 mg (0.42 mmol) of 7-bromo-4-(2,4-dichloro-5-methoxyanilino)-3-quinolinecarbonitrile (Reference Example 8) was reacted with crude 1-ethyl-4-[4-(4,4,5,5-tetramethyl-1,3,2-dioxaborolan-2-yl)benzyl]piperazine and 147 mg (0.13 mmol) of tetrakis(triphenylphosphine)palladium(0) in 7 mL of ethylene glycol dimethyl ether and 4 mL of saturated aqueous sodium bicarbonate to provide 70 mg of 4-(2,4-dichloro-5-methoxyanilino)-7-{4-[(4-ethyl-1-piperazinyl)methyl]phenyl}-3-quinolinecarbonitrile as a yellow solid after purification, mp>155° C. (dec);

$^1$H NMR (DMSO-d$_6$) δ 10.04 (broad s, 1H), 8.56 (broad s, 2H), 8.20–8.18 (m, 1H), 8.05–7.93 (m, 1H), 7.88–7.79 (m, 2H), 7.77–7.68 (m, 1H), 7.48 (s, 1H), 7.45 (s, 1H), 7.39–7.35 (m, 1H), 3.86 (s, 3H), 3.54 (s, 2H), 2.50–2.31 (m, 10H), 1.00 (t, J=7 Hz, 3H); MS (ES) m/z 546.1, 548.1 (M+1). Analysis for $C_{30}H_{29}Cl_2N_5O \cdot 1.0MeOH \cdot 0.94H_2O$: Calcd: C, 62.53; H, 5.90; N, 11.76. Found: C, 62.33; H, 5.50; N, 11.36.

EXAMPLE 31

4-(2,4-Dichloro-5-methoxyanilino)-7-{4-[(4-ethyl-1-piperazinyl)methyl]phenyl}-6-methoxy-3-quinolinecarbonitrile By the procedure for Example 26, 221 mg (0.59 mmol) of 3-cyano-4-(2,4-dichloro-5-methoxyanilino)-6-methoxy-7-quinolinyl trifluoromethanesulfonate (Reference Example 22) was reacted with half of the crude 1-ethyl-4-[4-(4,4,5,5-tetramethyl-1,3,2-dioxaborolan-2-yl)benzyl]piperazine intermediate generated for the synthesis of Example 30 and 147 mg (0.13) mmol) of tetrakis(triphenylphosphine)palladium(0) in 7 mL of ethylene glycol dimethyl ether and 4 mL of saturated aqueous sodium bicarbonate to provide 85 mg of 4-(2,4-dichloro-5-methoxyanilino)-7-{4-[(4-ethyl-1-piperazinyl)methyl]-phenyl}-6-methoxy-3-quinolinecarbonitrile as a yellow solid after purification, mp 126–130° C.;

$^1$H NMR (DMSO-d$_6$) δ 9.86 (broad s, 1H), 8.45 (s, 1H), 7.97 (s, 1H), 7.82–7.73 (m, 3H), 7.58 (d, J=8 Hz, 2H), 7.40 (d, J=8 Hz, 2H), 3.95 (s, 3H), 3.88 (s, 3H), 3.52 (s, 2H), 2.50–2.28 (m, 8H), 2.32 (q, J=7 Hz, 2H), 0.99 (t, J=7 Hz, 3H); MS (ES) m/z 576.1, 578.0 (M+1). Analysis for $C_{31}H_{31}Cl_2N_5O_2 \cdot 0.75H_2O$: Calcd: C, 63.10; H, 5.54; N, 11.85. Found: C, 63.50; H, 5.74; N, 11.47.

EXAMPLE 32

4-(2,4-Dichloro-5-methoxyanilino)-7-{4-[2-(4-ethyl-1-piperazinyl)ethyl])phenyl}-3-quinolinecarbonitrile By the procedure used to prepare 4-[3-(4,4,5,5-tetramethyl-1,3,2-dioxaborolan-2-yl)benzyl]morpholine in Example 26, 800 mg (2.32 mmol) of 1-ethyl-4-[2-(4-iodophenyl)ethyl]piperazine, was reacted with 649 mg (2.56 mmol) of bis(pinacolato)diboron, 684 mg (6.87 mmol) of potassium acetate and 95 mg (0.12 mmol) of [1,1'-bis(diphenylphosphino)ferrocene]dichloropalladium(II), complex with dichloromethane in 15 mL of anhydrous dimethylsulfoxide to provide crude 1-ethyl-4-[4-(4,4,5,5-tetramethyl-1,3,2-dioxaborolan-2-yl)phenethyl]piperazine. This material was divided into two equal portions, one of which was used in the subsequent step.

By the procedure of Example 26, 147 mg (0.35 mmol) of 7-bromo-4-(2,4-dichloro-5-methoxyanilino)-3-quinolinecarbonitrile (Reference Example 8) was reacted with crude 1-ethyl-4-[4-(4,4,5,5-tetramethyl-1,3,2-dioxaborolan-2-yl)-phenethyl]piperazine and 121 mg (0.10 mmol) of tetrakis(triphenylphosphine)palladium(0) in 7 mL of ethylene glycol dimethyl ether and 4 mL of saturated aqueous sodium bicarbonate to provide 48 mg of 4-(2,4-dichloro-5-methoxyanilino)-7-{4-[2-(4-ethyl-1-piperazinyl)ethyl]phenyl}-3-3-quinolinecarbonitrile as a yellow solid after purification, mp 75–78° C.;

$^1$H NMR (DMSO-d$_6$) δ 10.25–9.85 (broad s, 1H), 8.54 (broad s, 2H), 8.09 (s, 1H), 8.00–7.92 (m, 1H), 7.85–7.75 (m, 3H), 7.71 (s, 1H), 7.42 (s, 1H), 7.40 (s, 1H), 3.86 (s, 3H), 2.81 (t, J=7 Hz, 2H), 2.55 (t, J=7 Hz, 2H), 2.51–2.25 (m, 10H), 0.99 (t, J=7 Hz, 3H); MS (ES) m/z 533.1, 535.1 (M+1). Analysis for $C_{31}H_{31}Cl_2N_5O \cdot 1.0EtOAc$: Calcd: C, 64.81; H, 6.06; N, 10.80. Found: C, 64.55; H, 5.95; N, 10.86.

EXAMPLE 33

4-{3-Chloro-4-[(1-methyl-1H-imidazol-2-yl)sulfanyl]anilino}-7-[5-(4-morpholinylmethyl)-3-thienyl]-3-quinolinecarbonitrile By the procedure used to prepare 4-[3-(4,4,5,5-tetramethyl-1,3,2-dioxaborolan-2-yl)benzyl]morpholine in Example 26, 400 mg (1.53 mmol) of 4-[(4-bromo-2-thienyl)methyl]morpholine was reacted with 426 mg (1.68 mmol) of bis(pinacolato)diboron, 449 mg (4.58 mmol) of potassium acetate and 62 mg (0.076 mmol) of [1,1'-bis(diphenylphosphino)ferrocene]dichloropalladium(II), complex with dichloromethane in 7 mL of anhydrous dimethylsulfoxide to provide crude 4-{[4-(4,4,5,5-tetramethyl-1,3,2-dioxaborolan-2-yl)-2-thienyl]methyl}morpholine.

By the procedure of Example 26, 215 mg (0.63 mmol) of 7-bromo-4-{3-chloro-4-[(1-methyl-1H-imidazol-2-yl)sulfanyl]anilino}-3-quinolinecarbonitrile (Reference Example 14) was reacted with crude 4-{[4-(4,4,5,5-tetramethyl-1,3,2-dioxaborolan-2-yl)-2-thienyl]methyl}morpholine and 159 mg (0.14 mmol) of tetrakis(triphenylphosphine)palladium(0) in 7 mL of ethylene glycol dimethyl ether and 4 mL of saturated aqueous sodium bicarbonate to provide 104 mg of 4-{3-chloro-4-[(1-methyl-1H-imidazol-2-yl)sulfanyl]anilino}-7-[5-(4-morpholinylmethyl)-3-thienyl]-3-quinolinecarbonitrile as a yellow solid after purification, mp 110–113° C.;

$^1$H NMR (DMSO-d$_6$) δ 9.89 (s, 1H), 8.64 (s, 1H), 8.41 (d, J=10 Hz, 1H), 8.22 (s, 1H), 8.16 (s, 1H), 8.06 (d, J=9 Hz, 1H), 7.67 (s, 1H), 7.55 (d, J=1 Hz, 1H); 7.48 (d, J=2 Hz, 1H), 7.20 (dd, J=9, 2 Hz, 1H), 7.17 (d, J=1 Hz, 1H), 6.55 (d, J=9

Hz, 1H), 3.74 (s, 2H), 3.61 (s, 3H), 3.60 (t, J=5 Hz, 4H), 2.45 (t, J=4 Hz, 4H); MS (ES) m/z 573.3, 575.3 (M+1). Analysis for $C_{29}H_{25}ClN_6OS_2 \cdot 0.25CH_2Cl_2$: Calcd: C, 59.01; H, 4.32; N, 14.14. Found: C, 59.32; H, 4.32; N, 13.75.

EXAMPLE 34

7-[3,4-bis(4-Morpholinylmethyl)phenyl]-4-(2,4-dichloro-5-methoxyanilino)-3-quinolinecarbonitrile By the procedure used to prepare 4-[3-(4,4,5,5-tetramethyl-1,3,2-dioxaborolan-2-yl)benzyl]morpholine in Example 26, 800 mg (2.25 mmol) of 4-[4-bromo-2-(4-morpholinylmethyl)benzyl]morpholine was reacted with 629 mg (2.48 mmol) of bis(pinacolato)diboron, 663 mg (6.75 mmol) of potassium acetate and 115 mg (0.14 mmol) of [1,1'-bis(diphenylphosphino)ferrocene] dichloropalladium(II), complex with dichloromethane in 15 mL of anhydrous dimethylsulfoxide to provide crude 4-[2-(4-morpholinylmethyl)-4-(4,4,5,5-tetramethyl-1,3,2-dioxaborolan-2-yl)benzyl]morpholine. This material was divided into two equal portions, one of which was used in the subsequent step.

By the procedure of Example 26, 143 mg (0.34 mmol) of 7-bromo-4-(2,4-dichloro-5-methoxyanilino)-3-quinolinecarbonitrile (Reference Example 8) was reacted with crude 4-[2-(4-morpholinylmethyl)-4-(4,4,5,5-tetramethyl-1,3,2-dioxaborolan-2-yl)benzyl]morpholine and 117 mg (0.10 mmol) of tetrakis(triphenylphosphine)palladium(0) in 5 mL of ethylene glycol dimethyl ether and 3 mL of saturated aqueous sodium bicarbonate to provide 105 mg of 7-[3,4-bis(4-morpholinylmethyl)phenyl]-4-(2,4-dichloro-5-methoxyanilino)-3-quinolinecarbonitrile as a yellow solid after purification, mp 198–00° C.;

$^1$H NMR (DMSO-$d_6$) δ 10.04 (s, 1H), 8.60 (broad s, 2H), 8.18 (s, 1H), 8.08–8.98 (m, 1H), 7.85–7.74 (m, 3H), 7.48 (d, J=8 Hz, 1H), 7.42 (s, 1H), 3.86 (s, 3H), 3.69 (s, 2H), 3.66 (s, 2H), 3.58 (broad s, 8H), 2.46–2.38 (m, 8H); MS (ES) m/z 618.2, 620.2 (M+1). Analysis for $C_{33}H_{33}Cl_2N_5O_3$: Calcd: C, 64.08; H, 5.38; N, 11.32. Found: C, 63.91; H, 5.56; N, 11.02.

EXAMPLE 35

7-[3,4-bis(4-Morpholinylmethyl)phenyl]-4-{3-chloro-4-[(1-methyl-1H-imidazol-2-yl)sulfanyl]anilino}-3-quinolinecarbonitrile By the procedure for Example 26, 221 mg (0.59 mmol) of 7-bromo-4-{3-chloro-4-[(1-methyl-1H-imidazol-2-yl)sulfanyl]anilino}-3-quinolinecarbonitrile (Reference Example 14) was reacted with half of the crude 4-[2-(4-morpholinylmethyl)-4-(4,4,5,5-tetramethyl-1,3,2-dioxaborolan-2-yl)benzyl]morpholine intermediate generated for the synthesis of Example 34 and 117 mg (0.10 mmol) of tetrakis(triphenylphosphine)palladium(0) in 5 mL of ethylene glycol dimethyl ether and 3 mL of saturated aqueous sodium bicarbonate to provide 90 mg of 7-[3,4-bis (4-morpholinylmethyl)phenyl]-4-{3-chloro-4-[(1-methyl-1H-imidazol-2-yl)sulfanyl]anilino}-3-quinolinecarbonitrile as a yellow solid after purification, mp>25° C. (dec);

$^1$H NMR (DMSO-$d_6$): δ 9.95 (s, 1H), 8.67 (s, 1H), 8.48 (d, J=9 Hz, 1H), 8.20 (s, 1H), 8.02 (d, J=9 Hz, 1H), 7.80 (s, 1H), 7.76 (d, J=8 Hz, 1H), 7.55 (s, 1H), 7.50–7.46 (m, 2H), 7.21 (dd, J=8, 2 Hz, 1H), 7.17 (s, 1H), 6.56 (d, J=9 Hz, 1H), 3.69 (s, 2H), 3.66 (s, 2H), 3.62 (s, 3H), 3.58 (broad s, 8H), 2.41 (broad s, 8H); MS (ES) m/z 666.2, 668.2 (M+1). Analysis for $C_{36}H_{36}ClN_7O_2S \cdot 0.25CH_2Cl_2$: Calcd: C, 63.33; H, 5.35; N, 14.26. Found: C, 63.19; H, 5.60; N, 13.87.

EXAMPLE 36

4-(2,4-Dichloro-5-methoxyanilino)-6-methoxy-7-[5-(4-morpholinylmethyl)-3-thienyl]-3-quinolinecarbonitrile Using an analogous procedure to that described for Example 24, 3-cyano-4-(2,4-dichloro-5-methoxyanilino)-6-methoxy-7-quinolinyl trifluoromethanesulfonate (Reference Example 22) was converted to 4-(2,4-dichloro-5-methoxyanilino)-6-methoxy-7-[5-(4-morpholinyl-methyl)-3-thienyl]-3-quinolinecarbonitrile in 47% yield, mp 148–150° C.;

$^1$H NMR (DMSO-$d_6$) δ 9.87 (s, 1H), 8.47 (s, 1H), 8.09 (s, 1H), 7.97 (s, 2H), 7.79 (s, 1H), 7.40 (s, 1H), 4.69 (s, 3H), 3.88 (s, 3H), 3.61 (s, 2H), 3.47 (m, 4H), 2.50 (m, 4H); MS (ES) m/z 556.4 (M+1). Analysis for $C_{27}H_{24}Cl_2N_4O_3S \cdot 1.3H_2O$: Calcd: C, 56.01; H, 4.27; N, 9.66. Found: C, 55.67; H, 4.27; N, 9.65.

EXAMPLE 37

4-(2,4-Dichloro-5-methoxyanilino)-6-methoxy-7-[4-(4-morpholinylmethyl)phenyl]-3-quinolinecarbonitrile Using an analogous procedure to that described for Example 29, 3-cyano-4(2,4-dichloro-5-methoxyanilino)-6-methoxy-7-quinolinyl trifluoromethanesulfonate (Reference Example 22) was converted to 4-(2,4-dichloro-5-methoxyanilino)-6-methoxy-7-[4-(4-morpholinyl-methyl) phenyl]-3-quinolinecarbonitrile in 42% yield, mp 108–110° C.;

$^1$H NMR (DMSO-$d_6$) δ 9.85 (s, 1H), 8.47 (s, 1H), 7.90 (s, 1H), 7.83 (s, 1H), 7.78 (s, 1H), 7.60 (d, J=8 Hz, 2H), 7.43 (d, J=10 Hz, 3H), 3.96 (s, 3H), 3.88 (s, 3H), 3.61 (t, J=4 Hz, 4H), 3.52 (s, 2H), 2.40 (br s, 4H); MS (ES) m/z 549.1 (M+1). Analysis for $C_{29}H_{26}Cl_2N_4O_3 \cdot 0.7H_2O$: Calcd: C, 61.94; H, 4.92; N, 9.95. Found: C, 61.95; H, 4.96; N, 9.63.

EXAMPLE 38

4-(2,4-Dichloro-5-methoxyanilino)-6-methoxy-7-{3-[2-(4-morpholinyl)ethyl]phenyl}-3-quinolinecarbonitrile Using an analogous procedure to that described for Example 28, 3-cyano-4-(2,4-dichloro-5-methoxyanilino)-6-methoxy-7-quinolinyl trifluoromethanesulfonate (Reference Example 22) was converted to 4-(2,4-dichloro-5-methoxyanilino)-6-methoxy-7-{3-[2-(4-morpholinyl)ethyl]phenyl}-3-quinolinecarbonitrile in 45% yield, mp 193–195° C.;

$^1$H NMR (DMSO-$d_6$) δ 9.85 (s, 1H), 8.47 (s, 1H), 7.97 (s, 1H), 7.82 (s, 1H), 7.78 (s, 1H), 7.47 (m, 3H), 7.30 (s, 1H), 7.27 (s, 1H), 3.95 (s, 3H), 3.88 (s, 3H), 3.60 (t, J=4 Hz, 4H), 3.52 (t, J=6 Hz, 2H), 2.59 (t, J=8 Hz, 2H), 2.40 (br s, 4H); MS (ES) m/z 563.1 (M+1). Analysis for $C_{29}H_{26}Cl_2N_4O_3 \cdot 0.98H_2O$: Calcd: C, 61.98; H, 5.20; N, 9.62. Found: C, 61.98; H, 4.95; N, 9.24.

EXAMPLE 39

4-(2,4-Dichloro-5-methoxyanilino)-6-methoxy-7-[3-(4-morpholinylmethyl]phenyl}-3-quinolinecarbonitrile Using an analogous procedure to that described for Example 26, 3-cyano-4-(2,4-dichloro-5-methoxyanilino)-6- methoxy-7-quinolinyl trifluoromethanesulfonate (Reference Example 22) was converted to 4-(2,4-dichloro-5-methoxyanilino)-6-methoxy-7-[3-(4-morpholinylmethyl)phenyl]-3-quinolinecarbonitrile in 59% yield, mp 155–158° C.;

$^1$H NMR (DMSO-d$_6$) δ 9.88 (s, 1H), 8.48 (s, 1H), 7.98 (s, 1H), 7.83 (s, 1H), 7.79 (s, 1H), 7.55 (m, 5H), 3.95 (s, 3H), 3.88 (s, 3H), 3.61 (t, J=4 Hz, 4H), 3.58 (s, 2H), 2.40 (br s, 4H); MS (ES) m/z 549.1 (M+1). Analysis for C$_{29}$H$_{26}$Cl$_2$N$_4$O$_3$-0.2H$_2$O: Calcd: C, 62.97; H, 4.82; N, 9.91. Found: C, 63.01; H, 4.87; N, 9.52.

EXAMPLE 40

4-(2,4-Dichloro-5-methoxyanilino)-6-methoxy-7-{4-[2-(4-morpholinyl)ethyl]phenyl}-3-quinolinecarbonitrile Using an analogous procedure to that described for Example 27, 3-cyano-4-(2,4-dichloro-5-methoxyanilino)-6-methoxy-7-quinolinyl trifluoromethanesulfonate (Reference Example 22) was converted to 4-(2,4-dichloro-5-methoxyanilino)-6-methoxy-7-{4-[2-(4-morpholinyl)ethyl]phenyl}-3-quinolinecarbonitrile in 40% yield, mp 215–217° C.;

$^1$H NMR (DMSO-d$_6$) δ 9.86 (s, 1H), 8.47 (s, 1H), 7.97 (s, 1H), 7.81 (d, J=8 Hz, 2H), 7.55 (d, J=7 Hz, 2H), 7.40 (s, 1H), 7.35 (s, 1H), 7.33 (s, 1H), 3.95 (s, 3H), 3.88 (s, 3H), 3.61 (t, J=4 Hz, 4H), 2.89 (t, J=7 Hz, 2H), 2.59 (t, J=7 Hz, 2H), 2.46 (s, 4H); MS (ES) m/z 563.1 (M+1). Analysis for C$_{29}$H$_{26}$Cl$_2$N$_4$O$_3$-0.6H$_2$O: Calcd: C, 62.60; H, 5.13; N, 9.49. Found: C, 62.70; H, 5.00; N, 9.12.

EXAMPLE 41

4-(2,4-Dichloro-5-methoxyanilino)-7-{5-[(4-ethyl-1-piperazinyl)methyl]-2-furyl}-3-quinolinecarbonitrile N-Methylpiperazine (0.065 mL, 0.56 mmol) was added to a suspension of 4-(2,4-dichloro-5-methoxyanilino)-7-(5-formyl-2-furyl)-3-quinolinecarbonitrile (Example 6) (200 mg, 0.45 mmol) in 3 mL of methylene chloride and 1 mL of N,N-dimethylformamide. The reaction mixture was cooled to 0° C. and sodium triacetoxyborohydride (500 mg, 2.36 mmol) was added. After stirring at 0° C. for 1 hour, a catalytic amount of acetic acid was added and the reaction mixture was allowed to warm to room temperature. The reaction was quenched by the addition of water and then partitioned between saturated sodium bicarbonate and methylene chloride. The organic layer was dried over sodium sulfate, filtered and concentrated in vacuo. The residue was purified by flash column chromatography eluting with a gradient of 10% methanol in methylene chloride to 20% methanol in methylene chloride to provide 95 mg of 4-(2,4-dichloro-5-methoxyanilino)-7-{5-[(4-ethyl-1-piperazinyl)methyl]-2-furyl}-3-quinolinecarbonitrile (40% yield) mp 157–160° C.; MS (ES) m/z 522.3 (M+1). Analysis for C$_{27}$H$_{25}$Cl$_2$N$_5$O$_2$-0.9H$_2$O: Calcd: C, 60.20; H, 5.01; N, 13.00. Found: C, 60.05; H, 4.62; N, 13.00.

EXAMPLE 42

4-(2,4-Dichloro-5-methoxyanilino)-7-[5-(1,3-dioxolan-2-yl)-3-thienyl]-3-quinolinecarbonitrile A mixture of 4-(2,4-dichloro-5-methoxyanilino)-7-iodo-3-quinolinecarbonitrile (Reference Example 13) (2.50 g, 5.32 mmol), tributyl[5-(1,3-dioxolan-2-yl)-3-thienyl]stannane (2.98 g, 6.69 mmol), and a catalytic amount of dichlorobis(triphenylphosphine)palladium(II) in 60 mL of dioxane was heated at reflux for 4.5 hours. The mixture was concentrated in vacuo and partitioned between ethyl acetate and saturated sodium chloride. The organic layer was dried over sodium sulfate and concentrated in vacuo. A 300 mg portion was removed and triturated with ethyl acetate to provide 104 mg of 4-(2,4-dichloro-5-methoxyanilino)-7-[5-(1,3-dioxolan-2-yl)-3-thienyl]-3-quinoline-carbonitrile as a yellow solid, mp 234–236° C.;

$^1$H NMR (DMSO-d$_6$/trifluoroacetic acid) δ 3.88 (s, 3H), 3.80–4.12 (m, 4H), 6.15 (s, 1H), 7.57 (s, 1H), 7.87 (s, 2H), 8.23 (s, 1H), 8.31 (d, J=9 Hz, 1H), 8.36 (s, 1H), 8.76 (d, J=9 Hz, 1H), 9.13 (s, 1H); MS (ES) m/z 498.1, 500.1 (M+1). Analysis for C$_{24}$H$_{17}$Cl$_2$N$_3$O$_3$S-0.25H$_2$O: Calcd: C, 57.32; H, 3.51; N, 8.36. Found: C, 57.41; H, 3.26; N, 8.48.

EXAMPLE 43

4-(2,4-Dichloro-5-methoxyanilino)-7-(5-formyl-3-thienyl)-3-quinolinecarbonitrile A solution of crude 4-(2,4-dichloro-5-methoxyanilino)-7-[5-(1,3-dioxolan-2-yl)-3-thienyl]-3-quinolinecarbonitrile (Example 42) in 100 mL of tetrahydrofuran and 50 mL of 2N hydrochloric acid was stirred at room temperature overnight. Saturated sodium bicarbonate was slowly added and the product was extracted into ethyl acetate. The organic layer was washed with saturated sodium chloride, dried over magnesium sulfate, filtered and concentrated in vacuo. Ethyl acetate was added and the solid collected to provide 1.296 g of 4-(2,4-dichloro-5-methoxyanilino)-7-(5-formyl-3-thienyl)-3-quinolinecarbonitrile as a yellow solid, mp 259–262° C. (dec);

$^1$H NMR (DMSO-d$_6$/trifluoroacetic acid) δ 3.88 (s, 3H), 7.51 (s, 1H), 7.89 (s, 1H), 8.30 (s, 1H), 8.39 (d, J=9 Hz, 1H), 8.67 (s, 1H), 8.80–8.88 (m, 2H), 9.20 (s, 1H), 10.06 (s, 1H); MS (ES) m/z 454.1, 456.1 (M+1). Analysis for C$_{22}$H$_{13}$Cl$_2$N$_3$O$_2$S: Calcd: C, 58.16; H, 2.88; N, 9.25. Found: C, 57.93; H, 2.87; N, 9.22.

EXAMPLE 44

4-(2,4-Dichloroanilino)-7-(5-formyl-3-thienyl)-3-quinolinecarbonitrile

Following the procedures in Examples 42 and 43, 7-bromo-4-(2,4-dichloroanilino)-3-quinolinecarbonitrile (Reference Example 6) (370 mg, 0.94 mmol) was converted to 204 mg of 4-(2,4-dichloroanilino)-7-(5-formyl-3-thienyl)-3-quinolinecarbonitrile as a yellow solid, mp 286–288° C.;

$^1$H NMR (DMSO-d$_6$/trifluoroacetic acid) δ 7.63 (dd, J=7, 2 Hz, 1H), 7.74 (d, J=7 Hz, 1H), 7.92 (d, J=2 Hz, 1H), 8.06 (d, J=3 Hz, 1H), 8.14 (d, J=3 Hz, 1H), 8.31 (d, J=2 Hz, 1H), 8.40 (dd, J=7, 2 Hz, 1H), 8.82 (d, J=7 Hz, 1H), 9.24 (s, 1H), 10.00 (s, 1H); MS (ES) m/z 424.2, 426.2 (M+1). Analysis for C$_{21}$H$_{11}$Cl$_2$N$_3$OS: Calcd: C, 59.45; H, 2.61; N, 9.90. Found: C, 59.14; H, 2.50; N, 9.72.

EXAMPLE 45

4-(2,4-Dichloro-5-methoxyanilino)-6-(5-formyl-3-thienyl)-3-quinolinecarbonitrile Following the procedures in Examples 42 and 43, 6-bromo-4-(2,4-dichloro-5-methoxyanilino)-3-quinolinecarbonitrile (Reference Example 3) (226 mg, 0.53 mmol) was converted to 212 mg of 4-(2,4-dichloro-5-methoxyanilino)-6-(5-formyl-3-thienyl)-3-quinolinecarbonitrile as a yellow solid, mp 233–237° C.;

¹H NMR (DMSO-d₆/trifluoroacetic acid) δ 3.88 (s, 3H), 7.58 (s, 1H), 7.89 (s, 1H), 8.08 (d, J=9 Hz, 1H), 8.52 (d, J=9 Hz, 1H), 8.65 (s, 1H), 8.72 (s, 1H), 9.04–9.14 (m, 2H), 10.03 (s, 1H); MS (ES) m/z 454.1, 456.1 (M+1). Analysis for $C_{22}H_{13}Cl_2N_3O_2S$: Calcd: C, 58.16; H, 2.88; N, 9.25. Found: C, 57.77; H, 2.90; N, 8.87.

EXAMPLE 46

4-(2,4-Dichloro-5-methoxyanilino)-7-{5-[(4-methyl-1-piperazinyl)methyl]-3-thienyl}-3-quinolinecarbonitrile N-Methylpiperazine (0.080 mL, 0.72 mmol) was added to a suspension of 4-(2,4-dichloro-5-methoxyanilino)-7-(5-formyl-3-thienyl)-3-quinolinecarbonitrile (Example 43) (220 mg, 0.48 mmol) in 3 mL of methylene chloride and 1 mL of N,N-dimethylformamide. The reaction mixture was cooled to 0° C. and sodium triacetoxyborohydride (500 mg, 2.36 mmol) was added followed by a drop of acetic acid. After stirring at 0° C. for 10 minutes the ice bath was removed and the reaction mixture was stirred at room temperature for 3 hours. The reaction was quenched by the addition of water and then partitioned between saturated sodium bicarbonate and ethyl acetate. The organic layer was dried over magnesium sulfate, filtered and concentrated in vacuo. The residue was purified by flash column chromatography eluting with a gradient of 20% methanol in methylene chloride to 30% methanol in methylene chloride to provide 152 mg of 4-(2,4-dichloro-5-methoxyanilino)-7-{5-[(4-methyl-1-piperazinyl)methyl]-3-thienyl}-3-quinolinecarbonitrile (59% yield) as a white solid, mp 206–209° C.;

¹H NMR (DMSO-d₆/trifluoroacetic acid) δ 2.88 (s, 3H), 3.08–3.70 (br m, 8H), 3.88 (s, 3H), 4.48 (s, 2H), 7.58 (s, 1H), 7.85 (s, 1H), 7.88 (s, 1H), 8.24 (s, 1H), 8.30 (d, J=8 Hz, 1H), 8.43 (s, 1H), 8.80 (d, J=8 Hz, 1H), 9.20 (s, 1H); MS (ES) m/z 538.2, 540.2 (M+1). Analysis for $C_{27}H_{25}Cl_2N_5OS$: Calcd: C, 60.22; H, 4.68; N, 13.01. Found: C, 59.85; H, 4.60; N, 13.23.

EXAMPLE 47

(2R)-1-({5-[3-Cyano-4-(2,4-dichloro-5-methoxyanilino)-7-quinolinyl]-2-furyl}methyl)-2-pyrrolidinecarboxamide Prolinamide (77.0 mg, 0.67 mmol) was added to a suspension of 4-(2,4-dichloro-5-methoxyanilino)-7-(5-formyl-2-furyl)-3-quinolinecarbonitrile (Example 6) (245 mg, 0.56 mmol) in 3 ml of methylene chloride and 1 mL of N,N-dimethylformamide. The reaction mixture was cooled to 0° C. and sodium triacetoxyborohydride (620 mg, 2.93 mmol) was added. After stirring at 0° C. for 1 hour, a catalytic amount of acetic acid was added and the reaction mixture was slowly allowed to warm to room temperature. The reaction was quenched by the addition of saturated sodium bicarbonate and extracted with methylene chloride. The organic layer was washed with saturated sodium bicarbonate, dried over sodium sulfate, filtered and concentrated in vacuo. The residue was purified by flash column chromatography eluting with 10% methanol in methylene chloride to provide 210 mg of (2R)-1-({5-[3-cyano-4-(2,4-dichloro-5-methoxyanilino)-7-quinolinyl]-2-furyl}methyl)-2-pyrrolidinecarboxamide (70% yield) as a yellow solid, mp 121–126° C.; MS (ES) m/z 536.1 (M+1). Analysis for $C_{27}H_{23}Cl_2N_5O_3 \cdot 1.0H_2O$: Calcd: C, 58.49; H, 4.55; N, 12.63. Found: C, 58.77; H, 4.42; N, 12.43.

EXAMPLE 48

7-[5-(4-Morpholinylmethyl)-3-pyridinyl]-4-(4-phenoxyanilino)-3-quinolinecarbonitrile 4-[(5-Bromo-3-pyridinyl)methyl]morpholine (277 mg, 1.08 mmol) was dissolved in 15 mL of tetrahydrofuran and the solution was cooled to −78° C. 2.5M n-Butyl lithium in hexane (0.42 mL, 1.05 mmol) was added followed by tri-isopropylborate (209 mg, 1.11 mmol). The mixture was stirred at −78° C. for 30 min and then allowed to warm to room temperature. The solvent was removed in vacuo to provide the intermediate boronate. A mixture of this boronate, 7-bromo-4-(4-phenoxyanilino)-3-quinolinecarbonitrile (Reference Example 10)(250 mg, 0.60 mmol) and tetrakis(triphenylphosphine)palladium(0) (96 mg, 0.082 mmol) was heated at reflux in 8.0 mL of ethylene glycol dimethyl ether and 5.0 mL of saturated sodium bicarbonate for 2 hours. The reaction was cooled to room temperature, quenched with 4.1 mL of 1N sodium hydroxide, and partitioned between ethyl acetate and brine. The layers were separated and the ethyl acetate layer was dried over magnesium sulfate. Removal of the solvent in vacuo gave a residue which was purified by flash silica gel chromatography eluting with a gradient of ethyl acetate to 5% methanol in ethyl acetate to provide 102 mg (33% yield) of 7-[5-(4-morpholinylmethyl)-3-pyridinyl]-4-(phenoxyanilino)-3-quinolinecarbonitrile as a yellow solid: mp 185–187° C.;

¹H NMR (DMSO-d₆): δ 2.43 (t, J=4 Hz, 4H), 3.60 (t, J=4 Hz, 4H), 3.63 (s, 2H), 7.05 (dd, J=9, 1 Hz, 2H), 7.13 (m, 3H), 7.40 (m, 4H), 8.07 (dd, J=9, 2 Hz, 1H), 8.21 (s, 1H), 8.26 (s, 1H), 8.61 (m, 3H), 9.01 (d, J=2 Hz, 1H), 9.97 (s, 1H); MS (ES) m/z 514.2 (M+1). Analysis for $C_{32}H_{27}N_5O_2 \cdot 0.5H_2O$; Calcd: C, 73.55; H, 5.40; N, 13.40. Found: C, 73.64; H, 5.41; N, 13.31.

EXAMPLE 49

4-(2,4-Dichloro-5-methoxyanilino)-7-[5-(4-morpholinylmethyl)-3-pyridinyl]-3-quinolinecarbonitrile 4-[(5-Bromo-3-pyridinyl)methyl]morpholine (977 mg, 1.08 mmol) was dissolved in 15 mL of tetrahydrofuran and the solution was cooled to −78° C. 2.5 M n-Butyl lithium in hexane (0.42 mL, 1.05 mmol) was added followed by tri-isopropylborate (209 mg, 1.11 mmol). The mixture was stirred at −78° C. for 30 minutes and then allowed to warm to room temperature. The solvent was removed in vacuo to provide the intermediate boronate. A mixture of this boronate, 7-bromo-4-(2,4-dichloro-5-methoxyanilino)-3-quinolinecarbonitrile (Reference Example 8) (282 mg, 0.60 mmol) and tetrakis(triphenylphosphine)palladium(0) (96 mg, 0.082 mmol) was heated at reflux in 8.0 mL of ethylene glycol dimethyl ether and 5.0 mL of saturated sodium bicarbonate for 2 hours. The reaction was cooled to room temperature, quenched with 4.1 mL of 1N sodium hydroxide, and partitioned between ethyl acetate and brine. The layers were separated and the ethyl acetate layer was dried over magnesium sulfate. Removal of the solvent in vacuo gave a residue which was purified by flash silica gel chromatography eluting with a gradient of ethyl acetate to 5% methanol in ethyl acetate to provide 163 mg (52% yield) of 4-(2,4-dichloro-5-methoxyanilino)-7-[5-(4-morpholinylmethyl)-3-pyridinyl]-3-quinolinecarbonitrile as a yellow solid: mp 141–143° C.; ¹HNMR (DMSO-d₆/TFA): δ 3.19 (m, 2H), 3.44 (m, 2H), 3.74 (m, 2H), 3.92 (s, 3H), 3.98 (m, 2H), 4.65 (s, 2H), 7.63 (s, 1H), 7.89 (s, 1H), 8.38 (dd, J=9, 2 Hz, 1H), 8.46 (d, J=1Hz, 1H), 8.76 (s, 1H), 8.98 (d, J=10 Hz, 1H), 9.00 (s, 1H), 9.33 (s, 1H), 9.38 (d, J=2 Hz, 1H); MS (ES) m/z 520.1 (M+1). Analysis for $C_{27}H_{23}Cl_2N_5O_2$-0.5$H_2O$; Calcd: C, 61.27; H, 4.38; N, 13.46. Found: C, 61.26; H, 4.57; N, 13.23.

EXAMPLE 50

4-(2,4-Dichloro-5-methoxyanilino)-6-[5-(4-morpholinylmethyl)-3-thienyl]-3-quinolinecarbonitrile Morpholine (0.100 mL, 1.14 mmol) was added to a suspension of 4-(2,4-dichloro-5-methoxyanilino)-6-(5-formyl-3-thienyl)-3-quinolinecarbonitrile (Example 45) (150 mg, 0.33 mmol) in 3 mL of methylene chloride and 1 mL of N,N-dimethylformamide. The reaction mixture was cooled to 0° C. and sodium triacetoxyborohydride (340 mg, 1.60 mmol) was added followed by a drop of acetic acid. After stirring at 0° C. for 30 minutes the ice bath was removed and the reaction mixture was stirred at room temperature for 5.5 hours. The reaction was quenched by the addition of water and then partitioned between saturated sodium bicarbonate and ethyl acetate. The organic layer was dried over magnesium sulfate, filtered and concentrated in vacuo. The residue was purified by flash column chromatography eluting with a gradient of ethyl acetate to 10% methanol in ethyl acetate to provide 73 mg 4-(2,4-dichloro-5-methoxyanilino)-6-[5-(4-morpholinylmethyl)-3-thienyl]-3-quinolinecarbonitrile (42% yield) as a bright yellow solid, mp softens at 130° C., melts at 145–147° C.;

$^1$H NMR (DMSO-$d_6$) δ 2.50 (m, 4H), 3.59 (m, 4H), 3.73 (s, 2H), 3.87 (s, 3H), 7.36 (s, 1H), 7.65 (s, 1H), 7.75 (s, 1H), 7.88 (d, J=8 Hz, 1H), 8.01 (s, 1H), 8.22 (d, J=8 Hz, 1H), 8.49 (s, 1H), 8.77 (s, 1H); MS (ES) m/z 525.0 (M+1). Analysis for $C_{26}H_{22}Cl_2N_4O_2S$-0.25$H_2O$: Calcd: C, 58.92; H, 4.28; N, 10.57. Found: C, 58.78; H, 4.18; N, 10.31.

EXAMPLE 51

4-(2,4-Dichloro-5-methoxyanilino)-7-[5-(1,3-dioxolan-2-yl)-2-thienyl]-3-quinolinecarbonitrile A mixture of 4-(2,4-dichloro-5-methoxyanilino)-7-iodo-3-quinolinecarbonitrile (Reference Example 13) (2.00 g, 4.25 mmol), tributyl[5-(1,3-dioxolan-2-yl)-2-thienyl]stannane (2.38 g, 5.35 mmol), and a catalytic amount of dichlorobis(triphenylphosphine)palladium(II) in 60 mL of dioxane was heated at reflux for 6 hours then stirred at room temperature overnight. The mixture was concentrated in vacuo and partitioned between ethyl acetate and saturated sodium chloride. The organic layer was dried over sodium sulfate and concentrated in vacuo. A portion of this material was heated in ethyl acetate and the resultant suspension was filtered to provide an analytical sample of 4-(2,4-dichloro-5-methoxyanilino)-7-[5-(1,3-dioxolan-2-yl)-2-thienyl]-3-quinolinecarbonitrile as a yellow solid, mp 174–177° C. dec.;

$^1$H NMR (DMSO-$d_6$/trifluoroacetic acid) δ 3.87 (s, 3H), 3.95–4.02 (m, 2H), 4.05–4.13 (m, 4H), 6.13 (s, 1H), 7.38 (d, J=4 Hz, 1H), 7.59 (s, 1H), 7.84 (d, J=4 Hz, 1H), 7.87 (s, 1H), 8.14 (d, J=2 Hz, 1H), 8.29 (dd, J=9, 2 Hz, 1H), 8.75 (d, J=9 Hz, 1H), 9.16 (s, 1H); MS (ES) m/z 498.0, 500.0 (M+1). Analysis for $C_{24}H_{17}Cl_2N_3O_3S$-0.75$H_2O$: Calcd: C, 56.31; H, 3.64; N, 8.21. Found: C, 56.21; H, 3.84; N, 7.97.

EXAMPLE 52

4-(2,4-Dichloro-5-methoxyanilino)-7-(5-formyl-2-thienyl)-3-quinolinecarbonitrile A solution of crude 4-(2,4-dichloro-5-methoxyanilino)-7-[5-(1,3-dioxolan-2-yl)-2-thienyl]-3-quinolinecarbonitrile (Example 51) in 50 mL of tetrahydrofuran and 25 mL of 2N hydrochloric acid was stirred at room temperature overnight. Saturated sodium bicarbonate was slowly added. Upon attempting to extract the product into ethyl acetate a precipitate formed and was collected by filtration washing with water and ethyl acetate to provide 1.427 g of a bright yellow solid. A portion was heated in refluxing methanol and the resultant precipitate was filtered hot. The solid was washed with tetrahydrofuran, ethyl acetate and diethyl ether to provide an analytical sample of 4-(2,4-dichloro-5-methoxyanilino)-7-(5-formyl-2-thienyl)-3-quinolinecarbonitrile as a yellow solid, mp>300° C. (dec);

$^1$H NMR (DMSO-$d_6$) δ 3.85 (s, 3H), 7.19 (s, 1H), 7.64 (s, 1H), 7.98–8.07 (m, 2H), 8.12 (d, J=4 Hz, 1H), 8.16 (d, J=2 Hz, 1H), 8.46 (s, 1H), 8.56 (d, J=9 Hz, 1H), 9.96 (s, 1H); MS (ES) m/z 454.0, 456.0 (M+1). Analysis for $C_{22}H_{13}Cl_2N_3O_2S$-0.25$H_2O$: Calcd: C, 57.59; H, 2.97; N, 9.16. Found: C, 57.66; H, 2.91; N, 8.93.

EXAMPLE 53

4-(2,4-Dichloro-5-methoxyanilino)-7-[5-(4-morpholinylmethyl)-2-furyl]-3-quinolinecarbonitrile Morpholine (0.060 mL, 0.68 mmol) was added to a suspension of 4-(2,4-dichloro-5-methoxyanilino)-7-(5-formyl-2-furyl)-3-quinolinecarbonitrile (Example 6) (250 mg, 0.57 mmol) in 3 mL of methylene chloride and 1 mL of N,N-dimethylformamide. The reaction mixture was cooled to 0° C. and sodium triacetoxyborohydride (600 mg, 2.85 mmol) was added. After stirring at 0° C. for 1 hour, a catalytic amount of acetic acid was added and the reaction mixture was allowed to warm to room temperature. The reaction was quenched by the addition of water and then partitioned between saturated sodium bicarbonate and methylene chloride. The organic layer was dried over sodium sulfate, filtered and concentrated in vacuo. The residue was purified by flash column chromatography eluting with a gradient of 10% methanol in methylene chloride to 20) methanol in methylene chloride to provide 190 mg of 4-(2,4-dichloro-5-methoxyanilino)-7-[5-(4-morpholinylmethyl)-2-furyl]-3-quinolinecarbonitrile as a light yellow solid (65% yield) mp 182–183° C.; MS (ES) m/z 509.0, 511.0 (M+1). Analysis for $C_{26}H_{22}Cl_2N_4O_3$-0.5$H_2O$: Calcd: C, 60.24; H, 4.47; N, 10.81. Found: C, 60.40; H, 4.38; N, 10.52.

EXAMPLE 54

4-(2,4-Dichloro-5-methoxyanilino)-7-[(E)-2-(4-methoxyphenyl)ethenyl]-3-quinolinecarbonitrile A mixture of 7-iodo-4-(2,4-dichloro-5-methoxyanilino)-3-quinolinecarbonitrile (Reference Example 13) (250 mg, 0.53 mmol), 2-vinylanisole (0.11 mL, 0.85 mmol), palladium(II)acetate (1.3 mg, 0.006 mmol) and tri-o-tolylphosphine (6.4 mg, 0.02 mmol) in 5 mL of triethylamine was heated at reflux for 12 hours. The mixture was concentrated in vacuo and the resultant solid was partitioned between ethyl acetate and water. The organic layer was dried over sodium sulfate, filtered and concentrated to a small volume. The resultant solid was collected by filtration to provide 150 mg (59% yield) of 4-(2,4-dichloro-5-methoxyanilino)-7-[(E)-2-(4-methoxyphenyl)ethenyl]-3-quinolinecarbonitrile as a yellow solid, mp 216–220° C.;

$^1$H NMR (DMSO-$d_6$) δ 3.83 (s, 3H), 3.90 (s, 3H), 7.04 (d, J=9 Hz, 2H), 7.44 (d, J=16 Hz, 1H), 7.63–7.73 (m, 4H), 7.90 (s, 1H), 7.99 (s, 1H), 8.32 (d, J=9 Hz, 1H), 8.77 (d, J=9 Hz,

1H), 9.26 (s, 1H); MS (ES) m/z 476.1, 478.1 (M+1). Analysis for $C_{26}H_{19}Cl_2N_4O_2$: Calcd: C, 65.56; H, 4.02; N, 8.82. Found: C, 65.79; H, 3.98; N, 8.80.

EXAMPLE 55

4-(2,4-Dichloro-5-methoxyanilino)-7-{5-[(4-methyl-1-piperazinyl)methyl]-2-thienyl}-3-quinolinecarbonitrile N-Methylpiperazine (0.100 mL, 0.90 mmol) was added to a suspension of 4-(2,4-dichloro-5-methoxyanilino)-7-(5-formyl-2-thienyl)-3-quinolinecarbonitrile (Example 52) (224 mg, 0.49 mmol) in 3 mL of methylene chloride and 1 mL of N,N-dimethylformamide at room temperature. Sodium triacetoxyborohydride (500 mg, 2.36 mmol) was added followed by a drop of acetic acid. The reaction mixture was stirred at room temperature overnight to give a yellow solution. The reaction was quenched by the addition of water and then partitioned between saturated sodium bicarbonate and ethyl acetate. The organic layer was dried over magnesium sulfate, filtered and concentrated in vacuo. The residue was purified by flash column chromatography eluting with 20% methanol in methylene chloride to provide 108 mg of 4-(2,4-dichloro-5-methoxyanilino)-7-{5-[(4-methyl-1-piperazinyl)methyl]-2-thienyl}-3-quinolinecarbonitrile (41%, yield) as a white solid, mp 206–208° C.;

$^1$H NMR (DMSO-$d_6$/trifluoroacetic acid) δ 2.87 (s, 3H), 3.05–3.72 (br m, 8H), 3.88 (s, 3H), 4.47 (s, 2H), 7.39 (d, J=4 Hz, 1H), 7.57 (s, 1H), 7.87 (s, 1H), 7.91 (d, J=4 Hz, 1H), 8.15 (d, J=2 Hz, 1H), 8.30 ((dd, J=9, 2 Hz, 1H), 8.79 (d, J=9 Hz, 1H), 9.20 (s, 1H); MS (ES) m/z 538.1, 540.1 (M+1). Analysis for $C_{27}H_{25}Cl_2N_5OS$-$0.5H_2O$: Calcd: C, 59.23; H, 4.79; N, 12.79. Found: C, 59.12; H, 4.43; N, 12.88.

EXAMPLE 56

7-[5-(4-Morpholinylmethyl)-2-pyridinyl]-4-(4-phenoxyanilino)-3-quinolinecarbonitrile A mixture of 7-bromo-4-(4-phenoxyanilino)-3-quinolinecarbonitrile (Reference Example 10) (196.2 mg, 0.47 mmol), 4-{[6-(tributylstannyl)-3-pyridinyl]methyl}morpholine (396.9 mg, 0.52 mmol), and a catalytic amount of dichlorobis(triphenylphosphine)palladium(II) in 3 mL of tetrahydrofuran was heated at reflux for 4.5 days. The mixture was concentrated in vacuo and partitioned between ethyl acetate and saturated sodium chloride. The organic layer was dried over sodium sulfate and concentrated in vacuo. The residue was purified by preparative thin layer chromatography, with a developing solvent of 10% methanol in ethyl acetate, to give 134.8 mg of 7-[5-(4-morpholinylmethyl)-2-pyridinyl]-4-(4-phenoxyanilino)-3-quinolinecarbonitrile as a yellow solid, mp 219–221° C.;

$^1$H NMR (DMSO-$d_6$) δ 9.42 (t, J=4 Hz, 4H), 3.59 (m, 6H), 7.03–7.15 (m, 5H), 7.41 (m, 4H), 7.90 (dd, J=8, 2 Hz, 1H), 8.23 (d, J=8 Hz, 1H), 8.39 (dd, J=9, 2 Hz, 1H), 8.60 (d, J=3 Hz, 2H), 8.63 (s, 1H), 8.69 (d, J=2 Hz, 1H), 9.95 (s, 1H); MS (ES) m/z 514.2 (M+1). Analysis for $C_{32}H_{27}N_5O_2$-$0.5H_2O$: Calcd: C, 73.54; H, 5.40; N, 13.40. Found: C, 73.54; H, 5.35; N, 13.08.

EXAMPLE 57

4-(2,4-Dichloro-5-methoxyanilino)-7-[5-(4-morpholinylmethyl)-2-pyridinyl]-3-quinolinecarbonitrile A mixture of 4-(2,4-dichloro-5-methoxyanilino)-7-iodo-3-quinolinecarbonitrile (Reference Example 13) (200.0 mg, 0.43 mmol), 4-{[6-(tributylstannyl)-3-pyridinyl]methyl}morpholine (358.5 mg, 0.47 mmol), and a catalytic amount of dichlorobis(triphenylphosphine)palladium(I) in 4 mL of 1,4-dioxane was heated at reflux for 10 hours. The mixture was concentrated in vacuo and partitioned between ethyl acetate and saturated sodium chloride. The organic layer was dried over sodium sulfate and concentrated in vacuo. The residue was purified by preparative thin layer chromatography, with a developing solvent of 10% methanol in ethyl acetate, to give 70.2 mg of 4-(2,4-dichloro-5-methoxyanilino)-7-[5-(4-morpholinylmethyl)-2-pyridinyl]-3-quinolinecarbonitrile as a yellow solid, mp 220–22° C.;

$^1$H NMR (DMSO-$d_6$/TFA) δ 3.24–3.28 (m, 2H), 3.40–3.43 (m, 2H), 3.69 (t, J=12 Hz, 2H), 3.92 (s, 3H), 4.03 (d, J=13 Hz, 2H), 4.57 (s, 2H), 7.64 (s, 1H), 7.91 (s, 1H), 8.22 (dd, J=8, 2 Hz, 1H), 8.43 (d, J=8 Hz, 1H), 8.71 (dd, J=9, 2 Hz, 1H), 8.86 (d, J=2 Hz, 1H), 8.95 (s, 2H), 8.98 (s, 1H), 9.36 (s, 1H); MS (ES) m/z 520.1 (M+1). Analysis for $C_{27}H_{23}Cl_2N_5O_2$-$0.2H_2O$: Calcd: C, 61.88; H, 4.50; N, 13.36. Found: C, 61.87; H, 4.12; N, 13.25.

EXAMPLE 58

4-(2,4-Dichloro-5-methoxyanilino)-7-[5-({[2-(phenylsulfonyl)ethyl]amino}methyl)-2-furyl]-3-quinolinecarbonitrile 2-(Phenylsulfonyl)ethanamine (0.130 g, 0.68 mmol) was added to a suspension of 4-(2,4-dichloro-5-methoxyanilino)-7-(5-formyl-2-furyl)-3-quinolinecarbonitrile (Example 6) (250 mg, 0.57 mmol) in 3 mL of methylene chloride. Sodium triacetoxyborohydride (600 mg, 2.85 mmol) was added followed by 1 drop of acetic acid and the reaction mixture was stirred at room temperature overnight. The reaction was quenched by the addition of saturated sodium bicarbonate and then extracted with methylene chloride. The organic layer was dried over sodium sulfate, filtered and concentrated in vacuo. The residue was purified by flash column chromatography eluting with 10% methanol in methylene chloride to provide 160 mg of 4-(2,4-dichloro-5-methoxyanilino)-7-[5-({[2-(phenylsulfonyl)ethyl]amino}methyl)-2-furyl]-3-quinolinecarbonitrile as a yellow solid (46% yield) mp 123–128° C.;

MS (ES) m/z 607.0, 609.0 (M+1). Analysis for $C_{30}H_{24}Cl_2N_4O_4S$-$0.5H_2O$: Calcd: C, 58.44; H, 4.08; N, 9.09. Found: C, 58.19; H, 3.87; N, 9.07.

EXAMPLE 59

4-(2,4-Dichloro-5-methoxyanilino)-6-methoxy-7-(1H-pyrrol-1-yl)-3-quinolinecarbonitrile An amount of 200 mg of 7-amino-4-(2,4-dichloro-5-methoxyanilino)-6-methoxy-3-quinolinecarbonitrile (0.51 mmol) was stirred in N,N-dimethylformamide (4.5 mL), and to this were added 50 mg (0.33 mmol) of 4-chloropyridine hydrochloride, and 100 mg (0.77 mmol) of 2,5-dimethoxy-2,5-tetrahydrofuran. The reaction mixture was heated at 80° C. for 2 hours and subsequently cooled to room temperature, basified with saturated sodium bicarbonate solution, and extracted with ethyl acetate. The organic phase was dried over magnesium sulfate, filtered through a pad of silica gel and evaporated. The yellowish oily residue was purified by flash chromatography (ethyl acetate/methanol/triethylamine, 40:4:1) to give 95 mg (42% yield) of an orange solid, mp 229–230° C.;

$^1$H NMR (DMSO-$d_6$) δ 9.90 (s, 1H), 8.48 (s, 1H), 8.07 (s, 1H), 7.84 (s, 1H), 777 (s, 1H), 7.37 (broad s, 1H), 7.31 (t, J=2 Hz, 2H), 6.29 (t, J=2 Hz, 2H), 4.02 (s, 3H), 3.88 (s, 3H); HRMS (EI) m/z 439.07161 (M+1).

EXAMPLE 60

4-(3-Bromoanilino)-6-(2-formyl-1H-pyrrol-1-yl)-3-quinolinecarbonitrile

An amount of 100 mg (0.29 mmol) of 6-amino-4-[(3-bromophenyl)amino-3-quinolinecarbonitrile (prepared according to the procedure described in WO9843960-A1) was stirred in 2-ethoxyethanol (2 mL) at room temperature. To this was added 2-furaldehyde (42 mg, 0.43 mmol), and Amberlite IR-120 (29 mg), and the mixture was stirred for 2 days at room temperature during which an orange precipitate was formed. The reaction mixture was filtered and evaporated to dryness to give a yellow solid (107 mg, 87% yield), mp 94–95° C.;

$^1$H NMR (DMSO-d$_6$) δ 9.87 (s, 1H), 8.64 (d, J=2 Hz, 2H), 8.29 (d, J=2 Hz, 1H), 8.01 (s, 1H), 7.98 (s, 1H), 7.86 (d, J=2 Hz, 1H), 7.50 (s, 1H), 7.42–6.77 (m, 5H); MS (ES) m/z 417.0 (M+1). Analysis for $C_{21}H_{13}BrN_4O.1.3H_2O$: Calcd: C, 57.18; H, 3.54; N, 12.71. Found: C, 57.47; H, 3.46; N, 12.98.

EXAMPLE 61

4-(3-Chloro-4-fluoro-phenylamino)-7-methoxy-6-(1H-1-pyrrol-1-yl)-3-quinolinecarbonitrile A solution of 6-amino-4-(3-chloro-4-fluoroanilino)-7-methoxy-3-quinolinecarbonitrile (prepared by the procedure described in WO9843960-A1) (0.20 g, 0.58 mmol), 2,5-dimethoxytetrahydrofuran (0.1 mL, 0.77 mmol) and 4-chloropyridine hydrochloride (50 mg, 0.33 mmol) in N,N-dimethylformamide (4.5 mL) was heated at 108° C. for 16 hours then cooled to room temperature. The reaction solution was partitioned between saturated sodium bicarbonate solution and ethyl acetate. The organic phase was passed through a pad of silica gel and dried to give a light brown solid. Addition of ether to the light brown solid followed by filtration gave 119 mg of a cream colored solid, mp 192.5–193.5° C.;

$^1$H NMR (DMSO-d$_6$) δ 9.80 (s, 1H), 8.59 (s, 1H), 8.41 (s, 1H), 7.54 (m, 2H), 7.47 (t, J=9 Hz, 1H), 7.33 (m, 1H), 7.20 (t, J=2 Hz, 2H), 6.28 (t, J=2.1 Hz, 2 H), 4.01 (s, 3H); HRMS (ES) m/z 393.0913 (M+1). Analysis for $C_{21}H_{14}ClFN_4O$-0.25H$_2$O: Calcd: C, 63.48; H, 3.68; N, 14.10; Cl, 8.92; F, 4.78. Found: C, 63.83; H, 3.70; N, 13.85; Cl, 8.52; F, 4.86.

EXAMPLE 62

4-(3-Chloro-4-[(1-methyl-1H-imidazol-2-yl)sulfanyl]anilino)-7-(4-formylphenyl)-3-quinolinecarbonitrile By the procedure for Example 26, 500 mg (1.06 mmol) of 7-bromo-4-{3-chloro-4-[(1-methyl-1H-imidazol-2-yl)sulfanyl]}-3-quinolinecarbonitrile was reacted with 159 mg (1.06 mmol) of 4-formylphenylboronic acid and 184 mg (0.16 mmol) of tetrakis(triphenylphosphine)palladium (0) in 7 mL of ethylene glycol dimethyl ether and 4 mL of saturated aqueous sodium bicarbonate to provide 402 mg of 4-{3-chloro-4-[(1-methyl-1H-imidazol-2-yl)sulfanyl]anilino}-7-(4-formylphenyl)-3-quinolinecarbonitrile as a yellow solid after purification, mp>240° C. (dec);

$^1$H NMR (DMSO-d$_6$) δ 10.10 (s, 1H), 8.54–8.49 (m, 2H), 8.22 (s, 1H), 8.14–8.04 (m, 4H), 7.99 (d, J=9 Hz, 1H), 7.53 (s, 1H), 7.37 (s, 1H), 7.16 (s, 1H), 7.11 (d, J=8 Hz, 1H), 6.55 (d, J=9 Hz, 1H), 3.61 (s, 3H); MS (ES) m/z 496.0, 498.0 (M+1). Analysis for $C_{27}H_{18}ClN_5OS.0.80CH_2Cl_2$: Calcd: C, 59.21; H, 3.50; N, 12.42. Found: C, 59.59; H, 3.55; N, 12.50.

EXAMPLE 63

4-{3-Chloro-4-[(1-methyl-1H-imidazol-2-yl)sulfanyl]anilino}-7-[4-(4-morpholinylmethyl)phenyl]-3-quinolinecarbonitrile A mixture of 250 mg (0.50 mmol) of 4-{3-chloro-4-[(1-methyl-1H-imidazol-2-yl)sulfanyl]anilino}-7-(4-formylphenyl)-3-quinolinecarbonitrile 45 mg (0.50 mmol) of morpholine, 36 mg (0.61 mmol) of acetic acid and 41 mg (0.65 mmol) of sodium cyanoborohydride in 2 mL of ethanol, 0.5 mL of dimethyl formamide and 2 mL of methylene chloride were allowed to react at room temperature. After 12 hours, an additional 90 mg (1.03 mmol) of morpholine, 72 mg (1.2 mmol) of acetic acid and 82 mg (1.30 mmol) of sodium cyanoborohydride were added to the mixture. After stirring for a further 24 hours, the solvents were removed in vacuo, and the crude product was washed with saturated aqueous sodium bicarbonate solution. Purification by silica gel chromatography (eluting with 95:5 ethyl acetate/methanol, then 92:8 methylene chloride/methanol) provided 100 mg of 4-{3-chloro-4-[(1-methyl-1H-imidazol-2-yl)sulfanyl]anilino}-7-[4-(4-morpholinylmethyl)phenyl]-3-quinolinecarbonitrile as a yellow solid, mp 148–150° C.;

$^1$H NMR (DMSO-d$_6$) δ 9.95 (s, 1H), 8.67 (s, 1H), 8.47 (d, J=9 Hz, 1H), 8.21 (s, 1H), 8.04 (d, J=9 Hz, 1H), 7.87 (d, J=8 Hz, 2H), 7.55 (s, 1H), 7.49–7.46 (m, 3H; 7.21 (d, J=8 Hz, 1H), 7.17 (s, 1H), 6.46 (d, J=9 Hz, 1H), 3.62 (s, 3H), 3.60 (t, J=5 Hz, 4H), 3.54 (s, 2H), 2.40 (t, J=4 Hz, 4H); MS (ES) m/z 567.1, 569.2 (M+1). Analysis for $C_{31}H_{27}ClN_6OS$-0.5H$_2$O: Calcd: C, 64.63; H, 4.90; N, 14.59. Found: C, 64.28; H, 4.59; N, 14.66.

EXAMPLE 64

4-(2,4-Dichloro-5-methoxyanilino)-7-{1-[2-(4-morpholinyl)ethyl]-1H-imidazol-5-yl}-3-quinolinecarbonitrile A mixture of 4-{2-[5-(tributylstannyl)-1H-imidazol-1-yl]ethyl}morpholine (Reference Example 68) (367 mg, 0.78 mmol), 7-bromo-4-(2,4-dichloro-5-methoxyanilino)-3-quinolinecarbonitrile (Reference Example 8) (260 mg, 0.61 mmol), and dichlorobis(triphenylphosphine)palladium(II) (20 mg, 0.029 mmol) in 5 mL of dioxane was heated at reflux for 40 hours then concentrated in vacuo. The residue was partitioned between ethyl acetate and brine. The layers were separated and the aqueous layer was extracted with ethyl acetate. The combined organic extracts were washed with water and brine, dried over magnesium sulfate and filtered. Removal of the solvent in vacuo gave a residue which was purified by flash silica gel chromatography eluting with 10% methanol in ethyl acetate to provide 80 mg (25% yield) of 4-(2,4-dichloro-5-methoxyanilino)-7-{1-[2-(4-morpholinyl)ethyl]-1H-imidazol-5-yl}-3-quinolinecarbonitrile as a yellow solid, mp 150° C. (decomposed);

$^1$HNMR (DMSO-d$_6$/TFA): δ 3.31 (m, 4H), 3.58 (t, J=4 Hz, 2H), 3.80 (m, 4H), 3.92 (s, 3H), 4.83 (t, J=7 Hz, 2H), 7.56 (s, 1H), 7.89 (s, 1H), 8.14 (dd, J=9, 1 Hz, 1H), 8.23 (d, J=1 Hz, 1H), 8.27 (d, J=1 Hz, 1H), 8.95 (d, J=9 Hz, 1H), 9.31 (s, 1H), 9.50 (d, J=1 Hz, 1H); MS (ES) m/z 523.1 (M+1). Analysis for $C_{26}H_{24}Cl_2N_6O_2$-0.5EtOAc: Calcd: C, 59.26; H, 4.97; N, 14.81. Found: C, 59.56; H, 4.97; N, 14.63.

EXAMPLE 65

4-(2,4-Dichloro-5-methoxyanilino)-7-[4-(4-morpholinylmethyl)-3-thienyl]-3-quinolinecarbonitrile Using an analogous procedure to that described for Example 10, 4-(2,4-dichloro-5-methoxyanilino)-7-[4-(4-morpholinylmethyl)-3-thienyl]-3-quinolinecarbonitrile was prepared from 7-bromo-4-(2,4-dichloro-5-methoxyanilino)-3-quinolinecarbonitrile (Reference Example 8) and 4-[(4-bromo-3-thienyl)methyl]-morpholine (Reference Example 69) in 88% yield as a white solid, mp 188–190° C.;

$^1$H NMR (DMSO-d$_6$) δ 2.40–2.45 (m, 4H), 3.47 (s, 2H), 3.55–3.65 (m, 4H), 3.87 (s, 3H), 7.40 (s, 1H), 7.57 (d, J=3 Hz, 1H), 7.76 (s, 1H), 7.86 (d, J=3 Hz, 1H), 7.99 (d, J=9 Hz, 1H), 8.28 (s, 1H), 8.56 (d, J=9 Hz, 1H), 8.89 (s, 1H), 9.99 (s, 1H); MS (ES) m/z 525.0 (M+1). Analysis for C$_{26}$H$_{22}$Cl$_2$N$_4$O$_2$S: Calcd: C, 59.43; H, 4.22; N, 10.66. Found: C, 59.32; H, 4.50; N, 10.55.

EXAMPLE 66

4-(2,4-Dichloro-5-methoxyanilino)-7-[2-(4-morpholinylmethyl)-3-thienyl]-3-quinolinecarbonitrile Using an analogous procedure to that described for Example 10, 4-(2,4-dichloro-5-methoxyanilino)-7-[2-(4-morpholinylmethyl-3-thienyl]-3-quinolinecarbonitrile was prepared from 7-bromo-4-(2,4-dichloro-5-methoxyanilino)-3-quinolinecarbonitrile (Reference Example 8) and 4-[(3-bromo-2-thienyl)methyl]-morpholine (Reference Example 71) in 92% yield as a white solid, mp 98–100° C.;

$^1$NMR (DMSO-d$_6$) δ 2.45 (t, J=4 Hz, 4H), 3.60 (t, J=4 Hz, 4H), 3.78 (s, 2H), 3.86 (s, 3H), 7.30–7.55 (m, 2H), 7.57 (s, 1H), 7.70–7.85 (m, 2H), 8.03 (s, 1H), 8.55–8.65 (m, 2H), 10.01 (s, 1H); MS (ES) m/z 525.0 (M+1). Analysis for C$_{26}$H$_{22}$Cl$_2$N$_4$O$_2$S: Calcd: C, 59.43; H, 4.22; N, 10.66. Found: C, 59.22; H, 4.01; N, 10.75.

EXAMPLE 67

4-(2,4-Dichloro-5-methoxyanilino)-7-[4-(4-morpholinyl)phenyl]-3-quinolinecarbonitrile Using an analogous procedure to that described for Example 10, 4-(2,4-dichloro-5-methoxyanilino)-7-[4-(4-morpholinyl)phenyl]-3-quinolinecarbonitrile was prepared from 7-bromo-4-(2,4-dichloro-5-methoxyanilino)-3-quinolinecarbonitrile (Reference Example 8) and 4-[(4-bromophenyl)]morpholine (prepared according to the procedure of U.S. Pat. No. 4,1397,04) in 68% yield as a white solid, mp 235–237° C.:

$^1$H NMR (DMSO-d$_6$) δ 3.22 (t, J=5 Hz, 4H), 3.78 (t, J=5 Hz, 4H), 3.86 (s, 3H), 7.10 (d, J=8 Hz, 2H), 7.35 (s, 1H), 7.71 (s, 1H), 7.79 (d, J=8 Hz, 2H), 7.95–8.20 (m, 2H), 8.45–8.60 (m, 2H), 10.21 (s, 1H); MS (ES) m/z 505.1 (M+1). Analysis for C$_{27}$H$_{22}$Cl$_2$N$_4$O$_2$-0.4H$_2$O: Calcd: C, 63.25; H, 4.47; N, 10.93. Found: C, 63.33; H, 4.14; N, 10.74.

EXAMPLE 68

4-(2,4-Dichloro-5-methoxyanilino)-7-[4-(4-morpholinylmethyl)-2-thienyl]-3-quinolinecarbonitrile Using an analogous procedure to that described for Example 10, 4-(2,4-dichloro-5-methoxyanilino)-7-[4-(4-morpholinylmethyl)-2-thienyl]-3-quinolinecarbonitrile was prepared from 7-bromo-4-(2,4-dichloro-5-methoxyanilino)-3-quinolinecarbonitrile (Reference Example 8) and 4-[(5-bromo-3-thienyl)methyl]morpholine (Reference Example 73) in 96% yield as a white solid, mp 118–190° C.; $^1$H NMR (DMSO-d$_6$) δ 2.41 (t, J=7 Hz, 4H), 3.51 (s, 2H), 3.60 (t, J=7 Hz. (4H), 3.86 (s, 3H), 7.41 (s, 1H), 7.49 (s, 1H), 7.56–7.70 (m, 2H), 8.00–8.15 (m, 2H), 8.50–8.65 (m, 2H), 10.01 (s, 1H); MS (ES) m/z 525.0 (M+1). Analysis for C$_{26}$H$_{22}$Cl$_2$N$_4$O$_2$S-0.10CH$_2$Cl$_2$: Calcd: C, 58.81; H, 4.18; N, 10.49. Found: C, 59.54; H, 4.07; N, 10.15.

EXAMPLE 69

4-(2,4-Dichloro-5-methoxyanilino)-7-(5-formyl-1-methyl-1H-pyrrol-2-yl)-3-quinolinecarbonitrile Using an analogous procedure to that described for Example 5, 4-(2,4-dichloro-5-methoxyanilino)-7-(5-formyl-1-methyl-1H-pyrrol-2-yl)-3-quinolinecarbonitrile was prepared from 7-bromo-4-(2,4-dichloro-5-methoxyanilino)-3-quinolinecarbonitrile (Reference Example 8) and 1-methyl-5-(tributylstannyl)-1H-pyrrole-2-carbaldehyde (prepared according to the procedure of Denat, F. J. Organometallic Chem. 423, 173 (1992) in 64% yield as a light yellow solid, mp 200° C.(dec);

$^1$H NMR (DMSO-d$_6$) δ 3.87 (s, 3H), 4.00 (s, 3H), 6.66 (s, 1H), 7.19 (d, J=4 Hz, 1H), 7.42–8.09 (m, 4H), 8.60–8.70 (m, 2H), 9.65 (s, 1H), 10.10 (s, 1H); MS (ES) m/z 451.1 (M+1). Analysis for C$_{23}$H$_{16}$Cl$_2$N$_4$O$_2$-0.3CH$_2$Cl$_2$: Calcd: C, 58.69; H, 3.50; N, 11.45. Found: C, 58.85; H, 3.27; N, 11.13.

EXAMPLE 70

4-(2,4-Dichloro-5-methoxyanilino)-7-[1-methyl-5-(4-morpholinylmethyl)-1H-pyrrol-2-yl]-3-quinolinecarbonitrile 4-(2,4-Dichloro-5-methoxyanilino)-7-(5-formyl-1-methyl-1H-pyrrol-2-yl)-3-quinolinecarbonitrile (Example 69) (150 mg, 0.33 mmol) and morpholine (35 mg, 0.4 mmol) were dissolved in 3 mL of methylene chloride and 2 mL of N,N-dimethylformamide and cooled on an ice-water bath. Sodium triacetoxyborohydride (349 mg, 1.65 mmol) was added in portions. The resultant suspension was warmed to room temperature, stirred overnight, and partitioned between water and ethyl acetate. The combined organic layers were dried over sodium sulfate, filtered, concentrated in vacuo and purified by flash silica gel column chromatography eluting with 3% methanol in methylene chloride to give 115 mg (66% yield) of product as a white solid, mp 208–2101° C.;

$^1$H NMR (DMSO-d$_6$) δ 2.35–2.45 (m, 4H), 3.50 (s, 2H), 3.55–3.65 (m, 4H), 3.77 (s, 3H), 3.86 (s, 3H), 6.10 (s, 1H), 6.39 (s, 1H), 7.40 (s, 1H), 7.70–7.85 (m, 2H), 7.90 (s, 2H), 8.52–8.65 (m, 9H), 9.97 (s, 1H); MS (ES) m/z 522.1 (M+1). Analysis for C$_{27}$H$_{25}$Cl$_2$N$_5$O$_2$-0.3CH$_2$Cl$_2$: Calcd: C, 59.84; H, 4.70; N, 12.78. Found: C, 59.84; H, 4.66; N, 12.53.

EXAMPLE 71

4-(2,4-Dichloro-5-methoxyanilino)-7-{1-methyl-5-[(4-methyl-1-piperazinyl)methyl]-1H-pyrrol-2-yl}-3-quinolinecarbonitrile Using an analogous procedure to that described for Example 70, 4-(2,4-dichloro-5-methoxyanilino)-7-{1-methyl-5-[(4-methyl-1-piperazinyl)methyl]-1H-pyrrol-2- yl}-3-quinolinecarbonitrile was prepared from 4-(2,4-dichloro-5-methoxyanilino)-7-(5-formyl-1-methyl-1H-pyrrol-2-yl)-3-quinolinecarbonitrile (Example 69) and N-methyl piperazine in 71% yield as a white solid, mp 200° C. (dec);

$^1$H NMR (DMSO-d$_6$) δ 2.20 (s, 3H), 2.30–2.60 (m, 8H), 3.50 (s, 2H), 3.74 (s, 3H), 3.86 (s, 3H), 6.08 (d, J=4 Hz, 1H), 6.37 (s, 1H), 7.35–7.90 (m, 4H), 8.40–8.60 (m, 2H), 9.98 (s, 1H); MS (ES) m/z 535.1 (M+1). Analysis for C$_{28}$H$_{28}$Cl$_2$N$_6$O-0.8CH$_2$Cl$_2$: Calcd: C, 57.32; H, 4.93; N, 13.93. Found: C, 57.23; H, 4.78; N, 14.11.

EXAMPLE 72

4-(2,4-Dichloro-5-methoxyanilino)-7-[1-methyl-5-({[2-(phenylsulfonyl)ethyl]amino}methyl)-1H-pyrrol-2-yl]-3-quinolinecarbonitrile Using an analogous procedure to that described for Example 70, 4-(2,4-dichloro-5-methoxyanilino)-7-[1-methyl-5-({[2-(phenylsulfonyl)ethyl]amino}methyl)-1H-pyrrol-2-yl]-3-quinolinecarbonitrile was prepared from 4-(2,4-dichloro-5-methoxyanilino)-7-(5-formyl-1-methyl-1H-pyrrol-2-yl)-3-quinolinecarbonitrile (Example 69) and 2-(phenylsulfonyl)ethylamine (Reference Example 49) in 60% yield as a white solid, mp 178–1 80° C.;

$^1$H NMR (DMSO-d$_6$) δ 2.83 (t, J=7 Hz, 2H), 3.47 (t, J=7 Hz, 2H), 3.66 (s, 3H), 3.69 (s, 2), 3.86 (s, 3H), 6.00 (d, J=4 Hz, 1H), 6.33 (s, 1H), 7.32 (s, 1H), 7.58–7.82 (m, 7H), 7.90 (d, J=5 Hz, 2H), 8.45–8.60 (m, 2H), 10.00 (s, 1H); MS m/z 620.0 (M+1). Analysis for C$_{31}$H$_{27}$Cl$_2$N$_5$O$_3$S-0.2H$_2$O: Calcd: C, 59.65; H, 4.41; N, 11.22. Found: C, 59.45; H, 4.18; N, 1.13.

EXAMPLE 73

4-(2,4-Dichloro-5-methoxyanilino)-7-1-methyl-5-({[2-(methylsulfonyl)ethyl]amino}methyl)-1H-pyrrol-2]-3-quinolinecarbonitrile Using an analogous procedure to that described for Example 70, 4-(2,4-dichloro-5-methoxyanilino)-7-[1-methyl-5-({[2-(methylsulfonyl)ethyl]amino}-methyl)-1H-pyrrol-2-yl]-3-quinolinecarbonitrile was prepared from 4-(2,4-dichloro-5-methoxyanilino)-7-(5-formyl-1-methyl-1H-pyrrol-2-yl)-3-quinolinecarbonitrile (Example 69) and 2-(methylsulfonyl)ethylamine (Reference Example 72) in 38% yield as a white solid, mp 160–164° C.;

$^1$H NMR (DMSO-d$_6$) δ 2.99 (t, J=7 Hz, 2H), 3.02 (s, 3H), 3.28 (t, J=7 Hz, 2H), 3.73 (s, 3H), 3.78 (s, 2H), 3.86 (s, 3H), 6.12 (d, J=3 Hz, 1H), 6.39 (s, 1H), 7.30–7.55 (m, 2H), 7.70–8.00 (m, 3H), 8.45–8.70 (m, 2H), 9.97 (s, 1H); MS (ES) m/z 558.0 (M+1). Analysis for C$_{26}$H$_{25}$Cl$_2$N$_5$O$_3$S-0.15CH$_2$C$_2$: Calcd: C, 54.98; H, 4.45; N, 12.26. Found: C, 54.99; H, 4.40; N, 11.90.

EXAMPLE 74

4-(2,4-Dichloro-5-methoxyanilino)-7-[5-({[2-(2-pyridinyl)ethyl]amino}methyl)-2-furyl]-3-quinolinecarbonitrile 2-(2-Aminoethyl)pyridine (0.065 mL, 0.54 mmol) was added to a suspension of 4-(2,4-dichloro-5-methoxyanilino)-7-(5-formyl-2-furyl)-3-quinolinecarbonitrile (Example 6) (200 mg, 0.45 mmol) in 5 mL of methylene chloride at room temperature. Sodium triacetoxyborohydride (480 mg, 2.25 mmol) was added followed by a drop of acetic acid. The reaction mixture was stirred at room temperature overnight to give a yellow solution. The reaction was quenched by the addition of water and then partitioned between saturated sodium bicarbonate and ethyl acetate. The organic layer was dried over sodium sulfate, filtered and concentrated in vacuo. The residue was purified by flash silica gel column chromatography eluting with 10% methanol in methylene chloride to provide 55 mg of 4-(2,4-dichloro-5-methoxyanilino)-7-[5-({[2-(2-pyridinyl)ethyl]amino}methyl)-2-furyl]-3-quinolinecarbonitrile (23% yield) as a yellow solid, mp 130–135° C.;

$^1$H NMR (DMSO-d$_6$/trifluoroacetic acid) δ 3.45–3.60 (m, 4H), 6.94 (d, J=4 Hz, 1H), 7.52 (d, J=4 Hz, 1H), 7.62 (s, 1H), 7.89 (s, 1H), 7.99 (t, J=7 Hz, 1H), 8.04 (d, J=8 Hz, 1H), 8.28 (s, 1H), 8.35 (d, J=9 Hz, 1H), 8.56 (t, J=7 Hz, 1H), 8.87 (d, J=9 Hz, 1H), 8.94 (d, J=5 Hz, 1H), 9.30 (s, 1H); HRMS (ES) m/z 544.12947 (M+1).

EXAMPLE 75

4-(2,4-Dichloro-5-methoxyanilino)-7-(5-{[4-(2-hydroxyethyl)-1-piperazinyl]methyl}-2-furyl)-3-quinolinecarbonitrile N-Hydroxyethylpiperazine (0.072 mL, 0.55 mmol) was added to a suspension of 4-(2,4-dichloro-5-methoxyanilino)-7-(5-formyl-2-furyl)-3-quinolinecarbonitrile (Example 6) (200 mg, 0.45 mmol) in 3 mL of methylene chloride at room temperature. Sodium triacetoxyborohydride (480 mg, 2.25 mmol) was added followed by a drop of acetic acid. The reaction mixture was stirred at room temperature overnight to give a yellow solution. The reaction was quenched by the addition of water and then partitioned between saturated sodium bicarbonate and ethyl acetate. The organic layer was dried over sodium sulfate, filtered and concentrated in vacuo. The residue was purified by flash column chromatography eluting with 10% methanol in methylene chloride to provide 50 mg of 4-(2,4-dichloro-5-methoxyanilino)-7-(5-{[4-(2-hydroxyethyl)-1-piperazinyl]methyl}-2-furyl)-3-quinolinecarbonitrile (20% yield) as a light yellow solid, mp 176–181° C.; MS (ES) m/z 552.1, 554.1 (M+1). Analysis for C$_{28}$H$_{27}$Cl$_2$N$_5$O$_3$-1.6H$_2$O: Calcd: C, 57.85: H, 5.24; N, 12.05. Found: C, 58.07; H, 5.01; N, 11.67.

EXAMPLE 76

7-(5-{[bis(2-Hydroxyethyl)amino]methyl}-2-furyl)-4-(2,4-dichloro-5-methoxyanilino)-3-quinolinecarbonitrile Bis(2-hydroxyethyl)amine (0.052 mL, 0.55 mmol) was added to a suspension of 4-(2,4-dichloro-5-methoxyanilino)-7-(5-formyl-2-furyl)-3-quinolinecarbonitrile (Example 6) (200 mg, 0.45 mmol) in 5 mL of methylene chloride at room temperature. Sodium triacetoxyborohydride (480 mg, 2.25 mmol) was added followed by a drop of acetic acid. The reaction mixture was stirred at room temperature for 2 days. The reaction was quenched by the addition of water and then partitioned between saturated sodium bicarbonate and ethyl acetate. The organic layer was dried over sodium sulfate, filtered and concentrated in vacuo. The residue was purified by preparative thin layer chromatography with a developing solvent of 5% methanol in methylene chloride to provide 20 mg of 7-(5-{[bis(2-hydroxyethyl)amino]methyl}-2-furyl)-4-(2,4-dichloro-5-methoxyanilino)-3-quinolinecarbonitrile (8% yield) as a yellow solid, mp 155–160° C.; MS (ES) m/z 527.1, 529.1 (M+1). Analysis for $C_{26}H_{24}Cl_2N_4O_4 \cdot 1.5H_2O$: Calcd: C, 56.32: H, 4.91; N, 10.10. Found: C, 56.43; H, 4.70; N, 9.78.

EXAMPLE 77

4-(2,4-Dichloro-5-methoxyanilino)-7-[5-({[2-(methylsulfonyl)ethyl]amino}methyl)-2-furyl]-3-quinolinecarbonitrile The hydrochloride salt of 2-(methylsulfonyl)ethyl amine (Reference Example 72) (0.085 mg, 0.55 mmol) was added to a suspension of 4-(2,4-dichloro-5-methoxyanilino)-7-(5-formyl-2-furyl)-3-quinolinecarbonitrile (Example 6) (200 mg, 0.45 mmol) in 3 mL of methylene chloride and 1 mL of N,N-dimethylformamide. The mixture was cooled to 0° C. and sodium triacetoxyborohydride (480 mg, 2.25 mmol) was added followed by a drop of acetic acid. The reaction mixture was allowed to warm to room temperature and stirred for 2 hours to give a yellow solution. The reaction was quenched by the addition of water then partitioned between saturated sodium bicarbonate and ethyl acetate. The organic layer was dried over sodium sulfate, filtered and concentrated in vacuo. The residue was purified by preparative thin layer chromatography with a developing solvent of 5% methanol in methylene chloride to provide 50 mg of 4-(2,4-dichloro-5-methoxyanilino)-7-[5-({[2-(methylsulfonyl)ethyl]amino}methyl)-2-furyl]-3-quinolinecarbonitrile (20% yield) as an off-white solid, mp 171–174° C.;

MS (ES) m/z 545.1, 547.1 (M+1). Analysis for $C_{25}H_{22}Cl_2N_4O_4S$: Calcd: C, 55.05: H, 4.07; N, 10.27. Found: C, 54.87; H, 3.98; N, 9.94.

EXAMPLE 78

4-(2,4-Dichloro-5-methoxyanilino)-7-[5-(1-piperidinylmethyl)-2-thienyl]-3-quinolinecarbonitrile Piperidine (0.047 mL, 0.44 mmol) was added to a suspension of 4-(2,4-dichloro-5-methoxyanilino)-7-(5-formyl-2-thienyl)-3-quinolinecarbonitrile (Example 6) (200 mg, 0.44 mmol) in 2 mL of methylene chloride and 1 mL of N,N-dimethylformamide. The mixture was cooled to 0° C. and sodium triacetoxyborohydride (480 mg, 2.25 mmol) was added followed by a drop of acetic acid. The reaction mixture was allowed to warm to room temperature and stirred for 18 hours to give a yellow solution. The reaction was quenched by the addition of water then partitioned between saturated sodium bicarbonate and ethyl acetate. The organic layer was dried over sodium sulfate, filtered and concentrated in vacuo. The residue was purified by preparative thin layer chromatography with a developing solvent of 5% methanol in methylene chloride to provide 110 mg of 4-(2,4-dichloro-5-methoxyanilino)-7-[5-(1-piperidinylmethyl)-2-thienyl]-3-quinolinecarbonitrile (52% yield) as an off-white solid, mp 155–160° C.;

MS (ES) m/z 523.1, 525.1 (M+1). Analysis for $C_{27}H_{24}Cl_2N_4OS$: Calcd; C, 61.95; H, 4.62; N, 10.70. Found: C, 61.65; H, 3.59; N, 10.48.

EXAMPLE 79

4-{2-chloro-4-fluoro-5-methoxyanilino)-7-[5-(4-morpholinylmethyl}-3-thienyl]-3-quinolinecarbonitrile By the procedure of Example 26, 310 mg (0.76 mmol) of 7-bromo-4-(2-chloro-4-fluoro-5-methoxyanilino)-3-quinolinecarbonitrile (Reference Example 74) was reacted with 470 mg of crude 4-{[4-(4,4,5,5-tetramethyl-1,3,2-dioxaborolan-2-yl)-2-thienyl]methyl}morpholine and 30 mg (0.02 mmol) of tetrakis(triphenylphosphine)palladium (0) in 8 mL of ethylene glycol dimethyl ether and 3.2 mL of saturated aqueous sodium bicarbonate to provide 262 mg of 4-{2-chloro-4-fluoro-5-methoxyanilino)-7-[5-(4-morpholinylmethyl)-3-quinolinecarbonitrile as a white solid after purification 185–187° C.;

$^1$H NMR (DMSO-$d_6$) δ 9.93 (s, 1H), 8.57 (s, 1H), 8.54 (s, 1H), 8.22 (s, 1H), 8.16 (s, 1H), 8.06 (d, J=9 Hz, 1), 7.66 (m, 2H), 7.47 (d, J=9 Hz, 1H), 3.86 (s, 3H), 3.75 (s, 2H), 3.60 (t, J=4 Hz, 4H), 2.47 (t, J=4 Hz, 4H); MS (ES) m/z 509.0, 511.0 (M+1). Analysis for $C_{26}H_{22}ClFN_4O_2S$: Calcd: C, 61.35; H, 4.36; N, 11.01. Found: C, 60.96; H, 4.13; N, 10.69.

EXAMPLE 80

4-{2-Chloro-5-methoxy-4-methylanilino)-7-[5-(4-morpholinylmethyl)-3-thienyl}-3-quinolinecarbonitrile By the procedure of Example 26, 100 mg (0.25 mmol) of 7-bromo-4-(2-chloro-5-methoxy-4-methylanilino)-3-quinolinecarbonitrile (Reference Example 75) was reacted with 155 mg of crude 4-{[4-(4,4,5,5-tetramethyl-1,3,2-dioxaborolan-2-yl)-2-thienyl]methyl}morpholine and 20 mg (0.017 mmol) of tetrakis(triphenylphosphine)palladium (0) in 3 mL of ethylene glycol dimethyl ether and 1.1 mL of saturated aqueous sodium bicarbonate to provide 108 mg of 4-(2-chloro-5-methoxy-4-methylanilino)-7-[5-(4-morpholinylmethyl)-3-thienyl]-3-quinolinecarbonitrile as a white solid after purification, mp) 168–170° C.;

$^1$H NMR (DMSO-$d_6$) δ 9.9 (s, 1H), 8.56 (d, J=9 Hz, 1H), 8.52 (s, 1H), 8.19 (s, 1H), 8.16 (s, 1H), 8.04 (d, J=9 Hz, 1H), 7.67 (s, 1H), 7.38 (s, 1H), 7.14 (s, 1H, 3.80 (s, 3H), 3.75 (s, 2H), 3.60 (t, J=4 Hz, 4H), 2.47 (t, J=4 Hz, 4H), 2.21 (s, 3H); MS (ES) m/z 505.1, 507.1 (M+1). Analysis for $C_{27}H_{25}ClN_4O_2S \cdot 0.3H_2O$: Calcd: C, 63.53; H, 5.06; N, 10.98. Found: C, 63.42; H, 4.81; N, 10.60.

EXAMPLE 81

4-(2,4-Dichloro-5-methoxyanilino)-7-[6-(4-morpholinylmethyl)-3-pyridinyl]-3-quinolinecarbonitrile A mixture of 6-(4-morpholinylmethyl)-3-pyridinyl trifluoromethanesulfonate (65 mg, 0.20 mmol), 7-bromo-4-(2,4-dichloro-5-methoxyanilino)-3-quinolinecarbonitrile (85 mg, 0.20 mmol), tetrakis(triphenylphosphine)palladium(0) (22 mg, 0.02 mmol), anhydrous lithium chloride (25 mg, 0.60 mmol), and hexamethylditin (65 mg, 0.20 mmol) in 2 mL of 1,4-dioxane was heated at reflux for 16 hours. The mixture was cooled to room temperature, and partitioned between ethyl acetate and 10% sodium carbonate solution. The layers were separated and the organic layer was washed with brine, and dried over magnesium sulfate. Removal of the solvent in vacuo gave a residue which was purified by silica gel chromatography eluting with a gradient of ethyl acetate to 10% methanol in ethyl acetate to provide 28 mg (27% yield) of 4-(2,4-dichloro-5-methoxyanilino)-7-[6-(4-morpholinylmethyl)-3-pyridinyl]-3-quinolinecarbonitrile as a yellow solid, mp 195–197° C.; $^1$H NMR (DMSO-$d_6$/TFA) δ 3.39 (m, 4H), 3.93 (m, 7H), 4.68 (s, 2H), 7.64 (s, 1H), 7.81 (d, J=8 Hz, 1H), 7.90 (s, 1H), 8.42 (s, 1H), 8.43 (d, J=8 Hz, 1H), 8.49 (dd, J=8, 2 Hz, 1H), 8.96 (d, J=9 Hz, 1H), 9.24 (d, J=2 Hz, 1H), 9.37 (s, 1H); MS (ES) m/z 520.0 (M+1).

Analysis for $C_{27}H_{23}Cl_2N_5O_2$: Calcd: C, 62.31; H, 4.45; N, 13.46. Found: C, 62.02; H, 4.14; N, 13.16.

EXAMPLE 82

7-[4,5-bis(4-Morpholinylmethyl)-2-thienyl]-4-(2,4-dichloro-5-methoxyanilino)-6-methoxy-3-quinolinecarbonitrile 4-{[2-(4-Morpholinylmethyl)-3-thienyl]methyl}morpholine (Reference Example 24) (0.50 g, 1.77 mmol) was dissolved in 5 mL of anhydrous tetrahydrofuran and the mixture was cooled to −78° C. n-Butyl lithium (2.5M in hexanes) (2.12 mL, 5.31 mmol) was added dropwise to the reaction mixture and stirring was continued for 30 minutes. The cooling bath was removed and the mixture stirred at room temperature for 20 minutes. The reaction was then cooled to −78° C. and tributyltin chloride (1.5 mL, 5.31 mmol) was added. Stirring was continued for 15 minutes at −78° C., and then at room temperature overnight. The reaction was quenched with water and the product extracted into ethyl acetate. The organic layer was collected, dried over sodium sulfate and purified by flash column chromatography eluting with 5% methanol in methylene chloride to provide 859 mg of a yellow oil.

This oil was combined with 3-cyano-4-(2,4-dichloro-5-methoxyanilino)-6-methoxy-7-quinolinyl trifluoromethanesulfonate (Reference Example 22) (652 mg, 1.25 mmol) and dichlorobis(triphenylphosphine)palladium(II) (150 mg, 0.15 mmol) in 10 mL of dioxane and the mixture was heated at reflux for 6 hours. The reaction was cooled to room temperature and concentrated in vacuo. The residue was purified by flash column chromatography eluting with a gradient of 2% methanol in methylene chloride to 8% methanol in methylene chloride, followed by 5% methanol in ethyl acetate as an eluent to provide 300 mg (36%) of 7-[4,5-bis(4-morpholinylmethyl)-2-thienyl]-4-(2,4-dichloro-5-methoxyanilino)-6-methoxy-3-quinolinecarbonitrile as a yellow solid, mp 120–124° C.;

$^1$H NMR (DMSO-$d_6$) δ 2.47 (br s, 8H), 3.49 (s, 2H), 3.50 (br m, 8H), 3.77 (s, 2H), 3.87 (s, 3H), 4.04 (s, 3H), 7.39 (s, 1H), 7.68 (s, 1H), 7.77 (s, 1H), 7.98 (s, 1H), 8.16 (s, 1H), 8.46 (s, 1H), 9.82 (s, 1H); MS (ES) m/z 654.0 (M+1). Analysis for $C_{32}H_{33}Cl_2N_5O_4S$-0.4$H_2O$+0.2$C_4H_8O_2$: Calcd: C, 56.91; H, 5.20; N, 10.30. Found: C, 57.20; H, 5.10; N, 9.91.

EXAMPLE 83

4-(2,4-Dichloro-5-methoxyanilino)-7-(4-formylphenyl)-3-quinolinecarbonitrile

7-Bromo-4-(2,4-dichloro-5-methoxyanilino)-3-quinolinecarbonitrile (Reference Example 8) (3.00 g, 7.1 mmol) and 4-formylphenyl boronic acid (1.27 g, 8.5 mmol) were suspended in a mixture of ethylene glycol dimethyl ether (20 mL) and a saturated aqueous solution of sodium bicarbonate (20 mL). Tetrakis(triphenylphosphine)palladium(0) (0.30 g, 0.25 mmol) was added and the reaction mixture was heated to 80° C. The reaction was stirred at 80° C. for 4 hours and then cooled to room temperature. The reaction was partitioned between ethyl acetate and saturated sodium bicarbonate. The solid that precipitated was collected by filtration, washed with ethyl acetate, methylene chloride and then water to yield 3.00 g (94%) of 4-(2,4-dichloro-5-methoxyanilino)-7-(4-formylphenyl)-3-quinolinecarbonitrile as a yellow solid, mp 248–251° C.;

$^1$H NMR (DMSO-$d_6$) δ 3.87 (s, 3H), 7.43 (s, 1H), 7.78 (s, 1H), 7.99 (s, 1H), 8.09 (s, 1H), 8.16 (m, 3H), 8.32 (s, 1H), 8.67 (t, J=9 Hz, 2H), 10.10 (s, 1H), 10.11 (s, 1H); MS (ES) m/z 450.0 (M+1). Analysis for $C_{24}H_{15}Cl_2N_3O_2$-0.5$CH_2Cl_2$: Calcd: C, 56.91; H, 5.20; N, 10.30. Found: C, 57.20; H, 5.10; N, 9.91.

EXAMPLE 84

(2R)-1-{4-[3-Cyano-4-(2,4-dichloro-5-methoxyanilino)-7-quinolinyl]benzyl}-2-pyrrolidinecarboxamide L-Prolineamide (71.5 mg, 0.6 mmol) was added to a suspension of 4-(2,4-dichloro-5-methoxyanilino)-7-(4-formylphenyl)-3-quinolinecarbonitrile (Example 83) (200 mg, 0.42 mmol) in 5 mL of methylene chloride and 1 mL of N,N-dimethylformamide at room temperature. The reaction was cooled to 0° C. and sodium triacetoxyborohydride (500 mg, 2.36 mmol) was added followed by a drop of acetic acid. The reaction mixture was stirred at 0° C. for 30 minutes and then at room temperature for 3 hours to give a yellow solution. The reaction was quenched by the addition of water and partitioned between saturated sodium bicarbonate and ethyl acetate. The organic layer was dried over sodium sulfate, filtered and concentrated in vacuo. The residue was purified by flash column chromatography eluting with 10% methanol in methylene chloride to provide 159 mg (69%) of (2R)1-{4-[3-cyano-4-(2,4-dichloro-5-methoxyanilino)-7-quinolinyl]benzyl}-2-pyrrolidinecarboxamide as an off-white solid, mp 180–182° C.;

MS (ES) m/z 548.0 (M+1). Analysis for $C_{29}H_{25}Cl_2N_5O_2$-0.9$H_2O$: Calcd: C, 61.84; H, 4.80; N, 12.42. Found: C, 61.86; H, 4.41; N, 12.29.

EXAMPLE 85

4-(2,4-Dichloro-5-methoxyanilino)-7-[4-({[2-(phenylsulfonyl)ethyl]amino}methyl)phenyl]-3-quinolinecarbonitrile 2-(Phenylsulfonlyl)ethanamine (Reference Example 49) (116.1 mg, 0.63 mmol) was added to a suspension of 4-(2,4-dichloro-5-methoxyanilino)-7-(4-formylphenyl)-3-quinolinecarbonitrile (Example 83) (200 mg, 0.42 mmol) in 5 mL of methylene chloride and 1 mL of N,N-dimethylformamide at room temperature. The reaction was cooled to 0° C. and sodium triacetoxyborohydride (500 mg, 2.36 mmol) was added followed by a drop of acetic acid. The reaction mixture was stirred at 0° C. for 30 minutes and then at room temperature for 3 hours to give a yellow solution. The reaction was quenched by the addition of water and then partitioned between saturated sodium bicarbonate and ethyl acetate. The organic layer was dried over sodium sulfate, filtered and concentrated in vacuo. The residue was purified by flash column chromatography eluting with 10% methanol in methylene chloride to provide 159 mg (61%) of 4-(2,4-dichloro-5-methoxyanilino)-7-[4-({[2-(phenylsulfonyl)ethyl]amino}methyl)phenyl]-3-quinolinecarbonitrile as an off-white solid, mp 198–201° C.;

MS (ES) m/z 309.0 $(M+2)^{+2}$. Analysis for $C_{32}H_{26}Cl_2N_4O_3S$-0.8$H_2O$: Calcd: C, 60.82; H, 4.41; N, 8.55. Found: C, 60.83; H, 4.27; N, 8.74.

EXAMPLE 86

4-(2,4-Dichloro-5-methoxyanilino)-7-{4-[(dimethylamino)methyl]phenyl}-3-quinolinecarbonitrile Dimethylamine (2M solution in tetrahydrofuran) (0.31 mL, 0.63 mmol) was added to a suspension of 4-(2,4-dichloro-5-methoxyanilino)-7-(4-formylphenyl)-3- quinolinecarbonitrile (Example 83) (200 mg, 0.42 mmol) in 5 mL of methylene chloride and 1 mL of N,N-dimethylformamide it room temperature. The reaction was cooled to 0° C. and sodium triacetoxyborohydride (500 mg, 2.36 mmol) was added followed by a drop of acetic acid. The reaction mixture was stirred at 0° C. for 30 minutes and then at room temperature for 2 hours to give a yellow solution. The reaction was quenched by the addition of water and partitioned between saturated sodium bicarbonate and ethyl acetate. The organic layer was dried over sodium sulfate, filtered and concentrated in vacuo. The residue was purified by flash column chromatography eluting with 15% methanol in methylene chloride to provide 123 mg (62%) of 4-(2,4-dichloro-5-methoxyanilino)-7-{4-[(dimethylamino)methyl]phenyl}-3-quinolinecarbonitrile as an off-white solid, mp 187–189° C.;

$^1$NMR (DMSO-d$_6$) δ 2.20 (s, 6H), 3.48 (s, 2H), 3.86 (s, 3H), 7.45 (m, 3H), 7.70 (s, 1H), 7.85 (d, J=8 Hz, 2H), 8.0 (s, 1H), 8.11 (s, 1H), 8.54 (s, 1H); 10.11 (br s, 1H); MS (ES) m/z 478.0 (M+1). Analysis for $C_{26}H_{22}Cl_2N_4O$-0.1$H_2O$: Calcd: C, 65.16; H, 4.68; N, 11.69. Found: C, 64.95; H, 4.53; N, 11.61.

EXAMPLE 87

4-(2,4-Dichloro-5-methoxyanilino)-7-{4-[(diethylamino)methyl]phenyl}-3-quinolinecarbonitrile Diethylamine (0.065 mL, 0.9 mmol) was added to a suspension of 4-(2,4-dichloro-5-methoxyanilino)-7-(4-formylphenyl)-3-quinolinecarbonitrile (Example 83) (200 mg, 0.42 mmol) in 5 mL of methylene chloride and 1 mL of N,N-dimethylformamide at room temperature. The reaction was cooled to 0° C. and sodium triacetoxyborohydride (500 mg, 2.36 mmol) was added followed by a drop of acetic acid. The reaction mixture was stirred it 0° C. for 30 minutes and then at room temperature for 3 hours to give a yellow solution. The reaction was quenched by the addition of water and partitioned between saturated sodium bicarbonate and ethyl acetate. The organic layer was dried over sodium sulfate, filtered and concentrated in vacuo. The residue was purified by flash column chromatography elulting with 15% methanol in methylene chloride to provide 117 mg (55%) of 4-(2,4-dichloro-5-methoxyanilino)-7-{4-[(diethylamino)methyl]phenyl}-3-quinolinecarbonitrile as an off-white solid, mp 191–195° C.;

$^1$H NMR (DMSO-d$_6$) δ 1.00 (t, J=7 Hz, 6H) 2.48 (m, 4H), 3.62 (s, 2H), 3.86 (s, 3H), 7.50 (m, 3H), 7.71 (s, 1H), 7.85 (d, J=8 Hz, 2H), 7.99 (s, 1H), 8.12 (s, 1H), 8.55 (s, 1H), 10.04 (br s, 1H); MS (ES) m/z 506.0 (M+1). Analysis for $C_{28}H_{26}Cl_2N_4O$-0.77$H_2O$: Calcd: C, 64.74; H, 5.34; N, 10.79. Found: C, 64.74; H, 4.97; No 10.74.

EXAMPLE 88

4-(2,4-Dichloro-5-methoxyanilino)-7-[4-({[2-(methylsulfonyl)ethyl]amino}methyl)phenyl]-3-quinolinecarbonitrile 2-(Methylsulfonyl)ethylamine hydrochloride salt (Reference Example 72) (77.2 mg, 0.63 mmol) was added to a suspension of 4-(2,4-dichloro-5-methoxyanilino)-7-(4-formylphenyl)-3-quinolinecarbonitrile (Example 83) (200 mg, 0.42 mmol) in 5 mL of methylene chloride and 1 mL of N,N-dimethylformamide at room temperature. The reaction was cooled to 0° C. and sodium triacetoxyborohydride (500 mg, 2.36 mmol) was added followed by a drop of acetic acid. The reaction mixture was stirred at 0° C. for 30 minutes and then at room temperature overnight. The reaction was quenched by the addition of water and partitioned between saturated sodium bicarbonate and ethyl acetate. The organic layer was dried over sodium sulfate, filtered and concentrated in vacuo. The residue was purified by flash column chromatography eluting with 10% methanol in methylene chloride to provide 89 mg (38%) of 4-(2,4-dichloro-5-methoxyanilino)-7-[4-({[2-(methylsulfonyl)ethyl]amino}methyl)phenyl]-3-quinolinecarbonitrile as an off-white solid, mp 245–246° C.;

MS (ES) m/z 556.0 (M+1). Analysis for $C_{27}H_{24}Cl_2N_4O_3S$-0.8$H_2O$: Calcd: C, 56.89; H, 4.54; N, 9.82. Found: C, 56.87; H, 4.17; N, 9.75.

EXAMPLE 89

4-(2,4-Dichloro-5-methoxyanilino)-7-{5-[(4-hydroxy-1-piperidinyl)methyl]-2-thienyl}-3-quinolinecarbonitrile 4-Hydroxypiperidine (65 mg, 0.57 mmol) was added to a suspension of 4-(2,4-dichloro-5-methoxyanilino)-7-(5-formyl-2-thienyl)-3-quinolinecarbonitrile (Example 52) (200 mg, 0.44 mmol) in 4 mL of methylene chloride and 1 mL of N,N-dimethylformamide. The mixture was cooled to 0° C. and sodium triacetoxyborohydride (470 mg, 2.20 mmol) was added followed by a drop of acetic acid. The reaction mixture was allowed to warm to room temperature and stirred at room temperature for 18 hours to give a yellow solution. The reaction was quenched by the addition of water and partitioned between saturated sodium bicarbonate and ethyl acetate. The organic layer was dried over sodium sulfate, filtered and concentrated in vacuo. The residue was purified by preparative thin layer chromatography with a developing solvent of 5% methanol in methylene chloride to provide 70 mg of 4-(2,4-dichloro-5-methoxyanilino)-7-{5-[(4-hydroxy-1-piperidinyl)methyl]-2-thienyl}-3-quinolinecarbonitrile (30% yield) as an off-white solid, mp 120–123° C.; HRMS (ES): m/z 539.10639 (m+1).

EXAMPLE 90

4-(2,4-Dichloro-5-methoxyanilino)-7-[2-(4-methoxyphenyl)ethynyl]-3-quinolinecarbonitrile 7-Bromo-4-(2,4-dichloro-5-methoxyanilino)-3-quinolinecarbonitrile (Reference Example 8) (250 mg, 0.59 mmol), 1-ethynyl-4-methoxybenzene (0.23 mL, 1.77 mmol), copper iodide (20 mg, 0.11 mmol) and tetrakis (triphenylphosphine)palladium (21 mg, 0.018 mmol) were heated at reflux in 0.5 mL of triethylamine and 4 mL of N,N-dimethylformamide for 10 hours. The mixture was diluted with ethyl acetate and washed with brine. The organic layer was dried over sodium sulfate and concentrated in vacuo. The residue was purified by preparative thin layer chromatography with a developing solvent of 1:1 ethyl acetate and hexane to give 110 mg of 4-(2,4-dichloro-5-methoxyanilino)-7-[2-(4-methoxyphenyl)ethynyl]-3-quinolinecarbonitrile (39%) yield) as a yellow solid, mp 225–226° C.;

$^1$H NMR (DMSO-d$_6$) δ 3.85 (s, 3H), 3.91 (s, 3H), 7.07 (d, J=9 Hz, 2H), 7.62 (s, 1H), 7.65 (d, J=9 Hz, 2H), 7.89 (s, 1H), 8.07 (dd, J=9, 2 Hz, 1H), 8.10 (d, J=2 Hz, 1H), 8.83 (d, J=9 Hz, 1H), 9.33 (s, 1H); MS (ES) m/z 474.0, 476.0 (M+1). Analysis for $C_{26}H_{17}Cl_2N_3O_2$: Calcd; C, 65.84; H, 3.61; N, 8.86. Found: C, 65.58; H, 3.66; N, 8.61.

EXAMPLE 91

4-(2,4-Dichloro-5-methoxyanilino)-7-[2-(2-pyridinyl)ethynyl]-3-quinolinecarbonitrile 7-Bromo-4-(2,4-dichloro-5-methoxyanilino)-3-quinolinecarbonitrile (Reference Example 8) (250 mg, 0.59 mmol), 2-ethynylpyridine (0.18 mL, 1.77 mmol), copper iodide (20 mg, 0.11 mmol) and tetrakis(triphenylphosphine) palladium (21 mg, 0.018 mmol) were heated at reflux in 0.5 mL of triethylamine and 4 mL of N,N-dimethylformamide for 5 hours. The mixture was diluted with ethyl acetate and washed with brine. The organic layer was dried over sodium sulfate and concentrated in vacuo. The residue was purified by preparative thin layer chromatography with a developing solvent of 5% methanol in methylene chloride to give 110 mg of 4-(2,4-dichloro-5-methoxyanilino)-7-[2-(2-pyridinyl) ethynyl]-3-quinolinecarbonitrile (42% yield) as a yellow solid, mp 238–240° C.;

$^1$H NMR (DMSO-d$_6$/trifluoroacetic acid) δ 3.94 (s, 3H), 7.60 (s, 1H), 7.80–7.87 (m, 2H), 8.09 (d, J=8 Hz, 1H), 8.15 (dd, J=9, 2 Hz, 1H), 8.30–8.35 (m, 2H), 8.90 (d, J=5 Hz, 1H), 8.96 (d, J=9 Hz, 1H), 9.39 (s, 1H); MS (ES) m/z 445.1 (M+1). Analysis for $C_{24}H_{14}Cl_2N_4O$-1.5$H_2O$: Calcd; C, 61.02: H, 3.63; N, 11.86. Found: C, 60.97; H, 3.27; N, 11.98.

EXAMPLE 92

4-(2,4-Dichloro-5-methoxyanilino)-7-pyrrol-1-yl-3-quinolinecarbonitrile

An amount of 150 mg (0.42 mmol) of 7-amino-4-(2,4-dichloro-5-methoxyanilino)-3-quinolinecarbonitrile (Reference Example 81) was stirred in N,N-dimethylformamide (3.5 mL), and to this were added 2,5-dimethoxytetrahydrofuran (83 mg, 0.63 mmol), and 4-chloropyridine hydrochloride (41 mg, 0.27 mmol). The reaction mixture was heated at 80° C. for 2 hours, and subsequently evaporated to a brown oil, basified with saturated sodium bicarbonate solution, and extracted with ethyl acetate. The organic phase was washed with brine, dried over sodium sulfate and evaporated. The yellow oily residue was purified by preparative thin layer chromatography (40:4:1=ethyl acetate:methanol:triethylamine), to give a yellow solid (84 mg, 49% yield; contains 17% 5-pyrrole-isomer), mp 205–207° C.;

$^1$H NMR (DMSO-d$_6$) δ 9.95 (s, 1H), 8.62 (d, J=9 Hz, 1H), 8.59 (s, 1H), 8.10 (d, J=2 Hz, 1H), 8.04 (dd, J=9, 2 Hz, 1H), 7.77 (s, 1H), 7.71 (t, J=2 Hz, 2H), 7.43 (s, 1H), 6.37 (t, J=2 Hz, 2H), 3.87 (s, 3H); MS (ES) m/z 409.1 (M+1); HRMS (EI) 409.06058 (M+1). Analysis for $C_{21}H_{14}Cl_2N_4O$.2$H_2O$: Calcd: C, 56.59; H, 4.04; N, 12.58. Found: C, 56.39; H, 4.01; N, 12.30.

EXAMPLE 93

4-(2,4-Dichloro-5-methoxyanilino)-7-{(2-[(dimethlylamino)methyl]-1H-pyrrol-1-yl}-3-quinolinecarbonitrile An amount of 400 mg (0.98 mmol) of 4-(2,4-dichloro-5-methoxyanilino)-7-pyrrol-1-yl-3-quinolinecarbonitrile (Example 92) was stirred in ethanol (8 mL), tetrahydrofuran (1.6 mL), and ethyl acetate (2.4 mL), and to this were added paraformaldehyde (43 mg, 1.47 mmol), and dimethylamine hydrochloride (208 mg, 2.6 mmol). The reaction mixture was stirred at reflux for 16 hours, and subsequently evaporated, basified with saturated sodium bicarbonate solution, and extracted with ethyl acetate. The organic phase was washed with brine, dried over sodium sulfate and evaporated. The gummy residue was purified by flash chromatography (40:4:1=ethyl acetate:methanol:triethylamine), to give a cream solid (306 mg, 49% yield), mp 157–158° C.;

$^1$H NMR (DMSO-d$_6$/trifluoroacetic acid) δ 9.61 (bs, 1H), 8.69 (s, 1H), 8.68 (m, 1H), 7.89 (s, 1H), 7.76 (s, 1H), 7.74 (s, 1H), 7.30–7.29 (m, 2H), 6.68–6.67 (m, 1H), 6.43 (m, 1H), 4.43 (s, 1H), 4.41 (s, 1H), 3.87 (s, 3H), 2.57 (s, 3H), 2.55 (s, 3H); MS (ES) m/z 466.1 (M+1); HRMS (EI) 466.11952 (M+1). Analysis for $C_{24}H_{21}Cl_2N_5O$: Calcd: C, 61.81; H, 4.54; N, 15.02. Found: C, 61.72; H, 4.64; N, 14.90.

EXAMPLE 94

7-[5-(1,3-Dioxolan-2-yl)-3-thienyl]-4-[3-methyl-4-(2-pyridinylmethoxy)anilino]-3-quinolinecarbonitrile A mixture of 7-bromo-4-[3-methyl-4-(2-pyridinylmethoxy)anilino]-3-quinolinecarbonitrile (Reference Example 82) (1.00 g, 2.25 mmol), tributyl[5-(1,3-dioxolan-2-yl)-3-thienyl]stannane (1.19 g, 2.67 mmol), and a catalytic amount of dichlorobis(triphenylphosphine) palladium(II) in 30 mL of dioxane was heated at reflux for 6 hours and then stirred at room temperature overnight. The solution was concentrated and triturated with diethyl ether to provide 980 mg of a yellow solid. An analytical sample was obtained by flash column chromatography eluting with ethyl acetate to provide 7-[5-(1,3-dioxolan-2-yl)-3-thienyl]-4-[3-methyl-4-(2-pyridinylmethoxy)anilino]-3-quinolinecarbonitrile as a yellow solid, imp 194–196° C.;

MS (ES) m/z 521.1 (M+1). Analysis for $C_{30}H_{24}N_4O_3S$-0.75$H_2O$: Calcd: C, 67.46; H, 4.81; N, 10.49. Found: C, 67.48; H, 4.52; N, 10.35.

EXAMPLE 95

4-[3-Methyl-4-(2-pyridinylmethoxy)anilino]7-[5-(4-morpholinylmethyl)-3-thienyl-3-quinolinecarbonitrile A solution of 980 mg of crude 7-[5-(1,3-dioxolan-2-yl)-3-thienyl]-4-[3-methyl-4-(2-pyridinylmethoxy)anilino]-3-quinolinecarbonitrile (Example 94) in 40 ml of tetrahydrofuran and 20 mL of 2N hydrochloric acid was stirred at room temperature for 6 hours. Saturated sodium bicarbonate was slowly added. Ethyl acetate was added resulting in a large amount of insoluble material. The entire mixture was filtered and the solid was washed with water and ethyl acetate to provide 549 mg of the intermediate aldehyde. The organic layer of the filtrate was dried over magnesium sulfate, filtered and concentrated in vacuo to provide an additional 303 mg of the intermediate aldehyde.

Morpholine (0. 180 mL, 0. 21 mmol) was added to a suspension of the aldehyde (250 mg, 0.53 mmol) in 4 mL of methylene chloride and 1 mL of N,N-dimethylformamide. The reaction mixture was cooled to 0° C. and sodium triacetoxyborohydride (540 mg, 2.55 mmol) was added followed by a drop of acetic acid. After stirring at 0° C. for 20 minutes the ice bath was removed and the reaction mixture was stirred it room temperature for 5 hours. The reaction was quenched by the addition of saturated sodium bicarbonate and then partitioned between saturated sodium bicarbonate and ethyl acetate. The organic layer was dried over magnesium sulfate, filtered and concentrated in vacuo. The residue was triturated with methanol to provide 93 mg of 4-[3-methyl-4-(2-pyridinylmethoxy)anilino]-7-[5-(4-morpholinylmethyl)-3-thienyl]-3-quinolinecarbonitrile (33% yield) as an off-white solid, mp 217–219° C.;

MS (ES) m/z 548.1 (M+1). Analysis for $C_{32}H_{29}N_5O_2S$: Calcd: C, 70.18; H, 5.34; N, 12.79. Found: C, 69.94; H, 5.17; N, 12.52.

EXAMPLE 96

4-(2,4-Dichloro-5-methoxyanilino)-7-(2-formyl-1-methyl-1H-imidazol-5-yl)-3-quinolinecarbonitrile N-methylpiperazine (2.40 g, 20 mmol) was dissolved in 60 mL of hexanes and 50 mL of tetrahydrofuran. The mixture was cooled to 0° C. and n-butyl lithium (2.5M in hexanes) (8 mL, 20 mmol) was added slowly to the reaction mixture and stirring was continued for 40 minutes. To the reaction mixture was added 1-methyl-1H-imidazole-2-carbaldehyde (prepared by the procedure described in Alcalde, E., *Tetrahedron*, 52, 15171 (1996) in portions, followed by further stirring for 15 minutes. To this was added N,N,N',N'-tetramethylethylenediamine (4.64 g, 40 mmol), followed by n-butyl lithium (2.5M in hexanes) (16 mL, 40 mmol), while maintaining the reaction mixture at 0° C. The reaction was stirred for 18 hours, then 50 mL of tetrahydrofuran was added. The reaction was then cooled to −46° C. and tributyltin chloride (13.2 g, 40 mmol) dissolved in tetrahydrofuran (20 mL) was added. Stilling was continued for 15 minutes at −46° C., then the cooling bath was removed. The reaction was stirred for 6 hours, then quenched with saturated sodium bicarbonate and the product extracted into diethyl ether. The organic layer was collected, dried over sodium sulfate and purified by flash column chromatography eluting with 30% ethyl acetate in hexanes to provide 3.9 g of 1-methyl-5-tributylstannanyl-1H-imidazole-2-carbaldehyde as a yellow oil.

1-Methyl-5-tributylstannanyl-1H-imidazole-2-carbaldehyde (1.2 g, 30 mmol), 7-bromo-4-(2,4-dichloro-5-methoxyanilino)-3-quinolinecarbonitrile (0.5 g, 1.2 mmol) (Reference Example 8), dichlorobis(triphenylphosphine)palladium(II) (100 mg, 0.10 mmol) and triethylamine (0.133 g, 1.3 mmol) in 10 mL of dioxane was heated at reflux for 4 hours. The reaction was cooled to room temperature and partitioned between ethyl acetate and a saturated solution of sodium bicarbonate. The organic layer was collected, dried over sodium sulfate and passed through a plug of magnesol. After concentrating the solution, the resulting residue was purified by flash column chromatography, eluting with 5% methanol in methylene chloride to provide a semi-solid. This was triturated with a 1:1 mixture of diethyl ether/hexane to provide 370 mg (68%) of 4-(2,4-dichloro-5-methoxyanilino)-7-(2-formyl-1-methyl-1H-imidazol-5-yl)-3-quinolinecarbonitrile as a yellow solid, mp 186–189° C.; $^1$H NMR (DMSO-d$_6$) δ 3.87 (s, 3H), 4.07 (s, 3H), 7.44 (s, 1H), 7.72 (s, 1H), 7.79 (s, 1H), 7.93 (d, 1H), 8.17 (s, 1H), 8.65 (s, 1H), 8.67 (d, 1H), 9.81 (s, 1H), 10.14 (s, 1H); MS (ES) m/z 452.0 (M+1). Analysis for $C_{22}H_{15}Cl_2N_5O_2$-0.7H$_2$O: Calcd: C, 56.70; H, 3.56; N, 13.93. Found: C, 56.79; H, 3.77; N, 14.11.

EXAMPLE 97

4-({3-Chloro-4-[(1-methyl-1H-imidazol-2-yl)sulfanyl]phenyl}amino)-7-[4-(1-piperazinylmethyl)phenyl]-3-quinolinecarbonitrile A mixture of tert-butyl 4-{4-[4-({3-chloro-4-[(1-methyl-1H-imidazol-2-yl)sulfanyl]phenyl}amino)-3-cyano-7-quinolinyl]benzyl}-1-piperazinecarboxylate (Example 137) (2.05 g, 30.8 mmol) and 60 mL of methanolic HCl was stirred for 20 hours. The precipitated solid was collected by filtration, washed with ether, suspended in saturated aqueous sodium bicarbonate and stirred for 1 hour. The solids were collected by filtration, washing with water and diethyl ether to provide 1.97 g (99%) of 4-({3-chloro-4-[(1-methyl-1H-imidazol-2-yl)sulfanyl]phenyl}amino)-7-[4-(1-piperazinylmethyl)phenyl]-3-quinolinecarbonitrile as a yellow solid: mp 140–142° C.; MS 566 (M+H)+.

EXAMPLE 98

4-({3-Chloro-4-[(1-methyl-1H-imidazol-2-yl)sulfanyl]phenyl}amino)-7-{4-[(4-isopropyl-1-piperazinyl)methyl]phenyl}-3-quinolinecarbonitrile A mixture of 4-({3-chloro-4-[(1-methyl-1H-imidazol-2-yl)sulfanyl]phenyl}amino)-7-[4-(1-piperazinylmethyl)phenyl]-3-quinolinecarbonitrile (Example 97) (0.25 g, 0.44 mmol) and sodium cyanoborohydride (0.08 g, 1.27 mmol) in 30 mL of acetone was stirred for 1 hour. Two drops of glacial acetic acid were added and the mixture was stirred for 20 hours. The precipitated solid was collected by filtration, washed with diethyl ether, suspended in aqueous saturated sodium bicarbonate and stirred for 1 hour. The solids were collected by filtration, washing with water and diethyl ether. The solid was purified by flash silica gel chromatography eluting with a gradient of 5% methanol in dichloromethane to 20% methanol in dichloromethane to provide 0.075 g (28%) of 4-({3-chloro-4-[(1-methyl-1H-imidazol-2-yl)sulfanyl]phenyl}-amino)-7-{4-[(4-isopropyl-1-piperazinyl)methyl]phenyl}-3-quinolinecarbonitrile as a yellow solid: mp 193–195° C.; MS 608 (M+H)+.

EXAMPLE 99

(E)-3-[3-Cyano-4-(2,4-dichloro-5-methoxyanilino)-7-quinolinyl]-2-propenoic Acid (E)-tert-Butyl 3-[3-cyano-4-(2,4-dichloro-5-methoxyanilino)-7-quinolinyl]-2-propenoate (Example 142) (75 mg, 0.16 mmol) in 2 mL of dichloromethane and 0.3 mL of trifluoroacetic acid was stirred at room temperature for 5 hours. The mixture was diluted with diethyl ether and hexane. The resultant solid was collected by filtration to provide 45 mg (47% yield) of (E)-3-[3-cyano-4-(2,4-dichloro-5-methoxyanilino)-7-quinolinyl]-2-propenoic acid as a yellow solid: mp 237–240° C.; MS 398.0, 400.1 (M+H)+.

EXAMPLE 100

(1-{4-[3-Cyano-4-(2,4-dichloro-5-methoxyanilino)-7-quinolinyl]benzyl}-4-piperidinyl)acetic Acid Ethyl (1-{4-[3-cyano-4-(2,4-dichloro-5-methoxyanilino)-7-quinolinyl]benzyl}-4-piperidinyl)acetate (Example 144) (160 mg, 0.27 mmol) and 3 mL of 1 N sodium hydroxide in 3 mL of methanol was stirred at room temperature for 2.5 hours. The methanol was removed in vacuo and the aqueous solution was acidified with HCl. The solid was collected by filtration to provide 150 mg (97% yield) of (1-{4-[3-cyano-4-(2,4-dichloro-5-methoxyanilino)-7-quinolinyl]benzyl}-4-piperidinyl)acetic acid as a yellow solid: mp 239–240° C.; MS 424.2, 426.2 (M+H)+.

EXAMPLE 101

4-(2,4-Dichloro-5-methoxyanilino)-7-[4-(hydroxymethyl)phenyl]-3-quinolinecarbonitrile To a mixture of 4-(2,4-dichloro-5-methoxyanilino)-7-[4-(formylphenyl]-3-quinolinecarbonitrile (Example 83) (400 mg, 0.90 mmol) in 15 mL of methanol at 0° C., was added sodium borohydride (54 mg, 1.42 mmol) in portions. The mixture was allowed to warm to room temperature and stirred at room temperature for 2 hours. The mixture was partitioned between water and ethyl acetate. The organic layer was concentrated and purified by flash column chromatography, eluting with 1:1 hexane:ethyl acetate, to give 220 mg (54% yield) of 4-(2,4-dichloro-5-methoxyanilino)-7-[4-(hydroxymethyl)phenyl]-3-quinolinecarbonitrile as a yellow solid: mp 264–267° C.; MS 449.9, 451.9 (M+H)+.

EXAMPLE 102

7-[4-(Chloromethyl)phenyl]-4-(2,4-dichloro-5-methoxyanilino)-3-quinolinecarbonitrile To a mixture of 4-(2,4-dichloro-5-methoxyanilino)-7-[4-(hydroxymethyl)phenyl]-3-quinolinecarbonitrile (Example 101) (210 mg, 0.5 mmol) in 20 mL of dichloromethane and 75 μL of pyridine at −30° C. was added 1-chloro-N,N, 2-trimethyl propenylamine (81 mg, 0.65 mmol). The mixture was stirred at −30° C. for 2 hours and then at room temperature overnight. The mixture was concentrated and the residue was purified by flash column chromatography, eluting with 1:1 hexane:ethyl acetate, to give 90 mg (38% yield) of 7-[4-(chloromethyl)phenyl]-4-(2,4-dichloro-5-methoxyanilino)-3-quinolinecarbonitrile as a yellow solid: mp 236–239° C.;

MS 468.0, 470.0 (M+H)+.

EXAMPLE 103

4-[(2,4-Dichloro-5-methoxyphenyl)amino]-7-[4-(1H-1,2,3-triazol-1-ylmethyl)phenyl]-3-quinolinecarbonitrile A mixture of 7-[4-(chloromethyl)phenyl]-4-(2,4-dichloro-5-methoxyanilino)-3-quinolinecarbonitrile (Example 102) (0.25 g, 0.53 mmol), 1H-1,2,3-triazole (0.31 mL, 5.3 mmol), sodium hydroxide (85 mg, 2.1 mmol), and sodium iodide (40 mg, 0.26 mmol) was heated at 80° C. for 4 hours. The mixture was partitioned between ethyl acetate and water and the organic layer was dried over sodium sulfate and concentrated. The residue was purified by flash column chromatography, eluting with 1% methanol in dichloromethane to give 90 mg (34% yield) of 4-[(2,4-dichloro-5-methoxyphenyl)amino]-7-[4-(1H-1,2,3-triazol-1-ylmethyl)phenyl]-3-quinolinecarbonitrile as a yellow solid: mp 239–240° C.; MS 501.0, 503.0 (M+H)+.

EXAMPLE 104

4-(2,4-Dichloro-5-methoxyanilino)-7-(1H-pyrrol-2-yl)-3-quinolinecarbonitrile

A solution of tert-butyl 2-[3-cyano-4-(2,4-dichloro-5-methoxyanilino)-7-quinolinyl]-1H-pyrrole-1-carboxylate (90 mg, 0.177 mmol) (Example 164) in 2.0 mL of trifluoroacetic acid was stirred at 0° C. for 1 hour, then allowed to warm to room temperature and stirred for 2 hours. The resulting mixture was adjusted to pH of 8–9 with saturated aqueous sodium bicarbonate and then diluted with water. The crude product was collected by filtration, washed with water and purified by flash column chromatography to give 65 mg (90%) of 4-(2,4-dichloro-5-methoxyanilino)-7-(1H-pyrrol-2-yl)-3-quinolinecarbonitrile as a yellow solid: mp 240° C. dec; MS 409.2 (M+H)+.

EXAMPLE 105

4-[(2,4-Dichloro-5-methoxyanilino]-7-[4-(1H-tetraazol-5-yl)phenyl]-3-quinolinecarbonitrile A mixture of 4-(2,4-dichloro-5-methoxyphenylamino)-7-tributylstannanyl-3-quinolinecarbonitrile (200 mg, 0.32 mmol) (Reference Example 83), 5-(4-bromophenyl)-1H-tetrazole (106 mg, 0.47 mmol) and dichlorobis(triphenylphosphine)palladium(II) (11 mg, 0.016 mmol) in 3 mL of N,N-dimethylformamide was heated at reflux for 7 hours. The reaction mixture was diluted with dichloromethane, concentrated on silica gel, and purified by flash column chmomatography to give 39 mg (25%) of 4-[(2,4-dichloro-5-methoxyphenylamino]-7-[4-(1H-tetraazol-5-yl)phenyl]-3-quinolinecarbonitrile as a white solid: mp 270° C. dec; MS 487.6 (M+H)+.

EXAMPLE 106

4-({3-Chloro-4-[(1-methyl-1H-imidazol-2-yl)sulfanyl]phenyl}amino)-7-(5-{[(2-hydroxyethyl)(methyl)amino]methyl}-2-pyridinyl)-3-quinolinecarbonitrile A mixture of 2-[[(6-bromo-3-pyridinyl)methyl](methyl)amino]ethanol (245 mg, 10 mmol), 7-bromo-4-{3-chloro-4-[(1-methyl-1H-imidazol-2-yl)sulfanlyl]anilino}-3-quinolinecarbonitrile (471 mg, 1.0 mmol) (Reference Example 14), tetrakis(triphenylphosphine)palladium(0) (110 mg, 0.1 mmol), and hexamethylditin (328 mg, 1.0 mmol) in 10 mL of 1,4-dioxane was heated at reflux for 16 hours. The mixture was concentrated and the residue was chromatographed over silica gel, eluting with a gradient of methylene chloride to methylene chloride/methanol (3:1) to provide 4-({3-chloro-4-[(1-methyl-1H-imidazol-2-yl)sulfanyl]phenyl}amino)-7-(5-{[(2-hydroxyethyl)(methyl)amino]methyl}-2-pyridinyl)-3-quinolinecarbonitrile as a yellow solid, 198 mg (36%): mp 197–199° C.;

MS 556.4 (M+H)+.

EXAMPLE 107

Methyl 1-{[6-(4-{3-Chloro-4-[(1-methyl-1H-imidazol-2-yl)sulfanyl]anilino]-3-cyano-7-quinolinyl)-3-pyridinyl]methyl}-4-piperidinecarboxylate A mixture of 6-bromonicotinaldehyde (186 mg, 1.0 mmol), 7-bromo-4-{3-chloro-4-[(1-methyl-1H-imidazol-2-yl)sulfanyl]anilino}-3-quinolinecarbonitrile (471 mg, 1.0 mmol) (Reference Example 14), tetrakis(triphenylphosphine)palladium(0) (110 mg, 0.1 mmol), and hexamethylditin (328 mg, 1.0 mmol) in 10 mL of 1,4-dioxane was heated at reflux for 9 hours and concentrated. The residue was suspended in 10 mL of methylene chloride and 2 mL of N,N-dimethylformamide. Methyl isonipecotate (286 mg, 2.0 mmol) was added followed by two drops of glacial acetic acid and the mixture was stirred for 30 minutes. Sodium cyanoborohydride (1.0 g, 15.9 mmol) was added, and the mixture was stirred for 1 hour. Water was added to quench the reaction. The product was extracted into methylene chloride, and the combined extracts were washed with brine, dried, and concentrated. The residue was chromatographed over silica gel, eluting with a gradient of 10% to 20% methanol in ethyl acetate to provide methyl 1-{[6-(4-{3-chloro-4-[(1-methyl-1H-imidazol-2-yl)sulfanyl]anilino}-3-cyano-7-quinolinyl)-3-pyridinyl]methyl}-4-piperidinecarboxylate as a yellow solid, 164 mg (26%): mp 135–137° C.; MS 624.2 (M+H)+.

EXAMPLE 108

4-({3-Chloro-4-[(1-methyl-1H-imidazol-2-yl)sulfanyl]phenyl}amino)-7-[5-(4-ethyl-1-piperazinyl)-2-pyridinyl]-3-quinolinecarbonitrile To a solution of 1-(6-bromo-3-pyridinyl)-4-ethylpiperazine (405 mg, 1.5 mmol) in 10 mL of tetrahydrofuran at −78° C. was added n-butyllithium (2.5M in hexanes, 0.60 mL, 1.5 mmol). The solution was stirred at −78° C. for 15 minutes. Tributyltin chloride (585 mg, 1.8 mmol) was added, and the mixture was warmed to room temperature. The reaction was quenched with water, and the product was extracted with ethyl acetate. The organic layer was separated, dried over magnesium sulfate, and concentrated. The crude product was used directly in the next step. A mixture of this crude organotin compound, 7-bromo-4-{3-chloro-4-[(1-methyl-1H-imidazol-2-yl)sulfanyl]anilino}-3-quinolinecarbonitrile (236 mg, 0.50 mmol) (Reference Example 14), tetrakis(triphenylphosphine)palladium(0) (30 mg, 0.027 mmol), and dichlorobis(triphenylphosphine)palladium(II) (30 mg, 0.043 mmol) in 5 mL of 1,4-dioxane and 0.5 mL of dimethylformamide was heated at reflux for 10 h and concentrated. The residue was chromatographed over silica gel, eluting with a gradient of ethyl acetate to 30% methanol in ethyl acetate to provide 4-({3-chloro-4-[(1-methyl-1H-imidazol-2-yl)sulfanyl]phenyl}-amino)-7-[5-(4-ethyl-1-piperazinyl)-2-pyridinyl]-3-quinolinecarbonitrile as a yellow solid, 149 mg (51%): mp 246–248° C.; MS 580.9 (M+H)+.

EXAMPLE 109

4-({3-Chloro-4-[(1-methyl-1H-imidazol-2-yl)sulfanyl]phenyl}amino)-7-[6-(4-morpholinylmethyl)-3-pyridinyl]-3-quinolinecarbonitrile A mixture of 4-[(5-bromo-2-pyridinyl)methyl]morpholine (141 mg, 0.55 mmol), hexamethylditin (180 mg, 0.55 mmol), tetrakis(triphenylphosphine)palladium(0) (63 mg, 0.055 mmol) in 5 mL of 1,4-dioxane was heated at reflux for 45 minutes. 7-Bromo-4-{3-chloro-4-[(1-methyl-1H-imidazol-2-yl)sulfanyl]anilino}-3-quinolinecarbonitrile (200 mg, 0.42 mmol) (Reference Example 14) was added, followed by tetrakis(triphenylphosphine)palladium(0) (48 mg, 0.042 mmol) and 0.5 mL of dimethylformamide. The resulting reaction mixture was heated at reflux for 6 hours. After cooling to room temperature, the mixture was concentrated in vacuo and the residue was treated with water. The aqueous suspension was extracted with methylene chloride. The organic phase was washed with brine and dried over sodium sulfate. Removal of the solvent gave a semi-solid residue. The residue was purified by preparative thin layer chromatography developing with 10% methanol in dichloromethane to provide 63 mg (26%) of 4-({3-chloro-4-[(1-methyl-1H-imidazol-2-yl)sulfanyl]phenyl}-amino)-7-[6-(4-morpholinylmethyl)-3-pyridinyl]-3-quinolinecarbonitrile as a yellow solid: mp 233–235° C.; MS 568.05 (M+H)+.

EXAMPLE 110

4-({3-Chloro-4-[(1-methyl-1H-imidazol-2-yl)sulfanyl]phenyl}amino)-7-[6-(4-thiomorpholinyl)-3-pyridinyl]-3-quinolinecarbonitrile A mixture of 4-[(5-bromo-2-pyridinyl)thiomorpholine (119.2 mg, 0.46 mmol), hexamethylditin (150 mg, 0.46 mmol), tetrakis(triphenylphosphine)palladium(0) (48 mg, 0.042 mmol) in 4.0 mL of 1,4-dioxane was heated at reflux for 3.5 hours. 7-Bromo-4-{3-chloro-4-[(1-methyl-1H-imidazol-2-yl)sulfanyl]anilino}-3-quinolinecarbonitrile (200 mg, 0.42 mmol) (Reference Example 14) was added followed by tetrakis(triphenylphosphine)palladium(0) (48 mg, 0.042 mmol) and 0.5 mL of dimethylformamide. The resulting reaction mixture was heated at reflux for 19 hours. According to the work up procedure and purification reported for Example 109, 109 mg (45%) of 4-({3-chloro-4-[(1-methyl-1H-imidazol-2-yl)sulfanyl]phenyl}amino)-7-[6-(4-thiomorpholinyl)-3-pyridinyl]-3-quinolinecarbonitrile was obtained as a yellow solid: mp>260° C.; MS 569.8 (M+H)+.

EXAMPLE 111

4-(2,4-Dichloro-5-methoxyanilino)-7-[3-(morpholin-4-ylmethyl)-pyridin-2-yl]-3-quinolinecarbonitrile A mixture of 7-bomo-4-(2,4-dichloro-5-methoxyanilino)-3-quinolinecarbonitrile (494 mg, 1.17 mmol) (Reference Example 8), hexamethylditin (383 mg, 1.17 mmol) and tetrakis(triphenylphosphine)palladium(0) (68.2 mg, 0.059) in 1.5 mL of DMF(anhydrous) was head at 100° C. for 1.5 hours. 4-[2-Bromo-3-pyridinyl)methyl]morpholin (15 mg, 0.59 mmol) was added followed by tetrakis(triphenylphosphine)palladium(0) (68 mg, 0.059 mmol) and 6 mL of 1,4-dioxane. The resulting reaction mixture was heated at reflux for 22 h. According to the work up procedure and purification reported for Example 109, 28 mg (9%) of 4-(2,4-dichloro-5-methoxyanillino)-7-[3-(morpholin-4-ylmethyl)-pyridin-2-yl]-3-quinolinecarbonitrile was obtained as a yellow solid: mp 151–154° C.; MS 520.1 (M+H)+.

EXAMPLE 112

4-(2,4-Dichloro-5-methoxyanilino)-7-(3-formyl)-3-quinolinecarbonitrile

A mixture of 4-(2,4-dichloro-5-methoxyanilino)-7-iodo-3-quinolinecarbonitrile (0.118 g, 0.25 mmol) (Reference Example 13), 3-formylphenylboronic acid (0.075g, 0.50 mmol), tetrakis(triphenylphosphine)palladium(0) (0.020 g, 0.012 mmol), 10 mL of ethylene glycol dimethyl ether and 8 mL of a saturated sodium bicarbonate solution was placed in the vessel for microwave under nitrogen. The microwave heating (PROLABO unit, mono-mode regimen) was continued for 1 hour at 80° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.096 g (86%) of 4-(2,4-dichloro-5-methoxyanilino)-7-(3-formyl)-3-quinolinecarbonitrile 250–252° C.; MS 448.0 (M+H)+.

EXAMPLE 113

4-(2,4-Dichloro-5-methoxyanilino)-7-{3-[4-methyl-1-piperazinyl)methyl]phenyl}-3-quinolinecarbonitrile N-Methylpiperazine (0.045 mL, 0.37 mmol) was added to a suspension of 4-(2,4-dichloro-5-methoxyanilino)-7-(3-formyl)-3-quinolinecarbonitrile (0.130 g 0.30 mmol) (Example 112) in 3 mL of methylene chloride and 1 mL of N,N-dimethylformamide. The reaction mixture was cooled to 0° C. and sodium triacetoxyborohydride (0.330 g, 1.57 mmol) was added. After stirring at 0° C. for 1.5 hour, a catalytic amount of acetic acid was added and the reaction mixture was kept for 2 hours at 0° C. and then for 2 hours at room temperature. The reaction was quenched by the addition of water and then partitioned between saturated sodium bicarbonate and methylene chloride. The organic layer was dried over sodium sulfate, filtered and concentrated in vacuo. The residue was purified by column chromatography eluting with 10% methanol in methylene chloride to provide 0.070 g (45%) of 4-(2,4-dichloro-5-methoxyanilino)-7-{3-[(4-methyl-1-piperazinyl)methyl]phenyl}-3-quinolinecarbonitrile mp 104–106° C.; MS 532.1 (M+H)+.

EXAMPLE 114

4-(2,4-Dichloro-5-methoxyanilino)-7-(2-formylphenyl)-3-quinolinecarbonitrile

A mixture of 7-bromo-4-(2,4-dichloro-5-methoxyanilino)-3-quinolinecarbonitrile (0.250 g, 0.59 mmol) (Reference Example 8), 2-formylphenylboronic acid (0.149 g, 1.0 mmol), tetrakis(triphenylphosphine)palladium (0) (0.100 g, 0.060 mmol), 15 mL of ethylene glycol dimethyl ester and 10 mL of a saturated sodium bicarbonate solution was placed in the vessel for microwave under nitrogen. The microwave heating (PROLABO unit, monomode regimen) was continued for 1 hour at 80° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.200 g (75%) of 4-(2,4-dichloro-5-methoxyanilino)-7-(2-formyl)-3-quinolinecarbonitrile: mp 252–253° C., MS 448.0 (M+H)+.

EXAMPLE 115

4-(2,4-Dichloro-5-methoxyanilino)-7-[2-(4-morpholinylmethyl)phenyl]-3-quinolinecarbonitrile Morpholine (0.140 mL, 1.6 mmol) was added to a suspension of 4-(2,4-dichloro-5-methoxyanilino)-7-(2-formyl)-3-quinolinecarbonitrile (0.310 g, 0.69 mmol) (Example 114) in 5 mL of methylene chloride and 1 mL of N,N-dimethylformamide. The reaction mixture was cooled to 0° C. and sodium triacetoxyborohydride (0.500 g, 2.36 mmol) was added. After stirring at 0° C. for 1.5 hour, a catalytic amount of acetic acid was added and the reaction mixture was kept for 2 hours at 0° C. and then for 2 hours at room temperature. The reaction was quenched by the addition of water and then partitioned between saturated sodium bicarbonate and methylene chloride. The organic layer was dried over sodium sulfate, filtered and concentrated in vacuo. The residue was purified by column chromatography eluting with 10% methanol in methylene chloride to provide 0.154 g (43%) of 4-(2,4-dichloro-5-methoxyanilino)-7-[2-(4-morpholinylmethyl)phenyl]3-quinolinecarbonitrile: mp 107–109° C., MS 519.1 (M+H)+.

EXAMPLE 116

4-(2,4-Dichloro-5-methoxyanilino)-7-(1-naphthyl)-3-quinolinecarbonitrile

A mixture of 7-bromo-4-(2,4-dichloro-5-methoxyanilino)-3-quinolinecarbonitrile (0.141 g, 0.33 mmol) (Reference Example 8), 1-naphthylboronic acid (0.120 g, 0.70 mmol), tetrakis(triphenylphosphine) palladium(0) (0.020 g, 0.012 mmol), 15 mL of dimethylformamide and 10 mL of a saturated solution of sodium bicarbonate was placed in the vessel for microwave under nitrogen. The microwave heating (PROLABO unit, monomode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.116 g (75%) of 4-(2,4-dichloro-5-methoxyanilino)-7-(1-naphthyl)-3-quinolinecarbonitrile: mp 192–193° C., MS 470.0 (M+H)+.

EXAMPLE 117

4-(2,4-Dichloro-5-methoxyanilino)-7-(2-naphthyl)-3-quinolinecarbonitrile

A mixture of 7-bromo-4-(2,4-dichloro-5-methoxyanilino)-3-quinolinecarbonitrile (0.141 g, 0.33 mmol) (Reference Example 8), 2-naphthylboronic acid (0.120 g, 0.70 mmol), tetrakis(triphenylphosphine) palladium(0) (0.020 g, 0.012 mmol) 15 mL of dimethylformamide and 10 mL of a saturated solution of sodium bicarbonate was placed in the vessel for microwave under nitrogen. The microwave heating (PROLABO unit, monomode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.135 g (87%) of 4-(2,4-dichloro-5-methoxyanilino)-7-(2-naphthyl)-3-quinolinecarbonitrile: mp 243–244° C., MS 470.0 (M+H)+.

EXAMPLE 118

N-{3-[3-Cyano-4-(2,4-dichloro-5-methoxyanilino)-7-quinolinyl]phenyl}acetamide

A mixture of 7-bromo-4-(2,4-dichloro-5-methoxyanilino)-3-quinolinecarbonitrile (0.141 g, 0.33 mmol) (Reference Example 8), 3-acetamidophenylboronic acid (0.120 g, 0.67 mmol), tetrakis(triphenylphosphine) palladium(0) (0.020 g, 0.012 mmol), 15 mL of dimethylformamide and 10 mL of a saturated solution of sodium bicarbonate was placed in the vessel for microwave under nitrogen. The microwave heating (PROLABO unit, monomode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.105 g (65%) of N-{3-[3-cyano-4-(2,4-dichloro-5-methoxyanilino)-7-quinolinyl]phenyl}acetamide: mp 262–2630° C., MS 476.9 (M+H)+.

EXAMPLE 119

7-(1-Benzofuran-2-yl)-4-(2,4-dichloro-5-methoxyanilino)-3-quinolinecarbonitrile

A mixture of 7-bromo-4-(2,4-dichloro-5-methoxyanilino)-3-quinolinecarbonitrile (0.141 g, 0.33 mmol) (Reference Example 8), 1-benzofuranboronic acid (0.100 g, 0.62 mmol), tetrakis(triphenylphosphine) palladium(0) (0.020 g, 0.012 mmol), 15 mL of dimethylformamide and 10 mL of a saturated solution of sodium bicarbonate was placed in the vessel for microwave under nitrogen. The microwave heating (PROLABO unit, monomode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.130 g (86%) of 7-(1-benzofuran-2-yl)-4-(2,4-dichloro-5-methoxyanilino)-3-quinolinecarbonitrile: mp 276–277° C., MS 460.0 (M+H)+.

EXAMPLE 120

7-(-Benzothien-2-yl)-4-2,4-dichloro-5-methoxyanilino)-3-quinolinecarbonitrile

A mixture of 7-bromo-4-(2,4-dichloro-5-methoxyanilino)-3-quinolinecarbonitrile (0.141 g, 0.33 mmol) (Reference Example 8), 1-benzothiopheneboronic acid (0.120 g, 0.67 mmol), tetrakis(triphenylphosphine) palladium(0) (0.020 g, 0.012 mmol), 15 mL of dimethylformamide and 10 mL of a saturated solution of sodium bicarbonate was placed in the vessel for microwave under nitrogen. The microwave heating (PROLABO unit, mono-mode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.107 g (67%) of 7-(1-benzothien-2-yl)-4-(2,4-dichloro-5-methoxyanilino)-3-quinolinecarbonitrile: mp 269–270° C., MS 475.8 (M+H)+.

EXAMPLE 121

4-[3-Cyano-4-(2,4-dichloro-5-methoxyanilino)-7-quinolinyl]benzoic Acid

A mixture of 7-bromo-4-(2,4-dichloro-5-methoxyanilino)-3-quinolinecarbonitrile (0.141 g, 0.33 mmol) (Reference Example 8), 4-carboxyphenylboronic acid (0.100 g, 0.6 mmol), tetrakis(triphenylphosphine)palladium(0) (0.020 g, 0.012 mmol), 15 mL of dimethylformamide and 10 mL of a saturated solution of sodium bicarbonate was placed in the vessel for microwave under nitrogen. The microwave heating (PROLABO unit, mono-mode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.085 g (86%) of 4-[3-cyano-4-(2,4-dichloro-5-methoxyanilino)-7-quinolinyl]benzoic acid: mp 282–283° C., MS 65.8 (M+H)+.

EXAMPLE 122

4-(2,4-Dichloro-5-methoxyanilino)-7-(3-nitrophenyl)-3-quinolinecarbonitrile

A mixture of 7-bromo-4-(2,4-dichloro-5-methoxyanilino)-3-quinolinecarbonitrile (0.141 g, 0.33 mmol) (Reference Example 8), 3-nitrophenylboronic acid (0.090 g, 0.54 mmol), tetrakis(triphenylphosphine)palladium(0) (0.020 g, 0.012 mmol), 15 mL of dimethylformamide and 10 mL of a saturated solution of sodium bicarbonate was placed in the vessel for microwave under nitrogen. The microwave heating (PROLABO unit, mono-mode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.115 g (75%) of 4-(2,4-dichloro-5-methoxyanilino)-7-(3-quinolinecarbonitrile: mp 287–288° C., MS 464.9 (M+H)+.

EXAMPLE 123

4-{3-Chloro-4-[(1-methyl-1H-imidazol-2-yl)sulfanyl]anilino}-6-methoxy-7-[4-(4-morpholinylmethyl)phenyl]-3-quinolinecarbonitrile To a mixture of 4-(4-bromobenzyl)morpholine (0.20 g, 0.78 mmol) (Reference Example 46), potassium acetate (0.23 g, 0.23 mmol), bis(pinacolato)diboron (0.218 g, 0.86 mmol) in 5 mL dimethylsulfoxide was added [1,1'-bis(diphenylphosphino)ferrocene]dichloropalladium(II) complex with dichloromethane (0.032 g, 0.039 mmol). The mixture was stirred at 80° C. for 2 hours, cooled, diluted with ethyl acetate, washed with water, dried over MgSO$_4$ and evaporated under high vacuum to provide ~0.2 g of a dark solid material.

A mixture of this material, 4-{3-chloro-4-[(1-methyl-1H-imidazol-2-yl)sulfanyl]anilino}-3-cyano-6-methoxy-7-quinolinyl trifluoromethanesulfonate (0.06 g, 0.01 mmol) (Reference Example 120), 15 mL of dimethylformamide and 10 mL of a saturated solution of sodium bicarbonate was placed in the vessel for microwave under nitrogen. The microwave heating (PROLABO unit, mono-mode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.046 g (73%) of 4-{3-chloro-4-[(1-methyl-1H-imidazol-2-yl)sulfanyl]anilino}-6-methoxy-7-[4-(4-morpholinylmethyl)phenyl]-3-quinolinecarbonitrile: mp 260–262° C., MS 597.0 (M+H)+.

EXAMPLE 124

7-[3,4-Bis(4-morpholinylmethyl)phenyl]-4-{3-chloro-4-[(1-methyl-1H-imidazol-2-yl)sulfanyl]anilino}-6-methoxy-3-quinolinecarbonitrile To a mixture of 4-[4-bromo-2-(4-morpholinylmethyl)benzyl]morpholine (0.354 g, 0.1 mmol) (Reference Example 37), potassium acetate (0.23 g, 0.23 mmol), bis(pinacolato)diboron (0.218 g, 0.86 mmol) in 5 mL of dimethylsulfoxide was added [1,1'-bis(diphenylphosphino)ferrocene]dichloropalladium(II) complex with dichloromethane (0.032 g, 0.039 mmol). The mixture was stirred at 80° C. for 2 hours, cooled, diluted with ethyl acetate, washed with water, dried over magnesium sulfate and evaporated under high vacuum to provide ~0.4 g of a dark solid material.

A mixture of this material, 4-{3-chloro-4-[(1-methyl-1H-imidazol-2-yl)sulfanyl]anilino}-3-cyano-6-methoxy-7-quinolinyl trifluoromethanesulfonate (0.09 g, 0.015 mmol) (Reference Example 120), 15 mL of dimethylformamide and 10 mL of a saturated solution of sodium bicarbonate was placed in the vessel for microwave under nitrogen. The microwave heating (PROLABO unit, mono-mode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.09 g (82%) of 7-[3,4-bis(4-morpholinylmethyl)phenyl]-4-{3-chloro-4-[(1-methyl-1H-imidazol-2-yl)sulfanyl]anilino}-6-methoxy-3-quinolinecarbonitrile: mp 228–2300° C., MS 348.4 (M+2H)+2.

EXAMPLE 125

4-{3-Chloro-4-[(1-methyl-1H-imidazol-2-yl)sulfanyl]anilino}-6-methoxy-7-[5-(4-morpholinylmethyl)-3-thienyl]-3-quinolinecarbonitrile To a mixture of 4-[(4-bromo-2-thienyl)methyl]morpholine (0.26 g) 0.1 mmol) (prepared according to the procedure of U.S. Pat. No. 5,866,572), potassium acetate (0.23 g. 0.23 mmol) and bis(pinacolato)diboron (0.218 g) 0.86 mmol) in 5 mL of dimethylsulfoxide was added [1,1'-bis(diphenylphosphino)ferrocene]dichloropalladium(II)

complex with dichloromethane (0.032 g, 0.039 mmol). The mixture was stilled at 80° C. for 2 hours, cooled, diluted with ethyl acetate, washed with water, dried over magnesium sulfate and evaporated under high vacuum to provide 0.4 g of a dark solid material.

A mixture of this material, 4-{3-chloro-4-[(1-methyl-1H-imidazol-2-yl)sulfanyl]anilino}-3-cyano-6-methoxy-7-quinolinyl trifluoromethanesulfonate (0.09 g 0.015 mmol) (Reference Example 120), 15 mL of dimethylformamide and 10 mL of a saturated solution of sodium bicarbonate was placed in the vessel for microwave under nitrogen. The microwave heating (PROLABO unit, mono-mode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.035 g (0.37%) of 4-{3-chloro-4-[(1-methyl-1H-imidazol-2-yl)sulfanyl]anilino}-6-methoxy-7-[5-(4-morpholinylmethyl)-3-thienyl]-3-quinolinecarbonitrile: mp 238–240° C., MS 602.8 (M+H)+.

EXAMPLE 126

4-{3-Chloro-4-[(1-methyl-1H-imidazol-2-yl) sulfanyl]anilino}-6-methoxy-7-{5-[(4-methyl-1-piperazinyl)methyl]-3-thienyl}-3-quinolinecarbonitrile To the mixture of 1-[(4-bromo-2-thienyl)methyl]-4-methylpiperazine (0.275 g, 0.1 mmol) (Reference Example 97), potassium acetate (0.23 g, 0.23 mmol), bis(pinacolato) diboron (0.218 g, 0.86 mmol) in 5 mL of dimethylsulfoxide was added [ 1,1'-bis(diphenylphosphino)ferrocene] dichloropalladium(II) complex with dichloromethane (0.032 g, 0.039 mmol). The mixture was stirred at 80° C. for 2 hours, cooled, diluted with ethyl acetate, washed with water, dried over $MgSO_4$ and evaporated under high vacuum to provide ~0.4 g of a dark solid material.

A mixture of this material, 4-{3-chloro-4-[(1-methyl-1H-imidazol-2-yl)sulfanyl]anilino}-3-cyano-6-methoxy-7-quinolinyl trifluoromethanesulfonate (0.285 g, 0.05 mmol) (Reference Example 120), 15 mL of dimethylformamide and 10 mL of a saturated solution of sodium bicarbonate was placed in the vessel for microwave under nitrogen. The microwave heating (PROLABO unit, mono-mode regimen) was continued for 1 hour at 130° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.118 g (38%) of 4-{3-chloro-4-[(1-methyl-1H-imidazol-2-yl)sulfanyl]anilino}-6-methoxy-7-{5-[(4-methyl-1-piperazinyl)methyl]-3-thienyl}-3-quinolinecarbonitrile: mp 162–164° C., MS 615.7 (M+H)+.

EXAMPLE 127

4-{3-Chloro-4-[(1-methyl-1H-imidazol-2-yl) sulfanyl]anilino}-6-methoxy-7-(4-methoxyphenyl)3-quinolinecarbonitrile A mixture of 4-{3-chloro-4-[(1-methyl-1H-imidazol-2-yl)sulfanyl]anilino}-3-cyano-6-methoxy-7-quinolinyl trifluoromethanesulfonate (0.285 g, 0.05 mmol) (Reference Example 120), 4-methoxyphenylboronic acid (0.151 g, 1.0 mmol), tetrakis(triphenylphosphine)palladium(0) (0.100 g, 0.060 mmol), 15 mL of ethylene glycol dimethyl ether and 10 mL of a saturated solution of sodium bicarbonate was placed in the vessel for microwave under nitrogen. The microwave heating (PROLABO unit, mono-mode regimen) was continued for 1 hour at 80° C. with stirring. The reaction mixture was cooled to room temperature and then partitioned between water and ethyl acetate. The organic layer was dried over sodium sulfate, filtered and evaporated. The residue was purified by column chromatography eluting with chloroform to provide 0.190 g (72%) of 4-{3-chloro-4-[(1-methyl-1H-imidazol-2-yl)sulfanyl]anilino}-6-methoxy-7-(4-methoxyphenyl)-3-quinolinecarbonitrile: mp 227–229° C., MS 527.8 (M+H)+.

EXAMPLE 128

4-{2,4-Dichloro-5-methoxyphenyl)amino}-7-[4-(4-morpholinyl)phenyl]-3-quinolinecarbonitrile A mixture of 4-[3-cyano-4-(2,4-dichloro-5-methoxyanilino)-7-quinolinyl]benzoic acid (0.464 g, 0.10 mmol) (Example 121) and 3.0 mL of thionyl chloride was refluxed for 3 hours. The excess thionyl chloride was removed to provide 0.5 g of the intermediate chloroanhydride.

The chloroanhydride was dissolved in 10 mL of tetrahydrofuran and stirred with 2.0 mL of morpholine at room temperature for 2 hours. Solvent and excess morpholine were removed in vacuum. The residue was purified by column chromatography eluting with chloroform/methanol 30:1 to provide 0.288 g (54%) of 4-[(2,4-dichloro-5-methoxyphenyl)amino]-7-[4-(4-morpholinyl)phenyl]-3-quinolinecarbonitrile: mp 162–164° C., MS 533.1 (M+H)+.

EXAMPLE 129

4-({3-Chloro-4-[(1-methyl-1H-imidazol-2-yl) sulfanyl]phenyl}amino)-7-[4-(4-morpholinylcarbonyl)phenyl]-3-quinolinecarbonitrile A mixture of 7-bromo 4-({3-chloro-4-[(1-methyl-1H-imidazol-2-yl)sulfanyl]phenyl}-amino)-3-quinolinecarbonitrile (0.118 g, 0.25 mmol) (Reference Example 14), 4-carboxybenzeneboronic acid (0.083 g, 0.50 mmol), tetrakis(triphenylphosphine)palladium(0) (0.020 g, 0.012 mmol), 10 mL of ethylene glycol dimethyl ether and 8 mL of asaturated solution of sodium bicarbonate was placed in the vessel for microwave under nitrogen. The microwave heating (PROLABO unit, mono-mode regimen) was continued for 1 hour at 80° C. with stirring. The reaction mixture was cooled to room temperature and then partitioned between water and ethyl acetate. The organic layer was dried over sodium sulfate, filtered and evaporated to provide 0.070 g of crude acid.

A mixture of crude acid and 3.0 mL of thionyl chloride was heated at reflux for 3 hours. The excess thionyl chloride was removed to provide 0.07 g of crude chloroanhydride. The chloroanhydride was dissolved in 10 mL of tetrahydrofuran and stirred with 2.0 mL of morpholine at room temperature for 2 hours. Solvent and excess morpholine were removed in vacuum. The residue was purified by column chromatography, eluting with chloroform-methanol 30:1 to provide 0.045 g (31%) of 4-({3-chloro-4-[(1-methyl-1H-imidazol-2-yl)sulfanyl]phenyl}amino)-7-[4-(4-morpholinylcarbonyl)phenyl]-3-quinolinecarbonitrile: mp 98–101° C., MS 581.2 (M+H)+.

The Examples in Table 4 are listed with the chemical name, melting point and/or mass spectral data and the Example procedure used in the preparation of the compound.

TABLE 4

| Example | Chemical Name | MP ° C. | MS | Ex. Pro. Used |
|---|---|---|---|---|
| 130 | 4-(2,4-dichloro-5-methoxyanilino)-7-{4-[(2-methoxy)ethoxy]phenyl}-3-quinolinecarbonitrile | 205–207 | 494.3, 496.3 (M + H) + | 1 |
| 131 | 4-(2-chloro-5-methoxy-anilino)-7-[5-(4-morpholinylmethyl)-3-thienyl]-3-quinolinecarbonitrile | 110–115 | 491.0 (M + H) + | 1 |
| 132 | 4-[4-(benzyloxy)-3-chloroanilino]-7-[3,4-bis(4-morpholinylmethyl)phenyl]-3-quinolinecarbonitrile | foam | 660.2 (M + H) + | 35 |
| 133 | 7-[3,4-bis(4-morpholinylmethyl)phenyl]-4-(2-chloro-5-methoxy-4-methylanilino)-3-quinolinecarbonitrile | 186–188 | 597.9 (M + H) + | 35 |
| 134 | 4-{3-chloro-4-[(1-methyl-1H-imidazol-2-yl)sulfanyl]anilino}-7-{4-[(4-hydroxy-1-piperidinyl)methyl]phenyl}-3-quinolinecarbonitrile | 230–232 | 581.2 (M + H) + | 1 |
| 135 | 4-{3-chloro-4-[(1-methyl-1H-imidazol-2-yl)sulfanyl]anilino}-7-{4-[(4-methyl-1-piperazinyl)methyl]phenyl}-3-quinolinecarbonitrile | 202–203 | 290.5 (M + 2H)2 + | 70 |
| 136 | 4-{3-chloro-4-[(1-methyl-1H-imidazol-2-yl)sulfanyl]anilino}-7-[4-(1-pipendinylmethyl)phenyl]-3-quinolinecarbonitrile | 158–160 | 283.3 (M + 2H)2 + | 70 |
| 137 | tert-butyl-4-{4-[4-({3-chloro-4-[(1-methyl-1H-imidazol-2-yl)sulfanyl]-phenyl}amino)-3-cyano-7-quinolinyl]benzyl}-1-piperazinecarboxylate | 184–186 | 666.4 (M + H) + | 1 |
| 138 | 4-({3-chloro-4-[(1-methyl-1H-imidazol-2-yl)sulfanyl]phenyl}amino)-7-{4-[(4-morpholinylmethyl)-phenyl}-3-quinolinecarbonitrile | 205–210 | 553.4 (M + H) + | 10 |
| 139 | 4-(2,4-dichloro-5-methoxyanilino)-7-[(E)-2-phenylethenyl]-3-quinolinecarbonitrile | 230–232 | 446.0 (M + H) + | 2 |
| 140 | 4-(2,4-dichloro-5-methoxyanilino)-7-(2-phenylethynyl)-3-quinolinecarbonitrile | 210–212 | 444.0, 446.0 (M + H) + | 91 |
| 141 | 4-(2,4-dichloro-5-methoxyanilino)-7-[2-(4-methylphenyl)ethynyl]-3-quinolinecarbonitrile | 223–225 | 458.0 (M + H) + | 91 |
| 142 | tert-butyl (E)-3-[3-cyano-4-(2,4-dichloro-5-methoxyanilino)-7-quinolinyl]-2-propenoate | 203–204 | 470.0 (M + H) + | 2 |
| 143 | 4-(2,4-dichloro-5-methoxyanilino)-7-(3-hydroxy-1-propynyl)-3-quinolinecarbonitrile | 245 (dec) | 398.0 400.1 (M + H) + | 91 |
| 144 | ethyl(1-{4-[3-cyano-4-(2,4-dichloro-5-methoxyanilino)-7-quinolinyl]benzyl}-4-piperidinyl)acetate | 142–144 | 603.3 605.4 (M + H) + | 41 |

TABLE 4-continued

| Example | Chemical Name | MP ° C. | MS | Ex. Pro. Used |
|---|---|---|---|---|
| 145 | ethyl 1{4-[3-cyano-4-(2,4-dichloro-5-methoxyanilino)-7-quinolinyl]benzyl}-2-piperidinecarboxylate | 78–80 | 588.9, 590.9 (M + H) + | 41 |
| 146 | 4-(2,4-dichloro-5-methoxyanilino)-7-[3-(4-morpholinyl)-1-propynyl]-3-quinolinecarbonitrile | 190–191 | 466.93 468.8 (M + H) + | 91 |
| 147 | 1-{4-[3-cyano-4-(2,4-dichloro-5-inethoxy-anilino)-7-quinolinyl]benzyl}-2-piperidinecarboxylic acid | 230 (dec) | 560.83 562.8 (M + H) + | 100 |
| 148 | ethyl 1-(4-{3-cyano-4-[(2,4-dichloro-5-methoxyphenyl)amino]-7-quinolinyl}benzyl)-3-piperidinecarboxylate | 67–70 | 588.8, 590.8 (M + H) + | 41 |
| 149 | 1-(4-{3-cyano-4-[(2,4-dichloro-5-methoxyphenyl)amino]-7-quinolinyl}benzyl)-3-piperidinecarboxylic acid | 235 (dec) | 560.8, 100 562.8 (M + H) + | |
| 150 | 4-[(2,4-dichloro-5-methoxyphenyl)amino]-7-{4-[(1,1-dioxido-4-thiomorpholinyl)methyl]phenyl}-3-quinolinecarbonitrile | 248–251 | 567.2, 569.2 (M + H) + | 41 |
| 151 | 4-[(2,4-dichloro-5-methoxyphenyl)amino]-7-{4-[(1-oxido-4-thiomorpholinyl)methyl]phenyl}-3-quinolinecarbonitrile | 244–247 | 549.2, 551.2 (M − H) − | 41 |
| 152 | 7-(3-chloro-1-propynyl)-4-[(2,4-dichloro-5-methoxyphenyl)amino]-3-quinolinecarbonitrile | 215–217 | 416.26, 418.26 (M + H) + | 102 |
| 153 | 4-[(2,4-dichloro-5-methoxyphenyl)amino)-7-[4-(4-thiomorpholinylmethyl)phenyl]-3-quinolinecarbonitrile | 216–219 | 535.3, 537.3 (M + H) + | 41 |
| 154 | 4-{3-chloro-4-[(1-methyl-1H-imidazol-2-yl)sulfanyl]anilino}-7-[5-(4-morpholinylmethyl)-2-furyl]-3-quinolinecarbonitrile | 224–226 | 557.1 (M + H) + | 41 |
| 155 | 4-{3-chloro-4-[(1-methyl-1H-imidazol-2-yl)sulfanyl]anilino}-7-[5-(1-piperidinylmethyl)-2-furyl]-3-quinolinecarbonitrile | 214–215 | 553.2 (M − H) − | 41 |
| 156 | 4-{3-chloro-4-[(1-methyl-1H-imidazol-2-yl)sulfanyl]anilino}-7-{5-[(4-ethyl-1-piperazinyl)methyl]-2-furyl}-3-quinolinecarbonitrile | 212–215 | 583.1 (M + H) + | 41 |
| 157 | 4-{3-chloro-4-[(1-methyl-1H-imidazol-2-yl)sulfanyl]anilino}-7-(5-{[4-(2-hydroxyethyl)-1-piperazinyl]methyl}-2-furyl)-3-quinolinecarbonitrile | 206–209 | 600.1 (M + H) + | 41 |
| 158 | 4-({3-chloro-4-[(1-methyl-1H-imidazol-2-yl)sulfanyl]phenyl}amino)-7-(5-formyl-2-furyl)-3-quinolinecarbonitrile | 258–261 | 486.2 (M + H) + | 1 |

TABLE 4-continued

| Example | Chemical Name | MP °C | MS | Ex. Pro. Used |
|---|---|---|---|---|
| 159 | 4-{3-chloro-4-[(1-methyl-1H-imidazol-2-yl)sulfanyl]anilino}-7-{5-[(4-hydroxy-1-piperidinyl)methyl]-2-thienyl}-3-quinolinecarbonitrile | 147–149 | 586.9 (M + H) + | 41 |
| 160 | 4-{3-chloro-4-[(1-methyl-1H-imidazol-2-yl)sulfanyl]anilino}-7-[5-(1-piperidinylmethyl)-2-thienyl]-3-quinolinecarbonitrile | 100 (dec) | 570.8 (M + H) + | 41 |
| 161 | 4-{3-chloro-4 [(1-methyl-1H-imidazol-2-yl)sulfanyl]anilino}-7-(5-{[4-(2-hydroxyethyl)-1-piperazinyl]methyl}-2-thienyl)-3-quinolinecarbonitrile | 145–147 | 616.4 (M + H) + | 41 |
| 162 | 4-(2,4-dichloro-5-methoxyanilino)-7-[5-(hydroxymethyl)-1-methyl-1H-pyrrol-2-yl]-3-quinolinecarbonitrile | 175 (dec) | 453.0 (M + H) + | 70 |
| 163 | 4-(2,4-dichloro-5-methoxyanilino)-7-(3-formyl-2-thienyl)-3-quinolinecarbonitrile | 231–232 | 454.0 (M + H) + | 1 |
| 164 | tert-butyl 2-[3-cyano-4-(2,4-dichloro-5-methoxyanilino)-7-quinolinyl]-1H-pyrrole-1-carboxylate | 135 (dec) | 509.0 (M + H) + | 1 |
| 165 | 7-[1,1′-biphenyl]-4-yl-4-(2,4-dichloro-5-methoxyanilino)-3-quinolinecarbonitrile | 235–236 | 496.1 (M + H) + | 1 |
| 166 | 4-(2,4-dichloro-5-methoxyanilino)-6-methoxy-7-[3-(4-morpholinyl)-1-propynyl]-3-quinoline-carbonitrile | 105–108 | 497.2 (M + H) + | 11 |
| 167 | 4-(4-chloro-5-methoxy-2-methylanilino)-7-[5-(4-morpholinylmethyl)-2-thienyl]-3-quinolinecarbonitrile | dec > 108 | 505 (M + H) + | 33 |
| 168 | 7-[4,5-bis(4-morpholinylmethyl)-2-thienyl]-4-(4-phenoxyanilino)-3-quinolinecarbonitrile | 158–160 | 618 (M + H) + | 1 |
| 169 | 7-[4,5-bis(4-morpholinyl)methyl)-2-thienyl]-4-{3-chloro-4-[(1-methyl-1H-imidazol-2-yl)sulfanyl]anilino}-3-quinolinecarbonitrile | 173–175 | 672 (M + H) + | 1 |
| 170 | 4-{3-chloro-4-[(1-methyl-1H-imidazol-2-yl)sulfanyl]anilino}-7-(5-formyl-2-pyridinyl)-3-quinolinecarbonitrile | 130 (dec) | 494.9 (M − H) − | 106 |
| 171 | 4-{3-chloro-4-[(1-methyl-1H-imidazol-2-yl)sulfanyl)anilino}-7-{5-](4-ethyl-1-piperazinyl)methyl]-2-pyridinyl}-3-quinolinecarbonitrile | 125–130 | 595.4 (M + H) + | 107 |
| 172 | 4-{3-chloro-4-[(1-methyl-1H-imidazol-2-yl)sulfanyl]anilino}-7-{5-[(4-hydroxy-1-piperizinyl)methyl]-2-pyridinyl}-3-quinolinecarbonitrile | 194–196 | 291.8 (M + 2H) + 2 | 106 |
| 173 | 4-{3-chloro-[(1-methyl-1H-imidazol-2-yl)sulfanyl]anilino}-7-(5-{[4-(1-pyrrolidinyl)-1-piperidinyl]methyl}-2-pyridinyl)-3-quinolinecarbonitrile | 183–185 | 635.5 (M + H) + | 106 |
| 174 | 7-(3-aminophenyl)-4-(2,4-dichloro-5-methoxyanilino)-3-quinolinecarbonitrile | 221–222 | 434.9 (M + H) + | 117 |
| 175 | 1-{[6-(4-{3-chloro-4-[(1-methyl-1H-imidazol-2-yl)sulfanyl]anilino}-3-cyano-7-quinolinyl)-3-pyridinyl]methyl}-4-piperidinecarboxylic acid | 166–168 | 610.2 (M + H) + | 100 |
| 176 | 1-{6-[3-cyano-4-(2,4-dichloro-5-methoxy-phenylamino)-quinolin-7-yl)-pyridin-3-ylmethyl}-piperidine-4-carboxylic acid methyl ester | 186–188 | 576.2, (M + H) + | 107 |
| 177 | 1-{6-[3-cyano-4-(2,4-dichloro-5-methoxy-phenylamino)-quinolin-7-yl]-pyridin-3-ylmethyl}-piperidine-4-carboxylic acid | 150 (dec) | 562.3 (M + H) | 100 |
| 178 | 4-({3-chloro-4-[(1-methyl-1H-imidazol-2-yl)sulfanyl]phenyl}amino)-7-(5-chloro-2-pyridinyl)-3-quinoline-carbonitrile | 205–207 | 500.7 (M − H) − | 108 |
| 179 | 4-[(2,4-dichloro-5-methoxyphenyl)amino]-7-[5-(4-ethyl-1-piperazinyl)-2-pyridinyl]-3-quinolinecarbonitrile | 232–234 | 532.9 (M + H) + | 108 |
| 180 | 4-({3-chloro-4-[(1-methyl-1H-imidazol-2-yl)sulfanyl]phenyl}amino)-7-[5-(1-pyridinyl)]-3-quinolinecarbonitrile | 175–177 | 566.4 (M + H) + | 106 |
| 181 | 4-({3-chloro-4-[(1-methyl-1H-imidazol-2-yl)sulfanyl]phenyl}amino)-6-[5-(4-ethyl-1-piperazinyl)-2-pyridinyl]-3-quinolinecarbonitrile | 150 (dec) | 581.2 (M + H) + | 108 |
| 182 | 4-({3-chloro-4-[(1-methyl]-1H-imidazol-2-yl)sulfanyl]phenyl}amino)-6-[5-(4-morpholinylmethyl)-2-pyridinyl]-3-quinolinecarbonitrile | 238–241 | 568.1 (M + H) + | 108 |
| 183 | 4-({3-chloro-4-[(1-methyl-1H-imidazol-2-yl)sulfanyl]phenyl}amino)-6-{5-[(4-methyl-1-piperazinyl)methyl]-2-pyridinyl}-3-quinolinecarbonitrile | 260–262 | 579.3 (M − H) | 108 |
| 184 | 4-({3-chloro-4-[(1-methyl-1H-imidazol-2-yl)sulfanyl]phenyl}amino)-6-[6-(4-morpholinyl)-3-pyridinyl]-3-quinolinecarbonitrile | 276–278 | 554.1 (M + H) + | 108 |
| 185 | 4-(2,4-dichloro-5-methoxyanilino)-7-[6-(4-morpholinyl)-3-pyridinyl]-3-quinolinecarbonitrile | >260 | 506.0 (M + H) + | 108 |

TABLE 4-continued

| Example | Chemical Name | MP ° C. | MS | Ex. Pro. Used |
|---|---|---|---|---|
| 186 | 4-(2,4-dichloro-5-methoxyanilino)-7-[2-(4-morphpolinyl)-5-pyrimidinyl]-3-quinolinecarbonitrile | >260 | 508.8 (M + H) + | 108 |
| 187 | 4-{3-chloro-4-[(1-methyl-1H-imidazol-2-yl)sulfanyl]anilino}-7-[5-(4-morpholinylmethyl)-2-pyridinyl]-3-quinolinecarbonitrile | 225–227 | 567.7 (M + H) + | 108 |
| 188 | 4-(2,4-dichloro-5-methoxyanilino)-7-{5-[(4-methyl-1-piperazinyl)methyl]-2-pyridinyl}-3-quinolinecarbonitrile | 212–215 | 533.1 (M + H) + | 108 |
| 189 | 4-{3-chloro-4-[(1-methyl-1H-imidazol-2-yl)sulfanyl]anilino}-7-{5-[(4-methyl-1-pipeiazinyl)---methyl]-2-pyridinyl}-3-quinolinecarbonitrile | 197–199 | 581.1 (M + H) + | 108 |
| 190 | 4-{3-chloro-4-[(1-methyl-1H-imidazol-2-yl)sufanyl]anilino}-7-[6-(4-morpholinyl)-3-pyridinyl]-3-quinolinecarbonitrile | >250 | 553.8 (M + H) + | 108 |
| 191 | 4-{3-chloro-4-[(1-methyl-1H-imidazol-2-yl)sufanyl]anilino}-7-[2-(4-morpholinyl)-5-pyrimidinyl]-3-quinolinecarbonitrile | >250 | 555 (M + H) + | 108 |
| 192 | 4-(2,4-dichloro-5-methoxyanilino)-7-{5-[(4-hydroxy-1-piperidnyl)methyl]-3-thienyl}-3-quinolinecarbonitrile | 187–189 | 539.1, 541.2 (M + H) + | 41 |
| 193 | 4-(2,4-dichloro-5-methoxyanilino)-7-{6-[4-(4-morpholinyl-methyl)phenoxy)-3-pyridinyl)-3-quinolinecarbonitrile | 176–178 | 612 (M + H) + | 106 |
| 194 | 4-(2,4-dichloro-5-methoxyanilino)-7-(4-methoxyphenyl)-3-quinolinecarbonitrile | 210–212 | 449.7, 451.7 (M + H) + | 83 |
| 195 | 4-{3-chloro-4-[(1-methyl-1H-imidazol-2-yl)sulfanyl]anilino}-7-[6-(4-ethyl-1-piperazinyl)-3-pyridinyl]-3-quinolinecarbonitrile | 254–256 | 580.8 (M + H) + | 108 |
| 196 | 4-{3-chloro-4-[(1-methyl-1H-imidazol-2-yl)sulfanyl]anilino}-7-[6-(4-methyl-1-piperazinyl)-3-pyridinyl-3-quinolinecarbonitrile | 227–279 | 566.8 (M + H) + | 108 |
| 197 | 4-(2,4-dichloro-5-methoxyanilino)-7-[6-(4-ethyl-1-piperazinyl)-3-pyridinyl]-3-quinolinecarbonitrile | 264–266 | 533.0 (M + H) + | 108 |
| 198 | 4-(2,4-dichloro-5-methoxyanilino)-7-[6-(4-methyl-1-piperazinyl)-3-pyridinyl]-3-quinolinecarbonitrile | 240–242 | 519 (M + H) + | 108 |
| 199 | 4-{3-chloro-4-[(1-methyl-1H-imidazol-2-yl)sulfanyl]anilino}-7-[6-(4-morpholinylmethyl)-2-pyridinyl]-3-quinolinecarbonitrile | 232–234 | 567.8 (M + H) + | 108 |
| 200 | 4-(2,4-dichloro-5-methoxyanilino)-7-[6-(4-morpholinylmethyl)-2-pyridinyl]-3-quinolinecarbonitrile | 181–183 | 520.2 (M + H) + | 108 |
| 201 | 4-{3-chloro-4-[(1-methyl-1H-imidazol-2-yl)sulfanyl]anilino}-7-{6-[(4-ethyl-1-piperazinyl)methyl]-2-pyridinyl}-3-quinolinecarbonitrile | 214–216 | 595.2 (M + H) + | 108 |
| 202 | 4-{3-chloro-4-[(1-methyl-1H-imidazol-2-yl)sulfanyl)anilino}-7-{6-[(4-methyl-1-piperazinyl)methyl)-2-pyridinyl}-3-quinolinecarbonitrile | 157–159 | 581.4 (M + H) + | 108 |
| 203 | 4-({3-chloro-4-[(1-methyl-1H-imidazol-2-yl)sulfanyl]phenyl}amino)-7-[4-(4-morpholinylmethyl)-2-pyridinyl]-3-quinolinecarbonitrile | 205–207 | 568.4 (M + H) + | 108 |
| 204 | 4-[(2,4-dichloro-5-methoxyphenyl)amino]-7-[4-(4-morpholinylmethyl)-2-pyridinyl]-3-quinolinecarbonitrile | 180–182 | 520.2 (M + H) + | 108 |
| 205 | 4-({3-chloro-4-[(1-methyl-1H-imidazol-2-yl)sulfanyl]phenyl}amino)-7-{4-[(4-ethyl-1-piperazinyl)methyl]-2-pyridinyl}-3-quinolinecarbonitrile | 150–153 | 595.2 (M + H) + | 108 |
| 206 | 4-({3-chloro-4-[(1-methyl-1H-imidazol-2-yl)sulfanyl)phenyl}amino)-7-{4-[(4-methyl-1-piperazinyl)methyl]-2-pyridinyl}-3-quinolinecarbonitrile | 208–210 | 581.2 (M + H) + | 108 |
| 207 | 4-({3-chloro-4-[(1-methyl-1H-imidazol-2-yl)sulfanyl]phenyl}amino)-7-[3-(4-morpholinylmethyl)-2-pyridinyl]-3-quinolinecarbonitrile | 195 (dec) | 567.8 (M + H) + | 166 |
| 208 | 4-({3-chloro-4-[(1-methyl-1H-imidazol-2-yl)sulfanyl)phenyl}amino)-7-{3-[(4-ethyl-1-piperazinyl)methyl]-2-pyridinyl}-3-quinolinecarbonitrile | 187–190 | 595.38 (M + H) + | 106 |
| 209 | 4-({3-chloro-4-[(1-methyl-1H-imidazol-2-yl)sulfanyl]phenyl}amino)-7-{3-[(4-methyl-1-piperazinyl)methyl]-2-pyridinyl}-3-quinolinecarbonitrile | 217–220 | 581.35 (M + H) + | 106 |
| 210 | 4-({3-chloro-4-[(1-methyl-1H-imidazol-2-yl)sulfanyl]phenyl}amino)-7-{6-[4-(1-pyrrolidinyl)-1-piperidinyl-3-pyridinyl}-3-quinolinecarbonitrile | 230 (dec) | 621.2 (M + H) + | 110 |
| 211 | 4-({3-chloro-4-[(1-methyl-1H-imidazol-2-yl)sulfanyl]phenyl}amino)-7-[6-(1-piperidinyl)-3- | >260 | 551.0 (M + H) + | 110 |

TABLE 4-continued

| Example | Chemical Name | MP ° C. | MS | Ex. Pro. Used |
|---|---|---|---|---|
| | pyridinyl]-3-quinoline-carbonitrile | | | |
| 212 | 4-({3-chloro-4-[(1-methyl-1H-imidazol-2-yl)sulfanyl]phenyl}amino)-7-{6-[(2-methoxyethyl)(methyl)amino]-3-pyridinyl}-3-quinolinecarbonitrile | 224–226 | 555.9 (M + H) + | 110 |
| 213 | ethyl 1-{5-[4-({3-chloro-4-[(1-methyl-1H-imidazol-2-yl)sulfanyl]phenyl}amino)-3-cyano-7-quinolinyl]-2-pyridinyl}-4-piperidinecarboxylate | 253–255 | 624.2 (M + H) + | 109 |
| 214 | 4-({3-chloro-4-[(1-methyl-1H-imidazol-2-yl)sulfanyl)phenyl}amino)-7-[6-(4-hydroxy-1-piperidinyl)-3-pyridinyl]-3-quinolinecarbonitrile | 178–180 | 568.2 (M + H) + | 109 |
| 215 | 4-({3-chloro-4-[(1-methyl-1H-imidazol-2-yl)sulfanyl)phenyl}amino)-7-{6-[4-(2-hydroxyethyl)-1-piperazinyl]-3-pyridinyl}-3-quinoline-carbonitrile | 239–241 | 597.2 (M + H) + | 109 |
| 216 | 4-({3-chloro-4-[(1-methyl-1H-imidazol-2-yl)sulfanyl)phenyl}amino)-7-{6-[(2-hydroxyethyl)(methyl)amino]-3-pyridinyl}-3-quinolinecarbonitrile | 228 (dec) | 542.3 (M + H) + | 1 |
| 217 | 4-({3-chloro-4-[(1-methyl-1H-imidazol-2-yl)sulfanyl)phenyl}amino)-7-(5-{[4-(2-hyduoxyethyl)-1-piperazinyl]methyl}-2-pyridinyl)-3-quinolinecarbonitrile | 160–163 | 611.3 (M + H) + | 106 |
| 218 | 4-(2,4-dichloro-5-methoxyanilino)-7-{4-[(4-methyl-1-piperazinyl)]phenyl}-3-quinolinecarbonitrile | 190–192 | 532, 534 (M + H) + | 41 |
| 219 | 4-({3-chloro-4-[(1-methyl-1H-imidazol-2-yl)sulfanyl]phenyl}amino)-7-(5-thiomorpholinylmethyl)-2-pyridinyl]-3-quinolinecarbonitrile | 220–222 | 584.13 (M + H) + | 106 |
| 220 | 4-({3-chloro-4-[(1-methyl-1H-imidazol-2-yl)sulfanyl)phenyl}amino)-7-{6-[(4-ethyl-1-piperazinyl)methyl]-3-pyridinyl}-3-quinolinecarbonitrile | 192–195 | 595.58 (M + H) + | 109 |
| 221 | 4-({3-chloro-4-[(1-methyl-1H-imidazol-2-yl)sulfanyl)phenyl}amino)-7-{6-[(4-methyl-1-piperazinyl)methyl]-3-pyridinyl}-3-quinolinecarbonitrile | 228–230 | 581.2 (M + H) + | 109 |
| 222 | 4-({3-chloro-4-[(1-methyl-1H-imidazol-2-yl)sulfanyl)phenyl}amino)-7-(6-formyl-3-pyridinyl)-3-quinoline-carbonitrile | >250 | 497.41 (M + H) + | 110 |
| 223 | 4-({3-chloro-4-[(1-methyl-1H-imidazol-2-yl)sulfanyl)phenyl}amino)-7-{6-[(4-hydroxy-1-piperidinyl)methyl]-3-pyridinyl}-3-quinolinecarbonitrile | 242–244 | 580.2 (M − H) − | 109 |
| 224 | 4-({3-chloro-4-[(1-methyl-1H-imidazol-2-yl)sulfanyl)phenyl}amino)-7-[6-(1-piperidinylmethyl)-3-pyridinyl}-3-quinolinecarbonitrile | 246–248 | 565.94 (M + H) + | 109 |
| 225 | 4-({3-chloro-4-[(1-methyl-1H-imidazol-2-yl)sulfanyl)phenyl}amino)-7-{6-[(4-isopropyl-1-piperazinyl)methyl]-3-pyridinyl}-3-quinolinecarbonitrile | 225–227 | 609.94 (M + H) + | 41 |
| 226 | 4-(2,4-dichloro-5-methoxyanilino)-7-[1-methyl-2-(4-morpholinylmethyl)-1H-imidazol-5-yl]-3-quinolinecarbonitrile | 140–143 | 523.0 (M + H) | 41 |
| 227 | 4-(2,4-dichloro-5-methoxyanilino)-7-{1-methyl-2-[(4-methyl-1-piperazinyl)methyl]-1H-imidazol-5-yl}-3-quinolinecarbonitrile | 156–159 | 536.1 (M + H) | 41 |
| 228 | 4-(2,4-dichloro-5-methoxyanilino)-7-(2-formyl-1-methyl-1H-imidazol-5-yl)-6-methoxy-3-quinolinecarbonitrile | 141–144 | 482.0, 484.0 (M + H) | 130 |
| 229 | 4-(2,4-dichloro-5-methoxyanilino)-7-[4-({[2-(2-pyridinyl)ethyl]amino}methyl)phenyl]-3-quinolinecarbonitrile | 256–258 | 554.0 (M + H) | 41 |
| 230 | 4-(2,4-dichloro-5-methoxyanilino)-7-(4-{[4-(2-hydroxyethyl)-1-piperazinyl]methyl}phenyl)-3-quinolinecarbonitrile | 130–133 | 562.0, 564.1 (M + H) | 41 |
| 231 | methyl 1-{4-[3-cyano-4-(2,4-dichloro-5-methoxyanilino)-7-quinolinyl]benzyl}-4-piperidinecarboxylate | 278–280 | 575.0, 577.0 (M + H) | 41 |
| 232 | 4-(2,4-dichloro-5-methoxyanilino)-6-methoxy-7-[1-methyl-2-(4-morpholinylmethyl)-1H-imidazol-5-yl]-3-quinolinecarbonitrile | 248–252 | 553.0, 555.0 (M + H) | 41 |
| 233 | 4-(2,4-dichloro-5-methoxyanilino)-6-methoxy-7-{1-methyl-2-[(4-methyl-1-piperazinyl)methyl]-1H-imidazol-5-yl}-3-quinolinecarbonitrile | 234–236 | 566.0, 568.0 (M + H) | 41 |
| 234 | 4-(2-chloro-5-methoxy-4-methylanilino)-7-[4-(4-morpholinylmethyl)phenyl]-3-quinolinecarbonitrile | 140–143 | 499.1, 501.0 (M + H) | 26 |
| 235 | 4-(2-chloro-4-fluoro-5-methoxyanilino)-7-[4-(4-morpholinylmethyl)phenyl]-3-quinolinecarbonitrile | 174–178 | 503.0, 505.0 (M + H) | 26 |
| 236 | 4-(2-chloro-5-methoxyanilino)-7-[4-(4-morpholinylmethyl)phenyl]-3-quinolinecarbonitrile | 160–163 | 485.0, 487.1 (M + H) | 26 |

TABLE 4-continued

| Example | Chemical Name | MP ° C. | MS | Ex. Pro. Used |
|---|---|---|---|---|
| 237 | 1-{4-[3-cyano-4-(2,4-dichloro-5-methoxy-anilino)-7-quinolinyl]-benzyl}-4-piperidine-carboxylic acid | 248 | 560.9 (M + H) | 100 |

Representative compounds of Formula I of the invention may also be prepared by the following combinatorial procedures.

COMBINATORIAL PREPARATION OF EXAMPLE 135

4-{3-Chloro-4-[(1-methyl-1H-imidazol-2-yl) sulfanyl]anilino}-7-{4-[(4-methyl-1-piperazinyl) methyl]phenyl}-3-quinolinecarbonitrile Step A: To a mixture of 4-{3-chloro-4-[(1-methyl-1H-imidazol-2-yl)sulfanyl]anilino}-7-iodo-3-quinolinecarbonitrile (846 mg, 1.8 mmol), 4-formylbenzeneboronic acid (540 mg, 3.6 mmol) and sodium carbonate (954 mg, 9 mmol) in ethylene glycol dimethyl ether (20 mL) and water (10 mL) was added tetrakis(triphenylphosphine)palladium (207 mg, 10 mol %). The resulting mixture was heated at 85° C. for 6–18 hours. The mixture was cooled to room temperature and concentrated. The residue was suspended in N,N'-dimethylformamide (24 mL) and filtered. The filtrate containing 4-{3-chloro-4-[(1-methyl-1H-imidazol-2-yl) sulfanyl]anilino}-7-(4-formylphenyl)-3-quinolinecarbonitrile was used directly in Step B.

Step B: A solution of 4-{3-chloro-4-[(1-methyl-1H-imidazol-2-yl)sulfanyl]anilino}-7-(4-formylphenyl)-3-quinolinecarbonitrile in N,N'-dimethylformamide (0.15 mmol, 2 mL, 1/12 th of the solution prepared in Step A) was diluted with N,N'-dimethylformamide (4 mL) and dichloromethane (18 mL), then 1-methylpiperazine (45.5 mg, 0.45 mmol) and acetic acid (90 uL, 1.5 mmol) were added. The mixture was shaken on an orbital shaker for 10–30 minutes, then sodium cyanoborohydride (63 mg, 1.0 mmol) was added and shaking continued for 12–16 hours. The solvent was evaporated and the product purified by semi-preparative RP-HPLC to give 4-{3-chloro-4-[(1-methyl-1H-imidazol-2-yl)sulfanyl]anilino}-7-(4-[(4-methyl-1-piperazinyl)methyl]phenyl}-3-quinolinecarbonitrile (22 mg).

Semi-preparative Reverse Phase (RP)-HPLC conditions:

Sample dissolved in methanol (1.5 mL);

Column: YMC Pro C18 20 mm×50 mm 5 um;

Solvent A: 0.02% trifluoroacetic acid/water; Solvent B: 0.02% trifluoroacetic acid/acetonitrile;

Gradient: Time 0 min: 95% A; 2 min: 95% A; 15 min: 10% A; 16 min: 10% A;

Flow rate 22.5 mL/min;

Detection: 254 nm DAD.

Examples 238–271 in Table 5 were synthesized using 4-{3-chloro-4-[(1-methyl-1H-imidazol-2-yl)sulfanyl] anilino}-7-iodo-3-quinolinecarbonitrile with 4-formylbenzeneboronic acid, 3-formylbenzeneboronic acid, 2-formylfuran-5-boronic acid, 5-formyl-2-thiophene boronic acid, 2-bromo-5-formylpyridine* and 4-hydroxypiperidine, N,N-dimethylethylenediamine, 4-(1-pyrrolidinyl)-piperidine, 4-(aminomethyl)pyridine, dimethylamine, morpholine, ethanolamine, 1-methylpiperazine, N-(3-aminopropyl)morpholine, piperidine, 1-ethylpiperazine and 1-(2-hydroxyethyl) piperazine and following the combinatorial procedure outlined for Example 135:

*Note: 2-Bromo-5-formylpyridine was coupled with 7-bromo-4-{3-chloro-4-[(1-methyl-1H-imidazol-2-yl)sulfanyl]anilino}-3-quinolinecarbonitrile under the following conditions. A mixture of 7-bromo-4-{3-chloro-4-[(1-methyl-1H-imidazol-2-yl)sulfanyl]anilino}-3-quinolinecarbonitrile (942 mg, 2 mmol), 2-bromo-5-formylpyridine (372 mg, 2 mmol), hexamethylditin (655 mg, 2 mmol), tetrakis(triphenylphosphine)palladium (440 mg, 0.4 mmol) and lithium chloride (250 mg, 6 mmol) in dioxane (20 mL) was heated to 110° C. for 4 hours. The mixture was cooled to room temperature and concentrated. The residue was suspended in N,N'-dimethylformamide (24 mL) and filtered. The filtrate was used directly in Step B.

TABLE 5

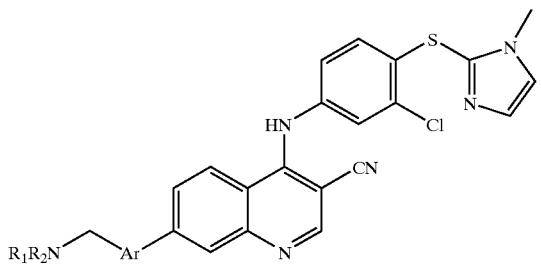

| Example | Ar | R1R2N | Theoretical (M + H)+ | Exptl. (M + H)+ | LCMS Retent. Time min. |
|---|---|---|---|---|---|
| 135 | 1,4-phenyl | 1-methylpiperazine | 580.20447 | 580.20344 | 1.86 |
| 238 | 1,4-phenyl | N,N-dimethylethylenediamine | 568.20447 | 568.20373 | 1.71 |
| 239 | 1,4-phenyl | 4-(1-pyrrolidinyl)-piperidine | 634.25142 | 634.25036 | 1.74 |
| 240 | 1,4-phenyl | 4-(aminomethyl)pyridine | 588.17317 | 588.17206 | 1.8 |
| 241 | 1,4-phenyl | dimethylamine | 525.16227 | 525.16159 | 1.85 |
| 243 | 1,4-phenyl | ethanolamine | 541.15719 | 541.15618 | 1.81 |
| 244 | 1,4-phenyl | N-(3-aminopropyl)morpholine | 624.23068 | 624.22949 | 1.72 |
| 245 | 1,4-phenyl | 1-ethylpiperazine | 594.22012 | 594.21914 | 1.87 |
| 246 | 1,4-phenyl | 1-(2-hydroxyethyl)piperazine | 610.21504 | 610.21412 | 1.84 |
| 247 | 1,3-phenyl | 4-hydroxypiperidine | 581.18849 | 581.18731 | 1.89 |

TABLE 5-continued

| Example | Ar | R1R2N | Theoretical (M + H)+ | Exptl. (M + H)+ | LCMS Retent. Time min. |
|---|---|---|---|---|---|
| 248 | 1,3-phenyl | N,N-dimethylethylenediamine | 568.20447 | 568.20383 | 1.75 |
| 249 | 1,3-phenyl | 4-(1-pyrrolidinyl)-piperidine | 634.25142 | 634.25042 | 1.78 |
| 250 | 1,3-phenyl | 4-(aminomethyl)pyridine | 588.17317 | 588.17203 | 1.84 |
| 251 | 1,3-phenyl | dimethylamine | 525.16227 | 525.16147 | 1.9 |
| 252 | 1,3-phenyl | morpholine | 567.17284 | 567.17187 | 1.91 |
| 253 | 1,3-phenyl | ethanolamine | 541.15719 | 541.15618 | 1.86 |
| 254 | 1,3-phenyl | 1-methylpiperazine | 580.20447 | 580.20358 | 1.81 |
| 255 | 1,3-phenyl | N-(3-aminopropyl)morpholine | 624.23068 | 624.22955 | 1.77 |
| 256 | 1,3-phenyl | piperidine | 565.19357 | 565.19275 | 2 |
| 257 | 1,3-phenyl | 1-ethylpiperazine | 594.22012 | 594.21928 | 1.83 |
| 258 | 1,3-phenyl | 1-(2-hydroxyethyl)piperazine | 610.21504 | 610.21434 | 1.9 |
| 259 | 2,5-furyl | 4-hydroxypiperidine | 571.16775 | 571.16671 | 1.81 |
| 260 | 2,5-furyl | N,N-dimethylethylenediamine | 558.18374 | 558.18267 | 1.69 |
| 261 | 2,5-furyl | 4-(1-pyrrolidinyl)-piperidine | 624.23069 | 624.22970 | 1.71 |
| 262 | 2,5-furyl | ethanolamine | 531.13645 | 531.13573 | 1.81 |
| 263 | 2,5-furyl | 1-methylpiperazine | 570.18374 | 570.18268 | 1.84 |
| 264 | 2,5-furyl | N-(3-aminopropyl)morpholine | 614.20995 | 614.20898 | 1.83 |
| 265 | 2,5-thienyl | N,N-dimethylethylenediamine | 574.16089 | 574.15973 | 1.73 |
| 266 | 2,5-thienyl | 4-(1-pyrrolidinyl)-piperidine | 640.20784 | 640.20653 | 1.76 |
| 267 | 2,5-thienyl | ethanolamine | 547.11361 | 547.11303 | 1.8 |
| 268 | 2,5-thienyl | N-(3-aminopropyl)morpholine | 630.18710 | 630.18600 | 1.8 |
| 269 | 2,5-thienyl | 1-ethylpiperazine | 600.17654 | 600.17561 | 1.93 |
| 270 | 2,5-pyridyl | N,N-dimethylethylenediamine | 569.19972 | 569.19879 | 1.66 |
| 271 | 2,5-pyridyl | N-(3-aminopropyl)morpholine | 625.22593 | 625.22502 | 1.66 |

LCMS conditions: Hewlett Packard 1100 MSD; YMC ODS-AM 2.0 mm×50 mm 5 u column at 23° C.; 3 μL injection; Solvent A: 0.02% TFA/water; Solvent B: 0.02% TFA/acetonitrile; Gradient: Time 0: 95% A; 0.3 min: 95% A; 4.7 min: 10% A; 4.9 min: 95% A; Post time 1 min. Flow rate 1.5 mL/min; Detection: 254 nm DAD; API-ES Scanning Mode Positive 150–700; Fragmentor 70 mV.

Examples 272–328 in Table 6 were synthesized using 4-(2,4-dimethylanilino)-7-iodo-3-quinolinecarbonitrile with 4-formylbenzeneboronic acid, 3-formylbenzenediamine acid, 2-formylfuran-5-boronic acid, 5-formyl-2-thiophene boronic acid, 5-formyl-3-thiophene boronic acid and 4-hydroxypiperidine, N,N-dimethylethylenediamine, 4-(1-pyrrolidinyl)piperidine, 4-(aminomethyl)pyridine, histamine, morpholine, ethanolamine, 1-methylpiperzine, N-(3-aminopropyl)morpholine, piperidine, 1-ethylpiperazine and 1-(2-hydroxyethyl)piperazine and following the combinatorial procedure outlined for Example 135:

TABLE 6

| Example | Ar | R1R2N | Ion observed | Theoretical | Exptl. | HPLC Retent. Time Min. |
|---|---|---|---|---|---|---|
| 272 | 1,4-phenyl | 4-hydroxypiperidine | [M + 2H]2+ | 232.12826 | 232.12798 | 2.01 |
| 273 | 1,4-phenyl | N,N-dimethylethylenediamine | [M + 2H]2+ | 225.63625 | 225.63614 | 1.78 |

TABLE 6-continued

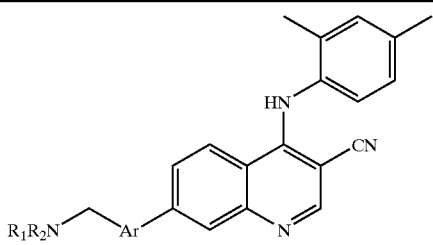

| Example | Ar | R1R2N | Ion observed | Theoretical | Exptl. | HPLC Retent. Time Min. |
|---|---|---|---|---|---|---|
| 274 | 1,4-phenyl | 4-(1-pyrrolidinyl)-piperidine | [M + 2H]2+ | 258.65973 | 258.65933 | 1.82 |
| 275 | 1,4-phenyl | 4-(aminomethyl)pyridine | [M + 2H]2+ | 235.62060 | 235.62029 | 1.97 |
| 276 | 1,4-phenyl | histamine | [M + 2H]2+ | 237.12605 | 237.12564 | 1.88 |
| 277 | 1,4-phenyl | morpholine | [M + 2H]2+ | 225.12043 | 225.12020 | 2.07 |
| 278 | 1,4-phenyl | ethanolamine | [M + 2H]2+ | 212.11261 | 212.11259 | 1.98 |
| 279 | 1,4-phenyl | 1-methylpiperazine | [M + 2H]2+ | 231.63625 | 231.63594 | 2.02 |
| 280 | 1,4-phenyl | N-(3-aminopropyl)morpholine | [M + 2H]2+ | 253.64936 | 253.64883 | 1.81 |
| 281 | 1,4-phenyl | piperidine | [M + 2H]2+ | 224.13080 | 224.13051 | 2.14 |
| 282 | 1,4-phenyl | 1-ethylpiperazine | [M + 2H]2+ | 238.64408 | 238.64370 | 2.02 |
| 283 | 1,4-phenyl | 1-(2-hydroxyethyl)piperazine | [M + 2H]2+ | 246.64153 | 246.64104 | 1.98 |
| 284 | 1,3-phenyl | 4-hydroxypiperidine | [M + 2H]2+ | 232.12826 | 232.12800 | 2.04 |
| 285 | 1,3-phenyl | N,N-dimethylethylenediamine | [M + 2H]2+ | 225.63625 | 225.63612 | 1.83 |
| 286 | 1,3-phenyl | 4-(1-pyrrolidinyl)-piperidine | [M + 2H]2+ | 258.65973 | 258.65934 | 1.85 |
| 287 | 1,3-phenyl | 4-(aminomethyl)pyridine | [M + 2H]2+ | 235.62060 | 235.62027 | 2.08 |
| 288 | 1,3-phenyl | histamine | [M + 2H]2+ | 237.12605 | 237.12565 | 1.86 |
| 289 | 1,3-phenyl | morpholine | [M + 2H]2+ | 225.12043 | 225.12021 | 2.06 |
| 290 | 1,3-phenyl | ethanolamine | [M + 2H]2+ | 212.11261 | 212.11254 | 1.96 |
| 291 | 1,3-phenyl | 1-methylpiperazine | [M + 2H]2+ | 231.63625 | 231.63591 | 2.11 |
| 292 | 1,3-phenyl | N-(3-aminopropyl)morpholine | [M + 2H]2+ | 253.64936 | 253.64931 | 1.96 |
| 293 | 1,3-phenyl | piperidine | [M + 2H]2+ | 224.13080 | 224.13055 | 2.25 |
| 294 | 1,3-phenyl | 1-ethylpiperazine | [M + 2H]2+ | 238.64408 | 238.64375 | 2.13 |
| 295 | 1,3-phenyl | 1-(2-hydroxyethyl)piperazine | [M + 2H]2+ | 246.64153 | 246.64109 | 2.1 |
| 296 | 2,5-furyl | 4-hydroxypiperidine | [M + 2H]2+ | 227.11789 | 227.11787 | 1.96 |
| 297 | 2,5-furyl | N,N-dimethylethylenediamine | [M + 2H]2+ | 220.62588 | 220.62579 | 1.8 |
| 298 | 2,5-furyl | 4-(1-pyrrolidinyl)-piperidine | [M + 2H]2+ | 253.64936 | 253.64889 | 1.79 |
| 299 | 2,5-furyl | 4-(aminomethyl)pyridine | [M + 2H]2+ | 230.61023 | 230.60992 | 1.87 |
| 300 | 2,5-furyl | histamine | [M + 2H]2+ | 232.11568 | 232.11548 | 1.73 |
| 301 | 2,5-furyl | morpholine | [M + 2H]2+ | 220.11007 | 220.11022 | 1.99 |
| 302 | 2,5-furyl | ethanolamine | [M + Na]1+ | 435.17915 | 435.17826 | 2 |
| 303 | 2,5-furyl | 1-methylpiperazine | [M + 2H]2+ | 226.62588 | 226.62557 | 1.99 |
| 304 | 2,5-furyl | piperidine | [M + 2H]2+ | 219.12043 | 219.12034 | 2.12 |
| 305 | 2,5-furyl | 1-ethylpiperazine | [M + 2H]2+ | 233.63371 | 233.63350 | 2.01 |
| 306 | 2,5-furyl | 1-(2-hydroxyethyl)piperazine | [M + 2H]2+ | 241.63117 | 241.63072 | 1.99 |
| 307 | 2,5-thienyl | 4-hydroxypiperidine | [M + 2H]2+ | 235.10647 | 235.10634 | 2.04 |
| 308 | 2,5-thienyl | N,N-dimethylethylenediamine | [2M + H]1+ | 911.43602 | 911.43583 | 1.84 |
| 309 | 2,5-thienyl | 4-(1-pyrrolidinyl)-piperidine | [M + 2H]2+ | 261.63794 | 261.63756 | 1.86 |
| 310 | 2,5-thienyl | 4-(aminomethyl)pyridine | [M + 2H]2+ | 238.59881 | 238.59845 | 1.95 |
| 311 | 2,5-thienyl | histamine | [M + 2H]2+ | 240.10426 | 240.10388 | 1.83 |
| 312 | 2,5-thienyl | morpholine | [M + 2H]2+ | 228.09864 | 228.09863 | 2.05 |
| 313 | 2,5-thienyl | ethanolamine | [M + 2H]2+ | 215.09082 | 215.09083 | 2.06 |
| 314 | 2,5-thienyl | 1-methylpiperazine | [M + 2H]2+ | 234.61446 | 234.61417 | 2.17 |
| 315 | 2,5-thienyl | 1-ethylpiperazine | [M + 2H]2+ | 241.62229 | 241.62195 | 2.18 |
| 316 | 2,5-thienyl | 1-(2-hydroxyethyl)piperazine | [M + 2H]2+ | 249.61974 | 249.61929 | 2.13 |
| 317 | 2,4-thienyl | 4-hydroxypiperidine | [M + 2H]2+ | 235.10647 | 235.10622 | 2.05 |
| 318 | 2,4-thienyl | N,N-dimethylethylenediamine | [M + 2H]2+ | 228.61446 | 228.61431 | 1.75 |
| 319 | 2,4-thienyl | 4-(1-pyrrolidinyl)-piperidine | [M + 2H]2+ | 261.63794 | 261.63739 | 1.96 |
| 320 | 2,4-thienyl | 4-(aminomethyl)pyridine | [M + 2H]2+ | 238.59881 | 238.59848 | 2 |
| 321 | 2,4-thienyl | histamine | [M + 2H]2+ | 240.10426 | 240.10389 | 1.93 |
| 322 | 2,4-thienyl | morpholine | [M + 2H]2+ | 228.09864 | 228.09856 | 2.08 |
| 323 | 2,4-thienyl | ethanolamine | [M + 2H]2+ | 215.09082 | 215.09055 | 2.06 |
| 324 | 2,4-thienyl | 1-methylpiperazine | [M + 2H]2+ | 234.61446 | 234.61414 | 2.12 |
| 325 | 2,4-thienyl | N-(3-aminopropyl)morpholine | [M + 2H]2+ | 256.62757 | 256.62711 | 1.96 |
| 326 | 2,4-thienyl | piperidine | [M + 2H]2+ | 227.10901 | 227.10880 | 2.18 |
| 327 | 2,4-thienyl | 1-ethylpiperazine | [M + 2H]2+ | 241.62229 | 241.62185 | 2.15 |
| 328 | 2,4-thienyl | 1-(2-hydroxyethyl)piperazine | [M + 2H]2+ | 249.61974 | 249.61930 | 2.12 |

Examples 329–350 in Table 7 were synthesized using 4-(4-bromo-2-chloro-6-methylanilino)-7-iodo-3-quinolinecarbonitrile with 2-formylfuran-5-boronic acid and 5-formyl-2-thiophene boronic acid and 4-hydroxypiperidine, N,N-dimethylethylenediamine, 4-(1-pyrrolidinyl)-piperidine, 4-(aminomethyl)pyridine, histamine, morpholine, ethanolamine, 1-methylpiperazine, N-(3-aminopropyl)morpholine, piperidine, 1-ethylpiperazine and 1-(2-hydroxyethyl)piperazine and following the combinatorial procedure outlined for Example 135:

TABLE 7

| Example | Ar | R1R2N | Ion observed | Theoretical | Exptl. | HPLC Ret. time |
|---|---|---|---|---|---|---|
| 329 | 2,5-furyl | 4-hydroxypiperidine | [M + 2H]2+ | 276.04584 | 276.04572 | 2.37 |
| 330 | 2,5-furyl | N,N-dimethylethylenediamine | [M + 2H]2+ | 269.55383 | 269.55343 | 2.17 |
| 331 | 2,5-furyl | 4-(1-pyrrolidinyl)-piperidine | [M + 3H]3+ | 202.05396 | 202.05603 | 2.19 |
| 332 | 2,5-furyl | 4-(aminomethyl)pyridine | [M + 2H]2+ | 279.53818 | 279.53778 | 2.19 |
| 333 | 2,5-furyl | histamine | [M + 2H]2+ | 281.04363 | 281.04341 | 2.3 |
| 334 | 2,5-furyl | morpholine | [M + 2H]2+ | 269.03801 | 269.03780 | 2.4 |
| 335 | 2,5-furyl | ethanolamine | [2M + H]1+ | 1021.09892 | 1021.09798 | 2.57 |
| 336 | 2,5-furyl | 1-methylpiperazine | [M + 2H]2+ | 275.55383 | 275.55330 | 2.58 |
| 337 | 2,5-furyl | N-(3-aminopropyl)morpholine | [M + 2H]2+ | 297.56694 | 297.56624 | 2.44 |
| 338 | 2,5-furyl | piperidine | [M + 2H]2+ | 268.04838 | 268.04842 | 2.78 |
| 339 | 2,5-furyl | 1-ethylpiperazine | [M + 2H]2+ | 282.56165 | 282.56102 | 2.65 |
| 340 | 2,5-furyl | 1-(2-hydroxyethyl)piperazine | [M + 2H]2+ | 290.55911 | 290.55849 | 2.54 |
| 341 | 2,5-thienyl | 4-hydroxypiperidine | [M + 2H]2+ | 284.03441 | 284.03424 | 2.64 |
| 342 | 2,5-thienyl | N,N-dimethylethylenediamine | [M + 2H]2+ | 277.54241 | 277.54183 | 2.43 |
| 343 | 2,5-thienyl | 4-(1-pyrrolidinyl)-piperidine | [M + 2H]2+ | 310.56588 | 310.56510 | 2.44 |
| 344 | 2,5-thienyl | 4-(aminomethyl)pyridine | [M + 2H]2+ | 287.52676 | 287.52607 | 2.57 |
| 345 | 2,5-thienyl | histamine | [M + 2H]2+ | 289.03221 | 289.03143 | 2.47 |
| 346 | 2,5-thienyl | Morpholine | [2M + H]1+ | 1105.08452 | 1105.08508 | 2.71 |
| 347 | 2,5-thienyl | ethanolamine | [M + 2H]2+ | 264.01876 | 264.01862 | 2.62 |
| 348 | 2,5-thienyl | 1-methylpiperazine | [M + 2H]2+ | 283.54241 | 283.54177 | 2.67 |
| 349 | 2,5-thienyl | N-(3-aminopropyl)morpholine | [M + 2H]2+ | 305.55551 | 305.55454 | 2.47 |
| 350 | 2,5-thienyl | piperidine | [M + H]+ | 551.01 | 551.07 | 2.84 |

Examples 351–382 in Table 8 were synthesized using 4-(4-bromo-2-chloro-6-methylanilino)-7-iodo-3-quinolinecarbonitrile with 4-formylbenzeneboronic acid, 3-formylbenzeneboronic acid and 5-formyl-3-thiophene boronic acid with 4-hydroxypiperidine, N,N-dimethylethylenediamine, 4-(1-pyrrolidinyl)-piperidine, 4-(aminomethyl)pyridine, histamine, morpholine, ethanolamine, 1-methylpiperazine, N-(3-aminopropyl)morpholine, piperidine, 1-ethylpiperazine and 1-(2-hydroxyethyl)piperazine and following the combinatorial procedure outlined for Example 135:

TABLE 8

| Example | Ar | R1R2N | Ion observed | Theoretical | Exptl. | HPLC Ret. time |
|---|---|---|---|---|---|---|
| 351 | 1,4-phenyl | 4-hydroxypiperidine | [M + 3H]3+ | 224.77484 | 224.77473 | 1.89 |
| 352 | 1,4-phenyl | N,N-dimethylethylenediamine | [M + 2H]2+ | 323.67461 | 323.67460 | 1.62 |
| 353 | 1,4-phenyl | 4-(1-pyrrolidinyl)-piperidine | [M + 3H]3+ | 260.15013 | 260.15025 | 1.67 |
| 354 | 1,4-phenyl | morpholine | [M + 2H]2+ | 322.64298 | 322.64280 | 1.91 |
| 355 | 1,4-phenyl | ethanolamine | [M + 2H]2+ | 296.62733 | 296.62702 | 1.81 |
| 356 | 1,4-phenyl | 1-methylpiperazine | [M + 3H]3+ | 224.11883 | 224.11891 | 1.91 |
| 357 | 1,4-phenyl | N-(3-aminopropyl)morpholine | [M + 3H]3+ | 253.46964 | 253.46929 | 1.93 |
| 358 | 1,4-phenyl | piperidine | [M + 3H]3+ | 214.11157 | 214.11140 | 2.1 |

TABLE 8-continued

| Example | Ar | R1R2N | Ion observed | Theoretical | Exptl. | HPLC Ret. time |
|---|---|---|---|---|---|---|
| 359 | 1,4-phenyl | 1-ethylpiperazine | [M + 3H]3+ | 233.46260 | 233.46228 | 1.94 |
| 360 | 1,4-phenyl | 1-(2-hydroxyethyl)piperazine | [M + 3H]3+ | 244.12588 | 244.12546 | 1.87 |
| 361 | 1,3-phenyl | 4-hydroxypiperidine | [M + 3H]3+ | 224.77484 | 224.77470 | 1.98 |
| 362 | 1,3-phenyl | N,N-dimethylethylenediamine | [M + H]+ | 646.34 | 646.3 | 1.73 |
| 363 | 1,3-phenyl | 4-(1-pyrrolidinyl)-piperidine | [M + 3H]3+ | 260.15013 | 260.15000 | 1.77 |
| 364 | 1,3-phenyl | 4-(aminomethyl)pyridine | [M + 3H]3+ | 229.43130 | 229.43129 | 1.89 |
| 365 | 1,3-phenyl | histamine | [M + 3H)3+ | 231.43857 | 231.43849 | 1.75 |
| 366 | 1,3-phenyl | morpholine | [M + 2H]2+ | 322.64298 | 322.64197 | 2 |
| 367 | 1,3-phenyl | ethanolamine | [M + 2H]2+ | 296.62733 | 296.62717 | 1.92 |
| 368 | 1,3-phenyl | 1-methylpiperazine | [M + 3H]3+ | 224.11883 | 224.11859 | 2.02 |
| 369 | 1,3-phenyl | N-(3-aminopropyl)morpholine | [M + 3H]3+ | 253.46964 | 253.46924 | 1.75 |
| 370 | 1,3-phenyl | piperidine | [M + 3H]3+ | 214.11157 | 214.11139 | 2.2 |
| 371 | 1,3-phenyl | 1-ethylpiperazine | [M + 3H]3+ | 233.46260 | 233.46223 | 2.05 |
| 372 | 1,3-phenyl | 1-(2-hydroxyethyl)piperazine | [M + 3H]3+ | 244.12588 | 244.12495 | 1.98 |
| 373 | 2,4-thienyl | N,N-dimethylethylenediamine | [M + 3H]3+ | 220.08978 | 220.08941 | 1.64 |
| 374 | 2,4-thienyl | 4-(1-pyrrolidinyl)-piperidine | [M + H]1+ | 790.34869 | 790.34843 | 1.67 |
| 375 | 2,4-thienyl | 4-(aminomethyl)pyridine | [M + 3H]3+ | 233.40225 | 233.40173 | 1.8 |
| 376 | 2,4-thienyl | histamine | [M + H]1+ | 704.21399 | 704.21442 | 1.98 |
| 377 | 2,4-thienyl | morpholine | [M + 2H]2+ | 328.59940 | 328.59852 | 1.95 |
| 378 | 2,4-thienyl | 1-methylpiperazine | [M + H]1+ | 682.25479 | 682.25389 | 2.04 |
| 379 | 2,4-thienyl | N-(3-aminopropyl)morpholine | [M + H]1+ | 770.30722 | 770.30775 | 1.67 |
| 380 | 2,4-thienyl | piperidine | [M + 3H]3+ | 218.08252 | 218.08236 | 2.14 |
| 381 | 2,4-thienyl | 1-ethylpiperazine | [M + 3H]3+ | 237.43355 | 237.43272 | 2.11 |
| 382 | 2,4-thienyl | 1-(2-hydroxyethyl)piperazine | [M + 3H]3+ | 248.09682 | 248.09584 | 2.01 |

Examples 383–421 in Table 9 were synthesized using 4-(3-chloro-4-phenoxyphenylamino)-7-iodo-3-quinolinecarbonitrile with 4-formylbenzeneboronic acid, 3-formylbenzeneboronic acid, 2-formylfuran-5-boronic acid, 5-formyl-2-thiophene boronic acid, 5-formyl-3-thiophene boronic acid, 2-bromo-5-formylpyridine* and 4-hydroxypiperidine, N,N-dimethylethylenediamine, 4-(1-pyrrolidinyl)-piperidine, 4-(aminomethyl)pyridine, histamine, morpholine, ethanolamine, 1-methylpiperazine, N-(3-aminopropyl)morpholine, piperidine, 1-ethylpiperazine and 1-(2-hydroxyethyl)piperazine and following the combinatorial procedure outlined for Example 135.

*Note: 2-Bromo-5-formylpyridine was coupled with 7-bromo-4-(3-chloro-4-phenoxyphenylamino)-3-quinolinecarbonitrile under the same conditions that were used for coupling with 7-bromo-4-{3-chloro-4-[(1-methyl-1H-imidazol-2-yl)sulfanyl]anilino}-3-quinolinecarbonitrile.

TABLE 9

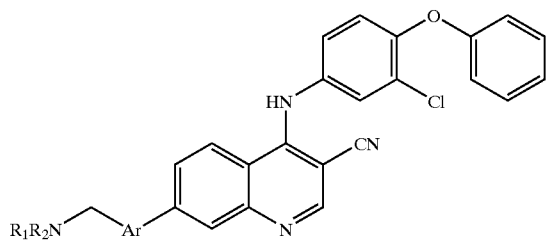

| Example | Ar | R1R2N | Theoretical (M + 2H)2+ | Exptl. (M + 2H)2+ | LCMS Retention time |
|---|---|---|---|---|---|
| 383 | 1,4-phenyl | N-(3-aminopropyl)morpholine | 302.62733 | 302.62675 | 2.13 |
| 384 | 1,4-phenyl | 1-ethylpiperazine | 287.62205 | 287.62155 | 2.27 |

TABLE 9-continued

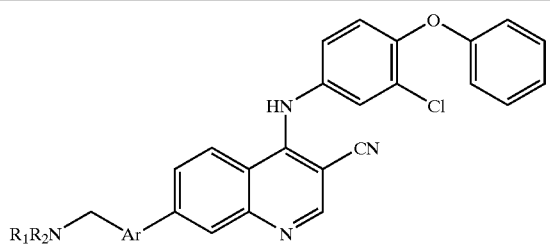

| Example | Ar | R1R2N | Theoretical (M + 2H)2+ | Exptl. (M + 2H)2+ | LCMS Retention time |
|---|---|---|---|---|---|
| 385 | 1,4-phenyl | 1-(2-hydroxyethyl)piperazine | 295.61950 | 295.61904 | 2.24 |
| 386 | 1,3-phenyl | N,N-dimethylethylenediamine | 274.61422 | 274.61410 | 2.14 |
| 387 | 1,3-phenyl | 4-(1-pyrrolidinyl)-piperidine | 307.63770 | 307.63710 | 2.17 |
| 388 | 1,3-phenyl | 4-(aminomethyl)pyridine | 284.59857 | 284.59810 | 2.21 |
| 389 | 1,3-phenyl | N-(3-aminopropyl)morpholine | 302.62733 | 302.62681 | 2.14 |
| 390 | 1,3-phenyl | 1-ethylpiperazine | 287.62205 | 287.62152 | 2.28 |
| 391 | 2,5-furyl | 4-hydroxypiperidine | 276.09586 | 276.09602 | 2.27 |
| 392 | 2,5-furyl | N,N-dimethylethylenediamine | 269.60385 | 269.60387 | 2.12 |
| 393 | 2,5-furyl | 4-(1-pyrrolidinyl)-piperidine | 302.62733 | 302.62666 | 2.13 |
| 394 | 2,5-furyl | 4-(aminomethyl)pyridine | 279.58820 | 279.58772 | 2.20 |
| 395 | 2,5-furyl | histamine | 281.09365 | 281.09374 | 2.10 |
| 396 | 2,5-furyl | morpholine | 269.08804 | 269.08825 | 2.30 |
| 397 | 2,5-furyl | ethanolamine | 533.13509[1] | 533.13339[1] | 2.24 |
| 398 | 2,5-furyl | 1-methylpiperazine | 275.60385 | 275.60331 | 2.24 |
| 399 | 2,5-furyl | N-(3-aminopropyl)morpholine | 297.61696 | 297.61630 | 2.10 |
| 400 | 2,5-furyl | piperidine | 535.18953[2] | 535.19000[2] | 2.11 |
| 401 | 2,5-furyl | 1-ethylpiperazine | 282.61168 | 282.61102 | 2.28 |
| 402 | 2,5-furyl | 1-(2-hydroxyethyl)piperazine | 290.60914 | 290.60843 | 2.24 |
| 403 | 2,5-thienyl | N,N-dimethylethylenediamine | 277.59243 | 277.59255 | 2.13 |
| 404 | 2,5-thienyl | 4-(1-pyrrolidinyl)-piperidine | 310.61591 | 310.61514 | 2.17 |
| 405 | 2,5-thienyl | 4-(aminomethyl)pyridine | 287.57678 | 287.57619 | 2.24 |
| 406 | 2,5-thienyl | morpholine | 553.14[2] | 553.01[2] | 2.37 |
| 407 | 2,5-thienyl | 1-methylpiperazine | 283.59243 | 283.59182 | 2.30 |
| 408 | 2,5-thienyl | 1-ethylpiperazine | 290.60026 | 290.59946 | 2.35 |
| 409 | 3,5-thienyl | 4-hydroxypiperidine | 284.08444 | 284.08400 | 2.27 |
| 410 | 3,5-thienyl | N,N-dimethylethylenediamine | 277.59243 | 277.59236 | 2.08 |
| 411 | 3,5-thienyl | 4-(1-pyrrolidinyl)-piperidine | 310.61591 | 310.61493 | 2.10 |
| 412 | 3,5-thienyl | 4-(aminomethyl)pyridine | 287.57678 | 287.57610 | 2.11 |
| 413 | 3,5-thienyl | histamine | 289.08223 | 289.08147 | 2.13 |
| 414 | 3,5-thienyl | morpholine | 553.14595[2] | 553.14540[2] | 2.30 |
| 415 | 3,5-thienyl | ethanolamine | 549.11224[1] | 549.11151[1] | 2.23 |
| 416 | 3,5-thienyl | 1-methylpiperazine | 283.59243 | 283.59182 | 2.28 |
| 417 | 3,5-thienyl | N-(3-aminopropyl)morpholine | 305.60554 | 305.60459 | 2.09 |
| 418 | 3,5-thienyl | piperidine | 276.08698 | 276.08710 | 2.41 |
| 419 | 3,5-thienyl | 1-ethylpiperazine | 290.60026 | 290.59949 | 2.30 |
| 420 | 3,5-thienyl | 1-(2-hydroxyethyl)piperazine | 298.59771 | 298.59690 | 2.25 |
| 421 | 2,4-pyridyl | N-(3-aminopropyl)morpholine | 303.12495 | 303.12490 | 2.10 |

[1][M + Na]+
[2][M + H]+

Examples 422–464 in Table 10 were synthesized using 4-(3-chloro-4-phenylsulfanylphenylamino)-7-iodo-3-quinolinecarbonitrile with 4-formylbenzeneboronic acid, 3-formylbenzeneboronic acid, 2-formylfuran-5-boronic acid, 5-formyl-2-thiophene boronic acid, 5-formyl-3-thiophene boronic acid and 4-hydroxypiperidine, N,N-dimethylethylenediamine, 4-(1-pyrrolidinyl)-piperidine, 4-(aminomethyl)pyridine, histamine, morpholine, ethanolamine, 1-methylpiperazine, N-(3-aminopropyl)morpholine, piperidine, 1-ethylpiperazine and 1-(2-hydroxyethyl)piperazine and following the combinatorial procedure outlined for Example 135:

TABLE 10

| Example | Ar | R1R2N | Theoretical (M + 2H)2+ | Exptl. (M + 2H)2+ | LCMS Retention time |
|---|---|---|---|---|---|
| 422 | 1,4-phenyl | 4-hydroxypiperidine | 577.18234[1] | 577.18295[1] | 2.87 |
| 423 | 1,4-phenyl | 4-(aminomethyl)pyridine | 292.58715 | 292.58655 | 2.74 |
| 424 | 1,4-phenyl | histamine | 294.09260 | 294.09187 | 2.61 |
| 425 | 1,4-phenyl | morpholine | 282.08698 | 282.08626 | 2.91 |
| 426 | 1,4-phenyl | ethanolamine | 269.07916 | 269.07861 | 2.84 |
| 427 | 1,4-phenyl | 1-methylpiperazine | 288.60280 | 288.60206 | 2.82 |
| 428 | 1,4-phenyl | N-(3-aminopropyl)morpholine | 310.61591 | 310.61527 | 2.64 |
| 429 | 1,4-phenyl | 1-ethylpiperazine | 295.61062 | 295.60985 | 2.37 |
| 430 | 1,4-phenyl | 1-(2-hydroxyethyl)piperazine | 303.60808 | 303.60740 | 2.34 |
| 431 | 1,3-phenyl | 4-hydroxypiperidine | 289.09481 | 289.09417 | 2.41 |
| 432 | 1,3-phenyl | N,N-dimethylethylenediamine | 282.60280 | 282.60225 | 2.21 |
| 433 | 1,3-phenyl | 4-(1-pyrrolidinyl)-piperidine | 315.62627 | 315.62597 | 2.23 |
| 434 | 1,3-phenyl | ethanolamine | 179.72186[3] | 179.72230[3] | 2.38 |
| 435 | 1,3-phenyl | N-(3-aminopropyl)morpholine | 310.61591 | 310.61550 | 2.24 |
| 436 | 1,3-phenyl | 1-(2-hydroxyethyl)piperazine | 303.60808 | 303.60778 | 2.35 |
| 437 | 2,5-furyl | 4-hydroxypiperidine | 567.16160[1] | 567.16421[1] | 2.38 |
| 438 | 2,5-furyl | N,N-dimethylethylenediamine | 277.59243 | 277.59188 | 2.61 |
| 439 | 2,5-furyl | 4-(1-pyrrolidinyl)-piperazine | 620.22[1] | 620.12[1] | 2.64 |
| 440 | 2,5-furyl | 4-(aminomethyl)pyridine | 287.57678 | 287.57642 | 2.74 |
| 441 | 2,5-furyl | histamine | 577.15[1] | 577.06[1] | 2.61 |
| 442 | 2,5-furyl | morpholine | 553.14595[1] | 553.14817[1] | 2.94 |
| 443 | 2,5-furyl | ethanolamine | 176.38162[2] | 176.38187[2] | 2.84 |
| 444 | 2,5-furyl | 1-methylpiperazine | 283.59243 | 283.59207 | 2.81 |
| 445 | 2,5-furyl | N-(3-aminopropyl)morpholine | 305.60554 | 305.60518 | 2.21 |
| 446 | 2,5-furyl | 1-ethylpiperazine | 580.19324[1] | 580.19320[1] | 2.37 |
| 447 | 2,5-thienyl | N,N-dimethylethylenediamine | 570.15474[1] | 570.15362[1] | 2.24 |
| 448 | 2,5-thienyl | 4-(1-pyrrolidinyl)-piperidine | 636.20169[1] | 636.20071[1] | 2.24 |
| 449 | 2,5-thienyl | morpholine | 569.12311[1] | 569.12237[1] | 2.47 |
| 450 | 2,5-thienyl | 1-methylpiperazine | 582.15474[1] | 582.15410[1] | 2.44 |
| 451 | 2,5-thienyl | N-(3-aminopropyl)morpholine | 626.18096[1] | 626.18051[1] | 2.24 |
| 452 | 2,5-thienyl | 1-ethylpiperazine | 298.58884 | 298.58852 | 2.47 |
| 453 | 3,5-thienyl | 4-hydroxypiperidine | 583.13876[1] | 583.13778[1] | 2.37 |
| 454 | 3,5-thienyl | N,N-dimethylethylenediamine | 285.58101 | 285.58062 | 2.21 |
| 455 | 3,5-thienyl | 4-(1-pyrrolidinyl)-piperidine | 318.60449 | 318.60415 | 2.21 |
| 456 | 3,5-thienyl | 4-(aminomethyl)pyridine | 295.56536 | 295.56502 | 2.27 |
| 457 | 3,5-thienyl | histamine | 297.07081 | 297.07052 | 2.20 |
| 458 | 3,5-thienyl | morpholine | 285.06519 | 285.06482 | 2.41 |
| 459 | 3,5-thienyl | ethanolamine | 543.10746[1] | 543.10928[1] | 2.34 |
| 460 | 3,5-thienyl | 1-methylpiperazine | 582.15475[1] | 582.15585[1] | 2.41 |
| 461 | 3,5-thienyl | N-(3-aminopropyl)morpholine | 313.59412 | 313.59399 | 2.21 |
| 462 | 3,5-thienyl | piperidine | 284.07556 | 284.07532 | 2.47 |
| 463 | 3,5-thienyl | 1-ethylpiperazine | 298.58884 | 298.58842 | 2.41 |
| 464 | 3,5-thienyl | 1-(2-hydroxyethyl)piperazine | 612.16531[1] | 612.16497[1] | 2.38 |

[1][M + H]+
[2][M + 3H]3+

Examples 465–476 in Table 11 were synthesized using 4-{[3-chloro-4-(3-furylmethyl)phenyl]amino})-7-(4-formylphenyl)-3-quinolinecarbonitrile with 4-hydroxypiperidine, N,N-dimethylethylenediamine, 4-(1-pyrrolidinyl)-piperidine, 4-aminomethyl)pyridine, histamine, morpholine, ethanolamine, 1-methylpiperazine, N-(3-aminopropyl)morpholine, piperidine, 1-ethylpiperazine and 1-(2-hydroxyethyl)piperazine and following the combinatorial procedure outlined for Example 135.

TABLE 11

| Example | Ar | R1R2N | Theoretical (M + H)+ | Exptl. (M + H)+ | LCMS Ret. time |
|---|---|---|---|---|---|
| 465 | 1,4-phenyl | 4-hydroxypiperidine | 549.2 | 549.1 | 2.54 |
| 466 | 1,4-phenyl | N,N-dimethylethylenediamine | 536.2 | 536.1 | 2.36 |
| 467 | 1,4-phenyl | 4-(1-pyrrolidinyl)-piperidine | 602.3 | 602.3 | 2.34 |
| 468 | 1,4-phenyl | 4-(aminomethyl)pyridine | 556.2 | 556.1 | 2.41 |
| 469 | 1,4-phenyl | histamine | 559.2 | 559.1 | 2.34 |
| 470 | 1,4-phenyl | morpholine | 535.2 | 535.1 | 2.58 |
| 471 | 1,4-phenyl | ethanolamine | 509.2 | 509.1 | 2.52 |
| 472 | 1,4-phenyl | 1-methylpiperazine | 548.2 | 548.1 | 2.47 |
| 473 | 1,4-phenyl | N-(3-aminopropyl)morpholine | 592.2 | 592.2 | 2.34 |
| 474 | 1,4-phenyl | piperidine | 533.2 | 533.1 | 2.67 |
| 475 | 1,4-phenyl | 1-ethylpiperazine | 562.2 | 562.1 | 2.48 |
| 476 | 1,4-phenyl | 1-(2-hydroxyethyl)piperazine | 578.2 | 578.3 | 2.44 |

Examples 477–510 in Table 12 were synthesized using 4-{[4-(3-furylmethyl)phenyl]amino}-7-iodo-3-quinolinecarbonitrile with 4-formylbenzeneboronic acid, 3-formylbenzeneboronic acid, 5-formyl-3-thiophene boronic acid, 2-bromo-5-formylpyridine* and 4-hydroxypiperidine, N,N-dimethylethylenediamine, 4-(1-pyrrolidinyl)-piperidine, 4-(aminomethyl)pyridine, histamine, morpholine, ethanolamine, 1-methylpiperazine, N-(3-aminopropyl)morpholine, piperidine, 1-ethylpiperazine and 1-(2-hydroxyethyl)piperazine and following the combinatorial procedure outlined for Example 135.

*Note: 2-Bromo-5-formylpyridine was coupled with 7-bromo-4-{[4-(3-furylmethyl)phenyl]amino}-3-quinolinecarbonitrile under the following conditions. A mixture of 7-bromo-4-{[4-(3-furylmethyl)phenyl]amino}-3-quinolinecarbonitrile (808 mg, 2 mmol), 2-bromo-5-formylpyridine (372 mg, 2 mmol), hexamethylditin (655 mg, 2 mmol), tetrakis(triphenylphosphine)palladium (440 mg, 0.4 mmol) and lithium chloride (250 mg, 6 mmol) in dioxane (20 mL) was heated to 110° C. for 4 hours. The mixture was cooled to room temperature and concentrated. The residue was suspended in N,N'-dimethylformamide (24 mL) and filtered. The filtrate was used directly in Step B.

TABLE 12

| Example | Ar | R1R2N | Theoretical (M + H)+ | Exptl. (M + H)+ | LCMS Ret. time |
|---|---|---|---|---|---|
| 477 | 1,4-phenyl | 4-(aminomethyl)pyridine | 522.2 | 522.1 | 2.15 |
| 478 | 1,4-phenyl | histamine | 525.2 | 525.2 | 2.07 |
| 479 | 1,4-phenyl | morpholine | 501.2 | 501.1 | 2.32 |
| 480 | 1,4-phenyl | ethanolamine | 475.2 | 475.2 | 2.27 |
| 481 | 1,4-phenyl | 1-methylpiperazine | 514.3 | 514.2 | 2.24 |
| 482 | 1,4-phenyl | piperidine | 499.2 | 499.2 | 2.40 |
| 483 | 1,4-phenyl | 1-ethylpiperazine | 528.3 | 528.2 | 2.27 |
| 484 | 1,4-phenyl | 1-(2-hydroxyethyl)piperazine | 544.3 | 544.3 | 2.21 |
| 485 | 1,3-phenyl | 4-hydroxypiperidine | 515.2 | 515.2 | 2.32 |
| 486 | 1,3-phenyl | N,N-dimethylethylenediamine | 502.3 | 502.2 | 2.10 |
| 487 | 1,3-phenyl | 4-(1-pyrrolidinyl)-piperidine | 568.3 | 568.5 | 2.14 |
| 488 | 1,3-phenyl | 4-(aminomethyl)pyridine | 522.2 | 522.1 | 2.20 |
| 489 | 1,3-phenyl | histamine | 525.2 | 525.2 | 2.11 |
| 490 | 1,3-phenyl | morpholine | 501.2 | 501.2 | 2.34 |
| 491 | 1,3-phenyl | ethanolamine | 475.2 | 475.2 | 2.28 |

TABLE 12-continued

| Example | Ar | R1R2N | Theoretical (M + H)+ | Exptl. (M + H)+ | LCMS Ret. time |
|---|---|---|---|---|---|
| 492 | 1,3-phenyl | 1-methylpiperazine | 514.3 | 514.2 | 2.28 |
| 493 | 1,3-phenyl | N-(3-aminopropyl)morpholine | 558.3 | 558.3 | 2.11 |
| 494 | 1,3-phenyl | 1-ethylpiperazine | 528.3 | 528.2 | 2.30 |
| 495 | 1,3-phenyl | 1-(2-hydroxyethyl)piperazine | 544.3 | 544.2 | 2.24 |
| 496 | 2,5-pyridyl | 4-hydroxypiperidine | 516.2 | 516.5 | 2.22 |
| 497 | 2,5-pyridyl | N,N-dimethylethylenediamine | 503.3 | 503.5 | 2.04 |
| 498 | 2,5-pyridyl | ethanolamine | 476.2 | 476.5 | 2.20 |
| 499 | 2,5-pyridyl | N-(3-aminopropyl)morpholine | 559.3 | 559.7 | 2.03 |
| 500 | 2,5-pyridyl | 1-(2-hydroxyethyl)piperazine | 545.3 | 545.5 | 2.20 |
| 501 | 3,5-thienyl | 4-hydroxypiperidine | 521.2 | 521.1 | 1.97 |
| 502 | 3,5-thienyl | 4-(1-pyrrolidinyl)-piperidine | 574.3 | 574.5 | 1.83 |
| 503 | 3,5-thienyl | 4-(aminomethyl)pyridine | 528.2 | 528.1 | 1.88 |
| 504 | 3,5-thienyl | morpholine | 507.2 | 507.0 | 1.97 |
| 505 | 3,5-thienyl | ethanolamine | 481.2 | 481.0 | 1.94 |
| 506 | 3,5-thienyl | 1-methylpiperazine | 520.2 | 520.1 | 2.00 |
| 507 | 3,5-thienyl | N-(3-aminopropyl)morpholine | 564.2 | 564.4 | 1.84 |
| 508 | 3,5-thienyl | piperidine | 505.2 | 505.1 | 2.04 |
| 509 | 3,5-thienyl | 1-ethylpiperazine | 534.2 | 534.2 | 2.01 |
| 510 | 3,5-thienyl | 1-(2-hydroxyethyl)piperazine | 550.2 | 550.4 | 1.97 |

Examples 511–535 in Table 13 were synthesized using 4-(2,4-dichloro-5-methoxyanilino)-7-iodo-3-quinolinecarbonitrile with 4-formylbenzeneboronic acid, 3-formylbenzeneboronic acid, 2-formylfuran-5-boronic acid, 5-formyl-2-thiophene boronic acid, 2-bromo-5-formylpyridine* and 4-hydroxypiperidine, histamine, dimethylethylenediamine, 4-(1-pyrrolidinyl)-piperidine, 4-(aminomethyl)pyridine, ethanolamine, N-(3-aminopropyl)morpholine, piperidine, 1-ethylpiperazine and 1-(2-hydroxyethyl)piperazine and following the combinatorial procedure outlined for Example 135.

*Note: 2-Bromo-5-formylpyridine was coupled with 7-bromo-4-(2,4-dichloro-5-methoxyanilino)-3-quinolinecarbonitrile under the following conditions. A mixture of 7-bromo-4-(2,4-dichloro-5-methoxyanilino)-3-quinolinecarbonitrile (942 mg, 2 mmol), 2-bromo-5-formylpyridine (372 mg, 2 mmol), hexamethylditin (655 mg, 2 mmol), tetrakis(triphenylphlosphine-)palladium (440 mg, 0.4 mmol) and lithium chloride (250 mg, 6 mmol) in dioxane (20 mL) was heated to 110° C. for 4 hours. The mixture was cooled to room temperature and concentrated. The residue was suspended in N,N'-dimethylformamide (24 mL) and filtered. The filtrate was used directly in Step B.

TABLE 13

| Example | Ar | R1R2N | Theoretical (M + H)+ | Exptl. (M + H)+ | LCMS Ret. time |
|---|---|---|---|---|---|
| 511 | 1,4-phenyl | 4-(1-pyrrolidinyl)-piperidine | 586.2 | 586.1 | 2.17 |
| 512 | 1,4-phenyl | 4-(aminomethyl)pyridine | 540.1 | 540 | 2.24 |
| 513 | 1,4-phenyl | histamine | 543.2 | 543.1 | 2.11 |
| 514 | 1,4-phenyl | ethanolamine | 493.1 | 493.1 | 2.34 |
| 515 | 1,4-phenyl | N-(3-aminopropyl)morpholine | 576.2 | 576.1 | 2.14 |
| 516 | 2,5-furyl | 4-hydroxypiperidine | 523.1 | 523.1 | 2.01 |
| 517 | 2,5-furyl | N,N-dimethylethylenediamine | 510.2 | 510.1 | 1.88 |
| 518 | 2,5-furyl | 4-(1-pyrrolidinyl)-piperidine | 576.2 | 576.1 | 1.88 |

TABLE 13-continued

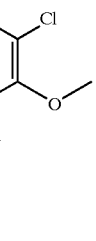

| Example | Ar | R1R2N | Theoretical (M + H)+ | Exptl. (M + H)+ | LCMS Ret. time |
|---|---|---|---|---|---|
| 519 | 2,5-furyl | 4-(aminomethyl)pyridine | 530.1 | 530 | 1.93 |
| 520 | 2,5-furyl | histamine | 533.1 | 533 | 1.85 |
| 521 | 2,5-furyl | ethanolamine | 483.1 | 483.1 | 1.98 |
| 522 | 2,5-furyl | N-(3-aminopropyl)morpholine | 566.2 | 566.1 | 1.87 |
| 523 | 2,5-furyl | piperidine | 507.1 | 507.1 | 2.14 |
| 524 | 2,5-furyl | 1-ethylpiperazine | 536.2 | 536.1 | 2.04 |
| 525 | 2,5-thienyl | 4-(1-pyrrolidinyl)-piperidine | 592.2 | 592 | 1.92 |
| 526 | 2,5-thienyl | 1-ethylpiperazine | 552.2 | 552 | 2.11 |
| 527 | 2,4-thienyl | N,N-dimethylethylenediamine | 526.1 | 526.1 | 1.88 |
| 528 | 2,4-thienyl | 4-(aminomethyl)pyridine | 546.1 | 546 | 1.93 |
| 529 | 2,4-thienyl | histamine | 549.1 | 549 | 1.87 |
| 530 | 2,5-pyrinyl | 4-hydroxypiperidine | 534.2 | 534.1 | 2 |
| 531 | 2,5-pyridyl | N,N-dimethylethylenediamine | 521.2 | 521.1 | 1.84 |
| 532 | 2,5-pyridyl | 4-(1-pyrrolidinyl)-piperidine | 587.2 | 587.2 | 1.87 |
| 533 | 2,5-pyridyl | ethanolamine | 494.1 | 494.1 | 1.98 |
| 534 | 2,5-pyridyl | N-(3-aminopropyl)morpholine | 577.2 | 577.2 | 1.84 |
| 535 | 2,5-pyridyl | 1-(2-hydroxyethyl)piperazine | 563.2 | 563.1 | 1.98 |

Examples 536–567 in Table 14 were synthesized using 7-iodo-4-(3,4,5-trimethyoxyanilino)-3-quinolinecarbonitrile with 4-formylbenzeneboronic acid, 3-formylbenzeneboronic acid, 2-formylfuran-5-boronic acid, 2-bromo-5-formylpyridine*, 5-formyl-2-thiophene boronic acid, 5-formyl-3-thiophene boronic acid 4-hydroxypiperidine, N,N-dimethylethylenediamine, 4-(1-pyrrolidinyl)-piperidine, 4-(aminomethyl)pyridine, histamine, morpholine, ethanolamine, 1-methylpiperazine, N-(3-aminopropyl)morpholine, piperidine, 1-ethylpiperazine and 1-(2-hydroxyethyl)piperazine and following the combinatorial procedure outlined for Example 135.

*Note: 2-Bromo-5-formylpyridine was coupled with 7-bromo-4-(3,4,5-trimethoxyanilino)-3-quinolinecarbonitrile under the following conditions. A mixture of 7-bromo-4-(2,4-dichloro-5-methoxyanilino)-3-quinolinecarbonitrile (942 mg, 2 mmol), 2-bromo-5-formylpyridine (372 mg, 2 mmol), hexamethylditin (655 mg, 2 mmol), tetrakis(triphenylphosphine)palladium (440 mg, 0.4 mmol) and lithium chloride (250 mg, 6 mmol) in dioxane (20 mL) was heated to 110° C. for 4 hours. The mixture was cooled to room temperature and concentrated. The residue was suspended in N,N'-dimethylformamide (24 mL) and filtered. The filtrate was used directly in Step B.

TABLE 14

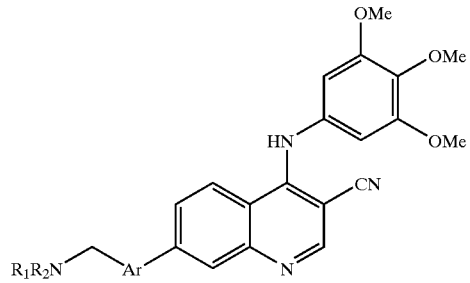

| Example | Ar | R1R2N | Theoretical (M + H)+ | Exptl. (M + H)+ | HPLC Ret. time |
|---|---|---|---|---|---|
| 536 | 1,4-phenyl | 4-hydroxypiperidine | 525.3 | 525.2 | 2.22 |
| 537 | 1,4-phenyl | morpholine | 511.2 | 511.3 | 2.45 |
| 538 | 1,4-phenyl | ethanolamine | 485.2 | 485.3 | 2.35 |
| 539 | 1,4-phenyl | 1-methylpiperazine | 524.3 | 524.3 | 2.36 |
| 540 | 1,4-phenyl | piperidine | 509.3 | 509.4 | 2.4 |
| 541 | 1,4-phenyl | 1-ethylpiperazine | 538.3 | 538.3 | 2.37 |
| 542 | 1,3-phenyl | 4-hydroxypiperidine | 525.3 | 525.4 | 2.24 |

TABLE 14-continued

[Structure: quinoline with 4-NH-(3,4,5-trimethoxyphenyl), 3-CN, and 7-Ar-CH2-NR1R2 substituent]

| Example | Ar | R1R2N | Theoretical (M + H)+ | Exptl. (M + H)+ | HPLC Ret. time |
|---|---|---|---|---|---|
| 543 | 1,3-phenyl | N,N-dimethylethylenediamine | 512.4 | 512.5 | 1.92 |
| 544 | 1,3-phenyl | 4-(1-pyrrolidinyl)-piperidine | 578.3 | 578.3 | 1.93 |
| 545 | 1,3-phenyl | 4-(aminomethyl)pyridine | 532.3 | 532.3 | 2.29 |
| 546 | 1,3-phenyl | histamine | 535.3 | 535.4 | 2.16 |
| 547 | 1,3-phenyl | morpholine | 511.2 | 511.3 | 2.45 |
| 548 | 1,3-phenyl | ethanolamine | 485.2 | 485.4 | 2.39 |
| 549 | 1,3-phenyl | 1-methylpiperazine | 524.3 | 524.4 | 2.36 |
| 550 | 1,3-phenyl | N-(3-aminopropyl)morpholine | 568.3 | 568.4 | 2.16 |
| 551 | 1,3-phenyl | piperidine | 509.3 | 509.5 | 2.42 |
| 552 | 1,3-phenyl | 1-(2-hydroxyethyl)piperazine | 554.3 | 554.4 | 2 |
| 553 | 2,5-furyl | 4-(1-pyrrolidinyl)-piperidine | 568.3 | 568.3 | 1.92 |
| 554 | 2,5-thienyl | 4-hydroxypiperidine | 531.2 | 531.3 | 1.92 |
| 555 | 2,5-thienyl | histamine | 541.2 | 541.2 | 1.86 |
| 556 | 2,5-thienyl | 1-methylpiperazine | 530.2 | 530.2 | 1.97 |
| 557 | 2,5-thienyl | 1-ethylpiperazine | 544.2 | 544.4 | 2.16 |
| 558 | 2,5-thienyl | 1-(2-hydroxyethyl)piperazine | 560.2 | 560.3 | 1.72 |
| 559 | 2,4-thienyl | 4-(aminomethyl)pyridine | 538.2 | 538.3 | 1.98 |
| 560 | 2,4-thienyl | morpholine | 517.2 | 517.2 | 2.15 |
| 561 | 2,4-thienyl | ethanolamine | 491.2 | 491.4 | 2.09 |
| 562 | 2,4-thienyl | 1-methylpiperazine | 530.2 | 530.3 | 2.06 |
| 563 | 2,5-pyridinyl | 4-hydroxypiperidine | 526.3 | 526.4 | 2.05 |
| 564 | 2,5-pyridinyl | 4-(1-pyrrolidinyl)-piperidine | 579.3 | 579.3 | 1.88 |
| 565 | 2,5-pyridinyl | ethanolamine | 486.2 | 486.2 | 1.92 |
| 566 | 2,5-pyridinyl | N-(3-aminopropyl)morpholine | 569.3 | 569.5 | 1.89 |
| 567 | 2,5-pyridinyl | 1-(2-hydroxyethyl)piperazine | 555.3 | 555.4 | 2.03 |

The chemical names of Examples 135 and 238–567 prepared by combinatorial means are listed in Table 15

TABLE 15

| Example # | ChemicaL Names of Examples |
|---|---|
| 135 | 4-{3-chloro-4-[(1-methyl-1H-imidazol-2-yl)sulfanyl]anilino}-7-{4-[(4-methyl-1-piperazinyl)methyl]phenyl}-3-quinolinecarbonitrile |
| 238 | 4-{3-chloro-4-[(1-methyl-1H-imidazol-2-yl)sulfanyl]anilino}-7-[4-{([2-(dimethylamino)ethyl]amino}methyl)phenyl]-3-quinolinecarbonitrile |
| 239 | 4-{3-chloro-4-[(1-methyl-1H-imidazol-2-yl)sulfanyl]anilino}-7-(4-{[4-(1-pyrrolidinyl)-1-piperidinyl]methyl}phenyl)-3-quinolinecarbonitrile |
| 240 | 4-{3-chloro-4-[(1-methyl-1H-imidazol-2-yl)sulfanyl]anilino}-7-(4-{[(4-pyridinylmethyl)amino]methyl}phenyl)-3-quinolinecarbonitrile |
| 241 | 4-{3-chloro-4-[(1-methyl-1H-imidazol-2-yl)sulfanyl]anilino}-7-{(4-[(dimethylamino)methyl]phenyl}-3-quinolinecarbonitrile |
| 243 | 4-{3-chloro-4-[(1-methyl-1H-imidazol-2-yl)sulfanyl]anilino}-7-(4-{[(2-hydroxyethyl)amino]methyl}phenyl)-3-quinolinecarbonitrile |
| 244 | 4-{3-chloro-4-[(1-methyl-1H-imidazol-2-yl)sulfanyl]anilino}-7-[4-({[3-(4-morpholinyl)propyl]amino}methyl)phenyl]-3-quinolinecarbonitrile |
| 245 | 4-{3-chloro-4-[(1-methyl-1H-imidazol-2-yl)sulfanyl]anilino}-7-{4-[(4-ethyl-1-piperazinyl)methyl]phenyl}-3-quinolinecarbonitrile |
| 246 | 4-{3-chloro-4-[(1-methyl-1H-imidazol-2-yl)sulfanyl]anilino}-7-(4-{[4-(2-hydroxyethyl)-1-piperazinyl]methyl}phenyl)-3-quinolinecarbonitrile |
| 247 | 4-{3-chloro-4-[(1-methyl-1H-imidazol-2-yl)sulfanyl]anilino}-7-{3-[(4-hydroxy-1-piperidinyl]methyl}phenyl)-3-quinolinecarbonitrile |
| 248 | 4-{3-chloro-4-[(1-methyl-1H-imidazol-2-yl)sulfanyl]anilino}-7-[3-({[2-(dimethylamino)ethyl]amino}methyl)phenyl]-3-quinolinecarbonitrile |
| 249 | 4-{3-chloro-4-[(1-methyl-1H-imidazol-2-yl)sulfanyl]anilino}-7-(3-{[4-(1-pyrrolidinyl)-1-piperidinyl]methyl}phenyl)-3-quinolinecarbonitrile |

TABLE 15-continued

| Example # | ChemicaL Names of Examples |
|---|---|
| 250 | 4-{3-chloro-4-[(1-methyl-1H-imidazol-2-yl)sulfanyl]anilino}-7-(3-{[(4-pyridinylmethyl)amino]methyl}phenyl)-3-quinolinecarbonitrile |
| 251 | 4-{3-chloro-4-[(1-methyl-1H-imidazol-2-yl)sulfanyl]anilino}-7-{3-[(dimethylamino)methyl]phenyl}-3-quinolinecarbonitrile |
| 252 | 4-{3-chloro-4-[(1-methyl-1H-imidazol-2-yl)sulfanyl]anilino}-7-[3-(4-morpholinylmethyl)phenyl]-3-quinolinecarbonitrile |
| 253 | 4-{3-chloro-4-[(1-methyl-1H-imidazol-2-yl)sulfanyl]anilino}-7-(3-{[(2-hydroxyethyl)amino]methyl}phenyl)-3-quinolinecarbonitrile |
| 254 | 4-{3-chloro-4-[(1-methyl-1H-imidazol-2-yl)sulfanyl]anilino}-7-{3-[(4-methyl-1-piperazinyl)methyl]phenyl}-3-quinolinecarbonitrile |
| 255 | 4-{3-chloro-4-[(1-methyl-1H-imidazol-2-yl)sulfanyl]anilino}-7-[3-({[3-(4-morpholinyl)propyl]amino}methyl)phenyl]-3-quinolinecarbonitrile |
| 256 | 4-{3-chloro-4-[(1-methyl-1H-imidazol-2-yl)sulfanyl]anilino}-7-[3-(1-piperidinylmethyl)phenyl]-3-quinolinecarbonitrile |
| 257 | 4-{3-chloro-4-[(1-methyl-1H-imidazol-2-yl)sulfanyl]anilino}-7-{3-[(4-ethyl-1-piperazinyl)methyl]phenyl}-3-quinolinecarbonitrile |
| 258 | 4-{3-chloro-4-[(1-methyl-1H-imidazol-2-yl)sulfanyl]anilino}-7-(3-{[4-(2-hydroxyethyl)-1-piperazinyl]methyl}phenyl)-3-quinolinecarbonitrile |
| 259 | 4-{3-chloro-4-[(1-methyl-1H-imidazol-2-yl)sulfanyl]anilino}-7-{5-[(4-hydroxy-1-piperidinyl)methyl]-2-furyl}-3-quinolinecarbonitrile |
| 260 | 4-{3-chloro-4-[(1-methyl-1H-imidazol-2-yl)sulfanyl]anilino}-7-[5-({[2-(dimethylamino)ethyl]amino}methyl)-2-furyl]-3-quinolinecarbonitrile |
| 261 | 4-{3-chloro-4-[(1-methyl-1H-imidazol-2-yl)sulfanyl]anilino}-7-(5-{[4-(1-pyrrolidinyl)-1-piperidinyl]methyl}-2-furyl)-3-quinolinecarbonltrile |
| 262 | 4-{3-chloro-4-[(1-methyl-1H-imidazol-2-yl)sulfanyl]anilino}-7-(5-{[(2-hydroxyethyl)amino]methyl}-2-furyl)-3-quinolinecarbonitrile |
| 263 | 4-{3-chloro-4-[(1-methyl-1H-imidazol-2-yl)sulfanyl]anilino}-7-{5-[(4-methyl-1-piperazinyl)methyl]-2-furyl}-3-quinolinecarbonitrile |
| 264 | 4-{3-chloro-4-[(1-methyl-1H-imidazol-2-yl)sulfanyl]anilino}-7-[5-({[3-(4-morpholinyl)propyl]amino}methyl)-2-furyl]-3-quinolinecarbonitrile |
| 265 | 4-{3-chloro-4-[(1-methyl-1H-imidazol-2-yl)sulfanyl]anilino}-7-[5-({[2-(dimethylamino)ethyl]amino}methyl)-2-thienyl]-3-quinolinecarbonitrile |
| 266 | 4-{3-chloro-4-[(1-methyl-1H-imidazol-2-yl)sulfanyl]anilino}-7-(5-{[4-(1-pyrrolidinyl)-1-piperidinyl]methyl}-2-thienyl)-3-quinolinecarbonitrile |
| 267 | 4-{3-chloro-4-[(1-methyl-1H-imidazol-2-yl)sulfanyl]anilino}-7-(5-{[(2-hydroxyethyl)amino]methyl}-2-thienyl)-3-quinolinecarbonitrile |
| 268 | 4-{3-chloro-4-[(1-methyl-1H-imidazol-2-yl)sulfanyl]anilino}-7-[5-({[3-(4-morpholinyl)propyl]amino}methyl)-2-thienyl]-3-quinolinecarbonitrile |
| 269 | 4-{3-chloro-4-[(1-methyl-1H-imidazol-2-yl)sulfanyl]anilino}-7-{5-[(4-ethyl-1-piperazinyl)methyl]-2-thienyl}-3-quinolinecarbonitrile |
| 270 | 4-{3-chloro-4-[(1-methyl-1H-imidazol-2-yl)sulfanyl]anilino}-7-[5-({[2-(dimethylamino)ethyl]amino}methyl)-2-pyridinyl]-3-quinolinecarbonitrile |
| 271 | 4-{3-chloro-4-[(1-methyl-1H-imidazol-2-yl)sulfanyl]anilino}-7-[5-({[3-(4-morpholinyl)propyl]amino}methyl)-2-pyridinyl]-3-quinolinecarbonitrile |
| 272 | 4-(2,4-dimethylanilino)-7-{4-[(4-hydroxy-1-piperidinyl)methyl]phenyl}-3-quinolinecarbonitrile |
| 273 | 7-[4-({[2-(dimethylamino)ethyl]amino}methyl)phenyl]-4-(2,4-dimethylanilino)-3-quinolinecarbonitrile |
| 274 | 4-(2,4-dimethylanilino)-7-(4-{[4-(1-pyrrolidinyl)-1-piperidinyl]methyl}phenyl)-3-quinolinecarbonitrile |
| 275 | 4-(2,4-dimethylanilino)-7-(4-{[(4-pyridinylmethyl)amino]methyl}phenyl)-3-quinolinecarbonitrile |
| 276 | 4-(2,4-dimethylanilino)-7-[4-({[2-(1H-imidazol-4-yl)ethyl]amino}methyl)phenyl]-3-quinolinecarbonitrile |
| 277 | 4-(2,4-dimethylanilino)-7-[4-(4-morpholinylmethyl)phenyl]-3-quinolinecarbonitrile |
| 278 | 4-(2,4-dimethylanilino)-7-(4-{[(2-hydroxyethyl)amino]methyl}phenyl)-3-quinolinecarbonitrile |
| 279 | 4-(2,4-dimethylanilino)-7-{4-[(4-methyl-1-piperazinyl)methyl]phenyl}-3-quinolinecarbonitrile |
| 280 | 4-(2,4-dimethylanilino)-7-[4-({[3-(4-morpholinyl)propyl]amino}methyl)phenyl]-3-quinolinecarbonitrile |
| 281 | 4-(2,4-dimethylanilino)-7-[4-(1-piperidinylmethyl)phenyl]-3-quinolinecarbonitrile |
| 282 | 4-(2,4-dimethylanilino)-7-{4-[(4-ethyl-1-piperazinyl)methyl]phenyl}-3-quinolinecarbonitrile |
| 283 | 4-(2,4-dimethylanilino)-7-{4-([4-(2-hydroxyethyl)-1-piperazinyl]methyl}phenyl)-3-quinolinecarbonitrile |
| 284 | 4-(2,4-dimethylanilino)-7-{3-[(4-hydroxy-1-piperidinyl)methyl]phenyl}-3-quinolinecarbonitrile |
| 285 | 7-[3-({[2-(dimethylamino)ethyl]amino}methyl)phenyl]-4-(2,4-dimethylanilino)-3-quinolinecarbonitrile |
| 286 | 4-(2,4-dimethylanilino)-7-(3-{[4-(1-pyrrolidinyl)-1-piperidinyl]methyl}phenyl)-3-quinolinecarbonitrile |
| 287 | 4-(2,4-dimethylanilino)-7-(3-{[(4-pyridinylmethyl)amino]methyl}phenyl)-3-quinolinecarbonitrile |
| 288 | 4-(2,4-dimethylanilino)-7-[3-({[2-(1H-imidazol-4- |

TABLE 15-continued

| Example # | Chemical Names of Examples |
|---|---|
| | yl)ethyl]amino}methyl)phenyl]-3-quinolinecarbonitrile |
| 289 | 4-(2,4-dimethylanilino)-7-[3-(4-morpholinylmethyl)phenyl]-3-quinolinecarbonitrile |
| 290 | 4-(2,4-dimethylanilino)-7-(3-{[(2-hydroxyethyl)amino]methyl}phenyl)-3-quinolinecarbonitrile |
| 291 | 4-(2,4-dimethylanilino)-7-{3-[(4-methyl-1-piperazinyl)methyl]phenyl}-3-quinolinecarbonitrile |
| 292 | 4-(2,4-dimethylanilino)-7-[3-({[3-(4-morpholinyl)propyl]amino}methyl)phenyl]-3-quinolinecarbonitrile |
| 293 | 4-(2,4-dimethylanilino)-7-[3-(1-piperidinylmethyl)phenyl]-3-quinolinecarbonitrile |
| 294 | 4-(2,4-dimethylanilino)-7-{3-[(4-ethyl-1-piperazinyl)methyl]phenyl}-3-quinolinecarbonitrile |
| 295 | 4-(2,4-dimethylanilino)-7-(3-{[4-(2-hydroxyethyl)-1-piperazinyl]methyl}phenyl)-3-quinolinecarbonitrile |
| 296 | 4-(2,4-dimethylanilino)-7-{5-[(4-hydroxy-1-piperidinyl)methyl]-2-furyl}-3-quinolinecarbonitrile |
| 297 | 7-[5-({[2-(dimethylamino)ethyl]amino}methyl)-2-furyl]-4-(2,4-dimethylanilino)-3-quinolinecarbonitrile |
| 298 | 4-(2,4-dimethylanilino)-7-(5-{[4-(1-pyrrolidinyl)-1-piperidinyl]methyl}-2-furyl)-3-quinolinecarbonitrile |
| 299 | 4-(2,4-dimethylanilino)-7-[5-({[4-pyridinylmethyl)amino]methyl}-2-furyl)-3-quinolinecarbonitrile |
| 300 | 4-(2,4-dimethylanilino)-7-[5-({[2-(1H-imidazol-4-yl)ethyl]amino}methyl)-2-furyl]-3-quinolinecarbonitrile |
| 301 | 4-(2,4-dimethylanilino)-7-[5-(4-morpholinylmethyl)-2-furyl]-3-quinolinecarbonitrile |
| 302 | 4-(2,4-dimethylanilino)-7-(5-{[(2-hydroxyethyl)amino]methyl}-2-furyl)-3-quinolinecarbonitrile |
| 303 | 4-(2,4-dimethylanilino)-7-{5-[(4-methyl-1 piperazinyl)methyl]-2-furyl}-3-quinolinecarbonitrile |
| 304 | 4-(2,4-dimethylanilino)-7-[5-(1-piperidinylmethyl)-2-furyl]-3-quinolinecarbonitrile |
| 305 | 4-(2,4-dimethylanilino)-7-{5-[(4-ethyl-1-piperazinyl)methyl]-2-furyl}-3-quinolinecarbonitrile |
| 306 | 4-(2,4-dimethylanilino)-7-(5-{[4-(2-hydroxyethyl)-1-piperazinyl]methyl}-2-furyl)-3-quinolinecarbonitrile |
| 307 | 4-(2,4-dimethylanilino)-7-{5-[(4-hydroxy-1-piperidinyl)methyl]-2-thienyl}-3-quinolinecarbonitrile |
| 308 | 7-[5-({[2-(dimethylamino)ethyl]amino}methyl)-2-thienyl]-4-(2,4-dimethylanilino)-3-quinolinecarbonitrile |
| 309 | 4-(2,4-dimethylanilino)-7-(5-{[4-(1-pyrrolidinyl)-1-piperidinyl]methyl}-2-thienyl)-3-quinolinecarbonitrile |
| 310 | 4-(2,4-dimethylanilino)-7-(5-{[(4-pyridinylmethyl)amino]methyl}-2-thienyl)-3-quinolinecarbonitrile |
| 311 | 4-(2,4-dimethylanilino)-7-[5-({[2-(1H-imidazol-4-yl)ethyl]amino}methyl)-2-thienyl]-3-quinolinecarbonitrile |
| 312 | 4-(2,4-dimethylanilino)-7-[5-(4-morpholinylmethyl)-2-thienyl]-3-quinolinecarbonitrile |
| 313 | 4-(2,4-dimethylanilino)-7-(5-{[(2-hydroxyethyl)amino]methyl}-2-thienyl)-3-quinolinecarbonitrile |
| 314 | 4-(2,4-dimethylanilino)-7-{5-[(4-methyl-1-piperazinyl)methyl]-2-thienyl}-3-quinolinecarbonitrile |
| 315 | 4-(2,4-dimethylanilino)-7-{5-[(4-ethyl-1-piperazinyl)methyl]-2-thienyl}-3-quinolinecarbonitrile |
| 316 | 4-(2,4-dimethylanilino)-7-(5-{[4-(2-hydroxyethyl)-1-piperazinyl]methyl}-2-thienyl)-3-quinolinecarbonitrile |
| 317 | 4-(2,4-dimethylanilino)-7-{5-[(4-hydroxy-1-piperidinyl)methyl]-3-thienyl}-3-quinolinecarbonitrile |
| 318 | 7-[5-({[2-(dimethylamino)ethyl]amino}methyl)-3-thienyl]-4-(2,4-dimethylanilino)-3-quinolinecarbonitrile |
| 319 | 4-(2,4-dimethylanilino)-7-(5-{[4-(1-pyrrolidinyl)-1-piperidinyl]methyl}-3-thienyl)-3-quinolinecarbonitrile |
| 320 | 4(2,4-dimethylanilino)-7-(5-{[(4-pyridinylmethyl)amino]methyl}-3-thienyl)-3-quinolinecarbonitrile |
| 321 | 4-(2,4-dimethylanilino)-7-[5-({[2-(1H-imidazol-4-yl)ethyl]amino}methyl)-3-thienyl]-3-quinolinecarbonitrile |
| 322 | 4-(2,4-dimethylanilino)-7-[5-(4-morpholinylmethyl)-3-thienyl}-3-quinolinecarbonitrile |
| 323 | 4-(2,4-dimethylanilino)-7-(5-{[(2-hydroxyethyl)amino]methyl}-3-thienyl)-3-quinolinecarbonitrile |
| 324 | 4-(2,4-dimethylanilino)-7-{5-[(4-methyl-1-piperazinyl)methyl]-3-thienyl}-3-quinolinecarbonitrile |
| 325 | 4-(2,4-dimethylanilino)-7-[5-({[3-(4-morpholinyl)propyl]amino}methyl)-3-thienyl]-3-quinolinecarbonitrile |
| 326 | 4-(2,4-dimethylanilino)-7-[5-(1-piperidinylmethyl)-3-thienyl]-3-quinolinecarbonitrile |

TABLE 15-continued

| Example # | ChemicaL Names of Examples |
|---|---|
| 327 | 4-(2,4-dimethylanilino)-7-{5-[(4-ethyl-1-piperazinyl)methyl]-3-thienyl}-3-quinolinecarbonitrile |
| 328 | 4-(2,4-dimethylanilino)-7-(5-{[4-(2-hydroxyethyl)-1-piperazinyl]methyl}-3-thienyl)-3-quinolinecarbonitrile |
| 329 | 4-(4-bromo-2-chloro-6-methylanilino)-7-{5-[(4-hydroxy-1-piperidinyl)methyl]-2-furyl}-3-quinolinecarbonitrile |
| 330 | 4-(4-bromo-2-chloro-6-methylanilino)-7-[5-({[2-(dimethylamino)ethyl]amino}methyl)-2-furyl]-3-quinolinecarbonitrile |
| 331 | 4-(4-bromo-2-chloro-6-methylanilino)-7-(5-{[4-(1-pyrrolidinyl)-1-piperidinyl]methyl}-2-furyl)-3-quinolinecarbonitrile |
| 332 | 4-(4-bromo-2-chloro-6-methylanilino)-7-(5-{[(4-pyridinylmethyl)amino]methyl}-2-furyl)-3-quinolinecarbonitrile |
| 333 | 4-(4-bromo-2-chloro-6-methylanilino)-7-[5-({[2-(1H-imidazol-4-yl)ethyl]amino}methyl)-2-furyl]-3-quinolinecarbonitrile |
| 334 | 4-(4-bromo-2-chloro-6-methylanilino)-7-[5-(4-morpholinylmethyl)-2-furyl]-3-quinolinecarbonitrile |
| 335 | 4-(4-bromo-2-chloro-6-methylanilino)-7-(5-{[(2-hydroxyethyl)amino]methyl}-2-furyl)-3-quinolinecarbonitrile |
| 336 | 4-(4-bromo-2-chloro-6-methylanilino)-7-{5-[(4-methyl-1-piperazinyl)methyl]-2-furyl}-3-quinolinecarbonitrile |
| 337 | 4-(4-bromo-2-chloro-6-methylanilino)-7-[5-({[3-(4-morpholinyl)propyl]amino}methyl)-2-furyl]-3-quinolinecarbonitrile |
| 338 | 4-(4-bromo-2-chloro-6-methylanilino)-7-[5-(1-piperidinylmethyl)-2-furyl]-3-quinolinecarbonitrile |
| 339 | 4-(4-bromo-2-chloro-6-methylanilino)-7-{5-[(4-ethyl-1-piperazinyl)methyl]-2-furyl}-3-quinolinecarbonitrile |
| 340 | 4-(4-bromo-2-chloro-6-methylanilino)-7-(5-{[4-(2-hydroxyethyl)-1-piperazinyl]methyl}-2-furyl)-3-quinolinecarbonitrile |
| 341 | 4-(4-bromo-2-chloro-6-methylanilino)-7-{5-[(4-hydroxy-1-piperidinyl)methyl]-2-thienyl}-3-quinolinecarbonitrile |
| 342 | 4-(4-bromo-2-chloro-6-methylanilino)-7-[5-({[2-(dimethylamino)ethyl]amino}methyl)-2-thienyl]-3-quinolinecarbonitrile |
| 343 | 4-(4-bromo-2-chloro-6-methylanilino)-7-(5-{[4-(1-pyrrolidinyl)-1-piperidinyl]methyl}-2-thienyl)-3-quinolinecarbonitrile |
| 344 | 4-(4-bromo-2-chloro-6-methylanilino)-7-(5-{[(4-pyridinylmethyl)amino]methyl}-2-thienyl)-3-quinolinecarbonitrile |
| 345 | 4-(4-bromo-2-chloro-6-methylanilino)-7-[5-({[2-(1H-imidazol-4-yl)ethyl]amino}methyl)-2-thienyl]-3-quinolinecarbonitrile |
| 346 | 4-(4-bromo-2-chloro-6-methylanilino)-7-[5-(4-morpholinylmethyl)-2-thienyl]-3-quinolinecarbonitrile |
| 347 | 4-(4-bromo-2-chloro-6-methylanilino)-7-(5-{[(2-hydroxyethyl)amino]methyl}-2-thienyl)-3-quinolinecarbonitrile |
| 348 | 4-(4-bromo-2-chloro-6-methylanilino)-7-{5-[(4-methyl-1-piperazinyl)methyl]-2-thienyl}-3-quinolinecarbonitrile |
| 349 | 4-(4-bromo-2-chloro-6-methylanilino)-7-[5-({[3-(4-morpholinyl)propyl]amino}methyl)-2-thienyl]-3-quinolinecarbonitrile |
| 350 | 4-(4-bromo-2-chloro-6-methylanilino)-7-[5-(1-piperidinylmethyl)-2-thienyl]-3-quinolinecarbonitrile |
| 351 | 4-([3-chloro-4'-[(4-hydroxy-1-piperidinyl)methyl]-5-methyl[1,1'-biphenyl]-4-yl)amino)-7-{4-[(4-hydroxy-1-piperidinyl)methyl]phenyl}-3-quinolinecarbonitrile |
| 352 | 4-([3-chloro-4'-({[2-(dimethylamino)ethyl]amino}methyl)-5-methyl[1,1'-biphenyl]-4-yl]amino)-7-[4-({[2-(dimethylamino)ethyl]amino}methyl)phenyl]-3-quinolinecarbonitrile |
| 353 | 4-[(3-chloro-5-methyl-4'-{[4-(1-pyrrolidinyl)-1-piperidinyl]methyl}[1,1'-biphenyl]-4-yl)amino]-7-(4-{[4-(1-pyrrolidinyl)-1-piperidinyl]methyl}phenyl)-3-quinolinecarbonitrile |
| 354 | 4-{[3-chloro-5-methyl-4'-(4-morpholinylmethyl)[1,1'-biphenyl]-4-yl]amino}-7-[4-(4-morpholinylmethyl)phenyl]-3-quinolinecarbonitrile |
| 355 | 4-[(3-chloro-4'-{[(2-hydroxyethyl)amino]methyl}-5-methyl[1,1'-biphenyl]-4-yl)amino]-7-(4-{[(2-hydroxyethyl)amino]methyl}phenyl)-3-quinolinecarbonitrile |
| 356 | 4-((3-chloro-5-methyl-4'-[(4-methyl-1-piperazinyl)methyl][1,1'-biphenyl]-4-yl]amino)-7-(4-[(4-methyl-1-piperazinyl)methyl]phenyl)-3-quinolinecarbonitrile |
| 357 | 4-([3-chloro-5-methyl-4'-({[3-(4-morpholinyl)propyl]amino)methyl}[1,1'-biphenyl]-4-yl]amino)-7-[4-({[3-(4-morpholinyl)propyl]amino)methyl)penyl]-3-quinolinecarbonitrile |
| 358 | 4-([3-chloro-5-methyl-4'-(1-piperidinylmethyl)[1,1'-biphenyl]-4-yl]amino)-7-[4-(1-piperidinylmethyl)phenyl]-3-quinolinecarbonitrile |
| 359 | 4-({3-chloro-4'-[(4-ethyl-1-piperazinyl)methyl]-5-methyl[1,1'-biphenyl]-4-yl}amino)-7-(4-[(4-ethyl-1-piperazinyl)methyl]phenyl)-3-quinolinecarbonitrile |
| 360 | 4-[(3-chloro-4'-([4-(2-hydroxyethyl)-1-piperazinyl]methyl)-5-methyl[1,1'-biphenyl]-4-yl)amino]-7-(4-([4-(2-hydroxyethyl)-1-piperazinyl]methyl}phenyl)-3-quinolinecarbonitrile |
| 361 | 4-({3-chloro-3'-[(4-hydroxy-1-piperidinyl)methyl]-5-methyl[1,1'-biphenyl]-4-yl}amino)-7-{3-[(4-hydroxy-1-piperidinyl)methyl]phenyl}-3- |

TABLE 15-continued

| Example # | ChemicaL Names of Examples |
|---|---|
| | quinolinecarbonitrile |
| 362 | 4-{[3-chloro-3'-({[2-(dimethylamino)ethyl]amino}methyl)-5-methyl[1,1'-biphenyl]-4-yl]amino}-7-[3-({[2-(dimethylamino}ethyl]amino)methyl)phenyl]-3-quinolinecarbonitrile |
| 363 | 4-[(3-chloro-5-methyl-3'-{[4-(1-pyrrolidinyl)-1-piperidinyl]methyl}[1,1'-biphenyl]-4-yl}amino]-7-(3-{[4-(1-pyrrolidinyl)-1-piperidinyl]methyl}phenyl)-3-quinolinecarbonitrile |
| 364 | 4-[(3-chloro-5-methyl-3'-{[(4-pyridinylmethyl)amino]methyl}[1,1'-biphenyl]-4-yl)amino]-7-(3-{[(4-pyridinylmethyl)amino]methyl}phenyl)-3-quinolinecarbonitrile |
| 365 | 4-{[3-chloro-3'-({[2-(1H-imidazol-4-yl)ethyl]amino}methyl)-5-methyl[1,1'-biphenyl]-4-yl]amino}-7-[3-({[2-(1H-imidazol-4-yl)ethyl]amino}methyl)phenyl]-3-quinolinecarbonitrile |
| 366 | 4-{[3-chloro-5-methyl-3'-(4-morpholinylmethyl)[1,1'-biphenyl]-4-yl]amino}-7-[3-(4-morpholinylmethyl)phenyl]-3-quinolinecarbonitrile |
| 367 | 4-[(3-chloro-3'-{[(2-hydroxyethyl)amino]methyl}-5-methyl[1,1'-biphenyl]-4-yl]amino]-7-(3-{[(2-hydroxyethyl)amino]methyl}phenyl)-3-quinolinecarbonitrile |
| 368 | 4-{(3-chloro-5-methyl-3'-[(4-methyl-1-piperazinyl)methyl][1,1'-bipheny]-4-yl}amino)-7-{3-[(4-methyl-1-piperazinyl)methyl]phenyl}-3-quinolinecarbonitrile |
| 369 | 4-{[3-chloro-5-methyl-3'-({[3-(4-morpholinyl)propyl]amino}methyl)[1,1'-biphenyl]-4-yl]amino}-7-[3-({[3-(4-morpholinyl)propyl]amino}methyl)phenyl]-3-quinolinecarbonitrile |
| 370 | 4-{[3-chloro-5-methyl-3'-(1-piperidinylmethyl)[1,1'-biphenyl]-4-yl]amino}-7-[3-(1-piperidinylmethyl)phenyl]-3-quinolinecarbonitrile |
| 371 | 4-({3-chloro-3'-[(4-ethyl-1-piperazinyl)methyl]-5-methyl[1,1'-biphenyl]-4-yl}amino)-7-{3-[(4-ethyl-1-piperazinyl)methyl]phenyl}-3-quinolinecarbonitrile |
| 372 | 4-[(3-chloro-3'-{[4-(2-hydroxyethyl)-1-piperazinyl]methyl}-5-methyl[1,1'-biphenyl]-4-yl)amino]-7-(3-{[4-(2-hydroxyethyl)-1-piperazinyl]methyl}phenyl)-3-quinolinecarbonitrile |
| 373 | 4-{2-chloro-4-[5-({[2-(dimethylamino)ethyl]amino}methyl)-3-thienyl]-6-methylanilino}-7-[5-({[2-(dimethylamino)ethyl]amino}methyl)-3-thienyl]-3-quinolinecarbonitrile |
| 374 | 4-[2-chloro-6-methyl-4-(5-{[4-(1-pyrrolidinyl)-1-piperidinyl]methyl}-3-thienyl)anilino]-7-(5-{[4-(1-pyrrolidinyl)-1-piperidinyl]methyl}-3-thienyl)-3-quinolinecarbonitrile |
| 375 | 4-[2-chloro-6-methyl-4-(5-{[(4-pyridinylmethyl)amino]methyl}-3-thienyl)anilino]-7-(5-{[(4-pyridinylmethyl)amino]methyl}-3-thienyl)-3-quinolinecarbonitrile |
| 376 | 4-(2-chloro-4-[5-({[2-(1H-imidazol-4-yl)ethyl]amino}methyl)-3-thienyl]-6-methylanilino}-7-[5-({[2-(1H-imidazol-4-yl)ethyl]amino}methyl)-3-thienyl]-3-quinolinecarbonitrile |
| 377 | 4-{2-chloro-6-methyl-4-[5-(4-morpholinylmethyl)-3-thienyl]anilino}-7-[5-(4-morpholinylmethyl)-3-thienyl]-3-quinolinecarbonitrile |
| 378 | 4-(2-chloro-6-methyl-4-{5-[(4-methyl-1-piperazinyl)methyl]-3-thienyl}anilino)-7-{5-[(4-methyl-1-piperazinyl)methyl]-3-thienyl}-3-quinolinecarbonitrile |
| 379 | 4-(2-chloro-6-methyl-4-[5-({[3-(4-morpholinyl)propyl]amino}methyl)-3-thienyl]anilino}-7-[5-({[3-(4-morpholinyl)propyl]amino}methyl)-3-thienyl]-3-quinolinecarbonitrile |
| 380 | 4-(2-chloro-6-methyl-4-[5-(1-piperidinylmethyl)-3-thienyl]anilino}-7-[5-(1-piperidinylmethyl)-3-thienyl]-3-quinolinecarbonitrile |
| 381 | 4-(2-chloro-4-{5-[(4-ethyl-1-piperazinyl)methyl]-3-thienyl}-6-methylanilino)-7-(5-[(4-ethyl-1-piperazinyl)methyl]-3-thienyl}-3-quinolinecarbonitrile |
| 382 | 4-[2-chloro-4-(5-{[4-(2-hydroxyethyl)-1-piperazinyl]methyl}-3-thienyl)-6-methylanilino]-7-{5-([4-(2-hydroxyethyl)-1-piperazinyl]methyl}-3-thienyl)-3-quinolinecarbonitrile |
| 383 | 4-[(3-chloro-4-phenoxyphenyl)amino]-7-[4-({[3-(4-morpholinyl)propyl]amino}methyl)phenyl]-3-quinolinecarbonitrile |
| 384 | 4-[(3-chloro-4-phenoxyphenyl)amino]-7-{4-[(4-ethyl-1-piperazinyl)methyl]phenyl}-3-quinolinecarbonitrile |
| 385 | 4-[(3-chloro-4-phenoxyphenyl)amino]-7-(4-{[4-(2-hydroxyethyl)-1-piperazinyl]methyl}phenyl)-3-quinolinecarbonitrile |
| 386 | 4-[(3-chloro-4-phenoxyphenyl)amino]-7-(3-({[2-(dimethylamino)ethyl]amino}methyl)phenyl]-3-quinolinecarbonitrile |
| 387 | 4-[(3-chloro-4-phenoxyphenyl)amino]-7-(3-{[4-(1-pyrrolidinyl)-1-piperidinyl]methyl}phenyl)-3-quinolinecarbonitrile |
| 388 | 4-[(3-chloro-4-phenoxyphenyl)amino]-7-(3-{((4-pyridinylmethyl)amino]methyl}phenyl)-3-quinolinecarbonitrile |
| 389 | 4-[(3-chloro-4-phenoxyphenyl)amino]-7-[3-({[3-(4-morpholinyl)propyl]amino}methyl)phenyl]-3-quinolinecarbonitrile |
| 390 | 4-[(3-chloro-4-phenoxyphenyl)amino]-7-{3-[(4-ethyl-1-piperazinyl)methyl]phenyl}-3-quinolinecarbonitrile |
| 391 | 4-[(3-chloro-4-phenoxyphenyl)amino]-7-{5-[(4-hydroxy-1-piperidinyl)methyl]-2-furyl}-3-quinolinecarbonitrile |
| 392 | 4-[(3-chloro-4-phenoxyphenyl)amino]-7-{5-({[2-(dimethylamino)ethyl]amino}methyl)-2-furyl]-3-quinolinecarbonitrile |

TABLE 15-continued

| Example # | Chemical Names of Examples |
|---|---|
| 393 | 4-[(3-chloro-4-phenoxyphenyl)amino]-7-(5-{[4-(1-pyrrolidinyl)-1-piperidinyl]methyl}-2-furyl)-3-quinolinecarbonitrile |
| 394 | 4-[(3-chloro-4-phenoxyphenyl)amino]-7-(5-{[(4-pyridinylmethyl)amino]methyl}-2-furyl)-3-quinolinecarbonitrile |
| 395 | 4-[(3-chloro-4-phenoxyphenyl)amino]-7-[5-({[2-(1H-imidazol-4-yl)ethyl]amino}methyl)-2-furyl]-3-quinolinecarbonitrile |
| 396 | 4-[(3-chloro-4-phenoxyphenyl)amino]-7-[5-(4-morpholinylmethyl)-2-furyl]-3-quinolinecarbonitrile |
| 397 | 4-[(3-chloro-4-phenoxyphenyl)amino]-7-[5-{[2-hydroxyethyl)amino]methyl}-2-furyl)-3-quinolinecarbonitrile |
| 398 | 4-[(3-chloro-4-phenoxyphenyl)amino]-7-{5-[(4-methyl-1-piperazinyl)methyl]-2-furyl}-3-quinolinecarbonitrile |
| 399 | 4-[(3-chloro-4-phenoxyphenyl)amino]-7-[5-({[3-(4-morpholinyl)propyl]amino}methyl)-2-furyl]-3-quinolinecarbonitrile |
| 400 | 4-[(3-chloro-4-phenoxyphenyl)amino]-7-[5-(1-piperidinylmethyl)-2-furyl]-3-quinolinecarbonitrile |
| 401 | 4-[(3-chloro-4-phenoxyphenyl)amino]-7-{5-[(4-ethyl-1-piperazinyl)methyl]-2-furyl}-3-quinolinecarbonitrile |
| 402 | 4-[(3-chloro-4-phenoxyphenyl)amino]-7-(5-{[4-(2-hydroxyethyl)-1-piperazinyl]methyl}-2-furyl)-3-quinolinocarbonitrile |
| 403 | 4-[(3-chloro-4-phenoxyphenyl)amino]-7-[5-({[2-(dimethylamino)ethyl]amino}methyl-2-thienyl]-3-quinolinecarbonitrile |
| 404 | 4-[(3-chloro-4-phenoxyphenyl)amino]-7-(5-{[4-(1-pyrrolidinyl)-1-piperidinyl]methyl}-2-thienyl)-3-quinolinecarbonitrile |
| 405 | 4-[(3-chloro-4-phenoxyphenyl)amino]-7-(5-{[(4-pyridinylmethyl)amino]methyl}-2-thienyl)-3-quinolinecarbonitrile |
| 406 | 4-[(3-chloro-4-phenoxyphenyl)amino]-7-[5-(4-morpholinylmethyl)-2-thienyl]-3-quinolinecarbonitrile |
| 407 | 4-[(3-chloro-4-phenoxyphenyl)amino]-7-{5-[(4-methyl-1-piperazinyl)methyl]-2-thienyl}-3-quinolinecarbonitrile |
| 408 | 4-[(3-chloro-4-phenoxyphenyl)amino]-7-{5-[(4-ethyl-1-piperazinyl)methyl]-2-thienyl)-3-quinolinecarbonitrile |
| 409 | 4-[(3-chloro-4-phenoxyphenyl)amino]-7-{5-[(4-hydroxy-1-piperidinyl)methyl]-3-thienyl}-3-quinolinecarbonitrile |
| 410 | 4-[(3-chloro-4-phenoxyphenyl)amino]-7-[5-({[2-(dimethylamino)ethyl]amino}methyl)-3-thienyl]-3-quinolinecarbonitrile |
| 411 | 4-[(3-chloro-4-phenoxyphenyl)amino]-7-(5-{[4-(1-pyrrolidinyl)-1-piperidinyl]methyl}-3-thienyl)-3-quinolinecarbonitrile |
| 412 | 4-[(3-chloro-4-phenoxyphenyl)amino]-7-(5-{[(4-pyridinylmethyl)amino]methyl}-3-thienyl)-3-quinolinecarbonitrile |
| 413 | 4-[(3-chloro-4-phenoxyphenyl)amino]-7-[5-({[2-(1H-imidazol-4-yl)ethyl]amino}methyl)-3-thienyl]-3-quinolinecarbonitrile |
| 414 | 4-[(3-chloro-4-phenoxyphenyl)amino]-7-[5-(4-morpholinylmethyl)-3-thienyl]-3-quinolinecarbonitrile |
| 415 | 4-[(3-chloro-4-phenoxyphenyl)amino]-7-(5-{[(2-hydroxyethyl)amino]methyl}-3-thienyl)-3-quinolinecarbonitrile |
| 416 | 4-[(3-chloro-4-phenoxyphenyl)amino]-7-{5-[(4-methyl-1-piperazinyl)methyl]-3-thienyl}-3-quinolinecarbonitrile |
| 417 | 4-[(3-chloro-4-phenoxyphenyl)amino]-7-[5-({[3-(4-morpholinyl)propyl]amino}methyl)-3-thienyl]-3-quinolinecarbonitrile |
| 418 | 4-[(3-chloro-4-phenoxyphenyl)amino]-7-[5-(1-piperidinylmethyl)-3-thienyl]-3-quinolinecarbonitrile |
| 419 | 4-[(3-chloro-4-phenoxyphenyl)amino]-7-{5-[(4-ethyl-1-piperazinyl)methyl]-3-thienyl}-3-quinolinecarbonitrile |
| 420 | 4-[(3-chloro-4-phenoxyphenyl)amino]-7-(5-{[4-(2-hydroxyethyl)-1-piperazinyl]methyl}-3-thienyl)-3-quinolinecarbonitrile |
| 421 | 4-[(3-chloro-4-phenoxyphenyl)amino]-7-[5-{[(3-(4-morpholinyl)propyl]amino}methyl)-2-pyridinyl]-3-quinolinecarbonitrile |
| 422 | 4-{[3-chloro-4-(phenylsulfanyl)phenyl]amino}-7-{4-[(4-hydroxy-1-piperidinyl)methyl]phenyl}-3-quinolinecarbonitrile |
| 423 | 4-{[3-chloro-4-(phenylsulfanyl)phenyl]amino}-7-(4-{[(4-pyridinylmethyl)amino]methyl}phenyl)-3-quinolinecarbonitrile |
| 424 | 4-{[3-chloro-4-(phenylsulfanyl)phenyl]amino}-7-[4-({[2-(1H-imidazol-4-yl)ethyl]amino}methyl)phenyl]-3-quinolinecarbonitrile |
| 425 | 4-{[3-chloro-4-(phenylsulfanyl)phenyl]amino}-7-[4-(4-morpholinylmethyl)phenyl]-3-quinolinecarbonitrile |
| 426 | 4-{[3-chloro-4-(phenylsulfanyl)phenyl]amino}-7-(4-{[(2-hydroxyethyl)amino]methyl}phenyl)-3-quinolinecarbonitrile |
| 427 | 4-{[3-chloro-4-(phenylsulfanyl)phenyl]amino}-7-{4-[(4-methyl-1-piperazinyl)methyl]phenyl}-3-quinolinecarbonitrile |
| 428 | 4-{[3-chloro-4-(phenylsulfanyl)phenyl]amino}-7-[4-({[3-(4-morpholinyl)propyl]amino}methyl)phenyl]-3-quinolinecarbonitrile |
| 429 | 4-{[3-chloro-4-(phenylsulfanyl)phenyl]amino}-7-(4-[(4-ethyl-1-piperazinyl)methyl]phenyl}-3-quinolinecarbonitrile |
| 430 | 4-{[3-chloro-4-(phenylsulfanyl)phenyl]amino}-7-(4-{[4-(2-hydroxyethyl)-1-piperazinyl]methyl}phenyl)-3-quinolinecarbonitrile |
| 431 | 4-{[3-chloro-4-(phenylsulfanyl)phenyl]amino}-7-{3-[(4-hydroxy-1- |

TABLE 15-continued

| Example # | ChemicaL Names of Examples |
|---|---|
| | piperidinyl)methyl]phenyl}-3-quinolinecarbonitrile |
| 432 | 4-{[3-chloro-4-(phenylsulfanyl)phenyl]amino}-7-[3-({[2-(dimethylamino)ethyl]amino}methyl)phenyl]-3-quinolinecarbonitrile |
| 433 | 4-{[3-chloro-4-(phenylsulfanyl)phenyl]amino}-7-(3-{[4-(1-pyrrolidinyl)-1-piperidinyl]methyl}phenyl)-3-quinolinecarbonitrile |
| 434 | 4-{[3-chloro-4-(phenylsulfanyl)phenyl]amino}-7-(3-{[(2-hydroxyethyl)amino]methyl}phenyl)-3-quinolinecarbonitrile |
| 435 | 4-{[3-chloro-4-(phenylsulfanyl)phenyl]amino}-7-[3-({[3-(4-morpholinyl)propyl]amino}methyl)phenyl]-3-quinolinecarbonitrile |
| 436 | 4-{[3-chloro-4-(phenylsulfanyl)phenyl]amino}-7-(3-{[4-(2-hydroxyethyl)-1-piperazinyl]methyl}phenyl)-3-quinolinecarbonitrile |
| 437 | 4-{[3-chloro-4-(phenylsulfanyl)phenyl]amino}-7-{5-[(4-hydroxy-1-piperidinyl)methyl]-2-furyl}-3-quinolinecarbonitrile |
| 438 | 4-{[3-chloro-4-(phenylsulfanyl)phenyl]amino}-7-[5-({[2-(dimethylamino)ethyl]amino}methyl)-2-furyl]-3-quinolinecarbonitrile |
| 439 | 4-{[3-chloro-4-(phenylsulfanyl)phenyl]amino}-7-(5-{[4-(1-pyrrolidinyl)-1-piperidinyl]methyl}-2-furyl)-3-quinolinecarbonitrile |
| 440 | 4-{[3-chloro-4-(phenylsulfanyl)phenyl]amino}-7-(5-{[(4-pyridinylmethyl)amino]methyl}-2-furyl)-3-quinolinecarbonitrile |
| 441 | 4-{[3-chloro-4-(phenylsulfanyl)phenyl]amino}-7-[5-({[2-(1H-imidazol-4-yl)ethyl]amino}methyl)-2-furyl]-3-quinolinecarbonitrile |
| 442 | 4-{[3-chloro-4-(phenylsulfanyl)phenyl]amino}-7-[5-(4-morpholinylmethyl)-2-furyl]-3-quinolinecarbonitrile |
| 443 | 4-{[3-chloro-4-(phenylsulfanyl)phenyl]amino}-7-(5-{[(2-hydroxyethyl)amino]methyl}-2-furyl)-3-quinolinecarbonitrile |
| 444 | 4-{[3-chloro-4-(phenylsulfanyl)phenyl]amino}-7-{5-[(4-methyl-1-piperazinyl)methyl]-2-furyl}-3-quinolinecarbonitrile |
| 445 | 4-{[3-chloro-4-(phenylsulfanyl)phenyl]amino}-7-[5-({[3-(4-morpholinyl)propyl]amino}methyl)-2-furyl]-3-quinolinecarbonitrile |
| 446 | 4-{[3-chloro-4-(phenylsulfanyl)phenyl]amino}-7-{5-[(4-ethyl-1-piperazinyl)methyl]-2-furyl}-3-quinolinecarbonitrile |
| 447 | 4-{[3-chloro-4-(phenylsulfanyl)phenyl]amino}-7-[5-({[2-(dimethylamino)ethyl]amino}methyl)-2-thienyl]-3-quinolinecarbonitrile |
| 448 | 4-{[3-chloro-4-(phenylsulfanyl)phenyl]amino}-7-(5-{[4-(1-pyrrolidinyl)-1-piperidinyl]methyl}-2-thienyl)-3-quinolinecarbonitrile |
| 449 | 4-{[3-chloro-4-(phenylsulfanyl)phenyl]amino}-7-[5-(4-morpholinylmethyl)-2-thienyl)-3-quinolinecarbonitrile |
| 450 | 4-{[3-chloro-4-(phenylsulfanyl)phenyl]amino}-7-{5-[(4-methyl-1-piperazinyl)methyl]-2-thienyl}-3-quinolinecarbonitrile |
| 451 | 4-{[3-chloro-4-(phenylsulfanyl)phenyl]amino}-7-[5-({[3-(4-morpholinyl)propyl]amino}methyl)-2-thienyl]-3-quinolinecarbonitrile |
| 452 | 4-{[3-chloro-4-(phenylsulfanyl)phenyl]amino}-7-{5-[(4-ethyl-1-piperazinyl)methyl]-2-thienyl}-3-quinolinecarbonitrile |
| 453 | 4-{[3-chloro-4-(phenylsulfanyl)phenyl]amino}-7-{5-[(4-hydroxy-1-piperidinyl)methyl]-3-thienyl}-3-quinolinecarbonitrile |
| 454 | 4-{[3-chloro-4-(phenylsulfanyl)phenyl]amino}-7-[5-({[2-(dimethylamino)ethyl]amino}methyl)-3-thienyl]-3-quinolinecarbonitrile |
| 455 | 4-{[3-chloro-4-(phenylsulfanyl)phenyl]amino}-7-(5-{[4-(1-pyrrolidinyl)-1-piperidinyl]methyl}-3-thienyl)-3-quinolinecarbonitrile |
| 456 | 4-{[3-chloro-4-(phenylsulfanyl)phenyl]amino}-7-(5-{[(4-pyridinylmethyl)amino]methyl}-3-thienyl)-3-quinolinecarbonitrile |
| 457 | 4-{[3-chloro-4-(phenylsulfanyl)phenyl]amino}-7-[5-({[2-(1H-imidazol-4-yl)ethyl]amino}methyl)-3-thienyl]-3-quinolinecarbonitrile |
| 458 | 4-{[3-chloro-4-(phenylsulfanyl)phenyl]amino}-7-[5-(4-morpholinylmethyl)-3-thienyl]-3-quinolinecarbonitrile |
| 459 | 4-{[3-chloro-4-(phenylsulfanyl)phenyl]amino}-7-(5-{[(2-hydroxyethyl)amino]methyl}-3-thienyl)-3-quinolinecarbonitrile |
| 460 | 4-{[3-chloro-4-(phenylsulfanyl)phenyl]amino}-7-{5-[(4-methyl-1-piperazinyl)methyl]-3-thienyl}-3-quinolinecarbonitrile |
| 461 | 4-{[3-chloro-4-(phenylsulfanyl)phenyl]amino}-7-[5-({[3-(4-morpholinyl)propyl]amino}methyl)-3-thienyl]-3-quinolinecarbonitrile |
| 462 | 4-{[3-chloro-4-(phenylsulfanyl)phenyl]amino}-7-[5-(1-piperidinylmethyl)-3-thienyl]-3-quinolinecarbonitrile |
| 463 | 4-{[3-chloro-4-(phenylsulfanyl)phenyl]amino}-7-{5-[(4-ethyl-1-piperazinyl)methyl]-3-thienyl}-3-quinolinecarbonitrile |
| 464 | 4-{[3-chloro-4-(phenylsulfanyl)phenyl]amino}-7-(5-{[4-(2-hydroxyethyl)-1-piperazinyl]methyl}-3-thienyl)-3-quinolinecarbonitrile |
| 465 | 4-{[3-chloro-4-(3-furylmethyl)phenyl]amino}-7-{4-[(4-hydroxy-1-piperidinyl)methyl]phenyl}-3-quinolinecarbonitrile |
| 466 | 4-{[3-chloro-4-(3-furylmethyl)phenyl]amino}-7-(4-({[2-(dimethylamino)ethyl]amino}methyl)phenyl]-3-quinolinecarbonitrile |
| 467 | 4-{[3-chloro-4-(3-furylmethyl)phenyl]amino}-7-(4-{[4-(1-pyrrolidinyl)-1-piperidinyl]methyl}phenyl)-3-quinolinecarbonitrile |
| 468 | 4-{[3-chloro-4-(3-furylmethyl)phenyl]amino}-7-(4-{[(4-pyridinylmethyl)amino]methyl}phenyl)-3-quinolinecarbonitrile |
| 469 | 4-{[3-chloro-4-(3-furylmethyl)phenyl]amino}-7-[4-({[2-(1H-imidazol-4-yl)ethyl]amino}methyl)phenyl]-3-quinolinecarbonitrile |

TABLE 15-continued

| Example # | ChemicaL Names of Examples |
|---|---|
| 470 | 4-{[3-chloro-4-(3-furylmethyl)phenyl]amino}-7-[4-(4-morpholinylmethyl)phenyl]-3-quinolinecarbonitrile |
| 471 | 4-{[3-chloro-4-(3-furylmethyl)phenyl]amino}-7-(4-{[(2-hydroxyethyl)amino]methyl}phenyl)-3-quinolinecarbonitrile |
| 472 | 4-{[3-chloro-4-(3-furylmethyl)phenyl]amino}-7-{4-[(4-methyl-1-piperazinyl)methyl]phenyl}-3-quinolinecarbonitrile |
| 473 | 4-{[3-chloro-4-(3-furylmethyl)phenyl]amino}-7-[4-({[3-(4-morpholinyl)propyl]amino}methyl)phenyl]-3-quinolinecarbonitrile |
| 474 | 4-{[3-chloro-4-(3-furylmethyl)phenyl]amino}-7-[4-(1-piperidinylmethyl)phenyl]-3-quinolinecarbonitrile |
| 475 | 4-{[3-chloro-4-(3-furylmethyl)phenyl]amino}-7-{4-[(4-ethyl-1-piperazinyl)methyl]phenyl}-3-quinolinecarbonitrile |
| 476 | 4-{[3-chloro-4-(3-furylmethyl)phenyl]amino}-7-(4-{[4-(2-hydroxyethyl)-1-piperazinyl]methyl}phenyl)-3-quinolinecarbonitrile |
| 477 | 4-{[4-(3-furylmethyl)phenyl]amino}-7-(4-{[(4-pyridinylmethyl)amino]methyl}phenyl)-3-quinolinecarbonitrile |
| 478 | 4-{[4-(3-furylmethyl)phenyl]amino}-7-[4-({[2-(1H-imidazol-4-yl)ethyl]amino}methyl)phenyl]-3-quinolinecarbonitrile |
| 479 | 4-{[4-(3-furylmethyl)phenyl]amino}-7-[4-(4-morpholinylmethyl)phenyl]-3-quinolinecarbonitrile |
| 480 | 4-{[4-(3-furylmethyl)phenyl]amino}-7-(4-{[(2-hydroxyethyl)amino]methyl}phenyl)-3-quinolinecarbonitrile |
| 481 | 4-{[4-(3-furylmethyl)phenyl]amino}-7-{4-[(4-methyl-1-piperazinyl)methyl]phenyl}-3-quinolinecarbonitrile |
| 482 | 4-{[4-(3-furylmethyl)phenyl]amino}-7-[4-(1-piperidinylmethyl)phenyl}-3-quinolinecarbonitrile |
| 483 | 7-{4-[(4-ethyl-1-piperazinyl)methyl]phenyl}-4-{[4-(3-furylmethyl)phenyl]amino}-3-quinolinecarbonitrile |
| 484 | 4-{[4-(3-furylmethyl)phenyl]amino}-7-(4-{[4-(2-hydroxyethyl)-1-piperazinyl]methyl}phenyl)-3-quinolinecarbonitrile |
| 485 | 4-{[4-(3-furylmethyl)phenyl]amino}-7-{3-[(4-hydroxy-1-piperidinyl)methyl]phenyl}-3-quinolinecarbonitrile |
| 486 | 7-[3-({[2-(dimethylamino)ethyl]amino}methyl)phenyl]-4-{[4-(3-furylmethyl)phenyl]amino}-3-quinolinecarbonitrile |
| 487 | 4-{[4-(3-furylmethyl)phenyl]amino}-7-(3-{[4-(1-pyrrolidinyl)-1-piperidinyl]methyl}phenyl)-3-quinolinecarbonitrile |
| 488 | 4-{[4-(3-furylmethyl)phenyl]amino}-7-(3-{[(4-pyridinylmethyl)amino]methyl}phenyl)-3-quinolinecarbonitrile |
| 489 | 4-{[4-(3-furylmethyl)phenyl]amino}-7-[3-({[2-(1H-imidazol-4-yl)ethyl]amino}methyl)phenyl]-3-quinolinecarbonitrile |
| 490 | 4-{[4-(3-furylmethyl)phenyl]amino}-7-[3-(4-morpholinylmethyl)phenyl]-3-quinolinecarbonitrile |
| 491 | 4-{[4-(3-furylmethyl)phenyl]amino}-7-(3-{[(2-hydroxyethyl)amino]methyl}phenyl)-3-quinolinecarbonitrile |
| 492 | 4-{[4-(3-furylmethyl)phenyl]amino}-7-{3-[(4-methyl-1-piperazinyl)methyl]phenyl}-3-quinolinecarbonitrile |
| 493 | 4-{[4-(3-furylmethyl)phenyl]amino}-7-[3-({[3-(4-morpholinyl)propyl]amino}methyl)phenyl]-3-quinolinecarbonitrile |
| 494 | 7-{3-[(4-ethyl-1-piperazinyl)methyl]phenyl}-4-{[4-(3-furylmethyl)phenyl]amino}-3-quinolinecarbonitrile |
| 495 | 4-{[4-(3-furylmethyl)phenyl]amino}-7-(3-{[4-(2-hydroxyethyl)-1-piperazinyl]methyl}phenyl)-3-quinolinecarbonitrile |
| 496 | 4-{[4-(3-furylmethyl)phenyl]amino}-7-{5-[(4-hydroxy-1-piperidinyl)methyl]-2-pyridinyl}-3-quinolinecarbonitrile |
| 497 | 7-[5-({[2-(dimethylamino)ethyl]amino}methyl)-2-pyridinyl]-4-{[4-(3-furylmethyl)phenyl]amino}-3-quinolinecarbonitrile |
| 498 | 4-{[4-(3-furylmethyl)phenyl]amino}-7-(5-{[(2-hydroxyethyl)amino]methyl}-2-pyridinyl)-3-quinolinecarbonitrile |
| 499 | 4-{[4-(3-furylmethyl)phenyl]amino}-7-[5-({[3-(4-morpholinyl)propyl]amino}methyl)-2-pyridinyl]-3-quinolinecarbonitrile |
| 500 | 4-{[4-(3-furylmethyl)phenyl]amino}-7-(5-{[4-(2-hydroxyethyl)-1-piperazinyl]methyl}-2-pyridinyl)-3-quinolinecarbonitrile |
| 501 | 4-{[4-(3-furylmethyl)phenyl]amino}-7-{5-[(4-hydroxy-1-piperidinyl)methyl]-3-thienyl}-3-quinolinecarbonitrile |
| 502 | 4-{[4-(3-furylmethyl)phenyl]amino}-7-(5-{[4-(1-pyrrolidlnyl)-1-piperidinyl]methyl}-3-thienyl)-3-quinolinecarbonitrile |
| 503 | 4-{[4-(3-furylmethyl)phenyl]amino}-7-(5-{[(4-pyridinylmethyl)amino]methyl}-3-thienyl)-3-quinolinecarbonitrile |
| 504 | 4-{[4-(3-furylmethyl)phenyl]amino}-7-[5-(4-morpholinylmethyl)-3-thienyl]-3-quinolinecarbonitrile |
| 505 | 4-{[4-(3-furylmethyl)phenyl]amino}-7-(5-{[(2-hydroxyethyl)amino]methyl}-3-thienyl)-3-quinolinecarbonitrile |
| 506 | 4-{[4-(3-furylmethyl)phenyl]amino}-7-{5-[(4-methyl-1-piperazinyl)methyl]-3-thienyl}-3-quinolinecarbonitrile |
| 507 | 4-{[4-(3-furylmethyl)phenyl]amino}-7-[5-{[3-(4-morpholinyl)propyl]amino}methyl)-3-thienyl]-3-quinolinecarbonitrile |
| 508 | 4-{[4-(3-furylmethyl)phenyl]amino}-7-[5-(1-piperidinylmethyl)-3-thienyl]-3- |

TABLE 15-continued

| Example # | Chemical Names of Examples |
|---|---|
| | quinolinecarbonitrile |
| 509 | 7-{5-[(4-ethyl-1-piperazinyl)methyl]-3-thienyl}-4-{[4-(3-furylmethyl)phenyl]amino}-3-quinolinecarbonitrile |
| 510 | 4-{[4-(3-furylmethyl)phenyl]amino}-7-(5-{[4-(2-hydroxyethyl)-1-piperazinyl]methyl}-3-thienyl)-3-quinolinecarbonitrile |
| 511 | 4-(2,4-dichloro-5-methoxyanilino)-7-(4-{[4-(1-pyrrolidinyl)-1-piperidinyl]methyl}phenyl)-3-quinolinecarbonitrile |
| 512 | 4-(2,4-dichloro-5-methoxyanilino)-7-(4-{[(4-pyridinylmethyl)amino]methyl}phenyl)-3-quinolinecarbonitrile |
| 513 | 4-(2,4-dichloro-5-methoxyanilino)-7-[4-({[2-(1H-imidazol-4-yl)ethyl]amino}methyl)phenyl]-3-quinolinecarbonitrile |
| 514 | 4-(2,4-dichloro-5-methoxyanilino)-7-(4-{[(2-hydroxyethyl)amino]methyl}phenyl)-3-quinolinecarbonitrile |
| 515 | 4-(2,4-dichloro-5-methoxyanilino)-7-[4-({[3-(4-morpholinyl)propyl]amino}methyl)phenyl]-3-quinolinecarbonitrile |
| 516 | 4-(2,4-dichloro-5-methoxyanilino)-7-{5-[(4-hydroxy-1-piperidinyl)methyl]-2-furyl}-3-quinolinecarbonitrile |
| 517 | 4-(2,4-dichloro-5-methoxyanilino)-7-[5-({[2-(dimethylamino)ethyl]amino}methyl)-2-furyl]-3-quinolinecarbonitrile |
| 518 | 4-(2,4-dichloro-5-methoxyanilino)-7-(5-{[4-(1-pyrrolidinyl)-1-piperidinyl]methyl}-2-furyl)-3-quinolinecarbonitrile |
| 519 | 4-(2,4-dichloro-5-methoxyanilino)-7-(5-{[(4-pyridinylmethyl)amino]methyl}-2-furyl)-3-quinolinecarbonitrile |
| 520 | 4-(2,4-dichloro-5-methoxyanilino)-7-[5-({[2-(1H-imidazol-4-yl)ethyl]amino}methyl)-2-furyl]-3-quinolinecarbonitrile |
| 521 | 4-(2,4-dichloro-5-methoxyanilino)-7-(5-{[(2-hydroxyethyl)amino]methyl}-2-furyl)-3-quinolinecarbonitrile |
| 522 | 4-(2,4-dichloro-5-methoxyanilino)-7-[5-({[3-(4-morpholinyl)propyl]amino}methyl)-2-furyl]-3-quinolinecarbonitrile |
| 523 | 4-(2,4-dichloro-5-methoxyanilino)-7-[5-(1-piperidinylmethyl)-2-furyl]-3-quinolinecarbonitrile |
| 524 | 4-(2,4-dichloro-5-methoxyanilino)-7-{5-[(4-ethyl-1-piperazinyl)methyl]-2-furyl}-3-quinolinecarbonitrile |
| 525 | 4-(2,4-dichloro-5-methoxyanilino)-7-(5-{[4-(1-pyrrolidinyl)-1-piperidinyl]methyl}-2-thienyl)-3-quinolinecarbonitrile |
| 526 | 4-(2,4-dichloro-5-methoxyanilino)-7-{5-[(4-ethyl-1-piperazinyl)methyl]-2-thienyl}-3-quinolinecarbonitrile |
| 527 | 4-(2,4-dichloro-5-methoxyanilino)-7-[5-({[2-(dimethylamino)ethyl]amino}methyl)-3-thienyl]-3-quinolinecarbonitrile |
| 528 | 4-(2,4-dichloro-5-methoxyanilino)-7-(5-}[(4-pyridinylmethyl)amino]methyl}-3-thienyl)-3-quinolinecarbonitrile |
| 529 | 4-(2,4-dichloro-5-methoxyanilino)-7-[5-({[2-(1H-imidazol-4-yl)ethyl]amino}methyl)-3-thienyl]-3-quinolinecarbonitrile |
| 530 | 4-(2,4-dichloro-5-methoxyanilino)-7-{5-[(4-hydroxy-1-piperidinyl)methyl]-2-pyridinyl}-3-quinolinecarbonitrile |
| 531 | 4-(2,4-dichloro-5-methoxyanilino)-7-[5-({[2-(dimethylamino)ethyl]amino}methyl)-2-pyridinyl]-3-quinolinecarbonitrile |
| 532 | 4-(2,4-dichloro-5-methoxyanilino)-7-(5-{[4-(1-pyrrolidinyl)-1-piperidinyl]methyl}-2-pyridinyl)-3-quinolinecarbonitrile |
| 533 | 4-(2,4-dichloro-5-methoxyanilino)-7-(5-{[(2-hydroxyethyl)amino]methyl}-2-pyridinyl)-3-quinolinecarbonitrile |
| 534 | 4-(2,4-dichloro-5-methoxyanilino)-7-[5-({[3-(4-morpholinyl)propyl]amino}methyl)-2-pyridinyl]-3-quinolinecarbonitrile |
| 535 | 4-(2,4-dichloro-5-methoxyanilino)-7-[(5-{[4-(2-hydroxyethyl)-1-piperazinyl]methyl}-2-pyridinyl]-3-quinolinecarbonitrile |
| 536 | 7-{4-[(4-hydroxy-1-piperidinyl)methyl]phenyl}-4-(3,4,5-trimethoxyanilino)-3-quinolinecarbonitrile |
| 537 | 7-[4-(4-morpholinylmethyl)phenyl]-4-(3,4,5-trimethoxyanilino)-3-quinolinecarbonitrile |
| 538 | 7-(4-{[(2-hydroxyethyl)amino]methyl}phenyl)-4-(3,4,5-trimethoxyanilino)-3-quinolinecarbonitrile |
| 539 | 7-{4-[(4-methyl-1-piperazinyl)methyl]phenyl}-4-(3,4,5-trimethoxyanilino)-3-quinolinecarbonitrile |
| 540 | 7-[4-(1-piperidinylmethyl)phenyl]-4-(3,4,5-trimethoxyanilino)-3-quinolinecarbonitrile |
| 541 | 7-{4-[(4-ethyl-1-piperazinyl)methyl]phenyl}-4-(3,4,5-trimethoxyanilino)-3-quinolinecarbonitrile |
| 542 | 7-{3-[(4-hydroxy-1-piperidinyl)methyl]phenyl}-4-(3,4,5-trimethoxyanilino)-3-quinolinecarbonitrile |
| 543 | 7-[3-({[2-(dimethylamino)ethyl]amino}methyl)phenyl]-4-(3,4,5-trimethoxyanilino)-3-quinolinecarbonitrile |
| 544 | 7-(3-{[4-(1-pyrrolidinyl)-1-piperidinyl]methyl}phenyl)-4-(3,4,5-trimethoxyanilino)-3-quinolinecarbonitrile |
| 545 | 7-(3-{[(4-pyridinylmethyl)amino]methyl}phenyl)-4-(3,4,5-trimethoxyanilino)-3-quinolinecarbonitrile |
| 546 | 7-[3-({[2-(1H-imidazol-4-yl)ethyl]amino}methyl)phenyl]-4-(3,4,5-trimethoxyanilino)-3-quinolinecarbonitrile |

TABLE 15-continued

| Example # | ChemicaL Names of Examples |
|---|---|
| 547 | 7-[3-(4-morpholinylmethyl)phenyl]-4-(3,4,5-trimethoxyanilino)-3-quinolinecarbonitrile |
| 548 | 7-(3-{[(2-hydroxyethyl)amino]methyl}phenyl)-4-(3,4,5-trimethoxyanilino)-3-quinolinecarbonitrile |
| 549 | 7-{3-[(4-methyl-1-piperazinyl)methyl]phenyl}-4-(3,4,5-trimethoxyanilino)-3-quinolinecarbonitrile |
| 550 | 7-[3-({[3-(4-morpholinyl)propyl]amino}methyl)phenyl]-4-(3,4,5-trimethoxyanilino)-3-quinolinecarbonitrile |
| 551 | 7-[3-(1-piperidinylmethyl)phenyl]-4-(3,4,5-trimethoxyanilino)-3-quinolinecarbonitrile |
| 552 | 7-((3-{[4-(2-hydroxyethyl)-1-piperazinyl]methyl}phenyl)-4-(3,4,5-trimethoxyanilino)-3-quinolinecarbonitrile |
| 553 | 7-(5-{[4-(1-pyrrolidinyl)-1-piperidinyl]methyl}-2-furyl)-4-(3,4,5-trimethoxyanilino)-3-quinolinecarbonitrile |
| 554 | 7-{5-[(4-hydroxy-1-piperidinyl)methyl]-2-thienyl}-4-(3,4,5-trimethoxyanilino)-3-quinolinecarbonitrile |
| 555 | 7-[5-({[2-(1H-imidazol-4-yl)ethyl]amino}methyl)-2-thienyl]-4-(3,4,5-trimethoxyanilino)-3-quinolinecarbonitrile |
| 556 | 7-{5-[(4-methyl-1-piperazinyl)methyl]-2-thienyl}-4-(3,4,5-trimethoxyanilino)-3-quinolinecarbonitrile |
| 557 | 7-{5-[(4-ethyl-1-piperazinyl)methyl]-2-thienyl}-4-(3,4,5-trimethoxyanilino)-3-quinolinecarbonitrile |
| 558 | 7-(5-{[4-(2-hydroxyethyl)-1-piperazinyl]methyl}-2-thienyl)-4-(3,4,5-trimethoxyanilino)-3-quinolinecarbonitrile |
| 559 | 7-(5-{[(4-pyridinylmethyl)amino]methyl}-3-thienyl)-4-(3,4,5-trimethoxyanilino)-3-quinolinecarbonitrile |
| 560 | 7-[5-(4-morpholinylmethyl)-3-thienyl]-4-(3,4,5-trimethoxyanilino)-3-quinolinecarbonitrile |
| 561 | 7-(5-[(2-hydroxyethyl)amino]methyl}-3-thienyl)-4-(3,4,5-trimethoxyanilino)-3-quinolinecarbonitrile |
| 562 | 7-{5-[(4-methyl-1-piperazinyl)methyl]-3-thienyl}-4-(3,4,5-trimethoxyanilino)-3-quinolinecarbonitrile |
| 563 | 7-{5-[(4-hydroxy-1-piperidinyl)methyl]-2-pyridinyl}-4-(3,4,5-trimethoxyanilino)-3-quinolinecarbonitrile |
| 564 | 7-(5-{[4-(1-pyrrolidinyl)-1-piperidinyl]methyl}-2-pyridinyl)-4-(3,4,5-trimethoxyanilino)-3-quinolinecarbonitrile |
| 565 | 7-(5-{[(2-hydroxyethyl)amino]methyl}-2-pyridinyl)-4-(3,4,5-trimethoxyanilino)-3-quinolinecarbonitrile |
| 566 | 7-[5-({[3-(4-morpholinyl)propyl]amino}methyl)-2-pyridinyl]-4-(3,4,5-trimethoxyanilino)-3-quinolinecarbonitrile |
| 567 | 7-[(5-{[4-(2-hydroxyethyl)-1-piperazinyl]methyl}-2-pyridinyl]-4-(3,4,5-trimethoxyanilino)-3-quinolinecarbonitrile |

What is claimed is:

1. A compound of Formula (I) represented by the structure:

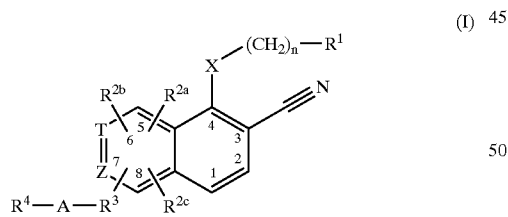

(I)

wherein:

X is —NH—, —NR$^5$—, —O—, or —S(O)$_m$—;
n is an integer of 0 or 1;
m is an integer of 0 to 2;
q is an integer of 0 to 5;
p is an integer of 2 to 5;
s is an integer of 0 to 5;
r is an integer of 0 to 5;
J is halogen;
A is absent;
T is N and Z is carbon;
R$^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$ R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$ R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —R$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$ (C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;

Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ring of 3 to 8 atoms, optionally containing 1 or 2 additional heteroatoms which may be the same or different selected from N, O and S;

R$^{2a}$, R$^{2b}$, and R$^{2c}$, are each, independently selected from —H, -aryl, —CH$_2$aryl, —Oaryl, —S(O)$_m$aryl, —J, —NO$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^7$OR$^5$, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$—R$^{12}$, —(C(R$^9$)$_2$)$_q$—R$^{12}$,

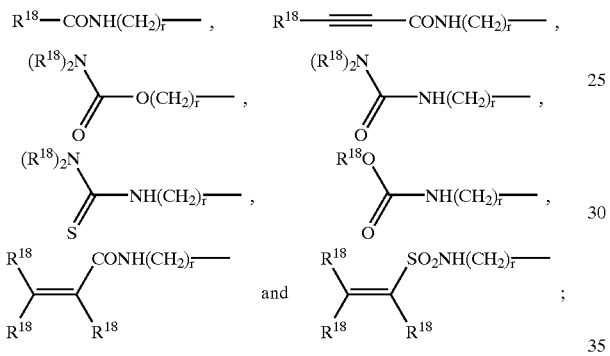

G is —NH—, —NR$^{10}$—, —O— or —S(O)$_m$—;

R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, CO$_2$H, —CONH$_2$, —CO$_2$R$^{10}$, —CONHR$^{10}$, —COR$^{10}$, —(C(R$^9$)$_2$)$_q$OH, (C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$ OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, (C(R$^9$)$_2$)$_q$OH, —(C(R$^9$)$_2$)$_q$OR$^{10}$, (C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

$R^6$ is a divalent group selected from alkyl of 1 to 6 carbon atoms, alkenyl of 2 to 6 carbon atoms, and alkynyl of 2 to 6 carbon atoms;

$R^7$ is a divalent alkyl group of 2 to 6 carbon atoms;

$R^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —R$^6$R$^{12}$, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —R$^6$R$^{12}$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$R$^{12}$, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O) NHR$^5$, —C(O)Q, —R$^6$C(O)H, —R$^6$C(O)R$^5$, —R$^6$C (O)OH, —R$^6$C(O)OR$^5$, —R$^6$C(O)NH$_2$, —R$^6$C(O) NHR$^5$, —R$^6$C(O)Q, —R$^6$OC(O)R$^5$, —R$^6$OC(O)NH$_2$, —R$^6$OC(O)NHR$^5$ and —R$^6$OC(O)Q;

$R^9$ is independently —H, —F or —R$^5$;

$R^{10}$ is an alkyl group of 1 to 12 carbon atoms, preferred is 1 to 6 carbon atoms;

$R^{11}$ is a cycloalkyl group of 3 to 10 carbon atoms;

$R^{12}$ is —N(O)$_n$R$^{13}$R$^{14}$ or —N$^+$(R$^{10}$R$^{13}$R$^{14}$)J$^-$;

provided that when $R^{12}$ is N(O)$_n$R$^{13}$R$^{14}$ and n is 1, $R^{13}$ or $R^{14}$ are not H;

$R^{13}$ and $R^{14}$ are independently selected from a group consisting of —H, —R$^5$, —R$^{11}$, —(C(R$^9$)$_2$)$_q$aryl-R$^{15}$, —(C(R$^9$)$_2$)$_q$heteroaryl-R$^{15}$, —(C(R$^9$)$_2$)$_q$heterocyclyl-R$^{15}$, —(C(R$^9$)$_2$)$_p$OR$^{16}$, —(C(R$^9$)$_2$)$_p$NR$^{16}$R$^{17}$, —(C(R$^9$)$_2$)$_p$S(O)$_m$R$^{16}$, —(C(R$^9$)$_2$)$_p$CO$_2$R$^{16}$, —(C(R$^9$)$_2$)$_p$C(O)NHR$^{16}$ and —(C(R$^9$)$_2$)$_p$C(O)R$^{15}$; further provided that $R^{13}$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, —R$^5$, —R$^{11}$, —(C(R$^9$)$_2$)$_q$arylR$^{15}$, —(C(R$^9$)$_2$)$_q$heteroarylR$^{15}$, —(C(R$^9$)$_2$)$_q$heterocyclyl-R$^{15}$, —(C(R$^9$)$_2$)$_q$CO$_2$R$^{16}$, —(C(R$^9$)$_2$)$_q$C(O)NHR$^{16}$, and —(C(R$^9$)$_2$)$_q$C(O)R$^{15}$; or optionally substituted on carbon by —F, —(C(R$^7$)$_2$)$_q$OR$^{16}$, —(C(R$^7$)$_2$)$_q$NR$^{16}$R$^{17}$, and —(C(R$^9$)$_2$)$_q$S(O)$_m$R$^{16}$; or optionally substituted on nitrogen by —(C(R$^9$)$_2$)$_p$OR$^{16}$, —(C(R$^9$)$_2$)$_p$NR$^{16}$R$^{17}$, and —(C(R$^9$)$_2$)$_p$S(O)$_m$R$^{16}$;

$R^{15}$ is independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_q$OH, —(C(R$^9$)$_2$)$_q$OR$^{10}$, —(C(R$^9$)$_2$)$_q$NH$_2$, —(C(R$^9$)$_2$)$_q$NHR$^{10}$, —(C(R$^9$)$_2$)$_q$R$^{10}$, —(C(R$^9$)$_2$)$_q$S(O)$_m$R$^{10}$, —(C(R$^9$)$_2$)$_q$CO$_2$R$^{10}$, —(C(R$^9$)$_2$)$_q$CONHR$^{10}$, —(C(R$^9$)$_2$)$_q$CONR$^{10}$R$^{10}$, —(C(R$^9$)$_2$)$_q$COR$^{10}$, —(C(R$^9$)$_2$)$_q$CO$_2$H, and —(C(R$^9$)$_2$)$_q$CONH$_2$; $R^{16}$ and $R^{17}$ are independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_p$OH, —(C(R$^9$)$_2$)$_p$OR$^{10}$, —(C(R$^9$)$_2$)$_p$NH$_2$, —(C(R$^9$)$_2$)$_p$NHR$^{10}$, —(C(R$^9$)$_2$)$_p$NR$^{10}$R$^{10}$, —(C(R$^9$)$_2$)$_p$S(O)$_m$R$^{10}$, —(C(R$^9$)$_2$)$_p$CO$_2$R$^{10}$, —(C(R$^9$)$_2$)$_p$CONHR$^{10}$, —(C(R$^9$)$_2$)$_p$CONR$^{10}$R$^{10}$, —(C(R$^9$)$_2$)$_p$COR$^{10}$, —(C(R$^9$)$_2$)$_p$CO$_2$H, and —(C(R$^9$)$_2$)$_p$CONH$_2$;

$R^{18}$ is independently selected from the group consisting of —H, -aryl, —R$^5$, —R$^6$NH$_2$, —R$^6$NHR$^5$ and —R$^6$Q;

provided that, the 7-position is substituted, or a pharmaceutically acceptable salt thereof.

2. The compound of claim 1, wherein X is —NH—, —NR$^5$, or —O— or a pharmaceutically acceptable salt thereof.

3. The compound of claim 1, wherein T is N and Z is carbon, n is 0 and X is —NH— or a pharmaceutically acceptable salt thereof.

4. The compound of claim 1, wherein T is N, Z is carbon, X is —NH—, n is 0 and $R^1$ is aryl or a pharmaceutically acceptable salt thereof.

5. A method of treating, inhibiting the growth of, or eradicating neoplasms in a mammal in need thereof which comprises administering to said mammal an effective amount of a compound of Formula (1) having the structure:

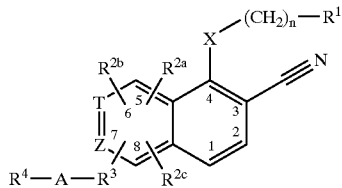

(I)

wherein:
X is —NH—, —NR⁵—, —O—, or —S(O)$_m$—;
n is an integer of 0 or 1;
m is an integer of 0 to 2;
q is an integer of 0 to 5;
p is an integer of 2 to 5;
s is an integer of 0 to 5;
r is an integer of 0 to 5;
J is halogen;
A is absent;
T is N and Z is carbon;
R¹ is a heteroaryl ring having 6 atoms containing 1 to 3 hetetoatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO₂, —NH₂, —OH, —SH, —CN, —N₃, —COOH, —CONH₂, —NHC(O)NH₂, —C(O)H, —CF₃, —OCF₃, —R⁵, —OR⁵, —NHR⁵, —Q, —S(O)$_m$ R⁵, —NHSO₂R⁵, —R⁶OH, —R⁶OR⁵, —R⁶NH₂, —R⁶NHR⁵, —R⁶Q, —R⁶SH, —R⁶S(O)$_m$ R⁵, —NHR⁷OH, —NHR⁷OR⁵, —N(R⁵)R⁷OH, —N(R⁵)R⁷OR⁵, —NHR⁷NH₂, —NHR⁷NHR⁵, —NHR⁷Q, —N(R⁵)R⁷NH₂, —N(R⁵)R⁷NHR⁵, —N(R⁵)R⁷Q, —OR⁷OH, —R⁷OR⁵, —OR⁷NH₂, —OR⁷NHR⁵, —OR⁷Q, —OC(O)R⁵, —NHC(O)R⁵, —NHC(O)NHR⁵, —R⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O)OR⁵, —R⁶C(O)NH₂, —R⁶C(O)NHR⁵, —R⁶C(O)Q, —R⁶OC(O)R⁵, —R⁶OC(O)NH₂, —R⁶OC(O)NHR⁵, —R⁶OC(O)Q and YR⁸ groups wherein Y is independently selected from —C(O)—, —C(O)O—, —OC(O)—, —C(O)NH—, —NHC(O)—, —NHSO₂—, —SO₂NH—, —C(OH)H—, —O(C(R⁹)₂)$_q$—, —S(O)$_m$(C(R⁹)₂)$_q$—, —NH(C(R⁹)₂)$_q$—, —NR¹⁰(C(R⁹)₂)$_q$—, —(C(R⁹)₂)$_q$—, —(C(R⁹)₂)$_q$O—, —(C(R⁹)₂)$_q$S(O)$_m$—, —(C(R⁹)₂)$_q$NH—; —(C(R⁹)₂)$_q$NR¹⁰—, —C≡C—, cis and trans —CH=CH— and cycloalkyl of 3 to 10 carbon atoms;
Q is —NR⁵R⁵ and further provided that when each R⁵ is independently selected from alkyl and alkenyl, R⁵R⁵ may optionally be taken together with the nitrogen atom to which they are attached forming a heterocyclyl ring of 3 to 8 atoms, optionally containing 1 or 2 additional heteroatoms which may be the same or different selected from N, O and S;
R²$^a$, R²$^b$, and R²$^c$, are each, independently selected from —H, -aryl, —CH₂aryl, —Oaryl, —S(O)$_m$aryl, —J, —NO₂, —OH, —SH, —CN, —N₃, —COOH, —CONH₂, —NHC(O)NH₂, —C(O)H, —CF₃, —OCF₃, —R⁵, —OR⁵, —S(O)$_m$R⁵, —NHSO₂R⁵, —R¹¹, —OR¹¹, —R⁶OH, —R⁶OR⁵, —R⁶SH, —R⁶S(O)$_m$R⁵, —OR⁷OH, —OR⁷OR⁵, —OC(O)R⁵, —NHC(O)R⁵, —NHC(O)NHR⁵, —OR⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O)OR⁵, —R⁶C(O)NH₂, —R⁶C(O)NHR⁵, —R⁶C(O)Q, —R⁶OC(O)R⁵, —R⁶OC(O)NH₂, —R⁶OC(O)NHR⁵, —R⁶OC(O)Q, —G—(C(R⁹)₂)$_p$—R¹², —(C(R⁹)₂)$_q$—R¹²,

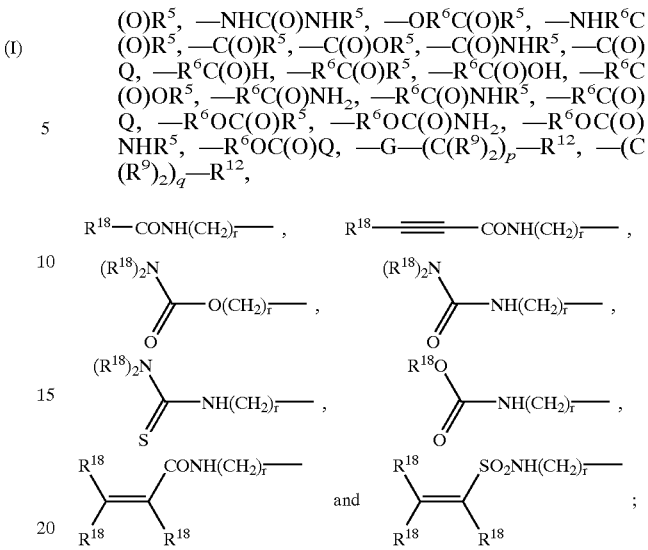

G is —NH—, —NR¹⁰—, —O— or —S(O)$_m$—;
R³ is selected from alkenyl of 2 to 6 carbon atoms, optionally substituted with one or more of —R¹⁰, —(C(R⁹)₂)$_s$R¹², —CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_q$H, —G(C(R⁹)₂)$_p$OR¹⁰, —G(C(R⁹)₂)$_p$R¹², and —G(C(R⁹)₂)$_p$OH; alkynyl of 2 to 6 carbon atoms, optionally substituted with one or more of —R¹⁰, —(C(R⁹)₂)$_s$R¹², —CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_q$H, —G(C(R⁹)₂)$_p$OR¹⁰, —G(C(R⁹)₂)$_p$R¹², and —G(C(R⁹)₂)$_p$OH; aryl of 6 to 12 carbon atoms optionally substituted with 1 to 4 substituents which may be the same or different selected from —R¹⁰, —(C(R⁹)₂)$_s$R¹², —CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_q$H, —G(C(R⁹)₂)$_p$OR¹⁰, —G(C(R⁹)₂)$_p$R¹², and —G(C(R⁹)₂)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R¹⁰, —(C(R⁹)₂)$_s$R¹², —CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_q$H, —G(C(R⁹)₂)$_p$OR¹⁰, —G(C(R⁹)₂)$_p$R¹², and —G(C(R⁹)₂)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R¹⁰, —(C(R⁹)₂)$_s$R¹²—CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_q$H, —G(C(R⁹)₂)$_p$OR¹⁰, —G(C(R⁹)₂)$_p$R¹², and —G(C(R⁹)₂)$_p$OH;

$R^4$ is selected from —$(C(R^9)_2)_rH$, optionally substituted with one or more of —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$;

alkenyl of 2 to 6 carbon atoms, optionally substituted with one or more of —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$;

alkynyl of 2 to 6 carbon atoms, optionally substituted with one or more of —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$;

aryl of 6 to 12 carbon atoms optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$;

$R^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

$R^6$ is a divalent group selected from alkyl of 1 to 6 carbon atoms, alkenyl of 2 to 6 carbon atoms, and alkynyl of 2 to 6 carbon atoms;

$R^7$ is a divalent alkyl group of 2 to 6 carbon atoms;

$R^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, $S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$R^6R^{12}$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$R^6R^{12}$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$; a bicyclic heteroaryl ling system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6R^{12}$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$;

$R^9$ is independently —H, —F or —$R^5$;

$R^{10}$ is an alkyl group of 1 to 12 carbon atoms, preferred is 1 to 6 carbon atoms;

$R^{11}$ is a cycloalkyl group of 3 to 10 carbon atoms;

$R^{12}$ is —$N(O)_nR^{13}R^{14}$ or —$N^+(R^{10}R^{13}R^{14})J^-$;

provided that when $R^{12}$ is $N(O)_nR^{13}R^{14}$ and n is 1, $R^{13}$ or $R^{14}$ are not H;

R$^{13}$ and R$^{14}$ are independently selected from a group consisting of —H, —R$^5$, —R$^{11}$, —(C(R$^9$)$_2$)$_q$aryl-R$^{15}$, —(C(R$^9$)$_2$)$_q$heteroaryl-R$^{15}$, —(C(R$^9$)$_2$)$_q$heterocyclyl-R$^{15}$, —(C(R$^9$)$_2$)$_p$OR$^{16}$, —(C(R$^9$)$_2$)$_p$NR$^{16}$R$^{17}$, —(C(R$^9$)$_2$)$_p$S(O)$_m$R$^{16}$, —(C(R$^9$)$_2$)$_p$CO$_2$R$^{16}$, —(C(R$^9$)$_2$)$_p$C(O)NHR$^{16}$ and —(C(R$^9$)$_2$)$_p$C(O)R$^{15}$ further provided that R$^{13}$ and R$^{14}$ may optionally be taken together with the nitrogen to which they are attached forming a heterocyclyl, heteroaryl or bicyclyl heteroaryl ring optionally substituted on either nitrogen or carbon by one or more selected from the group, —R$^5$, —R$^{11}$, —(C(R$^9$)$_2$)$_q$arylR$^{15}$, —(C(R$^9$)$_2$)$_q$heteroarylR$^{15}$, —(C(R$^9$)$_2$)$_q$heterocyclyl-R$^{15}$, —(C(R$^9$)$_2$)$_q$CO$_2$R$^{16}$, —(C(R$^9$)$_2$)$_q$C(O)NHR$^{16}$, and —(C(R$^9$)$_2$)$_q$C(O)R$^{15}$; or optionally substituted on carbon by —F, —(C(R$^7$)$_2$)$_q$OR$^{16}$, —(C(R$^7$)$_2$)$_q$NR$^{16}$R$^{17}$, and —(C(R$^9$)$_2$)$_q$S(O)$_m$R$^{16}$; or optionally substituted on nitrogen by —(C(R$^9$)$_2$)$_p$OR$^{16}$, —(C(R$^9$)$_2$)$_p$NR$^{16}$R$^{17}$, and —(C(R$^9$)$_2$)$_p$S(O)$_m$R$^{16}$;

R$^{15}$ is independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_q$OH, —(C(R$^9$)$_2$)$_q$OR$^{10}$, —(C(R$^9$)$_2$)$_q$NH$_2$, —(C(R$^9$)$_2$)$_q$NHR$^{10}$, —(C(R$^9$)$_2$)$_q$NR$^{10}$R$^{10}$, —(C(R$^9$)$_2$)$_q$COR$^{10}$, —(C(R$^9$)$_2$)$_q$CO$_2$R$^{10}$, —(C(R$^9$)$_2$)$_q$CONHR$^{10}$, —(C(R$^9$)$_2$)$_q$CONR$^{10}$R$^{10}$, —(C(R$^9$)$_2$)$_q$COR$^{10}$, —(C(R$^9$)$_2$)$_q$CO$_2$H, and —(C(R$^9$)$_2$)$_q$CONH$_2$;

R$^{16}$ and R$^{17}$ are independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_p$OH, —(C(R$^9$)$_2$)$_p$OR$^{10}$, —(C(R$^9$)$_2$)$_p$NH$_2$, —(C(R$^9$)$_2$)$_p$NHR$^{10}$, —(C(R$^9$)$_2$)$_p$NR$^{16}$R$^{10}$, —(C(R$^9$)$_2$)$_p$S(O)$_m$R$^{10}$, —(C(R$^9$)$_2$)$_p$CO$_2$R$^{10}$, —(C(R$^9$)$_2$)$_p$CONHR$^{10}$, —(C(R$^9$)$_2$)$_p$CONR$^{10}$R$^{10}$, —(C(R$^9$)$_2$)$_p$COR$^{10}$, —(C(R$^9$)$_2$)$_p$CO$_2$H, and —(C(R$^9$)$_2$)$_p$CONH$_2$;

R$^{18}$ is independently selected from the group consisting of —H, -aryl, —R$^5$, —R$^6$NH$_2$, —R$^6$NHR$^5$ and —R$^6$Q; provided that, the 7-position is substituted or a pharmaceutically acceptable salt thereof.

6. The method according to claim 5 wherein the neoplasm is selected from the group consisting of breast, kidney, bladder, mouth, larynx, esophagus, stomach, colon, ovary, lung, pancreas, skin, liver, prostate and brain.

7. The method of claim 5 wherein the neoplasm expresses Src or wherein the neoplasm depends at least in part on the Src pathway.

8. The method of claim 5 wherein the neoplasm expresses raf or wherein the neoplasm depends at least in part on the raf pathway.

9. The method of claim 5 wherein the neoplasm expresses EGFr, erbB-2, erbB-3 or erbB-4 or wherein the neoplasm depends at least in part on an EGFr, erbB-2, erbB-3 or erbB-4 pathway.

10. The method of claim 5 wherein the neoplasm expresses KDR or flt-1 or wherein the neoplasm depends at least in part on a KDR or flt-1 pathway.

11. The method of claim 5 wherein the neoplasm expresses PDGFr or wherein the neoplasm depends at least in part on the PDGFr pathway.

12. The method of claim 5 wherein the neoplasm expresses FGFr or wherein the neoplasm depends at least in part on the FGFr pathway.

13. The method of claim 5 wherein the neoplasm expresses tie-1 or tie-2 or wherein the neoplasm depends at least in part on a tie-1 or tie-2 pathway.

14. The method of claim 5 wherein the neoplasm expresses EPH or wherein the neoplasm depends at least in part on the EPH pathway.

15. The method of claim 5 wherein the neoplasm expresses a non-receptor tyrosine kinase including Abl, Jak, Fak, Syk or Csk or wherein the neoplasm depends at least in part on a Abl, Jak, Fak, Syk or Csk pathway.

16. The method of claim 5 wherein the neoplasm expresses mek or erk or wherein the neoplasm depends at least in part on the MAPK pathway.

17. The method of claim 5 wherein the neoplasm expresses a cyclin dependent kinase or wherein the neoplasm depends at least in part on a cyclin dependent kinase pathway.

18. The method of claim 5 wherein the neoplasm expresses a Src family kinase including Yes, Lck or Lyn or wherein the neoplasm depends at least in part on a Src family kinase pathway.

19. The method of claim 5 wherein the neoplasm expresses PKA, PKB or PKC or wherein the neoplasm depends at least in part on a PKA, PKB or PKC pathway.

20. A method of treating, inhibiting the progression of, or eradicating polycystic kidney disease in a mammal in need thereof which comprises administering to said mammal an effective amount of a compound of Formula (1) having the structure:

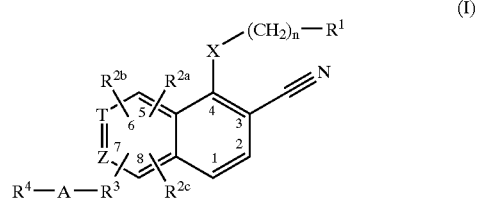

(I)

wherein:

X is —NH—, —NR$^5$—, —O—, or —S(O)$_m$—;

n is an integer of 0 or 1;

m is an integer of 0 to 2;

q is an integer of 0 to 5;

p is an integer of 2 to 5;

s is an integer of 0 to 5;

r is an integer of 0 to 5;

J is halogen;

A is absent;

T is N and Z is carbon;

R$^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR, —Q, —S(O)$_m$R, —NHSO$_2$R, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$R$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —R$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$—, —NR$^{10}$(C(R$^9$)$_2$)$_q$, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;

Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ring of 3 to 8 atoms, optionally containing 1 or 2 additional heteroatoms which may be the same or different selected from N, O and S;

R$^{2a}$, R$^{2b}$, and R$^{2c}$, are each, independently selected from —H, -aryl, —CH$_2$aryl, —Oaryl, —S(O)$_m$aryl, —J, —NO$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^7$OR$^5$, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$—R$^{12}$, —(C(R$^9$)$_2$)$_q$—R$^{12}$,

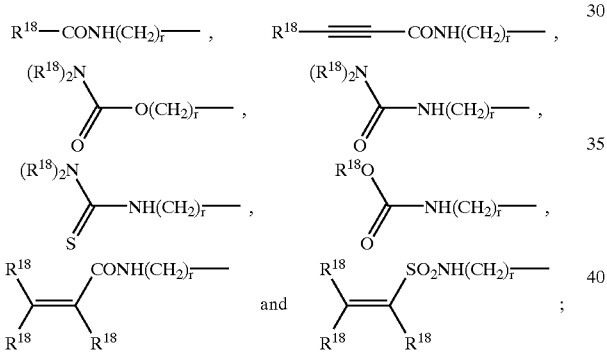

G is —NH—, —NR$^{10}$—, —O— or —S(O)$_m$—;

R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^5$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NH$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^{10}$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, CONHR$^{10}$, —COR$^{10}$, —C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_pH$, —$G(C(R^9)_2)_pOR^{10}$, —$G(C(R^9)_2)_pR^{12}$, and —$G(C(R^9)_2)_pOH$;

$R^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

$R^6$ is a divalent group selected from alkyl of 1 to 6 carbon atoms, alkenyl of 2 to 6 carbon atoms, and alkynyl of 2 to 6 carbon atoms;

$R^7$ is a divalent alkyl group of 2 to 6 carbon atoms;

$R^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6S(O)_mR$, —$NHR^7OH$, —$NHR^7OR^5$, —$N(R^5)R^7OH$, —$R^6R^{12}$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$R^6R^{12}$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6R^{12}$, —$R^6S(O)_mR^5$, —$NHR^7OH$, —$NHR^7OR^5$, —$N(R^5)R^7OH$, —$N(R^5)R^7R^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O) NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$;

$R^9$ is independently —H, —F or —$R^5$;

$R^{10}$ is an alkyl group of 1 to 12 carbon atoms, preferred is 1 to 6 carbon atoms;

$R^{11}$ is a cycloalkyl group of 3 to 10 carbon atoms;

$R^{12}$ is —$N(O)_nR^{13}R^{14}$ or —$N^+(R^{10}R^{13}R^{14})J^-$;

provided that when $R^{12}$ is $N(O)_nR^{13}R^{14}$ and n is 1, $R^{13}$ or $R^{14}$ are not H;

$R^{13}$ and $R^{14}$ are independently selected from a group consisting of —H, —$R^5$, —$R^{11}$, —$(C(R^9)_2)_q$aryl-$R^{15}$, —$(C(R^9)_2)_q$heteroaryl-$R^{15}$, —$(C(R^9)_2)_q$heterocyclyl-$R^{15}$, —$(C(R^9)_2)_pOR^{16}$, —$(C(R^9)_2)_pNR^{16}R^{17}$, —$(C(R^9)_2)_pS(O)_mR^{16}$, —$(C(R^9)_2)_pCO_2R^{16}$, —$(C(R^9)_2)_pC(O)NHR^{16}$ and —$(C(R^9)_2)_pC(O)R^{15}$; further provided that $R^{13}$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, —$R^5$, —$R^{11}$, —$(C(R^9)_2)_q$aryl$R^{15}$, —$(C(R^9)_2)_q$heteroaryl$R^{15}$, —$(C(R^9)_2)_q$heterocyclyl$R^{15}$, —$(C(R^9)_2)_qCO_2R^{16}$, —$(C(R^9)_2)_qC(O)NHR^{16}$, and —$(C(R^9)_2)_qC(O)R^{15}$; or optionally substituted on carbon by —F, —$(C(R^7)_2)_qOR^{16}$, —$(C(R^7)_2)_qNR^{16}R^{17}$, and —$(C(R^9)_2)_qS(O)_mR^{16}$; or optionally substituted on nitrogen by —$(C(R^9)_2)_pOR^{16}$, —$(C(R^9)_2)_pNR^{16}R^{17}$, and —$(C(R^9)_2)_pS(O)_mR^{16}$;

$R^{15}$ is independently selected from a group consisting of —H, —$R^5$, —$R^{11}$, —$(C(R^9)_2)_q$aryl, —$(C(R^9)_2)_q$heteroaryl, —$(C(R^9)_2)_q$heterocyclyl, —$(C(R^9)_2)_qOH$, —$(C(R^9)_2)_qOR^{10}$, —$(C(R^9)_2)_qNH_2$, —$(C(R^9)_2)_qNHR^{10}$, —$(C(R^9)_2)_qR^{10}$, —$(C(R^9)_2)_qS(O)_mR^{10}$, —$(C(R^9)_2)_qCO_2R^{10}$, —$(C(R^9)_2)_qCONHR^{10}$, —$(C(R^9)_2)_qCONR^{10}OR^{10}$, —$(C(R^9)_2)_qCOR^{10}$, —$(C(R^9)_2)_qCO_2H$, and —$(C(R^9)_2)_qCONH_2$;

$R^{16}$ and $R^{17}$ are independently selected from a group consisting of —H, —$R^5$, —$R^{11}$, —$(C(R^9)_2)_q$aryl, —$(C(R^9)_2)_q$heteroaryl, —$(C(R^9)_2)_q$heterocyclyl, —$(C(R^9)_2)_p$OH, —$(C(R^9)_2)_pOR^{10}$, —$(C(R^9)_2)_pNH_2$, —$(C(R^9)_2)_p$ NHR$^{10}$, —$(C(R^9)_2)_pNR^{16}R^{10}$, —$(C(R^9)_2)_p$ $S(O)_mR^{10}$, —$(C(R^9)_2)_pCO_2R^{10}$, —$(C(R^9)_2)_p$ CONHR$^{10}$, —$(C(R^9)_2)_pCONR^{10}R^{10}$, —$(C(R^9)_2)_p$ COR$^{10}$, —$(C(R^9)_2)_pCO_2H$, and —$(C(R^9)_2)_pCONH_2$;

$R^{18}$ is independently selected from the group consisting of —H, -aryl, —$R^5$, —$R^6NH_2$, —$R^6NHR^5$ and —$R^6Q$;

provided that, the 7-position is substituted
or a pharmaceutically acceptable salt thereof.

21. A method of treating, inhibiting, or eradicating colonic polyps in a mammal in need thereof which comprises providing to said mammal an effective amount of a compound of Formula (1) having the structure,

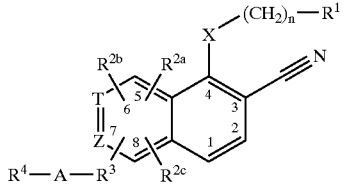

(I)

wherein:
X is —NH—, —NR⁵—, —O—, or —S(O)$_m$—;
n is an integer of 0 or 1;
m is an integer of 0 to 2;
q is an integer of 0 to 5;
p is an integer of 2 to 5;
s is an integer of 0 to 5;
r is an integer of 0 to 5;
J is halogen;
A is absent;
T is N and Z is carbon;
$R^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO₂, —NH₂, —OH, —SH, —CN, —N₃, —COOH, —CONH₂, —NHC(O)NH₂, —C(O)H, —CF₃, —OCF₃, —R⁵, —OR⁵, —NHR⁵, —Q, —S(O)$_m$ R⁵, —NHSO₂R⁵, —R⁶OH, —R⁶OR⁵, —R⁷NH₂, —R⁶NHR⁵, —R⁶Q, —R⁶SH, —R⁶S(O)$_m$ R⁵, —NHR⁷OH, —NHR⁷OR⁵, —N(R⁵)R⁷OH, —N(R⁵)R⁷OR⁵, —NHR⁷NH₂, —NHR⁷NHR⁵, —NHR⁷Q, —N(R⁵)R⁷NH₂, —N(R⁵)R⁷NHR⁵, —N(R⁵)R⁷Q, —OR⁷OH, —R⁷OR⁵, —OR⁷NH₂, —OR⁷NHR⁵, —OR⁷Q, —OC(O)R⁵, —NHC(O)R⁵, —NHC(O)NHR⁵, —R⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O)OR⁵, —R⁶C(O)NH₂, —R⁶C(O)NHR⁵, —R⁶C(O)Q, —R⁶OC(O)R⁵, —R⁶OC(O)NH₂, —R⁶OC(O)NHR⁵, —R⁶OC(O)Q and YR⁸ groups wherein Y is independently selected from —C(O)—, —C(O)O—, —OC(O)—, —C(O)NH—, —NHC(O)—, —NHSO₂—, —SO₂NH—, —C(OH)H—, —O(C(R⁹)₂)$_q$—, —S(O)$_m$ (C(R⁹)₂)$_q$—, —NH(C(R⁹)₂)$_q$—, —NR¹⁰(C(R⁹)₂)$_q$—, —(C(R⁹)₂)$_q$—, —(C(R⁹)₂)$_q$O—, —(C(R⁹)₂)$_q$S(O)$_m$—, —(C(R⁹)₂)$_q$NH—, —(C(R⁹)₂)$_q$NR¹⁰—, —C≡C—, cis and trans —CH=CH— and cycloalkyl of 3 to 10 carbon atoms;
Q is —NR⁵R⁵ and further provided that when each R⁵ is independently selected from alkyl and alkenyl, R⁵R⁵ may optionally be taken together with the nitrogen atom to which they are attached forming a heterocyclyl ring of 3 to 8 atoms, optionally containing 1 or 2 additional heteroatoms which may be the same or different selected from N, O and S;
$R^{2a}$, $R^{2b}$, and $R^{2c}$, are each, independently selected from —H, -aryl, —CH₂aryl, —Oaryl, —S(O)$_m$aryl, —J, —NO₂, —OH, —SH, —CN, —N₃, —COOH, —CONH₂, —NHC(O)NH₂, —C(O)H, —CF₃, —OCF₃, —R⁵, —OR⁵, —S(O)$_m$R⁵, —NHSO₂R⁵, —R¹¹, —OR¹¹, —R⁶OH, —R⁶OR⁵, R⁶SH, —R⁶S(O)$_m$ R⁵, —OR⁷OH, —OR⁷OR⁵, —OC(O)R⁵, —NHC(O)R⁵, —NHC(O)NHR⁵, —OR⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O)OR⁵, —R⁶C(O)NH₂, —R⁶C(O)NHR⁵, —R⁶C(O)Q, —R⁶OC(O)R⁵, —R⁶OC(O)NH₂, —R⁶OC(O)NHR⁵, —R⁶OC(O)Q, —G—(C(R⁹)₂)$_p$—R¹², —(C(R⁹)₂)$_q$—R¹², R¹⁸—CONH(CH₂)$_r$—, R¹⁸—≡—CONH(CH₂)$_r$—, (R¹⁸)₂N—C(O)—O(CH₂)$_r$—, (R¹⁸)₂N—C(O)—NH(CH₂)$_r$—, (R¹⁸)₂N—C(S)—NH(CH₂)$_r$—, R¹⁸O—C(O)—NH(CH₂)$_r$—, R¹⁸\C(R¹⁸)=C(R¹⁸)—CONH(CH₂)$_r$— and R¹⁸\C(R¹⁸)=C(R¹⁸)—SO₂NH(CH₂)$_r$—;

G is —NH—, —NR¹⁰—, —O— or S(O)$_m$;
$R^3$ is selected from alkenyl of 2 to 6 carbon atoms, optionally substituted with one or more of —R¹⁰, —(C(R⁹)₂)$_s$R¹²—CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_s$H, —G(C(R⁹)₂)$_p$OR¹⁰, —G(C(R⁹)₂)$_p$R¹², and —G(C(R⁹)₂)$_p$OH; alkynyl of 2 to 6 carbon atoms, optionally substituted with one or more of —R¹⁰, —(C(R⁹)₂)$_s$R¹², —CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_s$H, —G(C(R⁹)₂)$_p$OR¹⁰, —G(C(R⁹)₂)$_p$R¹², and —G(C(R⁹)₂)$_p$OH; aryl of 6 to 12 carbon atoms optionally substituted with 1 to 4 substituents which may be the same or different selected from —R¹⁰, —(C(R⁹)₂)$_s$R¹², —CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_s$H, —G(C(R⁹)₂)$_p$OR¹⁰, —G(C(R⁹)₂)$_p$R¹², and —G(C(R⁹)₂)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R¹⁰, —(C(R⁹)₂)$_s$R¹², —CHO, 1,3-dioxolane, —NO₂, —CN, CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_s$H, —G(C(R⁹)₂)$_p$OR¹⁰, —G(C(R⁹)₂)$_p$R¹², and —G(C(R⁹)₂)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R¹⁰, —(C(R⁹)₂)$_s$R¹², —CHO, 1,3-dioxolane, —NO₂, —CN, —CO₂H, —CONH₂, —CO₂R¹⁰, —CONHR¹⁰, —COR¹⁰, —(C(R⁹)₂)$_q$OH, —(C(R⁹)₂)$_q$OR¹⁰, —(C(R⁹)₂)$_q$NHR¹⁰, —(C(R⁹)₂)$_q$J, —(C(R⁹)₂)$_q$NH₂, —(C(R⁹)₂)$_s$H, —G(C(R⁹)₂)$_p$OR¹⁰, —G(C(R⁹)₂)$_p$R¹², and —G(C(⁹)₂)$_p$OH;

R⁴ is selected from —(C(R⁹)₂)ᵣH, optionally substituted with one or more of —R¹⁰, —(C(R⁹)₂)ₛR¹², —CHO, 1,3-dioxolane, —NO₂, —CN, —CO₂H, —CONHR₂, —CO₂R¹⁰, —CONHR¹⁰, —COR¹⁰, —(C(R⁹)₂)qOH, —(C(R⁹)₂)qOR¹⁰, —(C(R⁹)₂)qNHR¹⁰, —(C(R⁹)₂)qJ, —(C(R⁹)₂)qNH₂, —(C(R⁹)₂)rH, —G(C(R⁹)₂)pOR¹⁰, —G(C(R⁹)₂)pR¹², and —G(C(R⁹)₂)pOH;

alkenyl of 2 to 6 carbon atoms, optionally substituted with one or more of —R¹⁰, —(C(R⁹)₂)ₛR¹², —CHO, 1,3-dioxolane, —NO₂, —CN, —CO₂H, —CONH₂, —CO₂R¹⁰, —CONHR¹⁰, —COR¹⁰, —(C(R⁹)₂)qOH, —(C(R⁹)₂)qOR¹⁰, —(C(R⁹)₂)qNHR¹⁰, —(C(R⁹)₂)qJ, —(C(R⁹)₂)qNH₂, —(C(R⁹)₂)rH, —G(C(R⁹)₂)pOR¹⁰, —G(C(R⁹)₂)pR¹², and —G(C(R⁹)₂)pOH;

alkynyl of 2 to 6 carbon atoms, optionally substituted with one or more of —R¹⁰, —(C(R⁹)₂)ₛR¹², —CHO, 1,3-dioxolane, —NO₂, —CN, —CO₂H, —CONH₂, —CO₂R¹⁰, —CONHR¹⁰, —COR¹⁰, —(C(R⁹)₂)qOH, —(C(R⁹)₂)qOR¹⁰, —(C(R⁹)₂)qNHR¹⁰, —(C(R⁹)₂)qJ, —(C(R⁹)₂)qNH₂, —(C(R⁹)₂)rH, —G(C(R⁹)₂)pOR¹⁰, —G(C(R⁹)₂)pR¹², and —G(C(R⁹)₂)pOH;

aryl of 6 to 12 carbon atoms optionally substituted with 1 to 4 substituents which may be the same or different selected from —R¹⁰, —(C(R⁹)₂)ₛR¹², —CHO, 1,3-dioxolane, —NO₂, —CN, —CO₂H, —CONH₂, —CO₂R¹⁰, —CONHR¹⁰, —COR¹⁰, —(C(R⁹)₂)qOH, —(C(R⁹)₂)qOR¹⁰, —(C(R⁹)₂)qNHR¹⁰, —(C(R⁹)₂)qJ, —(C(R⁹)₂)qNH₂, —(C(R⁹)₂)rH, —G(C(R⁹)₂)pOR¹⁰, —G(C(R⁹)₂)pR¹², and —G(C(R⁹)₂)pOH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R¹⁰, —(C(R⁹)₂)ₛR¹², —CHO, 1,3-dioxolane, —NO₂, —CN, —CO₂H, —CONH₂, —CO₂R¹⁰, —CONHR¹⁰, —COR¹⁰, —(C(R⁹)₂)qOH, —(C(R⁹)₂)qOR¹⁰, —(C(R⁹)₂)qNHR¹⁰), —(C(R⁹)₂)qJ, —(C(R⁹)₂)qNH₂, —(C(R⁹)₂)rH, —G(C(R⁹)₂)pOR¹⁰, —G(C(R⁹)₂)pR¹², and —G(C(R⁹)₂)pOH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R¹⁰, —(C(R⁹)₂)ₛR¹², —CHO, 1,3-dioxolane, —NO₂, —CN, —CO₂H, —CONH₂, —CO₂R¹⁰, —CONHR¹⁰, —COR¹⁰, —(C(R⁹)₂)qOH, —(C(R⁹)₂)qOR¹⁰, —(C(R⁹)₂)qNHR¹⁰, —(C(R⁹)₂)qJ, —(C(R⁹)₂)qNH₂, —(C(R⁹)₂)rH, —G(C(R⁹)₂)pOR¹⁰, —G(C(R⁹)₂)pR¹², and —G(C(R⁹)₂)pOH;

R⁵ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

R⁶ is a divalent group selected from alkyl of 1 to 6 carbon atoms, alkenyl of 2 to 6 carbon atoms, and alkynyl of 2 to 6 carbon atoms;

R⁷ is a divalent alkyl group of 2 to 6 carbon atoms;

R⁸ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —CH₂aryl, —NHaryl, —Oaryl, —S(O)ₘaryl, —J, —NO₂, —NH₂, —OH, —SH, —CN, —N₃, —COOH, —CONH₂, —NHC(O)NH₂, —C(O)H, —CF₃, —OCF₃, —R⁵, —OR⁵, —NHR⁵, —Q, —S(O)ₘR⁵, —NHSO₂R⁵, —R¹¹, —OR¹¹, —NHR¹¹, —R⁶OH, —R⁶OR⁵, —R⁶NH₂, —R⁶NHR⁵, —R⁶Q, —R⁶SH, —R⁶S(O)ₘR⁵, —NHR⁷OH, —NHR⁷OR⁵, —N(R⁵)R⁷OH, —R⁶R¹², —N(R⁵)R⁷OR⁵, —NHR⁷NH₂, —NHR⁷NHR⁵, —NHR⁷Q, —N(R⁵)R⁷NH₂, —N(R⁵)R⁷NHR⁵, —N(R⁵)R⁷Q, —OR⁷OH, —OR⁷OR⁵, —OR⁷NH₂, —OR⁷NHR⁵, —OR⁷Q, —OC(O)R⁵, —NHC(O)R⁵, —NHC(O)NHR⁵, —OR⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O)OR⁵, —R⁶C(O)NH₂, —R⁶C(O)NHR⁵, —R⁶C(O)Q, —R⁶OC(O)R⁵, —R⁶OC(O)NH₂, —R⁶OC(O)NHR⁵ and —R⁶OC(O)Q; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —CH₂aryl, —NHaryl, —Oaryl, —S(O)ₘaryl, —J, —NO₂, —NH₂, —OH, —SH, —CN, —N₃, —COOH, —CONH₂, —NHC(O)NH₂, —C(O)H, —CF₃, —OCF₃, —R⁵, —OR⁵, —NHR⁵, —Q, —S(O)ₘR⁵, —NHSO₂R⁵, —R¹¹, —OR¹¹, —NHR¹¹, —R⁶OH, —R⁶OR⁵, —R⁶NH₂, —R⁶NHR⁵, —R⁶Q, —R⁶SH, —R⁶S(O)ₘR⁵, —NHR⁷OH, —NHR⁷OR, —N(R⁵)R⁷OH, —N(R⁵)R⁷OR, —NHR⁷NH₂, —NHR⁷NHR⁵, —NHR⁷Q, —N(R⁵)R⁷NH₂, —N(R⁵)R⁷NHR⁵, —N(R⁵)R⁷Q, —OR⁷OH, —OR⁷OR⁵, —OR⁷NH₂, —OR⁷NHR⁵, —OR⁷Q, —OC(O)R⁵, —NHC(O)R⁵, —R⁶R¹², —NHC(O)NHR⁵, —OR⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O) OR⁵, —R⁶C(O)NH₂, —R⁶C(O)NHR⁵, —R⁶C(O)Q, —R⁶OC(O)R⁵, —R⁶OC(O)NH₂, —R⁶OC(O)NHR⁵ and —R⁶OC(O)Q; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —CH₂aryl, —NHaryl, —Oaryl, —S(O)ₘaryl, —J, —NO₂, —NH₂, —OH, —SH, —CN, —N₃, —COOH, —CONH₂, —NHC(O)NH₂, —C(O)H, —CF₃, —OCF₃, —R⁵, —OR⁵, —NHR⁵, —Q, —S(O)ₘR⁵, —NHSO₂R⁵, —R¹¹, —OR¹¹, —NHR¹¹, —R⁶OH, —R⁶OR, —R⁶NH₂, —R⁶NHR⁵, —R⁶Q, —R⁶SH, —R⁶R¹², —R⁶S(O)ₘR⁵, —NHR⁷OH, —NHR⁷OR⁵, —N(R⁵)R⁷OH, —N(R⁵)R⁷OR⁵, —NHR⁷NH₂, —NHR⁷NHR⁵, —NHR⁷Q, —N(R⁵)R⁷NH₂, —N(R⁵)R⁷NHR⁵, —N(R⁵)R⁷Q, —OR⁷OH, —OR⁷OR⁵, —OR⁷NH₂, —OR⁷NHR⁵, —OR⁷Q, —OC(O)R⁵, —NHC(O)R⁵, —NHC(O)NHR⁵, —OR⁶C(O)R⁵, —NHR⁶C(O)R⁵, —C(O)R⁵, —C(O)OR⁵, —C(O)NHR⁵, —C(O)Q, —R⁶C(O)H, —R⁶C(O)R⁵, —R⁶C(O)OH, —R⁶C(O)OR⁵, —R⁶C(O)NH₂, —R⁶C(O)NHR⁵, —R⁶C(O)Q, —R⁶C(O)R⁵, —R⁶OC(O)R⁵, —ROC(O)NH₂, —ROC(O)NHR⁵ and —R⁶OC(O)Q;

R⁹ is independently —H, —F or —R⁵;

R¹⁰ is an alkyl group of 1 to 12 carbon atoms, preferred is 1 to 6 carbon atoms;

R¹¹ is a cycloalkyl group of 3 to 10 carbon atoms;

R¹² is —N(O)ₙR¹³R¹⁴ or —N⁺(R¹⁰R¹³R¹⁴)J;

provided that when R¹² is N(O), R¹³R¹⁴ and n is 1, R¹³ or R¹⁴ are not H;

$R^{13}$ and $R^{14}$ are independently selected from a group consisting of —H, —$R^5$, —$R^{11}$, —$(C(R^9)_2)_q$aryl-$R^{15}$, —$(C(R^9)_2)_q$heteroaryl-$R^{15}$, —$(C(R^9)_2)_q$heterocyclyl-$R^{15}$, —$(C(R^9)_2)_q OR^{16}$, —$(C(R^9)_2)_q NR^{16}R^{17}$, —$(C(R^9)_2)_p S(O)_m R^{16}$, —$(C(R^9)_2)_p CO_2 R^{16}$, —$(C(R^9)_2)_p C(O)NHR^{16}$ and —$(C(R^9)_2)_p C(O)R^{15}$; further provided that $R^{13}$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, —$R^5$, —$R^{11}$, —$(C(R^9)_2)_q$aryl$R^{15}$, —$(C(R^9)_2)_q$heteroaryl$R^{15}$, —$(C(R^9)_2)_q$heterocyclyl$R^{15}$, —$(C(R^9)_2)_q CO_2 R^{16}$, —$(C(R^9)_2)_q C(O)NHR^{16}$, and —$(C(R^9)_2)_q C(O)R^{15}$; or optionally substituted on carbon by —F, —$(C(R^7)_2)_q OR^{16}$, —$(C(R^7)_2)_q NR^{16}R^{17}$, and —$(C(R^9)_2)_q S(O)_m R^{16}$; or optionally substituted on nitrogen by —$(C(R^9)_2)_p OR^{16}$, —$(C(R^9)_2)_p NR^{16}R^{17}$, and —$(C(R^9)_2)_p S(O)_m R^{16}$;

$R^{15}$ is independently selected from a group consisting of —H, —$R^5$, —$R^{11}$, —$(C(R^9)_2)_q$aryl, —$(C(R^9)_2)_q$heteroaryl, —$(C(R^9)_2)_q$heterocyclyl, —$(C(R^9)_2)_q OH$, —$(C(R^9)_2)_q OR^{10}$, —$(C(R^9)_2)_q NH_2$, —$(C(R^9)_2)_q NHR^{10}$, —$(C(R^9)_2)_q R^{10}$, —$(C(R^9)_2)_q R^{10}$, —$(C(R^9)_2)_q CO_2 R^{10}$, —$(C(R^9)_2)_q CONHR^{10}$, —$(C(R^9)_2)_q CONR^{10}$, —$(C(R^9)_2)_q COR^{10}$, —$(C(R^9)_2)_q CO_2 H$, and —$(C(R^9)_2)_q CONH_2$;

$R^{16}$ and $R^{17}$ are independently selected from a group consisting of —H, —$R^5$, —$R^{11}$, —$(C(R^9)_2)_q$aryl, —$(C(R^9)_2)_q$heteroaryl, —$(C(R^9)_2)_q$heterocyclyl, —$(C(R^9)_2)_p OH$, —$(C(R^9)_2)_p OR^{10}$, —$(C(R^9)_2)_p NH_2$, —$(C(R^9)_2)_p NHR^{10}$, —$(C(R^9)_2)_p NR^{10}R^{10}$, —$(C(R^9)_2)_p S(O)_m R^{10}$, —$(C(R^9)_2)_p CO_2 R^{10}$, —$(C(R^9)_2)_p CONHR^{10}$, —$(C(R^9)_2)_p CONR^{10}R^{10}$, —$(C(R^9)_2)_p COR^{10}$, —$(C(R^9)_2)_p CO_2 H$, and —$(C(R^9)_2)_p CONH_2$;

$R^{18}$ is independently selected from the group consisting of —H, -aryl, —$R^5$, —$R^6 NH_2$, —$R^6 NHR^5$ and —$R^6 Q$;

provided that, the 7-position is substituted or a pharmaceutically acceptable salt thereof.

22. A method of treating a disease or inhibiting a disease state whose etiology is at least in part caused by a defect in a signaling pathway upstream from a protein kinase; by overexpression of a protein kinase; or by a dysregulated protein kinase in a mammal in need thereof which comprises providing said mammal an effective amount of a compound of Formula (1),

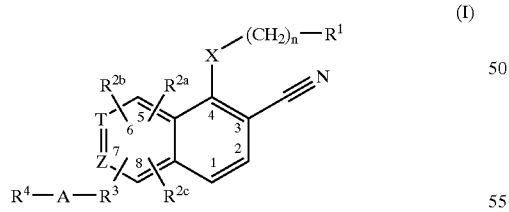

(I)

wherein:
X is —NH—, —$NR^5$—, —O—, or —$S(O)_m$—,
n is an integer of 0 or 1;
m is an integer of 0 to 2;
q is an integer of 0 to 5;
p is an integer of 2 to 5;
s is an integer of 0 to 5;
r is an integer of 0 to 5;
J is halogen;
A is absent;

T is N and Z is carbon;

$R^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, —$S(O)_m R^5$, —$NHSO_2 R^5$, —$R^6 H$, —$R^6 R$, —$R^6 NH_2$, —$R^6 NHR^5$, —$R^6 Q$, —$R^6 SH$, —$R^6 S(O)_m R^5$, —$NHR^7 OH$, —$NHR^7 OR^5$, —$N(R^5)R^7 OH$, —$N(R^5)R^7 OR^5$, —$NHR^7 NH_2$, —$NHR^7 NHR^5$, —$NHR^7 Q$, —$N(R^5)R^7 NH_2$, —$N(R^5)R^7 NHR^5$, —$N(R^5)R^7 Q$, —$OR^7 OH$, —$R^7 OR^5$, —$OR^7 NH_2$, —$OR^7 NHR^5$, —$OR^7 Q$, —$OC(O)R^5$, —$NHC(O)R^5$, —$NHC(O)NHR^5$, —$R^6 C(O)R^5$, —$NHR^6 C(O)R^5$, —$C(O)R^5$, —$C(O)OR^5$, —$C(O)NHR^5$, —$C(O)Q$, —$R^6 C(O)H$, —$R^6 C(O)R^5$, —$R^6 C(O)OH$, —$R^6 C(O)OR^5$, —$R^6 C(O)NH_2$, —$R^6 C(O)NHR$, —$R^6 C(O)Q$, —$R^6 OC(O)R^5$, —$R^6 OC(O)NH_2$, —$R^6 OC(O)NHR^5$, —$R^6 OC(O)Q$ and $YR^8$ groups wherein Y is independently selected from —$C(O)$—, —$C(O)O$—, —$OC(O)$—, —$C(O)NH$—, —$NHC(O)$—, —$NHSO_2$—, —$SO_2 NH$—, —$C(OH)H$—, —$O(C(R^9)_2)_q$—, —$S(O)_m(C(R^9)_2)_q$—, —$NH(C(R^9)_2)_q$—, —$NR^{10}(C(R^9)_2)_q$—, —$(C(R^9)_2)_q$—, —$(C(R^9)_2)_q O$—, —$(C(R^9)_2)_q S(O)_m$—, —$(C(R^9)_2)_q NH$—, —$(C(R^9)_2)_q NR^{10}$—, —C≡C—, cis and trans —CH=CH— and cycloalkyl of 3 to 10 carbon atoms;

Q is —$NR^5 R^5$ and further provided that when each $R^5$ is independently selected from alkyl and alkenyl, $R^5 R^5$ may optionally be taken together with the nitrogen atom to which they are attached forming a heterocyclyl ring of 3 to 8 atoms, optionally containing 1 or 2 additional heteroatoms which may be the same or different selected from N, O and S;

$R^{2a}$, $R^{2b}$, and $R^{2c}$, are each, independently selected from —H, -aryl, —$CH_2$aryl, —Oaryl, —$S(O)_m$aryl, —J, —$NO_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$S(O)_m R^5$, —$NHSO_2 R^5$, —$R^{11}$, —$OR^{11}$, —$R^6 OH$, —$R^6 OR^5$, —$R^6 SH$, —$R^6 S(O)_m R^5$, —$OR^7 OH$, —$OR^7 OR^5$, —$OC(O)R^5$, —$NHC(O)R^5$, —$NHC(O)NHR^5$, —$OR^6 C(O)R^5$, —$NHR^6 C(O)R^5$, —$C(O)R^5$, —$C(O)OR^5$, —$C(O)NHR^5$, —$C(O)Q$, —$R^6 C(O)H$, —$R^6 C(O)R^5$, —$R^6 C(O)OH$, —$R^6 C(O)OR^5$, —$R^6 C(O)NH_2$, —$R^6 C(O)NHR^5$, —$R^6 C(O)Q$, —$R^6 OC(O)R^5$, —$R^6 OC(O)NH_2$, —$R^6 OC(O)NHR^5$, —$R^6 OC(O)Q$, —G—$(C(R^9)_2)_p$—$R^{12}$,

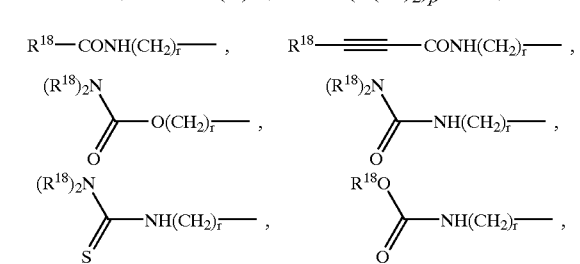

-continued

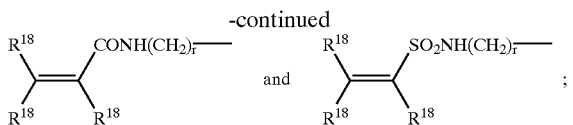

and ;

G is —NH—, —NR$^{10}$—, —O— or —S(O)$_m$—;

R$^3$ is selected from alkenyl of 2 to 6 carbon atoms, optionally substituted with one or more of —R$^{10}$, —(C(R$^9$)$_2$)R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)R$^{12}$, —CHO, 1,3-dioxolane, —NO$_2$, —CN, —CO$_2$H, —CONH$_2$—CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$ and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$—CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^1$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$—CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

R$^6$ is a divalent group selected from alkyl of 1 to 6 carbon atoms, alkenyl of 2 to 6 carbon atoms, and alkynyl of 2 to 6 carbon atoms;

R$^7$ is a divalent alkyl group of 2 to 6 carbon atoms;

R$^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —R$^6$R$^{12}$, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$R$^5$, —OR$^7$NH$_2$, —OR$^7$NHR$^5$, —OR$^7$Q, —OC(O)R$^5$, —NHC(O)R$^5$, —R$^6$R$^{12}$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$R$^{12}$, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$C(O)NHR$^5$ and —R$^6$C(O)Q;

R$^9$ is independently —H, —F or —R$^5$;

R$^{10}$ is an alkyl group of 1 to 12 carbon atoms, preferred is 1 to 6 carbon atoms;

R$^{11}$ is a cycloalkyl group of 3 to 10 carbon atoms;

R$^{12}$ is —N(O)$_n$R$^{13}$R$^{14}$ or —N$^+$(R$^{10}$R$^{13}$R$^{14}$)J$^-$;

provided that when R$^{12}$ is N(O)$^7$ R$^{13}$R$^{14}$ and n is 1, R$^{13}$ or R$^{14}$ are not H;

R$^{13}$ and R$^{14}$ are independently selected from a group consisting of —H, —R$^5$, —R$^{11}$, —(C(R$^9$)$_2$)$_q$aryl-R$^{15}$, —(C(R$^9$)$_2$)$_q$heteroaryl-R$^{15}$, —(C(R$^9$)$_2$)$_q$heterocyclyl-R$^{15}$, —(C(R$^9$)$_2$)$_p$OR$^{16}$, —(C(R$^9$)$_2$)$_p$NR$^{16}$R$^{17}$, —(C(R$^9$)$_2$)$_p$S(O)$_m$R$^{16}$, —(C(R$^9$)$_2$)$_p$CO$_2$R$^{16}$, —(C(R$^9$)$_2$)$_p$C(O)NHR$^{16}$ and —(C(R$^9$)$_2$)$_p$C(O)R$^{15}$; further provided that R$^{13}$ and R$^{14}$ may optionally be taken together with the nitrogen to which they are attached forming a heterocyclyl, heteroaryl or bicyclyl heteroaryl ring optionally substituted on either nitrogen or carbon by one or more selected from the group, —R$^5$, —R$^{11}$, —(C(R$^9$)$_2$)$_q$arylR$^{15}$, —(C(R$^9$)$_2$)$_q$heteroarylR$^{15}$, —(C(R$^9$)$_2$)$_q$heterocyclyl-R$^{15}$, —(C(R$^9$)$_2$)$_q$CO$_2$R$^{16}$, —(C(R$^9$)$_2$)$_q$C(O)NHR$^{16}$, and —(C(R$^9$)$_2$)$_q$C(O)R$^{15}$; or optionally substituted on carbon by —F, —(C(R$^7$)$_2$)$_q$ OR$^{16}$, —(C(R$^7$)$_2$)$_q$NR$^{16}$R$^{17}$, and —(C(R$^9$)$_2$)$_q$S(O)$_m$R$^{16}$; or optionally substituted on nitrogen by —(C(R$^9$)$_2$)$_p$OR$^{16}$, —(C(R$^9$)$_2$)$_p$NR$^{16}$R$^{17}$, and —(C(R$^9$)$_2$)$_p$S(O)$_m$R$^{16}$;

R$^{15}$ is independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_q$OH, —(C(R$^9$)$_2$)$_q$OR$^{10}$, —(C(R$^9$)$_2$)$_q$NH$_2$, —(C(R$^9$)$_2$)$_q$NHR$^{10}$, —(C(R$^9$)$_2$)$_q$R$^{10}$, —(C(R$^9$)$_2$)$_q$S(O)$_m$R$^{10}$, —(C(R$^9$)$_2$)$_q$CO$_2$R$^{10}$, —(C(R$^9$)$_2$)$_q$CONHR$^{10}$, —(C(R$^9$)$_2$)$_q$CONR$^{10}$R$^{10}$, —(C(R$^9$)$_2$)$_q$COR$^{10}$, —(C(R$^9$)$_2$)$_q$CO$_2$H, and —(C(R$^9$)$_2$)$_q$CONH$_2$;

R$^{16}$ and R$^{17}$ are independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_p$OH, —(C(R$^9$)$_2$)$_p$OR$^{10}$, —(C(R$^9$)$_2$)$_p$NH$_2$, —(C(R$^9$)$_2$)$_p$NHR$^{10}$, —(C(R$^9$)$_2$)$_p$NR$^{10}$R$^{10}$, —(C(R$^9$)$_2$)$_p$S(O)$_m$R$^{10}$, —(C(R$^9$)$_2$)$_p$CO$_2$R$^{10}$, —(C(R$^9$)$_2$)$_p$CONHR$^{10}$, —(C(R$^9$)$_2$)$_p$CONR$^{10}$R$^{10}$, —(C(R$^9$)$_2$)$_p$COR$^{10}$, —(C(R$^9$)$_2$)$_p$CO$_2$H, and —(C(R$^9$)$_2$)$_p$CONH$_2$;

R$^{18}$ is independently selected from the group consisting of —H, -aryl, —R$^5$, —R$^6$NH$_2$, —R$^6$NHR$^5$ and —R$^6$Q;

provided that, the 7-position is substituted or a pharmaceutically acceptable salt thereof.

23. A method of inhibiting the biological effects of a deregulated protein kinase in a mammal which comprises administering to said mammal an effective amount of a compound of Formula (1),

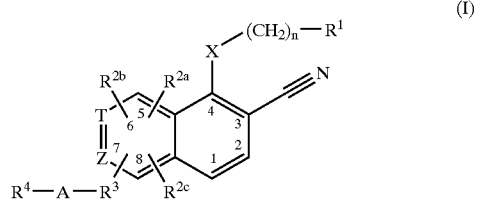

wherein:

X is —NH—, —NR$^5$—, —O—, or —S(O)$_m$—;

n is an integer of 0 or 1;

m is an integer of 0 to 2;

q is an integer of 0 to 5;

p is an integer of 2 to 5;

s is an integer of 0 to 5;

r is an integer of 0 to 5;

J is halogen;

A is absent;

T is N and Z is carbon; R$^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —R$^7$OR$^5$, —OR$^7$NH$_2$, —OR$^7$NHR$^5$, —OR$^7$Q, —OC(O)R$^5$, —NHC(O)R$^5$, —NHC(O)NH$^5$R, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$ (C(R$^9$)$_2$)$_q$—, —NH(C(R$^9$)$_2$)$_q$—, —NR$^{10}$(C(R$^9$)$_2$), —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH═CH— and cycloalkyl of 3 to 10 carbon atoms;

Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ring of 3 to 8 atoms, optionally containing 1 or 2 additional heteroatoms which may be the same or different selected from N, O and S;

R$^{2a}$, R$^{2b}$, and R$^{2c}$, are each, independently selected from —H, -aryl, —CH$_2$aryl, —Oaryl, —S(O)$_m$aryl, —J, —NO$_2$, —OH, —SH, —CN, —N, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^7$OR$^5$, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$—R$^{12}$, —(C(R$^9$)$_2$)$_q$—R$^{12}$,

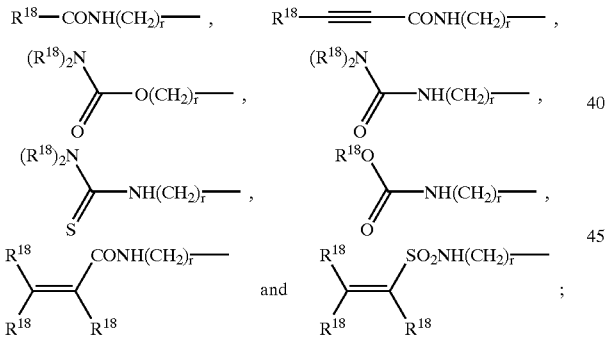

G is —NH—, —NR$^{10}$—, —O— or —S(O)$_m$—;

R$^3$ is selected from alkenyl of 2 to 6 carbon atoms, optionally substituted with one or more of —R$^{10}$, —(C(R$^5$)$_2$)$_s$R$^{12}$, —CHO, 1,3-dioxolane, —NO$_2$, —CN, —CO$_2$H, —CONH$_2$, CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$ R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;
a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;
a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C($R^9$)$_2$)$_p$$R^{12}$, and —G(C($R^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —$R^{10}$, —(C($R^9$)$_2$)$_s$$R^{12}$, —CHO, 1,3-dioxolane, —$NO_2$, —CN, —$CO_2$H, —$CONH_2$, —$CO_2$$R^{10}$, —CONH$R^{10}$, —COR$^{10}$, —(C($R^9$)$_2$)$_q$OH, —(C($R^9$)$_2$)$_q$O$R^{10}$, —(C($R^9$)$_2$)$_q$NH$R^{10}$, —(C($R^9$)$_2$)$_q$J, —(C($R^9$)$_2$)$_q$$NH_2$, —(C($R^9$)$_2$)$_q$H, —G(C($R^9$)$_2$)$_p$O$R^{10}$, —G(C($R^9$)$_2$)$_p$$R^{12}$, and —G(C($R^9$)$_2$)$_p$OH;

$R^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

$R^6$ is a divalent group selected from alkyl of 1 to 6 carbon atoms, alkenyl of 2 to 6 carbon atoms, and alkynyl of 2 to 6 carbon atoms;

$R^7$ is a divalent alkyl group of 2 to 6 carbon atoms;

$R^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —$CH_2$aryl, —NHaryl, —Oaryl, —S(O)$_m$aryl, —J, —$NO_2$, —$NH_2$, —OH, —SH, —CN, —$N_3$, —COOH, —$CONH_2$, —NHC(O)$NH_2$, —C(O)H, —$CF_3$, —$OCF_3$, —$R^5$, —O$R^5$, —NH$R^5$, —Q, —S(O)$_m$R, —NH$SO_2$$R^5$, —$R^{11}$, —O$R^{11}$, —NH$R^{11}$, —$R^6$OH, —$R^6$O$R^5$, —$R^6$$NH_2$, —$R^6$NH$R^5$, —$R^6$Q, —$R^6$SH, —$R^6$S(O)$_m$$R^5$, —NH$R^7$OH, —NH$R^7$O$R^5$, —N($R^5$)$R^7$OH, —$R^6$$R^{12}$, —N($R^5$)$R^7$O$R^5$, —NH$R^7$$NH_2$, —NH$R^7$NH$R^5$, —NH$R^7$Q, —N($R^5$)$R^7$$NH_2$, —N($R^5$)$R^7$NH$R^5$, —N($R^5$)$R^7$Q, —O$R^7$OH, —O$R^7$O$R^5$, —O$R^7$$NH_2$, —O$R^7$NH$R^5$, —O$R^7$Q, —OC(O)$R^5$, —NHC(O)$R^5$, —NHC(O)NH$R^5$, —O$R^6$C(O)R, —NH$R^6$C(O)$R^5$, —C(O)$R^5$, —C(O)O$R^5$, —C(O)NH$R^5$, —C(O)Q, —$R^6$C(O)H, —$R^6$C(O)$R^5$, —$R^6$C(O)OH, —$R^6$C(O)O$R^5$, —$R^6$C(O)$NH_2$, —$R^6$C(O)NH$R^5$, —$R^6$C(O)Q, —$R^6$OC(O)R, —$R^6$OC(O)$NH_2$, —$R^6$OC(O)NH$R^5$ and —$R^6$C(O)Q; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —$CH_2$aryl, —NHaryl, —Oaryl, —S(O)$_m$aryl, —J, —$NO_2$, —$NH_2$, —OH, —SH, —CN, —$N_3$, —COOH, —$CONH_2$, —NHC(O)$NH_2$, —C(O)H, —$CF_3$, —$OCF_3$, —$R^5$, —O$R^5$, —NH$R^5$, —Q, —S(O)$_m$$R^5$, —NH$SO_2$$R^5$, —$R^{11}$, —O$R^{11}$, —NH$R^{11}$, —$R^6$OH, —$R^6$O$R^5$, —$R^6$$NH_2$, —$R^6$NH$R^5$, —$R^6$Q, —$R^6$SH, —$R^6$S(O)$_m$$R^5$, —NH$R^7$OH, —NH$R^7$O$R^5$, —N($R^5$)$R^7$OH, —N($R^5$)$R^7$O$R^5$, —NH$R^7$$NH_2$, —NH$R^7$NH$R^5$, —NH$R^7$Q, —N($R^5$)$R^7$$NH_2$, —N($R^5$)$R^7$NH$R^5$, —N($R^5$)$R^7$Q, —O$R^7$OH, —O$R^7$O$R^5$, —O$R^7$$NH_2$, —O$R^7$NH$R^5$, —O$R^7$Q, —OC(O)$R^5$, —NHC(O)$R^5$, —$R^6$$R^{12}$, —NHC(O)NH$R^5$, —O$R^6$C(O)$R^5$, —NH$R^6$C(O)$R^5$, —C(O)$R^5$, —C(O)O$R^5$, —C(O)NH$R^5$, —C(O)Q, —$R^6$C(O)H, —$R^6$C(O)$R^5$, —$R^6$C(O)OH, —$R^6$C(O)OR$^5$, —$R^6$C(O)$NH_2$, —$R^6$C(O)NH$R^5$, —$R^6$C(O)Q, —$R^6$OC(O)$R^5$, —$R^6$OC(O)$NH_2$, —$R^6$OC(O)NH$R^5$ and —$R^6$OC(O)Q; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —$CH_2$aryl, —NHaryl, —Oaryl, —S(O)$_m$aryl, —J, —$NO_2$, —$NH_2$, —OH, —SH, —CN, —$N_3$, —COOH, —$CONH_2$, —NHC(O)$NH_2$, —C(O)H, —$CF_3$, —$OCF_3$, —$R^5$, —O$R^5$, —NH$R^5$, —Q, —S(O)$_m$$R^5$, —NH$SO_2$$R^5$, —$R^{11}$, —O$R^{11}$, —NH$R^{11}$, —$R^6$H, —$R^6$$R^5$, —$R^6$$NH_2$, —$R^6$NH$R^5$, —$R^6$Q, —$R^6$SH, —$R^6$$R^{12}$, —$R^6$S(O)$_m$$R^5$, —NH$R^7$OH, —NH$R^7$O$R^5$, —N($R^5$)$R^7$OH, —N($R^5$)$R^7$O$R^5$, —NH$R^7$$NH_2$, —NH$R^7$NH$R^5$, —NH$R^7$Q, —N($R^5$)$R^7$$NH_2$, —N($R^5$)$R^7$NH$R^5$, —N($R^5$)$R^7$Q, —O$R^7$OH, —O$R^7$O$R^5$, —O$R^7$$NH_2$, —O$R^7$NH$R^5$, —O$R^7$Q, —OC(O)$R^5$, —NHC(O)$R^5$, —NHC(O)NH$R^5$, —O$R^6$C(O)$R^5$, —NH$R^6$C(O)$R^5$, —C(O)$R^5$, —C(O)O$R^5$, —C(O) NH$R^5$, —C(O)Q, —$R^6$C(O)H, —$R^6$C(O)$R^5$, —$R^6$C (O)OH, —$R^6$C(O)O$R^5$, —$R^6$C(O)$NH_2$, —$R^6$C(O) NH$R^5$, —$R^6$C(O)Q, —$R^6$OC(O)$R^5$, —$R^6$OC(O)$NH_2$, —$R^6$OC(O)NH$R^5$ and —$R^6$C(O)Q;

$R^9$ is independently —H, —F or —$R^5$;

$R^{10}$ is an alkyl group of 1 to 12 carbon atoms, preferred is 1 to 6 carbon atoms;

$R^{11}$ is a cycloalkyl group of 3 to 10 carbon atoms;

$R^{12}$ is —N(O)$_n$$R^{13}$$R^{14}$ or —$N^+$($R^{10}$$R^{13}$$R^{14}$)$J^-$;

provided that when $R^{12}$ is N(O)$_n$$R^{13}$$R^{14}$ and n is 1, $R^{13}$ or $R^{14}$ are not H;

$R^{13}$ and $R^{14}$ are independently selected from a group consisting of —H, —$R^5$, —$R^{11}$, —(C($R^9$)$_2$)$_q$aryl-$R^{15}$, —(C($R^9$)$_2$)$_q$heteroaryl-$R^{15}$, —(C($R^9$)$_2$)$_q$heterocyclyl-$R^{15}$, —(C($R^9$)$_2$)$_p$O$R^{16}$, —(C($R^9$)$_2$)$_p$N$R^{16}$$R^{17}$, —(C($R^9$)$_2$)$_p$S(O)$_m$$R^{16}$, —(C($R^9$)$_2$)$_p$$CO_2$$R^{16}$, —(C($R^9$)$_2$)$_p$C(O)NH$R^{16}$ and —(C($R^9$)$_2$)$_p$C(O)$R^{15}$; further provided that $R^{13}$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, —$R^5$, —$R^{11}$, —(C($R^9$)$_2$)$_q$aryl$R^{15}$, —(C($R^9$)$_2$)$_q$heteroaryl$R^{15}$, —(C($R^9$)$_2$)$_q$heterocyclyl$R^{15}$, —(C($R^9$)$_2$)$_q$$CO_2$$R^{16}$, —(C($R^9$)$_2$)$_q$C(O)NH$R^{16}$, and —(C($R^9$)$_2$)$_q$C(O)$R^{15}$; or optionally substituted on carbon by —F, —(C($R^7$)$_2$)$_q$O$R^{16}$, —(C($R^7$)$_2$)$_q$N$R^{16}$$R^{17}$, and —(C($R^9$)$_2$)$_q$S(O)$_m$$R^{16}$; or optionally substituted on nitrogen by —(C($R^9$)$_2$)$_p$O$R^{16}$, —(C($R^9$)$_2$)$_p$N$R^{16}$$R^{17}$, and —(C($R^9$)$_2$)$_p$S(O)$_m$$R^{16}$;

$R^{15}$ is independently selected from a group consisting of —H, —$R^5$, —$R^{11}$, —(C($R^9$)$_2$)$_q$aryl, —(C($R^9$)$_2$)$_q$heteroaryl, —(C($R^9$)$_2$)$_q$heterocyclyl, —(C($R^9$)$_2$)$_q$OH, —(C($R^9$)$_2$)$_q$O$R^{10}$, —(C($R^9$)$_2$)$_q$$NH_2$, —(C($R^9$)$_2$)$_q$NH$R^{10}$, —(C($R^9$)$_2$)$_q$$R^{10}$, —(C($R^9$)$_2$)$_q$S(O)$_m$$R^{10}$, —(C($R^9$)$_2$)$_q$$CO_2$$R^{10}$, —(C($R^9$)$_2$)$_q$CONH$R^{10}$, —(C($R^9$)$_2$)$_q$CON$R^{10}$$R^{10}$, —(C($R^9$)$_2$)$_q$COR$^{10}$, —(C($R^9$)$_2$)$_q$$CO_2$H, and —(C($R^9$)$_2$)$_q$$CONH_2$;

$R^{16}$ and $R^{17}$ are independently selected from a group consisting of —H, —$R^5$, —$R^{11}$, —(C($R^9$)$_2$)$_q$aryl, —(C($R^9$)$_2$)$_q$heteroaryl, —(C($R^9$)$_2$)$_q$heterocyclyl, —(C($R^9$)$_2$)$_p$OH, —(C($R^9$)$_2$)$_p$O$R^{10}$, —(C($R^9$)$_2$)$_p$$NH_2$, —(C($R^9$)$_2$)$_p$NH$R^{10}$, —(C($R^9$)$_2$)$_p$N$R^{16}$$R^{10}$, —(C($R^9$)$_2$)$_p$S(O)$_m$$R^{10}$, —(C($R^9$)$_2$)$_p$$CO_2$$R^{10}$, —(C($R^9$)$_2$)$_p$CONH$R^{10}$, —(C($R^9$)$_2$)$_p$CON$R^{10}$$R^{10}$, —(C($R^9$)$_2$)$_p$COR$^{10}$, —(C($R^9$)$_2$)$_p$$CO_2$H, and —(C($R^9$)$_2$)$_p$$CONH_2$;

$R^{18}$ is independently selected from the group consisting of —H, -aryl, —$R^5$, —$R^6$$NH_2$, —$R^6$NH$R^5$ and —$R^6$Q;

provided that, the 7-position is substituted
or a pharmaceutically acceptable salt thereof.

24. A pharmaceutical composition for treating or inhibiting disease in a mammal characterized by abnormal growth of cells which comprises administering to a mammal in need thereof an effective amount of a compound of Formula (1) having the structure,

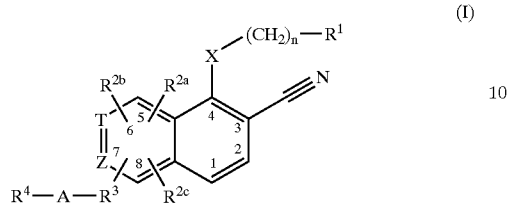

wherein:
X is —NH—, —NR$^5$—, —O—, or —S(O)$_m$—;
n is an integer of 0 or 1;
m is an integer of 0 to 2;
q is an integer of 0 to 5;
p is an integer of 2 to 5;
s is an integer of 0 to 5;
r is an integer of 0 to 5;
J is halogen;
A is absent;
T is N and Z is carbon;
R$^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$ R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$ R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —R$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;
Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ring of 3 to 8 atoms, optionally containing 1 or 2 additional heteroatoms which may be the same or different selected from N, O and S;
R$^{2a}$, R$^{2b}$, and R$^{2c}$, are each, independently selected from —H, -aryl, —CH$_2$aryl, —Oaryl, —S(O)$_m$aryl, —J, —NO$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^7$OR$^5$, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$—R$^{12}$, —(C(R$^9$)$_2$)$_q$R$^{12}$,

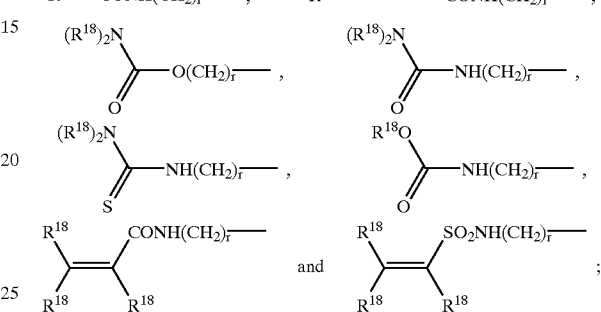

G is —NH—, —NR$^{10}$—, —O— or S(O)$_m$—;
R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(PR$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO, —CN, —CO$_2$H, —CONH$_2$, —CO$_2$R$^{10}$, —CONHR$^{10}$, —COR$^{10}$, —(C(R$^9$)$_2$)$_q$O, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$—CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)(NHR$^{10}$), —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

R$^6$ is a divalent group selected from alkyl of 1 to 6 carbon atoms, alkenyl of 2 to 6 carbon atoms, and alkynyl of 2 to 6 carbon atoms;

R$^7$ is a divalent alkyl group of 2 to 6 carbon atoms;

R$^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —R$^6$R$^{12}$, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —R$^6$R$^{12}$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$H, —R$^6$R$^5$, —R$^6$NH$_2$, —R$^6$NHR$^5$, —R$^6$Q, —R$^6$SH, —R$^6$R$^{12}$, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$) R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q;

R$^9$ is independently —H, —F or —R$^5$;

R$^{10}$ is an alkyl group of 1 to 12 carbon atoms, preferred is 1 to 6 carbon atoms;

$R^{11}$ is a cycloalkyl group of 3 to 10 carbon atoms;

$R^{12}$ is —N(O), $R^{13}R^{14}$ or —N$^+$($R^{10}R^{13}R^4$)J$^-$;

provided that when $R^{12}$ is N(O)$_n R^{13}R^{14}$ and n is 1, $R^{13}$ or $R^{14}$ are not H;

$R^{13}$ and $R^{14}$ are independently selected from a group consisting of —H, —$R^5$, —$R^{11}$, —(C($R^9$)$_2$)$_q$aryl-$R^{15}$, —(C($R^9$)$_2$)$_q$heteroaryl-$R^{15}$, —(C($R^9$)$_2$)$_q$heterocyclyl-$R^{15}$, —(C($R^9$)$_2$)$_p$O$R^{16}$, —(C($R^9$)$_2$)$_p$N$R^{16}R^{17}$, —(C($R^9$)$_2$)$_p$S(O)$_m R^{16}$, —(C($R^9$)$_2$)$_p$CO$_2 R^{16}$, —(C($R^9$)$_2$)$_p$C(O)NH$R^{16}$ and —(C($R^9$)$_2$)$_p$C(O)$R_5$; further provided that $R^{13}$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, —$R^5$, —$R^{11}$, —(C($R^9$)$_2$)$_q$aryl$R^{15}$, —(C($R^9$)$_2$)$_q$heteroaryl$R^{15}$, —(C($R^9$)$_2$)$_q$heterocyclyl$R^{15}$, —(C($R^9$)$_2$)$_q$CO$_2 R^{16}$, —(C($R^9$)$_2$)$_q$C(O)NH$R^{16}$, and —(C($R^9$)$_2$)$_q$C(O)$R^{15}$; or optionally substituted on carbon by —F, —(C($R^7$)$_2$)$_q$ (O$R^{10}$), —(C($R^7$)$_2$)$_q$N$R^{16}R^{17}$, and —(C($R^9$)$_2$)$_q$S(O)$_m R^{16}$ or optionally substituted on nitrogen by —(C($R^9$)$_2$)$_p$O$R^{16}$, —(C($R^9$)$_2$)$_p$N$R^{16}R^{17}$, and —(C($R^9$)$_2$)$_p$S(O)$_m R^{16}$;

$R^{15}$ is independently selected from a group consisting of —H, —$R^5$, —$R^{11}$, —(C($R^9$)$_2$)$_q$aryl, —(C($R^9$)$_2$)$_q$heteroaryl, —(C($R^9$)$_2$)$_q$heterocyclyl, —(C($R^9$)$_2$)$_q$OH, —(C($R^9$)$_2$)$_q$O$R^{10}$, —(C($R^9$)$_2$)$_q$NH$_2$, —(C($R^9$)$_2$)$_q$NH$R^{10}$, —(C($R^9$)$_2$)$_q$$R^{10}$, —(C($R^9$)$_2$)$_q$S(O)$_m R^{10}$, —(C($R^9$)$_2$)$_q$CO$_2 R^{10}$, —(C($R^9$)$_2$)$_q$CONH$R^{10}$, —(C($R^9$)$_2$)$_q$CON$R^{10}R^{10}$, —(C($R^9$)$_2$)$_q$CO$R^{10}$, —(C($R^9$)$_2$)$_q$CO$_2$H, and —(C($R^9$)$_2$)$_q$CONH$_2$;

$R^{16}$ and $R^{17}$ are independently selected from a group consisting of —H, —$R^5$, —$R^{11}$, —(C($R^9$)$_2$)$_q$aryl, —(C($R^9$)$_2$)$_q$heteroaryl, —(C($R^9$)$_2$)$_q$heterocyclyl, —(C($R^9$)$_2$)$_p$OH, —(C($R^9$)$_2$)$_q$O$R^{10}$, —(C($R^9$)$_2$)$_p$NH$_2$, —(C($R^9$)$_2$)$_p$NH$R^{10}$, —(C($R^9$)$_2$)$_p$N$R^{16}R^{16}$, —(C($R^9$)$_2$)$_p$S(O)$_m R^{10}$, —(C($R^9$)$_2$)$_p$CO$_2 R^{10}$, —(C($R^9$)$_2$)$_p$CONH$R^{10}$, —(C($R^9$)$_2$)$_p$CON$R^{10}R^{10}$, —(C($R^9$)$_2$)$_p$)COR$^{10}$, —(C($R^9$)$_2$)$_p$CO$_2$H, and —(C($R^9$)$_2$)$_p$CONH$_2$;

$R^{18}$ is independently selected from the group consisting of —H, -aryl, —$R^5$, —$R^6$NH$_2$, —$R^6$NH$R^5$ and —$R^6$Q;

provided that, the 7-position is substituted or a pharmaceutically acceptable salt thereof.

25. A method of treating or inhibiting the progression of restenosis in a mammal in need thereof which comprises providing to said mammal an effective amount of a PDGFr kinase inhibitor of Formula (1) having the structure,

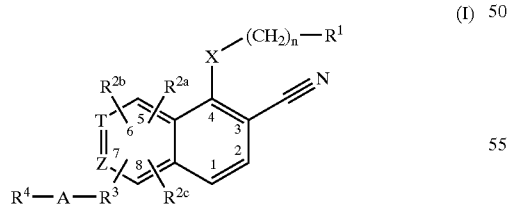

(I)

wherein:

X is —NH—, —N$R^5$—, —O—, or —S(O)$_m$—;

n is an integer of 0 or 1;

m is an integer of 0 to 2;

q is an integer of 0 to 5;

p is an integer of 2 to 5;

s is an integer of 0 to 5;

r is an integer of 0 to 5;

J is halogen;

A is absent;

T is N and Z is carbon;

$R^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —$R^5$, —O$R^5$, —NH$R^5$, —Q, —S(O)$_m$ $R^5$, —NHSO$_2 R^5$, —$R^6$OH, —$R^6$O$R^5$, —$R^6$NH$_2$, —$R^6$NH$R^5$, —$R^6$Q, —$R^6$SH, —$R^6$S(O)$_m$ $R^5$, —NH$R^7$OH, —NH$R^7$O$R^5$, —N($R^5$)$R^7$OH, —N($R^5$)$R^7$O$R^5$, —NH$R^7$NH$_2$, —NH$R^7$NH$R^5$, —NH$R^7$Q, —N($R^5$)$R^7$NH$_2$, —N($R^5$)$R^7$NH$R^5$, —N($R^5$)$R^7$Q, —O$R^7$OH, —$R^7$O$R^5$, —O$R^7$NH$_2$, —O$R^7$NH$R^5$, —O$R^7$Q, —OC(O)$R^5$, —NHC(O)$R^5$, —NHC(O)NH$R^5$, —$R^6$C(O)$R^5$, —NH$R^6$C(O)$R^5$, —C(O)$R^5$, —C(O)O$R^5$, —C(O)NH$R^5$, —C(O)Q, —$R^6$C(O)H, —$R^6$C(O)$R^5$, —$R^6$C(O)OH, —$R^6$C(O)O$R^5$, —$R^6$C(O)NH$_2$, —$R^6$C(O)NH$R^5$, —$R^6$C(O)Q, —$R^6$OC(O)$R^5$, —$R^6$OC(O)NH$_2$, —$R^6$OC(O)NH$R^5$, —$R^6$OC(O)Q and Y$R^8$ groups wherein Y is independently selected from —C(O)—, —C(O)O—, —OC (O)—, —C(O)NH—, —NHC(O)—, —NHSO$_2$—, —SO$_2$NH—, —C(OH)H—, —O(C($R^9$)$_2$)$_q$—, —S(O)$_m$ (C($R^9$)$_2$)$_q$—, —NH(C($R^9$)$_2$)$_q$—, —N$R^{10}$(C ($R^9$)$_2$)$_q$—, —(C($R^9$)$_2$)$_q$—, —(C($R^9$)$_2$)$_q$O—, —(C($R^9$)$_2$)$_q$S(O)$_m$—, —(C($R^9$)$_2$)$_q$NH—, —(C($R^9$)$_2$)$_q$N$R^{10}$—, —C≡C—, (is and trans —CH=CH— and cycloalkyl of 3 to 10 carbon atoms;

Q is —N$R^5R^5$ and further provided that when each $R^5$ is independently selected from alkyl and alkenyl, $R^5R^5$ may optionally be taken together with the nitrogen atom to which they are attached forming a heterocyclyl ring of 3 to 8 atoms, optionally containing 1 or 2 additional heteroatoms which may be the same or different selected from N, O and S;

$R^{2a}$, $R^{2b}$, and $R^{2c}$, are each, independently selected from —H, -aryl, —CH$_2$aryl, —Oaryl, —S(O)$_m$aryl, —J, —NO$_2$, —OH, —SH, —CN, —N$_3$, —COOH, —CONH$_2$, —NHC(O)NH$_2$, —C(O)H, —CF$_3$, —OCF$_3$, —$R^5$, —O$R^5$, —S(O)$_m R^5$, —NHSO$_2 R^5$, —$R^{11}$, —O$R^{11}$, —$R^6$OH, —$R^6$O$R^5$, —$R^6$SH, —$R^6$S(O)$_m R^5$, —O$R^7$OH, —O$R^7$O$R^5$, —OC(O)$R^5$, —NHC (O)$R^5$, —NHC(O)NH$R^5$, —O$R^6$C(O)$R^5$, —NH$R^{10}$C (O)$R^5$, —C(O)$R^5$, —C(O)O$R^5$, —C(O)NH$R^5$, —C(O) Q, —$R^6$C(O)H, —$R^6$C(O)$R^5$, —$R^6$C(O)OH, —$R^6$C (O)O$R^5$, —$R^6$C(O)NH$_2$, —$R^6$C(O)NH$R^5$, —$R^6$C(O) Q, —$R^6$OC(O)$R^5$, —$R^6$OC(O)NH$_2$, —$R^6$OC(O) NH$R^5$, —$R^6$OC(O)Q, —G—(C($R^9$)$_2$)$_p$—$R^{12}$, —(C ($R^9$)$_2$)$_q$—$R^{12}$, $R^{18}$—CONH(CH$_2$)$_r$—, $R^{18}$—≡≡≡—CONH(CH$_2$)$_r$—, ($R^{18}$)$_2$N—C(O)—O(CH$_2$)$_r$—, ($R^{18}$)$_2$N—C(O)—NH(CH$_2$)$_r$—, ($R^{18}$)$_2$N—C(S)—NH(CH$_2$)$_r$—, $R^{18}$O—C(O)—NH(CH$_2$)$_r$—,

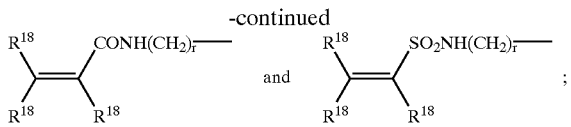

and ;

G is —N—, —NR$^{10}$—, —O— or —S(O)$_m$—;

R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

R$^6$ is a divalent group selected from alkyl of 1 to 6 carbon atoms, alkenyl of 2 to 6 carbon atoms, and alkynyl of 2 to 6 carbon atoms;

R$^7$ is a divalent alkyl group of 2 to 6 carbon atoms;

R$^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —R$^6$R$^{12}$, —N(R$^5$)R$^7$OR, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —R$^6$R$^{12}$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$R$^{12}$, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q;

R$^9$ is independently —H, —F or —R$^5$;

R$^{10}$ is an alkyl group of 1 to 12 carbon atoms, preferred is 1 to 6 carbon atoms;

R$^{11}$ is a cycloalkyl group of 3 to 10 carbon atoms;

R$^{12}$ is —N(O)$_n$R$^{13}$R$^{14}$ or —N$^+$(R$^{10}$R$^{13}$R$^{14}$)J$^-$;

provided that when R$^{12}$ is N(O)$_n$R$^{13}$R$^{14}$ and n is 1, R$^{13}$ or R$^{14}$ are not H;

R$^{13}$ and R$^{14}$ are independently selected from a group consisting of —H, —R$^5$, —R$^{11}$, —(C(R$^9$)$_2$)$_q$aryl-R$^{15}$, —(C(R$^9$)$_2$)$_q$heteroaryl-R$^{15}$, —(C(R$^9$)$_2$)$_q$heterocyclyl-R$^{15}$, —(C(R$^9$)$_2$)$_p$OR$^{16}$, —(C(R$^9$)$_2$)$_p$NR$^{16}$R$^{17}$, —(C(R$^9$)$_2$)$_p$S(O)$_m$R$^{16}$, —(C(R$^9$)$_2$)$_p$CO$_2$R$^{16}$, —(C(R$^9$)$_2$)$_p$C(O)NHR$^{16}$ and —(C(R$^9$)$_2$)$_p$C(O)R$^5$; further provided that R$^{13}$ and R$^{14}$ may optionally be taken together with the nitrogen to which they are attached forming a heterocyclyl, heteroaryl or bicyclyl heteroaryl ring optionally substituted on either nitrogen or carbon by one or more selected from the group, —R$^5$, —R$^{11}$, —(C(R$^9$)$_2$)$_q$arylR$^{15}$, —(C(R$^9$)$_2$)$_q$heteroarylR$^{15}$, —(C(R$^9$)$_2$)$_q$heterocyclylR$^{15}$, —(C(R$^9$)$_2$)$_q$CO$_2$R$^{16}$, —(C(R$^9$)$_2$)$_q$C(O)NHR$^{16}$, and —(C(R$^9$)$_2$)$_q$C(O)R$^{15}$; or optionally substituted on carbon by —F, —(C(R$^7$)$_2$)$_q$OR$^{16}$, —(C(R$^7$)$_2$)$_q$NR$^{16}$R$^{17}$, and —(C(R$^9$)$_2$)$_q$S(O)$_m$R$^{16}$; or optionally substituted on nitrogen by —(C(R$^9$)$_2$)$_p$OR$^{16}$, —(C(R$^9$)$_2$)$_p$NR$^{16}$R$^{17}$, and —(C(R$^9$)$_2$)$_p$S(O)$_m$R$^{16}$;

R$^{15}$ is independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_q$OH, —(C(R$^9$)$_2$)$_q$OR$^{10}$, —(C(R$^9$)$_2$)$_q$NH$_2$, —(C(R$^9$)$_2$)$_q$NHR$^{10}$, —(C(R$^9$)$_2$)$_q$R$^{10}$, —(C(R$^9$)$_2$)$_q$S(O)$_m$R$^{10}$, —(C(R$^9$)$_2$)$_q$CO$_2$R$^{10}$, —(C(R$^9$)$_2$)$_q$CONHR$^{10}$, —(C(R$^9$)$_2$)$_q$CONR$^{10}$R$^{10}$, —(C(R$^9$)$_2$)$_q$COR$^{10}$, —(C(R$^9$)$_2$)$_q$CO$_2$H, and —(C(R$^9$)$_2$)$_q$CONH$_2$;

R$^{16}$ and R$^{17}$ are independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_p$OH, —(C(R$^9$)$_2$)$_p$OR$^{10}$, —(C(R$^9$)$_2$)$_p$NH$_2$, —(C(R$^9$)$_2$)$_p$NHR$^{10}$, —(C(R$^9$)$_2$)$_p$NR$^{10}$R$^{10}$, —(C(R$^9$)$_2$)$_p$S(O)$_m$R$^{10}$, —(C(R$^9$)$_2$)$_p$CO$_2$R$^{10}$, —(C(R$^9$)$_2$)$_p$CONHR$^{10}$, —(C(R$^9$)$_2$)$_p$CONR$^{10}$R$^{10}$, —(C(R$^9$)$_2$)$_p$COR$^{10}$, —(C(R$^9$)$_2$)$_p$CO$_2$H, and —(C(R$^9$)$_2$)$_p$CONH$_2$;

R$^{18}$ is independently selected from the group consisting of —H, -aryl, —R$^5$, —R$^6$NH$_2$, —R$^6$NHR$^5$ and —R$^6$Q;

provided that, the 7-position is substituted or a pharmaceutically acceptable salt thereof.

26. A method of treating, inhibiting or eradicating autoimmune diseases which include rheumatoid arthritis, sepsis and transplant rejection in a mammal in need thereof which comprises providing to said mammal an effective amount of Zap-70 or Lck kinase inhibitor of Formula (1), having the structure,

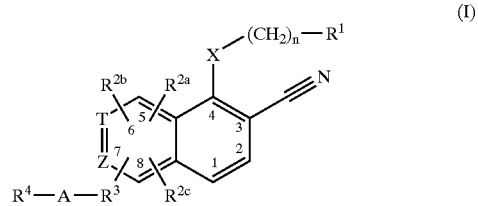

wherein:

X is —NH—, —NR$^5$—, —O—, or —S(O)$_m$—;

n is an integer of 0 or 1;

m is an integer of 0 to 2;

q is an integer of 0 to 5;

p is an integer of 2 to 5;

s is an integer of 0 to 5;

r is an integer of 0 to 5;

J is halogen;

A is absent;

T is N and Z is carbon;

R$^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$ R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —R$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$(C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;

Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ring of 3 to 8 atoms, optionally containing 1 or 2 additional heteroatoms which may be the same or different selected from N, O and S;

R$^{2a}$, R$^{2b}$, and R$^{2c}$, are each, independently selected from —H, -aryl, —CH$_2$aryl, —Oaryl, —S(O)$_m$aryl, —J, —NO$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^7$R$^5$, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$—R$^{12}$, —(C(R$^9$)$_2$)$_q$—R$^{12}$,

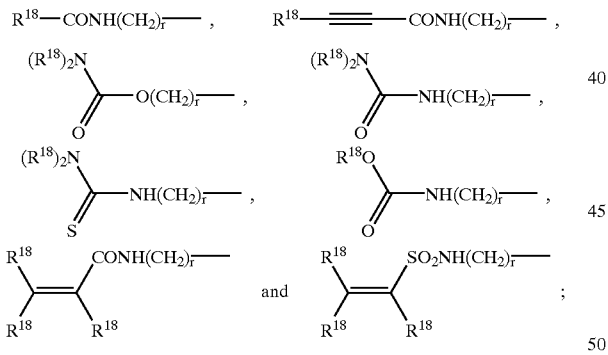

G is —NH—, —NR$^{10}$—, —O— or —S(O)$_m$—;

R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R), —CONHR$^{10}$, —COR$^{10}$), —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_qH$, —$G(C(R^9)_2)_pOR^{10}$, —$G(C(R^9)_2)_pR^{12}$, and —$G(C(R^9)_2)_pOH$;

$R^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

$R^6$ is a divalent group selected from alkyl of 1 to 6 carbon atoms, alkenyl of 2 to 6 carbon atoms, and alkynyl of 2 to 6 carbon atoms;

$R^7$ is a divalent alkyl group of 2 to 6 carbon atoms;

$R^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, $R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$R^6R^{12}$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —$CH_2$aryl, —NHaryl, —Oaryl, —$S(O)_m$aryl, —J, —$NO_2$, —$NHR_2$, —OH, —SH, —CN, —$N_3$, —COOH, —$CONH_2$, —NHC(O)$NH_2$, —C(O)H, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$R^6R^{12}$, —$NHC(O)NHR^5$, —$OR^6C(O)R^5$, —$NHR^6C(O)R^5$, —$C(O)R^5$, —$C(O)OR^5$, —$C(O)NHR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —$CH_2$aryl, —NHaryl, —Oaryl, —$S(O)_m$aryl, —J, —$NO_2$, —$NH_2$, —OH, —SH, —CN, —$N_3$, —COOH, —$CONH_2$, —$NHC(O)NH_2$, —$C(O)H$, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NR^5$, —$C(O)Q$, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$;

$R^9$ is independently —H, —F or —$R^5$;

$R^{10}$ is an alkyl group of 1 to 12 carbon atoms, preferred is 1 to 6 carbon atoms;

$R^{11}$ is a cycloalkyl group of 3 to 10 carbon atoms:

$R^{12}$ is —$N(O)_nR^{13}R^{14}$ or —$N^+(R^{10}R^{13}R^{14})J^-$;

provided that when $R^{12}$ is $N(O)_nR^{13}R^{14}$ and n is 1, $R^{13}$ or $R^{14}$ are not H;

$R^{13}$ and $R^{14}$ are independently selected from a group consisting of —H, —$R^5$, —$R^{11}$, —$(C(R^9)_2)_q$aryl-$R^{15}$, —$(C(R^9)_2)_q$heteroaryl-$R^{15}$, —$(C(R^9)_2)_q$heterocyclyl-$R^{15}$, —$(C(R^9)_2)_pOR^{16}$, —$(C(R^9)_2)_pNR^{16}R^{17}$, —$(C(R^9)_2)_pS(O)_mR^{16}$, —$(C(R^9)_2)_pCO_2R^{16}$, —$(C(R^9)_2)_pC(O)NHR^{16}$ and —$(C(R^9)_2)_pC(O)R^{15}$; further provided that $R^{13}$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, —$R^5$, —$R^{11}$, —$(C(R^9)_2)_q$aryl$R^{15}$, —$(C(R^9)_2)_q$heteroaryl$R^{15}$, —$(C(R^9)_2)_q$heterocyclyl-$R^{15}$, —$(C(R^9)_2)_qCO_2R^{16}$, —$(C(R^9)_2)_qC(O)NHR^{16}$, and —$(C(R^9)_2)_qC(O)R^{15}$; or optionally substituted on carbon by —F, —$(C(R^7)_2)_qOR^{16}$, —$(C(R^7)_2)_qNR^{16}R^{17}$, and —$(C(R^9)_2)_qS(O)_mR^{16}$; or optionally substituted on nitrogen by —$(C(R^9)_2)_pOR^{16}$, —$(C(R^9)_2)_pNR^{16}R^{17}$, and —$(C(R^9)_2)_pS(O)_mR^{16}$;

$R^{15}$ is independently selected from a group consisting of —H, —$R^5$, —$R^{11}$, —$(C(R^9)_2)_q$aryl, —$(C(R^9)_2)_q$heteroaryl, —$(C(R^9)_2)_q$heterocyclyl, —$(C(R^9)_2)_qOH$, —$(C(R^9)_2)_qOR^{10}$, —$(C(R^9)_2)_qNH_2$, —$(C(R^9)_2)_qNHR^{10}$, —$(C(R^9)_2)_qR^{10}$, —$(C(R^9)_2)_qS(O)R^{10}$, —$(C(R^9)_2)_qCO_2R^{10}$, —$(C(R^9)_2)_qCONHR^{10}$, —$(C(R^9)_2)_qCONR^{10}R^{10}$, —$(C(R^9)_2)_qCOR^{10}$, —$(C(R^9)_2)_qCO_2H$, and —$(C(R^9)_2)_qCONH_2$;

$R^{16}$ and $R^{17}$ are independently selected from a group consisting of —H, —$R^5$, —$R^{11}$, —$(C(R^9)_2)_q$aryl, —$(C(R^9)_2)_q$heteroaryl, —$(C(R^9)_2)_q$heterocyclyl, —$(C(R^9)_2)_pOH$, —$(C(R^9)_2)_pOR^{10}$, —$(C(R^9)_2)_pNH_2$, —$(C(R^9)_2)_pNHR^{10}$, —$(C(R^9)_2)_pNR^{16}R^{10}$, —$(C(R^9)_2)_pS(O)_mR^1$, —$(C(R^9)_2)_pCO_2R^{10}$, —$(C(R^9)_2)_pCONHR^{10}$, —$(C(R^9)_2)_pCONR^{10}R^{10}$, —$(C(R^9)_2)_pCOR^{10}$, —$(C(R^9)_2)_pCO_2H$, and —$(C(R^9)_2)_pCONH_2$;

$R^{18}$ is independently selected from the group consisting of —H, -aryl, —$R^5$, —$R^6NH_2$, —$R^6NHR^5$ and —$R^6Q$;

provided that, the 7-position is substituted or a pharmaceutically acceptable salt thereof.

27. A method of treating, inhibiting or eradicating viral infections in a mammal in need thereof which comprises providing to said mammal an effective amount of UL-97 kinase inhibitor of Formula (1) having the structure,

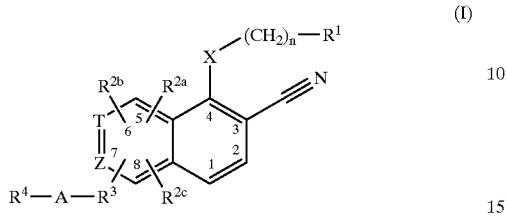

(I)

wherein:
X is —NH—, —NR$^5$—, —O—, or —S(O)$_m$—;
n is an integer of 0 or 1;
m is an integer of 0 to 2;
q is an integer of 0 to 5;
p is an integer of 2 to 5;
s is an integer of 0 to 5;
r is an integer of 0 to 5;
J is halogen;
A is absent;
T is N and Z is carbon;
R$^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH —R$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$C(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$ (C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$S(O)$_m$—, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;
Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ling of 3 to 8 atoms, optionally containing 1 or 2 additional heteroatoms which may be the same or different selected from N, O and S;
R$^{2a}$, R$^{2b}$, and R$^{2c}$, are each, independently selected from —H, -aryl, —CH$_2$aryl, —Oaryl, —S(O)$_m$aryl, —J, —NO$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^7$OR$^5$, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$—R$^{12}$, —(C(R$^9$)$_2$)$_q$—R$^{12}$,

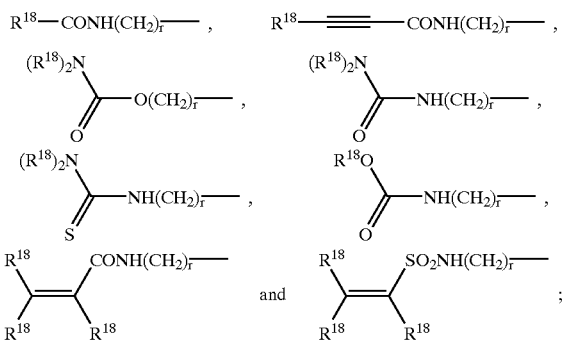

G is —NH—, —NR$^{10}$—, —O— or —S(O)$_m$—;
R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_p$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^5$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_rH$, —$G(C(R^9)_2)_pOR^{10}$, —$G(C(R^9)_2)_pR^{12}$, and —$G(C(R^9)_2)_pOH$;

$R^4$ is selected from —$(C(R^9)_2)_rH$, optionally substituted with one or more of —$R^{10}$, —$(C(R^9)_2)_sR^{12}$; —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_rH$, —$G(C(R^9)_2)_pOR^{10}$, —$G(C(R^9)_2)_pR^{12}$, and —$G(C(R^9)_2)_pOH$;

alkenyl of 2 to 6 carbon atoms, optionally substituted with one or more of —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_rH$, —$G(C(R^9)_2)_pOR^{10}$, —$G(C(R^9)_2)_pR^{12}$, and —$G(C(R^9)_2)_pOH$;

alkynyl of 2 to 6 carbon atoms, optionally substituted with one or more of —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_rH$, —$G(C(R^9)_2)_pOR^{10}$, —$G(C(R^9)_2)_pR^{12}$, and —$G(C(R^9)_2)_pOH$;

aryl of 6 to 12 carbon atoms optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_rH$, —$G(C(R^9)_2)_pOR^{10}$, —$G(C(R^9)_2)_pR^{12}$, and —$G(C(R^9)_2)_pOH$; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$COR^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_rH$, —$G(C(R^9)_2)_pOR^{10}$, —$G(C(R^9)_2)_pR^{12}$, and —$G(C(R^9)_2)_pOH$; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —$R^{10}$, —$(C(R^9)_2)_sR^{12}$, —CHO, 1,3-dioxolane, —$NO_2$, —CN, —$CO_2H$, —$CONH_2$, —$CO_2R^{10}$, —$CONHR^{10}$, —$COR^{10}$, —$(C(R^9)_2)_qOH$, —$(C(R^9)_2)_qOR^{10}$, —$(C(R^9)_2)_qNHR^{10}$, —$(C(R^9)_2)_qJ$, —$(C(R^9)_2)_qNH_2$, —$(C(R^9)_2)_rH$, —$G(C(R^9)_2)_pOR^{10}$, —$G(C(R^9)_2)_pR^{12}$, and —$G(C(R^9)_2)_qOH$;

$R^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

$R^6$ is a divalent group selected from alkyl of 1 to 6 carbon atoms, alkenyl of 2 to 6 carbon atoms, and alkynyl of 2 to 6 carbon atoms;

$R^7$ is a divalent alkyl group of 2 to 6 carbon atoms;

$R^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —$CH_2aryl$, —NHaryl, —Oaryl, —$S(O)_maryl$, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$R^6R^{12}$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R$, —$NHR^6C(O)R^5$, —$C(O)R^5$, —$C(O)OR^5$, —$C(O)NHR^5$, —C(O)Q, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —$CH_2aryl$, —NHaryl, —Oaryl, —$S(O)_maryl$, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6H$, —$R^6OR^5$, —$R^6NH_2$, —$R^6NHR^5$, —$R^6Q$, —$R^6SH$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)R^7NHR^5$, —$N(R^5)R^7Q$, —$OR^7OH$, —$OR^7R^5$, —$OR^7NH_2$, —$OR^7NHR^5$, —$OR^7Q$, —$OC(O)R^5$, —$NHC(O)R^5$, —$R^6R^{12}$, —$NHC(O)NHR^5$, —$OR^6C(O)R^5$, —$NHR^6C(O)R^5$, —$C(O)R^5$, —$C(O)OR^5$, —$C(O)NHR^5$, —C(O)Q, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^{10}C(O)R^5$, —$R^6OC(O)NH_2$, —$R^6OC(O)NHR^5$ and —$R^6OC(O)Q$; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —$CH_2aryl$, —NHaryl, —Oaryl, —S(O),aryl, —J, —$NO_2$, —$NH_2$, —OH, —SH, —CN, —$N_3$, —COOH, —$CONH_2$, —$NHC(O)NH_2$, —C(O)H, —$CF_3$, —$OCF_3$, —$R^5$, —$OR^5$, —$NHR^5$, —Q, —$S(O)_mR^5$, —$NHSO_2R^5$, —$R^{11}$, —$OR^{11}$, —$NHR^{11}$, —$R^6OH$, —$R^6OR^5$, —$R^6NH_2$, —$R^6NHR^5$, —$R^6Q$, —$R^6SH$, —$R^6R^{12}$, —$R^6S(O)_mR^5$, —$NHR^7OH$, —$NHR^7OR^5$, —$N(R^5)R^7OH$, —$N(R^5)R^7OR^5$, —$NHR^7NH_2$, —$NHR^7NHR^5$, —$NHR^7Q$, —$N(R^5)R^7NH_2$, —$N(R^5)$ $R^7NHR^5$, —$N(R^5)R^7Q$, —$OR^7OH$, —$OR^7OR^5$, —$OR^7NH_2$, —$OR^7NHR^5$, —$OR^7Q$, —$OC(O)R^5$, —$NHC(O)R^5$, —$NHC(O)NHR^5$, —$OR^6C(O)R^5$, —$NHR^6C(O)R^5$, —$C(O)R^5$, —$C(O)OR^5$, —$C(O)NHR^5$, —C(O)Q, —$R^6C(O)H$, —$R^6C(O)R^5$, —$R^6C(O)OH$, —$R^6C(O)OR^5$, —$R^6C(O)NH_2$, —$R^6C(O)NHR^5$, —$R^6C(O)Q$, —$R^6OC(O)R^5$, —$R^6OC(O)NH_2$, —$R^6OC(O)NHR^5$ and —$R^6OC(O)Q$;

$R^9$ is independently —H, —F or —$R^5$;

$R^{10}$ is an alkyl group of 1 to 12 carbon atoms, preferred is 1 to 6 carbon atoms;

$R^{11}$ is a cycloalkyl group of 3 to 10 carbon atoms;

$R^{12}$ is —N(O)$_n$R$^{13}$R$^{14}$ or —N$^+$(R$^{10}$R$^{13}$R$^{14}$)J$^-$;

provided that when $R^{12}$ is N(O)$_n$R$^{13}$R$^{14}$ and n is 1, $R^{13}$ or $R^{14}$ are not H;

$R^{13}$ and $R^{14}$ are independently selected from a group consisting of —H, —R$^5$, —R$^{11}$, —(C(R$^9$)$_2$)$_q$aryl-R$^{15}$, —(C(R$^9$)$_2$)$_q$heteroaryl-R$^{15}$, —(C(R$^9$)$_2$)$_q$heterocyclyl-R$^{15}$, —(C(R$^9$)$_2$)$_q$OR$^{16}$, —(C(R$^9$)$_2$)$_q$NR$^{16}$R$^{17}$, —(C(R$^9$)$_2$)$_p$S(O)$_m$R$^{16}$, —(C(R$^9$)$_2$)$_p$CO$_2$R$^{16}$, —(C(R$^9$)$_2$)$_p$C(O)NHR$^{16}$ and —(C(R$^9$)$_2$)$_p$C(O)R$^{15}$; further provided that $R^{13}$ and $R^{14}$ may optionally be taken together with the nitrogen to which they are attached forming a heterocyclyl, heteroaryl or bicyclyl heteroaryl ring optionally substituted on either nitrogen or carbon by one or more selected from the group, —R$^5$, —R$^{11}$, —(C(R$^9$)$_2$)$_q$arylR$^{15}$, —(C(R$^9$)$_2$)$_q$heteroarylR$^{15}$, —(C(R$^9$)$_2$)$_q$heterocyclylR$^{15}$, —(C(R$^9$)$_2$)$_q$CO$_2$R$^{16}$, —(C(R$^9$)$_2$)$_q$C(O)NHR$^{16}$, and —(C(R$^9$)$_2$)$_q$C(O)R$^{15}$; or optionally substituted on carbon by —F, —(C(R$^7$)$_2$)$_q$OR$^{16}$, —(C(R$^7$)$_2$)$_q$NR$^{16}$R$^{17}$, and —(C(R$^9$)$_2$)$_q$S(O)$_m$R$^{16}$; or optionally substituted on nitrogen by —(C(R$^9$)$_2$)$_q$OR$^{16}$, —(C(R$^9$)$_2$)$_p$NR$^{16}$R$^{17}$, and —(C(R$^9$)$_2$)$_p$S(O)$_m$R$^{16}$;

$R^{15}$ is independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_q$OH, —(C(R$^9$)$_2$)$_q$OR$^{10}$, —(C(R$^9$)$_2$)$_q$NH$_2$, —(C(R$^9$)$_2$)$_q$NHR$^{10}$, —(C(R$^9$)$_2$)$_q$R$^{10}$, —(C(R$^9$)$_2$)$_q$S(O)$_m$R$^{10}$, —(C(R$^9$)$_2$)$_q$CO$_2$R$^{10}$, —(C(R$^9$)$_2$)$_q$CONHR$^{10}$, —(C(R$^9$)$_2$)$_q$CONR$^{10}$R$^{10}$, —(C(R$^9$)$_2$)$_q$COR$^{10}$, —(C(R$^9$)$_2$)$_q$CO$_2$H, and —(C(R$^9$)$_2$)$_q$CONH$_2$;

$R^{16}$ and $R^{17}$ are independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_p$OH, —(C(R$^9$)$_2$)$_p$OR$^{10}$, —(C(R$^9$)$_2$)$_p$NH$_2$, —(C(R$^9$)$_2$)$_p$NHR$^{10}$, —(C(R$^9$)$_2$)$_p$NR$^{10}$R$^{10}$, —(C(R$^9$)$_2$)$_p$S(O)$_m$R$^{10}$, —(C(R$^9$)$_2$)$_p$CO$_2$R$^{10}$, —(C(R$^9$)$_2$)$_p$CONHR$^{10}$, —(C(R$^9$)$_2$)$_p$CONR$^{10}$R$^{10}$, —(C(R$^9$)$_2$)$_p$COR$^{10}$, —(C(R$^9$)$_2$)$_p$CO$_2$H, and —(C(R$^9$)$_2$)$_p$CONH$_2$;

$R^{18}$ is independently selected from the group consisting of —H, -aryl, —R$^5$, —R$^6$NH$_2$, —R$^6$NHR$^5$ and —R$^6$Q;

provided that, the 7-position is substituted or a pharmaceutically acceptable salt thereof.

28. A method of treating or inhibiting the progression of osteoporosis in a mammal in need thereof which comprises providing to said mammal an effective amount of Src kinase inhibitor of Formula (1) having the structure,

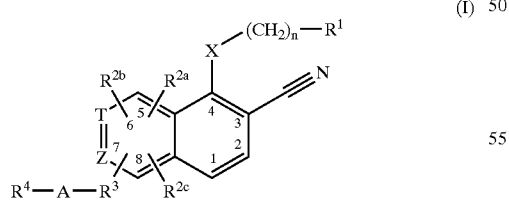

(I)

wherein:

X is —NH—, —NR$^5$—, —O—, or o—S(O)$_m$—;

n is an integer of 0 or 1;

m is an integer of 0 to 2;

q is an integer of 0 to 5;

p is an integer of 2 to 5;

s is an integer of 0 to 5;

r is an integer of 0 to 5;

J is halogen;

A is absent;

T is N and Z is carbon;

$R^1$ is a heteroaryl ring having 6 atoms containing 1 to 3 heteroatoms, 1 of which is N, or particularly 1 or 2 heteroatoms which may be the same or different, selected from N, O and S wherein the heteroaryl ring may be optionally substituted with 1 to 4 substituents which may be the same or different selected from —H, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$ R$^5$, —NHSO$_2$R, —R$^6$OH, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —R$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —R$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q and YR$^8$ groups wherein Y is independently selected from —C(O)—, —C(O)O—, —OC(O)—, —C(O)NH—, —NHC(O)—, —NHSO$_2$—, —SO$_2$NH—, —C(OH)H—, —O(C(R$^9$)$_2$)$_q$—, —S(O)$_m$ (C(R$^9$)$_2$)$_q$—, —NH(C(R$^9$)$_2$)$_q$—, —NR$^{10}$(C(R$^9$)$_2$)$_q$—, —(C(R$^9$)$_2$)$_q$—, —(C(R$^9$)$_2$)$_q$O—, —(C(R$^9$)$_2$)$_q$ S(O)$_m$, —(C(R$^9$)$_2$)$_q$NH—, —(C(R$^9$)$_2$)$_q$NR$^{10}$—, —C≡C—, cis and trans —CH=CH— and cycloalkyl of 3 to 10 carbon atoms;

Q is —NR$^5$R$^5$ and further provided that when each R$^5$ is independently selected from alkyl and alkenyl, R$^5$R$^5$ may optionally be taken together with the nitrogen atom to which they are attached forming a heterocyclyl ring of 3 to 8 atoms, optionally containing 1 or 2 additional heteroatoms which may be the same or different selected from N, O and S;

$R^{2a}$, $R^{2b}$, and $R^{2c}$, are each, independently selected from —H, -aryl, —CH$_2$aryl, —Oaryl, —S(O)$_m$aryl, —J, —NO$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —S(O)$_m$R$^5$, —NHSO$_2$R$^5$, —R$^{11}$, —OR$^{11}$, —R$^6$OH, —R$^6$OR$^5$, —R$^6$SH, —R$^6$S(O)$_m$R$^5$, —OR$^7$OH, —OR$^{10}$R, —OC(O)R$^5$, —NHC(O)R$^5$, —NHC(O)NHR$^5$, —OR$^6$C(O)R$^5$, —NHR$^6$C(O)R, —C(O)R$^5$, —C(O)OR$^5$, —C(O)NHR$^5$, —C(O)Q, —R$^6$C(O)H, R$^6$C(O)R$^5$, —R$^6$C(O)OR$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$, —R$^6$OC(O)Q, —G—(C(R$^9$)$_2$)$_p$—R$^{12}$, —(C(R$^9$)$_2$)$_q$—R$^{12}$,

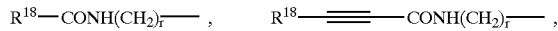

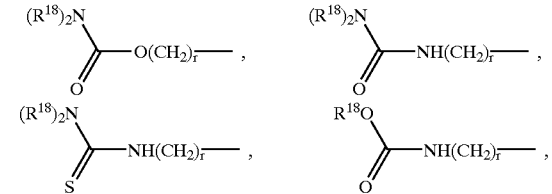

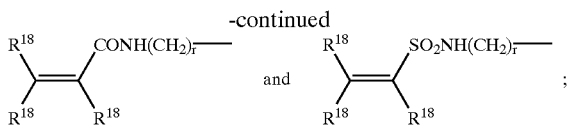

-continued
and ;

G is —NH—, —NR$^{10}$—, —O— or —S(O)$_m$—;

R$^3$ is selected from alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; alkynyl of 2 to 6 carbon atoms, optionally substituted with one or more of —R, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S where the heteroaryl ring may be optionally substituted with 1 to 4 substituents which may be the same or different selected from —R$^1$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^4$ is selected from —(C(R$^9$)$_2$)$_r$H, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkenyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

alkynyl of 2 to 6 carbon atoms, optionally substituted with one or more of —R$^{10}$, —(C(R$^9$)$_2$)$_s$R$^{12}$, —CHO, 1,3-dioxolane, —NO$_2$, —CN, —CO$_2$H, —CONHR$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

aryl of 6 to 12 carbon atoms optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —R$^{10}$, —(C(R$^9$)$_2$)$_s$R$^{12}$, —CHO, 1,3-dioxolane, —NO$_2$, —CN, —CO$_2$H, —CONH$_2$, —CO$_2$R$^{10}$, —CONHR$^{10}$, —COR$^{10}$, —(C(R$^9$)$_2$)$_q$OH, —(C(R$^9$)$_2$)$_q$OR$^{10}$, —(C(R$^9$)$_2$)$_q$NHR$^{10}$, —(C(R$^9$)$_2$)$_q$J, —(C(R$^9$)$_2$)$_q$NH$_2$, —(C(R$^9$)$_2$)$_r$H, —G(C(R$^9$)$_2$)$_p$OR$^{10}$, —G(C(R$^9$)$_2$)$_p$R$^{12}$, and —G(C(R$^9$)$_2$)$_p$OH;

R$^5$ is a monovalent group independently selected from alkyl of 1 to 12 carbon atoms, preferred is 1 to 6 carbon atoms, alkenyl of 2 to 6 carbon atoms, and alkynyl of 2 to 6 carbon atoms;

R$^6$ is a divalent group selected from alkyl of 1 to 6 carbon atoms, alkenyl of 2 to 6 carbon atoms, and alkynyl of 2 to 6 carbon atoms;

R$^7$ is a divalent alkyl group of 2 to 6 carbon atoms;

R$^8$ is a cycloalkyl ring of 3 to 10 carbon atoms that may optionally be substituted with one or more alkyl groups of 1 to 6 carbon atoms; aryl of 6 to 12 carbon atoms optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$S(O)$_m$R, —NHR$^7$OH, —NHR$^7$OR$^5$, —N(R$^5$)R$^7$OH, —R$^6$R$^7$, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$OC(O)NH$_2$, —R$^6$OC(O)NHR$^5$ and —R$^6$OC(O)Q; a heteroaryl ring having 5 or 6 atoms containing 1 to 4 heteroatoms or particularly 1 or 2 heteroatoms which may be the same or different, selected from N, O and S wherein the heteroaryl ring may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R, —R$^{11}$, —OR$^{11}$, —NHR$^{11}$, —R$^6$H, —R$^6$OR$^5$, —R$^6$NH$_2$, —R$^6$NHR$^5$, —R$^6$Q, —R$^6$SH, —R$^6$S(O)$_m$R$^5$, —NHR$^7$OH, —NHR$^7$OR$^5$, —N(R$^5$)R$^7$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —R$^6$R$^{12}$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R, —R$^6$OC(O)NH$_2$, —R$^6$OC(O)NHR$^5$ and —R$^6$OC(O)Q; a bicyclic heteroaryl ring system having 8 to 20 atoms containing 1 to 4 heteroatoms which may be the same or different selected from N, O and S wherein the bicyclic heteroaryl ring system may be optionally substituted with 1 to 4 substituents which may be the same or different selected from —H, -aryl, —CH$_2$aryl, —NHaryl, —Oaryl, —S(O)$_m$aryl, —J, —NO$_2$, —NH$_2$, —OH, —SH, —CN, —N$_3$, —COOH, —CONH$_2$, —NHC(O)NH$_2$, —C(O)H, —CF$_3$, —OCF$_3$, —R$^5$, —OR$^5$, —NHR$^5$, —Q, —S(O)$_m$R$^5$, —NHSO$_2$R$^5$, —R$^{11}$, —OR$^{11}$, —NHR$^{11}$, —R$^6$OH, —R$^6$OR$^5$, —R$^6$NH$_2$, —R$^6$NHR$^5$, —R$^6$Q, —R$^6$SH, —R$^6$R$^{12}$, —R$^6$S(O)$_m$R$^5$, —NHR$^7$OH, —NHR$^7$OR$^5$, —N(R$^5$)R$^6$OH, —N(R$^5$)R$^7$OR$^5$, —NHR$^7$NH$_2$, —NHR$^7$NHR$^5$, —NHR$^7$Q, —N(R$^5$)R$^7$NH$_2$, —N(R$^5$)R$^7$NHR$^5$, —N(R$^5$)R$^7$Q, —OR$^7$OH, —OR$^7$OR$^5$, —OR$^7$NH$_2$, —OR$^7$NHR$^5$, —OR$^7$Q, —OC(O)R$^5$, —NHC(O)R$^5$, —NHC(O)NHR$^5$, —OR$^6$C(O)R$^5$, —NHR$^6$C(O)R$^5$, —C(O)R$^5$, —C(O)OR$^5$, —C(O)NHR$^5$, —C(O)Q, —R$^6$C(O)H, —R$^6$C(O)R$^5$, —R$^6$C(O)OH, —R$^6$C(O)OR$^5$, —R$^6$C(O)NH$_2$, —R$^6$C(O)NHR$^5$, —R$^6$C(O)Q, —R$^6$OC(O)R$^5$, —R$^6$C(O)NH$_2$, —R$^6$OC(O)NHR$^5$ and —R$^6$OC(O)Q;

R$^9$ is independently —H, —F or —R$^5$;

R$^{10}$ is an alkyl group of 1 to 12 carbon atoms, preferred is 1 to 6 carbon atoms;

R$^{11}$ is a cycloalkyl group of 3 to 10 carbon atoms;

R$^{12}$ is —N(O)$_n$R$^{13}$R$^{14}$ or —N$^+$(R$^{10}$R$^{13}$R$^{14}$)J$^-$;

provided that when R$^{12}$ is N(O)$_n$R$^{13}$R$^{14}$ and n is 1, R$^{13}$ or R$^{14}$ are not H;

R$^{13}$ and R$^{14}$ are independently selected from a group consisting of —(C(R$^9$)$_2$)$_q$aryl-R$^{15}$, —(C(R$^9$)$_2$)$_q$heteroaryl-R$^{15}$, —(C(R$^9$)$_2$)$_q$heterocyclyl-R$^{15}$, —(C(R$^9$)$_2$)$_p$OR$^{16}$, —(C(R$^9$)$_2$)$_p$NR$^{16}$R$^{17}$, —(C(R$^9$)$_2$)$_p$S(O)$_m$R$^{16}$, —(C(R$^9$)$_2$)$_p$CO$_2$R$^{16}$, —(C(R$^9$)$_2$)$_p$C(O)NHR$^{16}$ and —(C(R$^9$)$_2$)$_p$C(O)R$^{15}$; further provided that R$^{13}$ and R$^{14}$ may optionally be taken together with the nitrogen to which they are attached forming a heterocyclyl, heteroaryl or bicyclyl heteroaryl ring optionally substituted on either nitrogen or carbon by one or more selected from the group, —R$^5$, —R$^{11}$, —(C(R$^9$)$_2$)$_q$arylR$^{15}$, —(C(R$^9$)$_2$)$_q$heteroarylR$^{15}$, —(C(R$^9$)$_2$)$_q$heterocyclylR$^{15}$, —(C(R$^9$)$_2$)$_q$CO$_2$R$^{16}$, —(C(R$^9$)$_2$)$_q$C(O)NHR$^{16}$, and —(C(R$^9$)$_2$)$_q$C(O)R$^{15}$; or optionally substituted on carbon by —F, —(C(R$^7$)$_2$)$_q$OR$^{16}$, —(C(R$^7$)$_2$)$_q$NR$^{16}$R$^{17}$, and —(C(R$^9$)$_2$)$_q$S(O)$_m$R$^{16}$; or optionally substituted on nitrogen by —(C(R$^9$)$_2$)$_p$OR$^{16}$, —(C(R$^9$)$_2$)$_p$NR$^{16}$R$^{17}$, and —(C(R$^9$)$_2$)$_p$S(O)$_m$R$^{16}$;

R$^{15}$ is independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_q$OH, —(C(R$^9$)$_2$)$_q$OR$^{10}$, —(C(R$^9$)$_2$)$_q$NH$_2$, —(C(R$^9$)$_2$)$_q$NHR$^{10}$, —(C(R$^9$)$_2$)$_q$R$^{10}$, —(C(R$^9$)$_2$)$_q$S(O)$_m$R$^{10}$, —(C(R$^9$)$_2$)$_q$CO$_2$R$^{10}$, —(C(R$^9$)$_2$)$_q$CONHR$^{10}$, —(C(R$^9$)$_2$)$_q$CONR$^{10}$R$^{10}$, —(C(R$^9$)$_2$)$_q$COR$^{10}$, —(C(R$^9$)$_2$)$_q$CO$_2$H, and —(C(R$^9$)$_2$)$_q$CONH$_2$;

R$^{16}$ and R$^{17}$ are independently selected from a group consisting of —H, —R$^5$, —R$^{11}$, —(C(R$^9$)$_2$)$_q$aryl, —(C(R$^9$)$_2$)$_q$heteroaryl, —(C(R$^9$)$_2$)$_q$heterocyclyl, —(C(R$^9$)$_2$)$_p$OH, —(C(R$^9$)$_2$)$_p$OR$^{10}$, —(C(R$^9$)$_2$)$_p$NH$_2$, —(C(R$^9$)$_2$)$_r$NHR$^{10}$, —(C(R$^9$)$_2$)$_p$NR$^{10}$R$^{10}$, —(C(R$^9$)$_2$)$_p$S(O)$_m$R$^{10}$, —(C(R$^9$)$_2$)$_p$CO$_2$R$^{10}$, —(C(R$^9$)$_2$)$_p$CONHR$^{10}$, —(C(R$^9$)$_2$)$_p$CONR$^{10}$R$^{10}$, —(C(R$^9$)$_2$)$_p$COR$^{10}$, —(C(R$^9$)$_2$)$_p$CO$_2$H, and —(C(R$^9$)$_2$)$_p$CONH$_2$;

R$^{18}$ is independently selected from the group consisting of —H, -aryl, —R$^5$, —R$^6$NH$_2$, —R$^6$NHR$^5$ and —R$^6$Q;

provided that, the 7-position is substituted or a pharmaceutically acceptable salt thereof.

* * * * *

UNITED STATES PATENT AND TRADEMARK OFFICE
CERTIFICATE OF CORRECTION

PATENT NO. : 6,689,772 B1
DATED : February 10, 2004
INVENTOR(S) : Diane H. Boschelli et al.

It is certified that error appears in the above-identified patent and that said Letters Patent is hereby corrected as shown below:

The structure found on the title page and Columns 6, 211, 217, 222, 227, 231, 236, 241, 245, 250, 255 and 259 should be replaced" with:

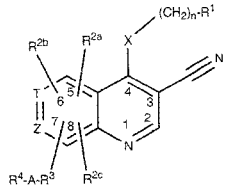

Column 215,
Line 16, replace "—$NHR^1$" with -- —$NHR^{11}$ --
Line 61, replace "—$NHSO^2R^5$" with -- $NHSO_2R^5$ --
Line 61, replace "—$R11$" with -- —$R^{11}$ --

Column 216,
Line 37, replace "—$(C(R^9)_qS(O)_mR^{10}$" with -- —$(C(R^9)_2)_qS(O)_mR^{10}$ --

Column 217,
Line 25, replace "—hetetoatoms" with -- —heteroatoms --

Column 218,
Line 55, replace "—$G(C(R^9)_2)R^{12}$" with -- —$G(C(R^9)_2)_pR^{12}$ --
Line 65, replace "—$G(C(R^9)_2)_2)_pOR^{10}$" with -- —$G(C(R^9)_2)_pOR^{10}$ --

Column 220,
Line 35, replace "—$R^6C(O)R$" with -- —$R^6C(O)R^5$ --
Line 38, replace "ling" with -- ring --

Column 221,
Line 4, replace "—$^{(C(R^9)}_2)_pOR^{16}$" with -- —$(C(R^9)_2)_pOR^{16}$ --
Line 13, replace "—$(C(R^9)_2)_q$heterocyclyl-$R^{15}$" with -- —$(C(R^9)_2)_q$heterocyclyl$R^{15}$ --
Line 24, replace "—$(C(R^9)_2)_qCOR^{10}$" with -- —$(C(R^9)_2)_qS(O)_mR^{10}$ --

Column 222,
Line 53, replace "—NO" with -- —$NO_2$ --
Line 55, replace "—NHR" with -- —$NHR^5$ --
Line 55, replace "—$S(O)_mR$" with -- —$S(O)_mR^5$ --
Line 56, replace "—$NHSO_2R$" with -- —$NHSO_2R^5$ --

Column 223
Line 50, replace "—$(C(R^9)_2)_q(OR^{10}$" with -- —$(C(R^9)_2)_qOR^{10}$ --
Line 50, replace "—$(C(R^5)_2)_qNHR^{10}$" with -- —$(C(R^9)_2)_qNHR^{10}$ --
Line 52, replace "—$G(C(R^9)_2)_p,OR^{10}$" with -- —$G(C(R^9)_2)_pOR^{10}$ --
Line 57, replace "—$(C(R^9)_2)_qNH^{10}$" with -- —$(C(R^9)_2)_qNHR^{10}$ --

UNITED STATES PATENT AND TRADEMARK OFFICE
CERTIFICATE OF CORRECTION

PATENT NO.   : 6,689,772 B1
DATED        : February 10, 2004
INVENTOR(S)  : Diane H. Boschelli et al.

It is certified that error appears in the above-identified patent and that said Letters Patent is hereby corrected as shown below:

Column 224,
Line 9, replace "—$(C(R^{10})_2)_qOR^{10}$" with -- —$(C(R^9)_2)_qOR^{10}$ --

Column 225,
Line 26, replace "—$R^6S(O)_mR$" with -- —$R^6S(O)_mR^5$ --

Column 226,
Line 5, replace "—$N(R^5)R^7R^5$" with -- —$N(R^5)R^7OR^5$ --

Column 227,
Line 34, replace "—$R^7NH_2$" with -- —$R^6NH_2$ --

Column 228,
Line 67, replace "—$G(C(^9)_2)_pOH$" with -- —$G(C(R^9)_2)_pOH$ --

Column 229,
Line 3, replace "—$CONHR_2$" with -- —$CONH_2$ --
Line 10, replace "—$CO,H$" with -- —$CO_2H$ --

Column 230,
Line 28, replace "—$NHR^7OR$" with -- —$NHR^7OR^5$ --
Line 28, replace "—$N(R^5)R^7OR$" with -- —$N(R^5)R^7OR^5$ --
Line 49, replace "—$R^6OR$" with -- —$R^6OR^5$ --
Line 59, replace "—$ROC(O)NH_2$" with -- —$R^6OC(O)NH_2$ --
Line 60, replace "—$ROC(O)NHR^5$" with -- —$R^6OC(O)NHR^5$ --
Line 66, replace "—$N(O),R^{13}R^{14}$" with -- —$N(O)_nR^{13}R^{14}$ --

Column 231,
Line 24, replace "—$(C(R^9)_2)_qR^{10}$" with -- —$(C(R^9)_2)_qS(O)_mR^{10}$ --
Line 25, replace "—$(C(R^9)_2)_qCONR^{10}$" with -- —$(C(R^9)_2)_qCONR^{10}R^{10}$ --

Column 232,
Line 11, replace "—$R^6H$" with -- —$R^6OH$ --
Line 11, replace "—$R^6R$" with -- —$R^6OR_5$ --
Line 21, replace "—$R^6C(O)NHR$" with -- $R^6C(O)NHR_5$ --
Line 51, insert -- —$(C(R^9)_2)_q-R^{12}$ -- at end of line before structures Column 233,
Lines 10, 17 and 46, replace "—$(C(R^9)_2)R^{12}$" with -- —$(C(R^9)_2)_sR^{12}$ --
Line 62, replace "—$COR$" with -- —$COR^{10}$ --
Line 67, replace "—$(C(R^9)_2)_sR^1$" with -- —$(C(R^9)_2)_sR^{12}$ --

UNITED STATES PATENT AND TRADEMARK OFFICE
CERTIFICATE OF CORRECTION

PATENT NO. : 6,689,772 B1
DATED : February 10, 2004
INVENTOR(S) : Diane H. Boschelli et al.

It is certified that error appears in the above-identified patent and that said Letters Patent is hereby corrected as shown below:

Column 234,
Line 10, replace "—$CO_2R$" with -- $CO_2R^{10}$ --

Column 235,
Line 15, replace "—$OR^7R^5$" with -- $OR^7OR^5$ --
Line 44, replace "—$R^6C(O)NHR^5$" with -- $R^6OC(O)NHR^5$ --
Line 44, replace "—$R6C(O)Q$" with -- —$R6OC(O)Q$ --
Line 50, replace $N(O)^7R^{13}R^{14}$" with -- $N(O)^nR^{13}R^{14}$ --

Column 237,
Line 1, replace "—$NHC(O)NH^5R$" with -- —$NHC(O)NHR^5$ --
Line 10, replace "—$NR^{10}(C(R^9)_2)$" with -- —$NR^{10}(C(R^9)_2)_q$ --
Line 24, replace "—N" with -- —$N_3$ --
Line 54, replace "—$(C(R^5)_2)_sR^{12}$" with -- —$(C(R^9)_2)_sR^{12}$ --

Column 238,
Line 39, replace "—$CONR^{10}$" with -- —$CONHR^{10}$ --

Column 239,
Line 29, replace "—$S(O)_mR$" with -- —$S(O)_mR^5$ --
Line 37, replace "—$OR^6C(O)R$" with -- —$OR^6C(O)R^5$ --
Line 41, replace "—$R^6OC(O)R$" with -- —$R^6OC(O)R^5$ --
Line 42, replace "—$R^6C(O)NHR^5$" with -- —$R^6OC(O)NHR^5$ --
Line 42, replace "—$R^6C(O)Q$" with -- —$R^6OC(O)Q$ --

Column 240,
Line 8, replace "—$R^6H$" with -- —$R^6OH$ --
Line 9, replace "—$R^6R^5$" with -- —$R^6OR^5$ --
Line 20, replace "—$R^6C(O)Q$" with -- —$R^6OC(O)Q$ --

Column 242,
Line 61, replace "—$G(C(PR^9)_2)_pOR^{10}$" with -- —$G(C(R^9)_2)_pOR^{10}$ --

Column 243,
Line 1, replace "—NO" with -- —$NO_2$ --
Line 2, replace "—$(C(R^9)_2)_qO$" with -- —$(C(R^9)_2)_qOH$ --
Line 44, replace "—$(C(R^9)_2)(NHR^{10}$" with -- —$(C(R^9)_2)_qNHR^{10}$ --

Column 244,
Line 53, replace "—$R^6H$" with -- —$R^6OH$ --
Line 54, replace "—$R^6R^5$" with -- —$R^6OR^5$ --

UNITED STATES PATENT AND TRADEMARK OFFICE
CERTIFICATE OF CORRECTION

PATENT NO. : 6,689,772 B1
DATED : February 10, 2004
INVENTOR(S) : Diane H. Boschelli et al.

It is certified that error appears in the above-identified patent and that said Letters Patent is hereby corrected as shown below:

Column 245,
Line 2, replace "—N(O),$R^{13}R^{14}$" with -- —N(O)$_n R^{13}R^{14}$ --
Line 2, replace "—$N^+(R^{10}R^{13}R^4)J^-$" with -- —$N^+(R^{10}R^{13}R^{14})J^-$ --
Line 10, replace "—$(C(R^9)_2)_p C(O)R_5$" with -- —$(C(R^9)_2)_p C(O)R^{15}$ --
Line 19, replace "—$(C(R^7)_2)_q(OR^{10}$" with -- —$(C(R^7)_2)_q OR^{16}$ --
Line 39, replace "—$(C(R^9)_2)_2)COR^{10}$" with -- —$(C(R^9)_2)_p COR^{10}$ --

Column 246,
Line 32, replace "(is" with -- cis --
Line 38, replace "ting" with -- ring --
Line 48, replace "—$NHR^{10}C(O)R^5$" with -- —$NHR^6 C(O)R^5$ --

Column 247,
Line 7, replace "—N-"— with -- —NH --
Line 47, replace "—NO" with -- —$NO_2$ --

Column 248,
Line 56, replace "—$N(R^5)R^7 OR$" with -- —$N(R^5)R^7 OR^5$ --

Column 249,
Line 49, replace "—$N(O)R_n R^{13}R^{14}$" with -- —$N(O)_n R^{13}R^{14}$ --
Line 57, replace "—$C(R^9)_2)_p C(O)R^5$" with -- —$C(R^9)_2)_p C(O)R^{15}$ --

Column 251,
Line 30, replace "—-$OR^7 R^5$" with -- —$OR^7 OR^5$ --
Line 63, replace "—$CO_2 R$)" with -- —$CO_2 R^{10}$ --
Line 64, replace "—$COR^{10}$)" with -- —$COR^{10}$ --

Column 252,
Lire 28, replace "—$(C(R^9)_2)_q NH$" with -- —$(C(R^9)_2)_q NH_2$ --
Line 65, replace "—1,3-dioxane" with -- —1,3-dioxolane --

Column 253,
Line 43, replace "—$R^6 C(O)R^5$" with -- —$R^6 OC(O)R^5$ --
Line 51, replace "—$NHR_2$" with -- —$NH_2$ --

Column 254,
Line 11, insert -- —$R^6 SH, -R^6 R^{12}$ -- after "—R6Q"
Line 18, replace "—$C(O)NR^5$" with -- —$C(O)NHR^5$ --
Line 53, replace "—$(C(R^9)_2)_q S(O)R^{10}$" with -- —$(C(R^9)_2)_q S(O)_m R^{10}$ --
Line 62, replace "—$(C(R^9)_2)_p S(O)_m R^1$" with -- —$(C(R^9)_2)_p S(O)_m R^{10}$ --

UNITED STATES PATENT AND TRADEMARK OFFICE
CERTIFICATE OF CORRECTION

PATENT NO. : 6,689,772 B1
DATED : February 10, 2004
INVENTOR(S) : Diane H. Boschelli et al.

It is certified that error appears in the above-identified patent and that said Letters Patent is hereby corrected as shown below:

<u>Column 255,</u>
Line 49, replace "—$R^6C(O)R^5$" with -- —$R^6OC(O)R^5$ --
Line 63, replace "ling" with -- ring --

<u>Column 256,</u>
Line 67, replace "—$C(R^9)_2)_sR^5$" with -- —$C(R^9)_2)_sR^{12}$ --

<u>Column 257,</u>
Line 14, replace "—$(C(R^9)_2)R12$" with -- —$(C(R^9)_2)_sR^{12}$ --
Line 18, replace "—$G(C(R^9)_2)_pOR^{10})$" with -- —$G(C(R^9)_2)_pOR^{10}$ --
Line 24, replace "—$(C(R^9)_2)J$" with -- —$(C(R^9)_2)_qJ$ --
Line 32, replace "—$^{(C(R^9)}_2)_qNHR^{10}$" with -- —$(C(R^9)_2)_qNHR^{10}$ --
Line 42, replace the first instance of "—$COR^{10}$" with -- $CO_2R^{10}$ --

<u>Column 258,</u>
Line 15, replace "—$OR^6C(O)R$" with -- —$OR^6C(O)R_5$ --
Line 31, replace "—$R^6H$" with -- —$R^6OH$ --
Line 36, replace "—$OR^{10}H$" with -- —$OR^7OH$ --
Line 36, replace "—$OR^7R^5$" with -- —$OR^7OR^5$ --
Line 42, replace "—$R^{10}C(O)R^5$" with -- —$R^6OC(O)R^5$ --
Line 49, replace "—$S(O),aryl$" with -- —$S(O)_maryl$ --

<u>Column 259,</u>
Line 22, replace "—$(C(R^9)_2)_qOR^{16}$" with -- —$(C(R^9)_2)_pOR^{16}$ --
Line 35, replace "—$(C(R^9)_2)_qNH^2$" with -- —$(C(R^9)_2)_pNH^2$ --
Line 60, replace "—$o-S(O)_m-$" with -- —$S(O)_m—$ --

<u>Column 260,</u>
Line 13, replace "—$NHSO_2R$" with -- —$NHSO_2R^5$ --
Line 47, replace "—$OR^{10}R$" with -- —$OR^7OR^5$ --
Line 48, replace "—$NHR^6C(O)R$" with -- —$NHR^6C(O)R^5$ --
Line 49, delete "—$R^6C(O)OR^5$" (it's a duplicate)

<u>Column 261,</u>
Line 16, replace "—R" with -- —$R^{10}$ --
Line 35, replace "—$R^1$" with -- —$R^{10}$ --
Line 60, replace "—$(C(R^9)_2)_5R^{12}$" with -- —$(C(R^9)_2)_sR^{12}$ --

UNITED STATES PATENT AND TRADEMARK OFFICE
CERTIFICATE OF CORRECTION

PATENT NO. : 6,689,772 B1
DATED : February 10, 2004
INVENTOR(S) : Diane H. Boschelli et al.

It is certified that error appears in the above-identified patent and that said Letters Patent is hereby corrected as shown below:

<u>Column 262,</u>
Line 1, replace "—CONHR$_2$" with -- —CONH$_2$ --
Line 55, replace "—R$^6$S(O)mR" with -- —R$^6$S(O)$_m$R$^5$ --
Line 56, replace "—R$^6$R7" with -- —R$^6$R$^{12}$ --
Line 62, replace "—R$^6$C(O)R" with -- —R$^6$C(O)R$^5$ --

<u>Column 263,</u>
Line 9, replace "—NHSO$_2$R" with -- —NHSO$_2$R$^5$ --
Line 10, replace "—R$^6$H" with -- —R$^6$OH --
Line 21, replace "—R$^6$OC(O)R" with -- —R$^6$OC(O)R$^5$ --
Line 35, replace "—N(R$^5$)R$^6$OH" with -- —N(R$^5$)R$^7$OH --
Line 43, replace "—R$^6$C(O)NH$_2$" with -- —R$^6$OC(O)NH$_2$ --

<u>Column 264,</u>
Line 6, insert -- —H, —R$^5$, —R$^{11}$ -- after "—consisting of"
Line 36, replace "—(C(R$^9$)$_2$)$_r$NHR$^{10}$" with -- —(CR$^9$)$_2$)$_p$NHR$^{10}$ --

Signed and Sealed this

Fourteenth Day of September, 2004

JON W. DUDAS
*Director of the United States Patent and Trademark Office*